United States Patent
Venkatraman et al.

(10) Patent No.: US 11,718,631 B2
(45) Date of Patent: Aug. 8, 2023

(54) SULPHONAMIDES AND COMPOSITIONS THEREOF FOR TREATING CONDITIONS ASSOCIATED WITH NLRP ACTIVITY

(71) Applicant: Novartis AG, Basel (CH)

(72) Inventors: Shankar Venkatraman, Lansdale, PA (US); Shomir Ghosh, Brookline, MA (US); William R. Roush, Jupiter, FL (US); Dong-Ming Shen, Boston, MA (US); Jason Katz, Newton, MA (US); Hans Martin Seidel, Concord, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/756,358

(22) PCT Filed: Oct. 12, 2018

(86) PCT No.: PCT/US2018/055576
§ 371 (c)(1),
(2) Date: Apr. 15, 2020

(87) PCT Pub. No.: WO2019/079119
PCT Pub. Date: Apr. 25, 2019

(65) Prior Publication Data
US 2022/0340591 A1    Oct. 27, 2022

Related U.S. Application Data

(60) Provisional application No. 62/573,562, filed on Oct. 17, 2017.

(51) Int. Cl.
| | | |
|---|---|---|
| *C07D 498/04* | (2006.01) | |
| *C07C 311/51* | (2006.01) | |
| *C07D 231/12* | (2006.01) | |
| *C07D 317/46* | (2006.01) | |
| *C07D 209/04* | (2006.01) | |
| *C07D 215/14* | (2006.01) | |
| *C07D 307/54* | (2006.01) | |
| *C07D 471/04* | (2006.01) | |
| *C07D 487/04* | (2006.01) | |
| *C07D 409/12* | (2006.01) | |
| *C07D 277/30* | (2006.01) | |

(52) U.S. Cl.
CPC .......... *C07D 498/04* (2013.01); *C07C 311/51* (2013.01); *C07D 209/04* (2013.01); *C07D 215/14* (2013.01); *C07D 231/12* (2013.01); *C07D 277/30* (2013.01); *C07D 307/54* (2013.01); *C07D 317/46* (2013.01); *C07D 409/12* (2013.01); *C07D 471/04* (2013.01); *C07D 487/04* (2013.01)

(58) Field of Classification Search
CPC .. C07D 209/04; C07D 215/14; C07D 231/12; C07D 277/30; C07D 307/54; C07D 311/51; C07D 317/46; C07D 409/12; C07D 471/04; C07D 487/04; C07D 498/04
See application file for complete search history.

(56) References Cited

U.S. PATENT DOCUMENTS 6,433,009 B1    8/2002  Dombroski et al.

FOREIGN PATENT DOCUMENTS

| CN | 103159674 A | 6/2013 |
| CN | 103172547 A | 6/2013 |
| EP | 1431267 A1 | 6/2004 |
| WO | 00/39077 A2 | 7/2000 |
| WO | 2001023349 A1 | 4/2001 |
| WO | 2017/129897 A1 | 8/2017 |
| WO | 2017/184604 A1 | 10/2017 |

OTHER PUBLICATIONS

STN Registry database entry for CAS RN 1625968-73-1, Accessed June 13, Entry Date Sep. 25, 2014.*
Ammazzalorso et al., "Titanium-Promoted Acylation of Sulfonamides to N-Acylsulfonamide PPARα Antagonists," Synthetic Communications 45(22):2546-54 (2015).
Luo et al., "Metronidazole acid acyl sulfonamide: A novel class of anticancer agents and potential EGFR tyrosine kinase inhibitors," Bioorg & Med Chem. 19(20):6069-76 (2011).

* cited by examiner

*Primary Examiner* — Alicia L Otton
(74) *Attorney, Agent, or Firm* — Sophie Binet Cross

(57) ABSTRACT

In one aspect, compounds of Formula AA, or a pharmaceutically acceptable salt thereof, are featured: wherein the variables shown in Formula AA can be as defined anywhere herein. Compounds AA are modulators of NLRP1 and/or NLRP3

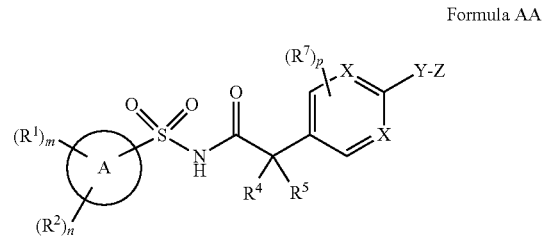

Formula AA

2 Claims, No Drawings
Specification includes a Sequence Listing.

SULPHONAMIDES AND COMPOSITIONS THEREOF FOR TREATING CONDITIONS ASSOCIATED WITH NLRP ACTIVITY

CROSS-REFERENCE TO RELATED APPLICATIONS

This application is a U.S. National Phase Application under 35 U.S.C. § 371 of International Patent Application No. PCT/US2018/055576, filed on Oct. 12, 2018, which claims priority to U.S. Patent Application No. 62/573,562, filed on Oct. 17, 2017.

SEQUENCE LISTING

The instant application contains a Sequence Listing which has been submitted electronically in ASCII format and is hereby incorporated by reference in its entirety. Said ASCII copy, created on Mar. 31, 2021 is named PAT058588-US-PCT_SL.txt and is 86,090 bytes in size.

TECHNICAL FIELD

This disclosure features chemical entities (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination of the compound) that are useful, e.g., for treating a condition, disease or disorder in which a decrease or increase in NLRP1/3 activity (e.g., an increase, e.g., a condition, disease or disorder associated with NLRP1/3 signaling) contributes to the pathology and/or symptoms and/or progression of the condition, disease or disorder in a subject (e.g., a human). This disclosure also features compositions as well as other methods of using and making the same.

BACKGROUND

The NLRP3 inflammasome is a component of the inflammatory process and its aberrant activation is pathogenic in inherited disorders such as the cryopyrin associated periodic syndromes (CAPS). The inherited CAPS Muckle-Wells syndrome (MWS), familial cold autoinflammatory syndrome (FCAS) and neonatal onset multi-system inflammatory disease (NOMID) are examples of indications that have been reported to be associated with gain of function mutations in NLRP3.

The NLRP1 inflammasome is a component of the inflammatory process and its aberrant activation is pathogenic in inherited disorders such as generalized vitiligo associated with autoimmune disease (autoimmune thyroid disease, latent autoimmune diabetes in adults, rheumatoid arthritis, psoriasis, pernicious anemia, systemic lupus erythematosus, and Addison's disease).

NLRP1 and NLRP3 can form a complex and they have been implicated in the pathogenesis of a number of complex diseases, including but not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In light of the above, it would be desirable to provide compounds that modulate (e.g., antagonize) NRLP1/3, wherein the compounds inhibit NLRP1 or NLRP3 or both NLRP3 and NLRP1.

SUMMARY

This disclosure features chemical entities (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination of the compound) that are useful, e.g., for treating a condition, disease or disorder in which a decrease or increase in NLRP1 or NLRP3 or both NLRP1 and NLRP3 activity, also referred to herein "NLRP1/3" activity (e.g., an increase, e.g., a condition, disease or disorder associated with NLRP1/3 signaling).

In some embodiments, provided herein is a compound of Formula AA

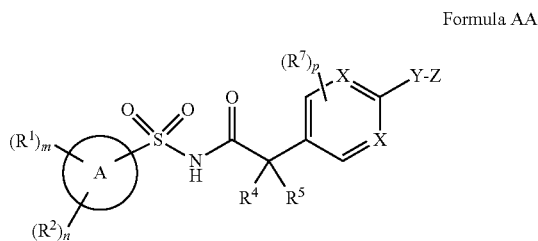

Formula AA or a pharmaceutically acceptable salt thereof, wherein the variables in Formula AA can be as defined anywhere herein.

This disclosure also features compositions as well as other methods of using and making the same.

An "antagonist" of NLRP1/3 includes compounds that inhibit the ability of NLRP1/3 to induce the production of IL-1β and/or IL-18 by directly binding to NLRP1/3, or by inactivating, destabilizing, altering distribution, of NLRP1/3 or otherwise.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, antagonizing) NLRP1 or NLRP3 or both NLRP1 and NLRP3 activity are featured that include contacting NLRP1 or NLRP3 or both NLRP1 and NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP1 or NLRP3 or both NLRP1 and NLRP3 (also referred to herein as "NLRP1/3"), as well as in vivo methods.

In a further aspect, methods of treatment of a disease in which NLRP1/3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which NLRP1/3 signaling contributes to the pathology and/or symptoms and/or progression of the disease, thereby treating the disease.

Embodiments can include one or more of the following features.

The chemical entity can be administered in combination with one or more additional therapies with one or more agents suitable for the treatment of the condition, disease or disorder.

Examples of the indications that may be treated by the compounds disclosed herein include but are not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune disease such as rheumatoid arthritis, systemic Lupus erythematosus, autoimmune thyroiditis; Addison's disease, pernicious anemia, cancer and aging.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "NLRP1/3" is meant to include, without limitation, nucleic acids, polynucleotides, oligonucleotides, sense and antisense polynucleotide strands, complementary sequences, peptides, polypeptides, proteins, homologous and/or orthologous NLRP molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a modulator of NLRP1/3, or a pharmaceutically acceptable salt and/or hydrate and/or cocrystal thereof;) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

The term "pharmaceutically acceptable salt" may refer to pharmaceutically acceptable addition salts prepared from pharmaceutically acceptable non-toxic acids including inorganic and organic acids. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. The term "pharmaceutically acceptable salt" may also refer to pharmaceutically acceptable addition salts prepared by reacting a compound having an acidic group with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The terms "hydrogen" and "H" are used interchangeably herein.

The term "halo" refers to fluoro (F), chloro (Cl), bromo (Br), or iodo (I).

The term "alkyl" refers to a hydrocarbon chain that may be a straight chain or branched chain, saturated or unsaturated, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "alkenyl" refers to a hydrocarbon chain including at least one double bond that may be a straight chain or branched chain, containing the indicated number of carbon atoms. For example, $C_{2-6}$ indicates that the group may have from 2 to 6 (inclusive) carbon atoms in it. Non-limiting examples include ethenyl and prop-1-en-2-yl.

The term "alkynyl" refers to a hydrocarbon chain including at least one triple bond that may be a straight chain or branched chain, containing the indicated number of carbon atoms. For example, $C_{2-6}$ indicates that the group may have from 2 to 6 (inclusive) carbon atoms in it. Non-limiting examples include ethynyl and 3,3-dimethylbut-1-yn-1-yl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "carbocyclic ring" as used herein includes an aromatic or nonaromatic cyclic hydrocarbon group having 3 to 10 carbons, such as 3 to 8 carbons, such as 3 to 7 carbons, which may be optionally substituted. Carbocyclic rings may be monocyclic or bicyclic, and when bicyclic, can be fused bicyclic, bridged bicyclic, or spirocyclic. Examples of carbocyclic rings include five-membered, six-membered, and seven-membered carbocyclic rings.

The term "heterocyclic ring" refers to an aromatic or nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. When bicyclic, a heterocyclic ring may have a nonaromatic ring and an aromatic ring (for example, chromanyl or methylenedioxyphenyl). When tricyclic, a heterocyclic ring may have 1 nonaromatic ring and 2 aromatic rings; or 2 nonaromatic rings and 1 aromatic ring. When a heterocyclic ring is bicyclic or tricyclic, any two connected rings of the bicycle or tricycle may be fused bicyclic, bridged bicyclic, or spirocyclic. Heterocyclic rings can also include oxidized ring members, such as —N(O)—, —S(O)—, and —S(O)$_2$—. Examples of heterocyclic rings include five-membered, six-membered, and seven-membered heterocyclic rings.

The term "cycloalkyl" as used herein includes a nonaromatic cyclic, bicylic, fused, or spiro hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. A cycloalkyl can include one or more elements of unsaturation; a cycloalkyl that includes an element of unsaturation is herein also referred to as a "cycloalkenyl". Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring fused or spiro system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Heterocycloalkyls can also include oxidized ring members, such as —N(O)—, —S(O)—, and —S(O)$_2$—. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

The term "aryl" is intended to mean an aromatic ring radical containing 6 to 10 ring carbons that may be a single ring or two fused rings wherein at least one of the fused rings is aromatic (i.e., the point of connection to the aryl is on an aromatic ring). Examples include phenyl and naphthyl.

The term "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N. Heteroaryls can also include oxidized ring members, such as —N(O)—, —S(O)—, and —S(O)$_2$—. Examples include furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Examples also include carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

The term "hydroxy" refers to an OH group.

The term "amino" refers to an NH$_2$ group.

The term "oxo" refers to O. By way of example, substitution of a CH$_2$ a group with oxo gives a C=O group.

As used herein, the terms "the ring A" or "A" are used interchangeably to denote in formula AA, wherein the bond that is shown as being broken by the wavy line connects A to the S(O)$_2$NHC(O)CR$^4$R$^5$ moiety of Formula AA.

As used herein, the term "the optionally substituted ring A" is used to denote in formula AA, wherein the bond that is shown as being broken by the wavy line connects A to the S(O)$_2$NHC(O)CR$^4$R$^5$ moiety of Formula AA.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The scope of the compounds disclosed herein includes tautomeric form of the compounds.

The details of one or more embodiments of the invention are set forth in the accompanying drawings and the description below. Other features and advantages of the invention will be apparent from the description and drawings, and from the claims.

DETAILED DESCRIPTION

In some embodiments, provided herein is a compound of Formula AA

Formula AA or a pharmaceutically acceptable salt thereof,
wherein
m=0, 1, or 2;
n=0, 1, or 2;
p=0, 1, or 2;
wherein
A is a 5-10-membered monocyclic or bicyclic heteroaryl, a 5-10-membered monocyclic or bicyclic heterocycloalkyl, a C$_6$-C$_{10}$ monocyclic or bicyclic aryl, or a C$_6$-C$_{10}$ monocyclic or bicyclic cycloalkyl;
R$^1$ and R$^2$ are each independently selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO—C$_6$-C$_{10}$ aryl, C(O)-5- to 10-membered heteroaryl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, NHCOC$_1$-C$_6$ alkyl, NHCOC$_6$-C$_{10}$ aryl, NHCO(5- to 10-membered heteroaryl), NHCO(3- to 7-membered heterocycloalkyl), NHCOC$_2$-C$_6$ alkynyl, NHCOOCC$_1$-C$_6$ alkyl, NH—(C=NR$^{13}$)NR$^{11}$R$^{12}$, CONR$^8$R$^9$, SF$_5$, SC$_1$-C$_6$ alkyl, S(O$_2$)C$_1$-C$_6$ alkyl, S(O)C$_1$-C$_6$ alkyl, S(O$_2$)NR$^{11}$R$^{12}$, SO$_2$NR$^8$R$^9$, NR$^{11}$SO$_2$NR$^{11}$R$^{12}$, NR$^{11}$CO$_2$R$^{12}$, NR$^{11}$CONR$^{11}$R$^{12}$, NR$^{11}$SO$_2$R$^{12}$, C$_3$-C$_7$ cycloalkyl and 3- to 7-membered heterocycloalkyl,
wherein the C$_1$-C$_6$ alkyl, C$_1$-C$_6$ haloalkyl, C$_3$-C$_7$ cycloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;
wherein each C$_1$-C$_6$ alkyl substituent and each C$_1$-C$_6$ alkoxy substituent of the R$^1$ or R$^2$ C$_3$-C$_7$ cycloalkyl or of the R$^1$ or R$^2$ 3- to 7-membered heterocycloalkyl is further optionally independently substituted with one to three hydroxy, halo, NR$^8$R$^9$, or oxo;
wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;
or at least one pair of R$^1$ and R$^2$ on adjacent atoms, taken together with the atoms connecting them, independently form at least one monocyclic or bicyclic C$_4$-C$_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$;

Y is selected from a bond, $-(Y^1)_o-(C_1$-$C_3$ alkyl$)_o$-, $-(CR^{16}R^{17})_o-(Y^1)_o-(CR^{16}R^{17})_o-$, and $C_{2\text{-}3}$ alkynylene;

$Y^1$ is selected from O, S, $SO_2$, $NR^{15}$, $CR^{16}OH$, $CR^{16}NR^8$, $C(O)NR^{15}$, and $C(O)$;

each occurrence of o is selected from 0 and 1, and wherein at least one o in $-(Y^1)_o-(C_1$-$C_3$ alkyl$)_o$- or $-(CR^{16}R^{17})_o-(Y^1)_o-(CR^{16}R^{17})_o-$ is 1;

Z is selected from a 5-10-membered monocyclic or bicyclic heteroaryl, a 5-10-membered monocyclic or bicyclic heterocyclic ring, a 5-10-membered monocyclic or bicyclic heterocycloalkyl, a $C_6$-$C_{10}$ monocyclic or bicyclic aryl, a $C_3$-$C_{10}$ monocyclic or bicyclic cycloalkyl, a $C_2$-$C_6$ alkenyl, and a $C_2$-$C_6$ alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, $C(O)OH$, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_3$-$C_{10}$ cycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, or wherein Z is optionally fused to a five-to-seven-membered carbocyclic ring or heterocyclic ring containing one or two heteroatoms independently selected from oxygen, sulfur and nitrogen;

each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

each X is independently N or $CR^6$;

each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

each of $R^4$ and $R^5$ is independently selected from hydrogen, $C_1$-$C_6$ alkyl, $C_1$-$C_6$ alkoxy, $NH_2$, $NHC_1$-$C_6$ alkyl, and $N(C_1$-$C_6$ alkyl$)_2$;

$R^{10}$ is $C_1$-$C_6$ alkyl;

each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$, and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl optionally substituted with halo, $C_1$-$C_6$ alkoxy, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^{15}$ is selected from H and $C_1$-$C_6$ alkyl;
$R^{16}$ is selected from H and $C_1$-$C_6$ alkyl; and
$R^{17}$ is selected from H and $C_1$-$C_6$ alkyl.

In some embodiments, provided herein is a compound of Formula AA

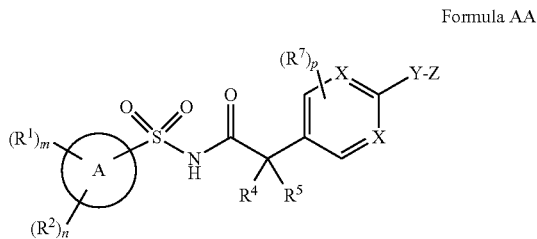

Formula AA or a pharmaceutically acceptable salt thereof,
wherein
m=0, 1, or 2;
n=0, 1, or 2;
p=0, 1, or 2;
wherein
A is a 5-10-membered monocyclic or bicyclic heteroaryl, a 5-10-membered monocyclic or bicyclic heterocycloalkyl, a $C_6$-$C_{10}$ monocyclic or bicyclic aryl, or a $C_6$-$C_{10}$ monocyclic or bicyclic cycloalkyl;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, C(O)-5- to 10-membered heteroaryl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)$ $C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^0$, $COOC_1$-$C_6$ alkyl, $C_6$-$C_{10}$ aryl, and $CONR^1R^9$;
Y is selected from a bond, —$(Y^1)_o$—$(C_1$-$C_3$ alkyl$)_o$-, —$(CR^{16}R^{17})_o$—$(Y^1)_o$—$(CR^{16}R^{17})_o$—, and $C_{2-3}$ alkynylene;
$Y^1$ is selected from O, S, $SO_2$, $NR^{15}$, $CR^{16}OH$, $CR^{16}NR^8$, $C(O)NR^{15}$, and C(O);
each occurrence of o is selected from 0 and 1, and wherein at least one o in —$(Y^1)_o$—$(C_1$-$C_3$ alkyl$)_o$- or —$(CR^{16}R^{17})_o$—$(Y^1)_o$—$(CR^{16}R^{17})_o$— is 1;
Z is selected from a 5-10-membered monocyclic or bicyclic heteroaryl, a 5-10-membered monocyclic or bicyclic heterocyclic ring, a 5-10-membered monocyclic or bicyclic heterocycloalkyl, a $C_6$-$C_{10}$ monocyclic or bicyclic aryl, a $C_3$-$C_{10}$ monocyclic or bicyclic cycloalkyl, a $C_2$-$C_6$ alkenyl, and a $C_2$-$C_6$ alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_3$-$C_{10}$ cycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, or wherein Z is optionally fused to a five-to-seven-membered carbocyclic ring or heterocyclic ring containing one or two heteroatoms independently selected from oxygen, sulfur and nitrogen;
wherein when Y is $Y^1$ and $Y^1$ is C(O), then Z is bonded to Y from a C ring member;
each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^1CO_2R^{12}$, $NR^{11}CONR^{11}R^{42}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl,
wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

each X is independently N or CR$^6$;
each R$^6$ is independently selected from hydrogen, C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, OH, NHC$_1$-C$_6$ alkyl, N(C$_1$-C$_6$ alkyl)$_2$, CONR$^8$R$^9$, SO$_2$NR$^8$R$^9$, NR$^{11}$SO$_2$NR$^{11}$R$^{12}$, NR$^{11}$CO$_2$R$^{12}$, NR$^{11}$CONR$^{11}$R$^{12}$, NR$^{11}$SO$_2$R$^{12}$, SF$_5$, S(O$_2$)C$_1$-C$_6$ alkyl, C$_3$-C$_7$ cycloalkyl, and 3- to 7-membered heterocycloalkyl, wherein the C$_1$-C$_6$ alkyl, C$_1$-C$_6$ haloalkyl, C$_1$-C$_6$ alkoxy, C$_3$-C$_7$ cycloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^6$ and R$^7$ on adjacent atoms, taken together with the atoms connecting them, independently form at least one C$_4$-C$_8$ carbocyclic ring or at least one 5-to-8-membered heterocyclic ring containing 1 or 2 heteroatoms and/or heteroatomic groups independently selected from O, N, NH, NR$^{13}$, S, S(O), and S(O)$_2$, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$;

each of R$^4$ and R$^5$ is independently selected from hydrogen, C$_1$-C$_6$ alkyl, C$_1$-C$_6$ alkoxy, NH$_2$, NHC$_1$-C$_6$ alkyl, and N(C$_1$-C$_6$ alkyl)$_2$;

R$^{10}$ is C$_1$-C$_6$ alkyl;
each of R$^8$ and R$^9$ at each occurrence is independently selected from hydrogen, C$_1$-C$_6$ alkyl, (C=NR$^{13}$)NR$^{11}$R$^{12}$, S(O$_2$)C$_1$-C$_6$ alkyl, S(O$_2$)NR$^{11}$R$^{12}$, COR$^{13}$, CO$_2$R$^{13}$, and CONR$^{11}$R$^{12}$; wherein the C$_1$-C$_6$ alkyl is optionally substituted with one or more hydroxy, halo, C$_1$-C$_6$ alkoxy, C$_6$-C$_{10}$ aryl, 5- to 10-membered heteroaryl, C$_3$-C$_7$ cycloalkyl or 3- to 7-membered heterocycloalkyl; or R$^8$ and R$^9$ taken together with the nitrogen they are attached to form a 3- to 7-membered ring optionally containing one or more heteroatoms in addition to the nitrogen they are attached to;

R$^{13}$ is C$_1$-C$_6$ alkyl optionally substituted with halo, C$_1$-C$_6$ alkoxy, C$_6$-C$_{10}$ aryl, or 5- to 10-membered heteroaryl;

each of R$^{11}$ and R$^{12}$ at each occurrence is independently selected from hydrogen and C$_1$-C$_6$ alkyl;
R$^{15}$ is selected from H and C$_1$-C$_6$ alkyl;
R$^{16}$ is selected from H and C$_1$-C$_6$ alkyl; and
R$^{17}$ is selected from H and C$_1$-C$_6$ alkyl.

In some embodiments, provided herein is a compound of Formula AA

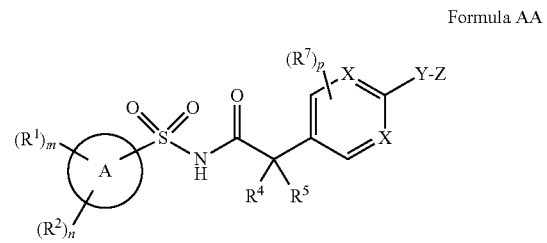

Formula AA or a pharmaceutically acceptable salt thereof,
wherein
m=0, 1, or 2
n=0, 1, or 2
p=0, 1 or 2
wherein
A is a 5-10-membered monocyclic or bicyclic heteroaryl, a 5-10-membered monocyclic or bicyclic heterocycloalkyl, a C$_6$-C$_{10}$ monocyclic or bicyclic aryl, or a C$_6$-C$_{10}$ monocyclic or bicyclic cycloalkyl;

R$^1$ and R$^2$ are each independently selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO—C$_6$-C$_{10}$ aryl, CO-5- to 10-membered heteroaryl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, NHCOC$_1$-C$_6$ alkyl, NHCOC$_6$-C$_{10}$ aryl, NHCO(5- to 10-membered heteroaryl), NHCO(3- to 7-membered heterocycloalkyl), NHCOC$_2$-C$_6$ alkynyl, NHCOOCC$_1$-C$_6$ alkyl, NH—(C=NR$^{13}$)NR$^{11}$R$^{12}$, CONR$^8$R$^9$, SO$_2$NR$^8$R$^9$, NR$^{11}$SO$_2$NR$^{11}$R$^{12}$, NR$^{11}$CO$_2$R$^{12}$, NR$^{11}$CONR$^{11}$R$^{12}$, NR$^{11}$SO$_2$R$^{12}$, SF$_5$, SC$_1$-C$_6$ alkyl, S(O$_2$)C$_1$-C$_6$ alkyl, S(O)C$_1$-C$_6$ alkyl, S(O$_2$)NR$^{11}$R$^{12}$, C$_3$-C$_7$ cycloalkyl and 3- to 7-membered heterocycloalkyl,
wherein the C$_1$-C$_6$ alkyl, C$_1$-C$_6$ haloalkyl, C$_3$-C$_7$ cycloalkyl and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein each C$_1$-C$_6$ alkyl substituent and each C$_1$-C$_6$ alkoxy substituent of the R$^1$ or R$^2$ C$_3$-C$_7$ cycloalkyl or of the R$^1$ or R$^2$ 3- to 7-membered heterocycloalkyl is further optionally independently substituted with one to three hydroxy, halo, NR$^8$R$^9$, or oxo;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

Y is selected from a bond, O, S, $SO_2$, $NR^{15}$, CO, $C_2$ alkynylene, and $CR^{16}R^{17}$;

Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_3$-$C_{10}$ cycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, or wherein Z is optionally fused to a five-to-seven-membered carbocyclic ring or heterocyclic ring containing one or two heteroatoms independently selected from oxygen, sulfur and nitrogen;

each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

each X is independently N or $CR^6$;

each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

each of $R^4$ and $R^5$ is independently selected from hydrogen, $C_1$-$C_6$ alkyl, $C_1$-$C_6$ alkoxy, $NH_2$, $NHC_1$-$C_6$ alkyl, and $N(C_1$-$C_6$ alkyl$)_2$;

$R^{10}$ is $C_1$-$C_6$ alkyl;

each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^3$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^{15}$ is selected from H and $C_1$-$C_6$ alkyl;

$R^{16}$ is selected from H and $C_1$-$C_6$ alkyl; and $R^{17}$ is selected from H and $C_1$-$C_6$ alkyl.

In some embodiments, provided herein is a compound of Formula AA

Formula AA

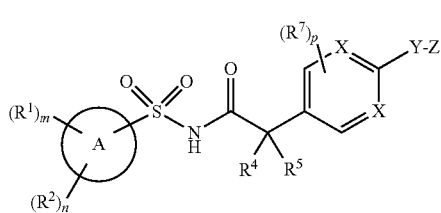

or a pharmaceutically acceptable salt thereof,
wherein
m=0, 1, or 2
n=0, 1, or 2
p=0, 1 or 2
wherein
A is a 5-10-membered monocyclic or bicyclic heteroaryl, a 5-10-membered monocyclic or bicyclic heterocycloalkyl, a $C_6$-$C_{10}$ monocyclic or bicyclic aryl, or a $C_6$-$C_{10}$ monocyclic or bicyclic cycloalkyl;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, CO-5- to 10-membered heteroaryl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—(C=$NR^3$)$NR^{11}R^{12}$, $CONR^1R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^1R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;
Y is selected from a bond, O, S, $SO_2$, $NR^{15}$, CO, and $CR^{16}R^{17}$;
Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen;
each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl)$_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl,
wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $NR^0$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
each X is independently N or $CR^6$;
each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl)$_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl,
wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{14}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$;

each of $R^4$ and $R^5$ is independently selected from hydrogen, $C_1$-$C_6$ alkyl, $C_1$-$C_6$ alkoxy, $NH_2$, $NHC_1$-$C_6$ alkyl, and $N(C_1$-$C_6$ alkyl$)_2$;

$R^{10}$ is $C_1$-$C_6$ alkyl;

each of $R^8$ and $R^9$ at each occurrence is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^{15}$ is selected from H and $C_1$-$C_6$ alkyl;

$R^{16}$ is selected from H and $C_1$-$C_6$ alkyl; and $R^{17}$ is selected from H and $C_1$-$C_6$ alkyl.

In some embodiments, provided herein is a compound of Formula AA

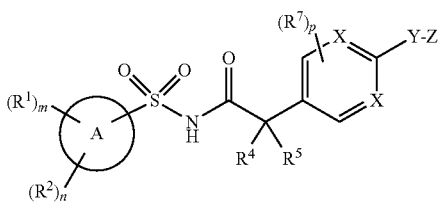

Formula AA or a pharmaceutically acceptable salt thereof,
wherein
m=0, 1, or 2
n=0, 1, or 2
p=0, 1 or 2 wherein

A is a 5-10-membered monocyclic or bicyclic heteroaryl, a 5-10-membered monocyclic or bicyclic heterocycloalkyl, a $C_6$-$C_{10}$ monocyclic or bicyclic aryl, or a $C_6$-$C_{10}$ monocyclic or bicyclic cycloalkyl;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, CO-5- to 10-membered heteroaryl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH(C=$NR^{13}$)$NR^{11}R^{12}$, $CONR^8R^9$, $SO_2NR^8R^9$, $NR^{11}SO_2NR^{11}R^{12}$, $NR^1CO_2R^{12}$, $NR^{11}CONR^{11}R^{12}$, $NR^{11}SO_2R^{12}$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$ wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;

Y is selected from a bond, O, S, $SO_2$, $NR^{15}$, CO, and $CR^{16}R^{17}$;

Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, NR$^{11}$SO$_2$R$^{12}$, 3- to 7-membered heterocycloalkyl, C$_6$-C$_{10}$ aryl, and CONR$^8$R$^9$, and wherein the C$_1$-C$_6$ alkyl or C$_1$-C$_6$ alkoxy that Z is substituted with is optionally substituted with one or more hydroxyl, C$_6$-C$_{10}$ aryl or NR$^8$R$^9$, or wherein Z is optionally fused to a five-to-seven-membered carbocyclic ring or heterocyclic ring containing one or two heteroatoms independently selected from oxygen, sulfur and nitrogen;

each R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, OH, NHC$_1$-C$_6$ alkyl, N(C$_1$-C$_6$ alkyl)$_2$, CONR$^8$R$^9$, SO$_2$NR$^8$R$^9$, NR$^{11}$SO$_2$NR$^{11}$R$^{12}$, NR$^{11}$CO$_2$R$^{12}$, NR$^{11}$CONR$^{11}$R$^{12}$, NR$^{11}$SO$_2$R$^{12}$, SF$_5$, S(O$_2$)C$_1$-C$_6$ alkyl, C$_3$-C$_7$ cycloalkyl, and 3- to 7-membered heterocycloalkyl, wherein the C$_1$-C$_6$ alkyl, C$_1$-C$_6$ haloalkyl, C$_1$-C$_6$ alkoxy, C$_3$-C$_7$ cycloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

each X is independently N or CR$^6$;

each R$^6$ is independently selected from hydrogen, C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_9$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, OH, NHC$_1$-C$_6$ alkyl, N(C$_1$-C$_6$ alkyl)$_2$, CONR$^8$R$^9$, SO$_2$NR$^8$R$^9$, NR$^{11}$SO$_2$NR$^{11}$R$^{12}$, NR$^{11}$CO$_2$R$^{12}$, NR$^{11}$CONR$^{11}$R$^{12}$, NR$^{11}$SO$_2$R$^{12}$, SF$_5$, S(O$_2$)C$_1$-C$_6$ alkyl, C$_3$-C$_7$ cycloalkyl, and 3- to 7-membered heterocycloalkyl, wherein the C$_1$-C$_6$ alkyl, C$_1$-C$_6$ haloalkyl, C$_1$-C$_6$ alkoxy, C$_3$-C$_7$ cycloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^6$ and R$^7$ on adjacent atoms, taken together with the atoms connecting them, independently form at least one C$_4$-C$_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$; each of R$^4$ and R$^5$ is independently selected from hydrogen, C$_1$-C$_6$ alkyl, C$_1$-C$_6$ alkoxy, NH$_2$, NHC$_1$-C$_6$ alkyl, and N(C$_1$-C$_6$ alkyl)$_2$;

R$^{10}$ is C$_1$-C$_6$ alkyl;

each of R$^8$ and R$^9$ at each occurrence is independently selected from hydrogen, C$_1$-C$_6$ alkyl, (C=NR$^{13}$)NR$^{11}$R$^{12}$, S(O$_2$)C$_1$-C$_6$ alkyl, S(O$_2$)NR$^{11}$R$^{12}$, COR$^{13}$, CO$_2$R$^{13}$ and CONR$^{11}$R$^{12}$; wherein the C$_1$-C$_6$ alkyl is optionally substituted with one or more hydroxy, halo, C$_1$-C$_6$ alkoxy, C$_6$-C$_{10}$ aryl, 5- to 10-membered heteroaryl, C$_3$-C$_7$ cycloalkyl or 3- to 7-membered heterocycloalkyl; or R$^8$ and R$^9$ taken together with the nitrogen they are attached to form a 3- to 7-membered ring optionally containing one or more heteroatoms in addition to the nitrogen they are attached to;

R$^{13}$ is C$_1$-C$_6$ alkyl, C$_6$-C$_{10}$ aryl, or 5- to 10-membered heteroaryl;

each of R$^{11}$ and R$^{12}$ at each occurrence is independently selected from hydrogen and C$_1$-C$_6$ alkyl;

R$^{15}$ is selected from H and C$_1$-C$_6$ alkyl;

R$^{16}$ is selected from H and C$_1$-C$_6$ alkyl; and

R$^{17}$ is selected from H and C$_1$-C$_6$ alkyl.

In some embodiments, provided herein is a compound of Formula AA

Formula AA

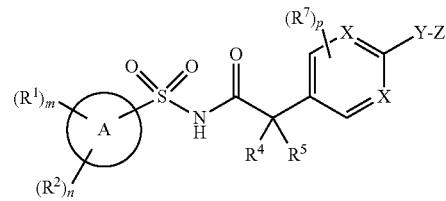

or a pharmaceutically acceptable salt thereof, wherein m=1 or 2;

n=1;

p=0, 1, or 2;

wherein

A is a 5-10-membered monocyclic or bicyclic heteroaryl, a 5-10-membered monocyclic or bicyclic heterocycloalkyl, a C$_6$-C$_{10}$ monocyclic or bicyclic aryl, or a C$_6$-C$_{10}$ monocyclic or bicyclic cycloalkyl;

wherein one pair of R$^1$ and R$^2$ is on adjacent atoms, and taken together with the atoms connecting them, independently form a monocyclic or bicyclic C$_4$-C$_{12}$ carbocyclic ring or a monocyclic or bicyclic 5-to-12-membered heterocyclic ring containing 1-3 heteroatoms and/or heteroatomic groups independently selected from O, N, NH, NR$^{13}$, S, S(O), and S(O)$_2$, wherein the carbocyclic ring or heterocyclic ring is optionally independently substituted with one or more substituents independently selected from hydroxy, halo, oxo, C$_1$-C$_6$ alkyl, C$_2$-C$_6$ alkenyl, C$_2$-C$_6$ alkynyl, C$_1$-C$_6$ alkoxy, OC$_3$-C$_{10}$ cycloalkyl, NR$^8$R$^9$, =NR$^{10}$, CN, COOC$_1$-C$_6$ alkyl, OS(O$_2$)C$_6$-C$_{10}$ aryl, S(O$_2$)C$_6$-C$_{10}$ aryl, C$_6$-C$_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$;

wherein when m is 2, then the $R^1$ that is not taken together with an adjacent $R^2$ and the atoms connecting them to form a ring is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO$—$C_6$-$C_{10}$ aryl, $C(O)$-5- to 10-membered heteroaryl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, $NH$—$(C=NR^{13})NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^2$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

Y is selected from a bond, $—(Y^1)_o—(C_1$-$C_3$ alkyl$)_o$-, $—(CR^{16}R^{17})_o—(Y^1)_o—(CR^{16}R^{17})_o—$, and $C_{2-3}$ alkynylene;

$Y^1$ is selected from O, S, $SO_2$, $NR^5$, $CR^{16}OH$, $CR^{16}NR^8$, $C(O)NR^{15}$, and C(O);

each occurrence of o is selected from 0 and 1, and wherein at least one o in $—(Y^1)_o—(C_1$-$C_3$ alkyl$)_o$- or $—(CR^{16}R^{17})_o—(Y^1)_o—(CR^{16}R^{17})_o—$ is 1;

Z is selected from a 5-10-membered monocyclic or bicyclic heteroaryl, a 5-10-membered monocyclic or bicyclic heterocyclic ring, a 5-10-membered monocyclic or bicyclic heterocycloalkyl, a $C_6$-$C_{10}$ monocyclic or bicyclic aryl, a $C_3$-$C_{10}$ monocyclic or bicyclic cycloalkyl, a $C_2$-$C_6$ alkenyl, and a $C_2$-$C_6$ alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_3$-$C_{10}$ cycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, or wherein Z is optionally fused to a five-to-seven-membered carbocyclic ring or heterocyclic ring containing one or two heteroatoms independently selected from oxygen, sulfur and nitrogen;

each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

each X is independently N or $CR^6$;

each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

each of $R^4$ and $R^5$ is independently selected from hydrogen, $C_1$-$C_6$ alkyl, $C_1$-$C_6$ alkoxy, $NH_2$, $NHC_1$-$C_6$ alkyl, and $N(C_1$-$C_6$ alkyl$)_2$;

$R^{10}$ is $C_1$-$C_6$ alkyl;

each of $R^8$ and $R^9$ at each occurrence is independently selected from hydrogen, $C_1$-$C_6$ alkyl, $C_3$-$C_6$ cycloalkyl, $(C=NR^3)NR^{11}R^{12}$, $S(O_2)C_1$-$C_6$ alkyl, $S(O_2)NR^{11}R^{12}$, $COR^{13}$, $CO_2R^{13}$, and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl optionally substituted with halo, $C_1$-$C_6$ alkoxy, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^{15}$ is selected from H and $C_1$-$C_6$ alkyl;

$R^{16}$ is selected from H and $C_1$-$C_6$ alkyl; and $R^7$ is selected from H and $C_1$-$C_6$ alkyl.

In some embodiments, provided herein is a compound of Formula AA

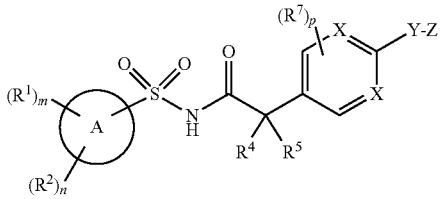

Formula AA or a pharmaceutically acceptable salt thereof,
wherein
m=1 or 2;
n=1;
p=0, 1, or 2;
wherein
A is a 5-10-membered monocyclic or bicyclic heteroaryl, a 5-10-membered monocyclic or bicyclic heterocycloalkyl, a $C_6$-$C_{10}$ monocyclic or bicyclic aryl, or a $C_6$-$C_{10}$ monocyclic or bicyclic cycloalkyl;
wherein one pair of $R^1$ and $R^2$ is on adjacent atoms, and taken together with the atoms connecting them, independently form a monocyclic or bicyclic $C_4$-$C_{12}$ carbocyclic ring or a monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$;

wherein when m is 2, then the $R^1$ that is not taken together with an adjacent $R^2$ and the atoms connecting them to form a ring is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, C(O)-5- to 10-membered heteroaryl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—$(C=NR^{13})NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_1$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

Y is selected from a bond, O, S, $SO_2$, $NR^{15}$, or $CR^{16}R^{17}$;

Z is selected from a 5-10-membered monocyclic or bicyclic heteroaryl, a 5-10-membered monocyclic or bicyclic heterocyclic ring, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_3$-$C_{10}$ cycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, or wherein Z is optionally fused to a five-to-seven-membered carbocyclic ring or heterocyclic ring containing one or two heteroatoms independently selected from oxygen, sulfur and nitrogen;

each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

each X is independently N or $CR^6$;
each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

each of $R^4$ and $R^5$ is independently selected from hydrogen, $C_1$-$C_6$ alkyl, $C_1$-$C_6$ alkoxy, $NH_2$, $NHC_1$-$C_6$ alkyl, and $N(C_1$-$C_6$ alkyl$)_2$;

$R^{10}$ is $C_1$-$C_6$ alkyl;

each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl optionally substituted with $C_1$-$C_6$ alkoxy, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^{15}$ is selected from H and $C_1$-$C_6$ alkyl;
$R^{16}$ is selected from H and $C_1$-$C_6$ alkyl; and
$R^{17}$ is selected from H and $C_1$-$C_6$ alkyl.

In some embodiments, the compound of Formula AA is a compound of formula AA-I

Formula AA-I

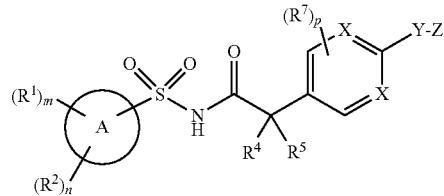

or a pharmaceutically acceptable salt thereof.

In some embodiments of a compound of Formula AA-I, m=0, 1, or 2;
n=0, 1, or 2;
p=0, 1, or 2;
wherein
A is a 5-10-membered monocyclic or bicyclic heteroaryl, a 5-10-membered monocyclic or bicyclic heterocycloalkyl, a $C_6$-$C_{10}$ monocyclic or bicyclic aryl, or a $C_6$-$C_{10}$ monocyclic or bicyclic cycloalkyl;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, CO-5- to 10-membered heteroaryl, $CO_2C_3$-$C_5$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—$(C=NR^{13})NR^{11}R^{12}$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $SC_1$-$C_6$ alkyl, $S(O_2)C_1$-$C_6$ alkyl, $S(O)C_1$-$C_6$ alkyl, $S(O_2)NR^1R^2$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;
Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_3$-$C_{10}$ monocyclic or bicyclic cycloalkyl, a $C_2$-$C_6$ alkenyl, and a $C_2$-$C_6$ alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, $SO_2NR^1R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl;
or wherein Z is optionally fused to a five-to-seven-membered carbocyclic ring or heterocyclic ring containing one or two heteroatoms independently selected from oxygen, sulfur and nitrogen;
each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl,
wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
each X is independently N or $CR^6$;
each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl,
wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$;
each of $R^4$ and $R^5$ is independently selected from hydrogen, $C_1$-$C_6$ alkyl, $C_1$-$C_6$ alkoxy, $NH_2$, $NHC_1$-$C_6$ alkyl, and $N(C_1$-$C_6$ alkyl$)_2$;
$R^{10}$ is $C_1$-$C_6$ alkyl;
each of $R^8$ and $R^9$ at each occurrence is independently selected from hydrogen, $C_1$-$C_6$ alkyl, $C_3$-$C_6$ cycloalkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^1$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl; and each of $R^{11}$ and $R^{12}$ at each occurrence is independently selected from hydrogen and $C_1$-$C_6$ alkyl.

In some embodiments of a compound of Formula AA-I, m=0, 1, or 2;
n=0, 1, or 2;
p=0, 1, or 2;
wherein A is a 5-10-membered monocyclic or bicyclic heteroaryl, a 5-10-membered monocyclic or bicyclic heterocycloalkyl, a $C_6$-$C_{10}$ monocyclic or bicyclic aryl, or a $C_6$-$C_{10}$ monocyclic or bicyclic cycloalkyl;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, CO-5- to 10-membered heteroaryl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^1R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;

Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl;

or wherein Z is optionally fused to a five-to-seven-membered carbocyclic ring or heterocyclic ring containing one or two heteroatoms independently selected from oxygen, sulfur and nitrogen;

each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^1R^9$, =$NR^{10}$, $COOC_1$-$C_6$ alkyl, $CONR^1R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

each X is independently N or $CR^6$;

each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, OH, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^6$ and R$^7$ on adjacent atoms, taken together with the atoms connecting them, independently form at least one C$_4$-C$_8$ carbocyclic ring or at least one 5-to-8-membered heterocyclic ring containing 1 or 2 heteroatoms and/or heteroatomic groups independently selected from O, N, NH, NR$^{13}$, S, S(O), and S(O)$_2$, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$;

each of R$^4$ and R$^5$ is independently selected from hydrogen, C$_1$-C$_6$ alkyl, C$_1$-C$_6$ alkoxy, NH$_2$, NHC$_1$-C$_6$ alkyl, and N(C$_1$-C$_6$ alkyl)$_2$;

R$^{10}$ is C$_1$-C$_6$ alkyl;

each of R$^8$ and R$^9$ at each occurrence is independently selected from hydrogen, C$_1$-C$_6$ alkyl, (C=NR$^{13}$)NR$^{11}$R$^{12}$, S(O$_2$)C$_1$-C$_6$ alkyl, S(O$_2$)NR$^{11}$R$^{12}$, COR$^{13}$, CO$_2$R$^{13}$ and CONR$^{11}$R$^{12}$; wherein the C$_1$-C$_6$ alkyl is optionally substituted with one or more hydroxy, halo, C$_1$-C$_6$ alkoxy, C$_6$-C$_{10}$ aryl, 5- to 10-membered heteroaryl, C$_3$-C$_7$ cycloalkyl or 3- to 7-membered heterocycloalkyl; or R$^8$ and R$^9$ taken together with the nitrogen they are attached to form a 3- to 7-membered ring optionally containing one or more heteroatoms in addition to the nitrogen they are attached to;

R$^{13}$ is C$_1$-C$_6$ alkyl, C$_6$-C$_{10}$ aryl, or 5- to 10-membered heteroaryl; and each of R$^{11}$ and R$^{12}$ at each occurrence is independently selected from hydrogen and C$_1$-C$_6$ alkyl.

In some embodiments of a compound of Formula AA or a compound of Formula AA-I, m=0, 1, or 2;
n=0, 1, or 2;
p=0, 1, or 2;
wherein A is a 5-10-membered monocyclic or bicyclic heteroaryl, a 5-10-membered monocyclic or bicyclic heterocycloalkyl, a C$_6$-C$_{10}$ monocyclic or bicyclic aryl, or a C$_6$-C$_{10}$ monocyclic or bicyclic cycloalkyl;

R$^1$ and R$^2$ are each independently selected from C$_1$-C$_6$ alkyl, C$_1$-C$_6$ alkoxy, halo, CN, NO$_2$, COC$_1$-C$_6$ alkyl, CO$_2$C$_1$-C$_6$ alkyl, NH$_2$, NHC$_1$-C$_6$ alkyl, N(C$_1$-C$_6$ alkyl)$_2$, NHCOC$_1$-C$_6$ alkyl, CONR$^8$R$^9$, S(O$_2$)C$_1$-C$_6$ alkyl, S(O)C$_1$-C$_6$ alkyl, S(O$_2$)NR$^{11}$R$^{12}$, C$_3$-C$_7$ cycloalkyl and 3- to 7-membered heterocycloalkyl, wherein the C$_1$-C$_6$ alkyl, C$_3$-C$_7$ cycloalkyl and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, and NR$^8$R$^9$, Z is selected from a 5-10-membered monocyclic or bicyclic heteroaryl, a 5-10-membered monocyclic or bicyclic heterocycloalkyl, a C$_6$-C$_{10}$ monocyclic or bicyclic aryl, a C$_3$-C$_{10}$ monocyclic or bicyclic cycloalkyl, a C$_2$-C$_6$ alkenyl, and a C$_2$-C$_6$ alkynyl, wherein Z is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, C$_6$-C$_{10}$ aryloxy, oxo, CN, halo, COOC$_1$-C$_6$ alkyl, C(O)OH, S(O$_2$)C$_1$-C$_6$ alkyl, 3- to 7-membered heterocycloalkyl, and CONR$^8$R$^9$, and wherein the C$_1$-C$_6$ alkyl or C$_1$-C$_6$ alkoxy that Z is substituted with is optionally substituted with one or more hydroxyl, NR$^8$R$^9$, or C$_6$-C$_{10}$ aryl;

or wherein Z is optionally fused to a five-to-seven-membered carbocyclic ring or heterocyclic ring containing one or two heteroatoms independently selected from oxygen, sulfur and nitrogen;

each R$^7$ is independently selected from C$_1$-C$_6$ alkyl, C$_1$-C$_6$ haloalkyl, C$_1$-C$_6$ alkoxy, halo, CN, COC$_1$-C$_6$ alkyl, CO$_2$C$_3$-C$_8$ cycloalkyl, NH$_2$, OH, S(O$_2$)C$_1$-C$_6$ alkyl, and C$_3$-C$_7$ cycloalkyl, wherein the C$_1$-C$_6$ alkyl and C$_1$-C$_6$ alkoxy is optionally substituted with one or more substituents each independently selected from hydroxy, halo, CN, oxo, C$_1$-C$_6$ alkyl, C$_1$-C$_6$ alkoxy, NR$^8$R$^9$, and C$_6$-C$_{10}$ aryl, each X is independently N or CR$^6$;

each R$^6$ is independently selected from hydrogen, C$_1$-C$_6$ alkyl, C$_1$-C$_6$ haloalkyl, C$_1$-C$_6$ alkoxy, halo, CN, COC$_1$-C$_6$ alkyl, CO$_2$C$_3$-C$_8$ cycloalkyl, NH$_2$, OH, S(O$_2$)C$_1$-C$_6$ alkyl, and C$_3$-C$_7$ cycloalkyl, wherein the C$_1$-C$_6$ alkyl and C$_1$-C$_6$ alkoxy is optionally substituted with one or more substituents each independently selected from hydroxy, halo, CN, oxo, C$_1$-C$_6$ alkyl, C$_1$-C$_6$ alkoxy, NR$^8$R$^9$, C$_6$-C$_{10}$ aryl;

each of R$^4$ and R$^5$ is independently selected from hydrogen, C$_1$-C$_6$ alkyl, C$_1$-C$_6$ alkoxy, NH$_2$, NHC$_1$-C$_6$ alkyl, and N(C$_1$-C$_6$ alkyl)$_2$;

each of R$^8$ and R$^9$ at each occurrence is independently selected from hydrogen, C$_1$-C$_6$ alkyl, C$_3$-C$_6$cycloalkyl, (C=NR$^{13}$)NR$^{11}$R$^{12}$, S(O$_2$)C$_1$-C$_6$ alkyl, S(O$_2$)NR$^{11}$R$^{12}$, COR$^{13}$, CO$_2$R$^{13}$ and CONR$^{11}$R$^{12}$; wherein the C$_1$-C$_6$ alkyl is optionally substituted with one or more hydroxy, halo, C$_1$-C$_6$ alkoxy, C$_6$-C$_{10}$ aryl, 5- to 10-membered heteroaryl, C$_3$-C$_7$ cycloalkyl or 3- to 7-membered heterocycloalkyl; or R$^8$ and R$^9$ taken together with the nitrogen they are attached to form a 3- to 7-membered ring optionally containing one or more heteroatoms in addition to the nitrogen they are attached to;

R$^{13}$ is C$_1$-C$_6$ alkyl, C$_6$-C$_{10}$ aryl, or 5- to 10-membered heteroaryl; and each of R$^{11}$ and R$^{12}$ at each occurrence is independently selected from hydrogen and C$_1$-C$_6$ alkyl.

In some embodiments of a compound of Formula AA or a compound of Formula AA-I, m=0, 1, or 2;
n=0, 1, or 2;
p=0, 1, or 2;
wherein A is a 5-10-membered monocyclic or bicyclic heteroaryl, a 5-10-membered monocyclic or bicyclic heterocycloalkyl, a C$_6$-C$_{10}$ monocyclic or bicyclic aryl, or a C$_6$-C$_{10}$ monocyclic or bicyclic cycloalkyl;

R$^1$ and R$^2$ are each independently selected from C$_1$-C$_6$ alkyl, C$_1$-C$_6$ alkoxy, halo, CN, NO$_2$, COC$_1$-C$_6$ alkyl, CO$_2$C$_1$-C$_6$ alkyl, NH$_2$, NHC$_1$-C$_6$ alkyl, N(C$_1$-C$_6$ alkyl)$_2$, NHCOC$_1$-C$_6$ alkyl, CONR$^8$R$^9$, S(O$_2$)C$_1$-C$_6$ alkyl, S(O)C$_1$-C$_6$ alkyl, S(O$_2$)NR$^{11}$R$^{12}$, C$_3$-C$_7$ cycloalkyl and 3- to 7-membered heterocycloalkyl, wherein the C$_1$-C$_6$ alkyl, C$_3$-C$_7$ cycloalkyl and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, and NR$^8$R$^9$, Z is selected from a 5-10-membered monocyclic or bicyclic heteroaryl, a 5-10-membered monocyclic or bicyclic heterocycloalkyl, a C$_6$-C$_{10}$ monocyclic or bicyclic aryl, a C$_6$-C$_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, CN, halo, COOC$_1$-$C_6$ alkyl, $S(O_2)$ $C_1$-$C_6$ alkyl, 3- to 7-membered heterocycloalkyl, and CONR$^8$R$^9$, and wherein the $C_1$-$C_6$ alkyl or $C_1$-$C_6$ alkoxy that Z is substituted with is optionally substituted with one or more hydroxyl, NR$^8$R$^9$, or $C_6$-$C_{10}$ aryl;

or wherein Z is optionally fused to a five-to-seven-membered carbocyclic ring or heterocyclic ring containing one or two heteroatoms independently selected from oxygen, sulfur and nitrogen;

each R$^7$ is independently selected from $C_1$-$C_6$ alkyl, $C_1$-$C_6$ haloalkyl, $C_1$-$C_6$ alkoxy, halo, CN, COC$_1$-$C_6$ alkyl, CO$_2$C$_3$-$C_8$ cycloalkyl, NH$_2$, OH, $S(O_2)C_1$-$C_6$ alkyl, and $C_3$-$C_7$ cycloalkyl, wherein the $C_1$-$C_6$ alkyl and $C_1$-$C_6$ alkoxy is optionally substituted with one or more substituents each independently selected from hydroxy, halo, CN, oxo, $C_1$-$C_6$ alkyl, $C_1$-$C_6$ alkoxy, NR$^8$R$^9$, and $C_6$-$C_{10}$ aryl, each X is independently N or CR$^6$;

each R$^6$ is independently selected from hydrogen, $C_1$-$C_6$ alkyl, $C_1$-$C_6$ haloalkyl, $C_1$-$C_6$ alkoxy, halo, CN, COC$_1$-$C_6$ alkyl, CO$_2$C$_3$-$C_9$ cycloalkyl, NH$_2$, OH, $S(O_2)C_1$-$C_6$ alkyl, and $C_3$-$C_7$ cycloalkyl, wherein the $C_1$-$C_6$ alkyl and $C_1$-$C_6$ alkoxy is optionally substituted with one or more substituents each independently selected from hydroxy, halo, CN, oxo, $C_1$-$C_6$ alkyl, $C_1$-$C_6$ alkoxy, NR$^8$R$^9$, $C_6$-$C_{10}$ aryl;

each of R$^4$ and R$^5$ is independently selected from hydrogen, $C_1$-$C_6$ alkyl, $C_1$-$C_6$ alkoxy, NH$_2$, NHC$_1$-$C_6$ alkyl, and N(C$_1$-$C_6$ alkyl)$_2$;

each of R$^8$ and R$^9$ at each occurrence is independently selected from hydrogen, $C_1$-$C_6$ alkyl, (C=NR$^{13}$)NR$^{11}$R$^{12}$, $S(O_2)C_1$-$C_6$ alkyl, $S(O_2)$NR$^{11}$R$^{12}$, COR$^{13}$, CO$_2$R$^{13}$ and CONR$^{11}$R$^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or R$^8$ and R$^9$ taken together with the nitrogen they are attached to to form a 3- to 7-membered ring optionally containing one or more heteroatoms in addition to the nitrogen they are attached to;

R$^{13}$ is $C_1$-$C_6$ alkyl, $C_6$-$C_{10}$ aryl, or 5- to 10-membered heteroaryl; and each of R$^{11}$ and R$^{12}$ at each occurrence is independently selected from hydrogen and $C_1$-$C_6$ alkyl.

In some embodiments of a compound of Formula AA or a compound of Formula AA-I, m=0 or 1;
n=0 or 1;
p=0, 1, or 2;
wherein
A is a 5-10-membered monocyclic or bicyclic heteroaryl, a 5-10-membered monocyclic or bicyclic heterocycloalkyl, a $C_6$-$C_{10}$ monocyclic or bicyclic aryl, or a $C_6$-$C_{10}$ monocyclic or bicyclic cycloalkyl;

R$^1$ and R$^2$ are each independently selected from $C_1$-$C_6$ alkyl, $C_1$-$C_6$ alkoxy, halo, COC$_1$-$C_6$ alkyl, CO$_2$C$_1$-$C_6$ alkyl, NH$_2$, NHC$_1$-$C_6$ alkyl, CONR$^8$R$^9$, $S(O_2)C_1$-$C_6$ alkyl, $S(O_2)$NR$^{11}$R$^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, and NR$^8$R$^9$, Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_3$-$C_{10}$ monocyclic or bicyclic cycloalkyl, a $C_2$-$C_6$ alkenyl, and a $C_2$-$C_6$ alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, oxo, CN, halo, COOC$_1$-$C_6$ alkyl, C(O)OH, $S(O_2)C_1$-$C_6$ alkyl, 3- to 7-membered heterocycloalkyl, and CONR$^8$R$^9$, and wherein the $C_1$-$C_6$ alkyl or $C_1$-$C_6$ alkoxy that Z is substituted with is optionally substituted with one or more hydroxyl, NR$^8$R$^9$, or $C_6$-$C_{10}$ aryl;

or wherein Z is optionally fused to a five-to-seven-membered carbocyclic ring or heterocyclic ring containing one or two heteroatoms independently selected from oxygen, sulfur and nitrogen;

each R$^7$ is independently selected from $C_1$-$C_6$ alkyl, $C_1$-$C_6$ haloalkyl, $C_1$-$C_6$ alkoxy, halo, CN, COC$_1$-$C_6$ alkyl, CO$_2$C$_3$-$C_8$ cycloalkyl, NH$_2$, OH, $S(O_2)C_1$-$C_6$ alkyl, and $C_3$-$C_7$ cycloalkyl, wherein the $C_1$-$C_6$ alkoxy is optionally substituted with one or more $C_6$-$C_{10}$ aryl, each X is independently N or CR$^6$;

each R$^6$ is independently selected from hydrogen, $C_1$-$C_6$ alkyl, $C_1$-$C_6$ haloalkyl, $C_1$-$C_6$ alkoxy, halo, CN, COC$_1$-$C_6$ alkyl, CO$_2$C$_3$-$C_8$ cycloalkyl, NH$_2$, OH, $S(O_2)C_1$-$C_6$ alkyl, and $C_3$-$C_7$ cycloalkyl, wherein the $C_1$-$C_6$ alkoxy is optionally substituted with one or more $C_6$-$C_{10}$ aryl;

each of R$^4$ and R$^5$ is independently selected from hydrogen, $C_1$-$C_6$ alkyl, $C_1$-$C_6$ alkoxy, NH$_2$, NHC$_1$-$C_6$ alkyl, and N(C$_1$-$C_6$ alkyl)$_2$; and each of R$^8$ and R$^9$ at each occurrence is independently selected from hydrogen, $C_1$-$C_6$ alkyl, and $C_3$-$C_6$ cycloalkyl.

In some embodiments of a compound of Formula AA or a compound of Formula AA-I, m=0 or 1;
n=0 or 1;
p=0, 1, or 2;
wherein
A is a 5-10-membered monocyclic or bicyclic heteroaryl, a 5-10-membered monocyclic or bicyclic heterocycloalkyl, a $C_6$-$C_{10}$ monocyclic or bicyclic aryl, or a $C_6$-$C_{10}$ monocyclic or bicyclic cycloalkyl;

R$^1$ and R$^2$ are each independently selected from $C_1$-$C_6$ alkyl, $C_1$-$C_6$ alkoxy, halo, COC$_1$-$C_6$ alkyl, CO$_2$C$_1$-$C_6$ alkyl, NH$_2$, NHC$_1$-$C_6$ alkyl, CONR$^8$R$^9$, $S(O_2)C_1$-$C_6$ alkyl, $S(O_2)$NR$^{11}$R$^{12}$, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, and NR$^8$R$^9$, Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, CN, halo, COOC$_1$-$C_6$ alkyl, $S(O_2)$ $C_1$-$C_6$ alkyl, 3- to 7-membered heterocycloalkyl, and CONR$^8$R$^9$, and wherein the $C_1$-$C_6$ alkyl or $C_1$-$C_6$ alkoxy that Z is substituted with is optionally substituted with one or more hydroxyl, NR$^8$R$^9$, or $C_6$-$C_{10}$ aryl;

or wherein Z is optionally fused to a five-to-seven-membered carbocyclic ring or heterocyclic ring containing one or two heteroatoms independently selected from oxygen, sulfur and nitrogen;
each $R^7$ is independently selected from $C_1$-$C_6$ alkyl, $C_1$-$C_6$ haloalkyl, $C_1$-$C_6$ alkoxy, halo, CN, $COC_1$-$C_6$ alkyl, $CO_2C_3$-$C_8$ cycloalkyl, $NH_2$, OH, $S(O_2)C_1$-$C_6$ alkyl, and $C_3$-$C_7$ cycloalkyl,
wherein the $C_1$-$C_6$ alkoxy is optionally substituted with one or more $C_6$-$C_{10}$ aryl;
each X is independently N or $CR^6$;
each $R^6$ is independently selected from hydrogen, $C_1$-$C_6$ alkyl, $C_1$-$C_6$ haloalkyl, $C_1$-$C_6$ alkoxy, halo, CN, $COC_1$-$C_6$ alkyl, $CO_2C_3$-$C_8$ cycloalkyl, $NH_2$, OH, $S(O_2)C_1$-$C_6$ alkyl, and $C_3$-$C_7$ cycloalkyl,
wherein the $C_1$-$C_6$ alkoxy is optionally substituted with one or more $C_6$-$C_{10}$ aryl;
each of $R^4$ and $R^5$ is independently selected from hydrogen, $C_1$-$C_6$ alkyl, $C_1$-$C_6$ alkoxy, $NH_2$, $NHC_1$-$C_6$ alkyl, and $N(C_1$-$C_6$ alkyl$)_2$; and
each of $R^8$ and $R^9$ at each occurrence is independently selected from hydrogen and $C_1$-$C_6$ alkyl.

In some embodiments of a compound of Formula AA or a compound of Formula AA-I,
m=1;
n=0;
p=0 or 2;
wherein
A is a phenyl;
$R^1$ is (dimethylamino)methyl;
Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_3$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, oxo, CN, halo, $COOC_1$-$C_6$ alkyl, C(O)OH, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl;
or wherein Z is optionally fused to a five-to-seven-membered carbocyclic ring or heterocyclic ring containing one or two heteroatoms independently selected from oxygen, sulfur and nitrogen;
each $R^7$ is independently selected from $C_1$-$C_6$ alkyl and $C_1$-$C_6$ alkoxy, wherein the $C_1$-$C_6$ alkoxy is optionally substituted with one or more $C_6$-$C_{10}$ aryl,
each X is $CR^6$;
each $R^6$ is independently selected from hydrogen, $C_1$-$C_6$ alkyl and $C_1$-$C_6$ alkoxy,
wherein the $C_1$-$C_6$ alkoxy is optionally substituted with one or more $C_6$-$C_{10}$ aryl;
each of $R^4$ and $R^5$ is hydrogen; and
each of $R^8$ and $R^9$ at each occurrence is independently selected from hydrogen, $C_1$-$C_6$ alkyl, and $C_3$-$C_6$ cycloalkyl.

In some embodiments of a compound of Formula AA or a compound of Formula AA-I,
m=1;
n=0;
p=0 or 2;
wherein
A is a phenyl;
$R^1$ is (dimethylamino)methyl;
Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl;
or wherein Z is optionally fused to a five-to-seven-membered carbocyclic ring or heterocyclic ring containing one or two heteroatoms independently selected from oxygen, sulfur and nitrogen;
each $R^7$ is independently selected from $C_1$-$C_6$ alkyl and $C_1$-$C_6$ alkoxy,
wherein the $C_1$-$C_6$ alkoxy is optionally substituted with one or more $C_6$-$C_{10}$ aryl,
each X is $CR^6$;
each $R^6$ is independently selected from hydrogen, $C_1$-$C_6$ alkyl and $C_1$-$C_6$ alkoxy,
wherein the $C_1$-$C_6$ alkoxy is optionally substituted with one or more $C_6$-$C_{10}$ aryl;
each of $R^4$ and $R^5$ is hydrogen; and
each of $R^8$ and $R^9$ at each occurrence is independently selected from hydrogen and $C_1$-$C_6$ alkyl.

In some embodiments, when Y is $Y^1$ and $Y^1$ is C(O), then Z is bonded to Y from a C ring member;
In some embodiments the variables shown in the formulae herein are as follows:
The Variables m and n
In some embodiments m=0, 1, or 2.
In some embodiments m=0 or 1.
In some embodiments m=1 or 2.
In some embodiments m=0.
In some embodiments m=1.
In some embodiments m=2.
In some embodiments n=0, 1, or 2.
In some embodiments n=0 or 1.
In some embodiments n=1 or 2.
In some embodiments n=0.
In some embodiments n=1.
In some embodiments n=2.
In some embodiments, m=0 and n=0.
In some embodiments, m=1 and n=0.
In some embodiments, m=1 and n=1.
In some embodiments, m=1 or 2; and n=1 or 2.
In certain embodiments of the foregoing, the sum of m and n is 2 or 3.
In some embodiments, m=1; and n=1 or 2.
In some embodiments, m=1 or 2; and n=1.
In some embodiments, m=2; and n=1.
The Ring a and Substitutions on the Ring A
In some embodiments, A is a 5-10-membered (e.g., 5-6-membered) monocyclic or bicyclic heteroaryl or a $C_6$-$C_{10}$ (e.g., $C_6$) monocyclic or bicyclic aryl, such as phenyl.
In some embodiments, A is a 5-10-membered (e.g., 5-6-membered) monocyclic or bicyclic heteroaryl.
In some embodiments, A is a 5-membered heteroaryl (e.g., pyrazolyl, thiophenyl, thiazolyl, and imidazolyl).
In some embodiments, A is a $C_6$-$C_{10}$ monocyclic or bicyclic aryl.
In some embodiments, A is phenyl optionally substituted with 1 or 2 $R^1$ and optionally substituted with 1 or 2 R.
In some embodiments, A is furanyl optionally substituted with 1 or 2 $R^1$ and optionally substituted with 1 or 2 $R^2$.

In some embodiments, A is thiophenyl optionally substituted with 1 or 2 $R^1$ and optionally substituted with 1 or 2 $R^2$.

In some embodiments, A is pyrrolyl optionally substituted with 1 or 2 $R^1$ and optionally substituted with 1 or 2 $R^2$.

In some embodiments, A is imidazolyl optionally substituted with 1 or 2 $R^1$ and optionally substituted with 1 or 2 $R^2$.

In some embodiments, A is oxazolyl optionally substituted with 1 or 2 $R^1$ and optionally substituted with 1 or 2 $R^2$.

In some embodiments, A is thiazolyl optionally substituted with 1 or 2 $R^1$ and optionally substituted with 1 or 2 $R^2$.

In some embodiments, A is isooxazolyl optionally substituted with 1 or 2 $R^1$ and optionally substituted with 1 or 2 $R^2$.

In some embodiments, A is isothiazolyl optionally substituted with 1 or 2 $R^1$ and optionally substituted with 1 or 2 $R^2$.

In some embodiments, A is pyrazolyl optionally substituted with 1 or 2 $R^1$ and optionally substituted with 1 or 2 $R^2$.

In some embodiments, A is triazolyl (e.g., 1,2,3-triazolyl or 1,2,4-triazolyl) optionally substituted with 1 or 2 $R^1$ and optionally substituted with 1 or 2 $R^2$.

In some embodiments, A is pyridyl optionally substituted with 1 or 2 $R^1$ and optionally substituted with 1 or 2 $R^2$.

In some embodiments, A is pyrimidinyl optionally substituted with 1 or 2 $R^1$ and optionally substituted with 1 or 2 $R^2$.

In some embodiments, A is pyrazinyl optionally substituted with 1 or 2 $R^1$ and optionally substituted with 1 or 2 $R^2$.

In some embodiments, A is pyridazinyl optionally substituted with 1 or 2 $R^1$ and optionally substituted with 1 or 2 $R^2$.

In some embodiments, A is triazinyl optionally substituted with 1 or 2 $R^1$ and optionally substituted with 1 or 2 $R^2$.

In some embodiments, A is phenyl substituted with 1 $R^1$ and optionally substituted with 1 $R^2$.

In some embodiments, A is furanyl substituted with 1 $R^1$ and optionally substituted with 1 $R^2$.

In some embodiments, A is thiophenyl substituted with 1 $R^1$ and optionally substituted with 1 $R^2$.

In some embodiments, A is oxazolyl substituted with 1 $R^1$ and optionally substituted with 1 $R^2$.

In some embodiments, A is thiazolyl substituted with 1 $R^1$ and optionally substituted with 1 $R^2$.

In some embodiments, A is pyrazolyl substituted with 1 $R^1$ and optionally substituted with 1 $R^2$.

In some embodiments, A is pyridyl substituted with 1 $R^1$ and optionally substituted with 1 $R^2$.

In some embodiments, A is phenyl substituted with 1 $R^1$ and substituted with 1 $R^2$.

In some embodiments, A is furanyl substituted with 1 $R^1$ and substituted with 1 $R^2$.

In some embodiments, A is thiophenyl substituted with 1 $R^1$ and substituted with 1 $R^2$.

In some embodiments, A is pyrrolyl substituted with 1 $R^1$ and substituted with 1 $R^2$.

In some embodiments, A is oxazolyl substituted with 1 $R^1$ and substituted with 1 $R^2$.

In some embodiments, A is thiazolyl substituted with 1 $R^1$ and substituted with 1 $R^2$.

In some embodiments, A is isooxazolyl substituted with 1 $R^1$ and substituted with 1 $R^2$.

In some embodiments, A is isothiazolyl substituted with 1 $R^1$ and substituted with 1 $R^2$.

In some embodiments, A is imidazolyl substituted with 1 $R^1$ and substituted with 1 $R^2$.

In some embodiments, A is triazolyl (e.g., 1,2,3-triazolyl or 1,2,4-triazolyl) substituted with 1 $R^1$ and substituted with 1 $R^2$.

In some embodiments, A is pyrazolyl substituted with 1 $R^1$ and substituted with 1 $R^2$.

In some embodiments, A is pyridyl substituted with 1 $R^1$ and substituted with 1 $R^2$.

In some embodiments, A is pyrimidyl substituted with 1 $R^1$ and substituted with 1 $R^2$.

In some embodiments, A is pyrazinyl substituted with 1 $R^1$ and substituted with 1 $R^2$.

In some embodiments, A is pyridazinyl substituted with 1 $R^1$ and substituted with 1 $R^2$.

In some embodiments, A is triazinyl substituted with 1 $R^1$ and substituted with 1 $R^2$.

In some embodiments, A is one of the rings disclosed hereinbelow, wherein in each case the bond that is shown as being broken by the wavy line  connects A to the $S(O)_2NHC(O)CR^4R^5$ moiety of Formula AA.

In some embodiments, the optionally substituted ring A is

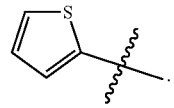 [SMILES: *c1cccs1]

In some embodiments, the optionally substituted ring A is

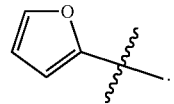 [SMILES: *c1ccco1]

In some embodiments, the optionally substituted ring A is

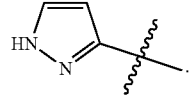 [SMILES: *c1cc[nH]n1]

In some embodiments, the optionally substituted ring A is

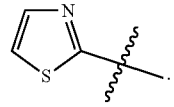 [SMILES: *c1nccs1]

In some embodiments, the optionally substituted ring A is

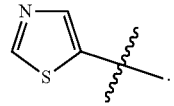

In some embodiments, the optionally substituted ring A is

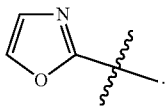 [SMILES: *c1ncco1]

In some embodiments, the optionally substituted ring A is

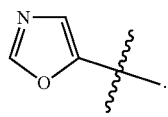 [SMILES: *c1cnco1]

In some embodiments, the optionally substituted ring A is

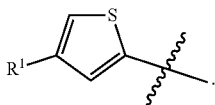

In some embodiments, the optionally substituted ring A is

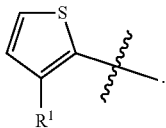

In some embodiments, the optionally substituted ring A is

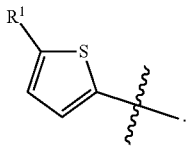

In some embodiments, the optionally substituted ring A is

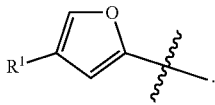

In some embodiments, the optionally substituted ring A is

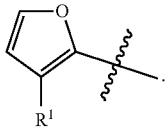

In some embodiments, the optionally substituted ring A is

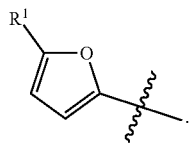

In some embodiments, the optionally substituted ring A is

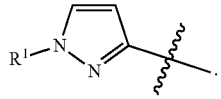

In some embodiments, the substituted ring A is

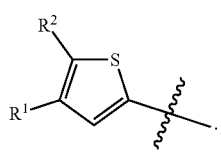

In some embodiments, the optionally substituted ring A is

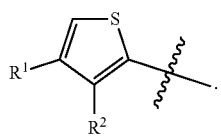

In some embodiments, the substituted ring A is

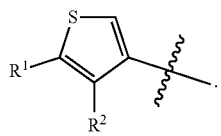

In some embodiments, the optionally substituted ring A is

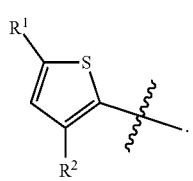

In some embodiments, the optionally substituted ring A is

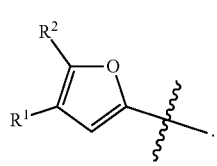

In some embodiments, the optionally substituted ring A is

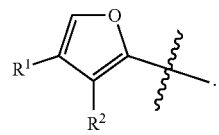

In some embodiments, the substituted ring A is

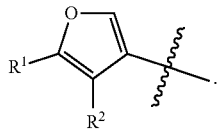

In some embodiments, the optionally substituted ring A is

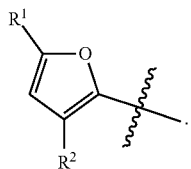

In some embodiments, the optionally substituted ring A is

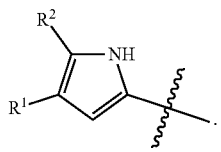

In some embodiments, the optionally substituted ring A is

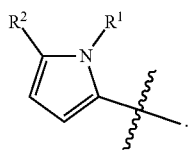

In some embodiments, the optionally substituted ring A is

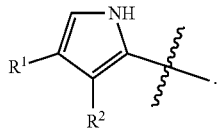

In some embodiments, the substituted ring A is

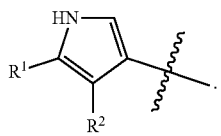

In some embodiments, the substituted ring A is

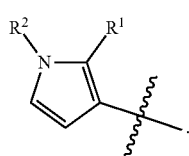

In some embodiments, the substituted ring A is

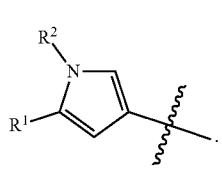

In some embodiments, the optionally substituted ring A is

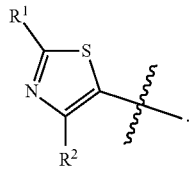

In some embodiments, the optionally substituted ring A is

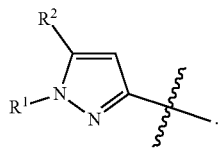

In some embodiments, the optionally substituted ring A is

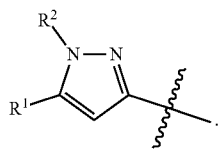

In some embodiments, the optionally substituted ring A is

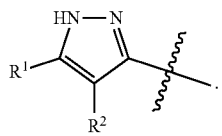

In some embodiments, the optionally substituted ring A is

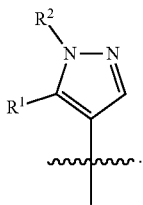

In some embodiments, the optionally substituted ring A is

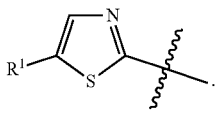

In some embodiments, the optionally substituted ring A is

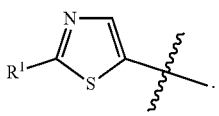

In some embodiments, the optionally substituted ring A is

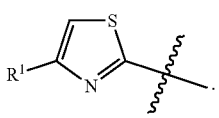

In some embodiments, the optionally substituted ring A is

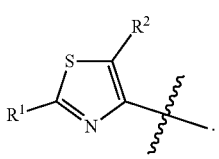

In some embodiments, the optionally substituted ring A is

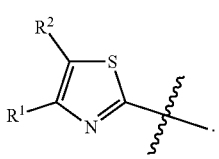

In some embodiments, the optionally substituted ring A is

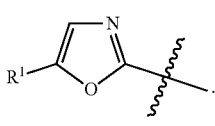

In some embodiments, the optionally substituted ring A is

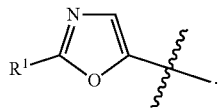

In some embodiments, the optionally substituted ring A is

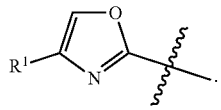

In some embodiments, the optionally substituted ring A is

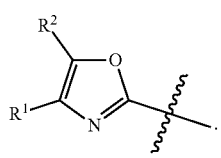

In some embodiments, the optionally substituted ring A is

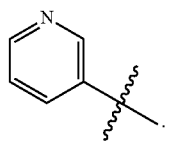 [SMILES: *c1cccnc1]

In some embodiments, the optionally substituted ring A is

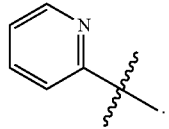 [SMILES: *c1ccccn1]

In some embodiments, the optionally substituted ring A is

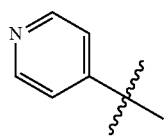

In some embodiments, the optionally substituted ring A is

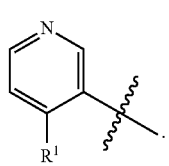

In some embodiments, the optionally substituted ring A is

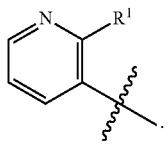

In some embodiments, the optionally substituted ring A is

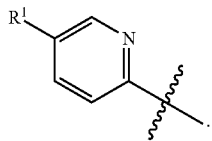

In some embodiments, the optionally substituted ring A is

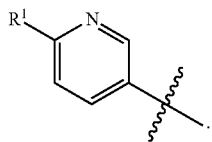

In some embodiments, the optionally substituted ring A is

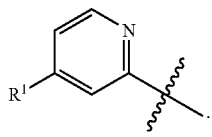

In some embodiments, the optionally substituted ring A is

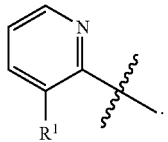

In some embodiments, the optionally substituted ring A is

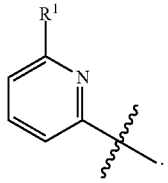

In some embodiments, the optionally substituted ring A is

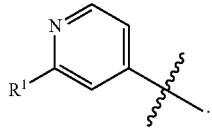

In some embodiments, the optionally substituted ring A is

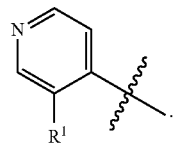

In some embodiments, the optionally substituted ring A is

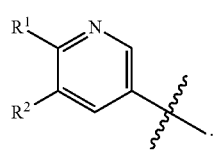

In some embodiments, the optionally substituted ring A is

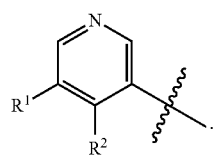

In some embodiments, the optionally substituted ring A is

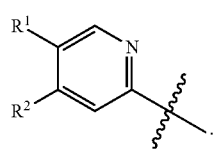

In some embodiments, the optionally substituted ring A is

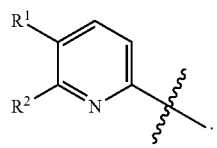

In some embodiments, the optionally substituted ring A is

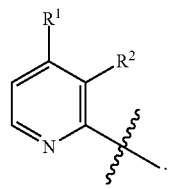

In some embodiments, the optionally substituted ring A is


In some embodiments, the optionally substituted ring A is

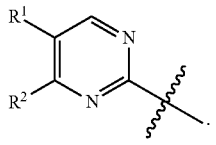

In some embodiments, the optionally substituted ring A is

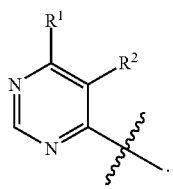

In some embodiments, the optionally substituted ring A is

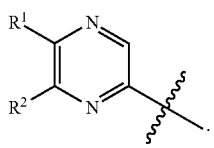

In some embodiments, the optionally substituted ring A is

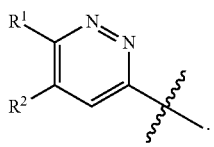

In some embodiments, the optionally substituted ring A is

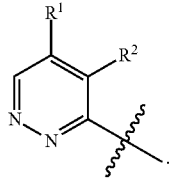

In some embodiments, the optionally substituted ring A is


In some embodiments, the optionally substituted ring A is

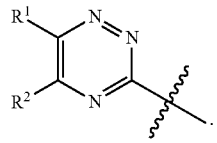

In some embodiments, the optionally substituted ring A is

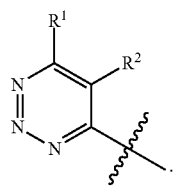

In some embodiments, the optionally substituted ring A is

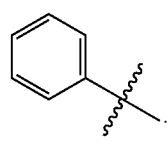

In some embodiments, the optionally substituted ring A is

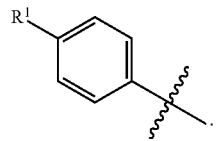

In some embodiments, the optionally substituted ring A is

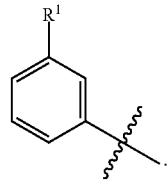

In some embodiments, the optionally substituted ring A is

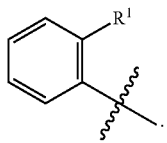

In some embodiments, the optionally substituted ring A is

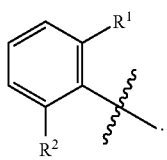

In some embodiments, the optionally substituted ring A is

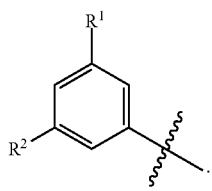

In some embodiments, the optionally substituted ring A is

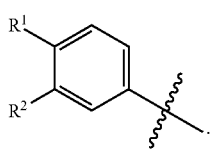

In some embodiments, the optionally substituted ring A is

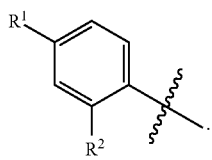

In some embodiments, the optionally substituted ring A is

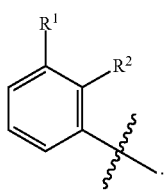

In some embodiments, the optionally substituted ring A is

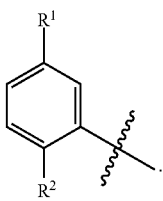

In some embodiments, the optionally substituted ring A is

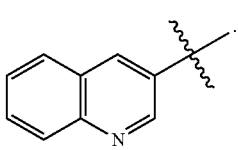 [SMILES: *c1cnc2ccccc2c1]

In some embodiments, the optionally substituted ring A is

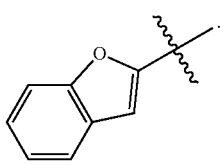 [SMILES: *c1cc2ccccc2o1]

In some embodiments, the optionally substituted ring A is

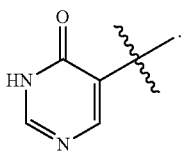

In some embodiments, the optionally substituted ring A is

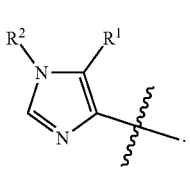

In some embodiments, the optionally substituted ring A is

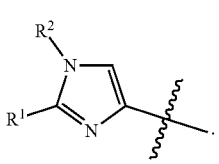

In some embodiments, the optionally substituted ring A is

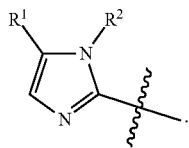

In some embodiments, the optionally substituted ring A is

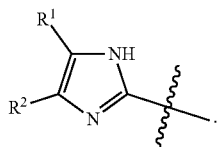

In some embodiments, the optionally substituted ring A is

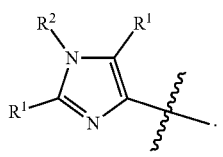

In some embodiments, the optionally substituted ring A is

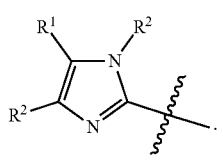

In some embodiments, the optionally substituted ring A is

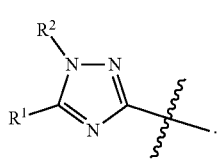

In some embodiments, the optionally substituted ring A is

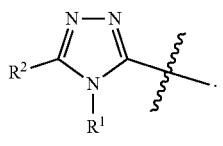

In some embodiments, the optionally substituted ring A is

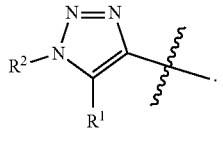

In some embodiments, the optionally substituted ring A is

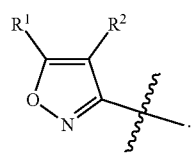

In some embodiments, the optionally substituted ring A is

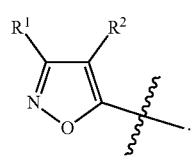

In some embodiments, the optionally substituted ring A is

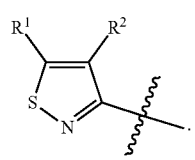

In some embodiments, the optionally substituted ring A is

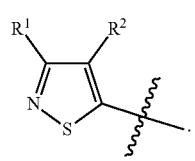

In some embodiments, the substituted ring A is

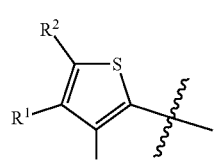

In some embodiments, the substituted ring A is

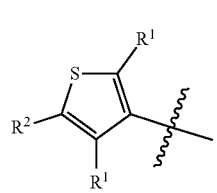

In some embodiments, the substituted ring A is

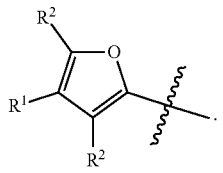

In some embodiments, the substituted ring A is

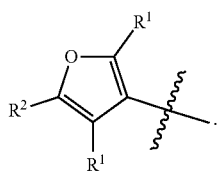

In some embodiments, the substituted ring A is

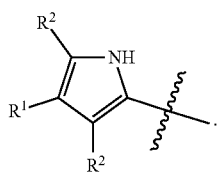

In some embodiments, the substituted ring A is

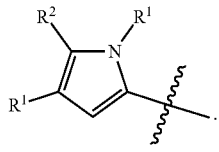

In some embodiments, the substituted ring A is

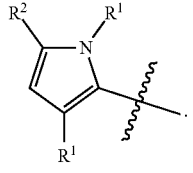

In some embodiments, the substituted ring A is

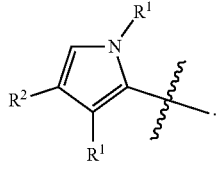

In some embodiments, the substituted ring A is

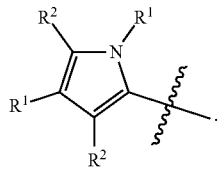

In some embodiments, the substituted ring A is

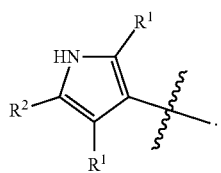

In some embodiments, the substituted ring A is

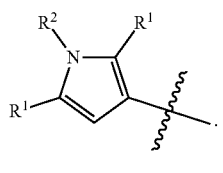

In some embodiments, the substituted ring A is

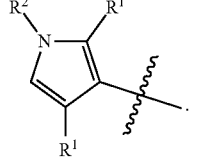

In some embodiments, the substituted ring A is

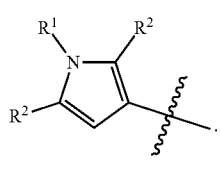

In some embodiments, the substituted ring A is

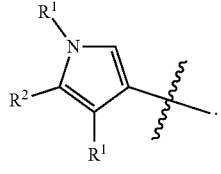

In some embodiments, the substituted ring A is

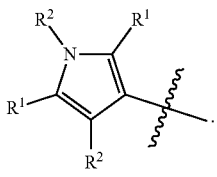

In some embodiments, the optionally substituted ring A is

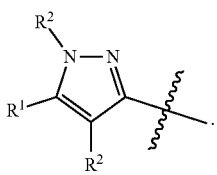

In some embodiments, the optionally substituted ring A is

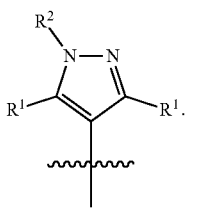

In some embodiments, the optionally substituted ring A is

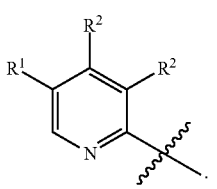

In some embodiments, the optionally substituted ring A is

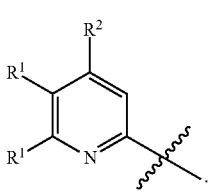

In some embodiments, the optionally substituted ring A is

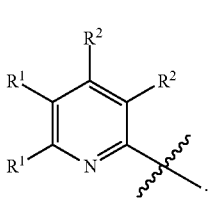

In some embodiments, the optionally substituted ring A is

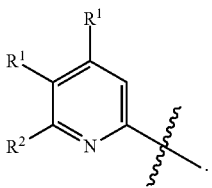

In some embodiments, the optionally substituted ring A is

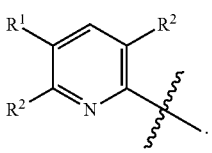

In some embodiments, the optionally substituted ring A is

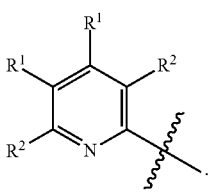

In some embodiments, the optionally substituted ring A is

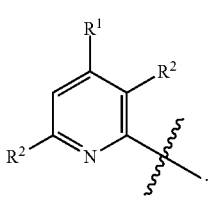

In some embodiments, the optionally substituted ring A is

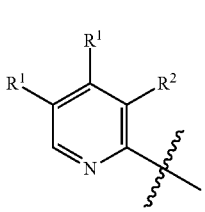

In some embodiments, the optionally substituted ring A is

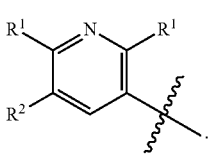

In some embodiments, the optionally substituted ring A is

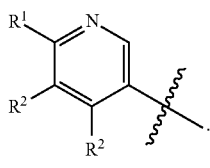

In some embodiments, the optionally substituted ring A is

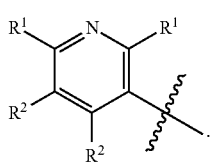

In some embodiments, the optionally substituted ring A is

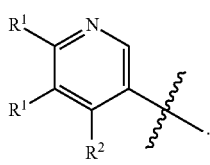

In some embodiments, the optionally substituted ring A is

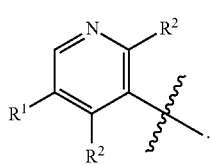

In some embodiments, the optionally substituted ring A is

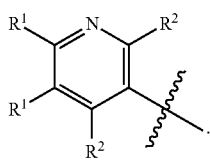

In some embodiments, the optionally substituted ring A is

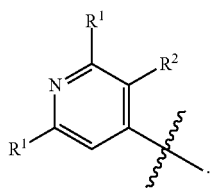

In some embodiments, the optionally substituted ring A is

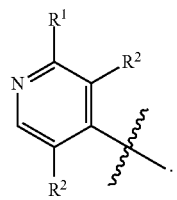

In some embodiments, the optionally substituted ring A is

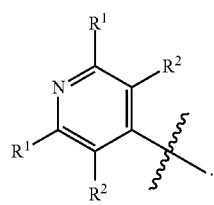

In some embodiments, the optionally substituted ring A is

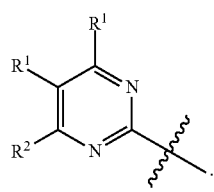

In some embodiments, the optionally substituted ring A is

In some embodiments, the optionally substituted ring A is

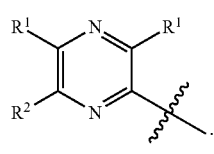

In some embodiments, the optionally substituted ring A is

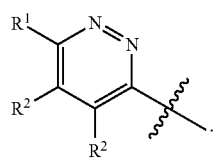

In some embodiments, the optionally substituted ring A is

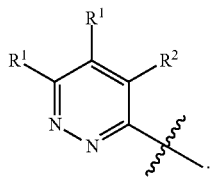

In some embodiments, the optionally substituted ring A is

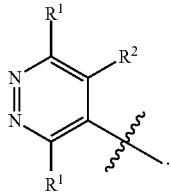

In some embodiments, the optionally substituted ring A is

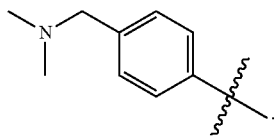 [SMILES: *c1ccc(CN(C)C)cc1]

In some embodiments, the optionally substituted ring A is selected from the group consisting of:

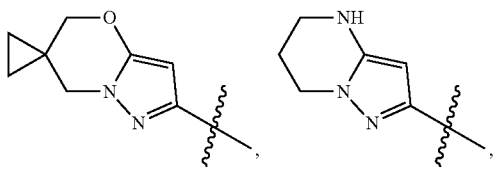

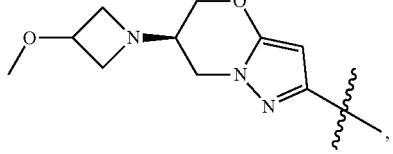

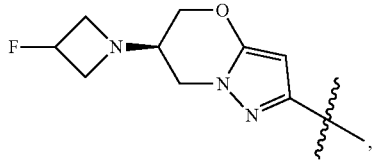

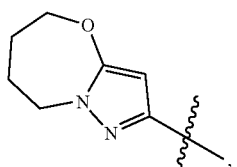

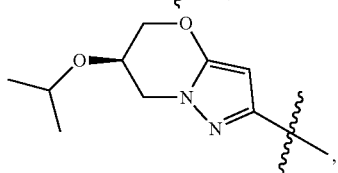

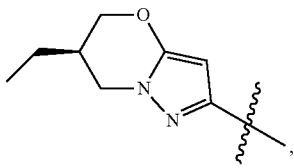

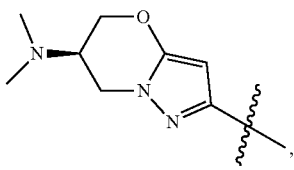

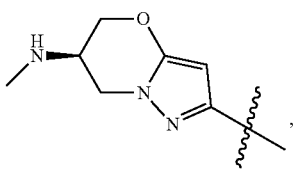

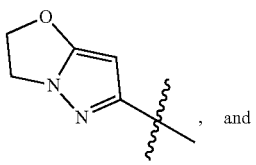

, and

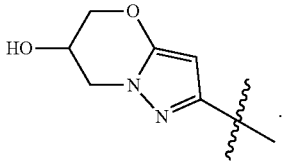

In some embodiments, the optionally substituted ring A is selected from the group consisting of:

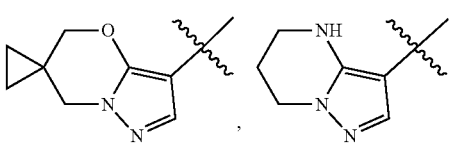

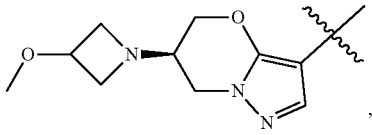

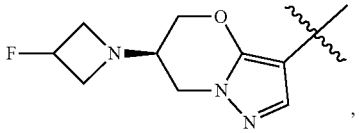

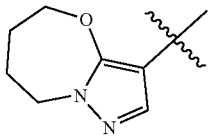

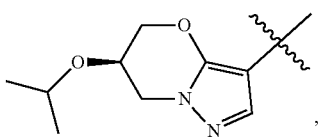

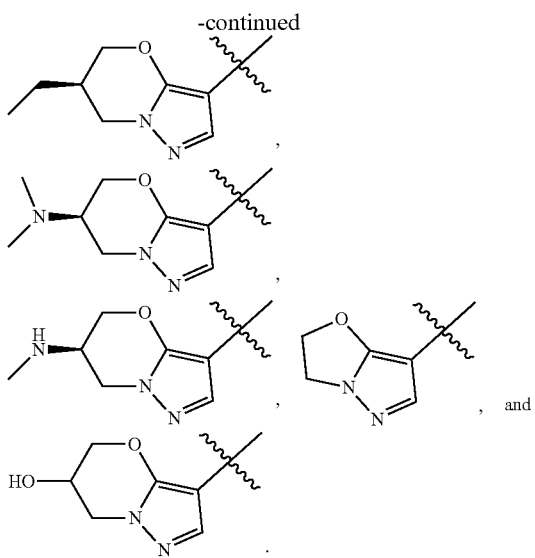

The groups $R^1$ and $R^2$

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, C(O)-5- to 10-membered heteroaryl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^1R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SO_2NR^1R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $SC_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $SC_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ alkyl, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^1R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ alkyl, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, —$NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is unsubstituted;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are unsubstituted;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
    wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is unsubstituted;
    wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are unsubstituted;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl are each unsubstituted;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
    wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl are each unsubstituted;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalor at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, at least one pair of $R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, one pair of $R^1$ and $R^2$ on adjacent atoms, taken together with the atoms connecting them, independently form one monocyclic or bicyclic $C_4$-$C_2$ carbocyclic ring or one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3-to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, one pair of $R^1$ and $R^2$ on adjacent atoms, taken together with the atoms connecting them, independently form one monocyclic or bicyclic $C_6$-$C_8$ carbocyclic ring or one monocyclic or bicyclic 5-to-8-membered heterocyclic ring containing 1 heteroatom or heteroatomic group independently selected from O, NH, and $NR^{13}$, wherein the carbocyclic ring or heterocyclic ring is optionally independently substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments, one pair of $R^1$ and $R^2$ on adjacent atoms, taken together with the atoms connecting them, independently form a monocyclic or bicyclic $C_6$-$C_8$ carbocyclic ring or a monocyclic or bicyclic 5-to-8-membered heterocyclic ring containing 1 heteroatom or heteroatomic group independently selected from O, NH, and $NR^{13}$, wherein the carbocyclic ring or heterocyclic ring is optionally independently substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments, one pair of $R^1$ and $R^2$ on adjacent atoms, taken together with the atoms connecting them, independently form a monocyclic or bicyclic $C_6$-$C_8$ carbocyclic ring or a monocyclic or bicyclic 5-to-8-membered heterocyclic ring containing 2 heteroatoms and/or heteroatomic groups each independently selected from O, NH, and $NR^{13}$, wherein the carbocyclic ring or heterocyclic ring is optionally independently substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments, one pair of $R^1$ and $R^2$ on adjacent atoms, taken together, forms:

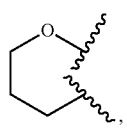

wherein each ⸸ represents a point of attachment to Ring A and wherein the

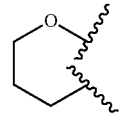

moiety is optionally substituted as described elsewhere herein.

In certain embodiments, the bottom ⸸ in the

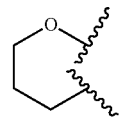

moiety represents a point of attachment to a ring nitrogen atom in Ring A.

In certain embodiments, one pair of $R^1$ and $R^2$ on adjacent atoms, taken together, forms:

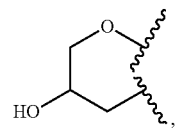

wherein each ⸸ represents a point of attachment to Ring A.

In certain embodiments, one pair of $R^1$ and $R^2$ on adjacent atoms, taken together, forms:

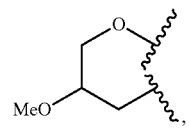

wherein each ⸸ represents a point of attachment to Ring A.

In certain embodiments, one pair of $R^1$ and $R^2$ on adjacent atoms, taken together, forms:

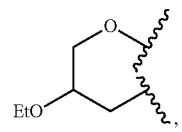

wherein each ⸸ represents a point of attachment to Ring A.

In certain embodiments, one pair of $R^1$ and $R^2$ on adjacent atoms, taken together, forms:

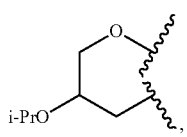

wherein each ⸹ represents a point of attachment to Ring A.
In certain embodiments, one pair of R¹ and R² on adjacent atoms, taken together, forms:

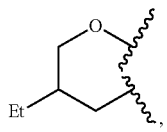

wherein each ⸹ represents a point of attachment to Ring A.
In certain embodiments, one pair of R¹ and R² on adjacent atoms, taken together, forms:

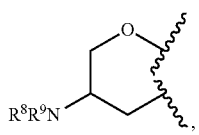

wherein each ⸹ represents a point of attachment to Ring A.
In certain embodiments, one pair of R¹ and R² on adjacent atoms, taken together, forms:

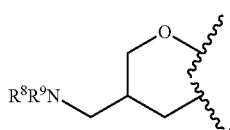

wherein each ⸹ represents a point of attachment to Ring A.
In certain embodiments, one pair of R¹ and R² on adjacent atoms, taken together, forms:

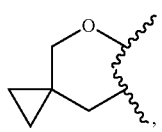

wherein each ⸹ represents a point of attachment to Ring A.
In certain embodiments, one pair of R¹ and R² on adjacent atoms, taken together, forms:

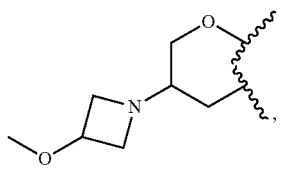

wherein each ⸹ represents a point of attachment to Ring A.
In some embodiments, one pair of R¹ and R² on adjacent atoms, taken together, forms:

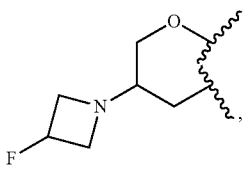

wherein each ⸹ represents a point of attachment to Ring A.
In some embodiments, one pair of R¹ and R² on adjacent atoms, taken together, forms:

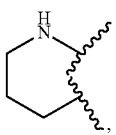

wherein each ⸹ represents a point of attachment to Ring A and wherein the

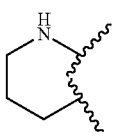

moiety is optionally substituted as described elsewhere herein.

In certain embodiments (where Ring A contains one or more nitrogen atoms), the bottom ⸹ in the

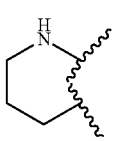

moiety represents a point of attachment to a ring nitrogen atom in Ring A.

In some embodiments, one pair of R¹ and R² on adjacent atoms, taken together, forms:

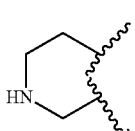

wherein each ⸹ represents a point of attachment to Ring A and wherein the

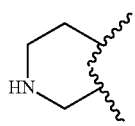

moiety is optionally substituted as described elsewhere herein.

In certain embodiments (where Ring A contains one or more nitrogen atoms), the bottom  in the

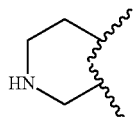

moiety represents a point of attachment to a ring nitrogen atom in Ring A.

In some embodiments, one pair of $R^1$ and $R^2$ on adjacent atoms, taken together, forms:

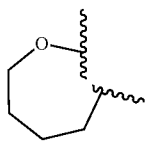 [SMILES: *CCCCO*]

wherein each  represents a point of attachment to Ring A and wherein the

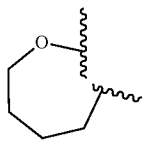 [SMILES: *CCCCO*]

moiety is optionally substituted as described elsewhere herein.

In certain embodiments (where Ring A contains one or more nitrogen atoms), the bottom  in the

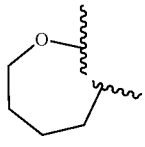 [SMILES: *CCCCO*]

moiety represents a point of attachment to a ring nitrogen atom in Ring A.

In some embodiments, one pair of $R^1$ and $R^2$ on adjacent atoms, taken together, forms:

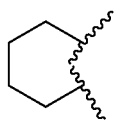

wherein each  represents a point of attachment to Ring A and wherein the

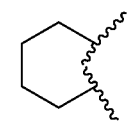

moiety is optionally substituted as described elsewhere herein.

In some embodiments, one pair of $R^1$ and $R^2$ on adjacent atoms, taken together, forms:

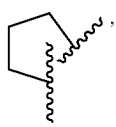

wherein each  represents a point of attachment to Ring A and wherein the

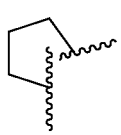

moiety is optionally substituted as described elsewhere herein.

In some embodiments, one pair of $R^1$ and $R^2$ on adjacent atoms, taken together, forms:

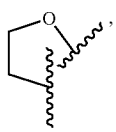 [SMILES: *CCO*]

wherein each  represents a point of attachment to Ring A and wherein the

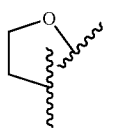

moiety is optionally substituted as described elsewhere herein.

In certain embodiments (where Ring A contains one or more nitrogen atoms), the bottom  in the

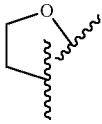 [SMILES: *CCO*]

moiety represents a point of attachment to a ring nitrogen atom in Ring A.

In some embodiments,
$R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, $S(O)C_1$-$C_6$ alkyl, 5- to 10-membered heteroaryl, and 3- to 7-membered heterocycloalkyl,
wherein the $C_1$-$C_6$ alkyl and 3- to 7-membered heterocycloalkyl is optionally substituted with one or more substituents each independently selected from hydroxy and oxo.

In some embodiments, m=1; n=0; and
$R^1$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-5- to 10-membered heteroaryl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, m=1; n=0; and
$R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl,
wherein the $C_1$-$C_6$ alkyl and 3- to 7-membered heterocycloalkyl is optionally substituted with one or more substituents each independently selected from hydroxy and oxo.

In some embodiments, m=1; n=1; and
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, CO—$C_6$-$C_{10}$ aryl, CO-5- to 10-membered heteroaryl, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heterocycloalkyl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, m=1; n=1; and,
$R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl,
wherein the $C_1$-$C_6$ alkyl and 3- to 7-membered heterocycloalkyl is optionally substituted with one or more substituents each independently selected from hydroxy and oxo.

In some embodiments, m=1; n=1; and
$R^1$ and $R^2$ are on adjacent atoms, and taken together with the atoms connecting them, form a $C_5$-$C_8$ carbocyclic ring or a 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, m=1; n=1; and
$R^1$ and $R^2$ are on adjacent atoms, and taken together with the atoms connecting them, form a $C_{5-8}$ carbocyclic ring or a 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, m=1; n=1; and
$R^1$ and $R^2$ are on adjacent atoms, and taken together with the atoms connecting them, form a $C_6$ carbocyclic ring or a 5-to-6-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, m=1; n=1; and
$R^1$ and $R^2$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, m=1 or 2; n=1; and one pair of $R^1$ and $R^2$ is on adjacent atoms, and taken together with the atoms connecting them, independently form a monocyclic or bicyclic $C_4$-$C_{12}$ carbocyclic ring or a monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$;

In certain embodiments of the foregoing (when m is 2), the $R^1$ that is not taken together with an adjacent $R^2$ and the atoms connecting them to form a ring is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, CO—$C_6$-$C_{10}$ aryl, C(O)-5- to 10-membered heteroaryl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3-to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $C_3$-$C_7$cycloalkyl and 3- to 7-membered heterocycloalkyl.

In some embodiments, m=1; n=1; and $R^1$ and $R^2$ are on adjacent atoms, and taken together with the atoms connecting them, independently form a monocyclic or bicyclic $C_4$-$C_{12}$ carbocyclic ring or a monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_5$-$C_8$ carbocyclic ring or a 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is unsubstituted.

In some embodiments, m=1; n=1; and $R^1$ and $R^2$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is unsubstituted.

Particular Embodiments Wherein m=1 and n=0:

In some embodiments, $R^1$ is $C_1$-$C_6$ alkyl optionally substituted with one or more hydroxy.

In some embodiments, $R^1$ is 1-hydroxy-2-methylpropan-2-yl.

In some embodiments, $R^1$ is $C_1$-$C_6$ alkyl.

In some embodiments, $R^1$ is methyl.

In some embodiments, $R^1$ is isopropyl.

In some embodiments, $R^1$ is $C_1$-$C_6$ alkyl substituted with hydroxy at the carbon directly connected to ring A.

In some embodiments, $R^1$ is 2-hydroxy-2-propyl.

In some embodiments, $R^1$ is hydroxymethyl.

In some embodiments, $R^1$ is 1-hydroxyethyl.

In some embodiments, $R^1$ is 2-hydroxyethyl.

In some embodiments, $R^1$ is 1-hydroxy-2-propyl.

In some embodiments, $R^1$ is $C_3$-$C_7$ cycloalkyl optionally substituted with one or more hydroxy.

In some embodiments, $R^1$ is $C_3$-$C_7$ cycloalkyl.

In some embodiments, $R^1$ is $C_3$-$C_7$ cycloalkyl substituted with hydroxy at the carbon directly connected to ring A.

In some embodiments, $R^1$ is 1-hydroxy-1-cyclopropyl.

In some embodiments, $R^1$ is 1-hydroxy-1-cyclobutyl.

In some embodiments, $R^1$ is 1-hydroxy-1-cyclopentyl.

In some embodiments, $R^1$ is 1-hydroxy-1-cyclohexyl.

In some embodiments, $R^1$ is 3- to 7-membered heterocycloalkyl optionally substituted with one or more hydroxy.

In some embodiments, $R^1$ is 3- to 7-membered heterocycloalkyl.

In some embodiments, $R^1$ is morpholinyl (e.g., 4-morpholinyl).

In some embodiments, $R^1$ is 1,3-dioxolan-2-yl.

In some embodiments, $R^1$ is 3- to 7-membered heterocycloalkyl substituted with hydroxy at the carbon directly connected to ring A.

In some embodiments, $R^1$ is $C_1$-$C_6$ alkyl optionally substituted with one or more oxo.

In some embodiments, $R^1$ is $COCH_3$.

In some embodiments, $R^1$ is $COCH_2CH_3$.

In some embodiments, $R^1$ is $C_3$-$C_7$ cycloalkyl optionally substituted with one or more oxo.

In some embodiments, $R^1$ is 3- to 7-membered heterocycloalkyl optionally substituted with one or more oxo.

In some embodiments, $R^1$ is $C_1$-$C_6$ alkyl optionally substituted with one or more $C_1$-$C_6$ alkoxy.

In some embodiments, $R^1$ is 2-methoxy-2-propyl.

In some embodiments, $R^1$ is $C_3$-$C_7$ cycloalkyl optionally substituted with one or more $C_1$-$C_6$ alkoxy.

In some embodiments, $R^1$ is 3- to 7-membered heterocycloalkyl optionally substituted with one or more $C_1$-$C_6$ alkoxy.

In some embodiments, $R^1$ is $C_1$-$C_6$ alkyl optionally substituted with one or more $NR^8R^9$.

In some embodiments, $R^1$ is (dimethylamino)methyl.

In some embodiments, $R^1$ is $C_3$-$C_7$ cycloalkyl optionally substituted with one or more $NR^8R^9$.

In some embodiments, $R^1$ is 3- to 7-membered heterocycloalkyl optionally substituted with one or more $NR^8R^9$.

In some embodiments, $R^1$ is $C_1$-$C_6$ haloalkyl optionally substituted with one or more hydroxy.

In some embodiments, $R^1$ is $C_1$-$C_6$ alkoxy.

In some embodiments, $R^1$ is $C_1$-$C_6$ haloalkoxy.

In some embodiments, $R^1$ is halo.

In some embodiments, $R^1$ is fluoro.

In some embodiments, $R^1$ is chloro.

In some embodiments, $R^1$ is CN.

In some embodiments, $R^1$ is $NO_2$.

In some embodiments, $R^1$ is $COC_1$-$C_6$ alkyl.

In some embodiments, $R^1$ is CO—$C_6$-$C_{10}$ aryl.

In some embodiments, $R^1$ is CO-5- to 10-membered heteroaryl.

In some embodiments, $R^1$ is $CO_2C_1$-$C_6$ alkyl.

In some embodiments, $R^1$ is $CO_2C_3$-$C_8$ cycloalkyl.

In some embodiments, $R^1$ is $OCOC_1$-$C_6$ alkyl.

In some embodiments, $R^1$ is $OCOC_6$-$C_{10}$ aryl.

In some embodiments, $R^1$ is OCO(5- to 10-membered heteroaryl).

In some embodiments, $R^1$ is OCO(3- to 7-membered heterocycloalkyl).

In some embodiments, $R^1$ is $C_6$-$C_{10}$ aryl.

In some embodiments, $R^1$ is phenyl.

In some embodiments, $R^1$ is 5- to 10-membered heteroaryl.

In some embodiments, $R^1$ is pyridyl (e.g., 4-pyridyl).

In some embodiments, $R^1$ is pyrazolyl (e.g., 1-pyrazolyl).

In some embodiments, $R^1$ is $NH_2$.

In some embodiments, $R^1$ is $NHC_1$-$C_6$ alkyl.

In some embodiments, $R^1$ is $N(C_1$-$C_6$ alkyl$)_2$.

In some embodiments, $R^1$ is $CONR^8R^9$.

In some embodiments, $R^1$ is $SF_5$.

In some embodiments, $R^1$ is $SC_1$-$C_6$ alkyl,

In some embodiments, $R^1$ is $S(O_2)C_1$-$C_6$ alkyl.

In some embodiments, $R^1$ is $S(O_2)CH_3$.

In some embodiments, $R^1$ is $S(O_2)NR^{11}R^{12}$.

In some embodiments, $R^1$ is $S(O_2)N(CH_3)_2$.

In some embodiments, $R^1$ is $S(O)C_1$-$C_6$ alkyl.

In some embodiments, $R^1$ is $S(O)CH_3$.

In some embodiments, $R^1$ is attached to a carbon of an aryl ring A.

In some embodiments, $R^1$ is attached to a carbon of a heteroaryl ring A.

In some embodiments, $R^1$ is attached to a nitrogen of a heteroaryl ring A.

Particular Embodiments Wherein m=1 and n=1:

In some embodiments, $R^1$ is $C_1$-$C_6$ alkyl optionally substituted with one or more hydroxy, and $R^2$ is $C_1$-$C_6$ alkyl optionally substituted with one or more hydroxy.

In some embodiments, $R^1$ is 1-hydroxy-2-methylpropan-2-yl, and $R^2$ is methyl.

In some embodiments, $R^1$ is 2-hydroxy-2-propyl and $R^2$ is methyl.

In some embodiments, $R^1$ is 2-hydroxy-2-propyl and $R^2$ is isopropyl.

In some embodiments, $R^1$ is 2-hydroxy-2-propyl and $R^2$ is 2-hydroxy-2-propyl.

In some embodiments, $R^1$ is 2-hydroxy-2-propyl and $R^2$ is 1-hydroxyethyl.

In some embodiments, $R^1$ is hydroxymethyl and $R^2$ is methyl.

In some embodiments, $R^1$ is 1-hydroxyethyl and $R^2$ is methyl.

In some embodiments, $R^1$ is 2-hydroxyethyl and $R^2$ is methyl.

In some embodiments, $R^1$ is 1-hydroxy-2-propyl and $R^2$ is methyl.

In some embodiments, $R^1$ is $C_1$-$C_6$ alkyl optionally substituted with one or more hydroxy, and $R^2$ is $C_6$-$C_{10}$ aryl.

In some embodiments, $R^1$ is 2-hydroxy-2-propyl and $R^2$ is phenyl.

In some embodiments, $R^1$ is $C_1$-$C_6$ alkyl optionally substituted with one or more hydroxy, and $R^2$ is 5- to 10-membered heteroaryl.

In some embodiments, $R^1$ is 2-hydroxy-2-propyl and $R^2$ is pyridyl.

In some embodiments, $R^1$ is 2-hydroxy-2-propyl and $R^2$ is pyrazolyl.

In some embodiments, $R^1$ is $C_1$-$C_6$ alkyl optionally substituted with one or more hydroxy, and $R^2$ is $SF_5$.

In some embodiments, $R^1$ is $C_1$-$C_6$ alkyl optionally substituted with one or more hydroxy, and $R^2$ is $SC_1$-$C_6$ alkyl.

In some embodiments, $R^1$ is $C_1$-$C_6$ alkyl optionally substituted with one or more hydroxy, and $R^2$ is $S(O_2)C_1$-$C_6$ alkyl.

In some embodiments, $R^1$ is $C_1$-$C_6$ alkyl optionally substituted with one or more hydroxy, and $R^2$ is $S(O_2)CH_3$.

In some embodiments, $R^1$ is $C_1$-$C_6$ alkyl optionally substituted with one or more hydroxy, and $R^2$ is halo.

In some embodiments, $R^1$ is 2-hydroxy-2-propyl and $R^2$ is chloro.

In some embodiments, $R^1$ is 2-hydroxy-2-propyl and $R^2$ is fluoro.

In some embodiments, $R^1$ is $C_3$-$C_7$ cycloalkyl optionally substituted with one or more hydroxy, and $R^2$ is $C_1$-$C_6$ alkyl.

In some embodiments, $R^1$ is 1-hydroxy-1-cyclopropyl, and $R^2$ is methyl.

In some embodiments, $R^1$ is 1-hydroxy-1-cyclobutyl, and $R^2$ is methyl.

In some embodiments, $R^1$ is 1-hydroxy-1-cyclopentyl, and $R^2$ is methyl.

In some embodiments, $R^1$ is 1-hydroxy-1-cyclohexyl, and $R^2$ is methyl.

In some embodiments, $R^1$ is 3- to 7-membered heterocycloalkyl optionally substituted with one or more hydroxy, and $R^2$ is $C_1$-$C_6$ alkyl.

In some embodiments, $R^1$ is morpholinyl, and $R^2$ is methyl.

In some embodiments, $R^1$ is 1,3-dioxolan-2-yl, and $R^2$ is methyl.

In some embodiments, $R^1$ is 3- to 7-membered heterocycloalkyl optionally substituted with one or more hydroxy, and $R^2$ is halo.

In some embodiments, $R^1$ is 1,3-dioxolan-2-yl, and $R^2$ is fluoro.

In some embodiments, $R^1$ is 1,3-dioxolan-2-yl, and $R^2$ is chloro.

In some embodiments, $R^1$ is $C_1$-$C_6$ alkyl optionally substituted with one or more oxo, and $R^2$ is methyl.

In some embodiments, $R^1$ is $COCH_3$, and $R^2$ is methyl.

In some embodiments, $R^1$ is $C_1$-$C_6$ alkyl optionally substituted with one or more $C_1$-$C_6$ alkoxy, and $R^2$ is $C_1$-$C_6$ alkyl.

In some embodiments, $R^1$ is 2-methoxy-2-propyl, and $R^2$ is methyl.

In some embodiments, $R^1$ is $C_1$-$C_6$ alkyl optionally substituted with one or more $NR^8R^9$, and $R^2$ is $C_1$-$C_6$ alkyl.

In some embodiments, $R^1$ is (dimethylamino)methyl, and $R^2$ is methyl.

In some embodiments, $R^2$ is 1-hydroxy-2-methylpropan-2-yl, and $R^1$ is methyl.

In some embodiments, $R^2$ is 2-hydroxy-2-propyl and $R^1$ is methyl.

In some embodiments, $R^2$ is 2-hydroxy-2-propyl and $R^1$ is isopropyl.

In some embodiments, $R^2$ is 2-hydroxy-2-propyl and $R^1$ is 1-hydroxyethyl.

In some embodiments, $R^2$ is hydroxymethyl and $R^1$ is methyl.

In some embodiments, $R^2$ is 1-hydroxyethyl and $R^1$ is methyl.

In some embodiments, $R^2$ is 2-hydroxyethyl and $R^1$ is methyl.

In some embodiments, $R^2$ is 1-hydroxy-2-propyl and $R^1$ is methyl.

In some embodiments, $R^2$ is $C_1$-$C_6$ alkyl optionally substituted with one or more hydroxy, and R is $C_6$-$C_{10}$ aryl.

In some embodiments, $R^2$ is 2-hydroxy-2-propyl and $R^1$ is phenyl.

In some embodiments, $R^2$ is $C_1$-$C_6$ alkyl optionally substituted with one or more hydroxy, and R is 5- to 10-membered heteroaryl.

In some embodiments, $R^2$ is 2-hydroxy-2-propyl and $R^1$ is pyridyl.

In some embodiments, $R^2$ is 2-hydroxy-2-propyl and $R^1$ is pyrazolyl.

In some embodiments, $R^2$ is $C_1$-$C_6$ alkyl optionally substituted with one or more hydroxy, and $R^1$ is $SF_5$.

In some embodiments, $R^2$ is $C_1$-$C_6$ alkyl optionally substituted with one or more hydroxy, and $R^1$ is $SC_1$-$C_6$ alkyl.

In some embodiments, $R^2$ is $C_1$-$C_6$ alkyl optionally substituted with one or more hydroxy, and $R^1$ is $S(O_2)C_1$-$C_6$ alkyl.

In some embodiments, $R^2$ is $C_1$-$C_6$ alkyl optionally substituted with one or more hydroxy, and $R^1$ is $S(O_2)CH_3$.

In some embodiments, $R^2$ is $C_1$-$C_6$ alkyl optionally substituted with one or more hydroxy, and $R^1$ is halo.

In some embodiments, $R^2$ is 2-hydroxy-2-propyl and $R^1$ is chloro.

In some embodiments, $R^2$ is 2-hydroxy-2-propyl and $R^1$ is fluoro.

In some embodiments, $R^2$ is $C_3$-$C_7$ cycloalkyl optionally substituted with one or more hydroxy, and $R^1$ is $C_1$-$C_6$ alkyl.

In some embodiments, $R^2$ is 1-hydroxy-1-cyclopropyl, and $R^1$ is methyl.

In some embodiments, $R^2$ is 1-hydroxy-1-cyclobutyl, and $R^1$ is methyl.

In some embodiments, $R^2$ is 1-hydroxy-1-cyclopentyl, and $R^1$ is methyl.

In some embodiments, $R^2$ is 1-hydroxy-1-cyclohexyl, and $R^1$ is methyl.

In some embodiments, $R^2$ is 3- to 7-membered heterocycloalkyl optionally substituted with one or more hydroxy, and $R^1$ is $C_1$-$C_6$ alkyl.

In some embodiments, $R^2$ is morpholinyl, and $R^1$ is methyl.

In some embodiments, $R^2$ is 1,3-dioxolan-2-yl, and $R^1$ is methyl.

In some embodiments, $R^2$ is 3- to 7-membered heterocycloalkyl optionally substituted with one or more hydroxy, and $R^1$ is halo.

In some embodiments, $R^2$ is 1,3-dioxolan-2-yl, and $R^1$ is fluoro.

In some embodiments, $R^2$ is 1,3-dioxolan-2-yl, and $R^1$ is chloro.

In some embodiments, $R^2$ is $C_1$-$C_6$ alkyl optionally substituted with one or more oxo, and $R^1$ is methyl.

In some embodiments, $R^2$ is $COCH_3$, and $R^1$ is methyl.

In some embodiments, $R^2$ is $C_1$-$C_6$ alkyl optionally substituted with one or more $C_1$-$C_6$ alkoxy, and $R^1$ is $C_1$-$C_6$ alkyl.

In some embodiments, $R^2$ is 2-methoxy-2-propyl, and $R^1$ is methyl.

In some embodiments, $R^2$ is $C_1$-$C_6$ alkyl optionally substituted with one or more $NR^8R^9$, and $R^1$ is $C_1$-$C_6$ alkyl.

In some embodiments, $R^2$ is (dimethylamino)methyl, and $R^1$ is methyl.

In some embodiments, $R^1$ and $R^2$ are each attached to a carbon of an aryl ring A.

In some embodiments, $R^1$ and $R^2$ are each attached to a carbon of a heteroaryl ring A.

In some embodiments, $R^1$ is attached to a carbon and $R^2$ is attached to a nitrogen of a heteroaryl ring A.

In some embodiments, $R^2$ is attached to a carbon and $R^1$ is attached to a nitrogen of a heteroaryl ring A.

In some embodiments, $R^1$ and $R^2$ on adjacent atoms, taken together with the atoms connecting them, independently form one monocyclic or bicyclic $C_4$-$C_{12}$ carbocyclic ring or one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ on adjacent atoms, taken together with the atoms connecting them, independently form one monocyclic or bicyclic $C_6$-$C_8$ carbocyclic ring or one monocyclic or bicyclic 5-to-8-membered heterocyclic ring containing 1 heteroatom or heteroatomic group independently selected from O, NH, and $NR^{13}$, wherein the carbocyclic ring or heterocyclic ring is optionally independently substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments, $R^1$ and $R^2$ on adjacent atoms, taken together with the atoms connecting them, independently form a monocyclic or bicyclic $C_6$-$C_8$ carbocyclic ring or a monocyclic or bicyclic 5-to-8-membered heterocyclic ring containing 1 heteroatom or heteroatomic group independently selected from O, NH, and $NR^{13}$, wherein the carbocyclic ring or heterocyclic ring is optionally independently substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments, $R^1$ and $R^2$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_5$ aliphatic carbocyclic ring.

In some embodiments, $R^1$ and $R^2$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_6$ aliphatic carbocyclic ring.

In some embodiments, $R^1$ and $R^2$ are on adjacent atoms, and taken together with the atoms connecting them, form a $C_6$ aromatic carbocyclic ring.

In some embodiments, $R^1$ and $R^2$ are on adjacent atoms, and taken together with the atoms connecting them, form a 5-membered heterocyclic ring containing 1 or 2 heteroatoms and/or heteroatomic groups independently selected from O, N, NH, $NR^{13}$, S, S(O), and S(O)$_2$, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 5-membered aliphatic heterocyclic ring containing 1 or 2 heteroatoms and/or heteroatomic groups independently selected from O, N, NH, $NR^{13}$, S, S(O), and S(O)$_2$.

In some embodiments, $R^1$ and $R^2$ are on adjacent atoms, and taken together with the atoms connecting them, form a 5-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 5-membered heteroaromatic ring containing 1 or 2 heteroatoms and/or heteroatomic groups independently selected from O, N, NH, $NR^{13}$, S, S(O), and S(O)$_2$. In some embodiments, $R^1$ and $R^2$ are on adjacent atoms, and taken together with the atoms connecting them, form a 5-membered heteroaromatic ring containing 1 or 2 heteroatoms independently selected from O, N, and S.

In some embodiments, $R^1$ and $R^2$ are on adjacent atoms, and taken together with the atoms connecting them, form a 6-membered heterocyclic ring containing 1 or 2 heteroatoms and/or heteroatomic groups independently selected from O, N, NH, $NR^{13}$, S, S(O), and S(O)$_2$, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 6-membered aliphatic heterocyclic ring containing 1 or 2 heteroatoms and/or heteroatomic groups independently selected from O, N, NH, $NR^{13}$, S, S(O), and S(O)$_2$.

In some embodiments, $R^1$ and $R^2$ are on adjacent atoms, and taken together with the atoms connecting them, form a 6-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 6-membered heteroaromatic ring containing 1 or 2 heteroatoms and/or heteroatomic groups independently selected from O, N, NH, $NR^{13}$, S, S(O), and S(O)$_2$.

In some embodiments, $R^1$ and $R^2$ are on adjacent atoms, and taken together with the atoms connecting them, form a 6-membered heteroaromatic ring containing 1 or 2 heteroatoms independently selected from O, N, and S.

In some embodiments, $R^1$ and $R^2$ are different.

In some embodiments, $R^1$ and $R^2$ are different, and $R^2$ comprises a carbonyl group.

In some embodiments, $R^1$ and $R^2$ are different, and $R^2$ comprises 1 or 2 (e.g., 1) nitrogen atoms.

In some embodiments, $R^1$ and $R^2$ are different, and $R^2$ comprises 1 or 2 (e.g., 1) oxygen atoms.

In some embodiments, $R^1$ and $R^2$ are different, and $R^2$ comprises a sulfur atom.

In some embodiments, $R^2$ and $R^1$ are different, and $R^2$ comprises a carbonyl group.

In some embodiments, $R^2$ and $R^1$ are different, and $R^2$ comprises 1 or 2 (e.g., 1) nitrogen atoms.

In some embodiments, $R^2$ and $R^1$ are different, and $R^2$ comprises 1 or 2 (e.g., 1) oxygen atoms.

In some embodiments, $R^2$ and $R^1$ are different, and $R^2$ comprises a sulfur atom.

In some embodiments, $R^1$ and $R^2$ are the same.

In some embodiments, $R^1$ is para or meta to $R^2$.

In some embodiments, $R^1$ is para or ortho to $R^2$.

In some embodiments, $R^1$ is ortho or meta to $R^2$. In some embodiments, $R^1$ is para to $R^2$.

In some embodiments, $R^1$ is meta to R.

In some embodiments, $R^1$ is ortho to $R^2$.

The Variable p

In some embodiments p=0, 1, or 2.

In some embodiments p=0.

In some embodiments p=1.

In some embodiments p=2.

The ring

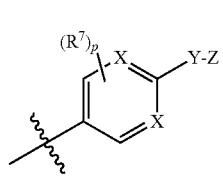

and the variable X

In some embodiments of ring

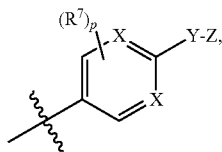

each X is N.

In some embodiments of ring

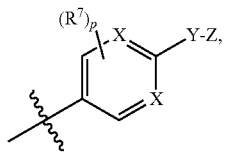

each X is CR⁶.

In some embodiments of ring

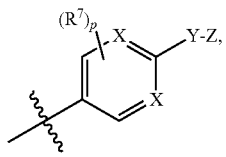

one X is N; and the other X is CR⁶.

In some embodiments of ring

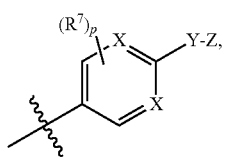

the ring is

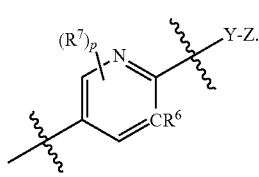

In some embodiments of

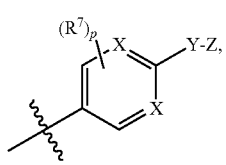

each X is CR⁶ and p is 0, 1 or 2.

In some embodiments of

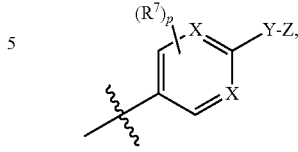

each X is CR⁶ and p is 1.

In some embodiments of

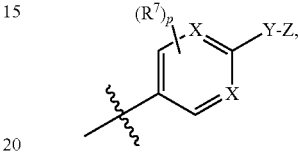

each X is CR⁶ and p is 2.

In some embodiments of

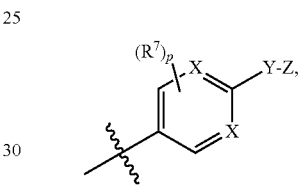

one X is N, one X is CR⁶, and p is 0, 1 or 2.

In some embodiments of

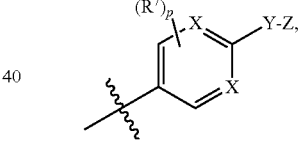

each X is N and p is 0, 1 or 2.

In some embodiments of

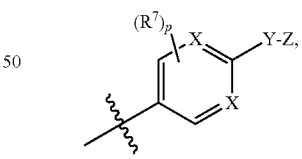 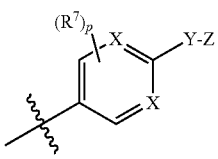

is

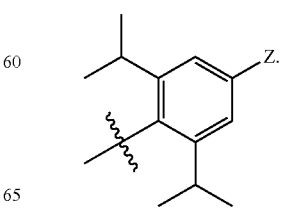

In some embodiments of

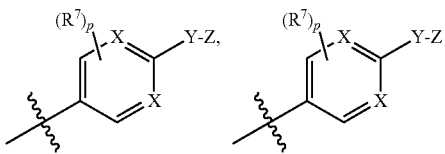

is

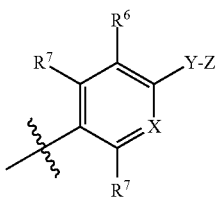

(e.g. X=N).

In some embodiments of

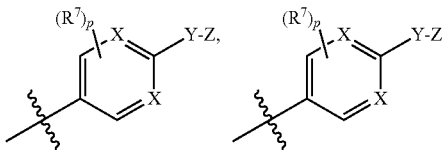

is

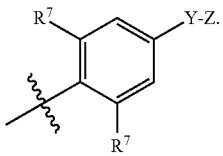

The groups $R^6$ and $R^7$

In some embodiments, each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

and each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

and each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_9$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, each $R^6$ is independently selected from hydrogen $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

and each $R^7$ is independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, each $R^6$ is independently selected from hydrogen $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

and each $R^7$ is independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^1R^9$, $SF_5$, $S(O_2)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^1R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments,
each $R^6$ is independently selected from hydrogen, $C_1$-$C_6$ alkyl, halo, CN, $NO_2$, $COC_1$-$C_6$ alkyl, $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

and
each $R^7$ is independently selected from $C_1$-$C_6$ alkyl, halo, CN, $NO_2$, $COC_1$-$C_6$ alkyl, $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
    wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments,
each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
    wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are unsubstituted;
and
each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
    wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are unsubstituted;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^1R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl are each unsubstituted; and each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl are each unsubstituted;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl are each unsubstituted; and each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl are each unsubstituted;

or at least one pair of $R^6$ and $R^7$ on adjacent atoms, taken together with the atoms connecting them, independently form at least one $C_5$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and NHCO$C_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, CO$C_1$-$C_6$ alkyl, CO$_2C_1$-$C_6$ alkyl, CO$_2C_3$-$C_6$ cycloalkyl, OCO$C_1$-$C_6$ alkyl, OCO$C_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CON$R^8R^9$, SF$_5$, S(O$_2$)$C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, N$R^8R^9$, =N$R^{10}$, COO$C_1$-$C_6$ alkyl, $C_6$-$C_{10}$ aryl, and CON$R^8R^9$.

In some embodiments, each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, NO$_2$, CO$C_1$-$C_6$ alkyl, CO$_2C_1$-$C_6$ alkyl, CO$_2C_3$-$C_8$ cycloalkyl, OCO$C_1$-$C_6$ alkyl, OCO$C_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, NH$_2$, OH, NH$C_1$-$C_6$ alkyl, N($C_1$-$C_6$ alkyl)$_2$, CON$R^8R^9$, SF$_5$, S(O$_2$)$C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, N$R^8R^9$, =N$R^{10}$, COO$C_1$-$C_6$ alkyl, CON$R^8R^9$, 3- to 7-membered heterocycloalkyl, $C_6$-$C_{10}$ aryl, 5- to 10-membered heteroaryl, OCO$C_1$-$C_6$ alkyl, OCO$C_6$-$C_{10}$ aryl, OCO(5- to 10-membered heteroaryl), OCO(3- to 7-membered heterocycloalkyl), NHCO$C_1$-$C_6$ alkyl, NHCO$C_6$-$C_{10}$ aryl, NHCO(5- to 10-membered heteroaryl), NHCO(3- to 7-membered heterocycloalkyl), and NHCO$C_2$-$C_6$ alkynyl;

wherein the 3- to 7-membered heterocycloalkyl, $C_6$-$C_{10}$ aryl, 5- to 10-membered heteroaryl, NHCO$C_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and O$C_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms and/or heteroatomic groups independently selected from O, N, NH, N$R^{13}$, S, S(O), and S(O)$_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, N$R^8R^9$, CH$_2$N$R^8R^9$, =N$R^{10}$, COO$C_1$-$C_6$ alkyl, $C_6$-$C_{10}$ aryl, and CON$R^8R^9$;

In some embodiments, each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, NO$_2$, CO$C_1$-$C_6$ alkyl, CO$_2C_1$-$C_6$ alkyl, CO$_2C_3$-$C_8$ cycloalkyl, OCO$C_1$-$C_6$ alkyl, OCO$C_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, NH$_2$, OH, NH$C_1$-$C_6$ alkyl, N($C_1$-$C_6$ alkyl)$_2$, CON$R^8R^9$, SF$_5$, S(O$_2$)$C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_1$-$C_6$ alkoxy, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, N$R^8R^9$, =N$R^{10}$, COO$C_1$-$C_6$ alkyl, CON$R^8R^9$, 3- to 7-membered heterocycloalkyl, $C_6$-$C_{10}$ aryl, 5- to 10-membered heteroaryl, OCO$C_1$-$C_6$ alkyl, OCO$C_6$-$C_{10}$ aryl, OCO(5- to 10-membered heteroaryl), OCO(3- to 7-membered heterocycloalkyl), NHCO$C_1$-$C_6$ alkyl, NHCO$C_6$-$C_{10}$ aryl, NHCO(5- to 10-membered heteroaryl), NHCO(3- to 7-membered heterocycloalkyl), and NHCO$C_2$-$C_6$ alkynyl;

wherein the 3- to 7-membered heterocycloalkyl, $C_6$-$C_{10}$ aryl, 5- to 10-membered heteroaryl, NHCO$C_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and O$C_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, N$R^1R^9$, CH$_2$N$R^8R^9$, =N$R^{10}$, COO$C_1$-$C_6$ alkyl, $C_6$-$C_{10}$ aryl, and CON$R^8R^9$;

In some embodiments, each $R^6$ is independently selected from hydrogen, $C_1$-$C_6$ alkyl, $C_1$-$C_6$ haloalkyl, $C_1$-$C_6$ alkoxy, halo, CN, CO$C_1$-$C_6$ alkyl, CO$_2C_3$-$C_8$ cycloalkyl, NH$_2$, OH, S(O$_2$)$C_1$-$C_6$ alkyl, and $C_3$-$C_7$ cycloalkyl, wherein the $C_1$-$C_6$ alkyl and $C_1$-$C_6$ alkoxy is optionally substituted with one or more substituents each independently selected from hydroxy, halo, CN, oxo, $C_1$-$C_6$ alkyl, $C_1$-$C_6$ alkoxy, N$R^8R^9$, $C_6$-$C_{10}$ aryl;

In some embodiments, each $R^6$ is independently selected from hydrogen, $C_1$-$C_6$ alkyl and $C_1$-$C_6$ alkoxy, wherein the $C_1$-$C_6$ alkoxy is optionally substituted with one or more $C_6$-$C_{10}$ aryl.

In some embodiments, each $R^6$ is independently selected from $C_1$-$C_6$ alkyl (e.g., 2-propyl), $C_1$-$C_6$ haloalkyl, $C_1$-$C_6$ alkoxy (e.g., methoxy), halo, CN, CO$C_1$-$C_6$ alkyl, CO$_2C_3$-$C_8$ cycloalkyl, NH$_2$, OH, S(O$_2$)$C_1$-$C_6$ alkyl, and $C_3$-$C_7$ cycloalkyl, wherein the $C_1$-$C_6$ alkoxy is optionally substituted with one or more $C_6$-$C_{10}$ aryl.

In some embodiments, each $R^6$ is independently selected from $C_1$-$C_6$ alkyl (e.g., 2-propyl) or $C_1$-$C_6$ alkoxy (e.g., methoxy), wherein the $C_1$-$C_6$ alkoxy is optionally substituted with one or more $C_6$-$C_{10}$ aryl.

In some embodiments, each $R^7$ is independently selected from $C_1$-$C_6$ alkyl (2-propyl), $C_1$-$C_6$ haloalkyl, $C_1$-$C_6$ alkoxy (e.g., methoxy), halo, CN, CO$C_1$-$C_6$ alkyl, CO$_2C_3$-$C_8$ cycloalkyl, NH$_2$, OH, S(O$_2$)$C_1$-$C_6$ alkyl, and $C_3$-$C_7$ cycloalkyl, wherein the $C_1$-$C_6$ alkoxy is optionally substituted with one or more $C_6$-$C_{10}$ aryl (e.g., phenyl).

In some embodiments, each $R^7$ is independently selected from $C_1$-$C_6$ alkyl (2-propyl) and $C_1$-$C_6$ alkoxy (e.g., methoxy), wherein the $C_1$-$C_6$ alkoxy is optionally substituted with one or more $C_6$-$C_{10}$ aryl (e.g., phenyl).

In some embodiments, each $R^7$ is independently selected from $C_1$-$C_6$ alkyl and $C_1$-$C_6$ alkoxy, wherein the $C_1$-$C_6$ alkoxy is optionally substituted with one or more $C_6$-$C_{10}$ aryl.

In some embodiments, each $R^6$ is independently selected from hydrogen, $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo; and each $R^7$ is independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_5$-$C_8$ carbocyclic ring, wherein the carbocyclic ring is optionally independently substituted with one or more hydroxy or oxo.

In some embodiments, one X is $CR^6$; p=0; and $R^6$ is selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, both X are $CR^6$; p=0; and each $R^6$ is selected from hydrogen, $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo.

In some embodiments, one X is $CR^6$; p=0; and $R^6$ is selected from hydrogen, $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo.

In some embodiments, one or both X are $CR^6$; p=1 or 2; and each $R^6$ is independently selected from hydrogen, $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

and each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

In some embodiments, both X are $CR^6$; p=1; and each $R^6$ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=1; and
each $R^6$ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2; and
each $R^6$ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^1R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$, In some embodiments, both X are $CR^6$; p=2; and
each $R^6$ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$.

In some embodiments, one or both X are $CR^6$; p=1 or 2; and
each $R^6$ is independently selected from hydrogen, $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo,
and
each $R^7$ is independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo,
or at least one pair of $R^6$ and $R^7$ on adjacent atoms, taken together with the atoms connecting them, independently form at least one $C_5$-$C_8$ carbocyclic ring, wherein the carbocyclic ring is optionally independently substituted with one or more hydroxy or oxo.

In some embodiments, one or both X are $CR^6$; p=1 or 2; and
each $R^6$ is independently selected from hydrogen, $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo;
and
each $R^7$ is independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo.

In some embodiments, both X are N; p=1 or 2; and
each $R^6$ is independently selected from hydrogen, $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo,
and
each $R^7$ is independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_5$-$C_8$ carbocyclic ring, wherein the carbocyclic ring is optionally independently substituted with one or more hydroxy or oxo.

In some embodiments, both X are N; p=1 or 2; and
each $R^6$ is independently selected from hydrogen, $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo;
and
each $R^7$ is independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo.

In some embodiments, one or both X are $CR^6$; p=1 or 2; and
one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, one or both X are $CR^6$; p=1 or 2; and
one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, one or both X are $CR^6$; p=1 or 2; and
one $R^6$ and one $R^7$ are on adjacent atoms, and taken together with the atoms connecting them, form a $C_6$ carbocyclic ring or a 5-to-6-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, one or both X are $CR^6$; p=1 or 2; and
one $R^6$ and one $R^7$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, one or both X are $CR^6$; p=1 or 2; and
one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is unsubstituted.

In some embodiments, one or both X are $CR^6$; p=1 or 2; and
one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is unsubstituted.

In some embodiments, both X are $CR^6$; p=2; and
two pairs, each of one $R^6$ and one $R^7$, are on adjacent atoms, and each pair of one $R^6$ and one $R^7$ taken together with the atoms connecting them independently form a $C_5$-$C_8$ carbocyclic ring or a 5-to-8-membered heterocyclic ring containing 1 or 2 heteroatoms and/or heteroatomic groups independently selected from O, N, NH, $NR^{13}$, S, S(O), and $S(O)_2$, wherein each carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $CO_0C_1$-$C_6$ alkyl, $C_6$-$C_{10}$ aryl, and $CONR^8R^9$.

In some embodiments, both X are $CR^6$; p=2; and
two pairs, each of one $R^6$ and one $R^7$, are on adjacent atoms, and each pair of one $R^6$ and one $R^7$ taken together with the atoms connecting them independently form a $C_5$-$C_8$ carbocyclic ring or a 5-to-8-membered heterocyclic ring containing 1 or 2 heteroatoms independently selected from O, N, and S, wherein each carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2; and
two pairs, each of one $R^6$ and one $R^7$, are on adjacent atoms, and each pair of one $R^6$ and one $R^7$ taken together with the atoms connecting them independently form a $C_6$ carbocyclic ring or a 5-to-6-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2; and
two pairs, each of one $R^6$ and one $R^7$, are on adjacent atoms, and each pair of one $R^6$ and one $R^7$ taken together with the atoms connecting them independently form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2; and
two pairs, each of one $R^6$ and one $R^7$, are on adjacent atoms, and each pair of one $R^6$ and one $R^7$ taken together with the atoms connecting them independently form a $C_5$-$C_8$ carbocyclic ring or a 5-to-8-membered heterocyclic ring containing 1 or 2 heteroatoms and/or heteroatomic groups independently selected from O, N, NH, $NR^{13}$, S, S(O), and $S(O)_2$, wherein the carbocyclic ring or heterocyclic ring is unsubstituted.

In some embodiments, both X are $CR^6$; p=2; and
two pairs, each of one $R^6$ and one $R^7$, are on adjacent atoms, and each pair of one $R^6$ and one $R^7$ taken together with the atoms connecting them independently form a $C_5$-$C_8$ carbocyclic ring or a 5-to-8-membered heterocyclic ring containing 1 or 2 heteroatoms independently selected from O, N, and S, wherein the carbocyclic ring or heterocyclic ring is unsubstituted.

Particular Embodiments Wherein One X is $CR^6$; p=0:

In some embodiments, $R^6$ is hydrogen.
In some embodiments, $R^6$ is $C_1$-$C_6$ alkyl.
In some embodiments, $R^6$ is isopropyl.
In some embodiments, $R^6$ is ethyl.
In some embodiments, $R^6$ is Methyl.
In some embodiments, $R^6$ is $C_1$-$C_6$ alkyl substituted with one or more halo.
In some embodiments, $R^6$ is trifluoromethyl.
In some embodiments, $R^6$ is trifluoromethoxy.
In some embodiments, $R^6$ is $C_3$-$C_7$ cycloalkyl.
In some embodiments, $R^6$ is cyclopropyl.
In some embodiments, $R^6$ is halo.
In some embodiments, $R^6$ is chloro.
In some embodiments, $R^6$ is fluoro.
In some embodiments, $R^6$ is cyano.
In some embodiments, $R^6$ is attached to a carbon of an aryl ring B.
In some embodiments, $R^6$ is attached to a carbon of a heteroaryl ring B.
In some embodiments, $R^6$ is attached to a nitrogen of a heteroaryl ring B.

Particular Embodiments Wherein One or Both X are $CR^6$; p=1 or 2:

In some embodiments, at least one $R^6$ is hydrogen, and at least one $R^7$ is $C_1$-$C_6$ alkyl optionally substituted with one or more halo.
In some embodiments, at least one $R^6$ is hydrogen, and at least one $R^7$ is $C_1$-$C_6$ alkyl.
In some embodiments, at least one $R^6$ is hydrogen, and at least one $R^7$ is methyl.
In some embodiments, at least one $R^6$ is hydrogen, and at least one $R^7$ is isopropyl.
In some embodiments, one X is $CR^6$; p=1; $R^6$ is hydrogen; and $R^7$ is isopropyl.
In some embodiments, at least one $R^6$ is hydrogen, and at least one $R^7$ is $C_1$-$C_6$ alkyl substituted with one or more halo.
In some embodiments, at least one $R^6$ is hydrogen, and at least one $R^7$ is trifluoromethyl.
In some embodiments, at least one $R^6$ is hydrogen, and at least one $R^7$ is $C_3$-$C_7$ cycloalkyl.
In some embodiments, at least one $R^6$ is hydrogen and at least one $R^7$ is cyclopropyl.
In some embodiments, one X is $CR^6$; p=1; $R^6$ is hydrogen; and $R^7$ is cyclopropyl.
In some embodiments, at least one $R^6$ is hydrogen, and at least one $R^7$ is halo.
In some embodiments, at least one $R^6$ is hydrogen, and at least one $R^7$ is chloro.
In some embodiments, at least one $R^6$ is hydrogen, and at least one $R^7$ is fluoro.
In some embodiments, one X is $CR^6$; p=1; $R^6$ is hydrogen; and $R^7$ is chloro.
In some embodiments, both X are $CR^6$; p=1; $R^6$ is hydrogen; and $R^7$ is chloro.
In some embodiments, one X is $CR^6$; p=1; $R^6$ is hydrogen; and $R^7$ is fluoro.
In some embodiments, both X are $CR^6$; p=1; $R^6$ is hydrogen; and $R^7$ is fluoro.

In some embodiments, both X are $CR^6$; p=2; $R^6$ is hydrogen; and $R^7$ is fluoro.

In some embodiments, both X are $CR^6$; p=2; $R^6$ is hydrogen; one $R^7$ is fluoro; and the other $R^7$ is cyano.

In some embodiments, both X are $CR^6$; p=3; $R^6$ is hydrogen; two $R^7$ are fluoro; and one $R^7$ is chloro.

In some embodiments, both X are $CR^6$; p=1; $R^6$ is hydrogen; and $R^7$ is fluoro.

In some embodiments, both X are $CR^6$; p=1; one $R^6$ is hydrogen; the other $R^6$ is trifluoromethyl; and $R^7$ is chloro.

In some embodiments, both X are $CR^6$; p=1; one $R^6$ is hydrogen; the other $R^6$ is isopropyl; and $R^7$ is chloro.

In some embodiments, at least one $R^6$ is hydrogen, and at least one $R^7$ is cyano.

In some embodiments, at least one $R^6$ is hydrogen and at least one $R^7$ is cyano.

In some embodiments, one X is $CR^6$; p=1; $R^6$ is hydrogen; and $R^7$ is cyano.

In some embodiments, both X are $CR^6$; p=1; $R^6$ is hydrogen; and $R^7$ is cyano.

In some embodiments, at least one $R^6$ is hydrogen, and at least one $R^7$ is $C_1$-$C_6$ alkoxy optionally substituted with one or more halo.

In some embodiments, at least one $R^6$ is hydrogen, and at least one $R^7$ is $C_1$-$C_6$ alkoxy.

In some embodiments, at least one $R^6$ is hydrogen, and at least one $R^7$ is methoxy.

In some embodiments, one X is $CR^6$; p=1; $R^6$ is hydrogen, and $R^7$ is methoxy.

In some embodiments, both X are $CR^6$; p=1; $R^6$ is hydrogen, and $R^7$ is methoxy.

In some embodiments, at least one $R^6$ is hydrogen, and at least one $R^7$ is $C_1$-$C_6$ alkoxy substituted with one or more halo.

In some embodiments, at least one $R^6$ is hydrogen, and at least one $R^7$ is trifluoromethoxy.

In some embodiments, at least one $R^6$ is hydrogen, and at least one $R^7$ is difluoromethoxy.

In some embodiments, at least one $R^6$ is hydrogen, and at least one $R^7$ is $C_1$-$C_6$ haloalkyl optionally substituted with hydroxy.

In some embodiments, one X is $CR^6$; p=1; $R^6$ is hydrogen, and $R^7$ is trifluoromethyl.

In some embodiments, at least one $R^6$ is hydrogen, and at least one $R^7$ is $C_1$-$C_6$ haloalkoxy.

In some embodiments, one X is $CR^6$; p=1; $R^6$ is hydrogen, and $R^7$ is trifluoromethoxy.

In some embodiments, one X is $CR^6$; p=2; $R^6$ is hydrogen; and $R^7$ is chloro.

In some embodiments, both X are $CR^6$; p=1; $R^7$ is isopropyl; and $R^6$ is hydrogen.

In some embodiments, both X are $CR^6$; p=2; $R^7$ is isopropyl; and $R^6$ is hydrogen.

In some embodiments, both X are $CR^6$; p=1; $R^7$ is ethyl; and $R^6$ is hydrogen.

In some embodiments, one X is $CR^6$; p=2; one $R^7$ is isopropyl; the other $R^7$ is trifluoromethyl; and $R^6$ is hydrogen.

In some embodiments, one X is $CR^6$; p=1; $R^7$ is cyclopropyl; and $R^6$ is hydrogen.

In some embodiments, one X is $CR^6$; p=2; $R^7$ is $C_1$-$C_6$ alkoxy; and $R^6$ is hydrogen.

In some embodiments, at least one $R^6$ is $C_1$-$C_6$ alkyl, and at least one $R^7$ is $C_1$-$C_6$ alkyl optionally substituted with one or more halo.

In some embodiments, at least one $R^6$ is $C_1$-$C_6$ alkyl and at least one $R^7$ is $C_1$-$C_6$ alkyl.

In some embodiments, at least one $R^6$ is isopropyl and at least one $R^7$ is methyl.

In some embodiments, at least one $R^6$ is isopropyl and at least one $R^7$ is isopropyl.

In some embodiments, one X is $CR^6$; p=1; $R^6$ is isopropyl; and $R^7$ is isopropyl.

In some embodiments, at least one $R^6$ is $C_1$-$C_6$ alkyl, and at least one $R^7$ is $C_1$-$C_6$ alkyl substituted with one or more halo.

In some embodiments, at least one $R^6$ is isopropyl and at least one $R^7$ is trifluoromethyl.

In some embodiments, at least one $R^6$ is $C_1$-$C_6$ alkyl, and at least one $R^7$ is $C_3$-$C_7$ cycloalkyl.

In some embodiments, at least one $R^6$ is isopropyl and at least one $R^7$ is cyclopropyl.

In some embodiments, one X is $CR^6$; p=1; $R^6$ is isopropyl; and $R^7$ is cyclopropyl.

In some embodiments, at least one $R^6$ is $C_1$-$C_6$ alkyl, and at least one $R^7$ is halo.

In some embodiments, at least one $R^6$ is isopropyl and at least one $R^7$ is halo.

In some embodiments, at least one $R^6$ is isopropyl and at least one $R^7$ is chloro.

In some embodiments, at least one $R^6$ is isopropyl and at least one $R^7$ is fluoro.

In some embodiments, one X is $CR^6$; p=1; $R^6$ is isopropyl; and $R^7$ is chloro.

In some embodiments, both X are $CR^6$; p=1; $R^6$ is isopropyl; and $R^7$ is chloro.

In some embodiments, one X is $CR^6$; p=1; $R^6$ is isopropyl; and $R^7$ is fluoro.

In some embodiments, both X are $CR^6$; p=1; $R^6$ is isopropyl; and $R^7$ is fluoro.

In some embodiments, both X are $CR^6$; p=2; $R^6$ is isopropyl; and $R^7$ is fluoro.

In some embodiments, both X are $CR^6$; p=2; $R^6$ is isopropyl; one $R^7$ is fluoro; and the other $R^7$ is cyano.

In some embodiments, both X are $CR^6$; p=3; $R^6$ is isopropyl; two $R^7$ are fluoro; and one $R^7$ is chloro.

In some embodiments, both X are $CR^6$; p=1; $R^6$ is ethyl; and $R^7$ is fluoro.

In some embodiments, both X are $CR^6$; p=1; one $R^6$ is isopropyl; the other $R^6$ is trifluoromethyl; and $R^7$ is chloro.

In some embodiments, at least one $R^6$ is $C_1$-$C_6$ alkyl, and at least one $R^7$ is cyano.

In some embodiments, at least one $R^6$ is isopropyl and at least one $R^7$ is cyano.

In some embodiments, one X is $CR^6$; p=1; $R^6$ is isopropyl; and $R^7$ is cyano.

In some embodiments, both X are $CR^6$; p=1; $R^6$ is isopropyl; and $R^7$ is cyano.

In some embodiments, at least one $R^6$ is $C_3$-$C_7$ cycloalkyl, and at least one $R^7$ is $C_3$-$C_7$ cycloalkyl.

In some embodiments, at least one $R^6$ is cyclopropyl, and at least one $R^7$ is cyclopropyl.

In some embodiments, at least one $R^6$ is $C_3$-$C_7$ cycloalkyl, and at least one $R^7$ is halo.

In some embodiments, at least one $R^6$ is cyclopropyl and at least one $R^7$ is halo.

In some embodiments, at least one $R^6$ is cyclopropyl and at least one $R^7$ is chloro.

In some embodiments, at least one $R^6$ is cyclopropyl and at least one $R^7$ is fluoro.

In some embodiments, one X is $CR^6$; p=1; $R^6$ is cyclopropyl; and $R^7$ is chloro.

In some embodiments, one X is $CR^6$; p=1; $R^6$ is cyclopropyl; and $R^7$ is fluoro.

In some embodiments, at least one $R^6$ is $C_1$-$C_6$ alkyl, and at least one $R^7$ is $C_1$-$C_6$ alkoxy optionally substituted with one or more halo.

In some embodiments, at least one $R^6$ is isopropyl, and at least one $R^7$ is $C_1$-$C_6$ alkoxy.

In some embodiments, at least one $R^6$ is isopropyl, and at least one $R^7$ is methoxy.

In some embodiments, one X is $CR^6$; p=1; $R^6$ is isopropyl, and $R^7$ is methoxy.

In some embodiments, both X are $CR^6$; p=1; $R^6$ is isopropyl, and $R^7$ is methoxy.

In some embodiments, at least one $R^6$ is $C_1$-$C_6$ alkyl, and at least one $R^7$ is $C_1$-$C_6$ alkoxy substituted with one or more halo.

In some embodiments, at least one $R^6$ is isopropyl, and at least one $R^7$ is trifluoromethoxy.

In some embodiments, at least one $R^6$ is isopropyl, and at least one $R^7$ is difluoromethoxy.

In some embodiments, at least one $R^6$ is halo, and at least one $R^7$ is $C_1$-$C_6$ haloalkyl optionally substituted with hydroxy.

In some embodiments, one X is $CR^6$; p=1; $R^6$ is chloro, and $R^7$ is trifluoromethyl.

In some embodiments, at least one $R^6$ is halo, and at least one $R^7$ is $C_1$-$C_6$ haloalkoxy.

In some embodiments, at least one $R^6$ is chloro, and at least one $R^7$ is trifluoromethoxy.

In some embodiments, one X is $CR^6$; p=1; $R^6$ is chloro, and $R^7$ is trifluoromethoxy.

In some embodiments, at least one $R^6$ is $C_1$-$C_6$ alkoxy; and at least one $R^7$ is halo.

In some embodiments, one X is $CR^6$; p=2; $R^6$ is $C_1$-$C_6$ alkoxy; and $R^7$ is chloro.

In some embodiments, at least one $R^7$ is $C_1$-$C_6$ alkyl, and at least one $R^6$ is $C_1$-$C_6$ alkyl optionally substituted with one or more halo.

In some embodiments, at least one $R^7$ is isopropyl and at least one $R^6$ is methyl.

In some embodiments, at least one $R^7$ is $C_1$-$C_6$ alkyl, and at least one $R^6$ is $C_1$-$C_6$ alkyl substituted with one or more halo.

In some embodiments, at least one $R^7$ is isopropyl and at least one $R^6$ is trifluoromethyl.

In some embodiments, at least one $R^7$ is $C_1$-$C_6$ alkyl, and at least one $R^6$ is $C_3$-$C_7$ cycloalkyl.

In some embodiments, at least one $R^7$ is isopropyl and at least one $R^6$ is cyclopropyl.

In some embodiments, one X is $CR^6$; p=1; $R^7$ is isopropyl; and $R^6$ is cyclopropyl.

In some embodiments, at least one $R^7$ is $C_1$-$C_6$ alkyl, and at least one $R^6$ is halo.

In some embodiments, at least one $R^7$ is isopropyl and at least one $R^6$ is halo.

In some embodiments, at least one $R^7$ is isopropyl and at least one $R^6$ is chloro.

In some embodiments, at least one $R^7$ is isopropyl and at least one $R^6$ is fluoro.

In some embodiments, one X is $CR^6$; p=1; $R^7$ is isopropyl; and $R^6$ is chloro.

In some embodiments, both X are $CR^6$; p=1; $R^7$ is isopropyl; and $R^6$ is chloro.

In some embodiments, one X is $CR^6$; p=1; $R^7$ is isopropyl; and $R^6$ is fluoro.

In some embodiments, both X are $CR^6$; p=1; $R^7$ is isopropyl; and $R^6$ is fluoro.

In some embodiments, both X are $CR^6$; p=2; $R^7$ is isopropyl; and $R^6$ is fluoro.

In some embodiments, both X are $CR^6$; p=2; $R^7$ is isopropyl; one $R^6$ is fluoro; and the other $R^6$ is cyano.

In some embodiments, both X are $CR^6$; p=1; $R^7$ is ethyl; and $R^6$ is fluoro.

In some embodiments, one X is $CR^6$; p=2; one $R^7$ is isopropyl; the other $R^7$ is trifluoromethyl; and $R^6$ is chloro.

In some embodiments, at least one $R^7$ is $C_1$-$C_6$ alkyl, and at least one $R^6$ is cyano.

In some embodiments, at least one $R^7$ is isopropyl and at least one $R^6$ is cyano.

In some embodiments, one X is $CR^6$; p=1; $R^7$ is isopropyl; and $R^6$ is cyano.

In some embodiments, both X are $CR^6$; p=1; $R^7$ is isopropyl; and $R^6$ is cyano.

In some embodiments, at least one $R^7$ is $C_3$-$C_7$ cycloalkyl, and at least one $R^6$ is $C_3$-$C_7$ cycloalkyl.

In some embodiments, at least one $R^7$ is cyclopropyl, and at least one $R^6$ is cyclopropyl.

In some embodiments, at least one $R^7$ is $C_3$-$C_7$ cycloalkyl, and at least one $R^6$ is halo.

In some embodiments, at least one $R^7$ is cyclopropyl and at least one $R^6$ is halo.

In some embodiments, at least one $R^7$ is cyclopropyl and at least one $R^6$ is chloro.

In some embodiments, at least one $R^7$ is cyclopropyl and at least one $R^6$ is fluoro.

In some embodiments, one X is $CR^6$; p=1; $R^7$ is cyclopropyl; and $R^6$ is chloro.

In some embodiments, one X is $CR^6$; p=1; $R^7$ is cyclopropyl; and $R^6$ is fluoro.

In some embodiments, at least one $R^7$ is $C_1$-$C_6$ alkyl, and at least one $R^6$ is $C_1$-$C_6$ alkoxy optionally substituted with one or more halo.

In some embodiments, at least one $R^7$ is isopropyl, and at least one $R^6$ is $C_1$-$C_6$ alkoxy.

In some embodiments, at least one $R^7$ is isopropyl, and at least one $R^6$ is methoxy.

In some embodiments, one X is $CR^6$; p=1; $R^7$ is isopropyl, and $R^6$ is methoxy.

In some embodiments, both X are $CR^6$; p=1; $R^7$ is isopropyl, and $R^6$ is methoxy.

In some embodiments, at least one $R^7$ is $C_1$-$C_6$ alkyl, and at least one $R^6$ is $C_1$-$C_6$ alkoxy substituted with one or more halo.

In some embodiments, at least one $R^7$ is isopropyl, and at least one $R^6$ is trifluoromethoxy.

In some embodiments, at least one $R^7$ is halo, and at least one $R^6$ is $C_1$-$C_6$ haloalkyl optionally substituted with hydroxy.

In some embodiments, one X is $CR^6$; p=1; $R^7$ is chloro, and $R^6$ is trifluoromethyl.

In some embodiments, at least one $R^7$ is halo, and at least one $R^6$ is $C_1$-$C_6$ haloalkoxy.

In some embodiments, at least one $R^7$ is chloro, and at least one $R^6$ is trifluoromethoxy.

In some embodiments, one X is $CR^6$; p=1; $R^7$ is chloro, and $R^6$ is trifluoromethoxy.

In some embodiments, at least one $R^7$ is $C_1$-$C_6$ alkoxy; and at least one $R^6$ is halo.

In some embodiments, one X is $CR^6$; p=2; $R^7$ is $C_1$-$C_6$ alkoxy; and $R^6$ is chloro.

In some embodiments, one $R^6$ and one $R^7$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_5$ aliphatic carbocyclic ring.

In some embodiments, $R^6$ and $R^7$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_6$ aliphatic carbocyclic ring.

In some embodiments, $R^6$ and $R^7$ are on adjacent atoms, and taken together with the atoms connecting them, form a $C_6$ aromatic carbocyclic ring.

In some embodiments, $R^6$ and $R^7$ are on adjacent atoms, and taken together with the atoms connecting them, form a 5-membered heterocyclic ring containing 1 or 2 heteroatoms and/or heteroatomic groups independently selected from O, N, NH, $NR^{13}$, S, S(O), and $S(O)_2$, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 5-membered aliphatic heterocyclic ring containing 1 or 2 heteroatoms and/or heteroatomic groups independently selected from O, N, NH, $NR^{13}$, S, S(O), and $S(O)_2$.

In some embodiments, $R^6$ and $R^7$ are on adjacent atoms, and taken together with the atoms connecting them, form a 5-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 5-membered heteroaromatic ring containing 1 or 2 heteroatoms and/or heteroatomic groups independently selected from O, N, NH, $NR^{13}$, S, S(O), and $S(O)_2$.

In some embodiments, $R^6$ and $R^7$ are on adjacent atoms, and taken together with the atoms connecting them, form a 5-membered heteroaromatic ring containing 1 or 2 heteroatoms independently selected from O, N, and S.

In some embodiments, $R^6$ and $R^7$ are on adjacent atoms, and taken together with the atoms connecting them, form a 6-membered heterocyclic ring containing 1 or 2 heteroatoms and/or heteroatomic groups independently selected from O, N, NH, $NR^D$, S, S(O), and $S(O)_2$, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^0$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 6-membered aliphatic heterocyclic ring containing 1 or 2 heteroatoms and/or heteroatomic groups independently selected from O, N, NH, $NR^{13}$, S, S(O), and $S(O)_2$.

In some embodiments, $R^6$ and $R^7$ are on adjacent atoms, and taken together with the atoms connecting them, form a 6-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 6-membered heteroaromatic ring containing 1 or 2 heteroatoms and/or heteroatomic groups independently selected from O, N, NH, $NR^{13}$, S, S(O), and $S(O)_2$.

In some embodiments, $R^6$ and $R^7$ are on adjacent atoms, and taken together with the atoms connecting them, form a 6-membered heteroaromatic ring containing 1 or 2 heteroatoms independently selected from O, N, and S.

In some embodiments, one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms and/or heteroatomic groups independently selected from O, N, NH, $NR^{13}$, S, S(O), and $S(O)_2$, In some embodiments, one $R^6$ and one $R^7$ are on adjacent atoms, and taken together with the atoms connecting them, form a $C_5$-$C_8$ carbocyclic ring or a 5-to-8-membered heterocyclic ring containing 1 or 2 heteroatoms independently selected from O, N, and S, wherein the ring is fused to the B ring at the 2- and 3-positions relative to the bond connecting the B ring to the $C(R^4R^5)$ group.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a $C_6$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a $C_6$ aliphatic carbocyclic ring.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a $C_6$ aromatic carbocyclic ring.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 5-membered heterocyclic ring containing 1 or 2 heteroatoms and/or heteroatomic groups independently selected from O, N, NH, $NR^{13}$, S, S(O), and $S(O)_2$, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^1R^9$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 5-membered aliphatic heterocyclic ring containing 1 or 2 heteroatoms and/or heteroatomic groups independently selected from O, N, NH, $NR^{13}$, S, S(O), and $S(O)_2$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 5-membered aliphatic heterocyclic ring containing 1 or 2 heteroatoms independently selected from O, N, and S.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 5-membered heteroaromatic ring containing 1 or 2 heteroatoms and/or heteroatomic groups independently selected from O, N, NH, $NR^{13}$, S, S(O), and $S(O)_2$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 5-membered heteroaromatic ring containing 1 or 2 heteroatoms independently selected from O, N, and S.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 6-membered heterocyclic ring containing 1 or 2 heteroatoms and/or heteroatomic groups independently selected from O, N, NH, $NR^{13}$, S, S(O), and $S(O)_2$, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 6-membered aliphatic heterocyclic ring containing 1 or 2 heteroatoms and/or heteroatomic groups independently selected from O, N, NH $NR^{13}$S, S(O), and $S(O)_2$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 6-membered aliphatic heterocyclic ring containing 1 or 2 heteroatoms independently selected from O, N, and S.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 6-membered heteroaromatic ring containing 1 or 2 heteroatoms and/or heteroatomic groups independently selected from O, N, NH, $NR^{13}$, S, S(O), and $S(O)_2$.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them form a 6-membered heteroaromatic ring containing 1 or 2 heteroatoms independently selected from O, N, and S.

In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them independently form a $C_5$-$C_5$ carbocyclic ring or a 5-to-8-membered heterocyclic ring containing 1 or 2 heteroatoms and/or heteroatomic groups independently selected from O, N, NH, $NR^{13}$, S, S(O), and $S(O)_2$, In some embodiments, both X are $CR^6$; p=2 or 3; and two pairs, each of one $R^6$ and one $R^7$, are on adjacent atoms, and each pair of one $R^6$ and one $R^7$ taken together with the atoms connecting them independently form a $C_5$-$C_8$ carbocyclic ring or a 5-to-8-membered heterocyclic ring containing 1 or 2 heteroatoms independently selected from O, N, and S,
wherein one of the two rings is fused to the B ring at the 2- and 3-positions relative to the bond connecting the B ring to the $C(R^4R^5)$ group, and the other of the two rings is fused to the B ring at the 5- and 6-positions relative to the bond connecting the B ring to the $C(R^4R^5)$ group.

In some embodiments, both X are $CR^6$; p=2; and two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, both X are $CR^6$; p=2; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is halo (e.g., $C_1$ or F).

In some embodiments, both X are $CR^6$; p=2; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is CN.

Particular embodiments wherein one or both X are $CR^6$; p=1 or 2:

In some embodiments, at least one $R^7$ is $C_1$-$C_6$ alkyl optionally substituted with one or more halo.

In some embodiments, at least one $R^7$ is $C_1$-$C_6$ alkyl.

In some embodiments, at least one $R^7$ is methyl.

In some embodiments, at least one $R^7$ is isopropyl.

In some embodiments, p=1; and $R^7$ is isopropyl.

In some embodiments, at least one $R^7$ is $C_1$-$C_6$ alkyl substituted with one or more halo.

In some embodiments, at least one $R^7$ is trifluoromethyl.

In some embodiments, at least one $R^7$ is $C_3$-$C_7$ cycloalkyl.

In some embodiments, at least one $R^7$ is cyclopropyl.

In some embodiments, p=1; and $R^7$ is cyclopropyl.

In some embodiments, at least one $R^7$ is halo.

In some embodiments, at least one $R^7$ is chloro.

In some embodiments, at least one $R^7$ is fluoro.

In some embodiments, p=1; and $R^7$ is chloro.

In some embodiments, p=1; and $R^7$ is fluoro.

In some embodiments, p=2; one $R^7$ is fluoro; and the other $R^7$ is cyano.

In some embodiments, at least one $R^7$ is cyano.

In some embodiments, p=1; and $R^7$ is cyano.

In some embodiments, at least one $R^7$ is $C_1$-$C_6$ alkoxy optionally substituted with one or more halo.

In some embodiments, at least one $R^7$ is $C_1$-$C_6$ alkoxy.

In some embodiments, at least one $R^7$ is methoxy.

In some embodiments, p=1; and $R^7$ is methoxy.

In some embodiments, at least one $R^7$ is trifluoromethoxy.

In some embodiments, at least one $R^7$ is difluoromethoxy.

In some embodiments, at least one $R^7$ is $C_1$-$C_6$ haloalkyl optionally substituted with hydroxy.

In some embodiments, p=1; and $R^7$ is trifluoromethyl.

In some embodiments, at least one $R^7$ is $C_1$-$C_6$ haloalkoxy.

In some embodiments, p=1; and $R^7$ is trifluoromethoxy.

In some embodiments, p=2; and $R^7$ is chloro.

In some embodiments, p=2; and $R^7$ is isopropyl.

In some embodiments, p=1; and $R^7$ is ethyl.

In some embodiments, p=2; one $R^7$ is isopropyl; and the other $R^7$ is trifluoromethyl.

In some embodiments, p=1; and $R^7$ is cyclopropyl.

In some embodiments, p=2; and $R^7$ is $C_1$-$C_6$ alkoxy.

In some embodiments, p=2; and $R^7$ is fluoro.

Particular embodiments wherein one or both X are N; p=1 or 2: In some embodiments, at least one $R^7$ is $C_1$-$C_6$ alkyl optionally substituted with one or more halo.

In some embodiments, at least one $R^7$ is $C_1$-$C_6$ alkyl.

In some embodiments, at least one $R^7$ is methyl.

In some embodiments, at least one $R^7$ is isopropyl.

In some embodiments, p=1; and $R^7$ is isopropyl.

In some embodiments, at least one $R^7$ is $C_1$-$C_6$ alkyl substituted with one or more halo.

In some embodiments, at least one $R^7$ is trifluoromethyl.

In some embodiments, at least one $R^7$ is $C_3$-$C_7$ cycloalkyl.

In some embodiments, at least one $R^7$ is cyclopropyl.

In some embodiments, p=1; and $R^7$ is cyclopropyl.

In some embodiments, at least one $R^7$ is halo.

In some embodiments, at least one $R^7$ is chloro.

In some embodiments, at least one $R^7$ is fluoro.

In some embodiments, p=1; and $R^7$ is chloro.

In some embodiments, p=1; and $R^7$ is fluoro.

In some embodiments, p=2; one $R^7$ is fluoro; and the other $R^7$ is cyano.

In some embodiments, at least one $R^7$ is cyano.

In some embodiments, p=1; and $R^7$ is cyano.

In some embodiments, at least one $R^7$ is $C_1$-$C_6$ alkoxy optionally substituted with one or more halo.

In some embodiments, at least one $R^7$ is $C_1$-$C_6$ alkoxy.

In some embodiments, at least one $R^7$ is methoxy.

In some embodiments, p=1; and $R^7$ is methoxy.

In some embodiments, at least one $R^7$ is trifluoromethoxy.

In some embodiments, at least one $R^7$ is difluoromethoxy.

In some embodiments, at least one $R^7$ is $C_1$-$C_6$ haloalkyl optionally substituted with hydroxy.

In some embodiments, p=1; and $R^7$ is trifluoromethyl.

In some embodiments, at least one $R^7$ is $C_1$-$C_6$ haloalkoxy.

In some embodiments, p=1; and $R^7$ is trifluoromethoxy.

In some embodiments, p=2; and $R^7$ is chloro.

In some embodiments, p=2; and $R^7$ is isopropyl.

In some embodiments, p=1; and $R^7$ is ethyl.

In some embodiments, p=2; one $R^7$ is isopropyl; and the other $R^7$ is trifluoromethyl.

In some embodiments, p=1; and $R^7$ is cyclopropyl.

In some embodiments, p=2; and $R^7$ is $C_1$-$C_6$ alkoxy.

In some embodiments, p=2; and $R^7$ is fluoro.

The Group Y

In some embodiments, Y is selected from a bond, O, S, $SO_2$, $NR^{15}$, or $CR^{16}R^{17}$.

In some embodiments, Y is selected from a bond, $-(Y^1)_o-(C_1$-$C_3$ alkyl$)_o$-, and $-(CR^{16}R^{17})_o-(Y^1)_o-(CR^{16}R^{17})_o-$.

In some embodiments, Y is a bond.

In some embodiments, Y is O.

In some embodiments, Y is S.

In some embodiments, Y is $SO_2$.

In some embodiments, Y is $NR^{15}$.

In some embodiments, Y is NH.

In some embodiments, Y is $CR^{16}R^{17}$.

In some embodiments, Y is $CH_2$.

In some embodiments, Y is $-CH(CH_3)-$.

In some embodiments, Y is selected from $-(Y^1)_o-(C_1$-$C_3$ alkyl$)_o$-, and $-(CR^{16}R^{17})_o-(Y^1)_o-(CR^{16}R^{17})_o-$.

In some embodiments, Y is $-(Y^1)_o-(C_1$-$C_3$ alkyl$)_o$-.

In certain embodiments when Y is $-(Y^1)_o-(C_1$-$C_3$ alkyl$)_o$-, Y is $-Y^1$.

In certain embodiments when Y is $-(Y^1)_o-(C_1$-$C_3$ alkyl$)_o$-, Y is $-(C_1$-$C_3$ alkyl)-. As a non-limiting example, Y is $CH_2CH_2$.

In certain embodiments when Y is $-(Y^1)_o-(C_1$-$C_3$ alkyl$)_o$-, Y is $-(Y^1)-(C_1$-$C_3$ alkyl)-.

In some embodiments, Y is $C_{2-3}$ alkynylene.

In some embodiments, Y is $C_2$ alkynylene.

In some embodiments, Y is $-(CR^{16}R^{17})_o-(Y^1)_o-(CR^{16}R^{17})_o-$.

The group $Y^1$

In some embodiments, $Y^1$ is selected from O, S, $SO_2$, $NR^{15}$, and C(O).

In some embodiments, $Y^1$ is selected from O, S, $SO_2$, and $NR^{15}$.

In some embodiments, $Y^1$ is selected from $CR^{16}OH$ and $CR^{16}NR^B$.

In certain embodiments of the foregoing, $Y^1$ is $CR^{16}OH$ (e.g., $Y^1$ is CHOH).

In some embodiments, $Y^1$ is O.

In some embodiments, $Y^1$ is S.

In some embodiments, $Y^1$ is $SO_2$.

In some embodiments, $Y^1$ is $NR^{15}$ (e.g., NH).

In some embodiments, $Y^1$ is C(O).

In some embodiments, $Y^1$ is $C(O)NR^{15}$ (e.g., C(O)NH).

The Variable o

In some embodiments, each occurrence of o is selected from 0 and 1, and wherein at least one o in $-(Y^1)_o-(C_1$-$C_3$ alkyl$)_o$- or $-(CR^{16}R^{17})_o-(Y^1)_o-(CR^{16}R^{17})_o-$ is 1;

In some embodiments (where Y is $-(Y^1)_o-(C_1$-$C_3$ alkyl$)_o$-), one occurrence of o is 0 and the other occurrence of o is 1.

In some embodiments (where Y is $-(Y^1)_o-(C_1$-$C_3$ alkyl$)_o$-), one occurrence of o is 1 and the other occurrence of o is 1. In some embodiments (where Y is $-(CR^{16}R^{17})_o-(Y^1)_o-(CR^{16}R^{17})_o-$), one occurrence of o is 1 and the remaining occurrences of o are 0.

In some embodiments (where Y is $-(CR^{16}R^{17})_o-(Y^1)_o-(CR^{16}R^{17})_o-$), two occurrences of o are 1 and the other occurrence of o is 0.

In some embodiments (where Y is $-(CR^{16}R^{17})_o-(Y^1)_o-(CR^{16}R^{17})_o-$), each occurrence of o is 1.

The Group Z

In some embodiments, Z is selected from a 5-10-membered monocyclic or bicyclic heteroaryl, a 5-10-membered monocyclic or bicyclic heterocyclic ring, a 5-10-membered monocyclic or bicyclic heterocycloalkyl, a $C_6$-$C_{10}$ monocyclic or bicyclic aryl, a $C_3$-$C_{10}$ monocyclic or bicyclic cycloalkyl, a $C_2$-$C_6$ alkenyl, and a $C_2$-$C_6$ alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_3$-$C_{10}$ cycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, or wherein Z is optionally fused to a five-to-seven-membered carbocyclic ring or heterocyclic ring containing one or two heteroatoms independently selected from oxygen, sulfur and nitrogen.

In some embodiments, Z is selected from a 5-10-membered monocyclic or bicyclic heteroaryl, a 5-10-membered monocyclic or bicyclic heterocyclic ring, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_3$-$C_{10}$ cycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, or wherein Z is optionally fused to a five-to-seven-membered carbocyclic ring or heterocyclic ring containing one or two heteroatoms independently selected from oxygen, sulfur and nitrogen.

In some embodiments, Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_3$-$C_{10}$ monocyclic or bicyclic cycloalkyl, a $C_2$-$C_6$ alkenyl, and a $C_2$-$C_6$ alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In some embodiments, Z is selected from a 5-10-membered monocyclic or bicyclic heteroaryl, a 5-10-membered monocyclic or bicyclic heterocycloalkyl, a $C_6$-$C_{10}$ monocyclic or bicyclic aryl, a $C_6$-$C_{10}$ monocyclic or bicyclic cycloalkyl, and a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring containing one or two heteroatoms independently selected from oxygen, sulfur and nitrogen.

In some embodiments, Z is selected from a 5-10-membered monocyclic or bicyclic heteroaryl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, CN, halo, $NR^8R^9$, $COOC_1$-$C_6$ alkyl, C(O)OH, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In some embodiments, Z is 5-10-membered monocyclic or bicyclic heteroaryl, wherein Z is optionally substituted with one or more substituents independently selected from $C_1$-$C_6$ alkyl, hydroxy, $C_1$-$C_6$ haloalkyl, $C_1$-$C_6$ haloalkoxy, oxo, C(O)OH, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, $C_3$-$C_{10}$ cycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is selected from a 5-10-membered monocyclic or bicyclic heteroaryl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In some embodiments, Z is 5-10-membered monocyclic or bicyclic heteroaryl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is 5-10-membered monocyclic or bicyclic heteroaryl, wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is selected from a 5-10-membered monocyclic or bicyclic heterocycloalkyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^1R^9$, $COOC_1$-$C_6$ alkyl, C(O)OH, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$.

In some embodiments, Z is selected from a 5-10-membered monocyclic or bicyclic heterocycloalkyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$.

In some embodiments, Z is a 5-10-membered monocyclic or bicyclic heterocycloalkyl, wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is a 5-10-membered monocyclic or bicyclic heterocycloalkyl, wherein Z is optionally substituted with one or more substituents independently selected from $C_1$-$C_6$ alkyl, hydroxy, $C_1$-$C_6$ haloalkyl, $C_1$-$C_6$ haloalkoxy, oxo, C(O)OH, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, $C_3$-$C_{10}$ cycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is 3,4-dihydropyrrole, tetrahydropyran, pyrrolidine, or tetrahydrofuran, wherein Z is optionally substituted with $C_1$-$C_6$ alkyl, hydroxy, $C_1$-$C_6$ haloalkyl, $C_1$-$C_6$ haloalkoxy, oxo, C(O)OH, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, $C_3$-$C_{10}$ cycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is chromanyl, isoindoline, isochromanyl, 1,2,3,6-tetrahydropyridyl, dihydroisobenzofuran, or methylenedioxyphenyl, wherein Z is optionally substituted with $C_1$-$C_6$ alkyl, hydroxy, $C_1$-$C_6$ haloalkyl, $C_1$-$C_6$ haloalkoxy, oxo, C(O)OH, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is selected from a $C_6$-$C_{10}$ monocyclic or bicyclic aryl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, CN, halo, $NR^8R^9$, $COOC_1$-$C_6$ alkyl, C(O)OH, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In some embodiments, Z is selected from a $C_6$-$C_{10}$ monocyclic or bicyclic aryl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^1R^9$, $COOC_1$-$C_6$ alkyl, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen, or wherein Z is optionally fused to a five-to-seven-membered carbocyclic ring or heterocyclic ring containing one or two heteroatoms independently selected from oxygen, sulfur and nitrogen.

In some embodiments, Z is a $C_6$-$C_{10}$ monocyclic or bicyclic aryl, wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is phenyl, naphthyl, or methylenedioxyphenyl, wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is dihydroindene or 1,2,3,4-tetrahydronaphthalene, wherein Z is optionally substituted with $C_1$-$C_6$ alkyl, hydroxy, $C_1$-$C_6$ haloalkyl, $C_1$-$C_6$ haloalkoxy, oxo, C(O)OH, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, $C_3$-$C_{10}$ cycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, and $C_6$-$C_{10}$ aryl.

In some embodiments, Z is selected from a $C_3$-$C_{11}$ monocyclic or bicyclic cycloalkyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In some embodiments, Z is selected from a $C_6$-$C_{10}$ monocyclic or bicyclic cycloalkyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In some embodiments, Z is selected from a $C_6$-$C_{10}$ monocyclic or bicyclic cycloalkyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, 3-to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In some embodiments, Z is a $C_6$-$C_{10}$ monocyclic or bicyclic cycloalkyl, wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is cycloalkenyl, wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is a 5-10-membered monocyclic or bicyclic heterocyclic ring wherein Z is optionally substituted with one or more substituents independently selected from $C_1$-$C_6$ alkyl, $C_1$-$C_6$ haloalkyl $C_1$-$C_6$ alkoxy, $C_1$-$C_6$ haloalkoxy, $C_6$-$C_{10}$ aryloxy, oxo, CN, halo, $COOC_1$-$C_6$ alkyl, C(O)OH, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is a 5-10-membered monocyclic or bicyclic heterocyclic ring wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is selected from a $C_2$-$C_6$ alkenyl, wherein Z is optionally substituted with one or more substituents independently selected from $C_1$-$C_6$ alkyl, $C_1$-$C_6$ alkoxy, $C_6$-$C_{10}$ aryloxy, hydroxy, CN, halo, $NR^8R^9$, $COOC_1$-$C_6$ alkyl, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$.

In some embodiments, Z is selected from a $C_2$-$C_6$ alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, $SO_2NR^8R^9$, $NR^{11}SO_2NR^{11}R^{12}$, $NR^{11}CO_2R^{12}$, $NR^{11}CONR^{11}R^{12}$, $NR^{11}SO_2R^{12}$, 3- to 7-membered heterocycloalkyl, $C_3$-$C_{10}$ cycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is selected from a $C_2$-$C_6$ (e.g., $C_2$-$C_3$) alkynyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, and $CONR^8R^9$, and wherein the $C_1$-$C_6$ alkyl or $C_1$-$C_6$ alkoxy that Z is substituted with is optionally substituted with one or more hydroxyl or $NR^8R^9$.

In some embodiments, Z is selected from pyrazolyl, thiazolyl, pyridinyl, pyrimidinyl, quinolinyl, isoquinolinyl, benzofuranyl, benzothiophenyl, indazolyl, quinoxalinyl, quinozolinyl, tetrahydropyridinyl, piperidinyl, pyrrolidinyl, piperazinyl, phenyl, naphthyl, methylenedioxyphenyl, cycloalkenyl (e.g., cyclopentenyl or cyclohexenyl), cycloalkyl (e.g., cyclopropyl, cyclopentyl, or cyclohexyl), C≡C, or alkenyl.

In some embodiments, Z is selected from pyrazolyl, pyridinyl, pyrimidinyl, piperidinyl, piperazinyl, phenyl, naphthyl, methylenedioxyphenyl, cycloalkenyl, or alkenyl.

In some embodiments, Z is phenyl, naphthyl, or methylenedioxyphenyl, wherein Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is pyrimidine, benzothiophene, indazole, quinoxaline, quinazoline benzofuran, or isoquinoline, wherein Z is optionally substituted with $C_1$-$C_6$ alkyl, hydroxyl, $C_1$-$C_6$ haloalkyl, $C_1$-$C_6$ haloalkoxy, oxo, C(O)OH, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, $C_3$-$C_{10}$ cycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is chromanyl or methylenedioxyphenyl, wherein Z is optionally substituted with one or more halo.

In certain embodiments of the foregoing, Z is methylenedioxyphenyl which is optionally substituted with one or more halo (e.g., $C_1$ or Br).

In some embodiments, Z is a 5-6 partially saturated monocyclic heterocyclic ring wherein Z is optionally substituted with one or more substituents independently selected from $C_1$-$C_6$ alkyl, $C_1$-$C_6$ haloalkyl $C_1$-$C_6$ alkoxy, $C_1$-$C_6$ haloalkoxy, $C_6$-$C_{10}$ aryloxy, oxo, CN, halo, $COOC_1$-$C_6$ alkyl, C(O)OH, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In certain embodiments of the foregoing, Z is

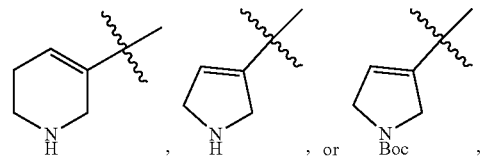 [SMILES: *C1=CCCNC1 ; *C1=CCNC1 ; *C1=CCN(C(=O)OC(C)(C)C)C1]

each of which is optionally substituted (e.g., unsubstituted) as described elsewhere herein.

In some embodiments, Z is a 9-10 partially saturated bicyclic heterocyclic ring wherein Z is optionally substituted with one or more substituents independently selected from $C_1$-$C_6$ alkyl, $C_1$-$C_6$ haloalkyl $C_1$-$C_6$ alkoxy, $C_1$-$C_6$ haloalkoxy, $C_6$-$C_{10}$ aryloxy, oxo, CN, halo, $COOC_1$-$C_6$ alkyl, C(O)OH, S(O$_2$)C$_1$-C$_6$ alkyl, 3- to 7-membered heterocycloalkyl, and CONR$^8$R$^9$, and wherein the C$_1$-C$_6$ alkyl or C$_1$-C$_6$ alkoxy that Z is substituted with is optionally substituted with one or more hydroxyl, NR$^8$R$^9$, or C$_6$-C$_{10}$ aryl.

In certain embodiments of the foregoing, Z is each of which is optionally substituted (e.g., unsubstituted) as described elsewhere herein.

In some embodiments, Z is 5-6-membered monocyclic heteroaryl, wherein Z is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, C$_6$-C$_{10}$ aryloxy, CN, halo, COOC$_1$-C$_6$ alkyl, S(O$_2$)C$_1$-C$_6$ alkyl, 3- to 7-membered heterocycloalkyl, and CONR$^8$R$^9$, and wherein the C$_1$-C$_6$ alkyl or C$_1$-C$_6$ alkoxy that Z is substituted with is optionally substituted with one or more hydroxyl, NR$^8$R$^9$, or C$_6$-C$_{10}$ aryl.

In some embodiments, Z is selected from 3-pyrazolyl, 4-pyrazolyl, 5-pyrazolyl, 3-pyridinyl, 4-pyridinyl, 5-pyrimidinyl, 2-pyrimidinyl, 8-quinolinyl, 5-indolyl, 5-pyrimidin-2-one, 4-thiazolyl, 5-thiazolyl, 4-isoxazolyl, 2-furyl, 5-(1,2,3,6-tetrahydropyridin)-yl, 1-cyclopentenyl, or vinyl.

In some embodiments, Z is pyrazolyl.
In some embodiments, Z is 3-pyrazolyl.
In some embodiments, Z is 4-pyrazolyl.
In some embodiments, Z is 5-pyrazolyl.
In some embodiments, Z is thiazolyl.
In some embodiments, Z is 4-thiazolyl.
In some embodiments, Z is 5-thiazolyl.
In some embodiments, Z is furyl.
In some embodiments, Z is 2-furyl.
In some embodiments, Z is thiophenyl.
In some embodiments, Z is 2-thiophenyl.
In some embodiments, Z is selected from pyrazolyl, pyridinyl, and pyrimidinyl.

In some embodiments, Z is selected from 3-pyrazolyl, 4-pyrazolyl, 5-pyrazolyl, 3-pyridinyl, 4-pyridinyl, 5-pyrimidinyl, 2-pyrimidinyl, 3-pyrazolyl, 4-pyrazolyl, 5-pyrazolyl, 3-pyridinyl, 4-pyridinyl, 5-pyrimidinyl, 2-pyrimidinyl, 8-quinolinyl, 5-indolyl, 5-pyrimidin-2-one, 4-thiazolyl, 5-thiazolyl, 4-isoxazolyl, and 2-furyl.

In some embodiments, Z is 9-10-membered bicyclic heteroaryl, wherein Z is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, C$_6$-C$_{10}$ aryloxy, CN, halo, COOC$_1$-C$_6$ alkyl, S(O$_2$)C$_1$-C$_6$ alkyl, 3- to 7-membered heterocycloalkyl, and CONR$^8$R$^9$, and wherein the C$_1$-C$_6$ alkyl or C$_1$-C$_6$ alkoxy that Z is substituted with is optionally substituted with one or more hydroxyl, NR$^8$R$^9$, or C$_6$-C$_{10}$ aryl.

In some embodiments, Z is selected from isoquinolinyl, quinolinyl, qunioxalinyl, quinozalinyl, indazolyl, benzofuranyl, and benzothiophenyl, each of which is optionally substituted as described elsewhere herein.

In certain embodiments, Z is isoquinolinyl or quinolinyl.
In certain embodiments, Z is quinoxalinyl or quinozalinyl.
In certain embodiments, Z is indazolyl.
In certain embodiments, Z is benzofuranyl or benzothiophenyl.

In some embodiments, Z is selected from a 5-6-membered monocyclic heterocycloalkyl, wherein Z is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, C$_6$-C$_{10}$ aryloxy, hydroxy, oxo, CN, halo, NR$^8$R$^9$, COOC$_1$-C$_6$ alkyl, C(O)OH, S(O$_2$)C$_1$-C$_6$ alkyl, 3- to 7-membered heterocycloalkyl, C$_6$-C$_{10}$ aryl, and CONR$^8$R$^9$, and wherein the C$_1$-C$_6$ alkyl or C$_1$-C$_6$ alkoxy that Z is substituted with is optionally substituted with one or more hydroxyl, C$_6$-C$_{10}$ aryl or NR$^8$R$^9$.

In some embodiments, Z is selected from piperidine (e.g., 5-(1,2,3,6-tetrahydropyridin)-yl), and piperazine.
In some embodiments, Z is tetrahydrofuranyl.
In some embodiments, Z is tetrahydropyranyl.
In some embodiments, Z is selected from phenyl, naphthyl, and methylenedioxyphenyl.

In some embodiments, Z is phenyl, naphthyl, or methylenedioxyphenyl, wherein Z is optionally substituted with one or more substituents independently selected from C$_1$-C$_6$ alkyl, C$_1$-C$_6$ haloalkyl, C$_1$-C$_6$ alkoxy, C$_1$-C$_6$ haloalkoxy, C$_6$-C$_{10}$ aryloxy, hydroxy, oxo, CN, halo, COOC$_1$-C$_6$ alkyl, C(O)OH, S(O$_2$)C$_1$-C$_6$ alkyl, 3- to 7-membered heterocycloalkyl, and CONR$^8$R$^9$, and wherein the C$_1$-C$_6$ alkyl or C$_1$-C$_6$ alkoxy that Z is substituted with is optionally substituted with one or more hydroxyl, NR$^8$R$^9$, or C$_6$-C$_{10}$ aryl.

In some embodiments, Z is phenyl.

In some embodiments, Z is phenyl, naphthyl, or methylenedioxyphenyl, wherein Z is optionally substituted with one or more substituents independently selected from C$_1$-C$_6$ alkyl, C$_1$-C$_6$ alkoxy, C$_6$-C$_{10}$ aryloxy, CN, halo, COOC$_1$-C$_6$ alkyl, S(O$_2$)C$_1$-C$_6$ alkyl, 3- to 7-membered heterocycloalkyl, and CONR$^8$R$^9$, and wherein the C$_1$-C$_6$ alkyl or C$_1$-C$_6$ alkoxy that Z is substituted with is optionally substituted with one or more hydroxyl, NR$^8$R$^9$, or C$_6$-C$_{10}$ aryl.

In some embodiments, Z is phenyl.

In certain embodiments when Z is phenyl, Z is substituted with one or more substituents independently selected from C$_1$-C$_6$ alkyl and halo.

In some embodiments, Z is phenyl which is optionally substituted or fused as described elsewhere herein.

In some embodiments, Z is phenyl optionally substituted with one or more substituents each independently selected from halo, C$_1$-C$_6$ alkyl, C$_1$-C$_6$ alkoxy, CN, C(O)OH, C$_1$-C$_6$haloalkyl, C$_1$-C$_6$ haloalkoxy, and NR$^8$R$^9$.

In certain embodiments, Z is phenyl optionally substituted with one or more independently selected halo.
In certain embodiments, Z is phenyl optionally substituted with one or more independently selected C$_1$-C$_6$ alkyl.
In certain embodiments, Z is phenyl optionally substituted with one or more independently selected C$_1$-C$_6$ alkoxy.
In certain embodiments, Z is phenyl optionally substituted with one or more independently selected CN.
In certain embodiments, Z is phenyl optionally substituted with one or more independently selected C(O)OH.
In certain embodiments, Z is phenyl optionally substituted with one or more independently selected C$_1$-C$_6$ haloalkyl.

In certain embodiments, Z is phenyl optionally substituted with one or more independently selected $C_1$-$C_6$ haloalkoxy.

In certain embodiments, Z is phenyl optionally substituted with one or more independently selected $NR^8R^9$.

In some embodiments, Z is phenyl which is fused to a five-to-seven-membered carbocyclic ring. As non-limiting examples of the foregoing, Z is:

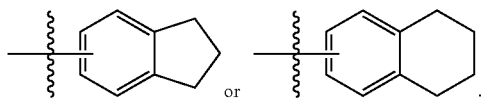

In some embodiments, Z is phenyl which is fused to a five-to-seven-membered heterocyclic ring containing one or two heteroatoms independently selected from oxygen, sulfur and nitrogen.

In some embodiments, Z is naphthyl.

In some embodiments, Z is methylenedioxyphenyl (e.g., methylenedioxyphenyl substituted with 2 halo (e.g., F)).

In some embodiments, Z is cycloalkenyl (e.g., cyclopentenyl, e.g., 1-cyclopentenyl).

In some embodiments, Z is selected from alkenyl (e.g., vinyl).

In some embodiments, Z is a $C_5$-$C_6$ monocyclic cycloalkyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In certain embodiments of the foregoing, Z is a cyclohexyl or cyclopentyl, each of which is optionally substituted as described above.

In some embodiments, Z is a $C_5$-$C_6$ monocyclic cycloalkyl, wherein Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $NR^8R^9$, $COOC_1$-$C_6$ alkyl, C(O)OH, $S(O_2)C_1$-$C_6$ alkyl, 3- to 7-membered heterocycloalkyl, $C_6$-$C_{10}$ aryl, and $CONR^8R^9$, and wherein the $C_1$-$C_6$ alkyl or $C_1$-$C_6$ alkoxy that Z is substituted with is optionally substituted with one or more hydroxyl, $C_6$-$C_{10}$ aryl or $NR^8R^9$, or wherein Z is optionally fused to a five-to-seven-membered carbocyclic ring or heterocyclic ring containing one or two heteroatoms independently selected from oxygen, sulfur and nitrogen.

In certain embodiments of the foregoing, Z is a cyclohexyl or cyclopentyl, each of which is optionally substituted as described above.

In some embodiments, Z is a $C_5$-$C_6$ monocyclic cycloalkyl which is fused to a 6-membered carbocyclic ring.

In certain embodiments of the foregoing, Z is

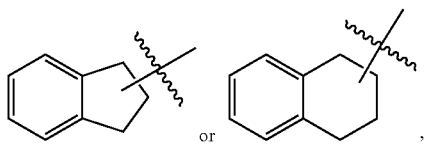

each of which is optionally substituted as described elsewhere herein.

In some embodiments, Z is $C_2$-$C_6$ alkynyl.

In certain embodiments of the foregoing, Z is C≡C.

In some embodiments, Z is optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryloxy, hydroxy, oxo, CN, halo, $COOC_1$-$C_6$ alkyl, C(O)OH, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, In some embodiments, Z is optionally substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl, In some embodiments, Z is substituted with one or more substituents independently selected from $C_1$-$C_6$ alkyl, $C_1$-$C_6$ alkoxy, $C_6$-$C_{10}$ aryloxy, CN, halo, $COOC_1$-$C_6$ alkyl, $S(O_2)C_1$-$C_6$ alkyl, 3- to 7-membered heterocycloalkyl, and $CONR^8R^9$, and wherein the $C_1$-$C_6$ alkyl or $C_1$-$C_6$ alkoxy that Z is substituted with is optionally substituted with one or more hydroxyl, $NR^8R^9$, or $C_6$-$C_{10}$ aryl.

In some embodiments, Z is optionally substituted with one or more $C_1$-$C_6$ alkyl (e.g., methyl or propyl, e.g., 2-propyl) optionally substituted with one or more hydroxyl, $NR^8R^9$ (e.g., dimethylamino), or $C_6$-$C_{10}$ aryl (e.g., phenyl, naphthyl, or methylenedioxyphenyl.

In some embodiments, Z is optionally substituted with one or more $C_1$-$C_6$ alkoxy (e.g., methoxy) optionally substituted with one or more hydroxyl, $NR^8R^9$ (e.g., dimethylamino), or $C_6$-$C_{10}$ aryl (e.g., phenyl, naphthyl, or methylenedioxyphenyl.

In some embodiments, Z is optionally substituted with one or more $C_1$-$C_6$ haloalkyl.

In some embodiments, Z is optionally substituted with one or more $C_1$-$C_6$ haloalkoxy.

In some embodiments, Z is optionally substituted with one or more $C_6$-$C_{10}$ aryloxy (e.g., phenoxy).

In some embodiments, Z is optionally substituted with one or more CN.

In some embodiments, Z is optionally substituted with one or more oxo.

In some embodiments, Z is optionally substituted with one or more halo (e.g., F, Cl).

In some embodiments, Z is optionally substituted with one or more $COOC_1$-$C_6$ alkyl (e.g., $CO_2$t-Bu).

In some embodiments, Z is optionally substituted with one or more C(O)OH.

In some embodiments, Z is optionally substituted with one or more $S(O_2)C_1$-$C_6$ alkyl (e.g., $S(O_2)$methyl).

In some embodiments, Z is optionally substituted with one or more 3- to 7-membered heterocycloalkyl (e.g., morpholinyl).

In some embodiments, Z is optionally substituted with one or more $CONR^8R^9$ (e.g., unsubstituted amido).

In some embodiments, Z is optionally substituted with one or more $C_1$-$C_6$ alkyl (e.g., methyl or propyl, e.g., 2-propyl) optionally substituted with one or more hydroxyl, $NR^8R^9$ (e.g., dimethylamino), or $C_6$-$C_{10}$ aryl (e.g., phenyl, naphthyl, or methylenedioxyphenyl.

In some embodiments, Z is optionally substituted with two or more substituents, wherein at least one of the substituents is a $C_1$-$C_6$ alkoxy (e.g., methoxy) optionally substituted with one or more hydroxyl, $NR^8R^9$ (e.g., dimethylamino), or $C_6$-$C_{10}$ aryl (e.g., phenyl, naphthyl, or methylenedioxyphenyl.

In some embodiments, Z is optionally substituted with two or more substituents, wherein at least one of the substituents is a $C_6$-$C_{10}$ aryloxy (e.g., phenoxy).

In some embodiments, Z is optionally substituted with two or more substituents, wherein at least one of the substituents is a CN.

In some embodiments, Z is optionally substituted with two or more substituents, wherein at least one of the substituents is a halo (e.g., F, Cl).

In some embodiments, Z is optionally substituted with two or more substituents, wherein at least one of the substituents is a $COOC_1$-$C_6$ alkyl (e.g., $CO_2$t-Bu).

In some embodiments, Z is optionally substituted with two or more substituents, wherein at least one of the substituents is a $S(O_2)C_1$-$C_6$ alkyl (e.g., $S(O_2)$methyl).

In some embodiments, Z is optionally substituted with two or more substituents, wherein at least one of the substituents is a 3- to 7-membered heterocycloalkyl (e.g., morpholinyl).

In some embodiments, Z is optionally substituted with two or more substituents, wherein at least one of the substituents is a $CONR^8R^9$ (e.g., unsubstituted amido).

In some embodiments, Z is phenyl optionally substituted with one or more $C_1$-$C_6$ alkyl (e.g., methyl or propyl, e.g., 2-propyl) optionally substituted with one or more hydroxyl, $NR^8R^9$ (e.g., dimethylamino), or $C_6$-$C_{10}$ aryl (e.g., phenyl, naphthyl, or methylenedioxyphenyl).

In some embodiments, Z is phenyl optionally substituted with one or more $C_1$-$C_6$ alkoxy (e.g., methoxy) optionally substituted with one or more hydroxyl, $NR^8R^9$ (e.g., dimethylamino), or $C_6$-$C_{10}$ aryl (e.g., phenyl, naphthyl, or methylenedioxyphenyl).

In some embodiments, Z is phenyl optionally substituted with one or more $C_6$-$C_{10}$ aryloxy (e.g., phenoxy).

In some embodiments, Z is phenyl optionally substituted with one or more CN.

In some embodiments, Z is phenyl optionally substituted with one or more halo (e.g., F, Cl). In some embodiments, Z is 3,4-dichlorophenyl.

In some embodiments, Z is phenyl optionally substituted with one or more $COOC_1$-$C_6$ alkyl (e.g., $CO_2$t-Bu).

In some embodiments, Z is phenyl optionally substituted with one or more $S(O_2)C_1$-$C_6$ alkyl (e.g., $S(O_2)$methyl).

In some embodiments, Z is phenyl optionally substituted with one or more 3- to 7-membered heterocycloalkyl (e.g., morpholinyl).

In some embodiments, Z is phenyl optionally substituted with one or more $CONR^1R^9$ (e.g., unsubstituted amido).

In some embodiments, Z is phenyl optionally substituted with one or more $C_1$-$C_6$ alkyl (e.g., methyl or propyl, e.g., 2-propyl) and with one or more halo (e.g., F, Cl).

The Groups $R^4$ and $R^5$

In some embodiments, each of $R^4$ and $R^5$ is independently selected from hydrogen and $C_1$-$C_6$ alkyl.

In some embodiments, $R^4$ is hydrogen.

In some embodiments, $R^5$ is hydrogen.

In some embodiments, each of $R^4$ and $R^1$ is hydrogen.

In some embodiments, $R^4$ is $C_1$-$C_6$ alkyl.

In some embodiments, $R^5$ is $C_1$-$C_6$ alkyl.

In some embodiments, each of $R^4$ and $R^1$ is $C_1$-$C_6$ alkyl.

In some embodiments, $R^4$ is hydrogen and $R^5$ is $C_1$-$C_6$ alkyl.

In some embodiments, $R^4$ is hydrogen and $R^5$ is $C_1$-$C_6$ alkyl, and the carbon bonded to $R^4$ and $R^5$ has ( ) stereochemistry.

In some embodiments, $R^4$ is hydrogen and $R^5$ is $C_1$-$C_6$ alkyl, and the carbon bonded to $R^4$ and $R^5$ has (R) stereochemistry.

The group $R^{10}$ In some embodiments, $R^{10}$ is $C_1$-$C_6$ alkyl.

In some embodiments, $R^{10}$ is methyl.

In some embodiments, $R^{10}$ is ethyl.

The groups $R^8$ and $R^9$

In some embodiments, each of $R^8$ and $R^9$ at each occurrence is independently selected from hydrogen, $C_1$-$C_6$ alkyl, $C_3$-$C_6$ cycloalkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.

In some embodiments, each of RB and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^3$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or RB and $R^9$ taken together with the nitrogen they are attached to form a 3- to 7-membered ring optionally containing one or more heteroatoms in addition to the nitrogen they are attached to.

In some embodiments, each of $R^8$ and $R^9$ at each occurrence is hydrogen,

In some embodiments, each $R^8$ at each occurrence is hydrogen and each $R^9$ at each occurrence is $C_1$-$C_6$ alkyl.

In some embodiments, each RB at each occurrence is hydrogen and each $R^9$ at each occurrence is methyl.

In some embodiments, each $R^8$ at each occurrence is hydrogen and each $R^9$ at each occurrence is ethyl.

In some embodiments, each of $R^8$ and $R^9$ at each occurrence is methyl.

In some embodiments, each of RB and $R^9$ at each occurrence is ethyl.

In some embodiments, each of $R^8$ and $R^9$ at each occurrence is $C_3$-$C_6$ cycloalkyl (e.g., cyclopropyl).

In some embodiments, RB at each occurrence is $C_3$-$C_6$ cycloalkyl (e.g., cyclopropyl); and $R^9$ at each occurrence is hydrogen.

In some embodiments, $R^8$ at each occurrence is $C(O)_2R^{13}$ (e.g., $C(O)_2$tBu); and $R^9$ at each occurrence is hydrogen.

In some embodiments, RB and $R^9$ taken together with the nitrogen they are attached to form a 3-membered ring.

In some embodiments, RB and $R^9$ taken together with the nitrogen they are attached to form a 4-membered ring.

In some embodiments, RB and $R^9$ taken together with the nitrogen they are attached to form a 5-membered ring.

In some embodiments, $R^8$ and $R^9$ taken together with the nitrogen they are attached to form a 6-membered ring optionally containing one or more oxygen atoms in addition to the nitrogen they are attached to.

In some embodiments, $R^8$ and $R^9$ taken together with the nitrogen they are attached to form a 6-membered ring optionally containing one or more nitrogen atoms in addition to the nitrogen they are attached to.

In some embodiments, $R^8$ and $R^9$ taken together with the nitrogen they are attached to form a 7-membered ring.

The Group $R^{13}$

In some embodiments, $R^{13}$ is $C_1$-$C_6$ alkyl optionally substituted with halo, $C_1$-$C_6$ alkoxy, $C_6$-$C_{10}$ aryl, or 5- to 10-membered heteroaryl;

In some embodiments, $R^{13}$ is $C_1$-$C_6$ alkyl substituted with halo, $C_1$-$C_6$ alkoxy, $C_6$-$C_{10}$ aryl, or 5-to 10-membered heteroaryl. In some embodiments, $R^{13}$ is $C_1$-$C_6$ alkyl.

In some embodiments, $R^{13}$ is $C_1$-$C_6$ alkoxy.
In some embodiments, $R^{13}$ is methyl.
In some embodiments, $R^{13}$ is ethyl.
In some embodiments, $R^{13}$ is $C_6$-$C_{10}$ aryl.
In some embodiments, $R^{13}$ is phenyl.
In some embodiments, $R^{13}$ is 5- to 10-membered heteroaryl.

The Groups $R^{11}$ and $R^{12}$

In some embodiments, each of $R^1$ and $R^{12}$ at each occurrence is independently selected from hydrogen and $C_1$-$C_6$ alkyl.

In some embodiments, each of $R^{11}$ and $R^{12}$ at each occurrence is hydrogen, In some embodiments, each $R^{11}$ at each occurrence is hydrogen and each $R^{12}$ at each occurrence is $C_1$-$C_6$ alkyl.

In some embodiments, each $R^{11}$ at each occurrence is hydrogen and each $R^{12}$ at each occurrence is methyl.

In some embodiments, each $R^{11}$ at each occurrence is hydrogen and each $R^{12}$ at each occurrence is ethyl.

In some embodiments, each of $R^{11}$ and $R^{12}$ at each occurrence is methyl.

In some embodiments, each of $R^{11}$ and $R^{12}$ at each occurrence is ethyl.

In some embodiments of the compound of formula AA, A is

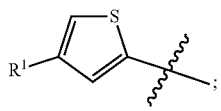

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, A is

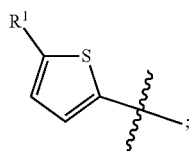

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, A is

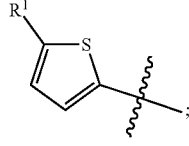

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, A is

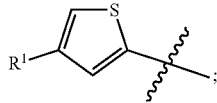

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, A is

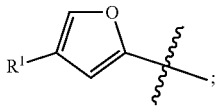

and R$^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, A is

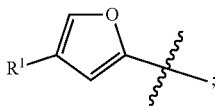

and R$^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, A is

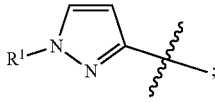

and R$^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, A is

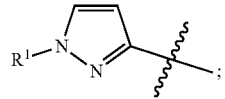

and R$^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, A is

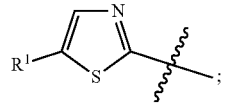

and R$^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, A is

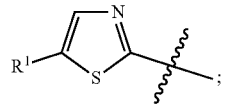

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, A is

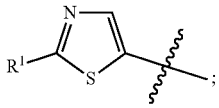

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, A is

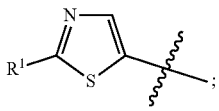

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, A is

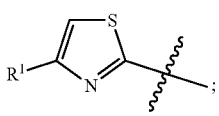

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, A is

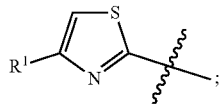

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, A is

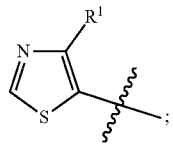

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl);

OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; $CONR^8R^9$; $SF_5$; and $S(O_2)C_1$-$C_6$ alkyl.

In some embodiments of the compound of formula AA, A is

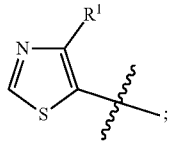

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, A is

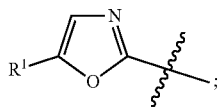

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; $CO$—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; $CONR^8R^9$; $SF_5$; and $S(O_2)C_1$-$C_6$ alkyl.

In some embodiments of the compound of formula AA, A is

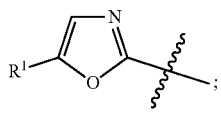

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, A is

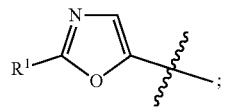

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; $CO$—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; $CONR^8R^9$; $SF_5$; and $S(O_2)C_1$-$C_6$ alkyl.

In some embodiments of the compound of formula AA, A is

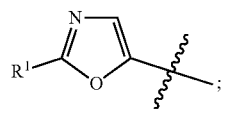

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, A is

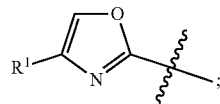

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, A is,

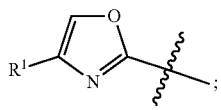

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, A is

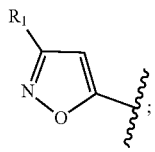

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, A is

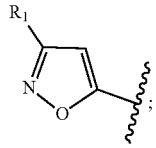

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, A is

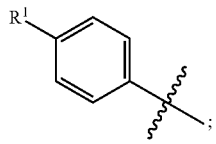

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; S(O₂)C₁-C₆ alkyl; and SO₂NR⁸R⁹.

In some embodiments of the compound of formula AA, A is

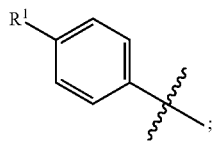

and R$^1$ is selected from:
  1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, A is

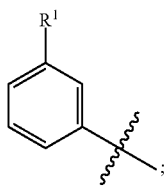

and R$^1$ is selected from:
  C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; S(O$_2$)C$_1$-C$_6$ alkyl; and SO$_2$ NR$^8$R$^9$.

In some embodiments of the compound of formula AA, A is

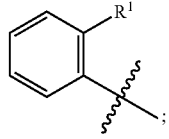

and R$^1$ is selected from:
  C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; S(O$_2$)C$_1$-C$_6$ alkyl; and SO$_2$ NR$^8$R$^9$.

In some embodiments of the compound of formula AA, A is

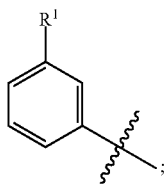

and R$^1$ is selected from:
  1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, A is

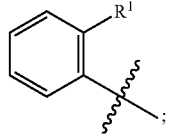

and R$^1$ is selected from:
  1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, A is

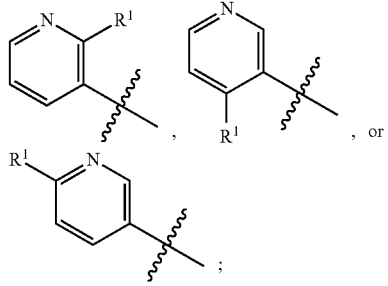

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; S(O₂)C₁-C₆ alkyl; and SO₂ NR⁸R⁹.

In some embodiments of the compound of formula AA, A is

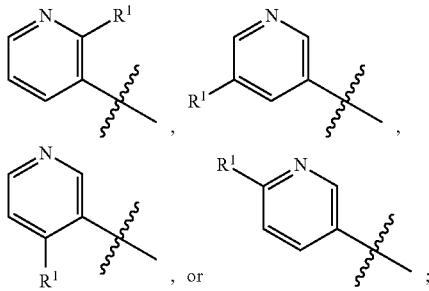

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

A is

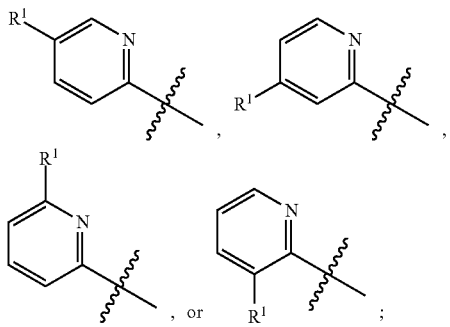

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy;
C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO-5- to 10-membered heteroaryl; CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; S(O₂)C₁-C₆ alkyl; and SO₂ NR⁸R⁹.

In some embodiments of the compound of formula AA, A is

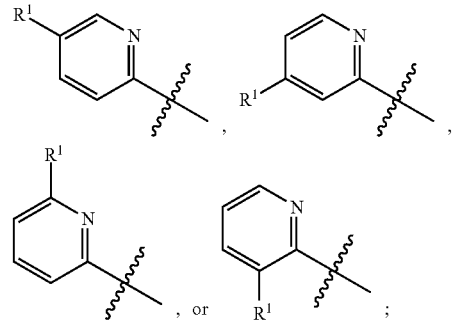

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

A is

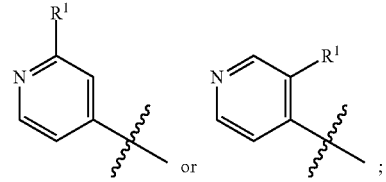

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-

$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)C_1$-$C_6$ alkyl; and $SO_2 NR^8R^9$.

In some embodiments of the compound of formula AA, A is

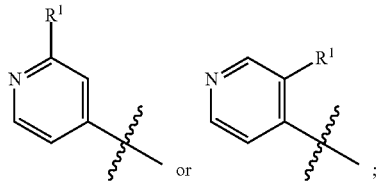

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, A is

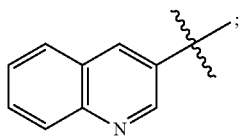 [SMILES: *c1cnc2ccccc2c1]

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)C_1$-$C_6$ alkyl; and $SO_2 NR^8R^9$.

A is

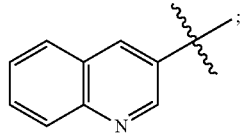 [SMILES: *c1cnc2ccccc2c1]

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

A is

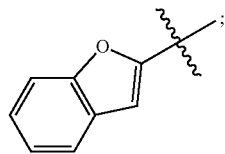 [SMILES: *c1cc2ccccc2o1]

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)C_1$-$C_6$ alkyl; and $SO_2 NR^8R^9$.

A is

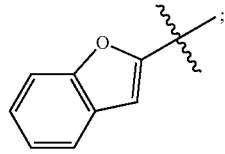 [SMILES: *c1cc2ccccc2o1]

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy- 2-propyl; (dimethylamino)methyl; 1-(dimethylamino)
ethyl; fluoro; chloro; phenyl; pyridyl; pyrazolyl; and
S(O$_2$)CH$_3$.

In some embodiments of the compound of formula AA,
A is

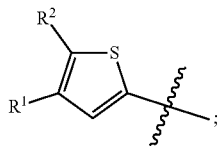

and R$^1$ and R$^2$ are one of the following combinations:
- R$^1$ is C$_1$-C$_6$ alkyl optionally substituted with one or more hydroxy, and R$^2$ is C$_1$-C$_6$ alkyl optionally substituted with one or more hydroxy;
- R$^1$ is C$_1$-C$_6$ alkyl optionally substituted with one or more hydroxy, and R$^2$ is C$_6$-C$_{10}$ aryl;
- R$^1$ is C$_1$-C$_6$ alkyl optionally substituted with one or more hydroxy, and R$^2$ is 5- to 10-membered heteroaryl;
- R$^1$ is C$_1$-C$_6$ alkyl optionally substituted with one or more hydroxy, and R$^2$ is SF$_5$;
- R$^1$ is C$_1$-C$_6$ alkyl optionally substituted with one or more hydroxy, and R$^2$ is S(O$_2$)C$_1$-C$_6$ alkyl;
- R$^1$ is C$_1$-C$_6$ alkyl optionally substituted with one or more hydroxy, and R$^2$ is halo;
- R$^1$ is C$_3$-C$_7$ cycloalkyl optionally substituted with one or more hydroxy, and R$^2$ is C$_1$-C$_6$ alkyl;
- R$^1$ is 3- to 7-membered heterocycloalkyl optionally substituted with one or more hydroxy, and R$^2$ is C$_1$-C$_6$ alkyl;
- R$^1$ is 3- to 7-membered heterocycloalkyl optionally substituted with one or more hydroxy, and R$^2$ is halo;
- R$^1$ is C$_1$-C$_6$ alkyl optionally substituted with one or more oxo, and R$^2$ is methyl;
- R$^1$ is C$_1$-C$_6$ alkyl optionally substituted with one or more C$_1$-C$_6$ alkoxy, and R$^2$ is C$_1$-C$_6$ alkyl;
- R$^1$ is C$_1$-C$_6$ alkyl optionally substituted with one or more NR$^8$R$^9$, and R$^2$ is C$_1$-C$_6$ alkyl;
- R$^1$ is C$_1$-C$_6$ alkyl optionally substituted with one or more NR$^8$R$^9$, and R$^2$ is halo;
- R$^2$ is C$_1$-C$_6$ alkyl optionally substituted with one or more hydroxy, and R$^1$ is C$_6$-C$_{10}$ aryl;
- R$^2$ is C$_1$-C$_6$ alkyl optionally substituted with one or more hydroxy, and R$^1$ is 5- to 10-membered heteroaryl;
- R$^2$ is C$_1$-C$_6$ alkyl optionally substituted with one or more hydroxy, and R$^1$ is SF$_5$.
- R$^2$ is C$_1$-C$_6$ alkyl optionally substituted with one or more hydroxy, and R$^1$ is S(O$_2$)C$_1$-C$_6$ alkyl;
- R$^2$ is C$_1$-C$_6$ alkyl optionally substituted with one or more hydroxy, and R$^1$ is halo;
- R$^2$ is C$_3$-C$_7$ cycloalkyl optionally substituted with one or more hydroxy, and R$^1$ is C$_1$-C$_6$ alkyl;
- R$^2$ is 3- to 7-membered heterocycloalkyl optionally substituted with one or more hydroxy, and R$^1$ is C$_1$-C$_6$ alkyl;
- R$^2$ is 3- to 7-membered heterocycloalkyl optionally substituted with one or more hydroxy, and R$^1$ is halo;
- R$^2$ is C$_1$-C$_6$ alkyl optionally substituted with one or more oxo, and R$^1$ is methyl;
- R$^2$ is C$_1$-C$_6$ alkyl optionally substituted with one or more C$_1$-C$_6$ alkoxy, and R$^1$ is C$_1$-C$_6$ alkyl;
- R$^2$ is C$_1$-C$_6$ alkyl optionally substituted with one or more NR$^8$R$^9$, and R$^1$ is C$_1$-C$_6$ alkyl; or
- R$^2$ is C$_1$-C$_6$ alkyl optionally substituted with one or more NR$^8$R$^9$, and R$^1$ is halo.

In some embodiments of the compound of formula AA, A is

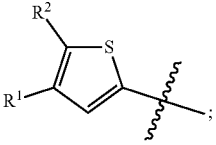

and R$^1$ and R$^2$ are one of the following combinations:
- R$^1$ is 1-hydroxy-2-methylpropan-2-yl, and R$^2$ is methyl;
- R$^1$ is 2-hydroxy-2-propyl and R$^2$ is methyl;
- R$^1$ is 2-hydroxy-2-propyl and R$^2$ is isopropyl;
- R$^1$ is 2-hydroxy-2-propyl and R$^2$ is 2-hydroxy-2-propyl;
- R$^1$ is 2-hydroxy-2-propyl and R$^2$ is 1-hydroxyethyl;
- R$^1$ is hydroxymethyl and R$^2$ is methyl;
- R$^1$ is 1-hydroxyethyl and R$^2$ is methyl;
- R$^1$ is 2-hydroxyethyl and R$^2$ is methyl;
- R$^1$ is 1-hydroxy-2-propyl and R$^2$ is methyl;
- R$^1$ is 2-hydroxy-2-propyl and R$^2$ is phenyl;
- R$^1$ is 2-hydroxy-2-propyl and R$^2$ is pyridyl;
- R$^1$ is 2-hydroxy-2-propyl and R$^2$ is pyrazolyl;
- R$^1$ is 2-hydroxy-2-propyl, and R$^2$ is S(O$_2$)CH$_3$;
- R$^1$ is 2-hydroxy-2-propyl and R$^2$ is chloro;
- R$^1$ is 2-hydroxy-2-propyl and R$^2$ is fluoro;
- R$^1$ is 1-hydroxy-1-cyclopropyl, and R$^2$ is methyl;
- R$^1$ is 1-hydroxy-1-cyclobutyl, and R$^2$ is methyl;
- R$^1$ is 1-hydroxy-1-cyclopentyl, and R$^2$ is methyl;
- R$^1$ is 1-hydroxy-1-cyclohexyl, and R$^2$ is methyl;
- R$^1$ is morpholinyl, and R$^2$ is methyl;
- R$^1$ is 1,3-dioxolan-2-yl, and R$^2$ is methyl;
- R$^1$ is 1,3-dioxolan-2-yl, and R$^2$ is fluoro;
- R$^1$ is 1,3-dioxolan-2-yl, and R$^2$ is chloro;
- R$^1$ is COCH$_3$, and R$^2$ is methyl;
- R$^1$ is 2-methoxy-2-propyl, and R$^2$ is methyl;
- R$^1$ is (dimethylamino)methyl, and R$^2$ is methyl;
- R$^2$ is 1-hydroxy-2-methylpropan-2-yl, and R$^1$ is methyl;
- R$^2$ is 2-hydroxy-2-propyl and R$^1$ is methyl;
- R$^2$ is 2-hydroxy-2-propyl and R$^1$ is isopropyl;
- R$^2$ is 2-hydroxy-2-propyl and R$^1$ is 1-hydroxyethyl;
- R$^2$ is hydroxymethyl and R$^1$ is methyl;
- R$^2$ is 1-hydroxyethyl and R$^1$ is methyl;
- R$^2$ is 2-hydroxyethyl and R$^1$ is methyl;
- R$^2$ is 1-hydroxy-2-propyl and R$^1$ is methyl;
- R$^2$ is 2-hydroxy-2-propyl and R$^1$ is phenyl;
- R$^2$ is C$_1$-C$_6$ alkyl optionally substituted with one or more hydroxy, and R$^1$ is 5- to 10-membered heteroaryl;
- R$^2$ is 2-hydroxy-2-propyl and R$^1$ is pyridyl;
- R$^2$ is 2-hydroxy-2-propyl and R$^1$ is pyrazolyl;
- R$^2$ is C$_1$-C$_6$ alkyl optionally substituted with one or more hydroxy, and R$^1$ is S(O$_2$)CH$_3$;
- R$^2$ is 2-hydroxy-2-propyl and R$^1$ is chloro;
- R$^2$ is 2-hydroxy-2-propyl and R$^1$ is fluoro;
- R$^2$ is C$_3$-C$_7$ cycloalkyl optionally substituted with one or more hydroxy, and R$^1$ is C$_1$-C$_6$ alkyl;
- R$^2$ is 1-hydroxy-1-cyclopropyl, and R$^1$ is methyl;
- R$^2$ is 1-hydroxy-1-cyclobutyl, and R$^1$ is methyl;
- R$^2$ is 1-hydroxy-1-cyclopentyl, and R$^1$ is methyl;
- R$^2$ is 1-hydroxy-1-cyclohexyl, and R$^1$ is methyl;
- R$^2$ is morpholinyl, and R$^1$ is methyl;
- R$^2$ is 1,3-dioxolan-2-yl, and R$^1$ is methyl;
- R$^2$ is 1,3-dioxolan-2-yl, and R$^1$ is fluoro;
- R$^2$ is 1,3-dioxolan-2-yl, and R$^1$ is chloro;

R² is C₁-C₆ alkyl optionally substituted with one or more oxo, and R¹ is methyl;
R² is COCH₃, and R¹ is methyl;
R² is 2-methoxy-2-propyl, and R¹ is methyl;
or
R² is (dimethylamino)methyl, and R¹ is methyl.
In some embodiments, of the compound of formula AA, A is

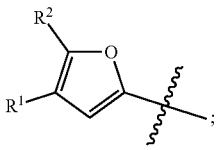

and R¹ and R² are one of the following combinations:
R¹ is C₁-C₆ alkyl optionally substituted with one or more hydroxy, and R² is C₁-C₆ alkyl optionally substituted with one or more hydroxy;
R¹ is C₁-C₆ alkyl optionally substituted with one or more hydroxy, and R² is C₆-C₁₀ aryl;
R¹ is C₁-C₆ alkyl optionally substituted with one or more hydroxy, and R² is 5- to 10-membered heteroaryl;
R¹ is C₁-C₆ alkyl optionally substituted with one or more hydroxy, and R² is SF₅;
R¹ is C₁-C₆ alkyl optionally substituted with one or more hydroxy, and R² is S(O₂)C₁-C₆ alkyl;
R¹ is C₁-C₆ alkyl optionally substituted with one or more hydroxy, and R² is halo;
R¹ is C₃-C₇ cycloalkyl optionally substituted with one or more hydroxy, and R² is C₁-C₆ alkyl;
R¹ is 3- to 7-membered heterocycloalkyl optionally substituted with one or more hydroxy, and R² is C₁-C₆ alkyl;
R¹ is 3- to 7-membered heterocycloalkyl optionally substituted with one or more hydroxy, and R² is halo;
R¹ is C₁-C₆ alkyl optionally substituted with one or more oxo, and R² is methyl;
R¹ is C₁-C₆ alkyl optionally substituted with one or more C₁-C₆ alkoxy, and R² is C₁-C₆ alkyl;
R¹ is C₁-C₆ alkyl optionally substituted with one or more NR⁸R⁹, and R² is C₁-C₆ alkyl;
R¹ is C₁-C₆ alkyl optionally substituted with one or more NR⁸R⁹, and R² is halo;
R² is C₁-C₆ alkyl optionally substituted with one or more hydroxy, and R¹ is C₆-C₁₀ aryl;
R² is C₁-C₆ alkyl optionally substituted with one or more hydroxy, and R¹ is 5- to 10-membered heteroaryl;
R² is C₁-C₆ alkyl optionally substituted with one or more hydroxy, and R¹ is SF₅.
R² is C₁-C₆ alkyl optionally substituted with one or more hydroxy, and R¹ is S(O₂)C₁-C₆ alkyl;
R² is C₁-C₆ alkyl optionally substituted with one or more hydroxy, and R¹ is halo;
R² is C₃-C₇ cycloalkyl optionally substituted with one or more hydroxy, and R¹ is C₁-C₆ alkyl;
R² is 3- to 7-membered heterocycloalkyl optionally substituted with one or more hydroxy, and R¹ is C₁-C₆ alkyl;
R² is 3- to 7-membered heterocycloalkyl optionally substituted with one or more hydroxy, and R¹ is halo;
R² is C₁-C₆ alkyl optionally substituted with one or more oxo, and R¹ is methyl;
R² is C₁-C₆ alkyl optionally substituted with one or more C₁-C₆ alkoxy, and R¹ is C₁-C₆ alkyl;

R² is C₁-C₆ alkyl optionally substituted with one or more NR⁸R⁹, and R¹ is C₁-C₆ alkyl;
or
R² is C₁-C₆ alkyl optionally substituted with one or more NR⁸R⁹, and R¹ is halo.
In some embodiments, of the compound of formula AA, A is

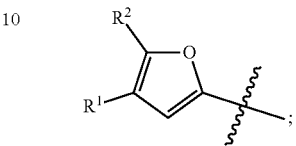

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is S(O₂)CH₃;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is COCH₃, and R² is methyl;
R¹ is 2-methoxy-2-propyl, and R² is methyl;
R¹ is (dimethylamino)methyl, and R² is methyl;
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;
R² is 2-hydroxy-2-propyl and R¹ is phenyl;
R² is C₁-C₆ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is C₁-C₆ alkyl optionally substituted with one or more hydroxy, and R¹ is S(O₂)CH₃;
R² is 2-hydroxy-2-propyl and R¹ is chloro;
R² is 2-hydroxy-2-propyl and R¹ is fluoro;
R² is C₃-C₇ cycloalkyl optionally substituted with one or more hydroxy, and R¹ is C₁-C₆ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;

$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is $COCH_3$, and $R^1$ is methyl;
$R^2$ is 2-methoxy-2-propyl, and $R^1$ is methyl;
or
$R^2$ is (dimethylamino)methyl, and $R^1$ is methyl.

In some embodiments, of the compound of formula AA, A is

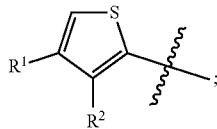

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$;
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more oxo, and $R^1$ is methyl;
$R^2$ is $C_1$-$C_6$ alkyl optionally substituted with one or more $C_1$-$C_6$ alkoxy, and $R^1$ is $C_1$-$C_6$ alkyl;
$R^2$ is $C_1$-$C_6$ alkyl optionally substituted with one or more $NR^8R^9$, and $R^1$ is $C_1$-$C_6$ alkyl;
or
$R^2$ is $C_1$-$C_6$ alkyl optionally substituted with one or more $NR^8R^9$, and $R^1$ is halo.

In some embodiments, of the compound of formula AA, A is

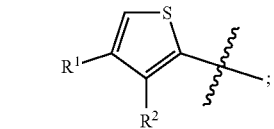

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl;
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;

R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is $C_1$-$C_6$ alkyl optionally substituted with one or more oxo, and R¹ is methyl;
R² is $COCH_3$, and R¹ is methyl;
R² is 2-methoxy-2-propyl, and R¹ is methyl;
or
R² is (dimethylamino)methyl, and R¹ is methyl.

In some embodiments, of the compound of formula AA, A is

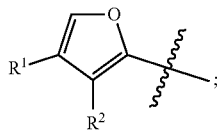

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy;
R¹ is $C_1$-$C_6$ alkyl optionally substituted with one or more hydroxy, and R² is $C_6$-$C_{10}$ aryl;
R¹ is $C_1$-$C_6$ alkyl optionally substituted with one or more hydroxy, and R² is 5- to 10-membered heteroaryl;
R¹ is $C_1$-$C_6$ alkyl optionally substituted with one or more hydroxy, and R² is $SF_5$;
R¹ is $C_1$-$C_6$ alkyl optionally substituted with one or more hydroxy, and R² is $S(O_2)C_1$-$C_6$ alkyl;
R¹ is $C_1$-$C_6$ alkyl optionally substituted with one or more hydroxy, and R² is halo;
R¹ is $C_3$-$C_7$ cycloalkyl optionally substituted with one or more hydroxy, and R² is $C_1$-$C_6$ alkyl;
R¹ is 3- to 7-membered heterocycloalkyl optionally substituted with one or more hydroxy, and R² is $C_1$-$C_6$ alkyl;
R¹ is 3- to 7-membered heterocycloalkyl optionally substituted with one or more hydroxy, and R² is halo;
R¹ is $C_1$-$C_6$ alkyl optionally substituted with one or more oxo, and R² is methyl;
R¹ is $C_1$-$C_6$ alkyl optionally substituted with one or more $C_1$-$C_6$ alkoxy, and R² is $C_1$-$C_6$ alkyl;
R¹ is $C_1$-$C_6$ alkyl optionally substituted with one or more $NR^8R^9$, and R² is $C_1$-$C_6$ alkyl;
R¹ is $C_1$-$C_6$ alkyl optionally substituted with one or more $NR^8R^9$, and R² is halo;
R² is $C_1$-$C_6$ alkyl optionally substituted with one or more hydroxy, and R¹ is $C_6$-$C_{10}$ aryl;
R² is $C_1$-$C_6$ alkyl optionally substituted with one or more hydroxy, and R¹ is 5- to 10-membered heteroaryl;
R² is $C_1$-$C_6$ alkyl optionally substituted with one or more hydroxy, and R¹ is $SF_5$.
R² is $C_1$-$C_6$ alkyl optionally substituted with one or more hydroxy, and R¹ is $S(O_2)C_1$-$C_6$ alkyl;
R² is $C_1$-$C_6$ alkyl optionally substituted with one or more hydroxy, and R¹ is halo;
R² is $C_3$-$C_7$ cycloalkyl optionally substituted with one or more hydroxy, and R¹ is $C_1$-$C_6$ alkyl;
R² is 3- to 7-membered heterocycloalkyl optionally substituted with one or more hydroxy, and R¹ is $C_1$-$C_6$ alkyl;
R² is 3- to 7-membered heterocycloalkyl optionally substituted with one or more hydroxy, and R¹ is halo;
R² is $C_1$-$C_6$ alkyl optionally substituted with one or more oxo, and R¹ is methyl;
R² is $C_1$-$C_6$ alkyl optionally substituted with one or more $C_1$-$C_6$ alkoxy, and R¹ is $C_1$-$C_6$ alkyl;
R² is $C_1$-$C_6$ alkyl optionally substituted with one or more $NR^8R^9$, and R¹ is $C_1$-$C_6$ alkyl;
or
R² is $C_1$-$C_6$ alkyl optionally substituted with one or more $NR^8R^9$, and R¹ is halo.

In some embodiments, of the compound of formula AA, A is

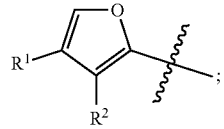

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is $S(O_2)CH_3$;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is $COCH_3$, and R² is methyl;
R¹ is 2-methoxy-2-propyl, and R² is methyl;
R¹ is (dimethylamino)methyl, and R² is methyl;
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;
R² is 2-hydroxy-2-propyl and R¹ is phenyl;
R² is $C_1$-$C_6$ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;

R² is C₁-C₆ alkyl optionally substituted with one or more hydroxy, and R¹ is S(O₂)CH₃;
R² is 2-hydroxy-2-propyl and R¹ is chloro;
R² is 2-hydroxy-2-propyl and R¹ is fluoro;
R² is C₃-C₇ cycloalkyl optionally substituted with one or more hydroxy, and R¹ is C₁-C₆ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is C₁-C₆ alkyl optionally substituted with one or more oxo, and R¹ is methyl;
R² is COCH₃, and R¹ is methyl;
R² is 2-methoxy-2-propyl, and R¹ is methyl;
or
R² is (dimethylamino)methyl, and R¹ is methyl.

In some embodiments, of the compound of formula AA, A is

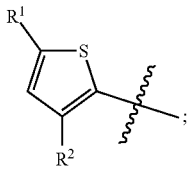

and R¹ and R² are one of the following combinations:
R¹ is C₁-C₆ alkyl optionally substituted with one or more hydroxy, and R² is C₁-C₆ alkyl optionally substituted with one or more hydroxy;
R¹ is C₁-C₆ alkyl optionally substituted with one or more hydroxy, and R² is C₆-C₁₀ aryl;
R¹ is C₁-C₆ alkyl optionally substituted with one or more hydroxy, and R² is 5- to 10-membered heteroaryl;
R¹ is C₁-C₆ alkyl optionally substituted with one or more hydroxy, and R² is SF₅;
R¹ is C₁-C₆ alkyl optionally substituted with one or more hydroxy, and R² is S(O₂)C₁-C₆ alkyl;
R¹ is C₁-C₆ alkyl optionally substituted with one or more hydroxy, and R² is halo;
R¹ is C₃-C₇ cycloalkyl optionally substituted with one or more hydroxy, and R² is C₁-C₆ alkyl;
R¹ is 3- to 7-membered heterocycloalkyl optionally substituted with one or more hydroxy, and R² is C₁-C₆ alkyl;
R¹ is 3- to 7-membered heterocycloalkyl optionally substituted with one or more hydroxy, and R² is halo;
R¹ is C₁-C₆ alkyl optionally substituted with one or more oxo, and R² is methyl;
R¹ is C₁-C₆ alkyl optionally substituted with one or more C₁-C₆ alkoxy, and R² is C₁-C₆ alkyl;
R¹ is C₁-C₆ alkyl optionally substituted with one or more NR⁸R⁹, and R² is C₁-C₆ alkyl;
R¹ is C₁-C₆ alkyl optionally substituted with one or more NR⁸R⁹, and R² is halo;
R² is C₁-C₆ alkyl optionally substituted with one or more hydroxy, and R¹ is C₆-C₁₀ aryl;
R² is C₁-C₆ alkyl optionally substituted with one or more hydroxy, and R¹ is 5- to 10-membered heteroaryl;
R² is C₁-C₆ alkyl optionally substituted with one or more hydroxy, and R¹ is SF₅;

R² is C₁-C₆ alkyl optionally substituted with one or more hydroxy, and R¹ is S(O₂)C₁-C₆ alkyl;
R² is C₁-C₆ alkyl optionally substituted with one or more hydroxy, and R¹ is halo;
R² is C₃-C₇ cycloalkyl optionally substituted with one or more hydroxy, and R¹ is C₁-C₆ alkyl;
R² is 3- to 7-membered heterocycloalkyl optionally substituted with one or more hydroxy, and R³ is C₁-C₆ alkyl;
R² is 3- to 7-membered heterocycloalkyl optionally substituted with one or more hydroxy, and R¹ is halo;
R² is C₁-C₆ alkyl optionally substituted with one or more oxo, and R¹ is methyl;
R² is C₁-C₆ alkyl optionally substituted with one or more C₁-C₆ alkoxy, and R¹ is C₁-C₆ alkyl;
R² is C₁-C₆ alkyl optionally substituted with one or more NR⁸R⁹, and R¹ is C₁-C₆ alkyl;
or
R² is C₁-C₆ alkyl optionally substituted with one or more NR⁸R⁹, and R¹ is halo.

In some embodiments, of the compound of formula AA, A is

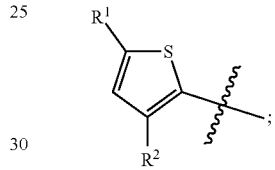

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is S(O₂)CH₃;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is COCH₃, and R² is methyl;
R¹ is 2-methoxy-2-propyl, and R² is methyl;
R¹ is (dimethylamino)methyl, and R² is methyl;
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;

R² is 2-hydroxy-2-propyl and R¹ is phenyl;
R² is $C_1$-$C_6$ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is $C_1$-$C_6$ alkyl optionally substituted with one or more hydroxy, and R¹ is $S(O_2)CH_3$;
R² is 2-hydroxy-2-propyl and R¹ is chloro;
R² is 2-hydroxy-2-propyl and R¹ is fluoro;
R² is $C_3$-$C_7$ cycloalkyl optionally substituted with one or more hydroxy, and R¹ is $C_1$-$C_6$ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is $C_1$-$C_6$ alkyl optionally substituted with one or more oxo, and R¹ is methyl;
R² is $COCH_3$, and R¹ is methyl;
R² is 2-methoxy-2-propyl, and R¹ is methyl; or
R² is (dimethylamino)methyl, and R¹ is methyl.

In some embodiments, of the compound of formula AA, A is

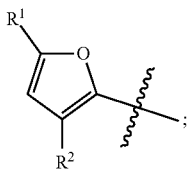

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy;
R¹ is $C_1$-$C_6$ alkyl optionally substituted with one or more hydroxy, and R² is $C_6$-$C_{10}$ aryl;
R¹ is $C_1$-$C_6$ alkyl optionally substituted with one or more hydroxy, and R² is 5- to 10-membered heteroaryl;
R¹ is $C_1$-$C_6$ alkyl optionally substituted with one or more hydroxy, and R² is $SF_5$;
R¹ is $C_1$-$C_6$ alkyl optionally substituted with one or more hydroxy, and R² is $S(O_2)C_1$-$C_6$ alkyl;
R¹ is $C_1$-$C_6$ alkyl optionally substituted with one or more hydroxy, and R² is halo;
R¹ is $C_3$-$C_7$ cycloalkyl optionally substituted with one or more hydroxy, and R² is $C_1$-$C_6$ alkyl;
R¹ is 3- to 7-membered heterocycloalkyl optionally substituted with one or more hydroxy, and R² is $C_1$-$C_6$ alkyl;
R¹ is 3- to 7-membered heterocycloalkyl optionally substituted with one or more hydroxy, and R² is halo;
R¹ is $C_1$-$C_6$ alkyl optionally substituted with one or more oxo, and R² is methyl;
R¹ is $C_1$-$C_6$ alkyl optionally substituted with one or more $C_1$-$C_6$ alkoxy, and R² is $C_1$-$C_6$ alkyl;
R¹ is $C_1$-$C_6$ alkyl optionally substituted with one or more $NR^8R^9$, and R² is $C_1$-$C_6$ alkyl;
R¹ is $C_1$-$C_6$ alkyl optionally substituted with one or more $NR^8R^9$, and R² is halo;

R² is $C_1$-$C_6$ alkyl optionally substituted with one or more hydroxy, and R¹ is $C_6$-$C_{10}$ aryl;
R² is $C_1$-$C_6$ alkyl optionally substituted with one or more hydroxy, and R¹ is 5- to 10-membered heteroaryl;
R² is $C_1$-$C_6$ alkyl optionally substituted with one or more hydroxy, and R¹ is $SF_5$;
R² is $C_1$-$C_6$ alkyl optionally substituted with one or more hydroxy, and R¹ is $S(O_2)C_1$-$C_6$ alkyl;
R² is $C_1$-$C_6$ alkyl optionally substituted with one or more hydroxy, and R¹ is halo;
R² is $C_3$-$C_7$ cycloalkyl optionally substituted with one or more hydroxy, and R¹ is $C_1$-$C_6$ alkyl;
R² is 3- to 7-membered heterocycloalkyl optionally substituted with one or more hydroxy, and R¹ is $C_1$-$C_6$ alkyl;
R² is 3- to 7-membered heterocycloalkyl optionally substituted with one or more hydroxy, and R¹ is halo;
R² is $C_1$-$C_6$ alkyl optionally substituted with one or more oxo, and R¹ is methyl;
R² is $C_1$-$C_6$ alkyl optionally substituted with one or more $C_1$-$C_6$ alkoxy, and R¹ is $C_1$-$C_6$ alkyl;
R² is $C_1$-$C_6$ alkyl optionally substituted with one or more $NR^8R^9$, and R¹ is $C_1$-$C_6$ alkyl; or
R² is $C_1$-$C_6$ alkyl optionally substituted with one or more $NR^8R^9$, and R¹ is halo.

In some embodiments, of the compound of formula AA, A is

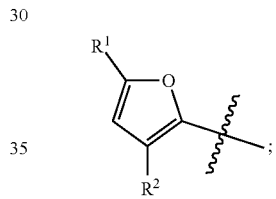

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R³ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is $S(O_2)CH_3$;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is $COCH_3$, and R² is methyl;
R¹ is 2-methoxy-2-propyl, and R² is methyl;
R¹ is (dimethylamino)methyl, and R² is methyl;
R² is 1-hydroxy-2-methylpropan-2-yl, and R¹ is methyl;
R² is 2-hydroxy-2-propyl and R¹ is methyl;

R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;
R² is 2-hydroxy-2-propyl and R¹ is phenyl;
R² is $C_1$-$C_6$ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is $C_1$-$C_6$ alkyl optionally substituted with one or more hydroxy, and R¹ is $S(O_2)CH_3$;
R² is 2-hydroxy-2-propyl and R¹ is chloro;
R² is 2-hydroxy-2-propyl and R¹ is fluoro;
R² is $C_3$-$C_7$ cycloalkyl optionally substituted with one or more hydroxy, and R¹ is $C_1$-$C_6$ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is $C_1$-$C_6$ alkyl optionally substituted with one or more oxo, and R¹ is methyl;
R² is $COCH_3$, and R¹ is methyl;
R² is 2-methoxy-2-propyl, and R¹ is methyl; or
R² is (dimethylamino)methyl, and R¹ is methyl.

In some embodiments, of the compound of formula AA, A is

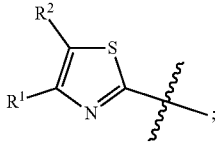

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy;
R¹ is $C_1$-$C_6$ alkyl optionally substituted with one or more hydroxy, and R² is $C_6$-$C_{10}$ aryl;
R¹ is $C_1$-$C_6$ alkyl optionally substituted with one or more hydroxy, and R² is 5- to 10-membered heteroaryl;
R¹ is $C_1$-$C_6$ alkyl optionally substituted with one or more hydroxy, and R² is $SF_5$;
R¹ is $C_1$-$C_6$ alkyl optionally substituted with one or more hydroxy, and R² is $S(O_2)C_1$-$C_6$ alkyl;
R¹ is $C_1$-$C_6$ alkyl optionally substituted with one or more hydroxy, and R² is halo;
R¹ is $C_3$-$C_7$ cycloalkyl optionally substituted with one or more hydroxy, and R² is $C_1$-$C_6$ alkyl;
R¹ is 3- to 7-membered heterocycloalkyl optionally substituted with one or more hydroxy, and R² is $C_1$-$C_6$ alkyl;
R¹ is 3- to 7-membered heterocycloalkyl optionally substituted with one or more hydroxy, and R² is halo;
R¹ is $C_1$-$C_6$ alkyl optionally substituted with one or more oxo, and R² is methyl;
R¹ is $C_1$-$C_6$ alkyl optionally substituted with one or more $C_1$-$C_6$ alkoxy, and R² is $C_1$-$C_6$ alkyl;
R¹ is $C_1$-$C_6$ alkyl optionally substituted with one or more $NR^8R^9$, and R² is $C_1$-$C_6$ alkyl;
R¹ is $C_1$-$C_6$ alkyl optionally substituted with one or more $NR^8R^9$, and R² is halo;
R² is $C_1$-$C_6$ alkyl optionally substituted with one or more hydroxy, and R¹ is $C_6$-$C_{10}$ aryl;
R² is $C_1$-$C_6$ alkyl optionally substituted with one or more hydroxy, and R¹ is 5- to 10-membered heteroaryl;
R² is $C_1$-$C_6$ alkyl optionally substituted with one or more hydroxy, and R¹ is $SF_5$;
R² is $C_1$-$C_6$ alkyl optionally substituted with one or more hydroxy, and R¹ is $S(O_2)C_1$-$C_6$ alkyl;
R² is $C_1$-$C_6$ alkyl optionally substituted with one or more hydroxy, and R¹ is halo;
R² is $C_3$-$C_7$ cycloalkyl optionally substituted with one or more hydroxy, and R¹ is $C_1$-$C_6$ alkyl;
R² is 3- to 7-membered heterocycloalkyl optionally substituted with one or more hydroxy, and R¹ is $C_1$-$C_6$ alkyl;
R² is 3- to 7-membered heterocycloalkyl optionally substituted with one or more hydroxy, and R¹ is halo;
R² is $C_1$-$C_6$ alkyl optionally substituted with one or more oxo, and R¹ is methyl;
R² is $C_1$-$C_6$ alkyl optionally substituted with one or more $C_1$-$C_6$ alkoxy, and R¹ is $C_1$-$C_6$ alkyl;
R² is $C_1$-$C_6$ alkyl optionally substituted with one or more $NR^8R^9$, and R¹ is $C_1$-$C_6$ alkyl; or
R² is $C_1$-$C_6$ alkyl optionally substituted with one or more $NR^8R^9$, and R¹ is halo.

In some embodiments, of the compound of formula AA, A is

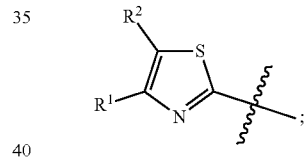

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is $S(O_2)CH_3$;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is $COCH_3$, and R² is methyl;
R¹ is 2-methoxy-2-propyl, and R² is methyl;

R¹ is (dimethylamino)methyl, and R² is methyl;
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;
R² is 2-hydroxy-2-propyl and R¹ is phenyl;
R² is $C_1$-$C_6$ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is $C_1$-$C_6$ alkyl optionally substituted with one or more hydroxy, and R¹ is $S(O_2)CH_3$;
R² is 2-hydroxy-2-propyl and R¹ is chloro;
R² is 2-hydroxy-2-propyl and R¹ is fluoro;
R² is $C_3$-$C_7$ cycloalkyl optionally substituted with one or more hydroxy, and R¹ is $C_1$-$C_6$ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is $C_1$-$C_6$ alkyl optionally substituted with one or more oxo, and R¹ is methyl;
R² is $COCH_3$, and R¹ is methyl;
R² is 2-methoxy-2-propyl, and R¹ is methyl; or
R² is (dimethylamino)methyl, and R¹ is methyl.

In some embodiments, of the compound of formula AA, A is

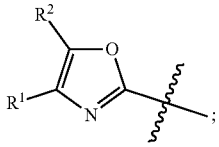

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy;
R¹ is $C_1$-$C_6$ alkyl optionally substituted with one or more hydroxy, and R² is $C_6$-$C_{10}$ aryl;
R¹ is $C_1$-$C_6$ alkyl optionally substituted with one or more hydroxy, and R² is 5- to 10-membered heteroaryl;
R¹ is $C_1$-$C_6$ alkyl optionally substituted with one or more hydroxy, and R² is $SF_5$;
R¹ is $C_1$-$C_6$ alkyl optionally substituted with one or more hydroxy, and R² is $S(O_2)C_1$-$C_6$ alkyl;
R¹ is $C_1$-$C_6$ alkyl optionally substituted with one or more hydroxy, and R² is halo;
R¹ is $C_3$-$C_7$ cycloalkyl optionally substituted with one or more hydroxy, and R² is $C_1$-$C_6$ alkyl;
R¹ is 3- to 7-membered heterocycloalkyl optionally substituted with one or more hydroxy, and R² is $C_1$-$C_6$ alkyl;
R¹ is 3- to 7-membered heterocycloalkyl optionally substituted with one or more hydroxy, and R² is halo;
R¹ is $C_1$-$C_6$ alkyl optionally substituted with one or more oxo, and R² is methyl;
R¹ is $C_1$-$C_6$ alkyl optionally substituted with one or more $C_1$-$C_6$ alkoxy, and R² is $C_1$-$C_6$ alkyl;
R¹ is $C_1$-$C_6$ alkyl optionally substituted with one or more $NR^8R^9$, and R² is $C_1$-$C_6$ alkyl;
R¹ is $C_1$-$C_6$ alkyl optionally substituted with one or more $NR^8R^9$, and R² is halo;
R² is $C_1$-$C_6$ alkyl optionally substituted with one or more hydroxy, and R¹ is $C_6$-$C_{10}$ aryl;
R² is $C_1$-$C_6$ alkyl optionally substituted with one or more hydroxy, and R¹ is 5- to 10-membered heteroaryl;
R² is $C_1$-$C_6$ alkyl optionally substituted with one or more hydroxy, and R³ is $SF_5$.
R² is $C_1$-$C_6$ alkyl optionally substituted with one or more hydroxy, and R¹ is $S(O_2)C_1$-$C_6$ alkyl;
R² is $C_1$-$C_6$ alkyl optionally substituted with one or more hydroxy, and R¹ is halo;
R² is $C_3$-$C_7$ cycloalkyl optionally substituted with one or more hydroxy, and R¹ is $C_1$-$C_6$ alkyl;
R² is 3- to 7-membered heterocycloalkyl optionally substituted with one or more hydroxy, and R¹ is $C_1$-$C_6$ alkyl;
R² is 3- to 7-membered heterocycloalkyl optionally substituted with one or more hydroxy, and R¹ is halo;
R² is $C_1$-$C_6$ alkyl optionally substituted with one or more oxo, and R¹ is methyl;
R² is $C_1$-$C_6$ alkyl optionally substituted with one or more $C_1$-$C_6$ alkoxy, and R¹ is $C_1$-$C_6$ alkyl;
R² is $C_1$-$C_6$ alkyl optionally substituted with one or more $NR^8R^9$, and R¹ is $C_1$-$C_6$ alkyl; or
R² is $C_1$-$C_6$ alkyl optionally substituted with one or more $NR^8R^9$, and R¹ is halo.

In some embodiments, of the compound of formula AA, A is

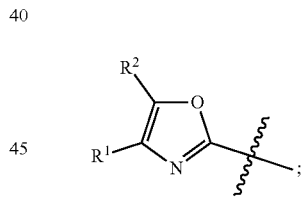

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is $S(O_2)CH_3$;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;

$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl;
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is $COCH_3$, and $R^3$ is methyl;
$R^2$ is 2-methoxy-2-propyl, and $R^1$ is methyl;
or
$R^2$ is (dimethylamino)methyl, and $R^1$ is methyl.

In some embodiments, of the compound of formula AA, A is

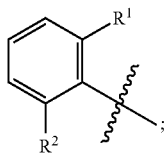

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^3$ is $C_1$-$C_6$ alkyl optionally substituted with one or more hydroxy, and $R^2$ is $C_6$-$C_{10}$ aryl;
$R^3$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^3$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more oxo, and $R^1$ is methyl;
$R^2$ is $C_1$-$C_6$ alkyl optionally substituted with one or more $C_1$-$C_6$ alkoxy, and $R^1$ is $C_1$-$C_6$ alkyl;
$R^2$ is $C_1$-$C_6$ alkyl optionally substituted with one or more $NR^8R^9$, and $R^1$ is $C_1$-$C_6$ alkyl;
or
$R^2$ is $C_1$-$C_6$ alkyl optionally substituted with one or more $NR^8R^9$, and $R^1$ is halo.

In some embodiments, of the compound of formula AA, A is

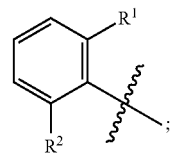

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;

R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is COCH₃, and R² is methyl;
R¹ is 2-methoxy-2-propyl, and R² is methyl;
R¹ is (dimethylamino)methyl, and R² is methyl;
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;
R² is 2-hydroxy-2-propyl and R¹ is phenyl;
R² is $C_1$-$C_6$ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is $C_1$-$C_6$ alkyl optionally substituted with one or more hydroxy, and R¹ is $S(O_2)CH_3$;
R² is 2-hydroxy-2-propyl and R¹ is chloro;
R² is 2-hydroxy-2-propyl and R¹ is fluoro;
R² is $C_3$-$C_7$ cycloalkyl optionally substituted with one or more hydroxy, and R¹ is $C_1$-$C_6$ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is $C_1$-$C_6$ alkyl optionally substituted with one or more oxo, and R¹ is methyl;
R² is COCH₃, and R¹ is methyl;
R² is 2-methoxy-2-propyl, and R¹ is methyl; or
R² is (dimethylamino)methyl, and R¹ is methyl.

In some embodiments, of the compound of formula AA, A is

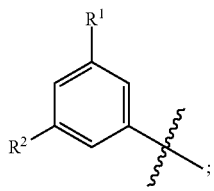

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy;
R¹ is $C_1$-$C_6$ alkyl optionally substituted with one or more hydroxy, and R² is $C_6$-$C_{10}$ aryl;
R¹ is $C_1$-$C_6$ alkyl optionally substituted with one or more hydroxy, and R² is 5- to 10-membered heteroaryl;
R¹ is $C_1$-$C_6$ alkyl optionally substituted with one or more hydroxy, and R² is $SF_5$;
R¹ is $C_1$-$C_6$ alkyl optionally substituted with one or more hydroxy, and R² is $S(O_2)C_1$-$C_6$ alkyl;
R¹ is $C_1$-$C_6$ alkyl optionally substituted with one or more hydroxy, and R² is halo;
R¹ is $C_3$-$C_7$ cycloalkyl optionally substituted with one or more hydroxy, and R² is $C_1$-$C_6$ alkyl;
R¹ is 3- to 7-membered heterocycloalkyl optionally substituted with one or more hydroxy, and R² is $C_1$-$C_6$ alkyl;
R¹ is 3- to 7-membered heterocycloalkyl optionally substituted with one or more hydroxy, and R² is halo;
R¹ is $C_1$-$C_6$ alkyl optionally substituted with one or more oxo, and R² is methyl;
R¹ is $C_1$-$C_6$ alkyl optionally substituted with one or more $C_1$-$C_6$ alkoxy, and R² is $C_1$-$C_6$ alkyl;
R¹ is $C_1$-$C_6$ alkyl optionally substituted with one or more $NR^8R^9$, and R² is $C_1$-$C_6$ alkyl;
R¹ is $C_1$-$C_6$ alkyl optionally substituted with one or more $NR^8R^9$, and R² is halo;
R² is $C_1$-$C_6$ alkyl optionally substituted with one or more hydroxy, and R¹ is $C_6$-$C_{10}$ aryl;
R² is $C_1$-$C_6$ alkyl optionally substituted with one or more hydroxy, and R¹ is 5- to 10-membered heteroaryl;
R² is $C_1$-$C_6$ alkyl optionally substituted with one or more hydroxy, and R¹ is $SF_5$.
R² is $C_1$-$C_6$ alkyl optionally substituted with one or more hydroxy, and R¹ is $S(O_2)C_1$-$C_6$ alkyl;
R² is $C_1$-$C_6$ alkyl optionally substituted with one or more hydroxy, and R¹ is halo;
R² is $C_3$-$C_7$ cycloalkyl optionally substituted with one or more hydroxy, and R¹ is $C_1$-$C_6$ alkyl;
R² is 3- to 7-membered heterocycloalkyl optionally substituted with one or more hydroxy, and R¹ is $C_1$-$C_6$ alkyl;
R² is 3- to 7-membered heterocycloalkyl optionally substituted with one or more hydroxy, and R¹ is halo;
R² is $C_1$-$C_6$ alkyl optionally substituted with one or more oxo, and R¹ is methyl;
R² is $C_1$-$C_6$ alkyl optionally substituted with one or more $C_1$-$C_6$ alkoxy, and R¹ is $C_1$-$C_6$ alkyl;
R² is $C_1$-$C_6$ alkyl optionally substituted with one or more $NR^8R^9$, and R¹ is $C_1$-$C_6$ alkyl; or
R² is $C_1$-$C_6$ alkyl optionally substituted with one or more $NR^8R^9$, and R¹ is halo.

In some embodiments, of the compound of formula AA, A is

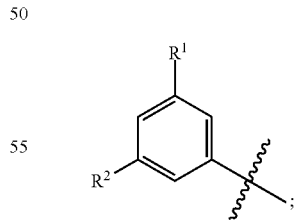

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;

$R^1$ is 2-hydroxyethyl and $R^2$ is methyl;
$R^1$ is 1-hydroxy-2-propyl and $R^2$ is methyl;
$R^3$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl;
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is $COCH_3$, and $R^1$ is methyl;
$R^2$ is 2-methoxy-2-propyl, and $R^1$ is methyl; or
$R^2$ is (dimethylamino)methyl, and $R^1$ is methyl.

In some embodiments, of the compound of formula AA, A is

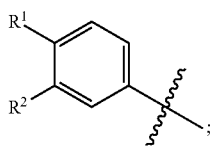

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more oxo, and $R^1$ is methyl;
$R^2$ is $C_1$-$C_6$ alkyl optionally substituted with one or more $C_1$-$C_6$ alkoxy, and $R^1$ is $C_1$-$C_6$ alkyl;
$R^2$ is $C_1$-$C_6$ alkyl optionally substituted with one or more $NR^8R^9$, and $R^1$ is $C_1$-$C_6$ alkyl; or
$R^2$ is $C_1$-$C_6$ alkyl optionally substituted with one or more $NR^8R^9$, and $R^1$ is halo.
$R^2$ is $C_1$-$C_6$ alkyl optionally substituted with one or more $NR^8R^9$, and $R^1$ is $SO_2NR^8R^9$.

In some embodiments, of the compound of formula AA, A is

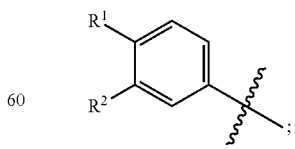

and $R^1$ and $R^2$ are one of the following combinations: $R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;

R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is $S(O_2)CH_3$;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is $COCH_3$, and R² is methyl;
R¹ is 2-methoxy-2-propyl, and R² is methyl;
R¹ is (dimethylamino)methyl, and R² is methyl;
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R³ is methyl;
R² is 2-hydroxy-2-propyl and R¹ is phenyl;
R² is $C_1$-$C_6$ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is $C_1$-$C_6$ alkyl optionally substituted with one or more hydroxy, and R¹ is $S(O_2)CH_3$;
R² is 2-hydroxy-2-propyl and R¹ is chloro;
R² is 2-hydroxy-2-propyl and R¹ is fluoro;
R² is $C_3$-$C_7$ cycloalkyl optionally substituted with one or more hydroxy, and R¹ is $C_1$-$C_6$ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is $C_1$-$C_6$ alkyl optionally substituted with one or more oxo, and R¹ is methyl;
R² is $COCH_3$, and R¹ is methyl;
R² is 2-methoxy-2-propyl, and R¹ is methyl;
or
R² is (dimethylamino)methyl, and R³ is methyl.

In some embodiments, of the compound of formula AA, A is

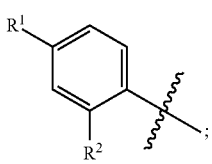

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy;
R¹ is $C_1$-$C_6$ alkyl optionally substituted with one or more hydroxy, and R² is $C_6$-$C_{10}$ aryl;
R¹ is $C_1$-$C_6$ alkyl optionally substituted with one or more hydroxy, and R² is 5- to 10-membered heteroaryl;
R¹ is $C_1$-$C_6$ alkyl optionally substituted with one or more hydroxy, and R² is $SF_5$;
R¹ is $C_1$-$C_6$ alkyl optionally substituted with one or more hydroxy, and R² is $S(O_2)C_1$-$C_6$ alkyl;
R¹ is $C_1$-$C_6$ alkyl optionally substituted with one or more hydroxy, and R² is halo;
R¹ is $C_3$-$C_7$ cycloalkyl optionally substituted with one or more hydroxy, and R² is $C_1$-$C_6$ alkyl;
R¹ is 3- to 7-membered heterocycloalkyl optionally substituted with one or more hydroxy, and R² is $C_1$-$C_6$ alkyl;
R¹ is 3- to 7-membered heterocycloalkyl optionally substituted with one or more hydroxy, and R² is halo;
R¹ is $C_1$-$C_6$ alkyl optionally substituted with one or more oxo, and R² is methyl;
R¹ is $C_1$-$C_6$ alkyl optionally substituted with one or more $C_1$-$C_6$ alkoxy, and R² is $C_1$-$C_6$ alkyl;
R¹ is $C_1$-$C_6$ alkyl optionally substituted with one or more $NR^8R^9$, and R² is $C_1$-$C_6$ alkyl;
R¹ is $C_1$-$C_6$ alkyl optionally substituted with one or more $NR^8R^9$, and R² is halo;
R² is $C_1$-$C_6$ alkyl optionally substituted with one or more hydroxy, and R¹ is $C_6$-$C_{10}$ aryl;
R² is $C_1$-$C_6$ alkyl optionally substituted with one or more hydroxy, and R¹ is 5- to 10-membered heteroaryl;
R² is $C_1$-$C_6$ alkyl optionally substituted with one or more hydroxy, and R¹ is $SF_5$.
R² is $C_1$-$C_6$ alkyl optionally substituted with one or more hydroxy, and R¹ is $S(O_2)C_1$-$C_6$ alkyl;
R² is $C_1$-$C_6$ alkyl optionally substituted with one or more hydroxy, and R¹ is halo;
R² is $C_1$-$C_6$ alkyl optionally substituted with one or more hydroxy, and R¹ is $SO_2NR^8R^9$;
R² is $C_3$-$C_7$ cycloalkyl optionally substituted with one or more hydroxy, and R¹ is $C_1$-$C_6$ alkyl;
R² is 3- to 7-membered heterocycloalkyl optionally substituted with one or more hydroxy, and R¹ is $C_1$-$C_6$ alkyl;
R² is 3- to 7-membered heterocycloalkyl optionally substituted with one or more hydroxy, and R¹ is halo;
R² is $C_1$-$C_6$ alkyl optionally substituted with one or more oxo, and R¹ is methyl;
R² is $C_1$-$C_6$ alkyl optionally substituted with one or more $C_1$-$C_6$ alkoxy, and R¹ is $C_1$-$C_6$ alkyl;
R² is $C_1$-$C_6$ alkyl optionally substituted with one or more $NR^8R^9$, and R¹ is $C_1$-$C_6$ alkyl;
or
R² is $C_1$-$C_6$ alkyl optionally substituted with one or more $NR^8R^9$, and R¹ is halo.

In some embodiments, of the compound of formula AA, A is

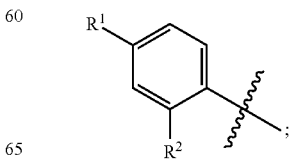

and $R^1$ and $R^2$ are one of the following combinations:
- $R^1$ is 1-hydroxy-2-methylpropan-2-yl, and $R^2$ is methyl;
- $R^1$ is 2-hydroxy-2-propyl and $R^2$ is methyl;
- $R^1$ is 2-hydroxy-2-propyl and $R^2$ is isopropyl;
- $R^1$ is 2-hydroxy-2-propyl and $R^2$ is 2-hydroxy-2-propyl;
- $R^1$ is 2-hydroxy-2-propyl and $R^2$ is 1-hydroxyethyl;
- $R^1$ is hydroxymethyl and $R^2$ is methyl;
- $R^1$ is 1-hydroxyethyl and $R^2$ is methyl;
- $R^1$ is 2-hydroxyethyl and $R^2$ is methyl;
- $R^1$ is 1-hydroxy-2-propyl and $R^2$ is methyl;
- $R^1$ is 2-hydroxy-2-propyl and $R^2$ is phenyl;
- $R^1$ is 2-hydroxy-2-propyl and $R^2$ is pyridyl;
- $R^1$ is 2-hydroxy-2-propyl and $R^2$ is pyrazolyl;
- $R^1$ is 2-hydroxy-2-propyl, and $R^2$ is $S(O_2)CH_3$;
- $R^1$ is 2-hydroxy-2-propyl and $R^2$ is chloro;
- $R^1$ is 2-hydroxy-2-propyl and $R^2$ is fluoro;
- $R^1$ is 1-hydroxy-1-cyclopropyl, and $R^2$ is methyl;
- $R^1$ is 1-hydroxy-1-cyclobutyl, and $R^2$ is methyl;
- $R^1$ is 1-hydroxy-1-cyclopentyl, and $R^2$ is methyl;
- $R^1$ is 1-hydroxy-1-cyclohexyl, and $R^2$ is methyl;
- $R^1$ is morpholinyl, and $R^2$ is methyl;
- $R^1$ is 1,3-dioxolan-2-yl, and $R^2$ is methyl;
- $R^1$ is 1,3-dioxolan-2-yl, and $R^2$ is fluoro;
- $R^1$ is 1,3-dioxolan-2-yl, and $R^2$ is chloro;
- $R^1$ is $COCH_3$, and $R^2$ is methyl;
- $R^1$ is 2-methoxy-2-propyl, and $R^2$ is methyl;
- $R^1$ is (dimethylamino)methyl, and $R^2$ is methyl;
- $R^2$ is 1-hydroxy-2-methylpropan-2-yl, and $R^1$ is methyl;
- $R^2$ is 2-hydroxy-2-propyl and $R^1$ is methyl;
- $R^2$ is 2-hydroxy-2-propyl and $R^1$ is isopropyl;
- $R^2$ is 2-hydroxy-2-propyl and $R^1$ is 1-hydroxyethyl;
- $R^2$ is hydroxymethyl and $R^1$ is methyl;
- $R^2$ is 1-hydroxyethyl and $R^1$ is methyl;
- $R^2$ is 2-hydroxyethyl and $R^1$ is methyl;
- $R^2$ is 1-hydroxy-2-propyl and $R^1$ is methyl;
- $R^2$ is 2-hydroxy-2-propyl and $R^1$ is phenyl;
- $R^2$ is $C_1$-$C_6$ alkyl optionally substituted with one or more hydroxy, and $R^1$ is 5- to 10-membered heteroaryl;
- $R^2$ is 2-hydroxy-2-propyl and $R^1$ is pyridyl;
- $R^2$ is 2-hydroxy-2-propyl and $R^1$ is pyrazolyl;
- $R^2$ is $C_1$-$C_6$ alkyl optionally substituted with one or more hydroxy, and $R^1$ is $S(O_2)CH_3$;
- $R^2$ is 2-hydroxy-2-propyl and $R^1$ is chloro;
- $R^2$ is 2-hydroxy-2-propyl and $R^1$ is fluoro;
- $R^2$ is $C_3$-$C_7$ cycloalkyl optionally substituted with one or more hydroxy, and $R^1$ is $C_1$-$C_6$ alkyl;
- $R^2$ is 1-hydroxy-1-cyclopropyl, and $R^1$ is methyl;
- $R^2$ is 1-hydroxy-1-cyclobutyl, and $R^1$ is methyl;
- $R^2$ is 1-hydroxy-1-cyclopentyl, and $R^1$ is methyl;
- $R^2$ is 1-hydroxy-1-cyclohexyl, and $R^1$ is methyl;
- $R^2$ is morpholinyl, and $R^1$ is methyl;
- $R^2$ is 1,3-dioxolan-2-yl, and $R^1$ is methyl;
- $R^2$ is 1,3-dioxolan-2-yl, and $R^1$ is fluoro;
- $R^2$ is 1,3-dioxolan-2-yl, and $R^1$ is chloro;
- $R^2$ is $C_1$-$C_6$ alkyl optionally substituted with one or more oxo, and $R^1$ is methyl;
- $R^2$ is $COCH_3$, and $R^1$ is methyl;
- $R^2$ is 2-methoxy-2-propyl, and $R^1$ is methyl; or
- $R^2$ is (dimethylamino)methyl, and $R^1$ is methyl.

In some embodiments, of the compound of formula AA, A is

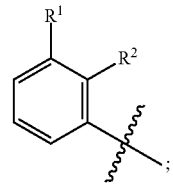

and $R^1$ and $R^2$ are one of the following combinations:
- $R^1$ is $C_1$-$C_6$ alkyl optionally substituted with one or more hydroxy, and $R^2$ is $C_1$-$C_6$ alkyl optionally substituted with one or more hydroxy;
- $R^1$ is $C_1$-$C_6$ alkyl optionally substituted with one or more hydroxy, and $R^2$ is $C_6$-$C_{10}$ aryl;
- $R^1$ is $C_1$-$C_6$ alkyl optionally substituted with one or more hydroxy, and $R^2$ is 5- to 10-membered heteroaryl;
- $R^1$ is $C_1$-$C_6$ alkyl optionally substituted with one or more hydroxy, and $R^2$ is $SF_5$;
- $R^1$ is $C_1$-$C_6$ alkyl optionally substituted with one or more hydroxy, and $R^2$ is $S(O_2)C_1$-$C_6$ alkyl;
- $R^1$ is $C_1$-$C_6$ alkyl optionally substituted with one or more hydroxy, and $R^2$ is halo;
- $R^1$ is $C_3$-$C_7$ cycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is halo;
- $R^1$ is $C_1$-$C_6$ alkyl optionally substituted with one or more oxo, and $R^2$ is methyl;
- $R^1$ is $C_1$-$C_6$ alkyl optionally substituted with one or more $C_1$-$C_6$ alkoxy, and $R^2$ is $C_1$-$C_6$ alkyl;
- $R^1$ is $C_1$-$C_6$ alkyl optionally substituted with one or more $NR^8R^9$, and $R^2$ is $C_1$-$C_6$ alkyl;
- $R^1$ is $C_1$-$C_6$ alkyl optionally substituted with one or more $NR^8R^9$, and $R^2$ is halo;
- $R^2$ is $C_1$-$C_6$ alkyl optionally substituted with one or more hydroxy, and $R^1$ is $C_6$-$C_{10}$ aryl;
- $R^2$ is $C_1$-$C_6$ alkyl optionally substituted with one or more hydroxy, and $R^1$ is 5- to 10-membered heteroaryl;
- $R^2$ is $C_1$-$C_6$ alkyl optionally substituted with one or more hydroxy, and $R^1$ is $SF_5$.
- $R^2$ is $C_1$-$C_6$ alkyl optionally substituted with one or more hydroxy, and $R^1$ is $S(O_2)C_1$-$C_6$ alkyl;
- $R^2$ is $C_1$-$C_6$ alkyl optionally substituted with one or more hydroxy, and $R^1$ is halo;
- $R^2$ is $C_3$-$C_7$ cycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is halo;
- $R^2$ is $C_1$-$C_6$ alkyl optionally substituted with one or more oxo, and $R^1$ is methyl;
- $R^2$ is $C_1$-$C_6$ alkyl optionally substituted with one or more $C_1$-$C_6$ alkoxy, and $R^1$ is $C_1$-$C_6$ alkyl;
- $R^2$ is $C_1$-$C_6$ alkyl optionally substituted with one or more $NR^8R^9$, and $R^1$ is $C_1$-$C_6$ alkyl; or
- $R^2$ is $C_1$-$C_6$ alkyl optionally substituted with one or more $NR^8R^9$, and $R^1$ is halo.

In some embodiments, of the compound of formula AA, A is

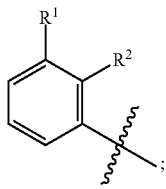

and $R^1$ and $R^2$ are one of the following combinations: $R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl;
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is $COCH_3$, and $R^1$ is methyl;
$R^2$ is 2-methoxy-2-propyl, and $R^1$ is methyl; or
$R^2$ is (dimethylamino)methyl, and $R^1$ is methyl.

In some embodiments, of the compound of formula AA, A is

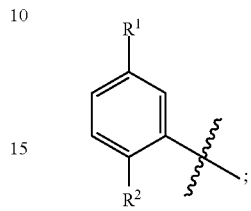

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more oxo, and $R^1$ is methyl;
$R^2$ is $C_1$-$C_6$ alkyl optionally substituted with one or more $C_1$-$C_6$ alkoxy, and $R^1$ is $C_1$-$C_6$ alkyl;

R² is C₁-C₆ alkyl optionally substituted with one or more NR⁸R⁹, and R¹ is C₁-C₆ alkyl; or R² is C₁-C₆ alkyl optionally substituted with one or more NR⁸R⁹, and R¹ is halo.

In some embodiments, of the compound of formula AA, A is

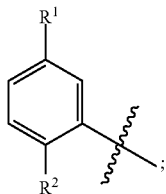

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is S(O₂)CH₃;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is COCH₃, and R² is methyl;
R¹ is 2-methoxy-2-propyl, and R² is methyl;
R¹ is (dimethylamino)methyl, and R² is methyl;
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;
R² is 2-hydroxy-2-propyl and R¹ is phenyl;
R² is C₁-C₆ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is C₁-C₆ alkyl optionally substituted with one or more hydroxy, and R¹ is S(O₂)CH₃;
R² is 2-hydroxy-2-propyl and R¹ is chloro;
R² is 2-hydroxy-2-propyl and R¹ is fluoro;
R² is C₃-C₇ cycloalkyl optionally substituted with one or more hydroxy, and R¹ is C₁-C₆ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is C₁-C₆ alkyl optionally substituted with one or more oxo, and R¹ is methyl;
R² is COCH₃, and R¹ is methyl;
R² is 2-methoxy-2-propyl, and R¹ is methyl; or
R² is (dimethylamino)methyl, and R¹ is methyl.

In some embodiments of the compound of Formula AA, A is

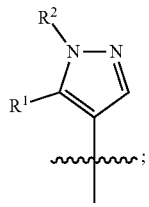

and R¹ and R², taken together forms

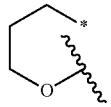

wherein the asterisk represents point of attachment to the nitrogen that is attached to R²,
wherein the

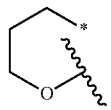

moiety is optionally substituted with one or more substituents independently selected from halo, oxo, C₁-C₆ alkyl, C₁-C₆ alkoxy NR⁸R⁹, and 3- to 10-membered heterocycloalkyl, wherein the C₁-C₆ alkyl, C₁-C₆ alkoxy, and 3- to 10-membered heterocycloalkyl are optionally substituted with one or more substituents selected from halo, C₁-C₆ alkoxy, oxo, and NR⁸R⁹.

In some embodiments of the compound of Formula AA, A is

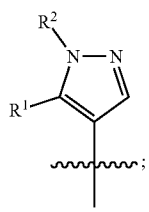

and R¹ and R², taken together forms

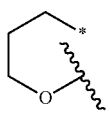

wherein the asterisk represents point of attachment to the nitrogen that is attached to R²,
wherein the

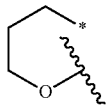

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is,

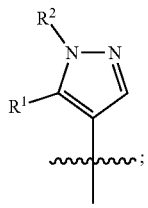

and R¹ and R², taken together forms

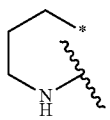

wherein the asterisk represents point of attachment to the nitrogen that is attached to R²,
wherein the

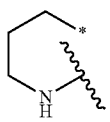

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

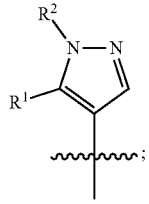

and R¹ and R², taken together forms

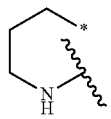

wherein the asterisk represents point of attachment to the nitrogen that is attached to R²,
wherein the

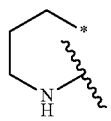

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

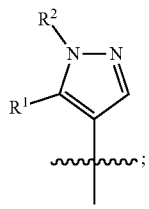

and R¹ and R², taken together forms

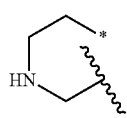

wherein the asterisk represents point of attachment to the nitrogen that is attached to R², wherein the

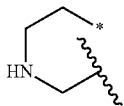

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

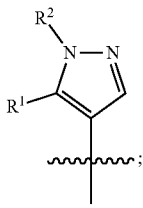

and $R^1$ and $R^2$, taken together forms

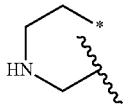

wherein the asterisk represents point of attachment to the nitrogen that is attached to $R^2$,
wherein the

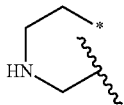

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

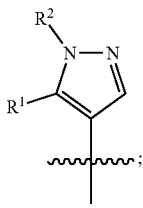

and $R^1$ and $R^2$, taken together forms

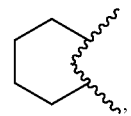

wherein the

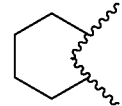

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

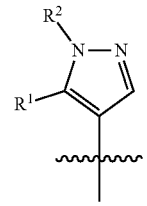

and $R^1$ and $R^2$, taken together forms

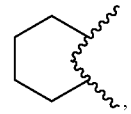

wherein the

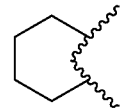

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

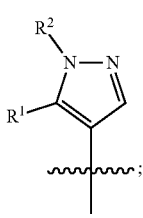

and R¹ and R², taken together forms

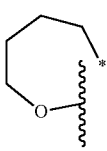

wherein the asterisk represents point of attachment to the nitrogen that is attached to R²,
wherein the

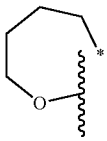

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

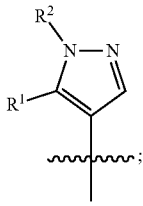

and R¹ and R², taken together forms

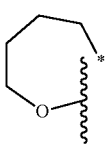

wherein the asterisk represents point of attachment to the nitrogen that is attached to R², wherein the

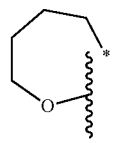 [SMILES: *CCCCO*]

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

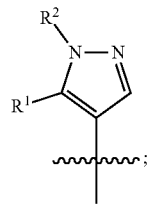

and R¹ and R², taken together forms

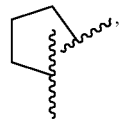

wherein the

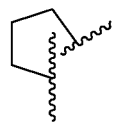

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

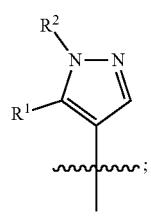

and R¹ and R², taken together forms

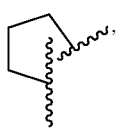

wherein the

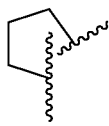

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

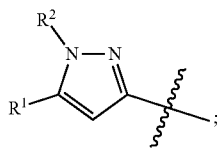

and R¹ and R², taken together forms

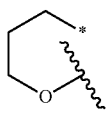

wherein the asterisk represents point of attachment to the nitrogen that is attached to R²,
wherein the

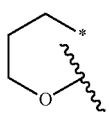

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

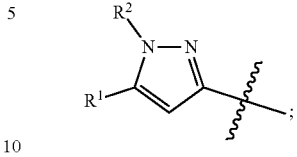

and R¹ and R², taken together forms

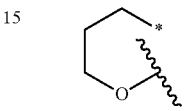

wherein the asterisk represents point of attachment to the nitrogen that is attached to R²,
wherein the

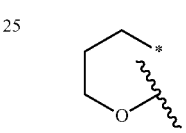

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

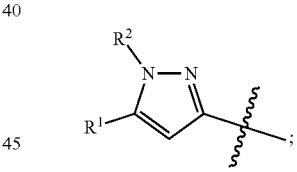

and R¹ and R², taken together forms

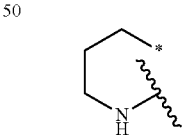

wherein the asterisk represents point of attachment to the nitrogen that is attached to R²,
wherein the

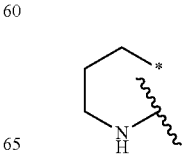

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

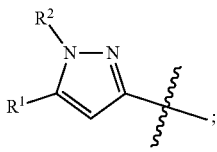

and $R^1$ and $R^2$, taken together forms

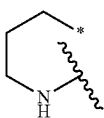

wherein the asterisk represents point of attachment to the nitrogen that is attached to $R^2$,
wherein the

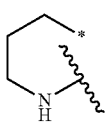

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

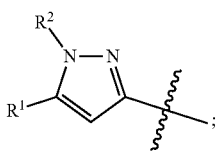

and $R^1$ and $R^2$, taken together forms

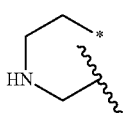

wherein the asterisk represents point of attachment to the nitrogen that is attached to $R^2$
wherein the

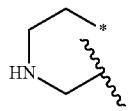

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

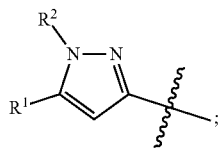

and $R^1$ and $R^2$, taken together forms

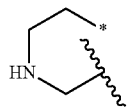

wherein the asterisk represents point of attachment to the nitrogen that is attached to $R^2$,
wherein the

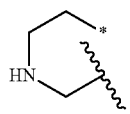

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

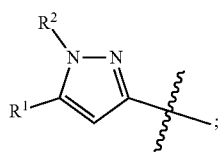

and R¹ and R², taken together forms

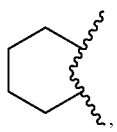

wherein the

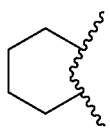

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

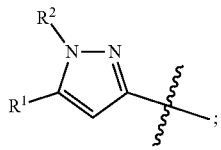

and R¹ and R², taken together forms

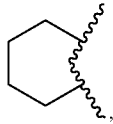

wherein the

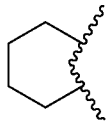

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

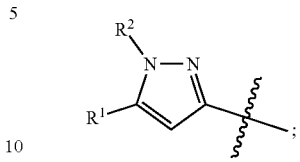

and R¹ and R², taken together forms

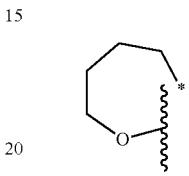

wherein the asterisk represents point of attachment to the nitrogen that is attached to R², wherein the

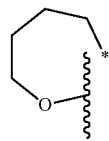 [SMILES: *CCCCO*]

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

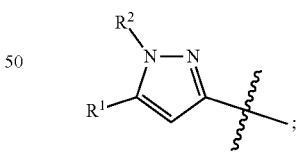

and R¹ and R², taken together forms

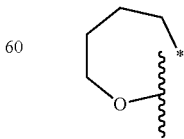

wherein the asterisk represents point of attachment to the nitrogen that is attached to R², wherein the

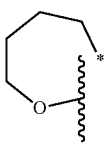

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

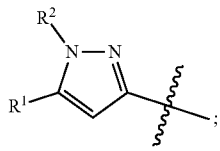

and $R^1$ and $R^2$, taken together forms

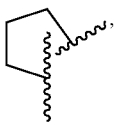

wherein the

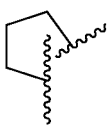

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

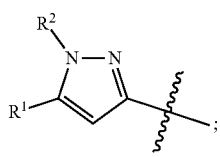

and $R^1$ and $R^2$, taken together forms

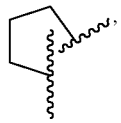

wherein the

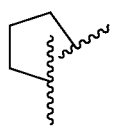

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

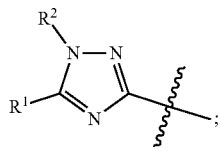

and $R^1$ and $R^2$, taken together forms

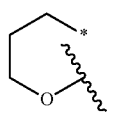

wherein the asterisk represents point of attachment to the nitrogen that is attached to $R^2$, wherein the

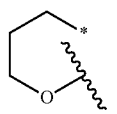

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

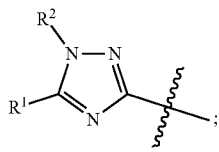

and R¹ and R², taken together forms

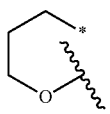

wherein the asterisk represents point of attachment to the nitrogen that is attached to R²,
wherein the

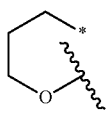

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

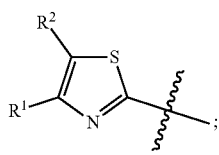

and R¹ and R², taken together forms

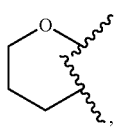

wherein the

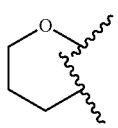

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

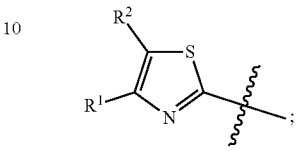

and R¹ and R², taken together forms

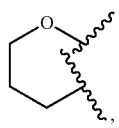 [SMILES: *CCCO*]

wherein the

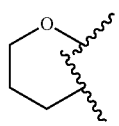

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

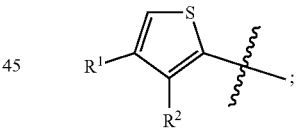

and R¹ and R², taken together forms

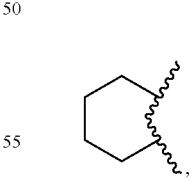

wherein the

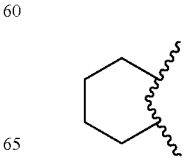

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

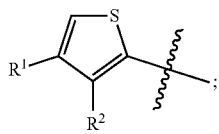

and $R^1$ and $R^2$, taken together forms

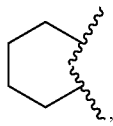

wherein the

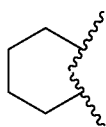

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of Formula AA, A is

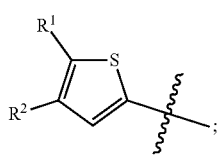

and $R^1$ and $R^2$, taken together forms

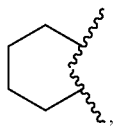

wherein the

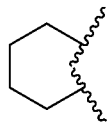

moiety is optionally substituted with one or more substituents independently selected from halo, oxo, $C_1$-$C_6$ alkyl, $C_1$-$C_6$ alkoxy $NR^8R^9$, and 3- to 10-membered heterocycloalkyl, wherein the $C_1$-$C_6$ alkyl, $C_1$-$C_6$ alkoxy, and 3- to 10-membered heterocycloalkyl are optionally substituted with one or more substituents selected from halo, $C_1$-$C_6$ alkoxy, oxo, and $NR^8R^9$.

In some embodiments of the compound of Formula AA, A is

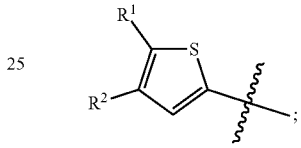

and $R^1$ and $R^2$, taken together forms

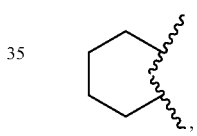

wherein the

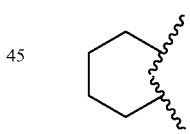

moiety is optionally substituted with one or more substituents independently selected from F, oxo, methyl, ethyl, methoxy, isopropoxy, methylamino, azetidinyl, wherein the methyl, ethyl, methoxy, isopropoxy, and azetidinyl are optionally substituted with one or more substituents selected from F, methoxy, oxo, and methylamino.

In some embodiments of the compound of formula AA,

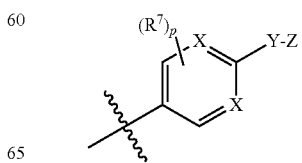

is

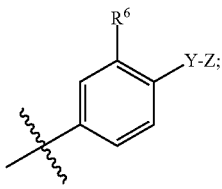

and $R^6$ is selected from:
hydrogen, $C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA,

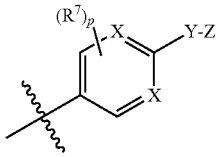

is

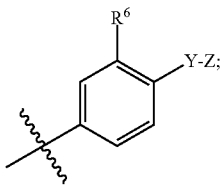

and $R^6$ is selected from:
isopropyl, ethyl, methyl, trifluoromethyl, trifluoromethoxy, cyclopropyl, halo, chloro, and fluoro.

In some embodiments of the compound of formula AA,

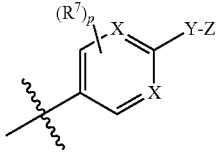

is

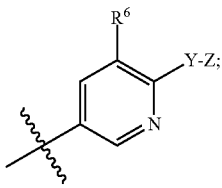

and $R^6$ is selected from:
hydrogen, $C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA,

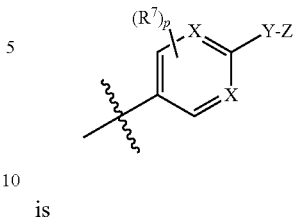

is

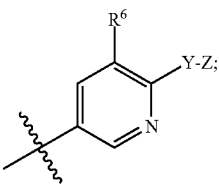

and $R^6$ is selected from:
isopropyl, ethyl, methyl, trifluoromethyl, trifluoromethoxy, cyclopropyl, halo, chloro, and fluoro.

In some embodiments, of the compound of formula AA,

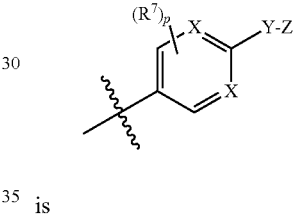

is

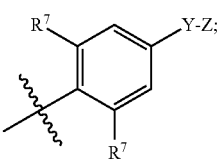

and the two $R^7$ are one of the following combinations:
One $R^7$ is $C_1$-$C_6$ alkyl, and the other $R^7$ is $C_1$-$C_6$ alkyl optionally substituted with one or more halo;
One $R^7$ is $C_1$-$C_6$ alkyl and the other $R^7$ is $C_1$-$C_6$ alkyl;
One $R^7$ is $C_1$-$C_6$ alkyl, and the other $R^7$ is $C_1$-$C_6$ alkyl substituted with one or more halo;
One $R^7$ is $C_1$-$C_6$ alkyl, and the other $R^7$ is $C_3$-$C_7$ cycloalkyl;
One $R^7$ is $C_1$-$C_6$ alkyl, and the other $R^7$ is halo;
One $R^7$ is $C_1$-$C_6$ alkyl, and the other $R^7$ is cyano;
One $R^7$ is $C_3$-$C_7$ cycloalkyl, and the other $R^7$ is $C_3$-$C_7$ cycloalkyl;
One $R^7$ is $C_3$-$C_7$ cycloalkyl, and the other $R^7$ is halo;
One $R^7$ is cyclopropyl and the other $R^7$ is halo;
One $R^7$ is $C_1$-$C_6$ alkyl, and the other $R^7$ is $C_1$-$C_6$ alkoxy optionally substituted with one or more halo;
One $R^7$ is $C_1$-$C_6$ alkyl, and the other $R^7$ is $C_1$-$C_6$ alkoxy;
One $R^7$ is $C_1$-$C_6$ alkyl, and the other $R^7$ is $C_1$-$C_6$ alkoxy substituted with one or more halo;
One $R^7$ is halo, and the other $R^7$ is $C_1$-$C_6$ haloalkyl;
One $R^7$ is halo, and the other $R^7$ is $C_1$-$C_6$ haloalkoxy;
One $R^7$ is $C_1$-$C_6$ alkoxy; and the other $R^7$ is halo;
One $R^7$ is $C_1$-$C_6$ alkoxy; and the other $R^7$ is chloro;
One $R^7$ is hydrogen; and the other $R^7$ is hydrogen;

One $R^7$ is hydrogen; and the other $R^7$ is halo;
One $R^7$ is hydrogen; and the other $R^7$ is chloro; or
One $R^7$ is hydrogen; and the other $R^7$ is cyano.

In some embodiments, of the compound of formula AA,

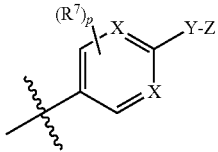

is

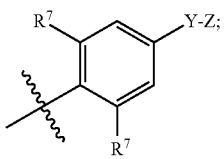

and the two $R^6$ are one of the following combinations:
One $R^7$ is isopropyl; and the other $R^7$ is methyl;
One $R^7$ is isopropyl; and the other $R^7$ is n-propyl;
One $R^7$ is isopropyl; and the other $R^7$ is isopropyl;
One $R^7$ is isopropyl; and the other $R^7$ is trifluoromethyl;
One $R^7$ is isopropyl; and the other $R^7$ is cyclopropyl;
One $R^7$ is isopropyl; and the other $R^7$ is chloro;
One $R^7$ is isopropyl; and the other $R^7$ is fluoro;
One $R^7$ is ethyl; and the other $R^7$ is fluoro;
One $R^7$ is isopropyl; and the other $R^7$ is cyano;
One $R^7$ is cyclopropyl; and the other $R^7$ is cyclopropyl;
One $R^7$ is cyclopropyl; and the other $R^7$ is chloro;
One $R^7$ is cyclopropyl; and the other $R^7$ is fluoro;
One $R^7$ is isopropyl; and the other $R^7$ is methoxy;
One $R^7$ is isopropyl; and the other $R^7$ is methoxy; or
One $R^7$ is isopropyl; and the other $R^7$ is trifluoromethoxy.

In some embodiments, of the compound of formula AA,

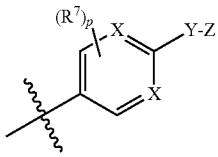

is

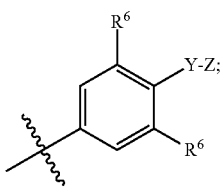

and the two $R^6$ are one of the following combinations:
One $R^6$ is $C_1$-$C_6$ alkyl, and the other $R^6$ is $C_1$-$C_6$ alkyl optionally substituted with one or more halo;
One $R^6$ is $C_1$-$C_6$ alkyl and the other $R^6$ is $C_1$-$C_6$ alkyl;
One $R^6$ is $C_1$-$C_6$ alkyl, and the other $R^6$ is $C_1$-$C_6$ alkyl substituted with one or more halo;
One $R^6$ is $C_1$-$C_6$ alkyl, and the other $R^6$ is $C_3$-$C_7$ cycloalkyl;
One $R^6$ is $C_1$-$C_6$ alkyl, and the other $R^6$ is halo;
One $R^6$ is $C_1$-$C_6$ alkyl, and the other $R^6$ is cyano;
One $R^6$ is $C_3$-$C_7$ cycloalkyl, and the other $R^6$ is $C_3$-$C_7$ cycloalkyl;
One $R^6$ is $C_3$-$C_7$ cycloalkyl, and the other $R^6$ is halo;
One $R^6$ is cyclopropyl and the other $R^6$ is halo;
One $R^6$ is $C_1$-$C_6$ alkyl, and the other $R^6$ is $C_1$-$C_6$ alkoxy optionally substituted with one or more halo;
One $R^6$ is $C_1$-$C_6$ alkyl, and the other $R^6$ is $C_1$-$C_6$ alkoxy;
One $R^6$ is $C_1$-$C_6$ alkyl, and the other $R^6$ is $C_1$-$C_6$ alkoxy substituted with one or more halo;
One $R^6$ is halo, and the other $R^6$ is $C_1$-$C_6$ haloalkyl;
One $R^6$ is halo, and the other $R^6$ is $C_1$-$C_6$ haloalkoxy;
One $R^6$ is $C_1$-$C_6$ alkoxy; and the other $R^6$ is halo;
One $R^6$ is $C_1$-$C_6$ alkoxy; and the other $R^6$ is chloro;
One $R^6$ is hydrogen; and the other $R^6$ is hydrogen;
One $R^6$ is hydrogen; and the other $R^6$ is halo;
One $R^6$ is hydrogen; and the other $R^6$ is chloro;
One $R^6$ is hydrogen; and the other $R^6$ is cyano; or
One $R^6$ is hydrogen; and the other $R^6$ is fluoro.

In some embodiments, of the compound of formula AA,

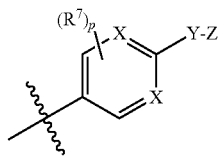

is

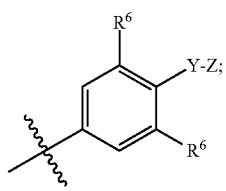

and the two $R^6$ are one of the following combinations:
One $R^6$ is isopropyl; and the other $R^6$ is methyl;
One $R^6$ is isopropyl; and the other $R^6$ is n-propyl;
One $R^6$ is isopropyl; and the other $R^6$ is isopropyl;
One $R^6$ is isopropyl; and the other $R^6$ is trifluoromethyl;
One $R^6$ is isopropyl; and the other $R^6$ is cyclopropyl;
One $R^6$ is isopropyl; and the other $R^6$ is chloro;
One $R^6$ is isopropyl; and the other $R^6$ is fluoro;
One $R^6$ is ethyl; and the other $R^6$ is fluoro;
One $R^6$ is isopropyl; and the other $R^6$ is cyano;
One $R^6$ is cyclopropyl; and the other $R^6$ is cyclopropyl;
One $R^6$ is cyclopropyl; and the other $R^6$ is chloro;
One $R^6$ is cyclopropyl; and the other $R^6$ is fluoro;
One $R^6$ is isopropyl; and the other $R^6$ is methoxy; or
One $R^6$ is isopropyl; and the other $R^6$ is trifluoromethoxy.

In some embodiments, of the compound of formula AA,

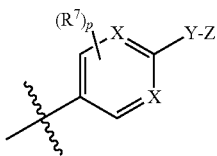

is

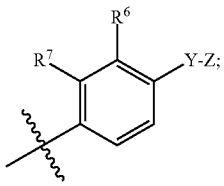

and $R^6$ and $R^7$ are one of the following combinations:
- $R^6$ is $C_1$-$C_6$ alkyl, and $R^7$ is $C_1$-$C_6$ alkyl optionally substituted with one or more halo;
- $R^6$ is $C_1$-$C_6$ alkyl and $R^7$ is $C_1$-$C_6$ alkyl;
- $R^6$ is $C_1$-$C_6$ alkyl, and $R^7$ is $C_1$-$C_6$ alkyl substituted with one or more halo;
- $R^6$ is $C_1$-$C_6$ alkyl, and $R^7$ is $C_3$-$C_7$ cycloalkyl;
- $R^6$ is $C_1$-$C_6$ alkyl, and $R^7$ is halo;
- $R^6$ is $C_1$-$C_6$ alkyl, and $R^7$ is cyano;
- $R^6$ is $C_3$-$C_7$ cycloalkyl, and $R^7$ is $C_3$-$C_7$ cycloalkyl;
- $R^6$ is $C_3$-$C_7$ cycloalkyl, and $R^7$ is halo;
- $R^6$ is cyclopropyl and $R^7$ is halo;
- $R^6$ is $C_1$-$C_6$ alkyl, and $R^7$ is $C_1$-$C_6$ alkoxy optionally substituted with one or more halo.
- $R^6$ is $C_1$-$C_6$ alkyl, and $R^7$ is $C_1$-$C_6$ alkoxy;
- $R^6$ is $C_1$-$C_6$ alkyl, and $R^7$ is $C_1$-$C_6$ alkoxy substituted with one or more halo;
- $R^6$ is halo, and $R^7$ is $C_1$-$C_6$ haloalkyl;
- $R^6$ is halo, and $R^7$ is $C_1$-$C_6$ haloalkoxy;
- $R^6$ is $C_1$-$C_6$ alkoxy; and $R^7$ is halo;
- $R^6$ is $C_1$-$C_6$ alkoxy; and $R^7$ is chloro;
- $R^7$ is $C_1$-$C_6$ alkyl, and $R^6$ is $C_1$-$C_6$ alkyl optionally substituted with one or more halo;
- $R^7$ is $C_1$-$C_6$ alkyl, and $R^6$ is $C_1$-$C_6$ alkyl substituted with one or more halo;
- $R^7$ is $C_1$-$C_6$ alkyl, and $R^6$ is $C_3$-$C_7$ cycloalkyl;
- $R^7$ is $C_1$-$C_6$ alkyl, and $R^6$ is halo;
- $R^7$ is $C_1$-$C_6$ alkyl and $R^6$ is halo;
- $R^7$ is $C_1$-$C_6$ alkyl, and $R^6$ is cyano;
- $R^7$ is $C_3$-$C_7$ cycloalkyl, and $R^6$ is $C_3$-$C_7$ cycloalkyl;
- $R^7$ is $C_3$-$C_7$ cycloalkyl, and $R^6$ is halo;
- $R^7$ is $C_3$-$C_7$ cycloalkyl and $R^6$ is halo;
- $R^7$ is $C_1$-$C_6$ alkyl, and $R^6$ is $C_1$-$C_6$ alkoxy optionally substituted with one or more halo;
- $R^7$ is $C_1$-$C_6$ alkyl, and $R^6$ is $C_1$-$C_6$ alkoxy;
- $R^7$ is $C_1$-$C_6$ alkyl, and $R^6$ is $C_1$-$C_6$ alkoxy substituted with one or more halo;
- $R^7$ is halo, and $R^6$ is $C_1$-$C_6$ haloalkyl;
- $R^7$ is halo, and $R^6$ is $C_1$-$C_6$ haloalkoxy;
- $R^7$ is $C_1$-$C_6$ alkoxy; and $R^6$ is halo;
- $R^7$ is $C_1$-$C_6$ alkoxy; and $R^6$ is chloro;
- $R^6$ is hydrogen, and $R^7$ is $C_1$-$C_6$ alkyl optionally substituted with one or more halo;
- $R^6$ is hydrogen, and $R^7$ is $C_1$-$C_6$ alkyl;
- $R^6$ is hydrogen, and $R^7$ is $C_1$-$C_6$ alkyl substituted with one or more halo;
- $R^6$ is hydrogen, and $R^7$ is $C_3$-$C_7$ cycloalkyl;
- $R^6$ is hydrogen, and $R^7$ is halo;
- $R^6$ is hydrogen, and $R^7$ is cyano;
- $R^6$ is hydrogen, and $R^7$ is $C_1$-$C_6$ alkoxy optionally substituted with one or more halo;
- $R^6$ is hydrogen, and $R^7$ is $C_1$-$C_6$ alkoxy;
- $R^6$ is hydrogen, and $R^7$ is $C_1$-$C_6$ alkoxy substituted with one or more halo;
- $R^6$ is hydrogen, and $R^7$ is $C_1$-$C_6$ haloalkyl;
- $R^6$ is hydrogen, and $R^7$ is $C_1$-$C_6$ haloalkoxy; or
- $R^6$ is hydrogen, and $R^7$ is chloro.

In some embodiments, of the compound of formula AA,

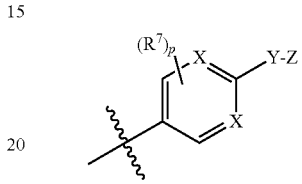

is

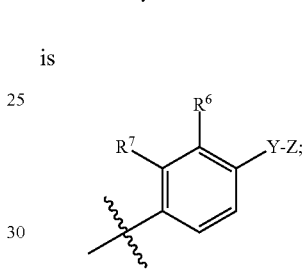

and $R^6$ and $R^7$ are one of the following combinations:
- $R^6$ is isopropyl; and $R^7$ is methyl;
- $R^6$ is isopropyl; and $R^7$ is isopropyl;
- $R^6$ is isopropyl; and $R^7$ is trifluoromethyl;
- $R^6$ is isopropyl; and $R^7$ is cyclopropyl;
- $R^6$ is isopropyl; and $R^7$ is chloro;
- $R^6$ is isopropyl; and $R^7$ is fluoro;
- $R^6$ is ethyl; and $R^7$ is fluoro;
- $R^6$ is isopropyl; and $R^7$ is cyano;
- $R^6$ is cyclopropyl; and $R^7$ is cyclopropyl;
- $R^6$ is cyclopropyl; and $R^7$ is chloro;
- $R^6$ is cyclopropyl; and $R^7$ is fluoro;
- $R^6$ is isopropyl; and $R^7$ is methoxy;
- $R^6$ is isopropyl; and $R^7$ is trifluoromethoxy;
- $R^6$ is chloro; and $R^7$ is trifluoromethyl;
- $R^6$ is chloro; and $R^7$ is trifluoromethoxy;
- $R^7$ is isopropyl; and $R^6$ is methyl;
- $R^7$ is isopropyl; and $R^6$ is trifluoromethyl;
- $R^7$ is isopropyl; and $R^6$ is cyclopropyl;
- $R^7$ is isopropyl; and $R^6$ is chloro;
- $R^7$ is ethyl; and $R^6$ is fluoro;
- $R^7$ is isopropyl; and $R^6$ is cyano;
- $R^7$ is cyclopropyl; and $R^6$ is cyclopropyl;
- $R^7$ is cyclopropyl; and $R^6$ is chloro;
- $R^7$ is cyclopropyl; and $R^6$ is fluoro;
- $R^7$ is isopropyl; and $R^6$ is methoxy;
- $R^7$ is isopropyl; and $R^6$ is trifluoromethoxy;
- $R^7$ is chloro; and $R^6$ is trifluoromethyl;
- $R^1$ is chloro; and $R^6$ is trifluoromethoxy;
- $R^6$ is hydrogen, and $R^7$ is methyl;
- $R^6$ is hydrogen, and $R^7$ is isopropyl;
- $R^6$ is hydrogen, and $R^7$ is trifluoromethyl;
- $R^6$ is hydrogen, and $R^7$ is cyclopropyl;
- $R^6$ is hydrogen, and $R^7$ is fluoro;
- $R^6$ is hydrogen, and $R^7$ is methoxy; or
- $R^6$ is hydrogen, and $R^7$ is trifluoromethoxy.

In some embodiments, of the compound of formula AA,

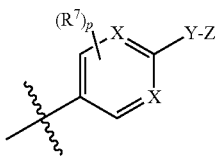

is

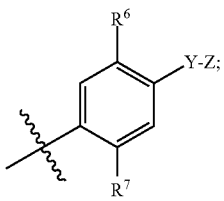

and $R^6$ and $R^7$ are one of the following combinations:
- $R^6$ is $C_1$-$C_6$ alkyl, and $R^7$ is $C_1$-$C_6$ alkyl optionally substituted with one or more halo;
- $R^6$ is $C_1$-$C_6$ alkyl and $R^7$ is $C_1$-$C_6$ alkyl;
- $R^6$ is $C_1$-$C_6$ alkyl, and $R^7$ is $C_1$-$C_6$ alkyl substituted with one or more halo;
- $R^6$ is $C_1$-$C_6$ alkyl, and $R^7$ is $C_3$-$C_7$ cycloalkyl;
- $R^6$ is $C_1$-$C_6$ alkyl, and $R^7$ is halo;
- $R^6$ is $C_1$-$C_6$ alkyl, and $R^7$ is cyano;
- $R^6$ is $C_3$-$C_7$ cycloalkyl, and $R^7$ is $C_3$-$C_7$ cycloalkyl;
- $R^6$ is $C_3$-$C_7$ cycloalkyl, and $R^7$ is halo;
- $R^6$ is cyclopropyl and $R^7$ is halo;
- $R^6$ is $C_1$-$C_6$ alkyl, and $R^7$ is $C_1$-$C_6$ alkoxy optionally substituted with one or more halo;
- $R^6$ is $C_1$-$C_6$ alkyl, and $R^7$ is $C_1$-$C_6$ alkoxy;
- $R^6$ is $C_1$-$C_6$ alkyl, and $R^7$ is $C_1$-$C_6$ alkoxy substituted with one or more halo;
- $R^6$ is halo, and $R^7$ is $C_1$-$C_6$ haloalkyl;
- $R^6$ is halo, and $R^7$ is $C_1$-$C_6$ haloalkoxy;
- $R^6$ is $C_1$-$C_6$ alkoxy; and $R^7$ is halo;
- $R^6$ is $C_1$-$C_6$ alkoxy; and $R^7$ is chloro;
- $R^7$ is $C_1$-$C_6$ alkyl, and $R^6$ is $C_1$-$C_6$ alkyl optionally substituted with one or more halo;
- $R^7$ is $C_1$-$C_6$ alkyl, and $R^6$ is $C_1$-$C_6$ alkyl substituted with one or more halo;
- $R^7$ is $C_1$-$C_6$ alkyl, and $R^6$ is $C_3$-$C_7$ cycloalkyl;
- $R^7$ is $C_1$-$C_6$ alkyl, and $R^6$ is halo;
- $R^7$ is $C_1$-$C_6$ alkyl and $R^6$ is halo;
- $R^7$ is $C_1$-$C_6$ alkyl, and $R^6$ is cyano;
- $R^7$ is $C_3$-$C_7$ cycloalkyl, and $R^6$ is $C_3$-$C_7$ cycloalkyl;
- $R^7$ is $C_3$-$C_7$ cycloalkyl, and $R^6$ is halo;
- $R^7$ is $C_3$-$C_7$ cycloalkyl and $R^6$ is halo;
- $R^7$ is $C_1$-$C_6$ alkyl, and $R^6$ is $C_1$-$C_6$ alkoxy optionally substituted with one or more halo;
- $R^7$ is $C_1$-$C_6$ alkyl, and $R^6$ is $C_1$-$C_6$ alkoxy;
- $R^7$ is $C_1$-$C_6$ alkyl, and $R^6$ is $C_1$-$C_6$ alkoxy substituted with one or more halo;
- $R^7$ is halo, and $R^6$ is $C_1$-$C_6$ haloalkyl;
- $R^7$ is halo, and $R^6$ is $C_1$-$C_6$ haloalkoxy;
- $R^7$ is $C_1$-$C_6$ alkoxy; and $R^6$ is halo;
- $R^7$ is $C_1$-$C_6$ alkoxy; and $R^6$ is chloro;
- $R^6$ is hydrogen, and $R^7$ is $C_1$-$C_6$ alkyl optionally substituted with one or more halo;
- $R^6$ is hydrogen, and $R^7$ is $C_1$-$C_6$ alkyl;
- $R^6$ is hydrogen, and $R^7$ is $C_1$-$C_6$ alkyl substituted with one or more halo;
- $R^6$ is hydrogen, and $R^7$ is $C_3$-$C_7$ cycloalkyl;
- $R^6$ is hydrogen, and $R^7$ is halo;
- $R^6$ is hydrogen, and $R^7$ is cyano;
- $R^6$ is hydrogen, and $R^7$ is $C_1$-$C_6$ alkoxy optionally substituted with one or more halo;
- $R^6$ is hydrogen, and $R^7$ is $C_1$-$C_6$ alkoxy;
- $R^6$ is hydrogen, and $R^7$ is $C_1$-$C_6$ alkoxy substituted with one or more halo;
- $R^6$ is hydrogen, and $R^7$ is $C_1$-$C_6$ haloalkyl;
- $R^6$ is hydrogen, and $R^7$ is $C_1$-$C_6$ haloalkoxy; or
- $R^6$ is hydrogen, and $R^7$ is chloro.

In some embodiments, of the compound of formula AA,

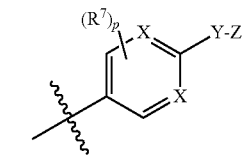

is

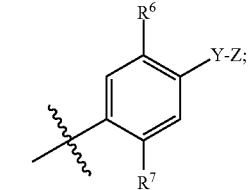

and $R^6$ and $R^7$ are one of the following combinations:
- $R^6$ is isopropyl; and $R^7$ is methyl;
- $R^6$ is isopropyl; and $R^7$ is isopropyl;
- $R^6$ is isopropyl; and $R^7$ is trifluoromethyl;
- $R^6$ is isopropyl; and $R^7$ is cyclopropyl;
- $R^6$ is isopropyl; and $R^7$ is chloro;
- $R^6$ is isopropyl; and $R^7$ is fluoro;
- $R^6$ is ethyl; and $R^7$ is fluoro;
- $R^6$ is isopropyl; and $R^7$ is cyano;
- $R^6$ is cyclopropyl; and $R^7$ is cyclopropyl;
- $R^6$ is cyclopropyl; and $R^7$ is chloro;
- $R^6$ is cyclopropyl; and $R^7$ is fluoro;
- $R^6$ is isopropyl; and $R^7$ is methoxy;
- $R^6$ is isopropyl; and $R^7$ is trifluoromethoxy;
- $R^6$ is chloro; and $R^7$ is trifluoromethyl;
- $R^6$ is chloro; and $R^7$ is trifluoromethoxy;
- $R^7$ is isopropyl; and $R^6$ is methyl;
- $R^7$ is isopropyl; and $R^6$ is trifluoromethyl;
- $R^7$ is isopropyl; and $R^6$ is cyclopropyl;
- $R^7$ is isopropyl; and $R^6$ is chloro;
- $R^7$ is ethyl; and $R^6$ is fluoro;
- $R^7$ is isopropyl; and $R^6$ is cyano;
- $R^7$ is cyclopropyl; and $R^6$ is cyclopropyl;
- $R^7$ is cyclopropyl; and $R^6$ is chloro;
- $R^7$ is cyclopropyl; and $R^6$ is fluoro;
- $R^7$ is isopropyl; and $R^6$ is methoxy;
- $R^7$ is isopropyl; and $R^6$ is trifluoromethoxy;
- $R^7$ is chloro; and $R^6$ is trifluoromethyl;
- $R^7$ is chloro; and $R^6$ is trifluoromethoxyl;
- $R^6$ is hydrogen, and $R^7$ is methyl;
- $R^6$ is hydrogen, and $R^7$ is isopropyl;
- $R^6$ is hydrogen, and $R^7$ is trifluoromethyl;

$R^6$ is hydrogen, and $R^1$ is cyclopropyl;
$R^6$ is hydrogen, and $R^7$ is fluoro;
$R^6$ is hydrogen, and $R^7$ is methoxy; or
$R^6$ is hydrogen, and $R^7$ is trifluoromethoxy.

In some embodiments, of the compound of formula AA,

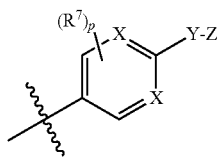

is

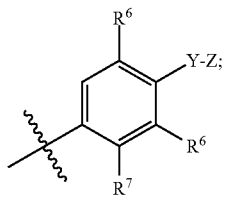

and $R^6$ and $R^7$ are one of the following combinations:
- each $R^6$ is independently $C_1$-$C_6$ alkyl, and $R^7$ is $C_1$-$C_6$ alkyl optionally substituted with one or more halo;
- each $R^6$ is independently $C_1$-$C_6$ alkyl and $R^7$ is $C_1$-$C_6$ alkyl;
- each $R^6$ is independently $C_1$-$C_6$ alkyl, and $R^7$ is $C_1$-$C_6$ alkyl substituted with one or more halo;
- each $R^6$ is independently $C_1$-$C_6$ alkyl, and $R^7$ is $C_3$-$C_7$ cycloalkyl;
- each $R^6$ is independently $C_1$-$C_6$ alkyl, and $R^7$ is halo;
- each $R^6$ is independently $C_1$-$C_6$ alkyl, and $R^7$ is cyano;
- each $R^6$ is independently $C_3$-$C_7$ cycloalkyl, and $R^7$ is $C_3$-$C_7$ cycloalkyl;
- each $R^6$ is independently $C_3$-$C_7$ cycloalkyl, and $R^7$ is halo;
- each $R^6$ is independently cyclopropyl and $R^7$ is halo;
- each $R^6$ is independently $C_1$-$C_6$ alkyl, and $R^7$ is $C_1$-$C_6$ alkoxy optionally substituted with one or more halo;
- each $R^6$ is independently $C_1$-$C_6$ alkyl, and $R^7$ is $C_1$-$C_6$ alkoxy;
- each $R^6$ is independently $C_1$-$C_6$ alkyl, and $R^7$ is $C_1$-$C_6$ alkoxy substituted with one or more halo;
- each $R^6$ is independently halo, and $R^7$ is $C_1$-$C_6$ haloalkyl;
- each $R^6$ is independently halo, and $R^7$ is $C_1$-$C_6$ haloalkoxy;
- each $R^6$ is independently $C_1$-$C_6$ alkoxy; and $R^7$ is halo;
- each $R^6$ is independently $C_1$-$C_6$ alkoxy; and $R^7$ is chloro;
- $R^7$ is $C_1$-$C_6$ alkyl, and each $R^6$ is independently $C_1$-$C_6$ alkyl optionally substituted with one or more halo;
- $R^7$ is $C_1$-$C_6$ alkyl, and each $R^6$ is independently $C_1$-$C_6$ alkyl substituted with one or more halo;
- $R^7$ is $C_1$-$C_6$ alkyl, and each $R^6$ is independently $C_3$-$C_7$ cycloalkyl;
- $R^7$ is $C_1$-$C_6$ alkyl, and each $R^6$ is independently halo;
- $R^7$ is $C_1$-$C_6$ alkyl and each $R^6$ is independently halo;
- $R^7$ is $C_1$-$C_6$ alkyl, and $R^6$ is cyano;
- $R^7$ is $C_3$-$C_7$ cycloalkyl, and each $R^6$ is independently $C_3$-$C_7$ cycloalkyl;
- $R^7$ is $C_3$-$C_7$ cycloalkyl, and each $R^6$ is independently halo;
- $R^7$ is $C_3$-$C_7$ cycloalkyl and each $R^6$ is independently halo;
- $R^7$ is $C_1$-$C_6$ alkyl, and each $R^6$ is independently $C_1$-$C_6$ alkoxy optionally substituted with one or more halo;
- $R^7$ is $C_1$-$C_6$ alkyl, and each $R^6$ is independently $C_1$-$C_6$ alkoxy;
- $R^7$ is $C_1$-$C_6$ alkyl, and each $R^6$ is independently $C_1$-$C_6$ alkoxy substituted with one or more halo;
- $R^7$ is halo, and each $R^6$ is independently $C_1$-$C_6$ haloalkyl;
- $R^7$ is halo, and each $R^6$ is independently $C_1$-$C_6$ haloalkoxy;
- $R^7$ is $C_1$-$C_6$ alkoxy; and each $R^6$ is independently halo;
- $R^7$ is $C_1$-$C_6$ alkoxy; and $R^6$ is chloro;
- each $R^6$ is hydrogen, and $R^7$ is $C_1$-$C_6$ alkyl optionally substituted with one or more halo;
- each $R^6$ is hydrogen, and $R^7$ is $C_1$-$C_6$ alkyl;
- each $R^6$ is hydrogen, and $R^7$ is $C_1$-$C_6$ alkyl substituted with one or more halo;
- each $R^6$ is hydrogen, and $R^7$ is $C_3$-$C_7$ cycloalkyl;
- each $R^6$ is hydrogen, and $R^7$ is halo;
- each $R^6$ is hydrogen, and $R^7$ is cyano;
- each $R^6$ is hydrogen, and $R^1$ is $C_1$-$C_6$ alkoxy optionally substituted with one or more halo;
- each $R^6$ is hydrogen, and $R^7$ is $C_1$-$C_6$ alkoxy;
- each $R^6$ is hydrogen, and $R^7$ is $C_1$-$C_6$ alkoxy substituted with one or more halo;
- each $R^6$ is hydrogen, and $R^7$ is $C_1$-$C_6$ haloalkyl;
- each $R^6$ is hydrogen, and $R^7$ is $C_1$-$C_6$ haloalkoxy; or
- each $R^6$ is hydrogen, and $R^7$ is chloro.

In some embodiments, of the compound of formula AA,

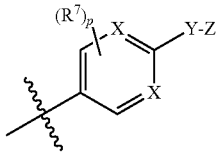

is

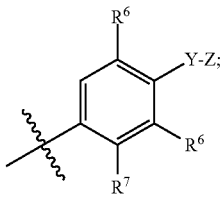

and $R^6$ and $R^7$ are one of the following combinations:
- each $R^6$ is isopropyl; and $R^7$ is methyl;
- each $R^6$ is isopropyl; and $R^7$ is isopropyl;
- each $R^6$ is isopropyl; and $R^7$ is trifluoromethyl;
- each $R^6$ is isopropyl; and $R^7$ is cyclopropyl;
- each $R^6$ is isopropyl; and $R^7$ is chloro;
- each $R^6$ is isopropyl; and $R^7$ is fluoro;
- each $R^6$ is ethyl; and $R^7$ is fluoro;
- each $R^6$ is isopropyl; and $R^7$ is cyano;
- each $R^6$ is cyclopropyl; and $R^7$ is cyclopropyl;
- each $R^6$ is cyclopropyl; and $R^7$ is chloro;
- each $R^6$ is cyclopropyl; and $R^7$ is fluoro;
- each $R^6$ is isopropyl; and $R^7$ is methoxy;
- each $R^6$ is isopropyl; and $R^7$ is trifluoromethoxy;
- each $R^6$ is chloro; and $R^7$ is trifluoromethyl;
- each $R^6$ is chloro; and $R^7$ is trifluoromethoxy;
- each $R^7$ is isopropyl; and $R^6$ is methyl;
- each $R^7$ is isopropyl; and $R^6$ is trifluoromethyl;
- each $R^7$ is isopropyl; and $R^6$ is cyclopropyl;
- each $R^7$ is isopropyl; and $R^6$ is chloro;

205

$R^7$ is ethyl; and $R^6$ is fluoro;
$R^7$ is isopropyl; and $R^6$ is cyano;
$R^7$ is cyclopropyl; and $R^6$ is cyclopropyl;
$R^7$ is cyclopropyl; and $R^6$ is chloro;
$R^7$ is cyclopropyl; and $R^6$ is fluoro;
$R^7$ is isopropyl; and $R^6$ is methoxy;
$R^7$ is isopropyl; and $R^6$ is trifluoromethoxy;
$R^7$ is chloro; and $R^6$ is trifluoromethyl;
$R^7$ is chloro; and $R^6$ is trifluoromethoxy;
one $R^6$ is isopropyl; the other $R^6$ is trifluoromethyl; and $R^7$ is chloro;
each $R^6$ is hydrogen, and $R^7$ is methyl;
each $R^6$ is hydrogen, and $R^7$ is isopropyl;
each $R^6$ is hydrogen, and $R^7$ is trifluoromethyl;
each $R^6$ is hydrogen, and $R^7$ is cyclopropyl;
each $R^6$ is hydrogen, and $R^7$ is fluoro;
each $R^6$ is hydrogen, and $R^7$ is methoxy; or
each $R^6$ is hydrogen, and $R^7$ is trifluoromethoxy.

In some embodiments, of the compound of formula AA,

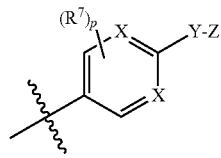

is

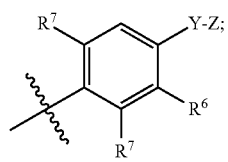

and $R^6$ and $R^7$ are one of the following combinations:
$R^6$ is $C_1$-$C_6$ alkyl, and each $R^7$ is independently $C_1$-$C_6$ alkyl optionally substituted with one or more halo;
$R^6$ is $C_1$-$C_6$ alkyl and each $R^7$ is independently $C_1$-$C_6$ alkyl;
$R^6$ is $C_1$-$C_6$ alkyl, and each $R^7$ is independently $C_1$-$C_6$ alkyl substituted with one or more halo;
$R^6$ is $C_1$-$C_6$ alkyl, and each $R^7$ is independently $C_3$-$C_7$ cycloalkyl;
$R^6$ is $C_1$-$C_6$ alkyl, and each $R^7$ is independently halo;
$R^6$ is $C_1$-$C_6$ alkyl, and $R^7$ is cyano;
$R^6$ is $C_3$-$C_7$ cycloalkyl, and each $R^7$ is independently $C_3$-$C_7$ cycloalkyl;
$R^6$ is $C_3$-$C_7$ cycloalkyl, and each $R^7$ is independently halo;
$R^6$ is cyclopropyl and each $R^7$ is independently halo;
$R^6$ is $C_1$-$C_6$ alkyl, and each $R^7$ is independently $C_1$-$C_6$ alkoxy optionally substituted with one or more halo;
$R^6$ is $C_1$-$C_6$ alkyl, and each $R^7$ is independently $C_1$-$C_6$ alkoxy;
$R^6$ is $C_1$-$C_6$ alkyl, and each $R^7$ is independently $C_1$-$C_6$ alkoxy substituted with one or more halo;
$R^6$ is halo, and each $R^7$ is independently $C_1$-$C_6$ haloalkyl;
$R^6$ is halo, and each $R^7$ is independently $C_1$-$C_6$ haloalkoxy;
$R^6$ is $C_1$-$C_6$ alkoxy; and each $R^7$ is independently halo;
$R^6$ is $C_1$-$C_6$ alkoxy; and $R^7$ is chloro;
each $R^7$ is independently $C_1$-$C_6$ alkyl, and $R^6$ is $C_1$-$C_6$ alkyl optionally substituted with one or more halo;

206 each $R^7$ is independently $C_1$-$C_6$ alkyl, and $R^6$ is $C_1$-$C_6$ alkyl substituted with one or more halo;
each $R^7$ is independently $C_1$-$C_6$ alkyl, and $R^6$ is $C_3$-$C_7$ cycloalkyl;
each $R^7$ is independently $C_1$-$C_6$ alkyl, and $R^6$ is halo;
each $R^7$ is independently $C_1$-$C_6$ alkyl and $R^6$ is halo;
each $R^7$ is independently $C_1$-$C_6$ alkyl, and $R^6$ is cyano;
each $R^7$ is independently $C_3$-$C_7$ cycloalkyl, and $R^6$ is $C_3$-$C_7$ cycloalkyl;
each $R^7$ is independently $C_3$-$C_7$ cycloalkyl, and $R^6$ is halo;
each $R^7$ is independently $C_3$-$C_7$ cycloalkyl and $R^6$ is halo;
each $R^7$ is independently $C_1$-$C_6$ alkyl, and $R^6$ is $C_1$-$C_6$ alkoxy optionally substituted with one or more halo;
each $R^7$ is independently $C_1$-$C_6$ alkyl, and $R^6$ is $C_1$-$C_6$ alkoxy;
each $R^7$ is independently $C_1$-$C_6$ alkyl, and $R^6$ is $C_1$-$C_6$ alkoxy substituted with one or more halo;
each $R^7$ is independently halo, and $R^6$ is $C_1$-$C_6$ haloalkyl;
each $R^7$ is independently halo, and $R^6$ is $C_1$-$C_6$ haloalkoxy;
each $R^7$ is independently $C_1$-$C_6$ alkoxy; and $R^6$ is halo;
each $R^6$ is independently $C_1$-$C_6$ alkoxy; and $R^6$ is chloro;
$R^6$ is hydrogen, and each $R^7$ is independently $C_1$-$C_6$ alkyl optionally substituted with one or more halo;
$R^6$ is hydrogen, and each $R^7$ is independently $C_1$-$C_6$ alkyl;
$R^6$ is hydrogen, and each $R^7$ is independently $C_1$-$C_6$ alkyl substituted with one or more halo;
$R^6$ is hydrogen, and each $R^7$ is independently $C_3$-$C_7$ cycloalkyl;
$R^6$ is hydrogen, and each $R^7$ is independently halo;
$R^6$ is hydrogen, and $R^7$ is cyano;
$R^6$ is hydrogen, and each $R^7$ is independently $C_1$-$C_6$ alkoxy optionally substituted with one or more halo;
$R^6$ is hydrogen, and each $R^7$ is independently $C_1$-$C_6$ alkoxy;
$R^6$ is hydrogen, and each $R^7$ is independently $C_1$-$C_6$ alkoxy substituted with one or more halo;
$R^6$ is hydrogen, and each $R^7$ is independently $C_1$-$C_6$ haloalkyl;
$R^6$ is hydrogen, and each $R^7$ is independently $C_1$-$C_6$ haloalkoxy; or
$R^6$ is hydrogen, and $R^7$ is chloro.

In some embodiments, of the compound of formula AA,

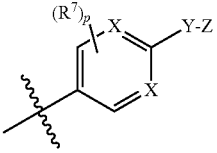

is

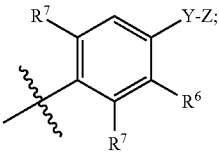

and $R^6$ and $R^7$ are one of the following combinations:
$R^6$ is isopropyl; and each $R^7$ is methyl;
$R^6$ is isopropyl; and each $R^7$ is isopropyl;
$R^6$ is isopropyl; and each $R^7$ is trifluoromethyl;

$R^6$ is isopropyl; and each $R^7$ is cyclopropyl;
$R^6$ is isopropyl; and each $R^7$ is chloro;
$R^6$ is isopropyl; and each $R^7$ is fluoro;
$R^6$ is ethyl; and each $R^7$ is fluoro;
$R^6$ is isopropyl; and each $R^7$ is cyano;
$R^6$ is cyclopropyl; and each $R^7$ is cyclopropyl;
$R^6$ is cyclopropyl; and each $R^7$ is chloro;
$R^6$ is cyclopropyl; and each $R^7$ is fluoro;
$R^6$ is isopropyl; and each $R^7$ is methoxy;
$R^6$ is isopropyl; and each $R^7$ is methoxy;
$R^6$ is isopropyl; and each $R^7$ is trifluoromethoxy;
$R^6$ is chloro; and each $R^7$ is trifluoromethyl;
$R^6$ is chloro; and each $R^7$ is trifluoromethoxy;
each $R^7$ is isopropyl; and $R^6$ is methyl;
each $R^7$ is isopropyl; and $R^6$ is trifluoromethyl;
each $R^7$ is isopropyl; and $R^6$ is cyclopropyl;
each $R^7$ is isopropyl; and $R^6$ is chloro;
each $R^7$ is ethyl; and $R^6$ is fluoro;
each $R^7$ is isopropyl; and $R^6$ is cyano;
each $R^7$ is cyclopropyl; and $R^6$ is cyclopropyl;
each $R^7$ is cyclopropyl; and $R^6$ is chloro;
each $R^7$ is cyclopropyl; and $R^6$ is fluoro;
each $R^7$ is isopropyl; and $R^6$ is methoxy;
each $R^7$ is isopropyl; and $R^6$ is trifluoromethoxy;
each $R^7$ is chloro; and $R^6$ is trifluoromethyl;
each $R^7$ is chloro; and $R^6$ is trifluoromethoxy;
$R^6$ is hydrogen, and each $R^7$ is methyl;
$R^6$ is hydrogen, and each $R^7$ is isopropyl;
$R^6$ is hydrogen, and each $R^7$ is trifluoromethyl;
$R^6$ is hydrogen, and each $R^7$ is cyclopropyl;
$R^6$ is hydrogen, and each $R^7$ is fluoro;
$R^6$ is hydrogen, and each $R^7$ is methoxy; or
$R^6$ is hydrogen, and each $R^7$ is trifluoromethoxy.

In some embodiments, of the compound of formula AA,

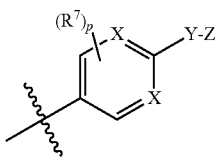

is

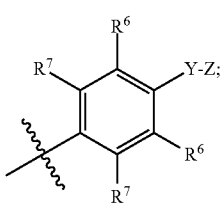

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl;
each $R^6$ is independently $C_1$-$C_6$ alkyl, and each $R^7$ is independently $C_1$-$C_6$ alkyl substituted with one or more halo;
each $R^6$ is independently $C_1$-$C_6$ alkyl, and each $R^7$ is independently $C_3$-$C_7$ cycloalkyl;
each $R^6$ is independently $C_1$-$C_6$ alkyl, and each $R^7$ is independently halo;
each $R^6$ is independently $C_1$-$C_6$ alkyl, and $R^7$ is cyano;
each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;
each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and $R^7$ is chloro;
each $R^7$ is independently $C_1$-$C_6$ alkyl, and each $R^6$ is independently $C_1$-$C_6$ alkyl optionally substituted with one or more halo;
each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and $R^6$ is chloro;
Two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring;
each $R^6$ is hydrogen, and each $R^7$ is independently $C_1$-$C_6$ alkyl optionally substituted with one or more halo;
each $R^6$ is hydrogen, and each $R^7$ is independently $C_1$-$C_6$ alkyl;

each $R^6$ is hydrogen, and each $R^7$ is independently $C_1$-$C_6$ alkyl substituted with one or more halo;
each $R^6$ is hydrogen, and each $R^7$ is independently $C_3$-$C_7$ cycloalkyl;
each $R^6$ is hydrogen, and each $R^7$ is independently halo;
each $R^6$ is hydrogen, and $R^7$ is cyano;
each $R^6$ is hydrogen, and each $R^7$ is independently $C_1$-$C_6$ alkoxy optionally substituted with one or more halo;
each $R^6$ is hydrogen, and each $R^7$ is independently $C_1$-$C_6$ alkoxy;
each $R^6$ is hydrogen, and each $R^7$ is independently $C_1$-$C_6$ alkoxy substituted with one or more halo;
each $R^6$ is hydrogen, and each $R^7$ is independently $C_1$-$C_6$ haloalkyl;
each $R^6$ is hydrogen, and each $R^7$ is independently $C_1$-$C_6$ haloalkoxy;
each $R^6$ is hydrogen, and $R^7$ is chloro; or
one $R^6$ is hydrogen, and one $R^6$ and one $R^7$, on adjacent atoms, taken together with the atoms connecting them form a $C_4$-$C_8$ aliphatic carbocyclic ring.

In some embodiments, of the compound of formula AA,

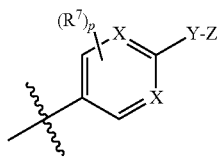

is

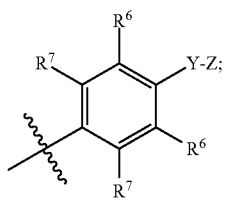

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and $R^7$ is chloro;
$R^6$ is isopropyl; one $R^7$ is fluoro; and the other $R^7$ is cyano;
each $R^6$ is hydrogen, and each $R^7$ is methyl;
each $R^6$ is hydrogen, and each $R^7$ is isopropyl;
each $R^6$ is hydrogen, and each $R^7$ is trifluoromethyl;
each $R^6$ is hydrogen, and each $R^7$ is cyclopropyl;
each $R^6$ is hydrogen, and each $R^7$ is fluoro;
each $R^6$ is hydrogen, and each $R^7$ is methoxy;
each $R^6$ is hydrogen, and each $R^7$ is trifluoromethoxy; or
two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, each of $R^1$ and $R^2$ is independently selected from the group consisting of $C_1$-$C_6$ alkyl optionally substituted with one or more hydroxy, halo, oxo, $C_1$-$C_6$ alkoxy, or $NR^8R^9$; $C_3$-$C_7$ cycloalkyl optionally substituted with one or more hydroxy, halo, oxo, $C_1$-$C_6$ alkoxy, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; 3- to 7-membered heterocycloalkyl optionally substituted with one or more hydroxy, halo, oxo, $C_1$-$C_6$ alkyl, or $NR^8R^9$ wherein the $C_1$-$C_6$ alkoxy or $C_1$-$C_6$ alkyl is further optionally substituted with one to three hydroxy, halo, $NR^8R^9$, or oxo; $C_1$-$C_6$ haloalkyl; $C_1$-$C_6$ alkoxy; $C_1$-$C_6$ haloalkoxy; halo; CN; CO—$C_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; $CONR^8R^9$; $SF_5$; $S(O_2)NR^{11}R^{12}$; $S(O)C_1$-$C_6$ alkyl; and $S(O_2)C_1$-$C_6$ alkyl.

In some embodiments, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; $S(O_2)CH_3$; and $S(O_2)NR^{11}R^{12}$.

In some embodiments, $R^2$ is selected from the group consisting of fluoro, chloro, cyano, methyl; methoxy; ethoxy; isopropyl; 1-hydroxy-2-methylpropan-2-yl; 2-hydroxy-2-propyl; hydroxymethyl; 1-hydroxyethyl; 2-hydroxyethyl; 1-hydroxy-2-propyl; 1-hydroxy-1-cyclopropyl; $COCH_3$; COPh; 2-methoxy-2-propyl; (dimethylamino)methyl; $S(O_2)CH_3$; and $S(O_2)NR^{11}R^{12}$.

In some embodiments,

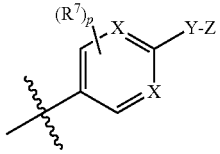

is

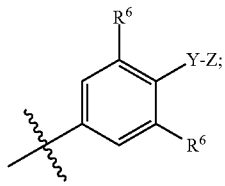

and each $R^6$ is independently selected from the group consisting of: hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^8$R$^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR$^8$R$^9$, =NR$^{10}$, COOC$_1$-$C_6$ alkyl, CONR$^8$R$^9$, 4- to 6-membered heterocycloalkyl, $C_6$-$C_{10}$ aryl, 5-to 10-membered heteroaryl, OCOC$_1$-$C_6$ alkyl, OCOC$_6$-$C_{10}$ aryl, OCO(5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl.

In some embodiments,

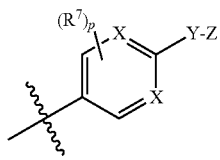

is

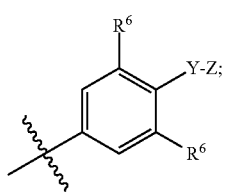

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, wherein the $C_1$-$C_6$ alkyl, $C_1$-$C_6$ haloalkyl, and $C_3$-$C_7$ cycloalkyl is optionally substituted with one or more substituents each independently selected from hydroxy, halo, CN, or oxo.

In some embodiments,

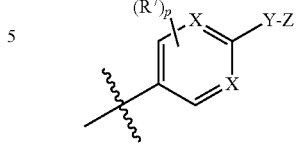

is

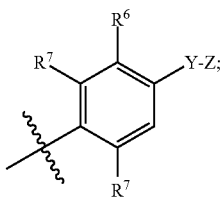

wherein each $R^6$ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^8$R$^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR$^8$R$^9$, =NR$^{10}$, COOC$_1$-$C_6$ alkyl, CONR$^8$R$^9$, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO (5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, CONR$^8$R$^9$, SF$_5$, S(O$_2$)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form a $C_4$-$C_7$ carbocyclic ring or 5-to-7-membered heterocyclic ring containing 1 or 2 heteroatoms and/or heteroatomic groups independently selected from O, N, NH, NR$^{13}$, S, S(O), and S(O)$_2$, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR$^8$R$^9$, =NR$^{10}$, COOC$_1$-$C_6$ alkyl, $C_6$-$C_{10}$ aryl, and CONR$^8$R$^9$.

In some embodiments,

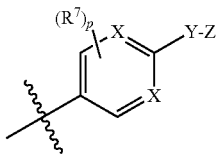

is

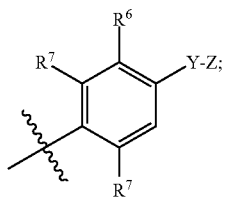

wherein each R⁶ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR⁸R⁹, =NR¹⁰, COOC$_1$-$C_6$ alkyl, CONR⁸R⁹, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO (5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;
wherein R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, CONR⁸R⁹, SF₅, S(O₂)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;
or R⁶ and R⁷, taken together with the atoms connecting them, independently form a $C_4$-$C_7$ carbocyclic ring or 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR⁸R⁹, =NR¹⁰, COOC$_1$-$C_6$ alkyl, $C_6$-$C_{10}$ aryl, and CONR⁸R⁹.

In some embodiments,

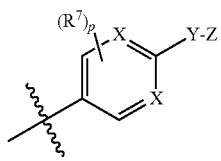

is

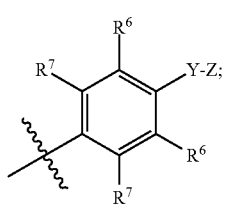

wherein each R⁶ is independently selected from hydrogen, $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR⁸R⁹, =NR¹⁰, COOC$_1$-$C_6$ alkyl, CONR⁸R⁹, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO (5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;
wherein each R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR⁸R⁹, SF₅, S(O₂)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;
or at least one pair of R⁶ and R⁷ on adjacent atoms, taken together with the atoms connecting them, independently form at least one $C_4$-$C_7$ carbocyclic ring or at least one 5-to-7-membered heterocyclic ring containing 1 or 2 heteroatoms and/or heteroatomic groups independently selected from O, N, NH, NR¹³, S, S(O), and S(O)₂, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR⁸R⁹, =NR¹⁰, COOC$_1$-$C_6$ alkyl, $C_6$-$C_{10}$ aryl, and CONR⁸R⁹.

In some embodiments,

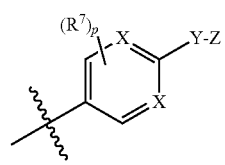

is

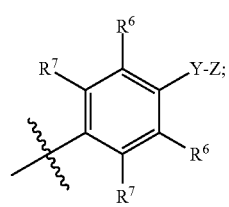

selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments of

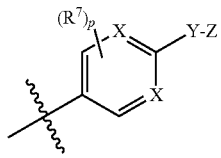

in Formula AA, each X is $CR^6$, p is 0, 1 or 2, and Z is:
5-10-membered heteroaryl; $C_5$-$C_6$ cycloalkyl; 5-6-membered heterocycloalkyl; or $C_6$-$C_{10}$ aryl, wherein Z is (i) optionally substituted with one or more halo, CN, $S(O_2)C_1$-$C_6$ alkyl, $C_6$-$C_{10}$ aryloxy, $CONR^8R^9$, $COOC_1$-$C_6$ alkyl, $C_1$-$C_6$ alkoxy optionally substituted with phenyl, or $C_1$-$C_6$ alkyl optionally substituted with hydroxyl or with $NR^8R^9$, and (ii) optionally fused to a five-to-seven-membered carbocyclic ring or heterocyclic ring containing one or two heteroatoms independently selected from oxygen, sulfur and nitrogen.

In some embodiments of

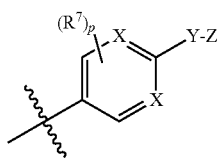

in Formula AA, each X is $CR^6$, p is 2, and Z is:
5-10-membered heteroaryl; $C_5$-$C_6$ cycloalkyl; 5-6-membered heterocycloalkyl; or $C_6$-$C_{10}$ aryl, wherein Z is (i) optionally substituted with one or more halo, CN, $S(O_2)C_1$-$C_6$ alkyl, $C_6$-$C_{10}$ aryloxy, $CONR^8R^9$, $COOC_1$-$C_6$ alkyl, $C_1$-$C_6$ alkoxy optionally substituted with phenyl, or $C_1$-$C_6$ alkyl optionally substituted with hydroxyl or with $NR^8R^9$, and (ii) optionally fused to a five-to-seven-membered carbocyclic ring or heterocyclic ring containing one or two heteroatoms independently selected from oxygen, sulfur and nitrogen.

In some embodiments of

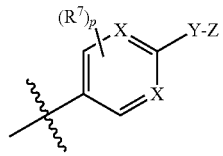

in Formula AA, each X is $CR^6$, p is 0, 1 or 2, and Z is:
5-10-membered heteroaryl optionally substituted with one or more $C_1$-$C_6$ alkyl or $COOC_1$-$C_6$ alkyl; $C_5$-$C_6$ cycloalkyl;
5-6-membered heterocycloalkyl optionally substituted with $COOC_1$-$C_6$ alkyl; $C_6$-$C_{10}$ aryl (i) optionally substituted with one or more halo, CN, $S(O_2)C_1$-$C_6$ alkyl, $C_6$-$C_{10}$ aryloxy, $CONR^8R^9$, $C_1$-$C_6$ alkoxy optionally substituted with phenyl, or $C_1$-$C_6$ alkyl optionally substituted with hydroxyl or with $NR^8R^9$, and (ii) optionally fused to a five-to-seven-membered carbocyclic ring or heterocyclic ring containing one or two heteroatoms independently selected from oxygen, sulfur and nitrogen.

In some embodiments of

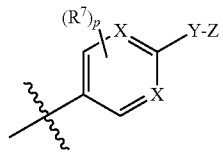

in Formula AA, each X is $CR^6$, p is 2, and Z is:
5-10-membered heteroaryl optionally substituted with one or more $C_1$-$C_6$ alkyl or $COOC_1$-$C_6$ alkyl;
$C_5$-$C_6$ cycloalkyl;
5-6-membered heterocycloalkyl optionally substituted with $COOC_1$-$C_6$ alkyl;
$C_6$-$C_{10}$ aryl (i) optionally substituted with one or more halo, CN, $S(O_2)C_1$-$C_6$ alkyl, $C_6$-$C_{10}$ aryloxy, $CONR^8R^9$, $C_1$-$C_6$ alkoxy optionally substituted with phenyl, or $C_1$-$C_6$ alkyl optionally substituted with hydroxyl or with $NR^8R^9$, and (ii) optionally fused to a five-to-seven-membered carbocyclic ring or heterocyclic ring containing one or two heteroatoms independently selected from oxygen, sulfur and nitrogen.

In some embodiments of

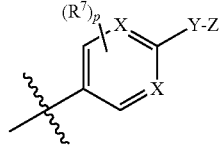

in Formula AA, each X is $CR^6$, p is 2;
is:
5-10-membered heteroaryl optionally substituted with one or more $C_1$-$C_6$ alkyl or $COOC_1$-$C_6$ alkyl; $C_5$-$C_6$ cycloalkyl;

5-6-membered heterocycloalkyl optionally substituted with COOC$_1$-C$_6$ alkyl; C$_6$-C$_{10}$ aryl (i) optionally substituted with one or more halo, CN, S(O$_2$)C$_1$-C$_6$ alkyl, C$_6$-C$_{10}$ aryloxy, CONR$^8$R$^9$, C$_1$-C$_6$ alkoxy optionally substituted with phenyl, or C$_1$-C$_6$ alkyl optionally substituted with hydroxyl or with NR$^8$R$^9$, and (ii) optionally fused to a five-to-seven-membered carbocyclic ring or heterocyclic ring containing one or two heteroatoms independently selected from oxygen, sulfur and nitrogen; and Y is C$_2$ alkynylene.

In some embodiments of

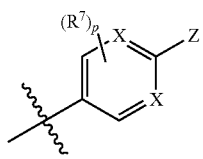

in Formula AA-I, each X is CR$^6$, p is 0, 1 or 2, and Z is:
5-10-membered heteroaryl; C$_5$-C$_6$ cycloalkyl; 5-6-membered heterocycloalkyl; or C$_6$-C$_{10}$ aryl, wherein Z is (i) optionally substituted with one or more halo, CN, S(O$_2$)C$_1$-C$_6$ alkyl, C$_6$-C$_{10}$ aryloxy, CONR$^8$R$^9$, COOC$_1$-C$_6$ alkyl, C$_1$-C$_6$ alkoxy optionally substituted with phenyl, or C$_1$-C$_6$ alkyl optionally substituted with hydroxyl or with NR$^8$R$^9$, and (ii) optionally fused to a five-to-seven-membered carbocyclic ring or heterocyclic ring containing one or two heteroatoms independently selected from oxygen, sulfur and nitrogen.

In some embodiments of

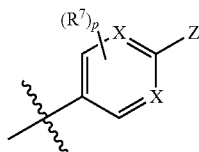

in Formula AA-I, each X is CR$^6$, p is 2, and Z is:
5-10-membered heteroaryl; C$_5$-C$_6$ cycloalkyl; 5-6-membered heterocycloalkyl; or C$_6$-C$_{10}$ aryl, wherein Z is (i) optionally substituted with one or more halo, CN, S(O$_2$)C$_1$-C$_6$ alkyl, C$_6$-C$_{10}$ aryloxy, CONR$^8$R$^9$, COOC$_1$-C$_6$ alkyl, C$_1$-C$_6$ alkoxy optionally substituted with phenyl, or C$_1$-C$_6$ alkyl optionally substituted with hydroxyl or with NR$^8$R$^9$, and (ii) optionally fused to a five-to-seven-membered carbocyclic ring or heterocyclic ring containing one or two heteroatoms independently selected from oxygen, sulfur and nitrogen.

In some embodiments of

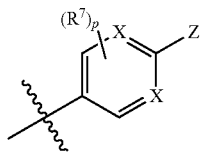

in Formula AA-I, each X is CR$^6$, p is 0, 1 or 2, and Z is:
5-10-membered heteroaryl optionally substituted with one or more C$_1$-C$_6$ alkyl or COOC$_1$-C$_6$ alkyl;
C$_5$-C$_6$ cycloalkyl;
5-6-membered heterocycloalkyl optionally substituted with COOC$_1$-C$_6$ alkyl; C$_6$-C$_{10}$ aryl (i) optionally substituted with one or more halo, CN, S(O$_2$)C$_1$-C$_6$ alkyl, C$_6$-C$_{10}$ aryloxy, CONR$^8$R$^9$, C$_1$-C$_6$ alkoxy optionally substituted with phenyl, or C$_1$-C$_6$ alkyl optionally substituted with hydroxyl or with NR$^8$R$^9$, and (ii) optionally fused to a five-to-seven-membered carbocyclic ring or heterocyclic ring containing one or two heteroatoms independently selected from oxygen, sulfur and nitrogen.

In some embodiments of

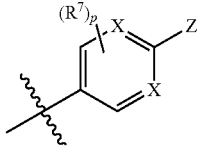

in Formula AA-I, each X is CR$^6$, p is 2, and Z is:
5-10-membered heteroaryl optionally substituted with one or more C$_1$-C$_6$ alkyl or COOC$_1$-C$_6$ alkyl;
C$_5$-C$_6$ cycloalkyl;
5-6-membered heterocycloalkyl optionally substituted with COOC$_1$-C$_6$ alkyl;
C$_6$-C$_{10}$ aryl (i) optionally substituted with one or more halo, CN, S(O$_2$)C$_1$-C$_6$ alkyl, C$_6$-C$_{10}$ aryloxy, CONR$^8$R$^9$, C$_1$-C$_6$ alkoxy optionally substituted with phenyl, or C$_1$-C$_6$ alkyl optionally substituted with hydroxyl or with NR$^8$R$^9$, and (ii) optionally fused to a five-to-seven-membered carbocyclic ring or heterocyclic ring containing one or two heteroatoms independently selected from oxygen, sulfur and nitrogen.

Non-Limiting Combinations and Formulas

In some embodiments, the compound of Formula AA is a compound of Formula AA-II:

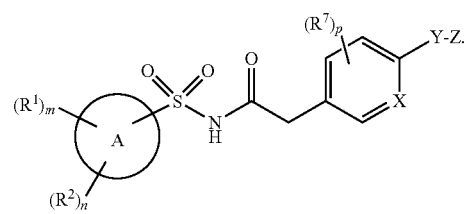

In some embodiments, the compound of Formula AA is a compound of Formula AA-II(i):

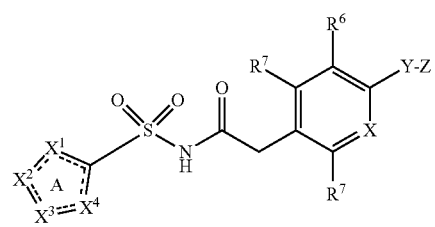

wherein
A is an aromatic heteroaryl;
X$^1$ is selected from the group consisting of CR$^1$, CH, NR$^1$, NH, N, O, and S;

X² is selected from the group consisting of CR², CH, NR², NH, N, O, and S;

X³ is selected from the group consisting of CR¹, CH, NR¹, NH, N, O, and S;

X⁴ is selected from the group consisting of CR², CH, NR², NH, N, O, and S;

wherein at least one of X¹, X², X³, and X⁴ is other than CR¹ and CR²;

wherein one pair of R¹ and R² on adjacent atoms, taken together with the atoms connecting them, form a monocyclic or bicyclic $C_4$-$C_{12}$ carbocyclic ring or a monocyclic or bicyclic 5-to-12-membered heterocyclic ring containing 1-3 heteroatoms and/or heteroatomic groups independently selected from O, N, NH, NR¹³, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, NR⁸R⁹, =NR¹⁰, CN, COOC₁-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and CONR⁸R⁹, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with NR⁸R⁹, $C_2$-$C_6$ alkenyl, $C_2$-$C_6$ alkynyl, $C_3$-$C_{10}$ cycloalkyl, $C_1$-$C_6$ alkoxy, oxo, NR⁸R⁹, =NR¹⁰, COOC₁-$C_6$ alkyl, $C_6$-$C_{10}$ aryl, and CONR⁸R⁹.

In certain embodiments of the compound of Formula AA-II(i), Y is a bond.

In certain other embodiments of the compound of Formula AA-II(i), Y is O or S.

In some embodiments of the compound of Formula AA-II(i),

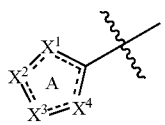

is

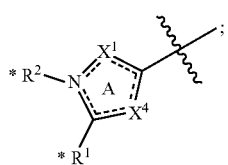

X¹ and X⁴ are each independently selected from N and CH; and the R¹ and R² that the asterisks are closest to are taken together with the atoms connecting them to form a monocyclic or bicyclic $C_4$-$C_{12}$ carbocyclic ring or a monocyclic or bicyclic 5-to-12-membered heterocyclic ring containing 1-3 heteroatoms and/or heteroatomic groups independently selected from O, N, NH, NR¹³, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_1$a cycloalkyl, NR⁸R⁹, =NR¹⁰, CN, COOC₁-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and CONR⁸R⁹, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with NR⁸R⁹, $C_2$-$C_6$ alkenyl, $C_2$-$C_6$ alkynyl, $C_3$-$C_{10}$ cycloalkyl, $C_1$-$C_6$ alkoxy, oxo, NR⁸R⁹, =NR¹⁰, COOC₁-$C_6$ alkyl, $C_6$-$C_{10}$ aryl, and CONR⁸R⁹.

In some embodiments of the compound of Formula AA-II(i),

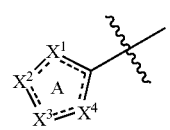

is

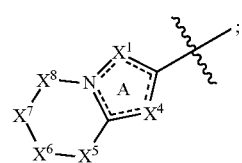

X¹ and X⁴ are each independently selected from N and CH;

X⁵ is selected from O, NH, $CH_2$, and CHR³⁰;

X⁶ is selected from $CH_2$, NR³¹, and C(O);

X⁷ is selected from a bond, O, $CH_2$, $CH_2CH_2$, CHR³²ᵃ, and CHR³²ᵃR³²ᵇ;

X⁸ is selected from $CH_2$ and C(O);

R³⁰ is $C_1$-$C_6$ alkyl (e.g., methyl);

R³¹ is $C_1$-$C_6$ alkyl (e.g., ethyl) optionally substituted with $C_1$-$C_6$ alkoxy (e.g., methoxy; and R³²ᵃ and R³²ᵇ are each independently selected from hydroxy, $C_1$-$C_6$ alkyl optionally substituted with NR⁸R⁹ (e.g., methoxycarbamoylmethyl), $C_1$-$C_6$ alkoxy (e.g., methoxy or isopropoxy), NR⁸R⁹ (e.g., methylamino or dimethylamino), and 3- to 10-membered heterocycloalkyl (e.g., azetidinyl) optionally substituted with halo (e.g., fluoro) or $C_1$-$C_6$ alkoxy (e.g., methoxy), or, alternatively, R³²ᵃ and R³²ᵇ are taken together with the atoms connecting them to form a $C_3$-$C_6$ carbocyclic ring (e.g., cyclopropyl).

In certain embodiments of foregoing, X¹ is N; and X⁴ is CH.

In some embodiments of the compound of Formula AA-II(i), is

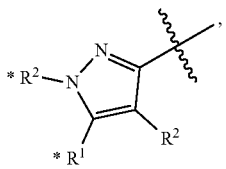

and the $R^1$ and $R^2$ that the asterisks are closest to are taken together with the atoms connecting them to form a monocyclic or bicyclic $C_4$-$C_{12}$ carbocyclic ring or a monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments of the compound of Formula AA-II(i),

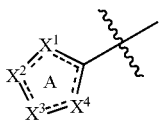

is

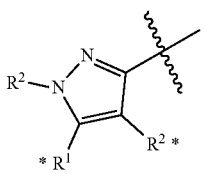

and the $R^1$ and $R^2$ that the asterisks are closest to are taken together with the atoms connecting them to form a monocyclic or bicyclic $C_4$-$C_{12}$ carbocyclic ring or a monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^1R^9$.

In some embodiments of the compound of Formula AA-II(i),

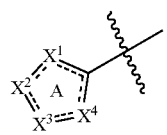

is

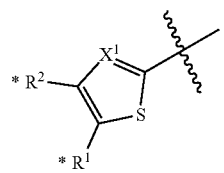

$X^1$ is selected from N and S, and the $R^1$ and $R^2$ that the asterisks are closest to are taken together with the atoms connecting them to form a monocyclic or bicyclic $C_4$-$C_{12}$ carbocyclic ring or a monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, —$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, —$NR^{10}$, $COOC_1$-$C_6$ alkyl, $C_6$-$C_{10}$ aryl, and $CONR^8R^9$.

In some embodiments of the compound of Formula AA-II(i), the $R^1$ and $R^2$ that the asterisks are closest to are taken together with the atoms connecting them to form $C_5$-$C_6$ carbocyclic ring or a 5-to-6-membered heterocyclic ring containing 1 heteroatom and/or heteroatomic group selected from O, NH, and $NR^{13}$, wherein the carbocyclic ring or heterocyclic ring is optionally independently substituted with one or more substituents independently selected from, oxo, methyl, ethyl, isopropyl, methoxy, isopropoxy, and azetidinyl, wherein the methyl, ethyl, isopropyl, methoxy, isopropoxy, and azetidinyl are optionally substituted with one or more substituents selected from hydroxy, fluoro, methoxy, and $NR^8R^9$; wherein $R^8$ and $R^9$ are each independently selected from H, methyl, and $CO_2R^{13}$; and wherein $R^{13}$ is selected from methyl and difluoromethyl.

In some embodiments of the compound of Formula AA-II(i), $R^6$ is selected from hydrogen and halo (e.g., fluoro); each $R^7$ is independently selected from $C_1$-$C_6$ alkyl (e.g., isopropyl, isobutyl, or n-propyl) and $C_3$-$C_{10}$ cycloalkyl (e.g., cyclopropyl); X is selected from N and $CR^6$; Y is selected from a bond, O, S, and $CR^{16}R^{17}$ (e.g., 2-ethyl); and Z is selected from 5-10-membered monocyclic or bicyclic heteroaryl (e.g., pyrimidinyl (e.g., 2-pyrimidinyl or 4-pyrimidinyl) or thiazolyl), a 5-10-membered monocyclic or bicyclic heterocyclic ring (e.g., chromanyl or methylenedioxyphenyl), a $C_6$-$C_{10}$ monocyclic or bicyclic aryl (e.g., phenyl), wherein Z is optionally substituted with one or more substituents independently selected from $C_1$-$C_6$ alkyl (e.g., methyl), halo (e.g., fluoro or chloro), and $C_3$-$C_{10}$ cycloalkyl (e.g., cyclopropyl).

In some embodiments of the compound of Formula AA-II(i), $R^6$ is selected from hydrogen and fluoro; each $R^7$ is independently selected from isopropyl, isobutyl, n-propyl, and cyclopropyl; X is selected from N and $CR^6$; Y is selected from a bond, O, S, and 2-ethyl; and Z is selected from pyrimidinyl, thiazolyl, chromanyl, methylenedioxyphenyl, and phenyl, wherein Z is optionally substituted with one or more substituents independently selected from methyl, fluoro, chloro, and cyclopropyl.

In some embodiments, the optionally substituted ring A is

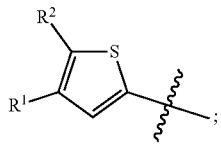

and $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the optionally substituted ring A is

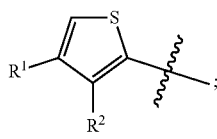

and $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

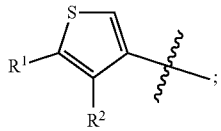

and $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the optionally substituted ring A is

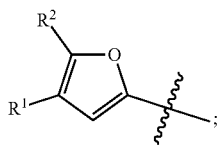

and $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, the optionally substituted ring A is

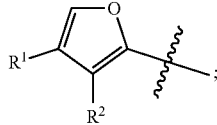

and $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, the substituted ring A is

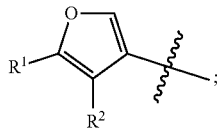

and $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, the optionally substituted ring A is

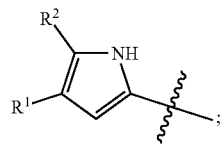

and $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, the optionally substituted ring A is

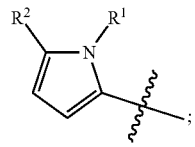

and $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and CONR⁸R⁹, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with NR⁸R⁹, $C_2$-$C_6$ alkenyl, $C_2$-$C_6$ alkynyl, $C_3$-$C_{10}$ cycloalkyl, $C_1$-$C_6$ alkoxy, oxo, NR⁸R⁹, =NR¹⁰, COOC₁-$C_6$ alkyl, $C_6$-$C_{10}$ aryl, and CONR⁸R⁹.

In some embodiments, the optionally substituted ring A is

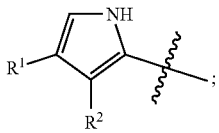

and
R¹ and R², taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, NR¹³, S, S(O), and S(O)₂, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, NR⁸R⁹, =NR¹⁰, CN, COOC₁-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and CONR⁸R⁹, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with NR⁸R⁹, $C_2$-$C_6$ alkenyl, $C_2$-$C_6$ alkynyl, $C_3$-$C_{10}$ cycloalkyl, $C_1$-$C_6$ alkoxy, oxo, NR⁸R⁹, =NR¹⁰, COOC₁-$C_6$ alkyl, $C_6$-$C_{10}$ aryl, and CONR⁸R⁹.

In some embodiments, the substituted ring A is

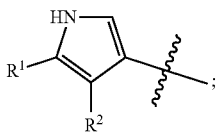

and
R¹ and R², taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, NR¹³, S, S(O), and S(O)₂, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, NR⁸R⁹, =NR¹⁰, CN, COOC₁-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and CONR⁸R⁹, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with NR⁸R⁹, $C_2$-$C_6$ alkenyl, $C_2$-$C_6$ alkynyl, $C_3$-$C_{10}$ cycloalkyl, $C_1$-$C_6$ alkoxy, oxo, NR⁸R⁹, =NR¹⁰, COOC₁-$C_6$ alkyl, $C_6$-$C_{10}$ aryl, and CONR⁸R⁹.

In some embodiments, the substituted ring A is

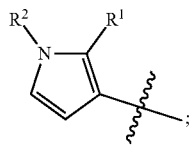

and
R¹ and R², taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, NR¹³, S, S(O), and S(O)₂, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, NR⁸R⁹, =NR¹⁰, CN, COOC₁-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and CONR⁸R⁹, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with NR⁸R⁹, $C_2$-$C_6$ alkenyl, $C_2$-$C_6$ In some embodiments, the substituted ring A is

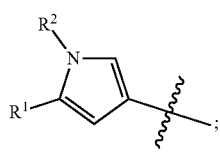

and
R¹ and R², taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, NR¹³, S, S(O), and S(O)₂, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, NR⁸R⁹, =NR¹⁰, CN, COOC₁-$C_6$ alkyl, $OS(O_2)$ $C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and CONR⁸R⁹, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with NR⁸R⁹, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the optionally substituted ring A is

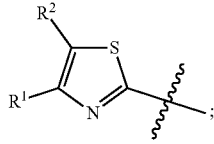

and
$R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$. In some embodiments, the optionally substituted ring A is

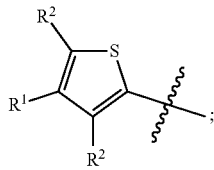

and
or one pair of $R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

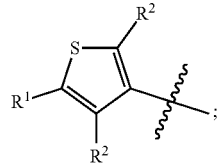

and
$R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the optionally substituted ring A is

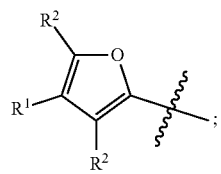

and
or one pair of $R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

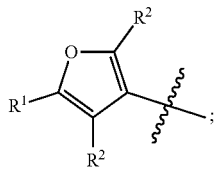

and
R¹ and R² on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^1R^9$.

In some embodiments, the optionally substituted ring A

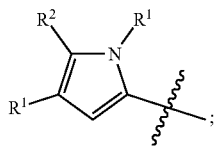

and
one pair of R¹ and R² on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, the optionally substituted ring A is

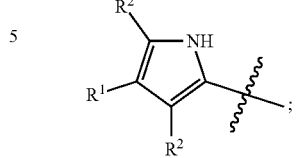

and
one pair of R¹ and R² on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, the optionally substituted ring A is

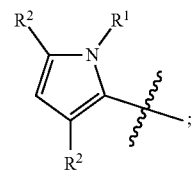

and
one pair of R¹ and R² on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, and $CONR^8R^9$.

In some embodiments, the optionally substituted ring A is

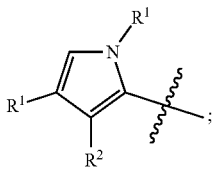

and
one pair of $R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^1R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

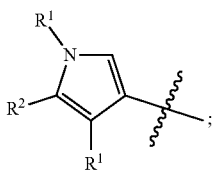

and
one pair of $R^1$ and $R^2$, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

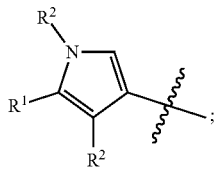

and
one pair of $R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

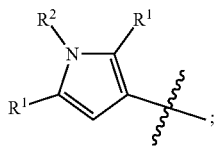

and
one pair of $R^1$ and $R^2$ on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

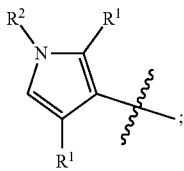

and

R¹ and R² on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

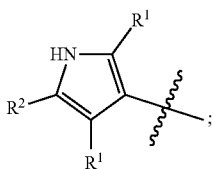

and

R¹ and R² on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

In some embodiments, the substituted ring A is

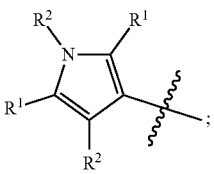

and one pair of R¹ and R² on adjacent atoms, taken together with the atoms connecting them, independently form at least one monocyclic or bicyclic $C_4$-$C_{12}$ carbocyclic ring or at least one monocyclic or bicyclic 5-to-12-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally independently substituted with one or more substituents independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, 5- to 10-membered heteroaryl, $C_3$-$C_{10}$ cycloalkyl, 3- to 10-membered heterocycloalkyl, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents selected from hydroxy, halo, $C_1$-$C_6$ alkyl optionally substituted with $NR^8R^9$, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, and $CONR^8R^9$.

Unless otherwise indicated, when a disclosed compound is named or depicted by a structure without specifying the stereochemistry and has one or more chiral centers, it is understood to represent all possible stereoisomers of the compound.

It is understood that the combination of variables in the formulae herein is such that the compounds are stable.

In some embodiments, provided herein is a compound that is selected from the group consisting of the compounds in Table 1A:

TABLE 1A
| Compound | Structure |
|---|---|
| 101 | 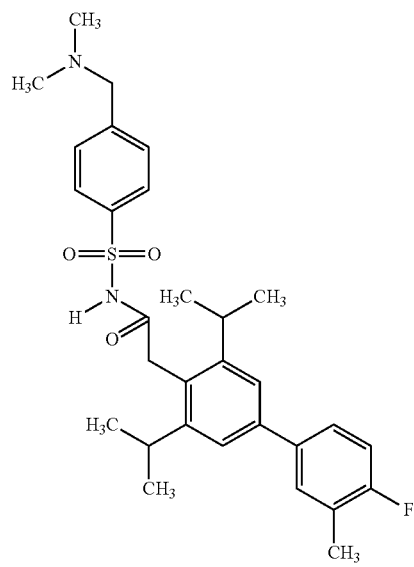 [SMILES: Cc1cc(-c2cc(C(C)C)c(CC(=O)NS(=O)(=O)c3ccc(CN(C)C)cc3)c(C(C)C)c2)ccc1F] |
| 102 | 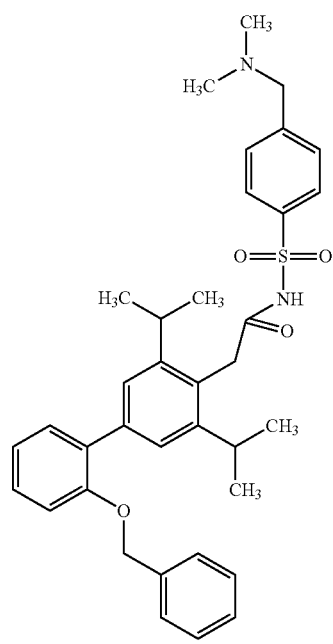 [SMILES: CC(C)c1cc(-c2ccccc2OCc2ccccc2)cc(C(C)C)c1CC(=O)NS(=O)(=O)c1ccc(CN(C)C)cc1] |

TABLE 1A-continued

| Compound | Structure |
|---|---|
| 103 | 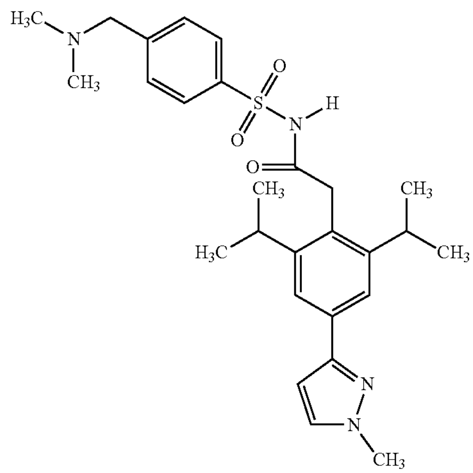 [SMILES: CC(C)c1cc(-c2ccn(C)n2)cc(C(C)C)c1CC(=O)NS(=O)(=O)c1ccc(CN(C)C)cc1] |
| 104 | 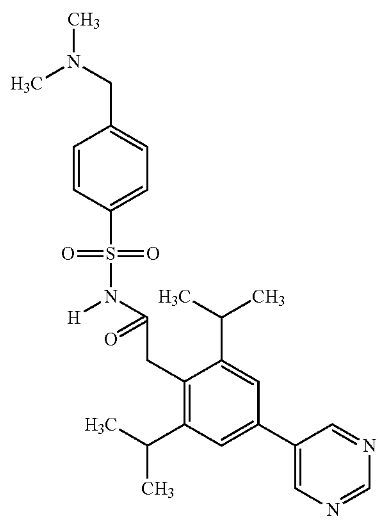 [SMILES: CC(C)c1cc(-c2cncnc2)cc(C(C)C)c1CC(=O)NS(=O)(=O)c1ccc(CN(C)C)cc1] |
| 105 | 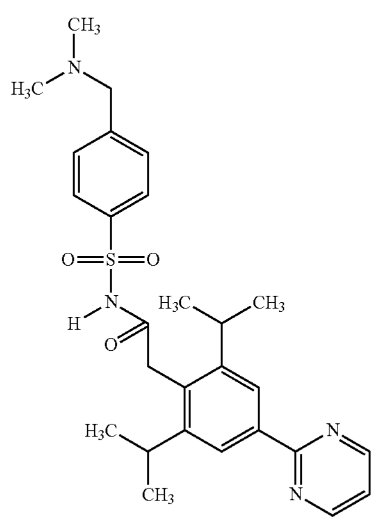 [SMILES: CC(C)c1cc(-c2ncccn2)cc(C(C)C)c1CC(=O)NS(=O)(=O)c1ccc(CN(C)C)cc1] |

TABLE 1A-continued

| Compound | Structure |
|---|---|
| 106 | 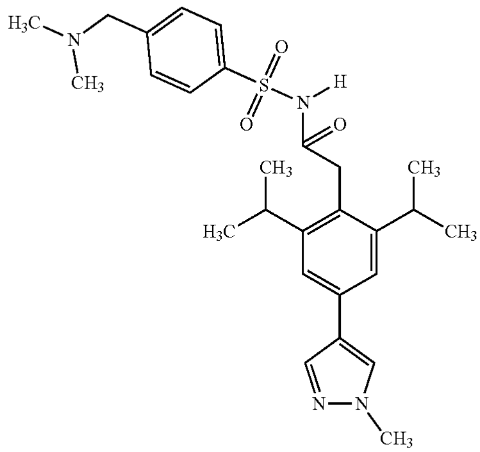 [SMILES: CC(C)c1cc(-c2cnn(C)c2)cc(C(C)C)c1CC(=O)NS(=O)(=O)c1ccc(CN(C)C)cc1] |
| 107 | 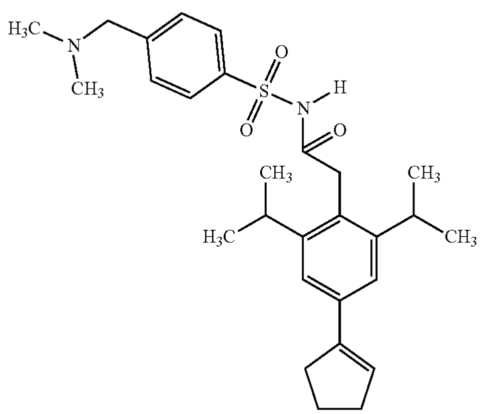 [SMILES: CC(C)c1cc(C2=CCCC2)cc(C(C)C)c1CC(=O)NS(=O)(=O)c1ccc(CN(C)C)cc1] |
| 108 | 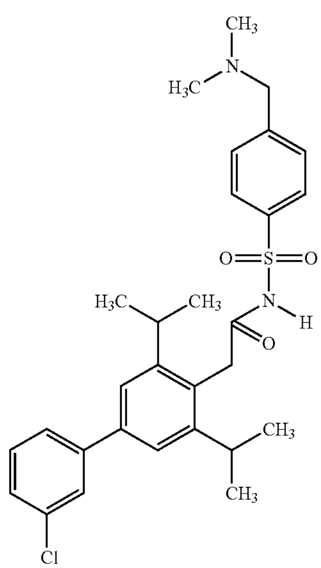 [SMILES: CC(C)c1cc(-c2cccc(Cl)c2)cc(C(C)C)c1CC(=O)NS(=O)(=O)c1ccc(CN(C)C)cc1] |

TABLE 1A-continued
| Compound | Structure |
|---|---|
| 109 | 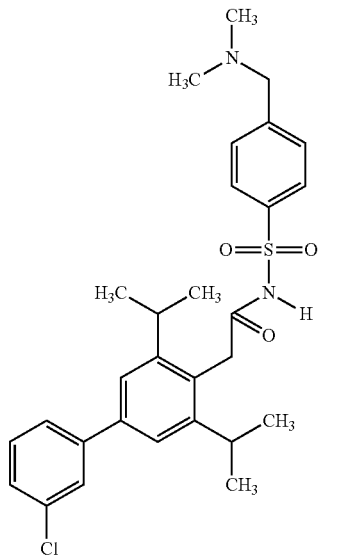 [SMILES: CC(C)c1cc(-c2cccc(Cl)c2)cc(C(C)C)c1CC(=O)NS(=O)(=O)c1ccc(CN(C)C)cc1] |
| 110 | 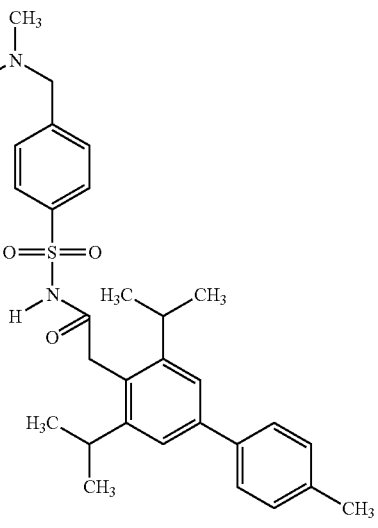 |
| 111 | 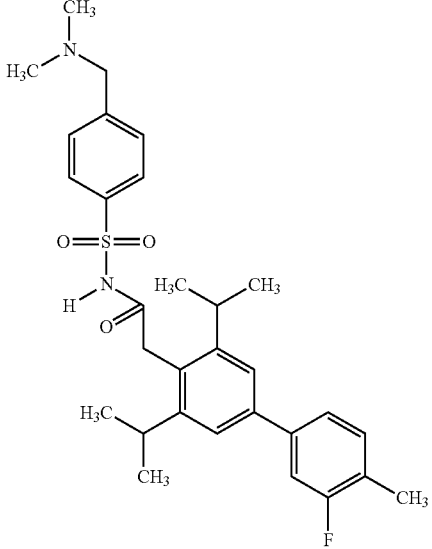 |

TABLE 1A-continued
| Compound | Structure |
|---|---|
| 112 | 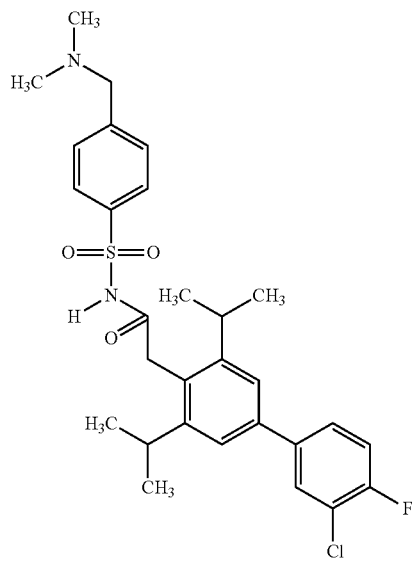 [SMILES: CC(C)c1cc(-c2ccc(F)c(Cl)c2)cc(C(C)C)c1CC(=O)NS(=O)(=O)c1ccc(CN(C)C)cc1] |
| 113 | 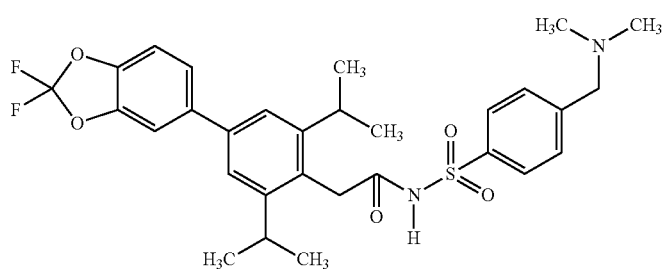 [SMILES: CC(C)c1cc(-c2ccc3c(c2)OC(F)(F)O3)cc(C(C)C)c1CC(=O)NS(=O)(=O)c1ccc(CN(C)C)cc1] |
| 114 | 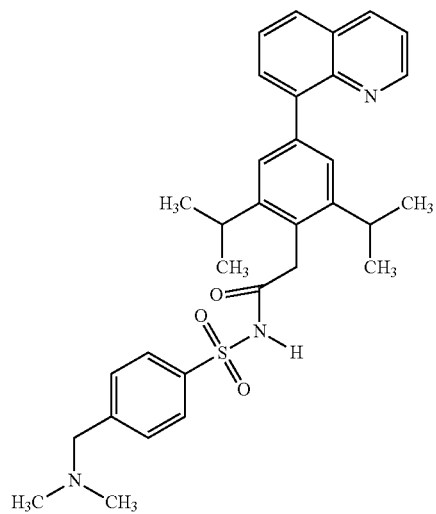 [SMILES: CC(C)c1cc(-c2cccc3cccnc23)cc(C(C)C)c1CC(=O)NS(=O)(=O)c1ccc(CN(C)C)cc1] |

TABLE 1A-continued

| Compound | Structure |
|---|---|
| 115 | 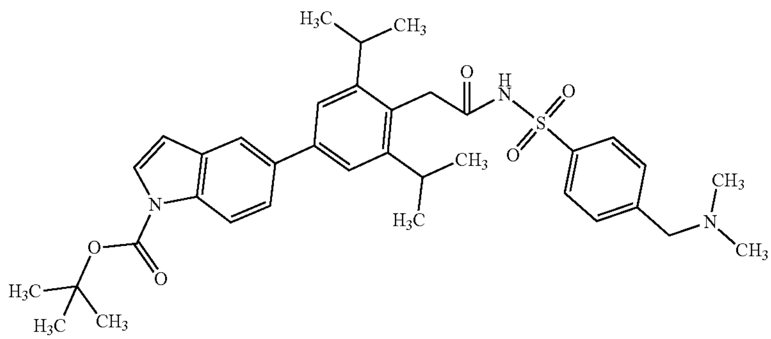 [SMILES: CC(C)c1cc(-c2ccc3c(ccn3C(=O)OC(C)(C)C)c2)cc(C(C)C)c1CC(=O)NS(=O)(=O)c1ccc(CN(C)C)cc1] |
| 116 | 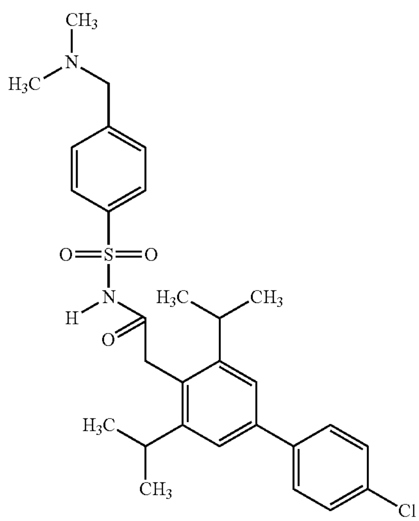 [SMILES: CC(C)c1cc(-c2ccc(Cl)cc2)cc(C(C)C)c1CC(=O)NS(=O)(=O)c1ccc(CN(C)C)cc1] |
| 117 | 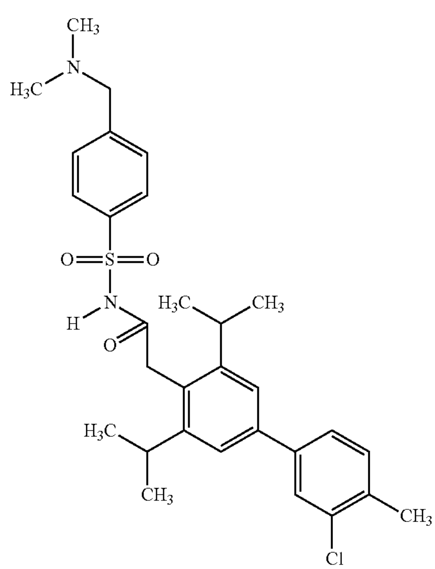 |

TABLE 1A-continued
| Compound | Structure |
|---|---|
| 118 | 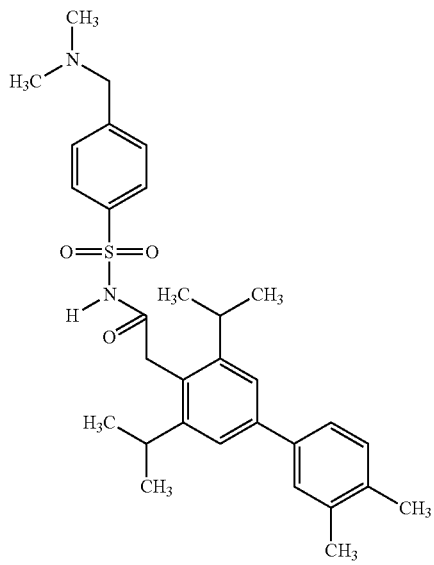 |
| 119 | 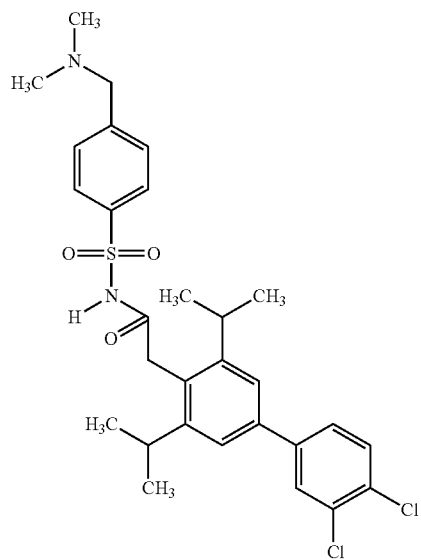 |

TABLE 1A-continued
| Compound | Structure |
|---|---|
| 120 | 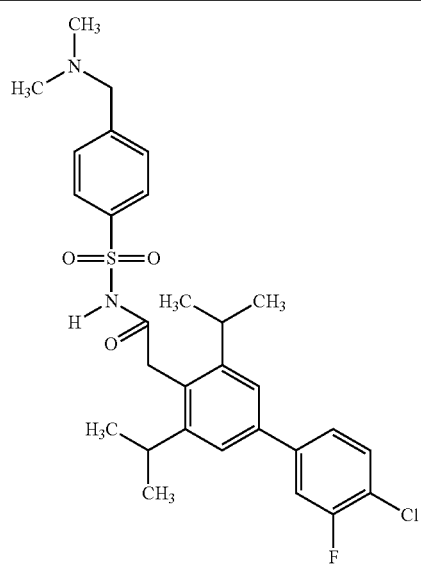 |
| 121 | 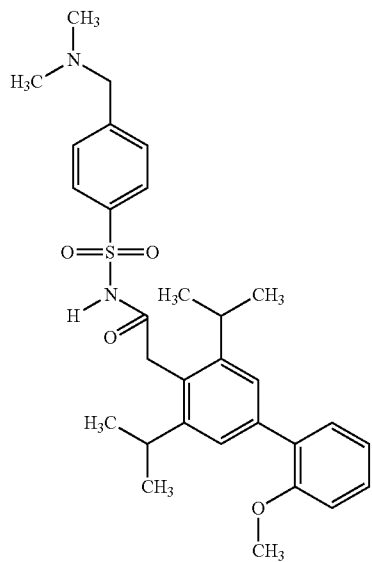 [SMILES: COc1ccccc1-c1cc(C(C)C)c(CC(=O)NS(=O)(=O)c2ccc(CN(C)C)cc2)c(C(C)C)c1] |

TABLE 1A-continued
| Compound | Structure |
|---|---|
| 122 | 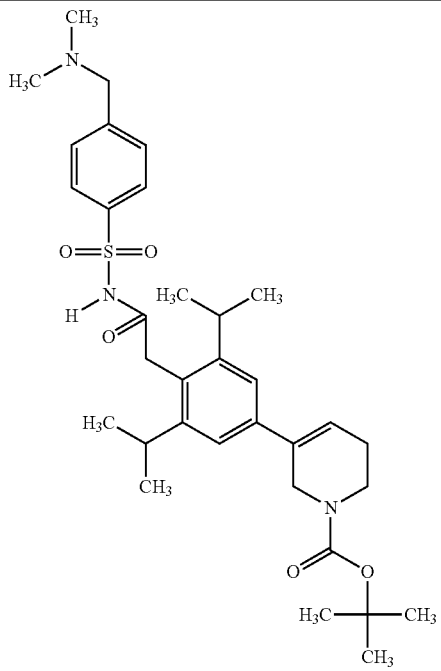 |
| 123 | 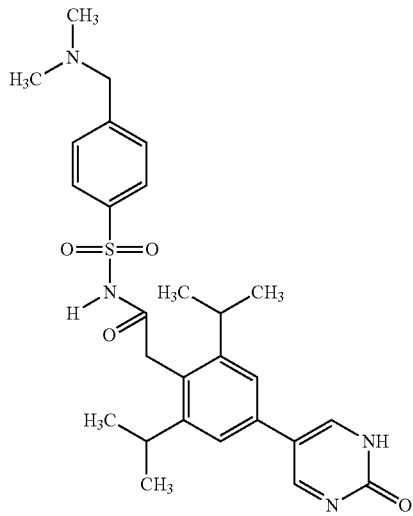 [SMILES: CC(C)c1cc(-c2cnc(=O)[nH]c2)cc(C(C)C)c1CC(=O)NS(=O)(=O)c1ccc(CN(C)C)cc1] |

TABLE 1A-continued
| Compound | Structure |
|---|---|
| 124 | 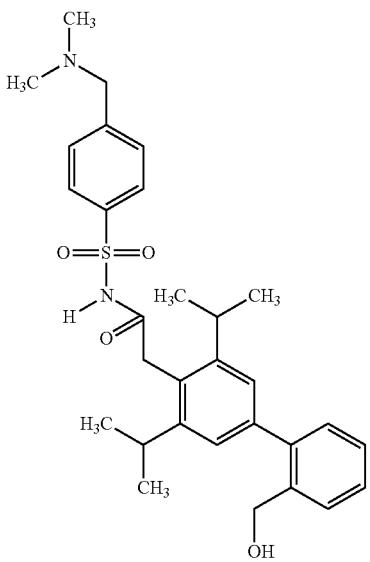 [SMILES: CC(C)c1cc(-c2ccccc2CO)cc(C(C)C)c1CC(=O)NS(=O)(=O)c1ccc(CN(C)C)cc1] |
| 125 | 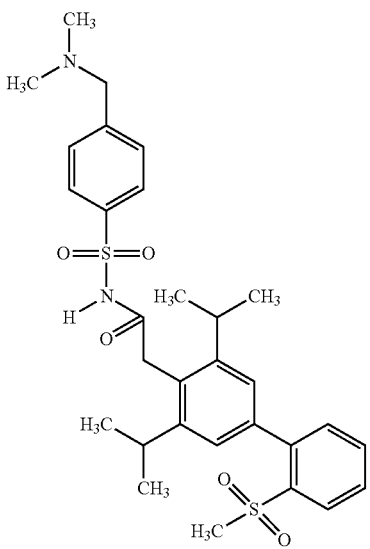 [SMILES: CC(C)c1cc(-c2ccccc2S(C)(=O)=O)cc(C(C)C)c1CC(=O)NS(=O)(=O)c1ccc(CN(C)C)cc1] |
| 126 | 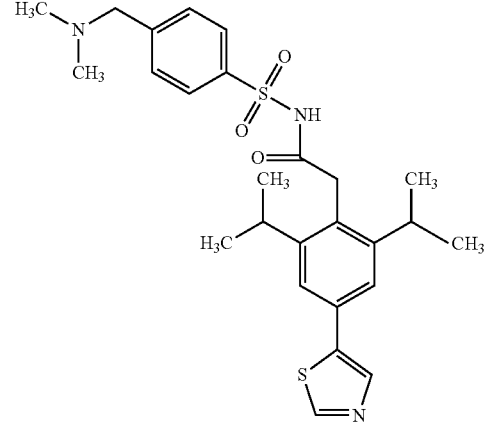 |

TABLE 1A-continued

| Compound | Structure |
|---|---|
| 127 | 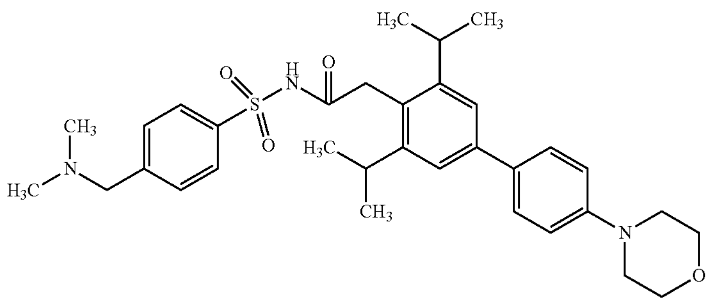 [SMILES: CC(C)c1cc(-c2ccc(N3CCOCC3)cc2)cc(C(C)C)c1CC(=O)NS(=O)(=O)c1ccc(CN(C)C)cc1] |
| 128 | 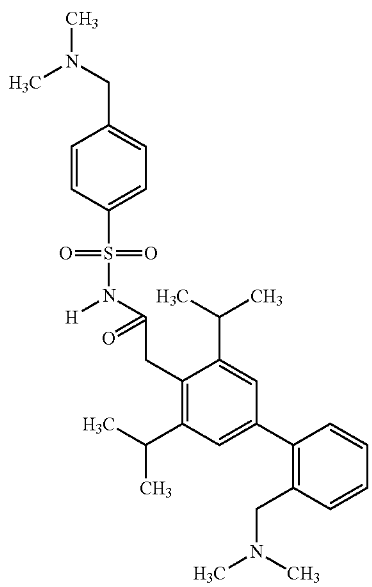 [SMILES: CC(C)c1cc(-c2ccccc2CN(C)C)cc(C(C)C)c1CC(=O)NS(=O)(=O)c1ccc(CN(C)C)cc1] |
| 129 | 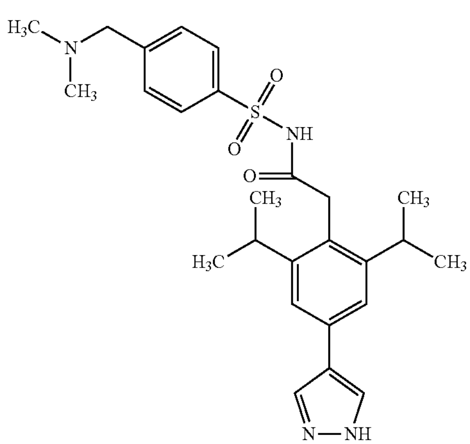 [SMILES: CC(C)c1cc(-c2cn[nH]c2)cc(C(C)C)c1CC(=O)NS(=O)(=O)c1ccc(CN(C)C)cc1] |

TABLE 1A-continued
| Compound | Structure |
|---|---|
| 130 | 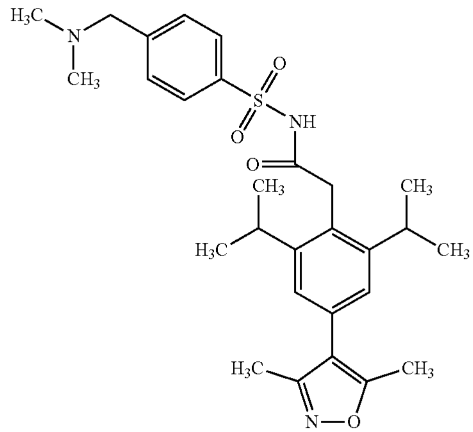 [SMILES: Cc1noc(C)c1-c1cc(C(C)C)c(CC(=O)NS(=O)(=O)c2ccc(CN(C)C)cc2)c(C(C)C)c1] |
| 131 | 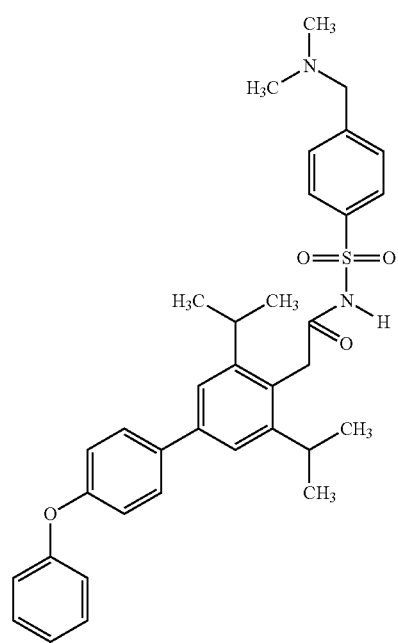 [SMILES: CC(C)c1cc(-c2ccc(Oc3ccccc3)cc2)cc(C(C)C)c1CC(=O)NS(=O)(=O)c1ccc(CN(C)C)cc1] |

TABLE 1A-continued

| Compound | Structure |
|----------|-----------|
| 132 | 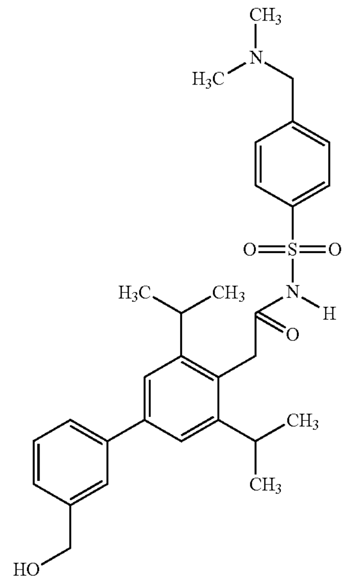 [SMILES: CC(C)c1cc(-c2cccc(CO)c2)cc(C(C)C)c1CC(=O)NS(=O)(=O)c1ccc(CN(C)C)cc1] |
| 133 | 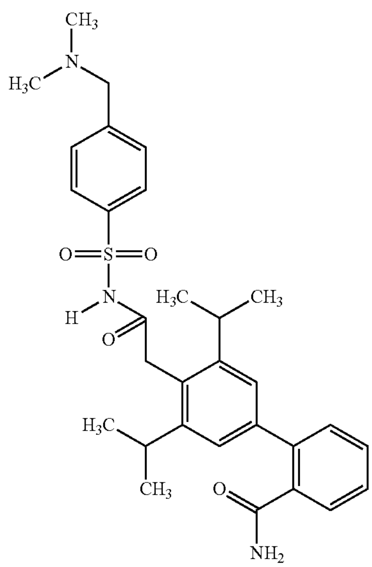 [SMILES: CC(C)c1cc(-c2ccccc2C(N)=O)cc(C(C)C)c1CC(=O)NS(=O)(=O)c1ccc(CN(C)C)cc1] |
| 134 | 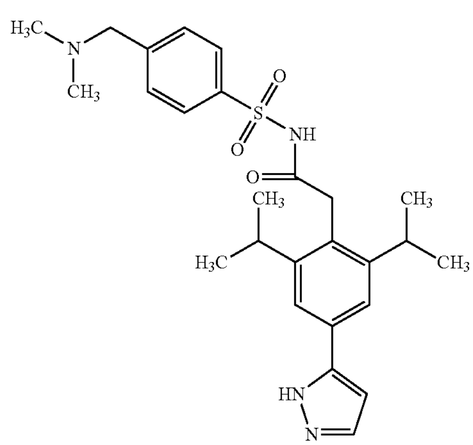 [SMILES: CC(C)c1cc(-c2ccn[nH]2)cc(C(C)C)c1CC(=O)NS(=O)(=O)c1ccc(CN(C)C)cc1] |

TABLE 1A-continued
| Compound | Structure |
|---|---|
| 135 | 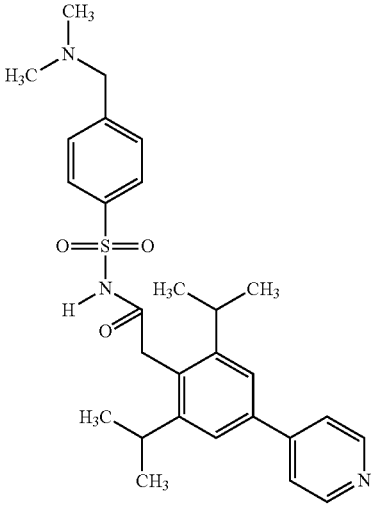 [SMILES: CC(C)c1cc(-c2ccncc2)cc(C(C)C)c1CC(=O)NS(=O)(=O)c1ccc(CN(C)C)cc1] |
| 136 | 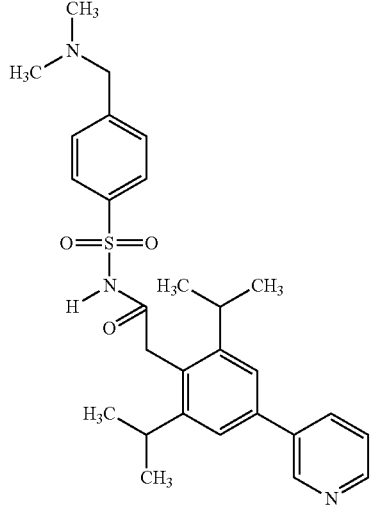 [SMILES: CC(C)c1cc(-c2cccnc2)cc(C(C)C)c1CC(=O)NS(=O)(=O)c1ccc(CN(C)C)cc1] |
| 137 | 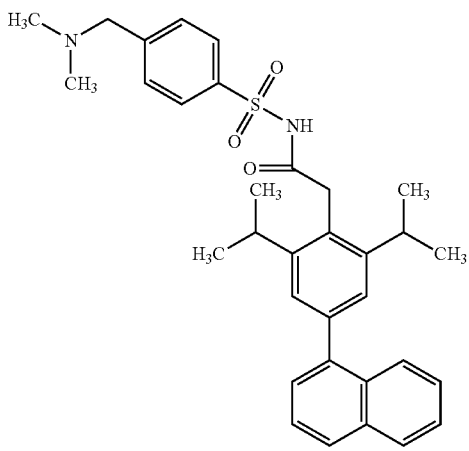 [SMILES: CC(C)c1cc(-c2cccc3ccccc23)cc(C(C)C)c1CC(=O)NS(=O)(=O)c1ccc(CN(C)C)cc1] |

TABLE 1A-continued
| Compound | Structure |
|---|---|
| 138 | 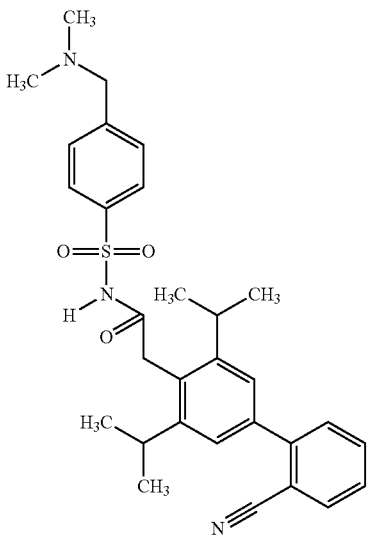 [SMILES: CC(C)c1cc(-c2ccccc2C#N)cc(C(C)C)c1CC(=O)NS(=O)(=O)c1ccc(CN(C)C)cc1] |
| 139 | 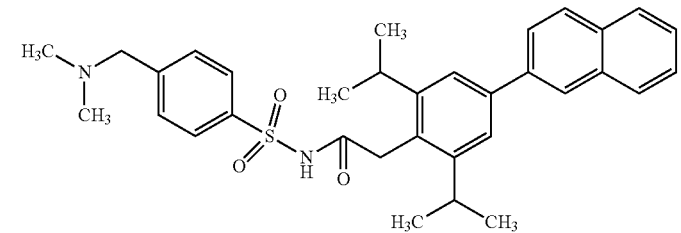 [SMILES: CC(C)c1cc(-c2ccc3ccccc3c2)cc(C(C)C)c1CC(=O)NS(=O)(=O)c1ccc(CN(C)C)cc1] |
| 140 | 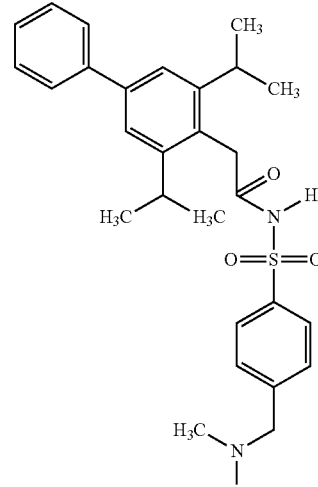 |

TABLE 1A-continued
| Compound | Structure |
|---|---|
| 141 | 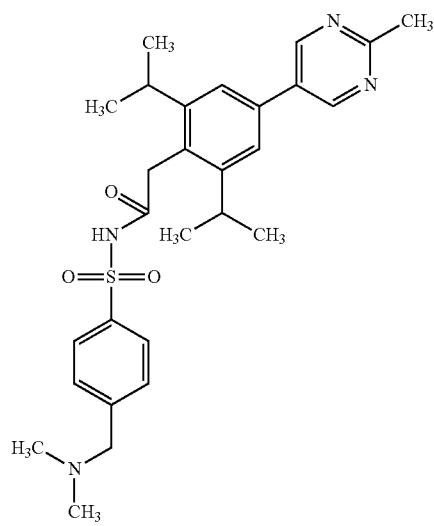 |
| 142 | 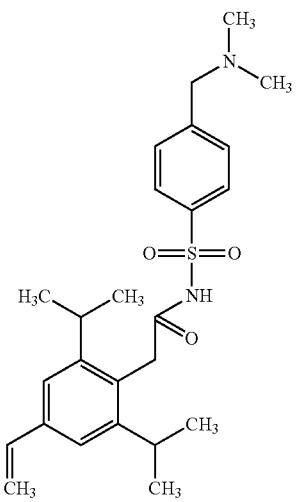 [SMILES: C=Cc1cc(C(C)C)c(CC(=O)NS(=O)(=O)c2ccc(CN(C)C)cc2)c(C(C)C)c1] |
| 143 | 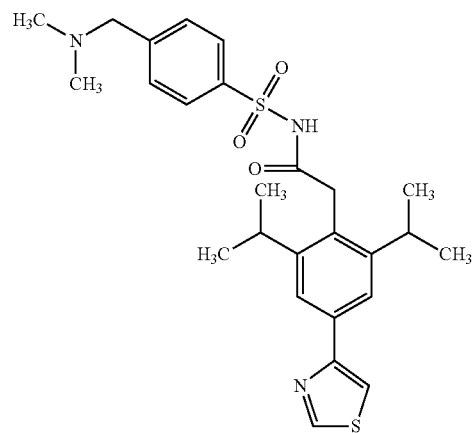 [SMILES: CC(C)c1cc(-c2cscn2)cc(C(C)C)c1CC(=O)NS(=O)(=O)c1ccc(CN(C)C)cc1] |

TABLE 1A-continued

| Compound | Structure |
|---|---|
| 144 | *(structure: 4-((dimethylamino)methyl)-N-(2-(2,6-diisopropyl-4-(furan-2-yl)phenyl)acetyl)benzenesulfonamide)* |
| 145 | *(structure: 4-((dimethylamino)methyl)-N-(2-(4-(but-2-en-2-yl)-2,6-diisopropylphenyl)acetyl)benzenesulfonamide)* |
| 146 | *(structure: 4-((dimethylamino)methyl)-N-(2-(4'-chloro-2,6-diisopropyl-3'-methyl-[1,1'-biphenyl]-4-yl)acetyl)benzenesulfonamide)* |

TABLE 1A-continued
| Compound | Structure |
|---|---|
| 147 | 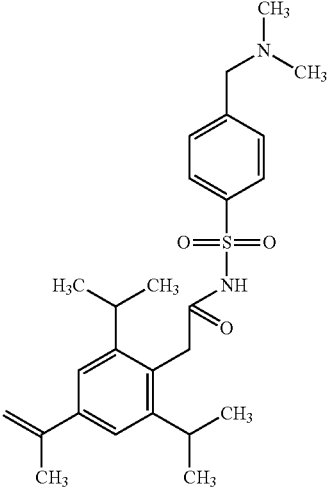 [SMILES: C=C(C)c1cc(C(C)C)c(CC(=O)NS(=O)(=O)c2ccc(CN(C)C)cc2)c(C(C)C)c1] |
| 148 | 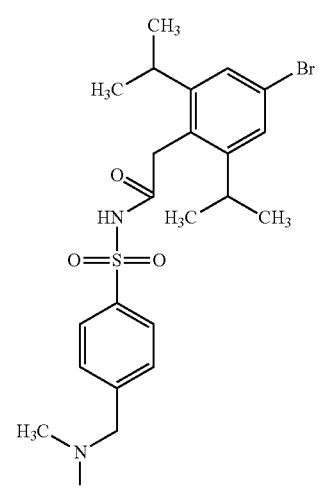 |
| 149 | 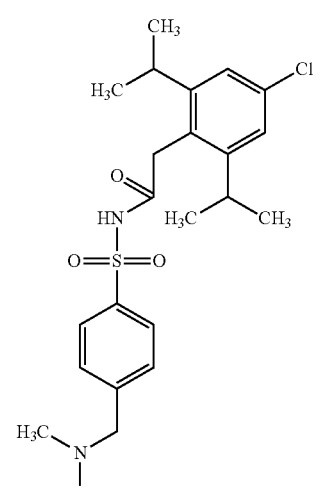 |

TABLE 1A-continued
| Compound | Structure |
|---|---|
| 150 | 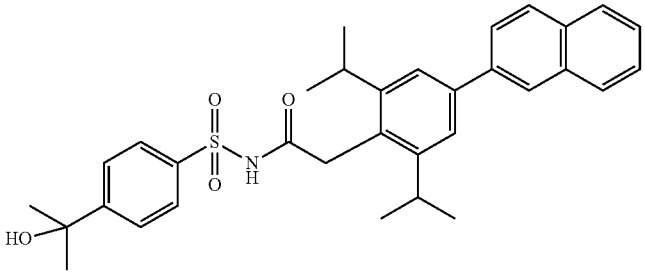 [SMILES: CC(C)c1cc(-c2ccc3ccccc3c2)cc(C(C)C)c1CC(=O)NS(=O)(=O)c1ccc(C(C)(C)O)cc1] |
| 151 | 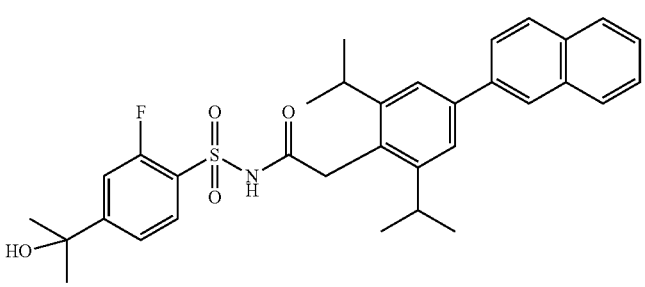 [SMILES: CC(C)c1cc(-c2ccc3ccccc3c2)cc(C(C)C)c1CC(=O)NS(=O)(=O)c1ccc(C(C)(C)O)cc1F] |
| 152 | 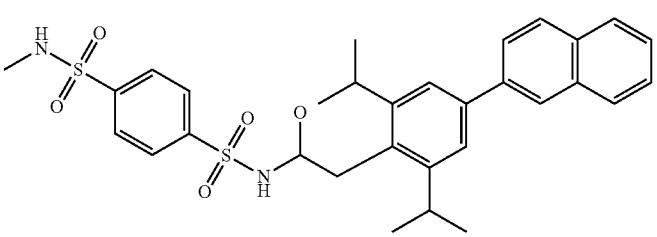 [SMILES: CNS(=O)(=O)c1ccc(S(=O)(=O)NC(O)Cc2c(C(C)C)cc(-c3ccc4ccccc4c3)cc2C(C)C)cc1] |
| 153 | 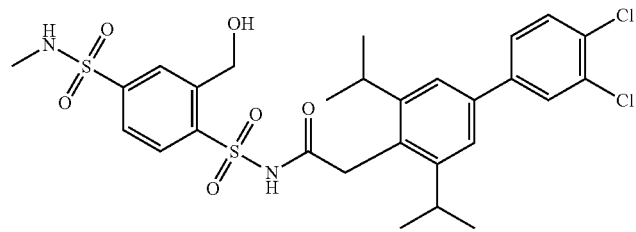 [SMILES: CNS(=O)(=O)c1ccc(S(=O)(=O)NC(=O)Cc2c(C(C)C)cc(-c3ccc(Cl)c(Cl)c3)cc2C(C)C)c(CO)c1] |
| 154 | 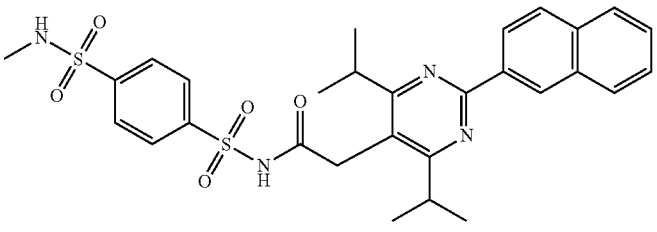 [SMILES: CNS(=O)(=O)c1ccc(S(=O)(=O)NC(=O)Cc2c(C(C)C)nc(-c3ccc4ccccc4c3)nc2C(C)C)cc1] |
| 155 | 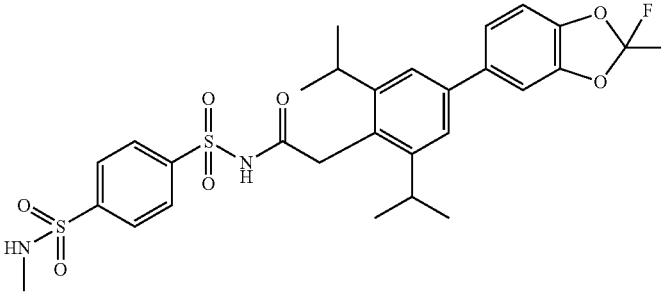 |

TABLE 1A-continued

| Compound | Structure |
|---|---|
| 156 | 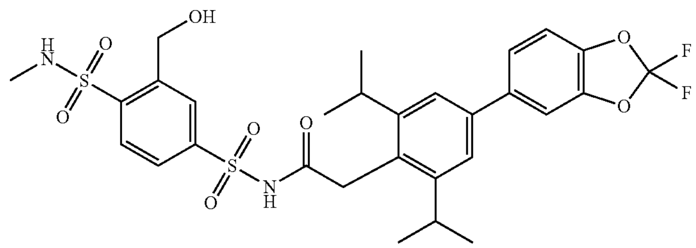 |
| 157 | 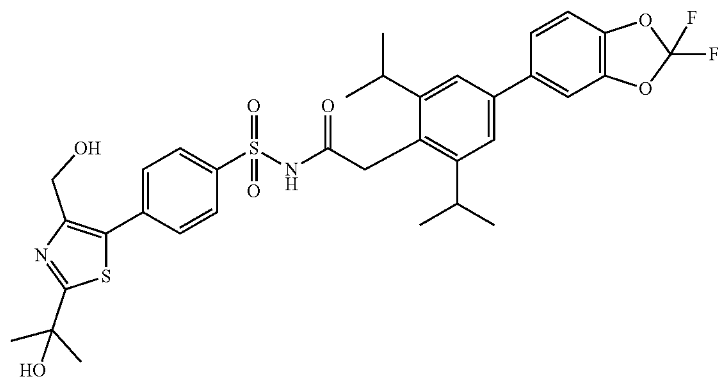 |
| 158 | 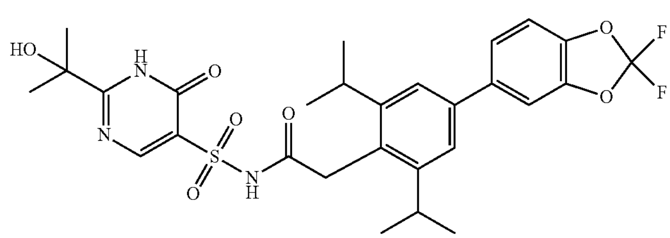 |
| 159 | 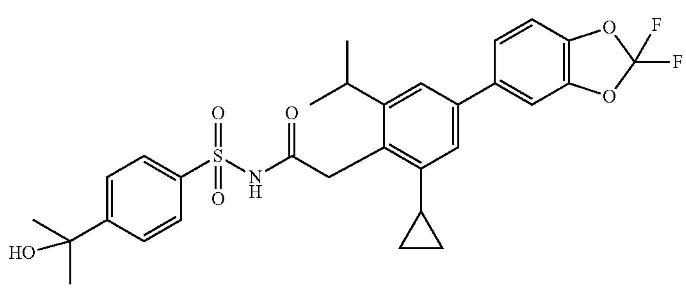 |

TABLE 1A-continued
| Compound | Structure |
|---|---|
| 160 | 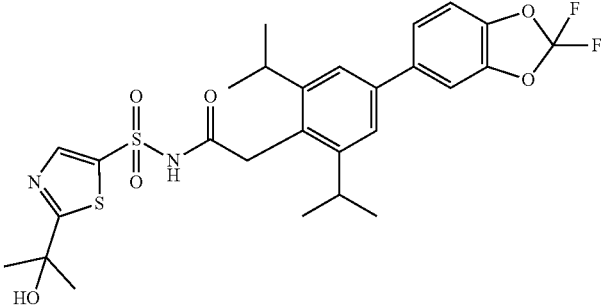 |
| 161 | 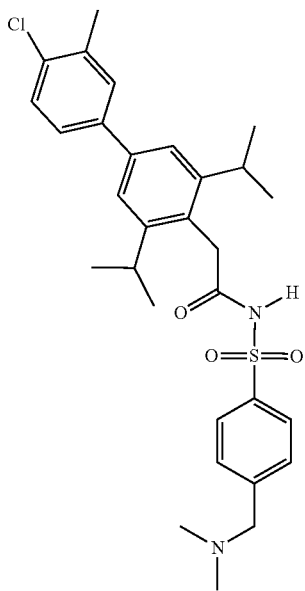 [SMILES: Cc1cc(-c2cc(C(C)C)c(CC(=O)NS(=O)(=O)c3ccc(CN(C)C)cc3)c(C(C)C)c2)ccc1Cl] |
or a pharmaceutically acceptable salt thereof.

In some embodiments, provided herein is a compound that is selected from the group consisting of the compounds in Table 1B:
TABLE 1B
| Compound | Structure |
|---|---|
| 101 | 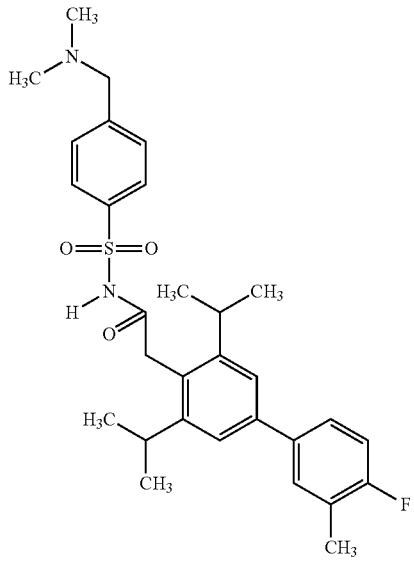 [SMILES: Cc1cc(-c2cc(C(C)C)c(CC(=O)NS(=O)(=O)c3ccc(CN(C)C)cc3)c(C(C)C)c2)ccc1F] |
| 102 | 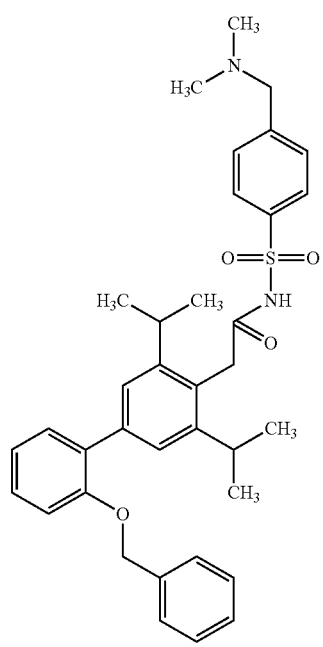 [SMILES: CC(C)c1cc(-c2ccccc2OCc2ccccc2)cc(C(C)C)c1CC(=O)NS(=O)(=O)c1ccc(CN(C)C)cc1] |

TABLE 1B-continued

| Compound | Structure |
|---|---|
| 103 | 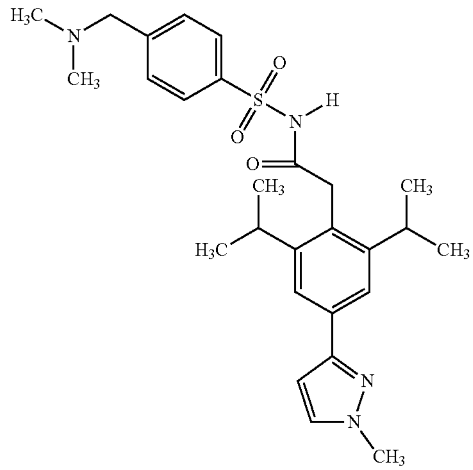 [SMILES: CC(C)c1cc(-c2ccn(C)n2)cc(C(C)C)c1CC(=O)NS(=O)(=O)c1ccc(CN(C)C)cc1] |
| 104 | 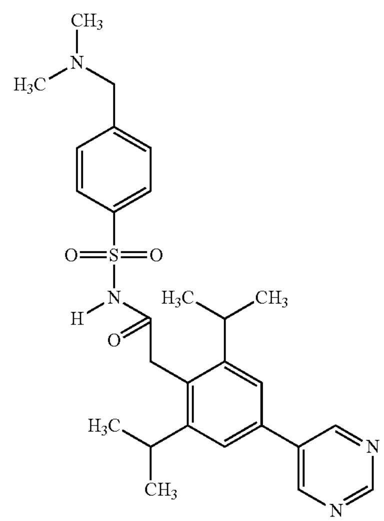 [SMILES: CC(C)c1cc(-c2cncnc2)cc(C(C)C)c1CC(=O)NS(=O)(=O)c1ccc(CN(C)C)cc1] |
| 105 | 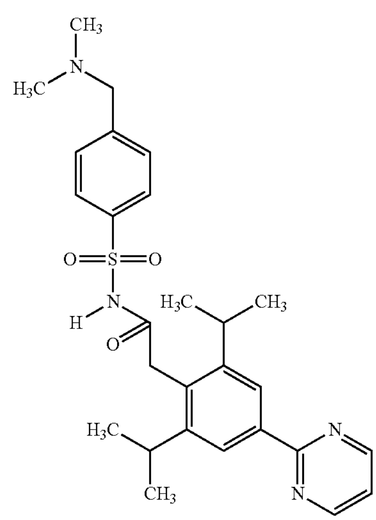 [SMILES: CC(C)c1cc(-c2ncccn2)cc(C(C)C)c1CC(=O)NS(=O)(=O)c1ccc(CN(C)C)cc1] |

TABLE 1B-continued
| Compound | Structure |
|---|---|
| 106 | 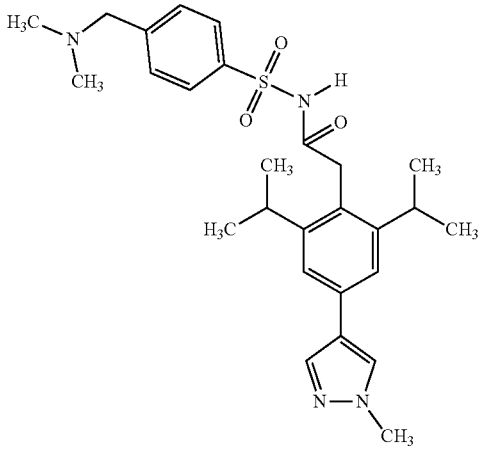 [SMILES: CC(C)c1cc(-c2cnn(C)c2)cc(C(C)C)c1CC(=O)NS(=O)(=O)c1ccc(CN(C)C)cc1] |
| 107 | 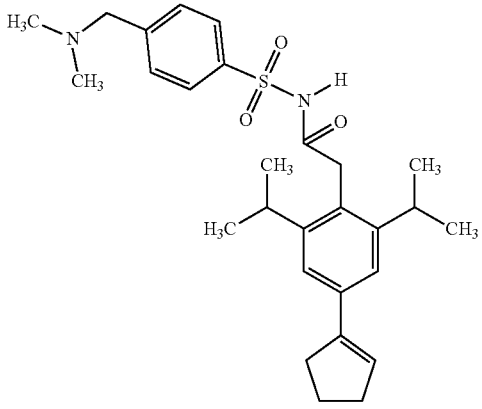 [SMILES: CC(C)c1cc(C2=CCCC2)cc(C(C)C)c1CC(=O)NS(=O)(=O)c1ccc(CN(C)C)cc1] |
| 108 | 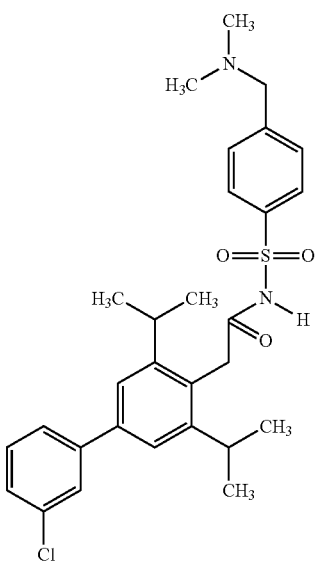 [SMILES: CC(C)c1cc(-c2cccc(Cl)c2)cc(C(C)C)c1CC(=O)NS(=O)(=O)c1ccc(CN(C)C)cc1] |

TABLE 1B-continued
| Compound | Structure |
|---|---|
| 109 | 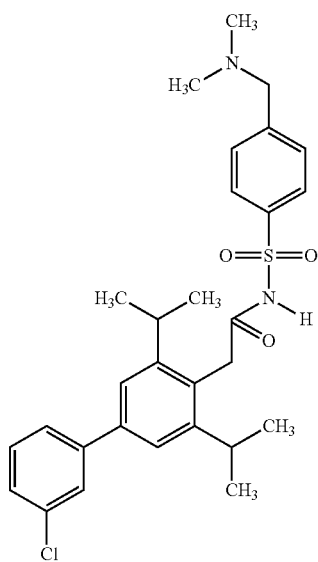 [SMILES: CC(C)c1cc(-c2cccc(Cl)c2)cc(C(C)C)c1CC(=O)NS(=O)(=O)c1ccc(CN(C)C)cc1] |
| 110 | 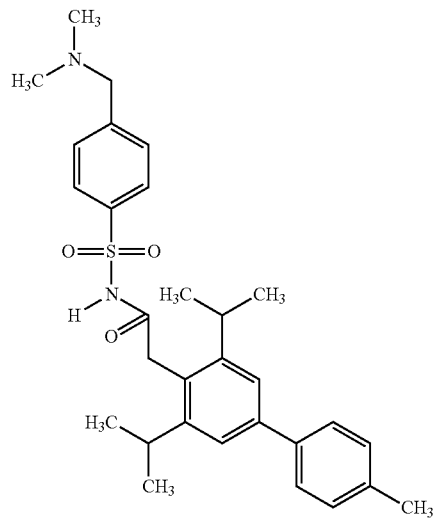 |

TABLE 1B-continued
| Compound | Structure |
|---|---|
| 111 | 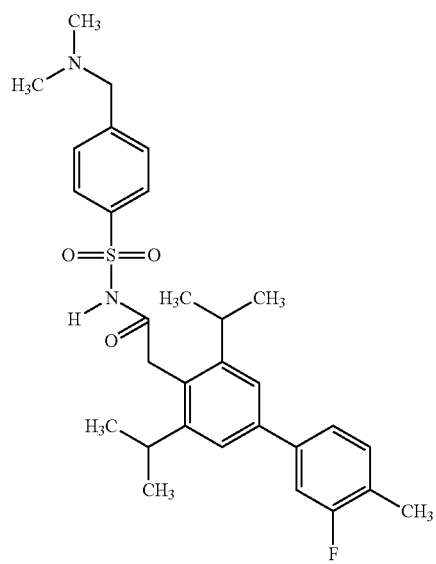 |
| 112 | 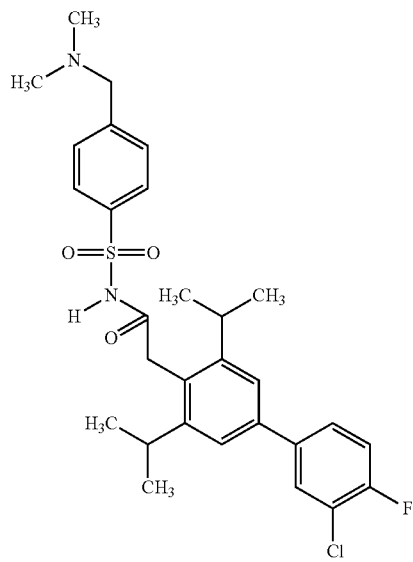 [SMILES: CC(C)c1cc(-c2ccc(F)c(Cl)c2)cc(C(C)C)c1CC(=O)NS(=O)(=O)c1ccc(CN(C)C)cc1] |
| 113 | 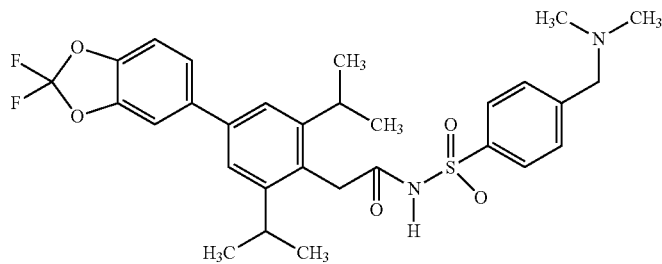 |

TABLE 1B-continued

| Compound | Structure |
| --- | --- |
| 114 | 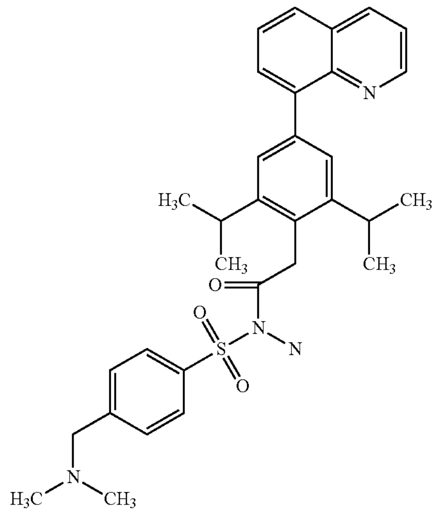 [SMILES: CC(C)c1cc(-c2cccc3cccnc23)cc(C(C)C)c1CC(=O)N(N)S(=O)(=O)c1ccc(CN(C)C)cc1] |
| 115 | 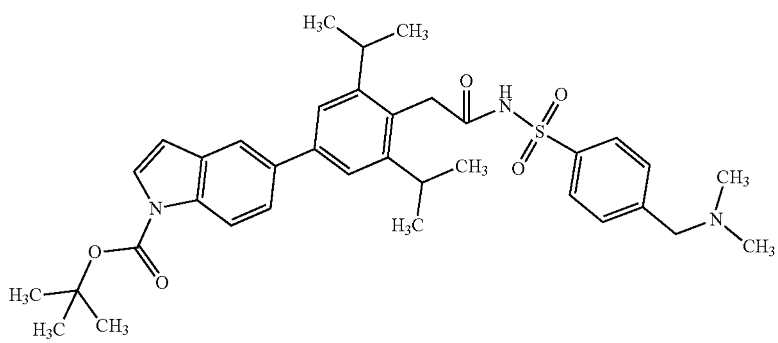 [SMILES: CC(C)c1cc(-c2ccc3c(ccn3C(=O)OC(C)(C)C)c2)cc(C(C)C)c1CC(=O)NS(=O)(=O)c1ccc(CN(C)C)cc1] |
| 116 | 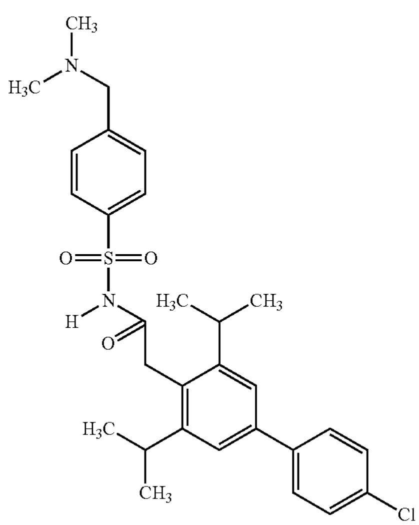 [SMILES: CC(C)c1cc(-c2ccc(Cl)cc2)cc(C(C)C)c1CC(=O)NS(=O)(=O)c1ccc(CN(C)C)cc1] |

TABLE 1B-continued
| Compound | Structure |
|---|---|
| 117 | 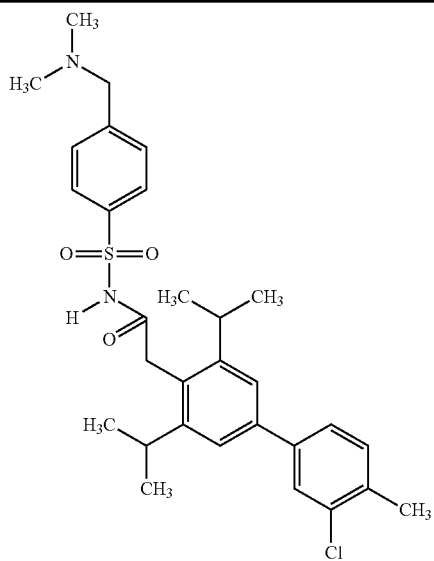 |
| 118 | 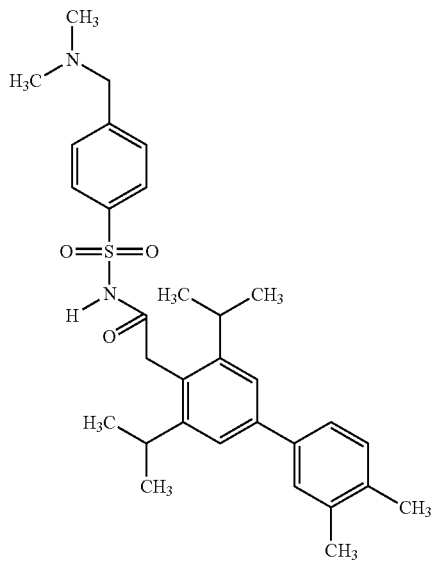 |

TABLE 1B-continued
| Compound | Structure |
|---|---|
| 119 | 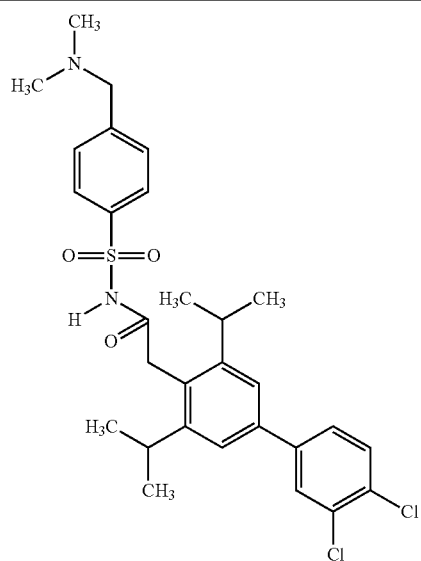 |
| 120 | 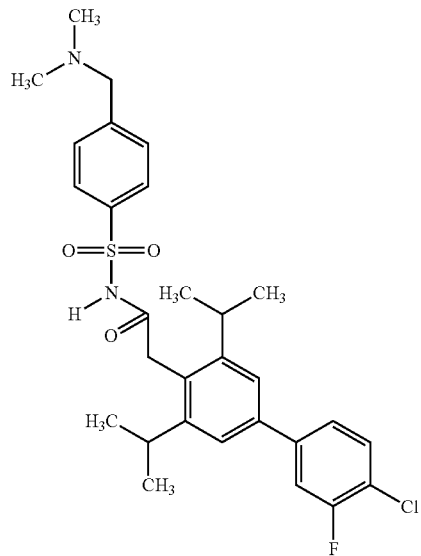 |

TABLE 1B-continued
| Compound | Structure |
|---|---|
| 121 | 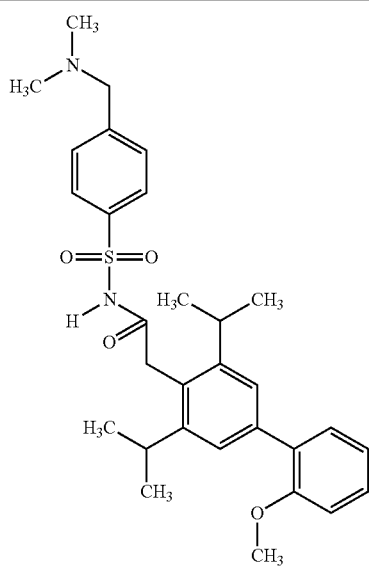 [SMILES: COc1ccccc1-c1cc(C(C)C)c(CC(=O)NS(=O)(=O)c2ccc(CN(C)C)cc2)c(C(C)C)c1] |
| 122 | 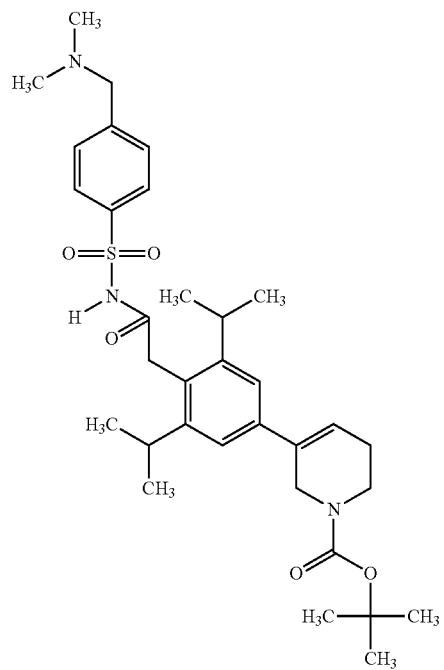 [SMILES: CC(C)c1cc(C2=CCCN(C(=O)OC(C)(C)C)C2)cc(C(C)C)c1CC(=O)NS(=O)(=O)c1ccc(CN(C)C)cc1] |

TABLE 1B-continued

| Compound | Structure |
|---|---|
| 123 | 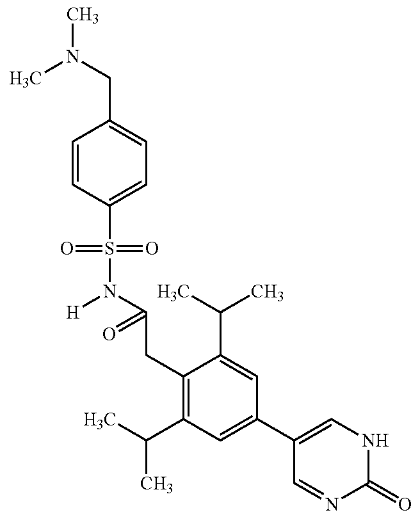 [SMILES: CC(C)c1cc(-c2cnc(=O)[nH]c2)cc(C(C)C)c1CC(=O)NS(=O)(=O)c1ccc(CN(C)C)cc1] |
| 124 | 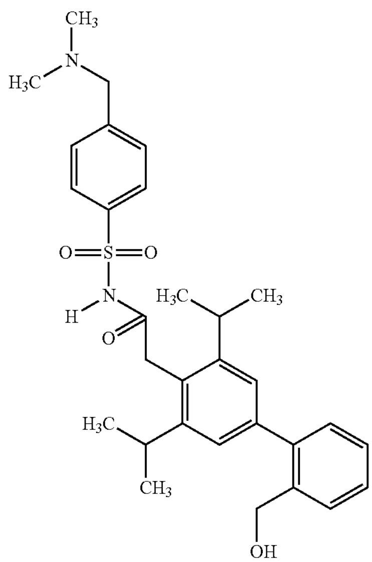 [SMILES: CC(C)c1cc(-c2ccccc2CO)cc(C(C)C)c1CC(=O)NS(=O)(=O)c1ccc(CN(C)C)cc1] |
| 125 | 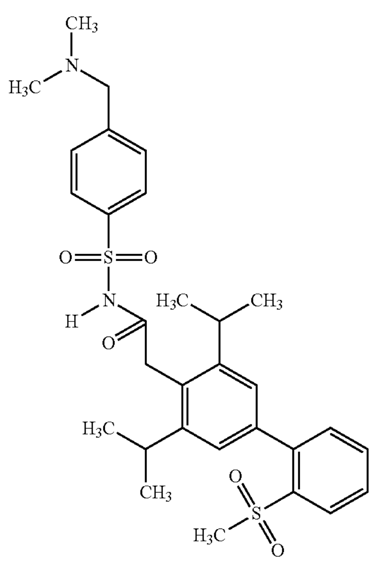 [SMILES: CC(C)c1cc(-c2ccccc2S(C)(=O)=O)cc(C(C)C)c1CC(=O)NS(=O)(=O)c1ccc(CN(C)C)cc1] |

TABLE 1B-continued

| Compound | Structure |
|---|---|
| 126 | 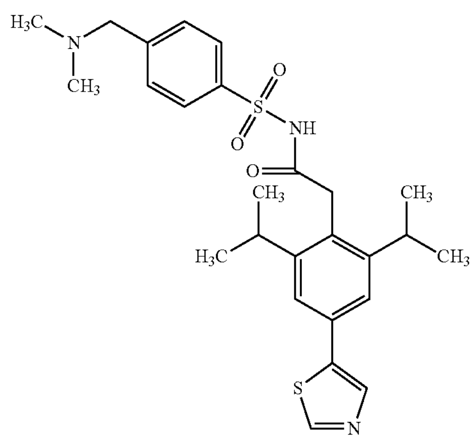 [SMILES: CC(C)c1cc(-c2cncs2)cc(C(C)C)c1CC(=O)NS(=O)(=O)c1ccc(CN(C)C)cc1] |
| 127 | 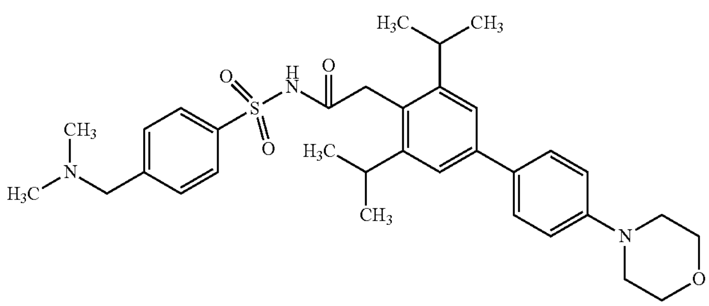 [SMILES: CC(C)c1cc(-c2ccc(N3CCOCC3)cc2)cc(C(C)C)c1CC(=O)NS(=O)(=O)c1ccc(CN(C)C)cc1] |
| 128 | 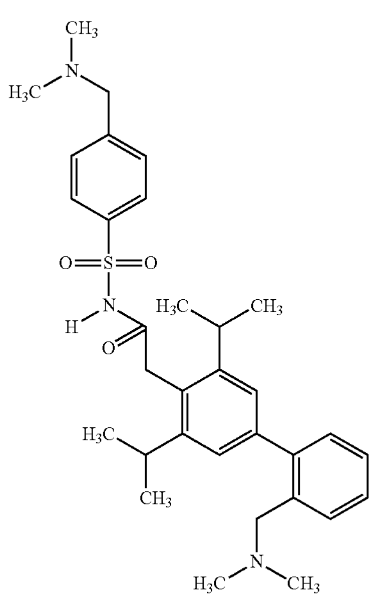 [SMILES: CC(C)c1cc(-c2ccccc2CN(C)C)cc(C(C)C)c1CC(=O)NS(=O)(=O)c1ccc(CN(C)C)cc1] |

TABLE 1B-continued
| Compound | Structure |
|---|---|
| 129 | 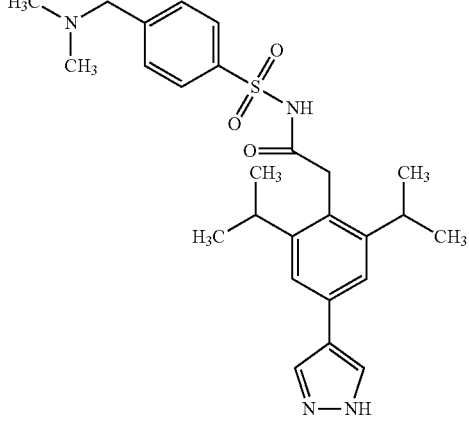 |
| 130 | 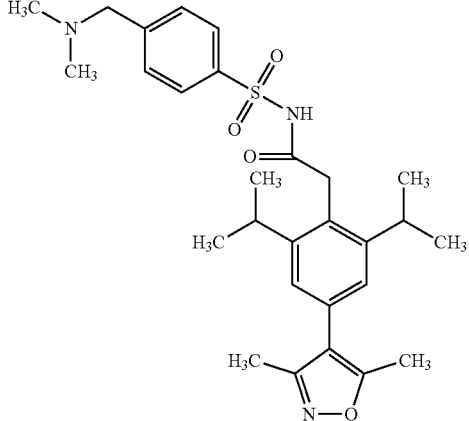 [SMILES: Cc1noc(C)c1-c1cc(C(C)C)c(CC(=O)NS(=O)(=O)c2ccc(CN(C)C)cc2)c(C(C)C)c1] |
| 131 | 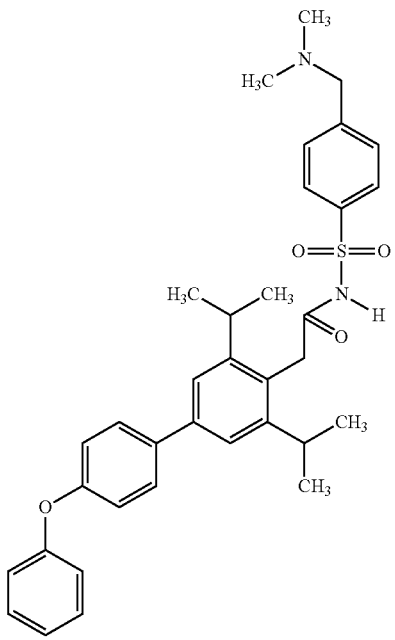 [SMILES: CC(C)c1cc(-c2ccc(Oc3ccccc3)cc2)cc(C(C)C)c1CC(=O)NS(=O)(=O)c1ccc(CN(C)C)cc1] |

TABLE 1B-continued

| Compound | Structure |
|---|---|
| 132 | 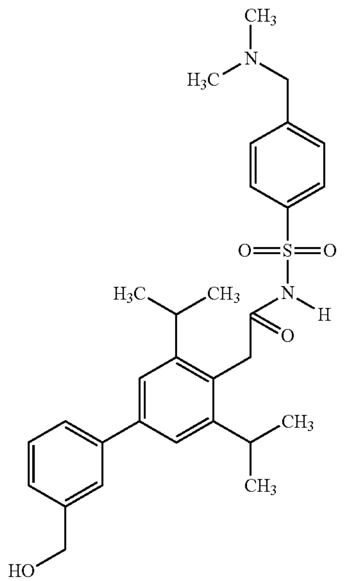 [SMILES: CC(C)c1cc(-c2cccc(CO)c2)cc(C(C)C)c1CC(=O)NS(=O)(=O)c1ccc(CN(C)C)cc1] |
| 133 | 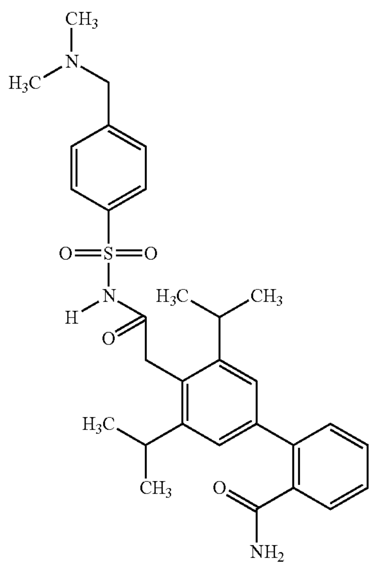 [SMILES: CC(C)c1cc(-c2ccccc2C(N)=O)cc(C(C)C)c1CC(=O)NS(=O)(=O)c1ccc(CN(C)C)cc1] |
| 134 | 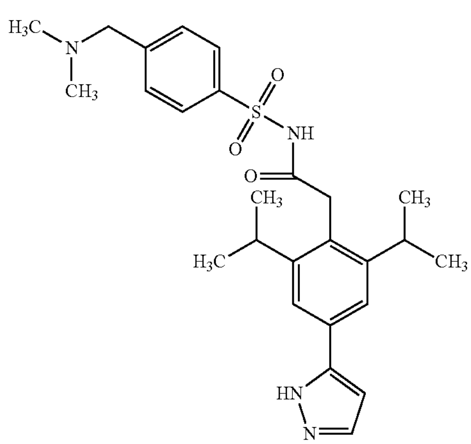 [SMILES: CC(C)c1cc(-c2ccn[nH]2)cc(C(C)C)c1CC(=O)NS(=O)(=O)c1ccc(CN(C)C)cc1] |

TABLE 1B-continued
| Compound | Structure |
|---|---|
| 135 | 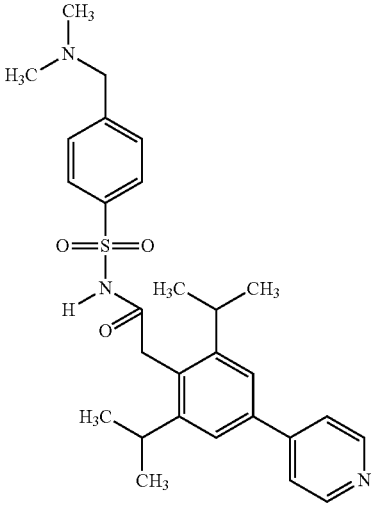 [SMILES: CC(C)c1cc(-c2ccncc2)cc(C(C)C)c1CC(=O)NS(=O)(=O)c1ccc(CN(C)C)cc1] |
| 136 | 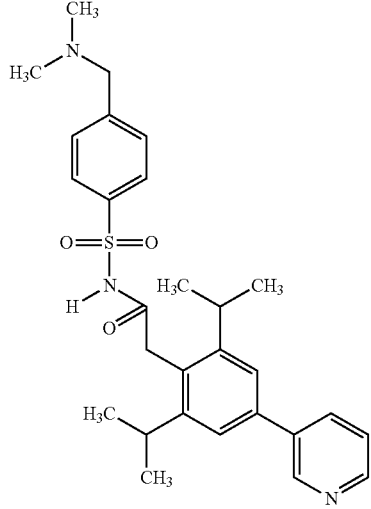 [SMILES: CC(C)c1cc(-c2cccnc2)cc(C(C)C)c1CC(=O)NS(=O)(=O)c1ccc(CN(C)C)cc1] |
| 137 | 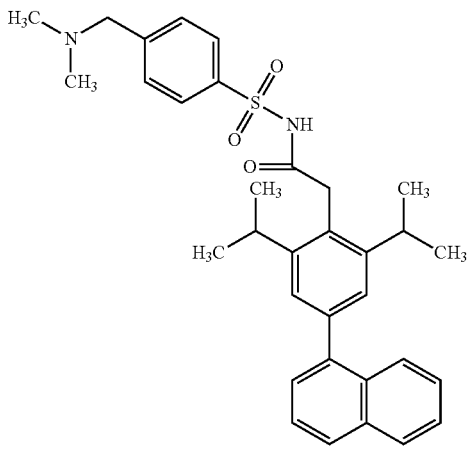 [SMILES: CC(C)c1cc(-c2cccc3ccccc23)cc(C(C)C)c1CC(=O)NS(=O)(=O)c1ccc(CN(C)C)cc1] |

TABLE 1B-continued
| Compound | Structure |
|---|---|
| 138 | 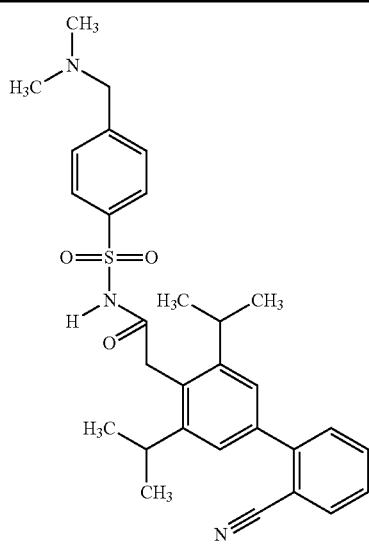 |
| 139 | 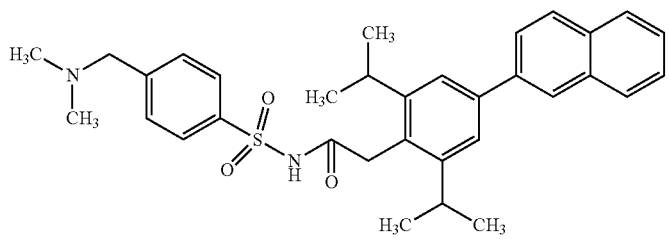 |
| 140 | 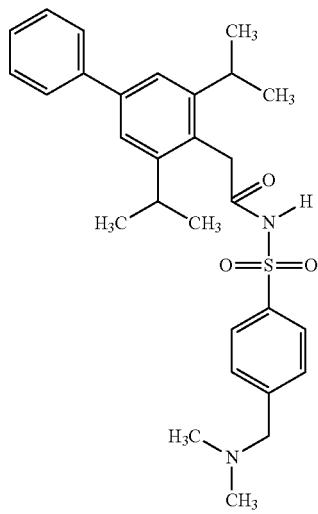 [SMILES: CC(C)c1cc(-c2ccccc2)cc(C(C)C)c1CC(=O)NS(=O)(=O)c1ccc(CN(C)C)cc1] |

TABLE 1B-continued

| Compound | Structure |
|---|---|
| 141 | *(structure)* |
| 142 | *(structure)* |
| 143 | *(structure)* |

TABLE 1B-continued
| Compound | Structure |
|---|---|
| 144 | 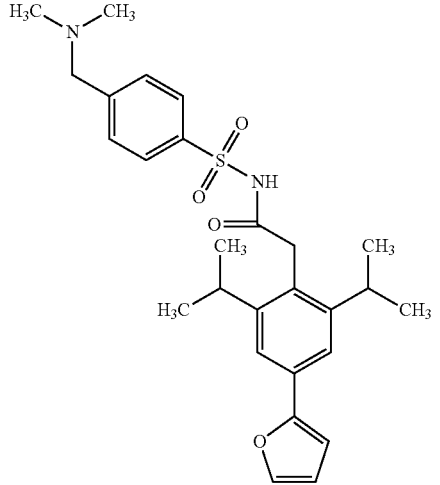 [SMILES: CC(C)c1cc(-c2ccco2)cc(C(C)C)c1CC(=O)NS(=O)(=O)c1ccc(CN(C)C)cc1] |
| 145 | 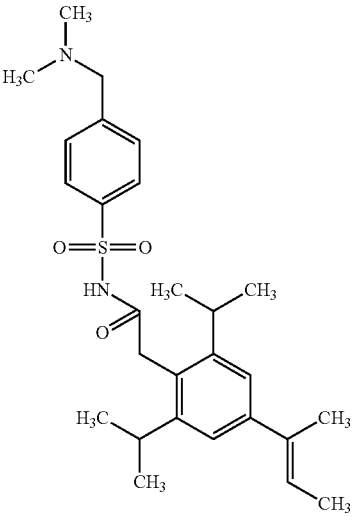 [SMILES: C/C=C(\C)c1cc(C(C)C)c(CC(=O)NS(=O)(=O)c2ccc(CN(C)C)cc2)c(C(C)C)c1] |
| 146 | 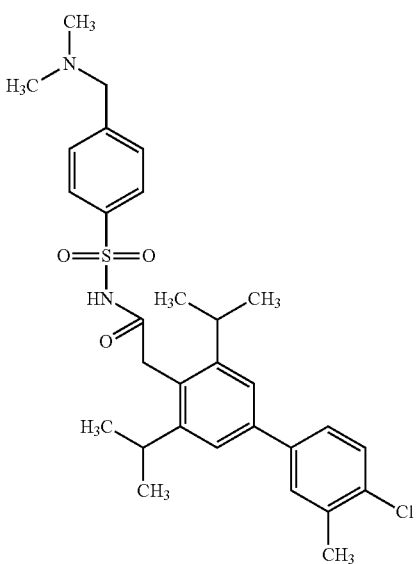 [SMILES: Cc1cc(-c2cc(C(C)C)c(CC(=O)NS(=O)(=O)c3ccc(CN(C)C)cc3)c(C(C)C)c2)ccc1Cl] |

TABLE 1B-continued

| Compound | Structure |
|---|---|
| 147 | 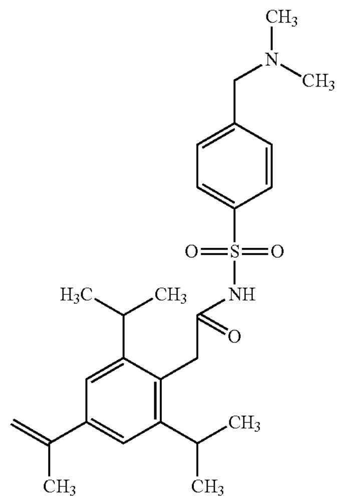 [SMILES: C=C(C)c1cc(C(C)C)c(CC(=O)NS(=O)(=O)c2ccc(CN(C)C)cc2)c(C(C)C)c1] |
| 150 | 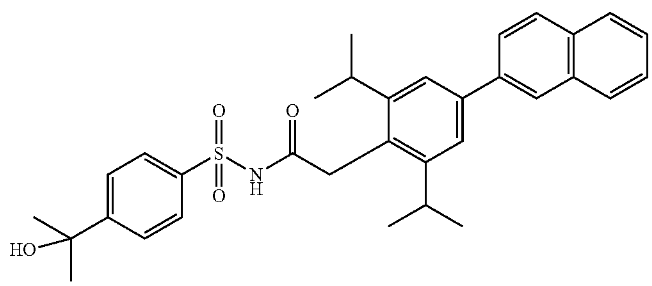 [SMILES: CC(C)c1cc(-c2ccc3ccccc3c2)cc(C(C)C)c1CC(=O)NS(=O)(=O)c1ccc(C(C)(C)O)cc1] |
| 151 | 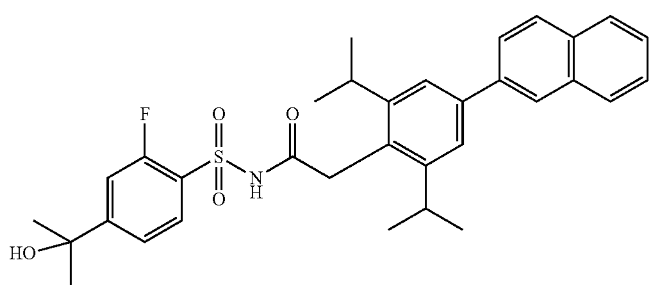 [SMILES: CC(C)c1cc(-c2ccc3ccccc3c2)cc(C(C)C)c1CC(=O)NS(=O)(=O)c1ccc(C(C)(C)O)cc1F] |
| 152 | 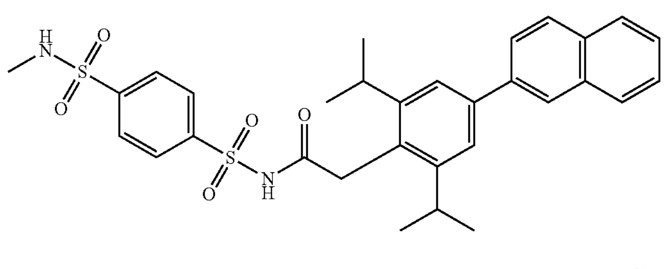 [SMILES: CNS(=O)(=O)c1ccc(S(=O)(=O)NC(=O)Cc2c(C(C)C)cc(-c3ccc4ccccc4c3)cc2C(C)C)cc1] |
| 153 | 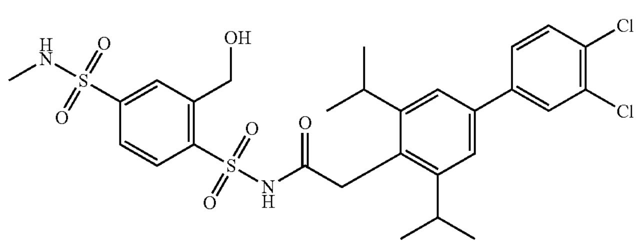 [SMILES: CNS(=O)(=O)c1ccc(S(=O)(=O)NC(=O)Cc2c(C(C)C)cc(-c3ccc(Cl)c(Cl)c3)cc2C(C)C)c(CO)c1] |

TABLE 1B-continued

| Compound | Structure |
|---|---|
| 154 | 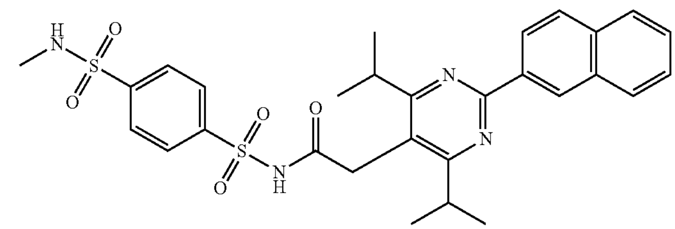 [SMILES: CNS(=O)(=O)c1ccc(S(=O)(=O)NC(=O)Cc2c(C(C)C)nc(-c3ccc4ccccc4c3)nc2C(C)C)cc1] |
| 155 | 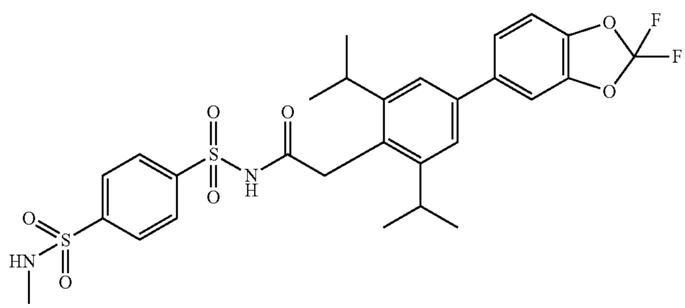 [SMILES: CNS(=O)(=O)c1ccc(S(=O)(=O)NC(=O)Cc2c(C(C)C)cc(-c3ccc4c(c3)OC(F)(F)O4)cc2C(C)C)cc1] |
| 156 | 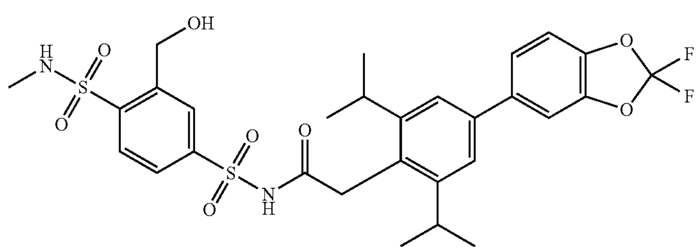 [SMILES: CNS(=O)(=O)c1ccc(S(=O)(=O)NC(=O)Cc2c(C(C)C)cc(-c3ccc4c(c3)OC(F)(F)O4)cc2C(C)C)cc1CO] |
| 157 | 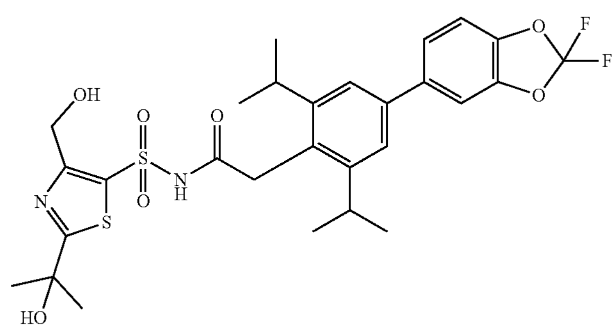 [SMILES: CC(C)c1cc(-c2ccc3c(c2)OC(F)(F)O3)cc(C(C)C)c1CC(=O)NS(=O)(=O)c1sc(C(C)(C)O)nc1CO] |
| 158 | 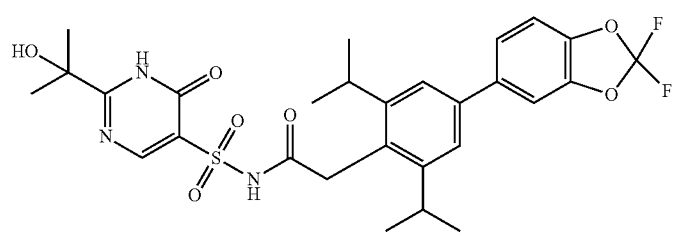 [SMILES: CC(C)c1cc(-c2ccc3c(c2)OC(F)(F)O3)cc(C(C)C)c1CC(=O)NS(=O)(=O)c1cnc(C(C)(C)O)[nH]c1=O] |

TABLE 1B-continued
| Compound | Structure |
|---|---|
| 159 | 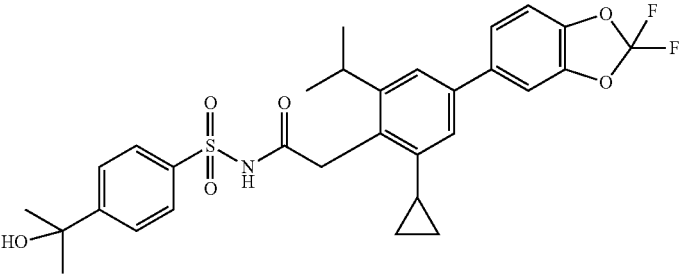 [SMILES: CC(C)c1cc(-c2ccc3c(c2)OC(F)(F)O3)cc(C2CC2)c1CC(=O)NS(=O)(=O)c1ccc(C(C)(C)O)cc1] |
| 160 | 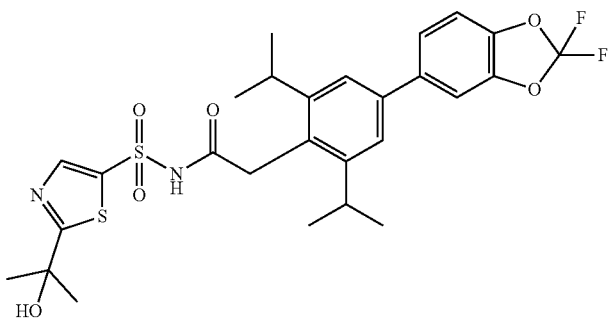 [SMILES: CC(C)c1cc(-c2ccc3c(c2)OC(F)(F)O3)cc(C(C)C)c1CC(=O)NS(=O)(=O)c1cnc(C(C)(C)O)s1] |
| 161 | 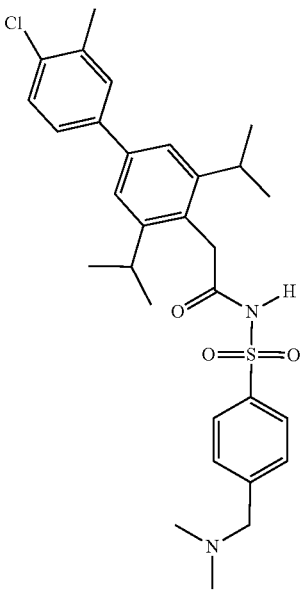 [SMILES: Cc1cc(-c2cc(C(C)C)c(CC(=O)NS(=O)(=O)c3ccc(CN(C)C)cc3)c(C(C)C)c2)ccc1Cl] |
or a pharmaceutically acceptable salt thereof.

In some embodiments, provided herein is a compound that is selected from the group consisting of the compounds in Table 1C:

TABLE 1C

| Compound | Structure |
|---|---|
| 201 | 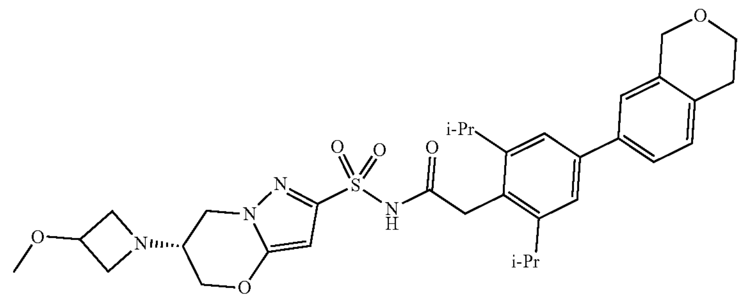 [SMILES: COC1CN([C@H]2COc3cc(S(=O)(=O)NC(=O)Cc4c(C(C)C)cc(-c5ccc6c(c5)COCC6)cc4C(C)C)nn3C2)C1] |
| 202 | 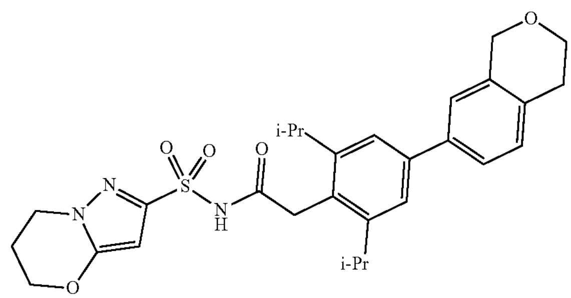 [SMILES: CC(C)c1cc(-c2ccc3c(c2)COCC3)cc(C(C)C)c1CC(=O)NS(=O)(=O)c1cc2n(n1)CCCO2] |
| 203 | 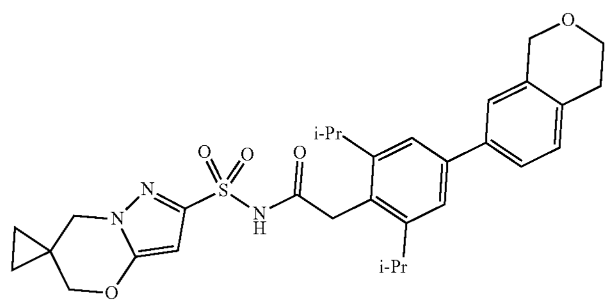 [SMILES: CC(C)c1cc(-c2ccc3c(c2)COCC3)cc(C(C)C)c1CC(=O)NS(=O)(=O)c1cc2n(n1)CC1(CC1)CO2] |
| 204 | 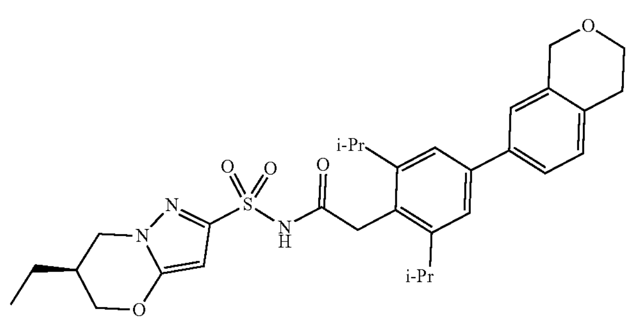 [SMILES: CC[C@@H]1COc2cc(S(=O)(=O)NC(=O)Cc3c(C(C)C)cc(-c4ccc5c(c4)COCC5)cc3C(C)C)nn2C1] |
| 205 | 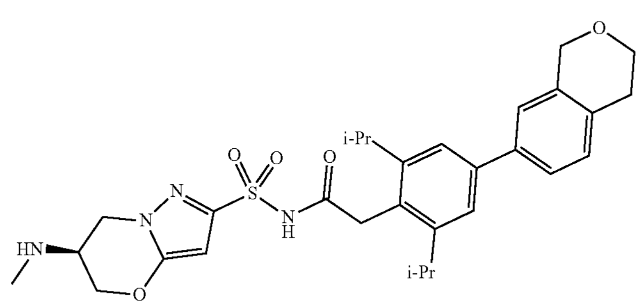 [SMILES: CN[C@@H]1COc2cc(S(=O)(=O)NC(=O)Cc3c(C(C)C)cc(-c4ccc5c(c4)COCC5)cc3C(C)C)nn2C1] |

TABLE 1C-continued
| Compound | Structure |
|---|---|
| 206 | 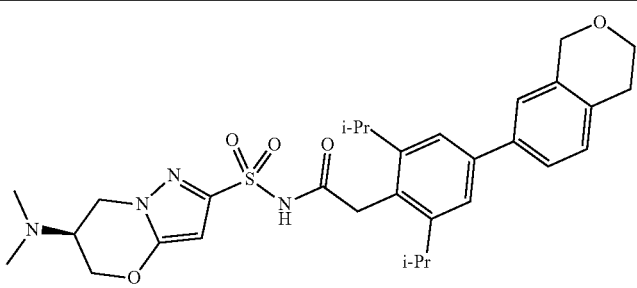 |
| 207 | 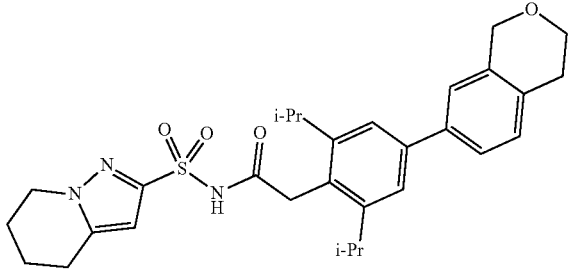 [SMILES: CC(C)c1cc(-c2ccc3c(c2)COCC3)cc(C(C)C)c1CC(=O)NS(=O)(=O)c1cc2n(n1)CCCC2] |
| 208 | 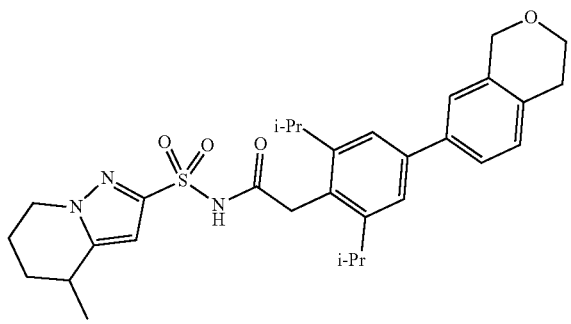 [SMILES: CC(C)c1cc(-c2ccc3c(c2)COCC3)cc(C(C)C)c1CC(=O)NS(=O)(=O)c1cc2n(n1)CCCC2C] |
| 209 | 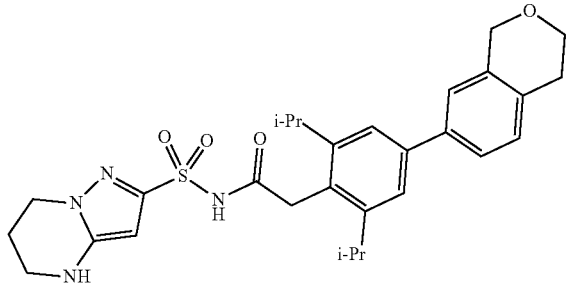 [SMILES: CC(C)c1cc(-c2ccc3c(c2)COCC3)cc(C(C)C)c1CC(=O)NS(=O)(=O)c1cc2n(n1)CCCN2] |
| 210 | 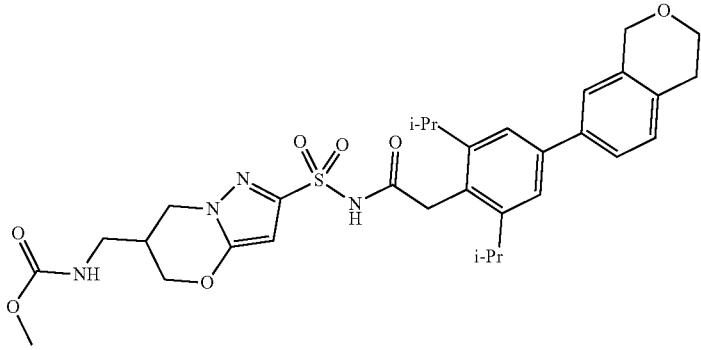 [SMILES: COC(=O)NCC1COc2cc(S(=O)(=O)NC(=O)Cc3c(C(C)C)cc(-c4ccc5c(c4)COCC5)cc3C(C)C)nn2C1] |

TABLE 1C-continued

| Compound | Structure |
|---|---|
| 211 | 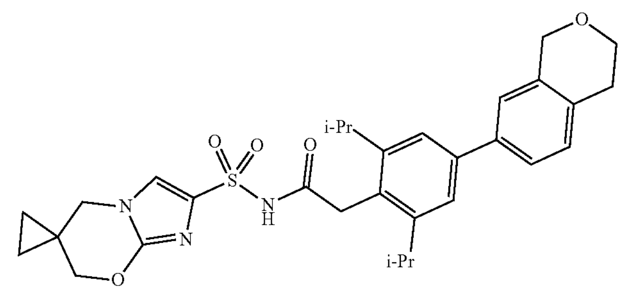 [SMILES: CC(C)c1cc(-c2ccc3c(c2)COCC3)cc(C(C)C)c1CC(=O)NS(=O)(=O)c1cn2c(n1)OCC1(CC1)C2] |
| 212 | 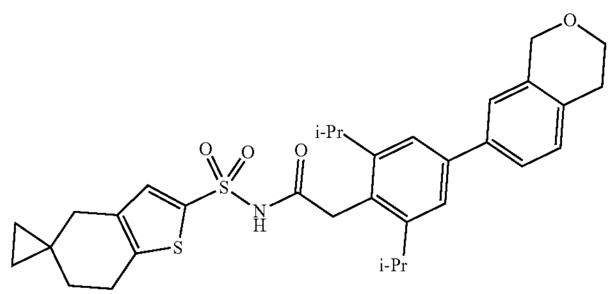 [SMILES: CC(C)c1cc(-c2ccc3c(c2)COCC3)cc(C(C)C)c1CC(=O)NS(=O)(=O)c1cc2c(s1)CCC1(CC1)C2] |
| 213 | 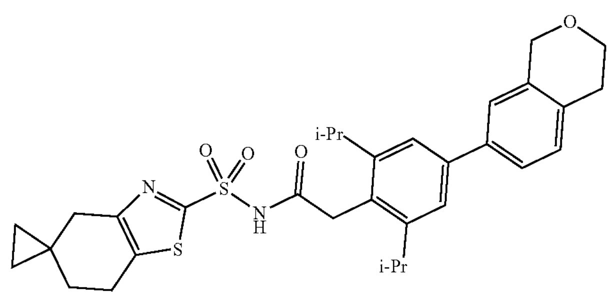 [SMILES: CC(C)c1cc(-c2ccc3c(c2)COCC3)cc(C(C)C)c1CC(=O)NS(=O)(=O)c1nc2c(s1)CCC1(CC1)C2] |
| 214 | 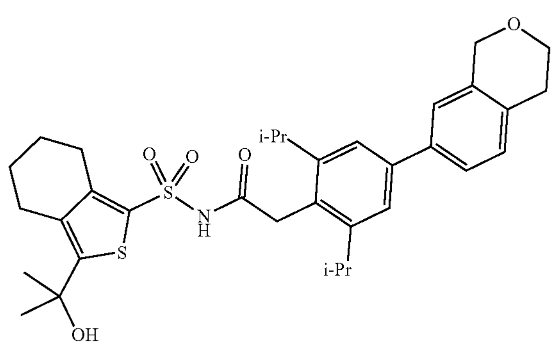 [SMILES: CC(C)c1cc(-c2ccc3c(c2)COCC3)cc(C(C)C)c1CC(=O)NS(=O)(=O)c1sc(C(C)(C)O)c2c1CCCC2] |
| 215 | 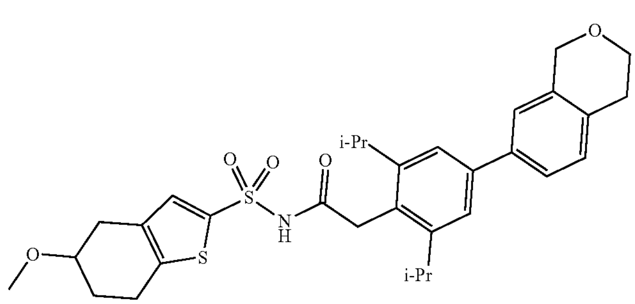 [SMILES: COC1CCc2sc(S(=O)(=O)NC(=O)Cc3c(C(C)C)cc(-c4ccc5c(c4)COCC5)cc3C(C)C)cc2C1] |

TABLE 1C-continued

| Compound | Structure |
|---|---|
| 216 | 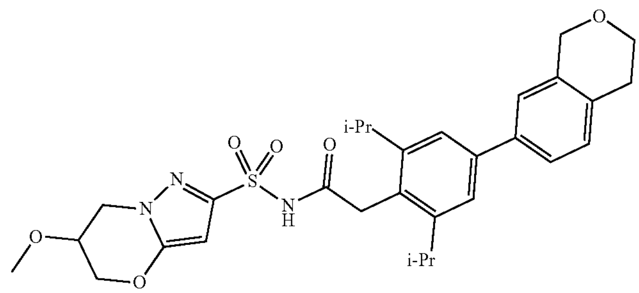 [SMILES: COC1COc2cc(S(=O)(=O)NC(=O)Cc3c(C(C)C)cc(-c4ccc5c(c4)COCC5)cc3C(C)C)nn2C1] |
| 217 | 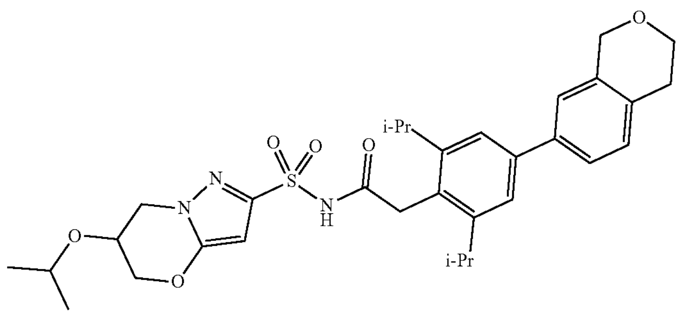 [SMILES: CC(C)OC1COc2cc(S(=O)(=O)NC(=O)Cc3c(C(C)C)cc(-c4ccc5c(c4)COCC5)cc3C(C)C)nn2C1] |
| 218 | 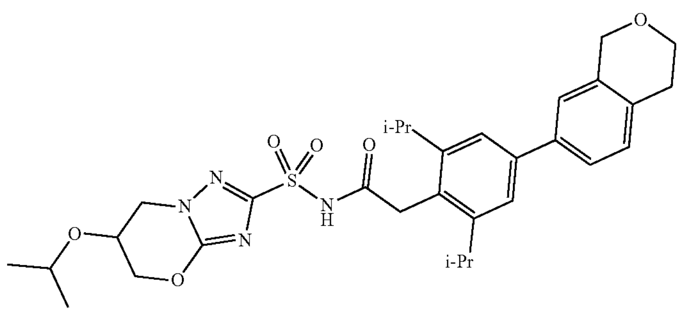 [SMILES: CC(C)OC1COc2nc(S(=O)(=O)NC(=O)Cc3c(C(C)C)cc(-c4ccc5c(c4)COCC5)cc3C(C)C)nn2C1] |
| 219 | 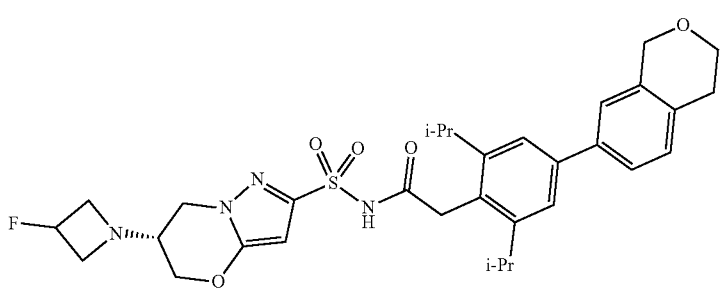 [SMILES: CC(C)c1cc(-c2ccc3c(c2)COCC3)cc(C(C)C)c1CC(=O)NS(=O)(=O)c1cc2n(n1)C[C@@H](N1CC(F)C1)CO2] |
| 220 | 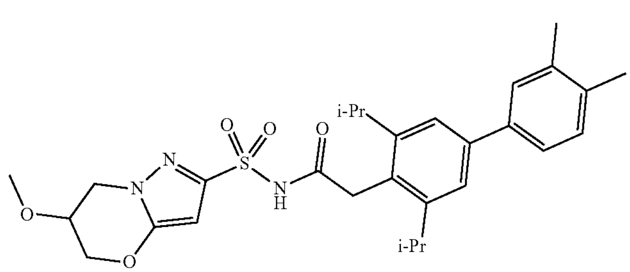 |

TABLE 1C-continued

| Compound | Structure |
|---|---|
| 221 | 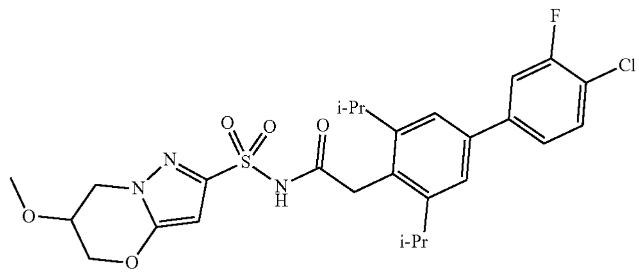 [SMILES: COC1COc2cc(S(=O)(=O)NC(=O)Cc3c(C(C)C)cc(-c4ccc(Cl)c(F)c4)cc3C(C)C)nn2C1] |
| 222 | 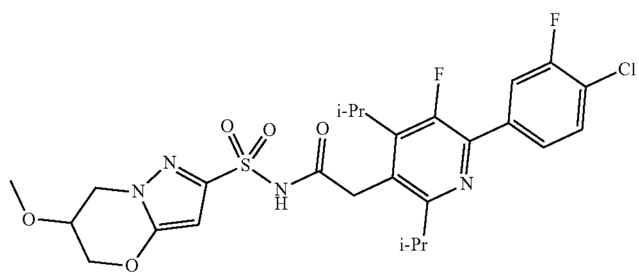 [SMILES: COC1COc2cc(S(=O)(=O)NC(=O)Cc3c(C(C)C)nc(-c4ccc(Cl)c(F)c4)c(F)c3C(C)C)nn2C1] |
| 223 | 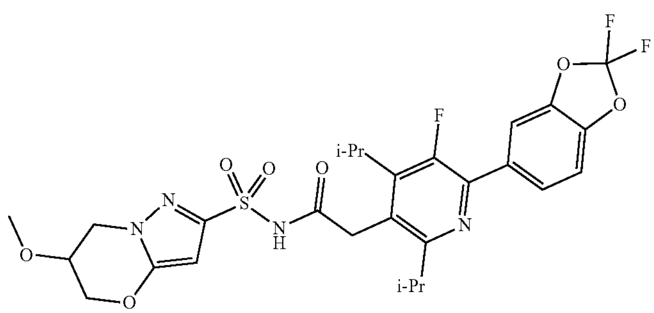 [SMILES: COC1COc2cc(S(=O)(=O)NC(=O)Cc3c(C(C)C)nc(-c4ccc5c(c4)OC(F)(F)O5)c(F)c3C(C)C)nn2C1] |
| 224 | 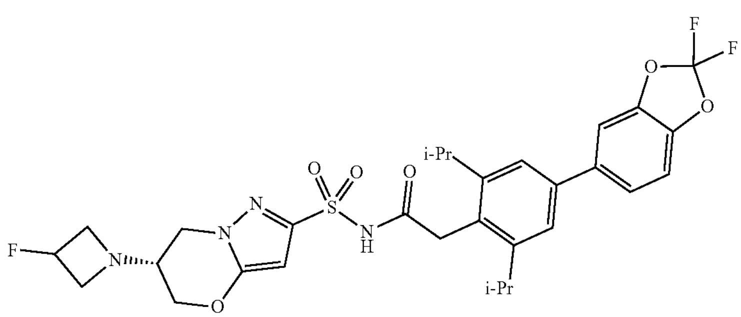 [SMILES: CC(C)c1cc(-c2ccc3c(c2)OC(F)(F)O3)cc(C(C)C)c1CC(=O)NS(=O)(=O)c1cc2n(n1)C[C@@H](N1CC(F)C1)CO2] |
| 225 | 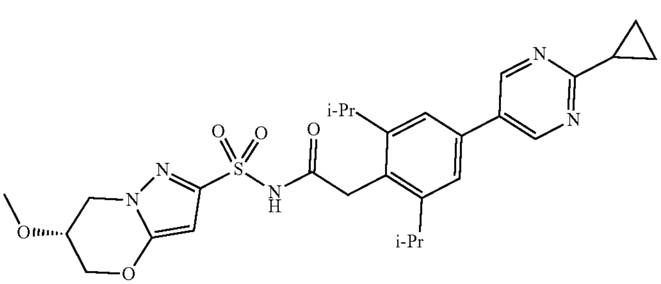 [SMILES: CO[C@H]1COc2cc(S(=O)(=O)NC(=O)Cc3c(C(C)C)cc(-c4cnc(C5CC5)nc4)cc3C(C)C)nn2C1] |

TABLE 1C-continued
| Compound | Structure |
|---|---|
| 226 | 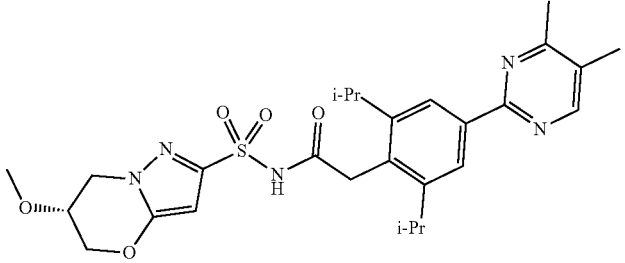 |
| 227 | 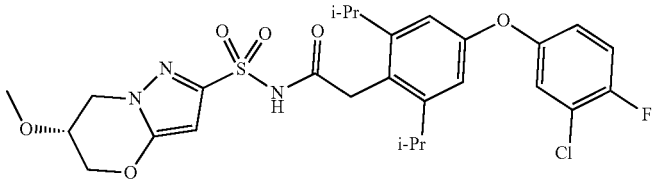 [SMILES: CO[C@H]1COc2cc(S(=O)(=O)NC(=O)Cc3c(C(C)C)cc(Oc4ccc(F)c(Cl)c4)cc3C(C)C)nn2C1] |
| 228 | 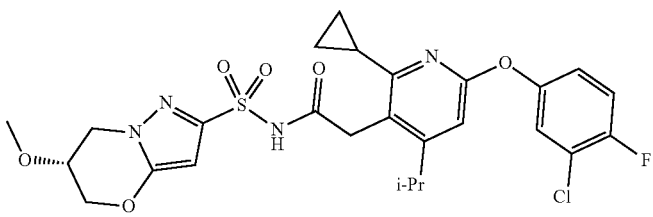 [SMILES: CO[C@H]1COc2cc(S(=O)(=O)NC(=O)Cc3c(C(C)C)cc(Oc4ccc(F)c(Cl)c4)nc3C3CC3)nn2C1] |
| 229 | 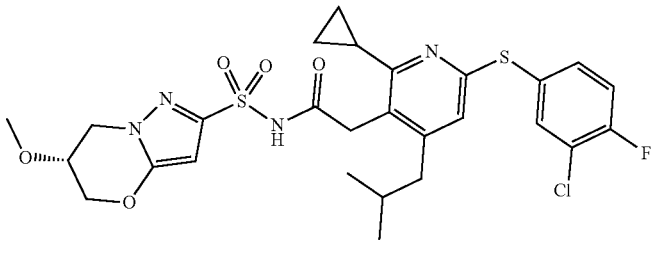 [SMILES: CO[C@H]1COc2cc(S(=O)(=O)NC(=O)Cc3c(CC(C)C)cc(Sc4ccc(F)c(Cl)c4)nc3C3CC3)nn2C1] |
| 230 | 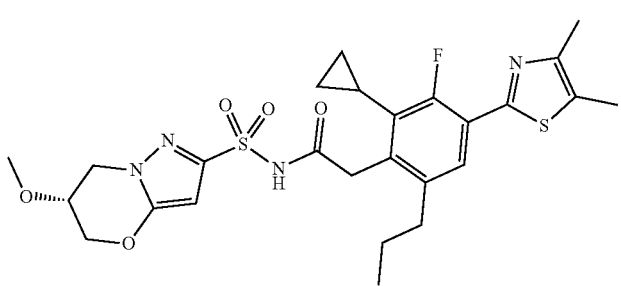 |

TABLE 1C-continued

| Compound | Structure |
| --- | --- |
| 231 | 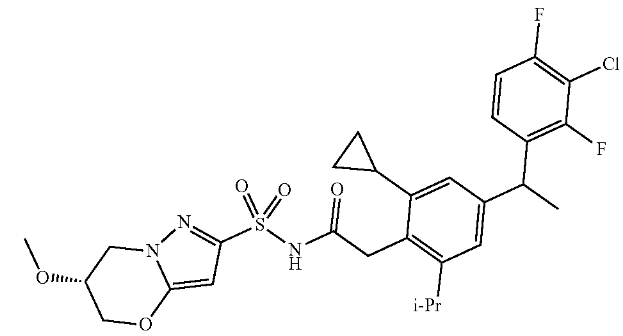 [SMILES: CO[C@H]1COc2cc(S(=O)(=O)NC(=O)Cc3c(C(C)C)cc(C(C)c4ccc(F)c(Cl)c4F)cc3C3CC3)nn2C1] |
| 232 | 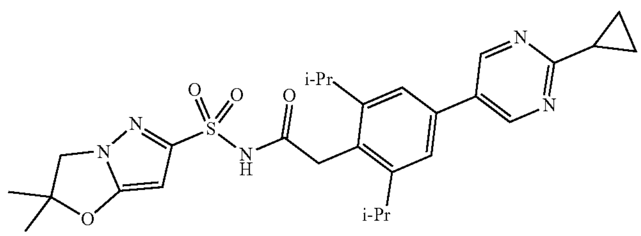 [SMILES: CC(C)c1cc(-c2cnc(C3CC3)nc2)cc(C(C)C)c1CC(=O)NS(=O)(=O)c1cc2n(n1)CC(C)(C)O2] |
| 233 | 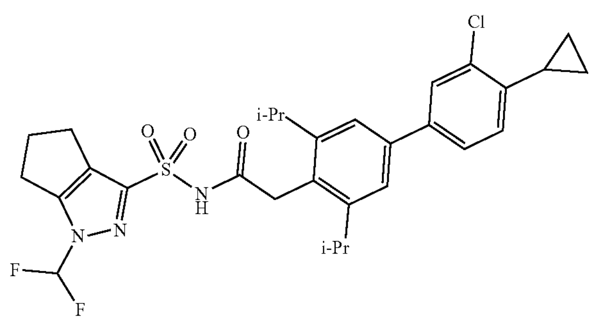 [SMILES: CC(C)c1cc(-c2ccc(C3CC3)c(Cl)c2)cc(C(C)C)c1CC(=O)NS(=O)(=O)c1nn(C(F)F)c2c1CCC2] |
| 234 | 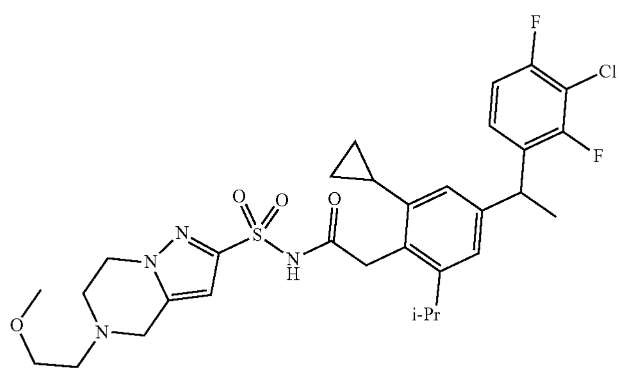 [SMILES: COCCN1CCn2nc(S(=O)(=O)NC(=O)Cc3c(C(C)C)cc(C(C)c4ccc(F)c(Cl)c4F)cc3C3CC3)cc2C1] |

TABLE 1C-continued

| Compound | Structure |
|---|---|
| 235 | *(chemical structure)* |
| 236 | *(chemical structure)* | or a pharmaceutically acceptable salt thereof.

In some embodiments, provided herein is a compound that is selected from the group consisting of the compounds in Table 1D:

TABLE 1D

| Compound # | Structure |
|---|---|
| 301 | *(chemical structure)* |
| 302 | *(chemical structure)* |

TABLE 1D-continued

| Compound # | Structure |
|---|---|
| 303 | 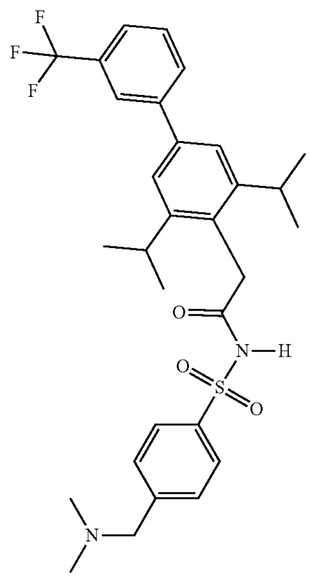 [SMILES: CC(C)c1cc(-c2cccc(C(F)(F)F)c2)cc(C(C)C)c1CC(=O)NS(=O)(=O)c1ccc(CN(C)C)cc1] |
| 304 | 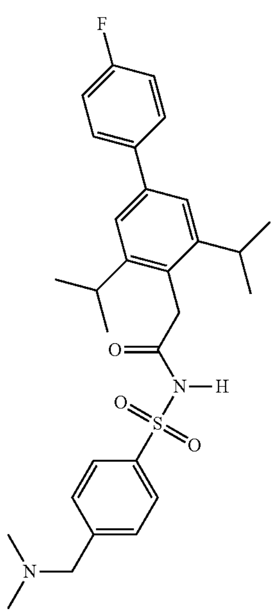 [SMILES: CC(C)c1cc(-c2ccc(F)cc2)cc(C(C)C)c1CC(=O)NS(=O)(=O)c1ccc(CN(C)C)cc1] |
| 305 | |
| 306 | |

TABLE 1D-continued
| Compound # | Structure |
|---|---|
| 307 | 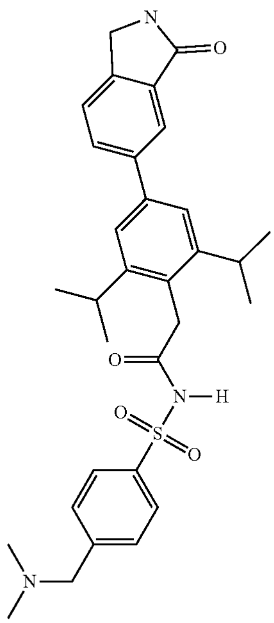 [SMILES: CC(C)c1cc(-c2ccc3c(c2)C(=O)NC3)cc(C(C)C)c1CC(=O)NS(=O)(=O)c1ccc(CN(C)C)cc1] |
| 308 | 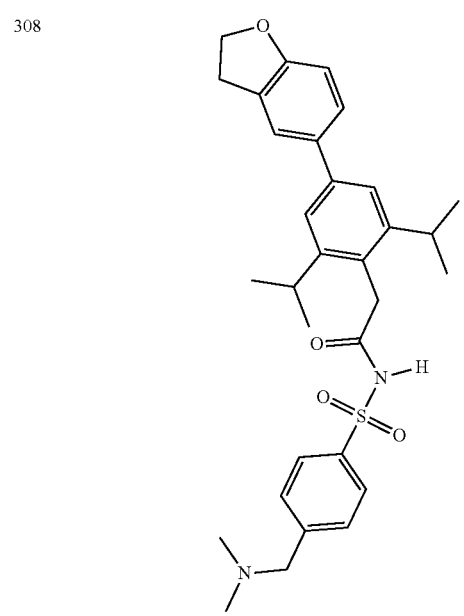 |
TABLE 1D-continued
| Compound # | Structure |
|---|---|
| 309 | 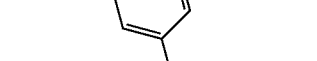 |
| 310 | 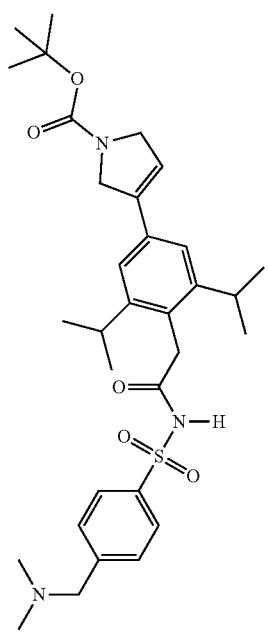 [SMILES: CC(C)c1cc(C2=CCN(C(=O)OC(C)(C)C)C2)cc(C(C)C)c1CC(=O)NS(=O)(=O)c1ccc(CN(C)C)cc1] |

TABLE 1D-continued

| Compound # | Structure |
|---|---|
| 311 | 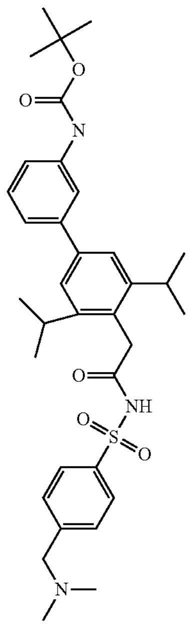 [SMILES: CC(C)c1cc(-c2cccc(NC(=O)OC(C)(C)C)c2)cc(C(C)C)c1CC(=O)NS(=O)(=O)c1ccc(CN(C)C)cc1] |
| 312 | 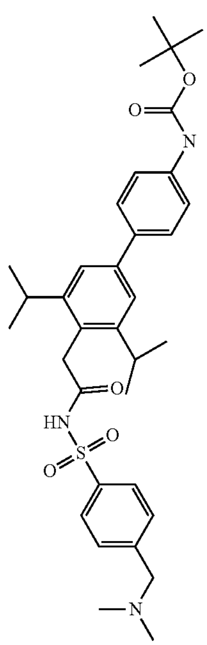 [SMILES: CC(C)c1cc(-c2ccc(NC(=O)OC(C)(C)C)cc2)cc(C(C)C)c1CC(=O)NS(=O)(=O)c1ccc(CN(C)C)cc1] |
| 313 | 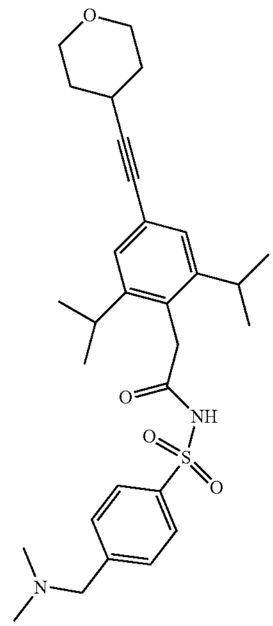 [SMILES: CC(C)c1cc(C#CC2CCOCC2)cc(C(C)C)c1CC(=O)NS(=O)(=O)c1ccc(CN(C)C)cc1] |
| 314 | 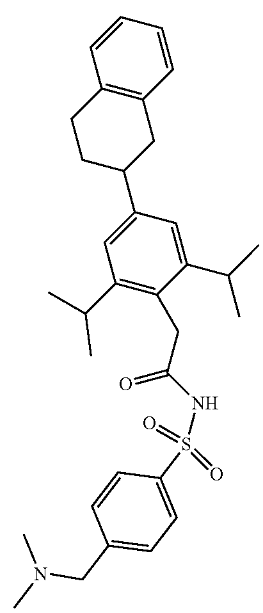 [SMILES: CC(C)c1cc(C2CCc3ccccc3C2)cc(C(C)C)c1CC(=O)NS(=O)(=O)c1ccc(CN(C)C)cc1] |

TABLE 1D-continued
| Compound # | Structure |
| --- | --- |
| 315 | 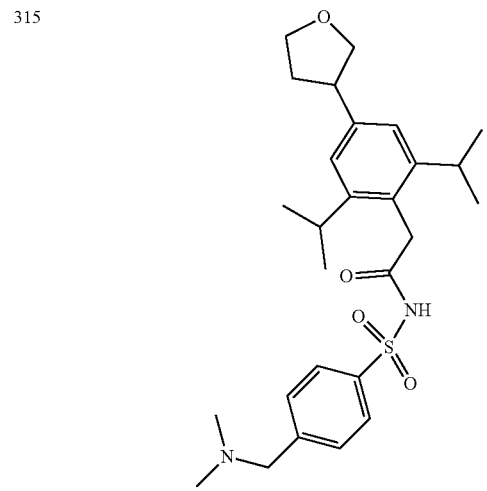 |
| 316 | 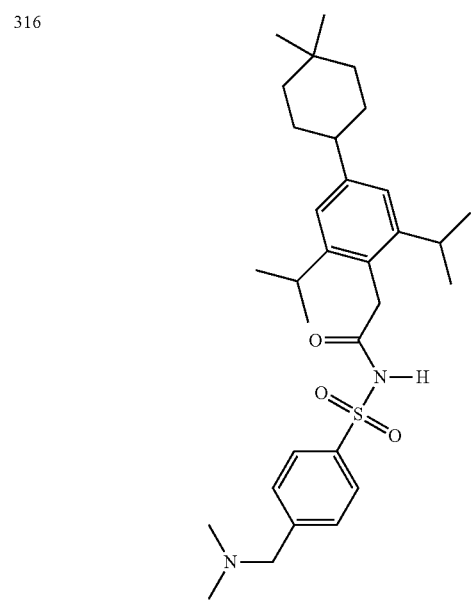 |
| 317 | 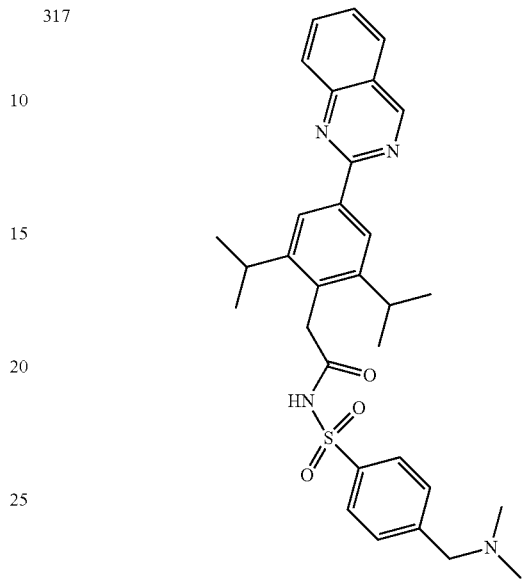 |
| 318 | 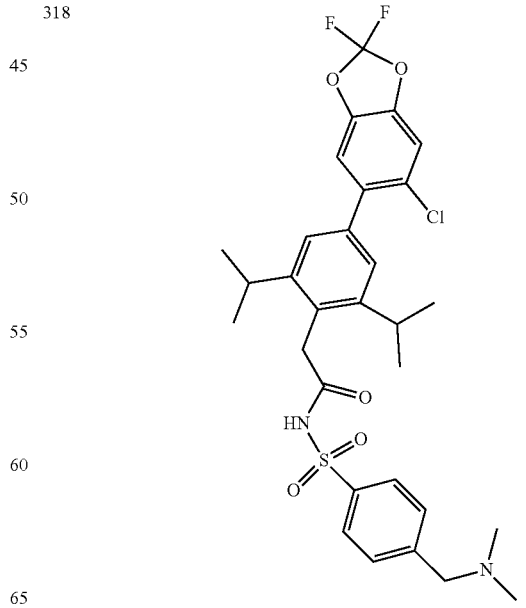 |

TABLE 1D-continued
| Compound # | Structure |
| --- | --- |
| 319 | 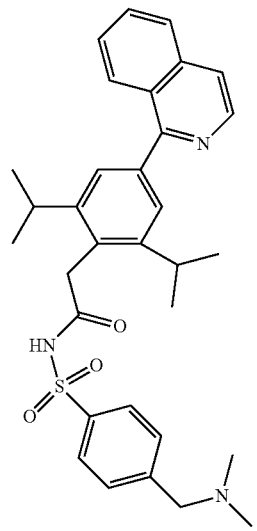 [SMILES: CC(C)c1cc(-c2nccc3ccccc23)cc(C(C)C)c1CC(=O)NS(=O)(=O)c1ccc(CN(C)C)cc1] |
| 320 | 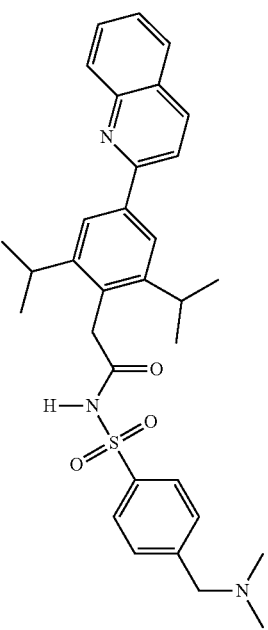 [SMILES: CC(C)c1cc(-c2ccc3ccccc3n2)cc(C(C)C)c1CC(=O)NS(=O)(=O)c1ccc(CN(C)C)cc1] |
TABLE 1D-continued
| Compound # | Structure |
| --- | --- |
| 321 | 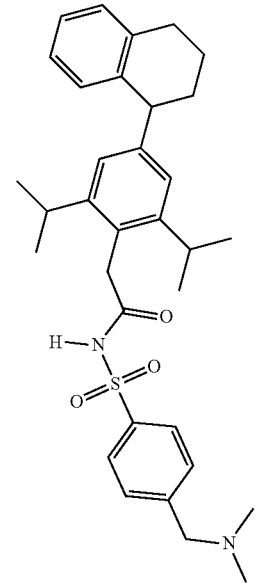 [SMILES: CC(C)c1cc(C2CCCc3ccccc32)cc(C(C)C)c1CC(=O)NS(=O)(=O)c1ccc(CN(C)C)cc1] |
| 322 | 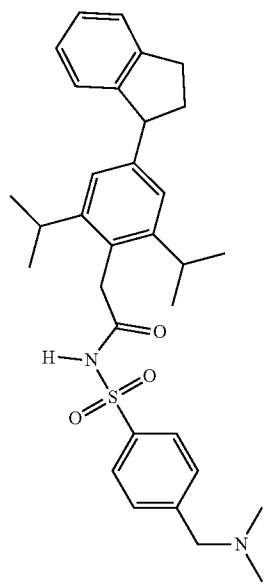 [SMILES: CC(C)c1cc(C2CCc3ccccc32)cc(C(C)C)c1CC(=O)NS(=O)(=O)c1ccc(CN(C)C)cc1] |

TABLE 1D-continued

| Compound # | Structure |
|---|---|
| 323 | 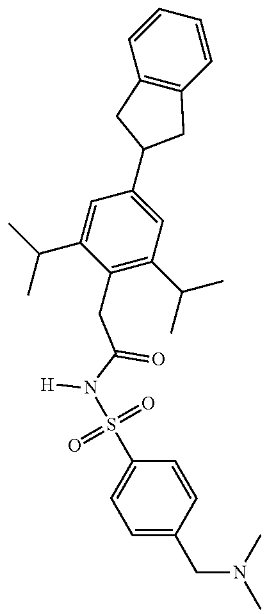 [SMILES: CC(C)c1cc(C2Cc3ccccc3C2)cc(C(C)C)c1CC(=O)NS(=O)(=O)c1ccc(CN(C)C)cc1] |
| 324 | 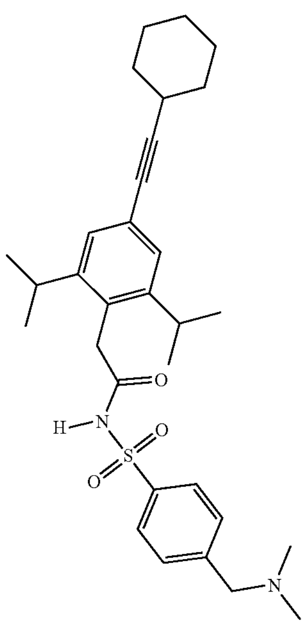 [SMILES: CC(C)c1cc(C#CC2CCCCC2)cc(C(C)C)c1CC(=O)NS(=O)(=O)c1ccc(CN(C)C)cc1] |
| 325 | |
| 326 | |

TABLE 1D-continued

| Compound # | Structure |
|---|---|
| 327 | (structure) |
| 328 | (structure) |
| 329 | (structure) |
| 330 | (structure) |

TABLE 1D-continued
| Compound # | Structure |
|---|---|
| 331 | 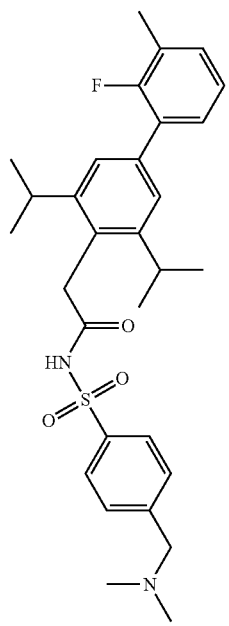 |
| 332 | 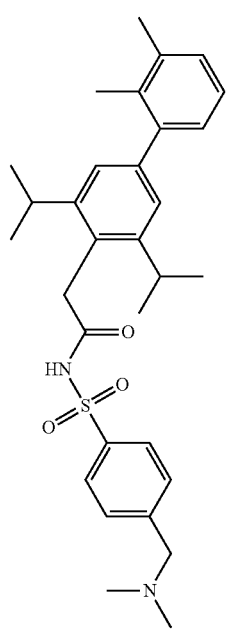 |
TABLE 1D-continued
| Compound # | Structure |
|---|---|
| 333 | 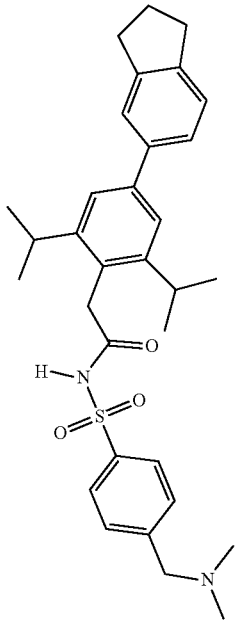 [SMILES: CC(C)c1cc(-c2ccc3c(c2)CCC3)cc(C(C)C)c1CC(=O)NS(=O)(=O)c1ccc(CN(C)C)cc1] |
| 334 | 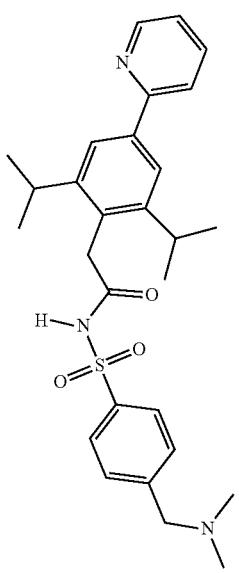 [SMILES: CC(C)c1cc(-c2ccccn2)cc(C(C)C)c1CC(=O)NS(=O)(=O)c1ccc(CN(C)C)cc1] |

TABLE 1D-continued
| Compound # | Structure |
|---|---|
| 335 | 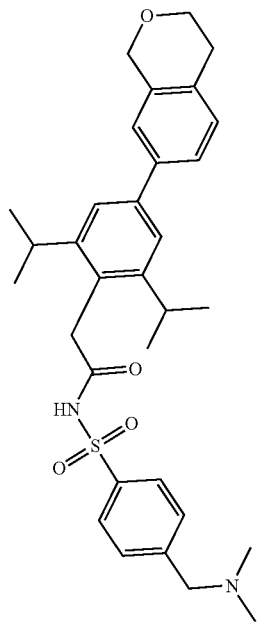 [SMILES: CC(C)c1cc(-c2ccc3c(c2)COCC3)cc(C(C)C)c1CC(=O)NS(=O)(=O)c1ccc(CN(C)C)cc1] |
| 336 | 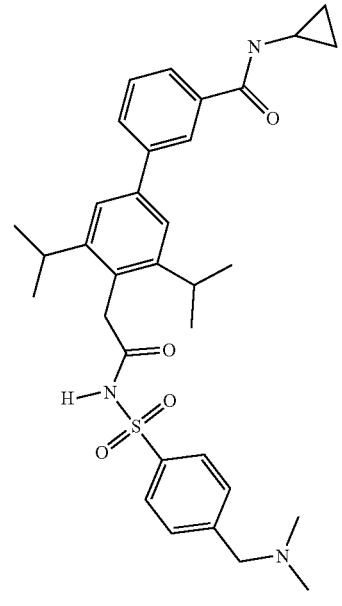 [SMILES: CC(C)c1cc(-c2cccc(C(=O)NC3CC3)c2)cc(C(C)C)c1CC(=O)NS(=O)(=O)c1ccc(CN(C)C)cc1] |
| 337 | 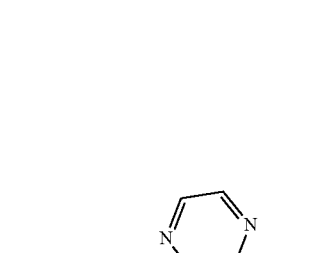 |
| 338 | 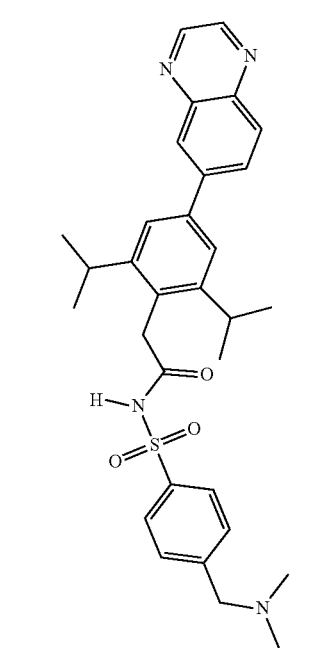 [SMILES: CC(C)c1cc(-c2ccc3nccnc3c2)cc(C(C)C)c1CC(=O)NS(=O)(=O)c1ccc(CN(C)C)cc1] |

TABLE 1D-continued

| Compound # | Structure |
|---|---|
| 339 | (structure) |
| 340 | (structure) |
| 341 | (structure) |
| 342 | (structure) |

TABLE 1D-continued
| Compound # | Structure |
|---|---|
| 343 | 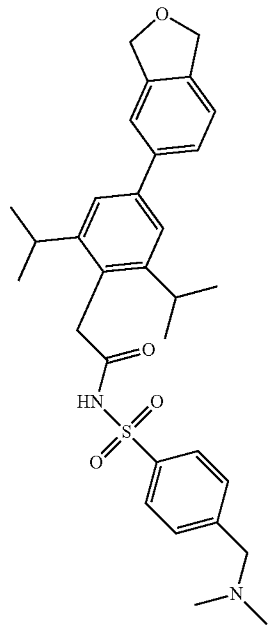 [SMILES: CC(C)c1cc(-c2ccc3c(c2)COC3)cc(C(C)C)c1CC(=O)NS(=O)(=O)c1ccc(CN(C)C)cc1] |
| 344 | 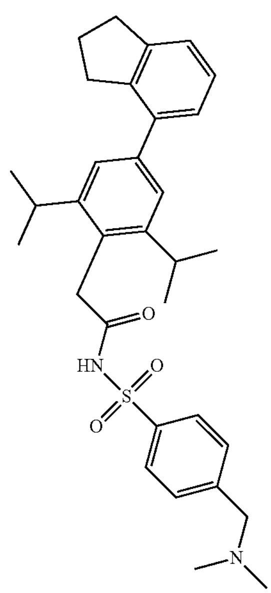 [SMILES: CC(C)c1cc(-c2cccc3c2CCC3)cc(C(C)C)c1CC(=O)NS(=O)(=O)c1ccc(CN(C)C)cc1] |
| 345 | |
| 346 | |
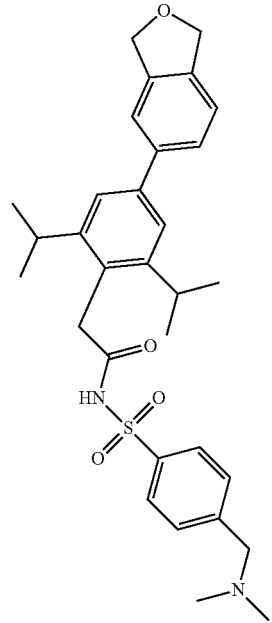

TABLE 1D-continued
| Compound # | Structure |
|---|---|
| 347 | 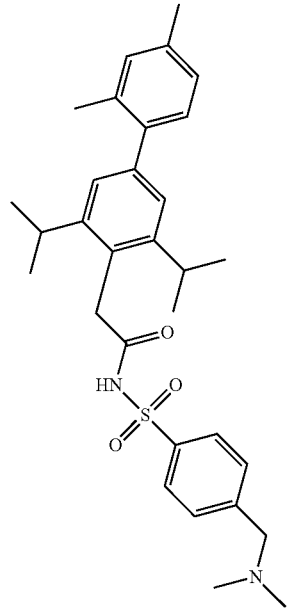 [SMILES: Cc1ccc(-c2cc(C(C)C)c(CC(=O)NS(=O)(=O)c3ccc(CN(C)C)cc3)c(C(C)C)c2)c(C)c1] |
| 348 | 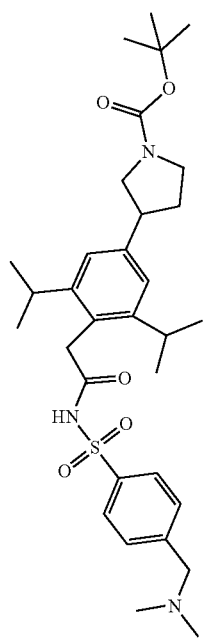 [SMILES: CC(C)c1cc(C2CCN(C(=O)OC(C)(C)C)C2)cc(C(C)C)c1CC(=O)NS(=O)(=O)c1ccc(CN(C)C)cc1] |
TABLE 1D-continued
| Compound # | Structure |
|---|---|
| 349 | 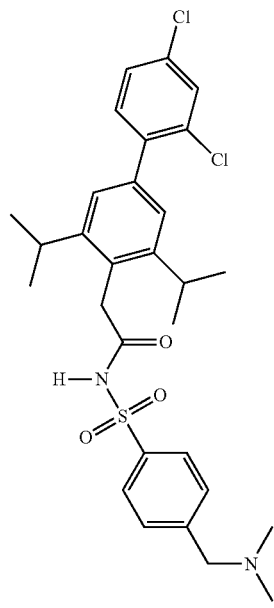 [SMILES: CC(C)c1cc(-c2ccc(Cl)cc2Cl)cc(C(C)C)c1CC(=O)NS(=O)(=O)c1ccc(CN(C)C)cc1] |
| 350 | 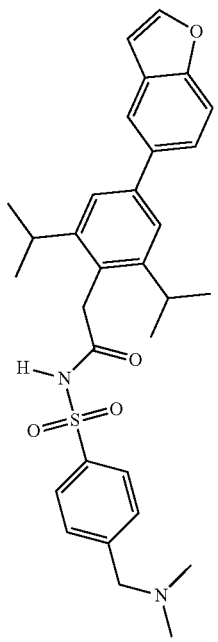 [SMILES: CC(C)c1cc(-c2ccc3occc3c2)cc(C(C)C)c1CC(=O)NS(=O)(=O)c1ccc(CN(C)C)cc1] |

TABLE 1D-continued

| Compound # | Structure |
|---|---|
| 351 | (isoquinolin-7-yl attached to 2,6-diisopropylphenyl-CH2-C(=O)-NH-S(=O)2-C6H4-CH2-N(CH3)2) |
| 352 | (5,6,7,8-tetrahydronaphthalen-2-yl attached to 2,6-diisopropylphenyl-CH2-C(=O)-NH-S(=O)2-C6H4-CH2-N(CH3)2) |
| 353 | (3,4-difluorophenyl attached to 2,6-diisopropylphenyl-CH2-C(=O)-NH-S(=O)2-C6H4-CH2-N(CH3)2) |
| 354 | (2-chlorophenyl attached to 2,6-diisopropylphenyl-CH2-C(=O)-NH-S(=O)2-C6H4-CH2-N(CH3)2) |

TABLE 1D-continued

| Compound # | Structure |
|---|---|
| 355 | 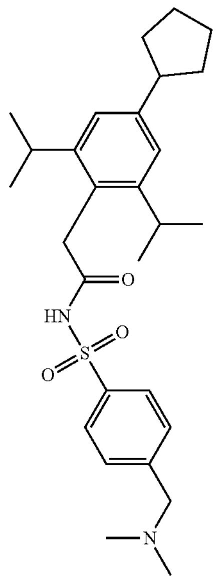 [SMILES: CC(C)c1cc(C2CCCC2)cc(C(C)C)c1CC(=O)NS(=O)(=O)c1ccc(CN(C)C)cc1] |
| 356 | 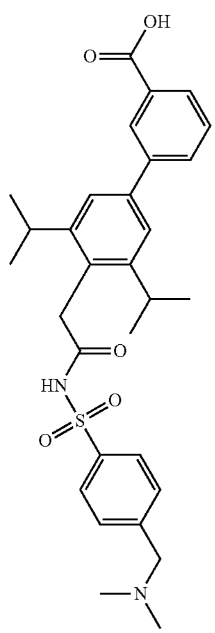 [SMILES: CC(C)c1cc(-c2cccc(C(=O)O)c2)cc(C(C)C)c1CC(=O)NS(=O)(=O)c1ccc(CN(C)C)cc1] |
| 357 | |
| 358 | |

TABLE 1D-continued
| Compound # | Structure |
|---|---|
| 359 | 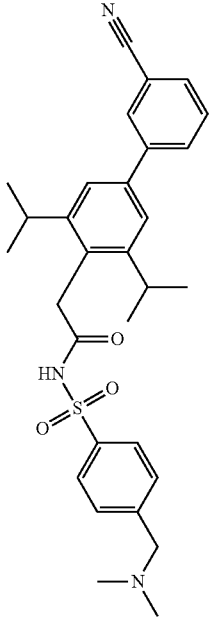 [SMILES: CC(C)c1cc(-c2cccc(C#N)c2)cc(C(C)C)c1CC(=O)NS(=O)(=O)c1ccc(CN(C)C)cc1] |
| 360 | 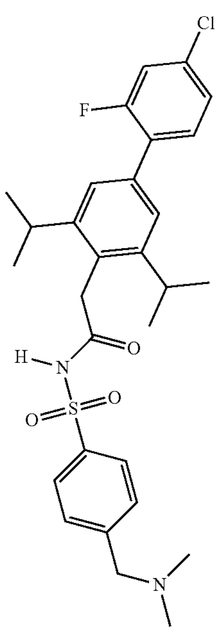 [SMILES: CC(C)c1cc(-c2ccc(Cl)cc2F)cc(C(C)C)c1CC(=O)NS(=O)(=O)c1ccc(CN(C)C)cc1] |
| 361 | 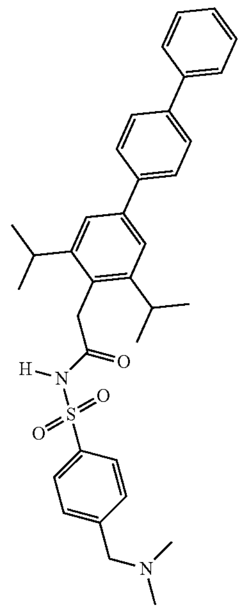 [SMILES: CC(C)c1cc(-c2ccc(-c3ccccc3)cc2)cc(C(C)C)c1CC(=O)NS(=O)(=O)c1ccc(CN(C)C)cc1] |
| 362 | 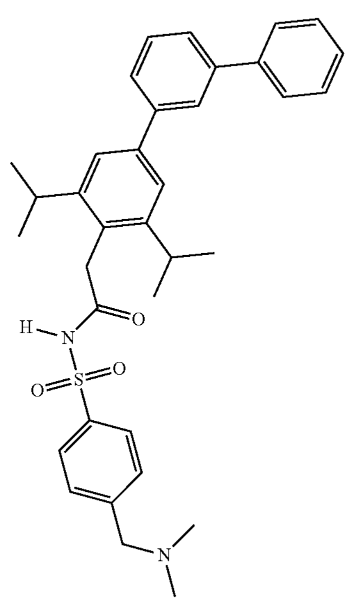 [SMILES: CC(C)c1cc(-c2cccc(-c3ccccc3)c2)cc(C(C)C)c1CC(=O)NS(=O)(=O)c1ccc(CN(C)C)cc1] |

TABLE 1D-continued
| Compound # | Structure |
|---|---|
| 363 | 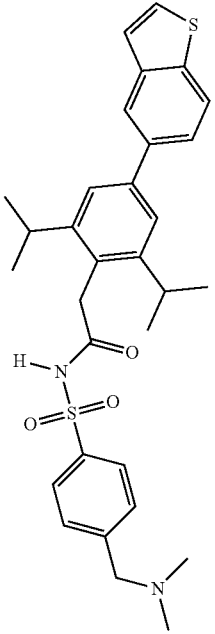 [SMILES: CC(C)c1cc(-c2ccc3sccc3c2)cc(C(C)C)c1CC(=O)NS(=O)(=O)c1ccc(CN(C)C)cc1] |
| 364 | 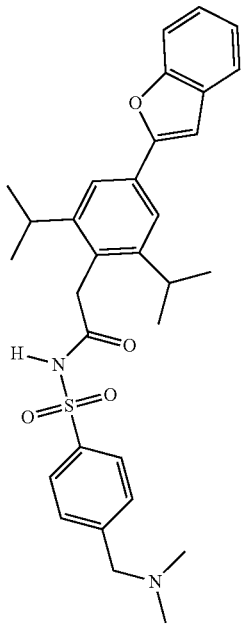 [SMILES: CC(C)c1cc(-c2cc3ccccc3o2)cc(C(C)C)c1CC(=O)NS(=O)(=O)c1ccc(CN(C)C)cc1] |
| 365 | 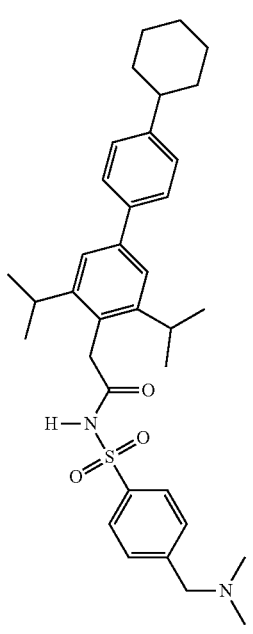 [SMILES: CC(C)c1cc(-c2ccc(C3CCCCC3)cc2)cc(C(C)C)c1CC(=O)NS(=O)(=O)c1ccc(CN(C)C)cc1] |
| 366 | 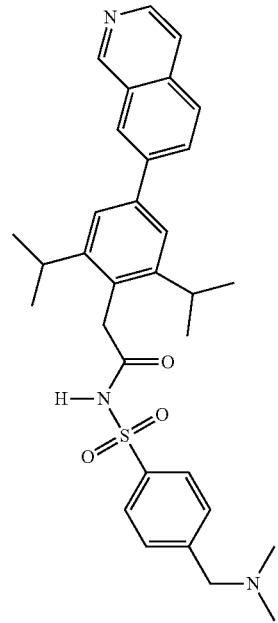 [SMILES: CC(C)c1cc(-c2ccc3ccncc3c2)cc(C(C)C)c1CC(=O)NS(=O)(=O)c1ccc(CN(C)C)cc1] |

TABLE 1D-continued
| Compound # | Structure |
|---|---|
| 367 | 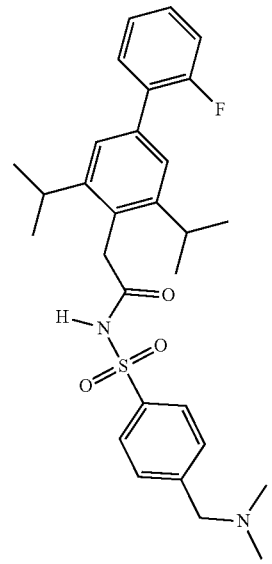 [SMILES: CC(C)c1cc(-c2ccccc2F)cc(C(C)C)c1CC(=O)NS(=O)(=O)c1ccc(CN(C)C)cc1] |
| 368 | 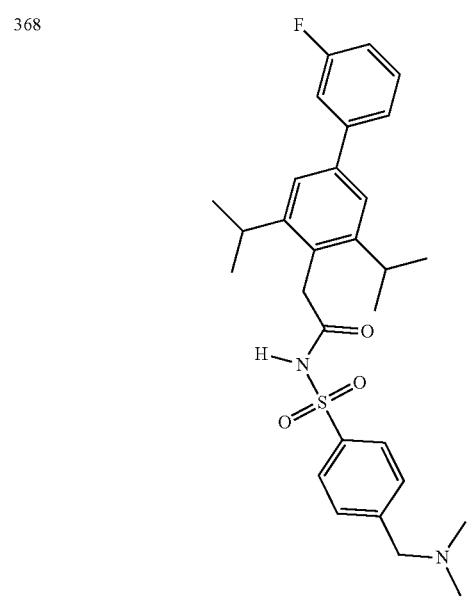 |
TABLE 1D-continued
| Compound # | Structure |
|---|---|
| 369 | 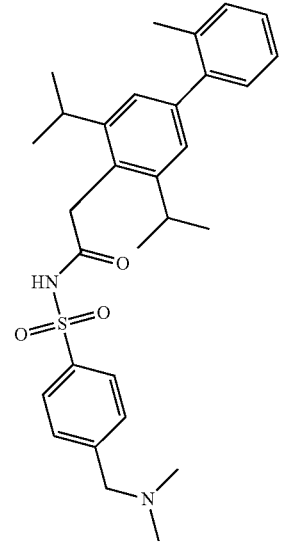 [SMILES: Cc1ccccc1-c1cc(C(C)C)c(CC(=O)NS(=O)(=O)c2ccc(CN(C)C)cc2)c(C(C)C)c1] |
| 370 | 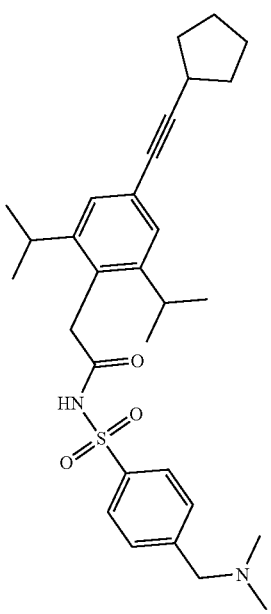 [SMILES: CC(C)c1cc(C#CC2CCCC2)cc(C(C)C)c1CC(=O)NS(=O)(=O)c1ccc(CN(C)C)cc1] |

TABLE 1D-continued

| Compound # | Structure |
|---|---|
| 371 | (structure) |
| 372 | (structure) |
| 373 | (structure) |
| 374 | (structure) |
| 375 | (structure) |
| 376 | (structure) |
| 377 | (structure) |
| 378 | (structure) |
| 379 | (structure) | or a pharmaceutically acceptable salt thereof.

In some embodiments, provided herein is a compound that is selected from the group consisting of the compounds in Table 1C and/or Table 1D.

Pharmaceutical Compositions and Administration

General

In some embodiments, a chemical entity (e.g., a compound that modulates (e.g., antagonizes) NLRP1 or NLRP3 or both NLRP1 and NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-p-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: *The Science and Practice of Pharmacy*, $22^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" *Neoplasia*. 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP1 or NLRP3 or both NLRP1 and NLRP3 activity (e.g., an increase, e.g., NLRP1/3 signaling) contributes to the pathology and/or symptoms and/or progression of the condition, disease or disorder are provided, comprising administering to a subject an effective amount of a chemical entity described herein (e.g., a compound described generically or specifically herein or a pharmaceutically acceptable salt thereof or compositions containing the same).

Indications

In some embodiments, the condition, disease or disorder is selected from: inappropriate host responses to infectious diseases where active infection exists at any body site, such as septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis, immune-based diseases such as acute and delayed hypersensitivity, graft rejection, and graft-versus-host disease; auto-immune diseases including Type 1 diabetes mellitus and multiple sclerosis. For example, the condition, disease or disorder may be an inflammatory disorder such as rheumatoid arthritis, osteoarthritis, septic shock, COPD and periodontal disease.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, the condition, disease or disorder is selected from major adverse cardiovascular events such as cardiovascular death, non-fatal myocardial infarction and non-fatal stroke in patients with a prior hear attack and inflammatory atherosclerosis (see for example, NCT01327846).

In some embodiments, the condition, disease or disorder is selected from metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In some embodiments, the condition, disease or disorder is a cardiovascular indication. In some embodiments, the condition, disease or disorder is myocardial infraction. In some embodiments, the condition, disease or disorder is stroke.

In some embodiments, the condition, disease or disorder is obesity.

In some embodiments, the condition, disease or disorder is Type 2 Diabetes.

In some embodiments, the condition, disease or disorder is NASH.

In some embodiments, the condition, disease or disorder is Alzheimer's disease.

In some embodiments, the condition, disease or disorder is gout.

In some embodiments, the condition, disease or disorder is SLE.

In some embodiments, the condition, disease or disorder is rheumatoid arthritis.

In some embodiments, the condition, disease or disorder is IBD.

In some embodiments, the condition, disease or disorder is multiple sclerosis.

In some embodiments, the condition, disease or disorder is COPD.

In some embodiments, the condition, disease or disorder is asthma.

In some embodiments, the condition, disease or disorder is scleroderma.

In some embodiments, the condition, disease or disorder is pulmonary fibrosis.

In some embodiments, the condition, disease or disorder is age related macular degeneration (AMD).

In some embodiments, the condition, disease or disorder is cystic fibrosis.

In some embodiments, the condition, disease or disorder is Muckle Wells syndrome.

In some embodiments, the condition, disease or disorder is familial cold autoinflammatory syndrome (FCAS).

In some embodiments, the condition, disease or disorder is chronic neurologic cutaneous and articular syndrome.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; acute myeloid leukemia (AML) chronic myeloid leukemia (CML); gastric cancer; and lung cancer metastasis.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; gastric cancer; and lung cancer metastasis.

In some embodiments, the indication is MDS.

In some embodiments, the indication is non-small lung cancer in patients carrying mutation or overexpression of NLRP3.

In some embodiments, the indication is ALL in patients resistant to glucocorticoids treatment.

In some embodiments, the indication is LCH.

In some embodiments, the indication is multiple myeloma.

In some embodiments, the indication is promyelocytic leukemia.

In some embodiments, the indication is gastric cancer.

In some embodiments, the indication is lung cancer metastasis.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of treatment for an indication related to NLRP3 activity, such as an indication related to NLRP3 polymorphism.

In some embodiments, the methods described herein further include the step of identifying a subject (e.g., a patient) in need of treatment for an indication related to NLRP3 activity, such as an indication related to NLRP3 where polymorphism is a gain of function In some embodiments, the methods described herein further include the step of identifying a subject (e.g., a patient) in need of treatment for an indication related to NLRP3 activity, such as an indication related to NLRP3 polymorphism found in CAPS syndromes.

In some embodiments, the methods described herein further include the step of identifying a subject (e.g., a patient) in need of treatment for an indication related to NLRP3 activity, such as an indication related NLRP3 polymorphism where the polymorphism is VAR_014104 (R262W)

In some embodiments, the methods described herein further include the step of identifying a subject (e.g., a patient) in need of treatment for an indication related to NLRP3 activity, such as an indication related NLRP3 polymorphism where the polymorphism is a natural variant reported in http://www.uniprot.org/uniprot/Q96P20

In some embodiments, the methods described herein further include the step of identifying a subject (e.g., a patient) in need of treatment for an indication related to NLRP1 activity, such as an indication related NLRP1 polymorphism.

In some embodiments, the methods described herein further include the step of identifying a subject (e.g., a patient) in need of treatment for an indication related to NLRP1 activity, such as an indication related to NLRP1 where polymorphism is a gain of function In some embodiments, the methods described herein further include the step of identifying a subject (e.g., a patient) in need of treatment for an indication related to NLRP1 activity, such as an indication related NLRP1 polymorphism found in vitiligo Vitiligo-Associated Autoimmune Disease.

In some embodiments, the methods described herein further include the step of identifying a subject (e.g., a patient) in need of treatment for an indication related to NLRP1 activity, such as an indication related where NLRP1 polymorphism is VAR_033239 (L155H)

In some embodiments, the methods described herein further include the step of identifying a subject (e.g., a patient) in need of treatment for an indication related to NLRP1 activity, such as an indication related where NLRP1 polymorphism is a natural variant reported in http://www.uniprot.org/uniprot/Q9C000

In some embodiments, the methods described herein further include the step of identifying a subject (e.g., a patient) in need of treatment for an indication related to NLRP1/3 activity, such as an indication related to point mutation of NLRP1/3 signaling.

Anti-TNFα Agents

The term "anti-TNFα agent" refers to an agent which directly or indirectly blocks, down-regulates, impairs, inhibits, impairs, or reduces TNFα activity and/or expression. In some embodiments, an anti-TNFα agent is an antibody or an antigen-binding fragment thereof, a fusion protein, a soluble TNFα receptor (a soluble tumor necrosis factor receptor superfamily member 1A (TNFR1) or a soluble tumor necrosis factor receptor superfamily 1B (TNFR2)), an inhibitory nucleic acid, or a small molecule TNFα antagonist. In some embodiments, the inhibitory nucleic acid is a ribozyme, small hairpin RNA, a small interfering RNA, an antisense nucleic acid, or an aptamer.

Exemplary anti-TNFα agents that directly block, down-regulate, impair, inhibit, or reduce TNFα activity and/or expression can, e.g., inhibit or decrease the expression level of TNFα or a receptor of TNFα (TNFR1 or TNFR2) in a cell (e.g., a cell obtained from a subject, a mammalian cell), or inhibit or reduce binding of TNFα to its receptor (TNFR1 and/or TNFR2) and/or. Non-limiting examples of anti-TNFα agents that directly block, down-regulate, impair, inhibit, or reduce TNFα activity and/or expression include an antibody or fragment thereof, a fusion protein, a soluble TNFα receptor (e.g., a soluble TNFR1 or soluble TNFR2), inhibitory nucleic acids (e.g., any of the examples of inhibitory nucleic acids described herein), and a small molecule TNFα antagonist.

Exemplary anti-TNFα agents that can indirectly block, down-regulate, impair, inhibitreduce TNFα activity and/or expression can, e.g., inhibit or decrease the level of downstream signaling of a TNFα receptor (e.g., TNFR1 or TNFR2) in a mammalian cell (e.g., decrease the level and/or activity of one or more of the following signaling proteins: AP-1, mitogen-activated protein kinase kinase kinase 5 (ASK1), inhibitor of nuclear factor kappa B (IKK), mitogen-activated protein kinase 8 (JNK), mitogen-activated protein kinase (MAPK), MEKK 1/4, MEKK 4/7, MEKK 3/6, nuclear factor kappa B (NF-κB), mitogen-activated protein kinase kinase kinase 14 (NIK), receptor interacting serine/threonine kinase 1 (RIP), TNFRSFIA associated via death domain (TRADD), and TNF receptor associated factor 2 (TRAF2), in a cell), and/or decrease the level of TNFα-induced gene expression in a mammalian cell (e.g., decrease the transcription of genes regulated by, e.g., one or more transcription factors selected from the group of activating transcription factor 2 (ATF2), c-Jun, and NF-κB). A description of downstream signaling of a TNFα receptor is provided in Wajant et al., *Cell Death Differentiation* 10:45-65, 2003 (incorporated herein by reference). For example, such indirect anti-TNFα agents can be an inhibitory nucleic acid that targets (decreases the expression) a signaling component downstream of a TNFα-induced gene (e.g., any TNFα-induced gene known in the art), a TNFα receptor (e.g., any one or more of the signaling components downstream of a TNFα receptor described herein or known in the art), or a transcription factor selected from the group of NF-κB, c-Jun, and ATF2.

In other examples, such indirect anti-TNFα agents can be a small molecule inhibitor of a protein encoded by a TNFα-induced gene (e.g., any protein encoded by a TNFα-induced gene known in the art), a small molecule inhibitor of a signaling component downstream of a TNFα receptor (e.g., any of the signaling components downstream of a TNFα receptor described herein or known in the art), and a small molecule inhibitor of a transcription factor selected from the group of ATF2, c-Jun, and NF-κB.

In other embodiments, anti-TNFα agents that can indirectly block, down-regulate, impair, or reduce one or more components in a cell (e.g., a cell obtained from a subject, a mammalian cell) that are involved in the signaling pathway that results in TNFα mRNA transcription, TNFα mRNA stabilization, and TNFα mRNA translation (e.g., one or more components selected from the group of CD14, c-Jun, ERK1/2, IKK, IκB, interleukin 1 receptor associated kinase 1 (IRAK), JNK, lipopolysaccharide binding protein (LBP), MEK1/2, MEK3/6, MEK4/7, MK2, MyD88, NF-κB, NIK, PKR, p38, AKT serine/threonine kinase 1 (rac), raf kinase (raf), ras, TRAF6, TTP). For example, such indirect anti-TNFα agents can be an inhibitory nucleic acid that targets (decreases the expression) of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, LBP, MEK1/2, MEK3/6, MEK4/7, MK2, MyD88, NF-κB, NIK, IRAK, lipopolysaccharide binding protein (LBP), PKR, p38, rac, raf, ras, TRAF6, TTP). In other examples, an indirect anti-TNFα agents is a small molecule inhibitor of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, lipopolysaccharide binding protein (LBP), MEK1/2, MEK3/6, MEK4/7, MK2, MyD88, NF-κB, NIK, IRAK, lipopolysaccharide binding protein (LBP), PKR, p38, rac, raf, ras, TRAF6, TTP).

Antibodies

In some embodiments, the anti-TNFα agent is an antibody or an antigen-binding fragment thereof (e.g., a Fab or a scFv). In some embodiments, an antibody or antigen-binding fragment of an antibody described herein can bind specifically to TNFα. In some embodiments, an antibody or antigen-binding fragment described herein binds specifically to any one of TNFα, TNFR1, or TNFR2. In some embodiments, an antibody or antigen-binding fragment of an antibody described herein can bind specifically to a TNFα receptor (TNFR1 or TNFR2).

In some embodiments, the antibody can be a humanized antibody, a chimeric antibody, a multivalent antibody, or a fragment thereof. In some embodiments, an antibody can be a scFv-Fc, a VHH domain, a VNAR domain, a (scFv)2, a minibody, or a BiTE.

In some embodiments, an antibody can be a crossmab, a diabody, a scDiabody, a scDiabody-CH3, a Diabody-CH3, a DutaMab, a DT-IgG, a diabody-Fc, a scDiabody-HAS, a charge pair antibody, a Fab-arm exchange antibody, a SEEDbody, a Triomab, a LUZ-Y, a Fcab, a kλ-body, an orthogonal Fab, a DVD-IgG, an IgG(H)-scFv, a scFv-(H) IgG, an IgG(L)-scFv, a scFv-(L)-IgG, an IgG (L,H)-Fc, an IgG(H)-V, a V(H)-IgG, an IgG(L)-V, a V(L)-IgG, an KIH IgG-scFab, a 2scFv-IgG, an IgG-2scFv, a scFv4-Ig, a Zybody, a DVI-IgG, a nanobody, a nanobody-HSA, a DVD-Ig, a dual-affinity re-targeting antibody (DART), a triomab, a kih IgG with a common LC, an ortho-Fab IgG, a 2-in-1-IgG, IgG-ScFv, scFv2-Fc, a bi-nanobody, tanden antibody, a DART-Fc, a scFv-HAS-scFv, a DAF (two-in-one or four-in-one), a DNL-Fab3, knobs-in-holes common LC, knobs-in-holes assembly, a TandAb, a Triple Body, a miniantibody, a minibody, a TriBi minibody, a scFv-CH3 KIH, a Fab-scFv, a scFv-CH-CL-scFv, a F(ab')2-scFV2, a scFv-KIH, a Fab-scFv-Fc, a tetravalent HCAb, a scDiabody-Fc, a tandem scFv-Fc, an intrabody, a dock and lock bispecific antibody, an ImmTAC, a HSAbody, a tandem scFv, an IgG-IgG, a Cov-X-Body, and a scFv1-PEG-scFv2.

Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); or an antigen-binding fragment of an IgM (e.g., an antigen-binding fragment of a human or humanized IgM).

Non-limiting examples of anti-TNFα agents that are antibodies that specifically bind to TNFα are described in Ben-Horin et al., *Autoimmunity Rev.* 13(1):24-30, 2014; Bongartz et al., *JAMA* 295(19):2275-2285, 2006; Butler et al., *Eur. Cytokine Network* 6(4):225-230, 1994; Cohen et al., *Canadian J. Gastroenterol. Hepatol.* 15(6):376-384, 2001; Elliott et al., *Lancet* 1994; 344: 1125-1127, 1994; Feldmann et al., *Ann. Rev. Immunol.* 19(1):163-196, 2001; Rankin et al., *Br. J. Rheumatol.* 2:334-342, 1995; Knight et al., *Molecular Immunol.* 30(16):1443-1453, 1993; Lorenz et al., *J. Immunol.* 156(4):1646-1653, 1996; Hinshaw et al., *Circulatory Shock* 30(3):279-292, 1990; Ordas et al., *Clin. Pharmacol. Therapeutics* 91(4):635-646, 2012; Feldman, *Nature Reviews Immunol.* 2(5):364-371, 2002; Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Wanner et al., *Shock* 11(6):391-395, 1999; and U.S. Pat. Nos. 6,090,382; 6,258,562; and 6,509,015).

In certain embodiments, the anti-TNFα agent can include or is golimumab (Golimumab™), adalimumab (Humira™), infliximab (Remicade™), CDP571, CDP 870, or certolizumab pegol (Cimzia™). In certain embodiments, the anti-TNFα agent can be a TNFα inhibitor biosimilar. Examples of approved and late-phase TNFα inhibitor biosimilars include, but are not limited to, infliximab biosimilars such as Flixabi™ (SB2) from Samsung Bioepis, Inflectra® (CT-P13) from Celltrion/Pfizer, GS071 from Aprogen, Remsima™, PF-06438179 from Pfizer/Sandoz, NI-071 from Nichi-Iko Pharmaceutical Co., and ABP 710 from Amgen; adalimumab biosimilars such as Amgevita® (ABP 501) from Amgen and Exemptia™ from Zydus Cadila, BMO-2 or MYL-1401-A from Biocon/Mylan, CHS-1420 from Coherus, FKB327 from Kyowa Kirin, and BI 695501 from Boehringer Ingelheim; Solymbic®, SB5 from Samsung Bioepis, GP-2017 from Sandoz, ONS-3010 from Oncobiologics, M923 from Momenta, PF-06410293 from Pfizer, and etanercept biosimilars such as Erelzi™ from Sandoz/Novartis, Brenzys™ (SB4) from Samsung Bioepis, GP2015 from Sandoz, TuNEX® from Mycenax, LBECO101 from LG Life, and CHS-0214 from Coherus.

In some embodiments of any of the methods described herein, the anti-TNFα agent is selected from the group consisting of: adalimumab, certolizumab, etanercept, golimumab, infliximabm, CDP571, and CDP 870.

In some embodiments, any of the antibodies or antigen-binding fragments described herein has a dissociation constant ($K_D$) of less than $1 \times 10^{-5}$ M (e.g., less than $0.5 \times 10^{-5}$ M, less than $1 \times 10^{-6}$ M, less than $0.5 \times 10^{-6}$ M, less than $1 \times 10^{-7}$ M, less than $0.5 \times 10^{-7}$ M, less than $1 \times 10^{-8}$ M, less than $0.5 \times 10^{-8}$ M, less than $1 \times 10^{-9}$ M, less than $0.5 \times 10^{-9}$ M, less than $1 \times 10^{-10}$ M, less than $0.5 \times 10^{-10}$ M, less than $1 \times 10^{-11}$ M, less than $0.5 \times 10^{-11}$ M, or less than $1 \times 10^{-12}$ M), e.g., as measured in phosphate buffered saline using surface plasmon resonance (SPR).

In some embodiments, any of the antibodies or antigen-binding fragments described herein has a $K_D$ of about $1 \times 10^{-12}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, about $0.5 \times 10^{-10}$ M, about $1 \times 10^{-11}$ M, or about $0.5 \times 10^{-11}$ M (inclusive); about $0.5 \times 10^{-11}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, about $0.5 \times 10^{-10}$ M, or about $1 \times 10^{-11}$ M (inclusive); about $1 \times 10^{-11}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, or about $0.5 \times 10^{-10}$ M (inclusive); about $0.5 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, or about $1 \times 10^{-10}$ M (inclusive); about $1 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, or about $0.5 \times 10^{-9}$ M (inclusive); about $0.5 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, or about $1 \times 10^{-9}$ M (inclusive); about $1 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, or about $0.5 \times 10^{-8}$ M (inclusive); about $0.5 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, or about $1 \times 10^{-8}$ M (inclusive); about $1 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, or about $0.5 \times 10^{-7}$ M (inclusive); about $0.5 \times 10^{-7}$ M to about $1 \times 10^{-5}$ M, about $0.5 \times 10^{-5}$ M, about $1 \times 10^{-6}$ M, about $0.5 \times 10^{-6}$ M, or about $1 \times 10^{-7}$ M (inclusive); about $1 \times 10^{-7}$ M to about $1 \times 10^{-5}$ M, about $0.5 \times 10^{-5}$ M, about $1 \times 10^{-6}$ M, or about $0.5 \times 10^{-6}$ M (inclusive); about $0.5 \times 10^{-6}$ M to about $1 \times 10^{-5}$ M, about $0.5 \times 10^{-5}$ M, or about $1 \times 10^{-6}$ M (inclusive); about $1 \times 10^{-6}$ M to about $1 \times 10^{-5}$ M or about $0.5 \times 10^{-5}$ M (inclusive); or about $0.5 \times 10^{-5}$ M to about $1 \times 10^{-5}$ M (inclusive), e.g., as measured in phosphate buffered saline using surface plasmon resonance (SPR).

In some embodiments, any of the antibodies or antigen-binding fragments described herein has a $K_{off}$ of about $1\times10^{-6}$ s$^{-1}$ to about $1\times10^{-3}$ s$^{-1}$, about $0.5\times10^{-3}$ s$^{-1}$, about $1\times10^{-4}$ s$^{-1}$, about $0.5\times10^{-4}$ s$^{-1}$, about $1\times10^{-5}$ s$^{-1}$, or about $0.5\times10^{-5}$ s$^{-1}$ (inclusive); about $0.5\times10^{-5}$ s$^{-1}$ to about $1\times10^{-3}$ s$^{-1}$, about $0.5\times10^{-3}$ s$^1$, about $1\times10^{-4}$ s$^{-1}$, about $0.5\times10^{-4}$ s$^{-1}$, or about $1\times10^{-5}$ s$^{-1}$ (inclusive); about $1\times10^{-5}$ s$^{-1}$ to about $1\times10^{-3}$ s$^{-1}$, about $0.5\times10^{-3}$ s$^{-1}$, about $1\times10^{-4}$ s$^{-1}$, or about $0.5\times10^{-4}$ s$^{-1}$ (inclusive); about $0.5\times10^{-4}$ s$^{-1}$ to about $1\times10^{-1}$ s$^{-1}$, about $0.5\times10^{-3}$ s$^{-1}$, or about $1\times10^{-1}$ s$^1$ (inclusive); about $1\times10^{-1}$ s$^{-1}$ to about $1\times10^{-3}$ s$^{-1}$, or about $0.5\times10^{-3}$ s$^{-1}$ (inclusive); or about $0.5\times10^{-5}$ s$^{-1}$ to about $1\times10^{-3}$ s$^{-1}$ (inclusive), e.g., as measured in phosphate buffered saline using surface plasmon resonance (SPR).

In some embodiments, any of the antibodies or antigen-binding fragments described herein has a $K_{on}$ of about $1\times10^2$ M$^{-1}$ s$^{-1}$ to about $1\times10^6$ M$^{-1}$ s$^{-1}$, about $0.5\times10^6$ M$^{-1}$ s$^{-1}$, about $1\times10^5$ M$^{-1}$ s$^{-1}$, about $0.5\times10^5$ M$^{-1}$ s$^{-1}$, about $1\times10^4$ M$^{-1}$ s$^{-1}$, about $0.5\times10^4$ M$^{-1}$ s$^{-1}$, about $1\times10^3$ M$^{-1}$ s$^{-1}$, or about $0.5\times10^3$ M$^{-1}$ s$^{-1}$ (inclusive); about $0.5\times10^3$ M$^{-1}$ s$^{-1}$ to about $1\times10^6$ M$^{-1}$ s$^{-1}$, about $0.5\times10^6$ M$^{-1}$ s$^{-1}$, about $1\times10^5$ M$^{-1}$ s$^{-1}$, about $0.5\times10^5$ M$^{-1}$ s$^{-1}$, about $1\times10^4$ M$^{-1}$ s$^{-1}$, about $0.5\times10^4$ M$^{-1}$ s$^{-1}$, or about $1\times10^3$ M$^{-1}$ s$^{-1}$ (inclusive); about $1\times10^3$ M$^{-1}$ s$^{-1}$ to about $1\times10^6$ M$^{-1}$ s$^{-1}$, about $0.5\times10^6$ M$^{-1}$ s$^{-1}$, about $1\times10^5$ M$^{-1}$ s$^{-1}$, about $0.5\times10^5$ M$^{-1}$ s$^{-1}$, about $1\times10^4$ M$^{-1}$ s$^{-1}$, or about $0.5\times10^4$ M$^{-1}$ s$^{-1}$ (inclusive); about $0.5\times10^4$ M$^{-1}$ s$^{-1}$ to about $1\times10^6$ M$^{-1}$ s$^{-1}$, about $0.5\times10^6$ M$^{-1}$ s$^{-1}$, about $1\times10^5$ M$^{-1}$ s$^{-1}$, about $0.5\times10^5$ M$^{-1}$ s$^{-1}$, or about $1\times10^4$ M$^{-1}$ s$^{-1}$ (inclusive); about $1\times10^4$ M$^{-1}$ s$^{-1}$ to about $1\times10^6$ M$^{-1}$ s$^{-1}$, about $0.5\times10^6$ M$^{-1}$ s$^{-1}$, about $1\times10^5$ M$^{-1}$ s$^{-1}$, or about $0.5\times10^5$ M$^{-1}$ s$^{-1}$ (inclusive); about $0.5\times10^5$ M$^{-1}$ s$^{-1}$ to about $1\times10^6$ M$^{-1}$ s$^{-1}$, about $0.5\times10^6$ M$^{-1}$ s$^{-1}$, or about $1\times10^5$ M$^{-1}$ s$^{-1}$ (inclusive); about $1\times10^5$ M$^{-1}$ s$^{-1}$ to about $1\times10^6$ M$^{-1}$ s$^{-1}$, or about $0.5\times10^6$ M$^{-1}$ s$^{-1}$ (inclusive); or about $0.5\times10^6$ M$^{-1}$ s$^{-1}$ to about $1\times10^6$ M$^{-1}$ s$^{-1}$ (inclusive), e.g., as measured in phosphate buffered saline using surface plasmon resonance (SPR).

Fusion Proteins

In some embodiments, the anti-TNFα agent is a fusion protein (e.g., an extracellular domain of a TNFR fused to a partner peptide, e.g., an Fc region of an immunoglobulin, e.g., human IgG) (see, e.g., Deeg et al., *Leukemia* 16(2):162, 2002; Peppel et al., *J. Exp. Med.* 174(6):1483-1489, 1991) or a soluble TNFR (e.g., TNFR1 or TNFR2) that binds specifically to TNFα. In some embodiments, the anti-TNFα agent includes or is a soluble TNFα receptor (e.g., Bjornberg et al., *Lymphokine Cytokine Res.* 13(3):203-211, 1994; Kozak et al., *Am. J. Physiol. Reg. Integrative Comparative Physiol.* 269(1):R23-R29, 1995; Tsao et al., *Eur Respir J.* 14(3):490-495, 1999; Watt et al., *J Leukoc Biol.* 66(6):1005-1013, 1999; Mohler et al., *J. Immunol.* 151(3):1548-1561, 1993; Nophar et al., *EMBO J.* 9(10):3269, 1990; Piguet et al., *Eur. Respiratory J.* 7(3):515-518, 1994; and Gray et al., *Proc. Natl. Acad. Sci. U.S.A.* 87(19):7380-7384, 1990). In some embodiments, the anti-TNFα agent includes or is etanercept (Enbrel™) (see, e.g., WO 91/03553 and WO 09/406,476, incorporated by reference herein). In some embodiments, the anti-TNFα agent inhibitor includes or is r-TBP-I (e.g., Gradstein et al., J. *Acquir. Immune Defic. Syndr.* 26(2): 111-117, 2001).

Inhibitory Nucleic Acids

Inhibitory nucleic acids that can decrease the expression of AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA expression in a mammalian cell include antisense nucleic acid molecules, i.e., nucleic acid molecules whose nucleotide sequence is complementary to all or part of a AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (e.g., complementary to all or a part of any one of SEQ ID NOs: 1-37).

```
Human TNFα CDS
                                                         (SEQ ID NO: 1)
ATGAGCACTGAAAGCATGATCCGGGACGTGGAGCTGGCCGAGGAGGCGCTCCCCAA

GAAGACAGGGGGCCCCAGGGCTCCAGGCGGTGCTTGTTCCTCAGCCTCTTCTCCTT

CCTGATCGTGGCAGGCGCCACCACGCTCTTCTGCCTGCTGCACTTTGGAGTGATCGG

CCCCCAGAGGGAAGAGTTCCCCAGGGACCTCTCTCTAATCAGCCCTCTGGCCCAGGC

AGTCAGATCATCTTCTCGAACCCCGAGTGACAAGCCTGTAGCCCATGTTGTAGCAAA

CCCTCAAGCTGAGGGGCAGCTCCAGTGGCTGAACCGCCGGGCCAATGCCCTCCTGG

CCAATGGCGTGGAGCTGAGAGATAACCAGCTGGTGGTGCCATCAGAGGGCCTGTAC

CTCATCTACTCCCAGGTCCTCTTCAAGGGCCAAGGCTGCCCCTCCACCCATGTGCTC

CTCACCCACACCATCAGCCGCATCGCCGTCTCCTACCAGACCAAGGTCAACCTCCTC

TCTGCCATCAAGAGCCCCTGCCAGAGGGAGACCCCAGAGGGGGCTGAGGCCAAGCC

CTGGTATGAGCCCATCTATCTGGGAGGGGTCTTCCAGCTGGAGAAGGGTGACCGACT

CAGCGCTGAGATCAATCGGCCCGACTATCTCGACTTTGCCGAGTCTGGGCAGGTCTA

CTTTGGGATCATTGCCCTGTGA

Human TNFR1 CDS
                                                         (SEQ ID NO: 2)
ATGGGCCTCTCCACCGTGCCTGACCTGCTGCTGCCACTGGTGCTCCTGGAGCTGTTG

GTGGGAATATACCCCTCAGGGGTTATTGGACTGGTCCCTCACCTAGGGGACAGGGA
```

```
GAAGAGAGATAGTGTGTGTCCCCAAGGAAAATATATCCACCCTCAAAATAATTCGA

TTTGCTGTACCAAGTGCCACAAAGGAACCTACTTGTACAATGACTGTCCAGGCCCGG

GGCAGGATACGGACTGCAGGGAGTGTGAGAGCGGCTCCTTCACCGCTTCAGAAAAC

CACCTCAGACACTGCCTCAGCTGCTCCAAATGCCGAAAGGAAATGGGTCAGGTGGA

GATCTCTTCTTGCACAGTGGACCGGGACACCGTGTGTGGCTGCAGGAAGAACCAGT

ACCGGCATTATTGGAGTGAAAACCTTTTCCAGTGCTTCAATTGCAGCCTCTGCCTCA

ATGGGACCGTGCACCTCTCCTGCCAGGAGAAACAGAACACCGTGTGCACCTGCCAT

GCAGGTTTCTTTCTAAGAGAAAACGAGTGTGTCTCCTGTAGTAACTGTAAGAAAAGC

CTGGAGTGCACGAAGTTGTGCCTACCCCAGATTGAGAATGTTAAGGGCACTGAGGA

CTCAGGCACCACAGTGCTGTTGCCCCTGGTCATTTTCTTTGGTCTTTGCCTTTTATCCC

TCCTCTTCATTGGTTTAATGTATCGCTACCAACGGTGGAAGTCCAAGCTCTACTCCAT

TGTTTGTGGGAAATCGACACCTGAAAAAGAGGGGGAGCTTGAAGGAACTACTACTA

AGCCCCTGGCCCCAAACCCAAGCTTCAGTCCCACTCCAGGCTTCACCCCCACCCTGG

GCTTCAGTCCCGTGCCCAGTTCCACCTTCACCTCCAGCTCCACCTATACCCCCGGTGA

CTGTCCCAACTTTGCGGCTCCCCGCAGAGAGGTGGCACCACCCTATCAGGGGCTGA

CCCCATCCTTGCGACAGCCCTCGCCTCCGACCCCATCCCCAACCCCCTTCAGAAGTG

GGAGGACAGCGCCCACAAGCCACAGAGCCTAGACACTGATGACCCCGCGACGCTGT

ACGCCGTGGTGGAGAACGTGCCCCCGTTGCGCTGGAAGGAATTCGTGCGGCGCCTA

GGGCTGAGCGACCACGAGATCGATCGGCTGGAGCTGCAGAACGGGCGCTGCCTGCG

CGAGGCGCAATACAGCATGCTGGCGACCTGGAGGCGGCGCACGCCGCGGCGCGAG

GCCACGCTGGAGCTGCTGGGACGCGTGCTCCGCGACATGGACCTGCTGGGCTGCCT

GGAGGACATCGAGGAGGCGCTTTGCGGCCCCGCCGCCCTCCCGCCCGCGCCCAGTC

TTCTCAGATGA
Human TNFR2 CDS
                                                    (SEQ ID NO: 3)
ATTCTTCCCCTGGTGGCCATGGGACCCAGGTCAATGTCACCTGCATCGTGAACGTCT

GTAGCAGCTCTGACCACAGCTCACAGTGCTCCTCCCAAGCCAGCTCCACAATGGGA

GACACAGATTCCAGCCCCTCGGAGTCCCCGAAGGACGAGCAGGTCCCCTTCTCCAA

GGAGGAATGTGCCTTTCGGTCACAGCTGGAGACGCCAGAGACCCTGCTGGGGAGCA

CCGAAGAGAAGCCCCTGCCCCTTGGAGTGCCTGATGCTGGGATGAAGCCCAGTTAA
Human TRADD CDS
                                                    (SEQ ID NO: 4)
ATGGCAGCTGGGCAAAATGGGCACGAAGAGTGGGTGGGCAGCGCATACCTGTTTGT

GGAGTCCTCGCTGGACAAGGTGGTCCTGTCGGATGCCTACGCGCACCCCCAGCAGA

AGGTGGCAGTGTACAGGGCTCTGCAGGCTGCCTTGGCAGAGAGCGGCGGGAGCCCG

GACGTGCTGCAGATGCTGAAGATCCACCGCAGCGACCCGCAGCTGATCGTGCAGCT

GCGATTCTGCGGGCGGCAGCCCTGTGGCCGCTTCCTCCGCGCCTACCGCGAGGGGGC

GCTGCGCGCCGCGCTGCAGAGGAGCCTGGCGGCCGCGCTCGCCCAGCACTCGGTGC

CGCTGCAACTGGAGCTGCGCGCCGGCGCCGAGCGGCTGGACGCTTTGCTGGCGGAC

GAGGAGCGCTGTTTGAGTTGCATCCTAGCCCAGCAGCCCGACCGGCTCCGGGATGA

AGAACTGGCTGAGCTGGAGGATGCGCTGCGAAATCTGAAGTGCGGCTCGGGGGCCC

GGGGTGGCGACGGGGAGGTCGCTTCGGCCCCCTTGCAGCCCCCGGTGCCCTCTCTGT
```

-continued

```
CGGAGGTGAAGCCGCCGCCGCCGCCGCCACCTGCCCAGACTTTTCTGTTCCAGGGTC

AGCCTGTAGTGAATCGGCCGCTGAGCCTGAAGGACCAACAGACGTTCGCGCGCTCT

GTGGGTCTCAAATGGCGCAAGGTGGGGCGCTCACTGCAGCGAGGCTGCCGGGCGCT

GCGGGACCCGGCGCTGGACTCGCTGGCCTACGAGTACGAGCGCGAGGGACTGTACG

AGCAGGCCTTCCAGCTGCTGCGGCGCTTCGTGCAGGCCGAGGGCCGCCGCGCCACG

CTGCAGCGCCTGGTGGAGGCACTCGAGGAGAACGAGCTCACCAGCCTGGCAGAGGA

CTTGCTGGGCCTGACCGATCCCAATGGCGGCCTGGCCTAG
```

Human TRAF2 CDS
(SEQ ID NO: 5)
```
ATGGCTGCAGCTAGCGTGACCCCCCCTGGCTCCCTGGAGTTGCTACAGCCCGGCTTC

TCCAAGACCCTCCTGGGGACCAAGCTGGAAGCCAAGTACCTGTGCTCCGCCTGCAG

AAACGTCCTCCGCAGGCCCTTCCAGGCGCAGTGTGGCCACCGGTACTGCTCCTTCTG

CCTGGCCAGCATCCTCAGCTCTGGGCCTCAGAACTGTGCTGCCTGTGTTCACGAGGG

CATATATGAAGAAGGCATTTCTATTTTAGAAAGCAGTTCGGCCTTCCCAGATAATGC

TGCCCGCAGGGAGGTGGAGAGCCTGCCGGCCGTCTGTCCCAGTGATGGATGCACCT

GGAAGGGGACCCTGAAAGAATACGAGAGCTGCCACGAAGGCCGCTGCCCGCTCATG

CTGACCGAATGTCCCGCGTGCAAAGGCCTGGTCCGCCTTGGTGAAAAGGAGCGCCA

CCTGGAGCACGAGTGCCCGGAGAGAAGCCTGAGCTGCCGGCATTGCCGGGCACCCT

GCTGCGGAGCAGACGTGAAGGCGCACCACGAGGTCTGCCCCAAGTTCCCCTTAACT

TGTGACGGCTGCGGCAAGAAGAAGATCCCCGGGAGAAGTTTCAGGACCACGTCAA

GACTTGTGGCAAGTGTCGAGTCCCTTGCAGATTCCACGCCATCGGCTGCCTCGAGAC

GGTAGAGGGTGAGAAACAGCAGGAGCACGAGGTGCAGTGGCTGCGGGAGCACCTG

GCCATGCTACTGAGCTCGGTGCTGGAGGCAAAGCCCCTCTTGGGAGACCAGAGCCA

CGCGGGGTCAGAGCTCCTGCAGAGGTGCGAGAGCCTGGAGAAGAAGACGGCCACTT

TTGAGAACATTGTCTGCGTCCTGAACCGGGAGGTGGAGAGGGTGGCCATGACTGCC

GAGGCCTGCAGCCGGCAGCACCGGCTGGACCAAGACAAGATTGAAGCCCTGAGTAG

CAAGGTGCAGCAGCTGGAGAGGAGCATTGGCCTCAAGGACCTGGCGATGGCTGACT

TGGAGCAGAAGGTCTTGGAGATGGAGGCATCCACCTACGATGGGGTCTTCATCTGG

AAGATCTCAGACTTCGCCAGGAAGCGCCAGGAAGCTGTGGCTGGCCGCATACCCGC

CATCTTCTCCCCAGCCTTCTACACCAGCAGGTACGGCTACAAGATGTGTCTGCGTAT

CTACCTGAACGGCGACGGCACCGGGCGAGGAACACACCTGTCCCTCTTCTTTGTGGT

GATGAAGGGCCCGAATGACGCCCTGCTGCGGTGGCCCTTCAACCAGAAGGTGACCT

TAATGCTGCTCGACCAGAATAACCGGGAGCACGTGATTGACGCCTTCAGGCCCGAC

GTGACTTCATCCTCTTTTCAGAGGCCAGTCAACGACATGAACATCGCAAGCGGCTGC

CCCCTCTTCTGCCCCGTCTCCAAGATGGAGGCAAAGAATTCCTACGTGCGGGACGAT

GCCATCTTCATCAAGGCCATTGTGGACCTGACAGGGCTCTAA
```

Human AP-1 CDS
(SEQ ID NO: 6)
```
ATGGAAACACCCTTCTACGGCGATGAGGCGCTGAGCGGCCTGGGCGGCGGCGCCAG

TGGCAGCGGCGGCAGCTTCGCGTCCCCGGGCCGCTTGTTCCCCGGGGCGCCCCGAC

GGCCGCGGCCGGCAGCATGATGAAGAAGGACGCGCTGACGCTGAGCCTGAGTGAGC

AGGTGGCGGCAGCGCTCAAGCCCTGCGGCCGCGCCGCCTCCTACCCCCCTGCGCGCC

GACGGCGCCCCCAGCGCGGCACCCCCCGACGGCCTGCTCGCCTCTCCCGACCTGGG
```

```
GCTGCTGAAGCTGGCCTCCCCCGAGCTCGAGCGCCTCATCATCCAGTCCAACGGGCT

GGTCACCACCACGCCGACGAGCTCACAGTTCCTCTACCCCAAGGTGGCGGCCAGCG

AGGAGCAGGAGTTCGCCGAGGGCTTCGTCAAGGCCCTGGAGGATTTACACAAGCAG

AACCAGCTCGGCGCGGGCGCGGCCGCTGCCGCCGCCGCCGCCGCCGGGGGGCC

CTCGGGCACGGCCACGGGCTCCGCGCCCCCGGCGAGCTGGCCCCGGCGGCGGCCG

CGCCCGAAGCGCCTGTCTACGCGAACCTGAGCAGCTACGCGGGCGGCGCCGGGGGC

GCGGGGGGCGCCGCGACGGTCGCCTTCGCTGCCGAACCTGTGCCCTTCCCGCCGCCG

CCACCCCCAGGCGCGTTGGGGCCGCCGCGCCTGGCTGCGCTCAAGGACGAGCCACA

GACGGTGCCCGACGTGCCGAGCTTCGGCGAGAGCCCGCCGTTGTCGC

CCATCGACATGGACACGCAGGAGCGCATCAAGGCGGAGCGCAAGCGGCTGCGCAA

CCGCATCGCCGCCTCCAAGTGCCGCAAGCGCAAGCTGGAGCGCATCTCGCGCCTGG

AAGAGAAAGTGAAGACCCTCAAGAGTCAGAACACGGAGCTGGCGTCCACGGCGAG

CCTGCTGCGCGAGCAGGTGGCGCAGCTCAAGCAGAAAGTCCTCAGCCACGTCAACA

GCGGCTGCCAGCTGCTGCCCCAGCACCAGGTGCCCGCGTACTGA

Human ASK1 CDS
                                                        (SEQ ID NO: 7)
ATGAGCACGGAGGCGGACGAGGGCATCACTTTCTCTGTGCCACCCTTCGCCCCCTCG

GGCTTCTGCACCATCCCCGAGGGCGGCATCTGCAGGAGGGGAGGAGCGGCGGCGGT

GGGCGAGGGCGAGGAGCACCAGCTGCCACCGCCGCCGCCGGGCAGTTTCTGGAACG

TGGAGAGCGCCGCTGCCCCTGGCATCGGTTGTCCGGCGGCCACCTCCTCGAGCAGTG

CCACCCGAGGCCGGGGCAGCTCTGTTGGCGGGGGCAGCCGACGGACCACGGTGGCA

TATGTGATCAACGAAGCGAGCCAAGGGCAACTGGTGGTGGCCGAGAGCGAGGCCCT

GCAGAGCTTGCGGGAGGCGTGCGAGACAGTGGGCGCCACCCTGGAACCCTGCATTT

TGGGAAACTCGACTTTGGAGAAACCACCGTGCTGGACCGCTTTTACAATGCAGATAT

TGCGGTGGTGGAGATGAGCGATGCCTTCCGGCAGCCGTCCTTGTTTTACCACCTTGG

GGTGAGAGAAAGTTTCAGCATGGCCAACAACATCATCCTCTACTGCGATACTAACTC

GGACTCTCTGCAGTCACTGAAGGAAATCATTTGCCAGAAGAATACTATGTGCACTGG

GAACTACACCTTTGTTCCTTACATGATAACTCCACATAACAAAGTCTACTGCTGTGA

CAGCAGCTTCATGAAGGGGTTGACAGAGCTCATGCAACCGAACTTCGAGCTGCTTCT

TGGACCCATCTGCTTACCTCTTGTGGATCGTTTTATTCAACTTTTGAAGGTGGCACAA

GCAAGTTCTAGCCAGTACTTCCGGGAATCTATACTCAATGACATCAGGAAAGCTCGT

AATTTATACACTGGTAAAGAATTGGCAGCTGAGTTGGCAAGAATTCGGCAGCGAGT

AGATAATATCGAAGTCTTGACAGCAGATATTGTCATAAATCTGTTACTTTCCTACAG

AGATATCCAGGACTATGATTCTATTGTGAAGCTGGTAGAGACTTTAGAAAAACTGCC

AACCTTTGATTTGGCCTCCCATCACCATGTGAAGTTTCATTATGCATTTGCACTGAAT

AGGAGAAATCTCCCTGGTGACAGAGCAAAAGCTCTTGATATTATGATTCCCATGGTG

CAAAGCGAAGGACAAGTTGCTTCAGATATGTATTGCCTAGTTGGTCGAATCTACAAA

GATATGTTTTTGGACTCTAATTTCACGGACACTGAAAGCAGAGACCATGGAGCTTCT

TGGTTCAAAAAGGCATTTGAATCTGAGCCAACACTACAGTCAGGAATTAATTATGCG

GTCCTCCTCCTGGCAGCTGGACACCAGTTTGAATCTTCCTTTGAGCTCCGGAAAGTT

GGGGTGAAGCTAAGTAGTCTTCTTGGTAAAAAGGGAAACTTGGAAAAACTCCAGAG
```

-continued

```
CTACTGGGAAGTTGGATTTTTTCTGGGGGCCAGCGTCCTAGCCAATGACCACATGAG

AGTCATTCAAGCATCTGAAAAGCTTTTTAAACTGAAGACACCAGCATGGTACCTCAA

GTCTATTGTAGAGACAATTTTGATATATAAGCATTTTGTGAAACTGACCACAGAACA

GCCTGTGGCCAAGCAAGAACTTGTGGACTTTTGGATGGATTTCCTGGTCGAGGCCAC

AAAGACAGATGTTACTGTGGTTAGGTTTCCAGTATTAATATTAGAACCAACCAAAAT

CTATCAACCTTCTTATTTGTCTATCAACAATGAAGTTGAGGAAAAGACAATCTCTAT

TTGGCACGTGCTTCCTGATGACAAGAAAGGTATACATGAGTGGAATTTTAGTGCCTC

TTCTGTCAGGGGAGTGAGTATTTCTAAATTTGAAGAAAGATGCTGCTTTCTTTATGTG

CTTCACAATTCTGATGATTTCCAAATCTATTTCTGTACAGAACTTCATTGTAAAAAGT

TTTTTGAGATGGTGAACACCATTACCGAAGAGAAGGGGAGAAGCACAGAGGAAGG

AGACTGTGAAAGTGACTTGCTGGAGTATGACTATGAATATGATGAAAATGGTGACA

GAGTCGTTTTAGGAAAAGGCACTTATGGGATAGTCTACGCAGGTCGGGACTTGAGC

AACCAAGTCAGAATTGCTATTAAGGAAATCCCAGAGAGAGACAGCAGATACTCTCA

GCCCCTGCATGAAGAAATAGCATTGCATAAACACCTGAAGCACAAAAATATTGTCC

AGTATCTGGGCTCTTTCAGTGAGAATGGTTTCATTAAAATCTTCATGGAGCAGGTCC

CTGGAGGAAGTCTTTCTGCTCTCCTTCGTTCCAAATGGGGTCCATTAAAAGACAATG

AGCAAACAATTGGCTTTTATACAAAGCAAATACTGGAAGGATTAAAATATCTCCATG

ACAATCAGATAGTTCACCGGGACATAAAGGGTGACAATGTGTTGATTAATACCTAC

AGTGGTGTTCTCAAGATCTCTGACTTCGGAACATCAAAGAGGCTTGCTGGCATAAAC

CCCTGTACTGAAACTTTTACTGGTACCCTCCAGTATATGGCACCAGAAATAATAGAT

AAAGGACCAAGAGGCTACGGAAAAGCAGCAGACATCTGGTCTCTGGGCTGTACAAT

CATTGAAATGGCCACAGGAAAACCCCCATTTTATGAACTGGGAGAACCACAAGCAG

CTATGTTCAAGGTGGGAATGTTTAAAGTCCACCCTGAGATCCCAGAGTCCATGTCTG

CAGAGGCCAAGGCATTCATACTGAAATGTTTTGAACCAGATCCTGACAAGAGAGCC

TGTGCTAACGACTTGCTTGTTGATGAGTTTTTAAAAGTTTCAAGCAAAAAGAAAAAG

ACACAACCTAAGCTTTCAGCTCTTTCAGCTGGATCAAATGAATATCTCAGGAGTATA

TCCTTGCCGGTACCTGTGCTGGTGGAGGACACCAGCAGCAGCAGTGAGTACGGCTC

AGTTTCACCCGACACGGAGTTGAAAGTGGACCCCTTCTCTTTCAAAACAAGAGCCAA

GTCCTGCGGAGAAAGAGATGTCAAGGGAATTCGGACACTCTTTTTGGGCATTCCAGA

TGAGAATTTTGAAGATCACAGTGCTCCTCCTTCCCCTGAAGAAAAGATTCTGGATT

CTTCATGCTGAGGAAGGACAGTGAGAGGCGAGCTACCCTTCACAGGATCCTGACGG

AAGACCAAGACAAAATTGTGAGAAACCTAATGGAATCTTTAGCTCAGGGGCTGAA

GAACCGAAACTAAAATGGGAACACATCACAACCCTCATTGCAAGCCTCAGAGAATT

TGTGAGATCCACTGACCGAAAAATCATAGCCACCACACTGTCAAAGCTGAAACTGG

AGCTGGACTTCGACAGCCATGGCATTAGCCAAGTCCAGGTGGTACTCTTTGGTTTTC

AAGATGCTGTCAATAAAGTTCTTCGGAATCATAACATCAAGCCGCACTGGATGTTTG

CCTTAGACAGTATCATTCGGAAGGCGGTACAGACAGCCATTACCATCCTGGTTCCAG

AACTAAGGCCACATTTCAGCCTTGCATCTGAGAGTGATACTGCTGATCAAGAAGACT

TGGATGTAGAAGATGACCATGAGGAACAGCCTTCAAATCAAACTGTCCGAAGACCT

CAGGCTGTCATTGAAGATGCTGTGGCTACCTCAGGCGTGAGCACGCTCAGTTCTACT

GTGTCTCATGATTCCCAGAGTGCTCACCGGTCACTGAATGTACAGCTTGGAAGGATG
```

```
                                           -continued
AAAATAGAAACCAATAGATTACTGGAAGAATTGGTTCGGAAAGAGAAAGAATTACA

AGCACTCCTTCATCGAGCTATTGAAGAAAAAGACCAAGAAATTAAACACCTGAAGC

TTAAGTCCCAACCCATAGAAATTCCTGAATTGCCTGTATTTCATCTAAATTCTTCTGG

CACAAATACTGAAGATTCTGAACTTACCGACTGGCTGAGAGTGAATGGAGCTGATG

AAGACACTATAAGCCGGTTTTTGGCTGAAGATTATACACTATTGGATGTTCTCTACT

ATGTTACACGTGATGACTTAAAATGCTTGAGACTAAGGGGAGGGATGCTGTGCACA

CTGTGGAAGGCTATCATTGACTTTCGAAACAAACAGACTTGA

Human CD14 CDS
                                                               (SEQ ID NO: 8)
ATGGAGCGCGCGTCCTGCTTGTTGCTGCTGCTGCTGCCGCTGGTGCACGTCTCTGCG

ACCACGCCAGAACCTTGTGAGCTGGACGATGAAGATTTCCGCTGCGTCTGCAACTTC

TCCGAACCTCAGCCCGACTGGTCCGAAGCCTTCCAGTGTGTGTCTGCAGTAGAGGTG

GAGATCCATGCCGGCGGTCTCAACCTAGAGCCGTTTCTAAAGCGCGTCGATGCGGA

CGCCGACCCGCGGCAGTATGCTGACACGGTCAAGGCTCTCCGCGTGCGGCGGCTCA

CAGTGGGAGCCGCACAGGTTCCTGCTCAGCTACTGGTAGGCGCCCTGCGTGTGCTAG

CGTACTCCCGCCTCAAGGAACTGACGCTCGAGGACCTAAAGATAACCGGCACCATG

CCTCCGCTGCCTCTGGAAGCCACAGGACTTGCACTTTCCAGCTTGCGCCTACGCAAC

GTGTCGTGGGCGACAGGGCGTTCTTGGCTCGCCGAGCTGCAGCAGTGGCTCAAGCC

AGGCCTCAAGGTACTGAGCATTGCCCAAGCACACTCGCCTGCCTTTTCCTGCGAACA

GGTTCGCGCCTTCCCGGCCCTTACCAGCCTAGACCTGTCTGACAATCCTGGACTGGG

CGAACGCGGACTGATGGCGGCTCTCTGTCCCCACAAGTTCCCGGCCATCCAGAATCT

AGCGCTGCGCAACACAGGAATGGAGACGCCCACAGGCGTGTGCGCCGCACTGGCGG

CGGCAGGTGTGCAGCCCCACAGCCTAGACCTCAGCCACAACTCGCTGCGCGCCACC

GTAAACCCTAGCGCTCCGAGATGCATGTGGTCCAGCGCCCTGAACTCCCTCAATCTG

TCGTTCGCTGGGCTGGAACAGGTGCCTAAAGGACTGCCAGCCAAGCTCAGAGTGCT

CGATCTCAGCTGCAACAGACTGAACAGGGCGCCGCAGCCTGACGAGCTGCCCGAGG

TGGATAACCTGACACTGGACGGGAATCCCTTCCTGGTCCCTGGAACTGCCCTCCCCC

ACGAGGGCTCAATGAACTCCGGCGTGGTCCCAGCCTGTGCACGTTCGACCCTGTCGG

TGGGGGTGTCGGGAACCCTGGTGCTGCTCCAAGGGGCCCGGGGCTTTGCCTAA

Human ERK1 CDS
                                                               (SEQ ID NO: 9)
ATGGCGGCGGCGGCGGCTCAGGGGGGCGGGGCGGGGAGCCCCGTAGAACCGAGG

GGGTCGGCCCGGGGGTCCCGGGGGAGGTGGAGATGGTGAAGGGGCAGCCGTTCGAC

GTGGGCCCGCGCTACACGCAGTTGCAGTACATCGGCGAGGGCGCGTACGGCATGGT

CAGCTCGGCCTATGACCACGTGCGCAAGACTCGCGTGGCCATCAAGAAGATCAGCC

CCTTCGAACATCAGACCTACTGCCAGCGCACGCTCCGGGAGATCCAGATCCTGCTGC

GCTTCCGCCATGAGAATGTCATCGGCATCCGAGACATTCTGCGGGCGTCCACCCTGG

AAGCCATGAGAGATGTCTACATTGTGCAGGACCTGATGGAGACTGACCTGTACAAG

TTGCTGAAAAGCCAGCAGCTGAGCAATGACCATATCTGCTACTTCCTCTACCAGATC

CTGCGGGGCCTCAAGTACATCCACTCCGCCAACGTGCTCCACCGAGATCTAAAGCCC

TCCAACCTGCTCATCAACACCACCTGCGACCTTAAGATTTGTGATTTCGGCCTGGCC

CGGATTGCCGATCCTGAGCATGACCACACCGGCTTCCTGACGGAGTATGTGGCTACG
```

-continued

CGCTGGTACCGGGCCCCAGAGATCATGCTGAACTCCAAGGGCTATACCAAGTCCAT

CGACATCTGGTCTGTGGGCTGCATTCTGGCTGAGATGCTCTCTAACCGGCCCATCTTC

CCTGGCAAGCACTACCTGGATCAGCTCAACCACATTCTGGGCATCCTGGGCTCCCCA

TCCCAGGAGGACCTGAATTGTATCATCAACATGAAGGCCCGAAACTACCTACAGTCT

CTGCCCTCCAAGACCAAGGTGGCTTGGGCCAAGCTTTTCCCCAAGTCAGACTCCAAA

GCCCTTGACCTGCTGGACCGGATGTTAACCTTTAACCCCAATAAACGGATCACAGTG

GAGGAAGCGCTGGCTCACCCCTACCTGGAGCAGTACTATGACCCGACGGATGAGCC

AGTGGCCGAGGAGCCCTTCACCTTCGCCATGGAGCTGGATGACCTACCTAAGGAGC

GGCTGAAGGAGCTCATCTTCCAGGAGACAGCACGCTTCCAGCCCGGAGTGCTGGAG

GCCCCCTAG

Human ERK2 CDS (SEQ ID NO: 10)
ATGGCGGCGGCGGCGGCGGGCGCGGGCCCGGAGATGGTCCGCGGGCAGGTGTT

CGACGTGGGGCCGCGCTACACCAACCTCTCGTACATCGGCGAGGGCGCCTACGGCA

TGGTGTGCTCTGCTTATGATAATGTCAACAAAGTTCGAGTAGCTATCAAGAAAATCA

GCCCCTTTGAGCACCAGACCTACTGCCAGAGAACCCTGAGGGAGATAAAAATCTTA

CTGCGCTTCAGACATGAGAACATCATTGGAATCAATGACATTATTCGAGCACCAACC

ATCGAGCAAATGAAAGATGTATATATAGTACAGGACCTCATGGAAACAGATCTTTA

CAAGCTCTTGAAGACACAACACCTCAGCAATGACCATATCTGCTATTTTCTCTACCA

GATCCTCAGAGGGTTAAAATATATCCATTCAGCTAACGTTCTGCACCGTGACCTCAA

GCCTTCCAACCTGCTGCTCAACACCACCTGTGATCTCAAGATCTGTGACTTTGGCCT

GGCCCGTGTTGCAGATCCAGACCATGATCACACAGGGTTCCTGACAGAATATGTGGC

CACACGTTGGTACAGGGCTCCAGAAATTATGTTGAATTCCAAGGGCTACACCAAGTC

CATTGATATTTGGTCTGTAGGCTGCATTCTGGCAGAAATGCTTTCTAACAGGCCCAT

CTTTCCAGGGAAGCATTATCTTGACCAGCTGAACCACATTTTGGGTATTCTTGGATCC

CCATCACAAGAAGACCTGAATTGTATAATAAATTTAAAAGCTAGGAACTATTTGCTT

TCTCTTCCACACAAAAATAAGGTGCCATGGAACAGGCTGTTCCCAAATGCTGACTCC

AAAGCTCTGGACTTATTGGACAAAATGTTGACATTCAACCCACACAAGAGGATTGA

AGTAGAACAGGCTCTGGCCCACCCATATCTGGAGCAGTATTACGACCCGAGTGACG

AGCCCATCGCCGAAGCACCATTCAAGTTCGACATGGAATTGGATGACTTGCCTAAGG

AAAAGCTCAAAGAACTAATTTTTGAAGAGACTGCTAGATTCCAGCCAGGATACAGA

TCTTAA

Human IKK CDS (SEQ ID NO: 11)
ATGTTTTCAGGGGGTGTCATAGCCCCGGGTTTGGCCGCCCCAGCCCCGCCTTCCCC

GCCCCGGGGAGCCCGCCCCCTGCCCCGCGTCCCTGCCGACAGGAAACAGGTGAGCA

GATTGCCATCAAGCAGTGCCGGCAGGAGCTCAGCCCCCGGAACCGAGAGCGGTGGT

GCCTGGAGATCCAGATCATGAGAAGGCTGACCCACCCCAATGTGGTGGCTGCCCGA

GATGTCCCTGAGGGGATGCAGAACTTGGCGCCCAATGACCTGCCCCTGCTGGCCATG

GAGTACTGCCAAGGAGGAGATCTCCGGAAGTACCTGAACCAGTTTGAGAACTGCTG

TGGTCTGCGGGAAGGTGCCATCCTCACCTTGCTGAGTGACATTGCCTCTGCGCTTAG

ATACCTTCATGAAAACAGAATCATCCATCGGGATCTAAAGCCAGAAAACATCGTCCT

GCAGCAAGGAGAACAGAGGTTAATACACAAAATTATTGACCTAGGATATGCCAAGG

-continued

```
AGCTGGATCAGGGCAGTCTTTGCACATCATTCGTGGGGACCCTGCAGTACCTGGCCC
CAGAGCTACTGGAGCAGCAGAAGTACACAGTGACCGTCGACTACTGGAGCTTCGGC
ACCCTGGCCTTTGAGTGCATCACGGGCTTCCGGCCCTTCCTCCCCAACTGGCAGCCC
GTGCAGTGGCATTCAAAAGTGCGGCAGAAGAGTGAGGTGGACATTGTTGTTAGCGA
AGACTTGAATGGAACGGTGAAGTTTTCAAGCTCTTTACCCTACCCCAATAATCTTAA
CAGTGTCCTGGCTGAGCGACTGGAGAAGTGGCTGCAACTGATGCTGATGTGGCACC
CCCGACAGAGGGGCACGGATCCCACGTATGGGCCCAATGGCTGCTTCAAGGCCCTG
GATGACATCTTAAACTTAAAGCTGGTTCATATCTTGAACATGGTCACGGGCACCATC
CACACCTACCCTGTGACAGAGGATGAGAGTCTGCAGAGCTTGAAGGCCAGAATCCA
ACAGGACACGGGCATCCCAGAGGAGGACCAGGAGCTGCTGCAGGAAGCGGGCCTG
GCGTTGATCCCCGATAAGCCTGCCACTCAGTGTATTTCAGACGGCAAGTTAAATGAG
GGCCACACATTGGACATGGATCTTGTTTTCTCTTTGACAACAGTAAAATCACCTAT
GAGACTCAGATCTCCCCACGGCCCCAACCTGAAAGTGTCAGCTGTATCCTTCAAGAG
CCCAAGAGGAATCTCGCCTTCTTCCAGCTGAGGAAGGTGTGGGGCCAGGTCTGGCA
CAGCATCCAGACCCTGAAGGAAGATTGCAACCGGCTGCAGCAGGGACAGCGAGCCG
CCATGATGAATCTCCTCCGAAACAACAGCTGCCTCTCCAAAATGAAGAATTCCATGG
CTTCCATGTCTCAGCAGCTCAAGGCCAAGTTGGATTTCTTCAAAACCAGCATCCAGA
TTGACCTGGAGAAGTACAGCGAGCAAACCGAGTTTGGGATCACATCAGATAAACTG
CTGCTGGCCTGGAGGGAAATGGAGCAGGCTGTGGAGCTCTGTGGGCGGGAGAACGA
AGTGAAACTCCTGGTAGAACGGATGATGGCTCTGCAGACCGACATTGTGGACTTAC
AGAGGAGCCCCATGGGCCGGAAGCAGGGGGGAACGCTGGACGACCTAGAGGAGCA
AGCAAGGGAGCTGTACAGGAGACTAAGGGAAAAACCTCGAGACCAGCGAACTGAG
GGTGACAGTCAGGAAATGGTACGGCTGCTGCTTCAGGCAATTCAGAGCTTCGAGAA
GAAAGTGCGAGTGATCTATACGCAGCTCAGTAAAACTGTGGTTTGCAAGCAGAAGG
CGCTGGAACTGTTGCCCAAGGTGGAAGAGGTGGTGAGCTTAATGAATGAGGATGAG
AAGACTGTTGTCCGGCTGCAGGAGAAGCGGCAGAAGGAGCTCTGGAATCTCCTGAA
GATTGCTTGTAGCAAGGTCCGTGGTCCTGTCAGTGGAAGCCCGGATAGCATGAATGC
CTCTCGACTTAGCCAGCCTGGGCAGCTGATGTCTCAGCCCTCCACGGCCTCCAACAG
CTTACCTGAGCCAGCCAAGAAGAGTGAAGAACTGGTGGCTGAAGCACATAACCTCT
GCACCCTGCTAGAAAATGCCATACAGGACACTGTGAGGGAACAAGACCAGAGTTTC
ACGGCCCTAGACTGGAGCTGGTTACAGACGGAAGAAGAAGAGCACAGCTGCCTGGA
GCAGGCCTCATGA
```

Human IκB CDS (SEQ ID NO: 12)

```
ATGTTCCAGGCGGCCGAGCGCCCCCAGGAGTGGGCCATGGAGGGCCCCCGCGACGG
GCTGAAGAAGGAGCGGCTACTGGACGACCGCCACGACAGCGGCCTGGACTCCATGA
AAGACGAGGAGTACGAGCAGATGGTCAAGGAGCTGCAGGAGATCCGCCTCGAGCC
GCAGGAGGTGCCGCGCGGCTCGGAGCCCTGGAAGCAGCAGCTCACCGAGGACGGG
GACTCGTTCCTGCACTTGGCCATCATCCATGAAGAAAAGGCACTGACCATGGAAGTG
ATCCGCCAGGTGAAGGGAGACCTGGCCTTCCTCAACTTCCAGAACAACCTGCAGCA
GACTCCACTCCACTTGGCTGTGATCACCAACCAGCCAGAAATTGCTGAGGCACTTCT
```

-continued

```
GGGAGCTGGCTGTGATCCTGAGCTCCGAGACTTTCGAGGAAATACCCCCCTACACCT

TGCCTGTGAGCAGGGCTGCCTGGCCAGCGTGGGAGTCCTGACTCAGTCCTGCACCAC

CCCGCACCTCCACTCCATCCTGAAGGCTACCAACTACAATGGCCACACGTGTCTACA

CTTAGCCTCTATCCATGGCTACCTGGGCATCGTGGAGCTTTTGGTGTCCTTGGGTGCT

GATGTCAATGCTCAGGAGCCCTGTAATGGCCGGACTGCCCTTCACCTCGCAGTGGAC

CTGCAAAATCCTGACCTGGTGTCACTCCTGTTGAAGTGTGGGGCTGATGTCAACAGA

GTTACCTACCAGGGCTATTCTCCCTACCAGCTCACCTGGGGCCGCCCAAGCACCCGG

ATACAGCAGCAGCTGGGCCAGCTGACACTAGAAAACCTTCAGATGCTGCCAGAGAG

TGAGGATGAGGAGAGCTATGACACAGAGTCAGAGTTCACGGAGTTCACAGAGGACG

AGCTGCCCTATGATGACTGTGTGTTTGGAGGCCAGCGTCTGACGTTATGA
```

Human IRAK CDS (SEQ ID NO: 13)
```
ATGGCCGGGGGCCGGGCCCGGGGGAGCCCGCAGCCCCCGGCGCCCAGCACTTCTT

GTACGAGGTGCCGCCCTGGGTCATGTGCCGCTTCTACAAAGTGATGGACGCCCTGGA

GCCCGCCGACTGGTGCCAGTTCGCCGCCCTGATCGTGCGCGACCAGACCGAGCTGC

GGCTGTGCGAGCGCTCCGGGCAGCGCACGGCCAGCGTCCTGTGGCCCTGGATCAAC

CGCAACGCCCGTGTGGCCGACCTCGTGCACATCCTCACGCACCTGCAGCTGCTCCGT

GCGCGGGACATCATCACAGCCTGGCACCCTCCCGCCCCGCTTCCGTCCCCAGGCACC

ACTGCCCCGAGGCCCAGCAGCATCCCTGCACCCGCCGAGGCCGAGGCCTGGAGCCC

CCGGAAGTTGCCATCCTCAGCCTCCACCTTCCTCTCCCCAGCTTTTCCAGGCTCCCAG

ACCCATTCAGGGCCTGAGCTCGGCCTGGTCCCAAGCCCTGCTTCCCTGTGGCCTCCA

CCGCCATCTCCAGCCCCTTCTTCTACCAAGCCAGGCCCAGAGAGCTCAGTGTCCCTC

CTGCAGGGAGCCCGCCCCTTTCCGTTTTGCTGGCCCCTCTGTGAGATTTCCCGGGGC

ACCCACAACTTCTCGGAGGAGCTCAAGATCGGGGAGGGTGGCTTTGGGTGCGTGTA

CCGGGCGGTGATGAGGAACACGGTGTATGCTGTGAAGAGGCTGAAGGAGAACGCTG

ACCTGGAGTGGACTGCAGTGAAGCAGAGCTTCCTGACCGAGGTGG

AGCAGCTGTCCAGGTTTCGTCACCCAAACATTGTGGACTTTGCTGGCTACTGTGCTC

AGAACGGCTTCTACTGCCTGGTGTACGGCTTCCTGCCCAACGGCTCCCTGGAGGACC

GTCTCCACTGCCAGACCCAGGCCTGCCCACCTCTCCTGGCCTCAGCGACTGGACA

TCCTTCTGGGTACAGCCCGGGCAATTCAGTTTCTACATCAGGACAGCCCCAGCCTCA

TCCATGGAGACATCAAGAGTTCCAACGTCCTTCTGGATGAGAGGCTGACACCCAAG

CTGGGAGACTTTGGCCTGGCCCGGTTCAGCCGCTTTGCCGGGTCCAGCCCCAGCCAG

AGCAGCATGGTGGCCCGGACACAGACAGTGCGGGGCACCCTGGCCTACCTGCCCGA

GGAGTACATCAAGACGGGAAGGCTGGCTGTGGACACGGACACCTTCAGCTTTGGGG

TGGTAGTGCTAGAGACCTTGGCTGGTCAGAGGGCTGTGAAGACGCACGGTGCCAGG

ACCAAGTATCTGAAAGACCTGGTGGAAGAGGAGGCTGAGGAGGCTGGAGTGGCTTT

GAGAAGCACCCAGAGCACACTGCAAGCAGGTCTGGCTGCAGATGCCTGGGCTGCTC

CCATCGCCATGCAGATCTACAAGAAGCACCTGGACCCCAGGCCCGGGCCCTGCCCA

CCTGAGCTGGGCCTGGGCCTGGGCCAGCTGGCCTGCTGCTGCCTGCACCGCCGGGCC

AAAAGGAGGCCTCCTATGACCCAGGTGTACGAGAGGCTAGAGAAGCTGCAGGCAGT

GGTGGCGGGGGTGCCCGGGCATTCGGAGGCCGCCAGCTGCATCCCCCCTTCCCCGC

AGGAGAACTCCTACGTGTCCAGCACTGGCAGAGCCCACAGTGGGGCTGCTCCATGG
```

-continued

CAGCCCCTGGCAGCGCCATCAGGAGCCAGTGCCCAGGCAGCAGAGCAGCTGCAGAG

AGGCCCCAACCAGCCCGTGGAGAGTGACGAGAGCCTAGGCGGCCTCTCTGCTGCCC

TGCGCTCCTGGCACTTGACTCCAAGC

TGCCCTCTGGACCCAGCACCCCTCAGGGAGGCCGGCTGTCCTCAGGGGACACGGC

AGGAGAATCGAGCTGGGGGAGTGGCCCAGGATCCCGGCCCACAGCCGTGGAAGGA

CTGGCCCTTGGCAGCTCTGCATCATCGTCGTCAGAGCCACCGCAGATTATCATCAAC

CCTGCCCGACAGAAGATGGTCCAGAAGCTGGCCCTGTACGAGGATGGGGCCCTGGA

CAGCCTGCAGCTGCTGTCGTCCAGCTCCCTCCCAGGCTTGGGCCTGGAACAGGACAG

GCAGGGGCCCGAAGAAAGTGATGAATTTCAGAGCTGA

Human JNK CDS (SEQ ID NO: 14)

ATGAGCAGAAGCAAGCGTGACAACAATTTTTATAGTGTAGAGATTGGAGATTCTAC

ATTCACAGTCCTGAAACGATATCAGAATTTAAAACCTATAGGCTCAGGAGCTCAAG

GAATAGTATGCGCAGCTTATGATGCCATTCTTGAAAGAAATGTTGCAATCAAGAAGC

TAAGCCGACCATTTCAGAATCAGACTCATGCCAAGCGGGCCTACAGAGAGCTAGTT

CTTATGAAATGTGTTAATCACAAAAATATAATTGGCCTTTTGAATGTTTTCACACCAC

AGAAATCCCTAGAAGAATTTCAAGATGTTTACATAGTCATGGAGCTCATGGATGCAA

ATCTTTGCCAAGTGATTCAGATGGAGCTAGATCATGAAAGAATGTCCTACCTTCTCT

ATCAGATGCTGTGTGGAATCAAGCACCTTCATTCTGCTGGAATTATTCATCGGGACT

TAAAGCCCAGTAATATAGTAGTAAAATCTGATTGCACTTTGAAGATTCTTGACTTCG

GTCTGGCCAGGACTGCAGGAACGAGTTTTATGATGACGCCTTATGTAGTGACTCGCT

ACTACAGAGCACCCGAGGTCATCCTTGGCATGGGCTACAAGGAAAACGTTGACATT

TGGTCAGTTGGGTGCATCATGGGAGAAATGATCAAAGGTGGTGTTTTGTTCCCAGGT

ACAGATCATATTGATCAGTGGAATAAAGTTATTGAACAGCTTGGAACACCATGTCCT

GAATTCATGAAGAAACTGCAACCAACAGTAAGGACTTACGTTGAAAACAGACCTAA

ATATGCTGGATATAGCTTTGAGAAACTCTTCCCTGATGTCCTTTTCCCAGCTGACTCA

GAACACAACAAACTTAAAGCCAGTCAGGCAAGGGATTTGTTATCCAAAATGCTGGT

AATAGATGCATCTAAAAGGATCTCTGTAGATGAAGCTCTCCAACACCCGTACATCAA

TGTCTGGTATGATCCTTCTGAAGCAGAAGCTCCACCACCAAAGATCCCTGACAAGCA

GTTAGATGAAAGGGAACACACAATAGAAGAGTGGAAAGAATTGATATATAAGGAA

GTTATGGACTTGGAGGAGAGAACCAAGAATGGAGTTATACGGGGGCAGCCCTCTCC

TTTAGGTGCAGCAGTGATCAATGGCTCTCAGCATCCATCATCATCGTCGTCTGTCAA

TGATGTGTCTTCAATGTCAACAGATCCGACTTTGGCCTCTGATACAGACAGCAGTCT

AGAAGCAGCAGCTGGGCCTCTGGGCTGCTGTAGATGA

Human LBP CDS (SEQ ID NO: 15)

ATGGGGGCCTTGGCCAGAGCCCTGCCGTCCATACTGCTGGCATTGCTGCTTACGTCC

ACCCCAGAGGCTCTGGGTGCCAACCCCGGCTTGGTCGCCAGGATCACCGACAAGGG

ACTGCAGTATGCGGCCCAGGAGGGGCTATTAGCTCTGCAGAGTGAGCTGCTCAGGA

TCACGCTGCCTGACTTCACCGGGGACTTGAGGATCCCCCACGTCGGCCGTGGGCGCT

ATGAGTTCCACAGCCTGAACATCCACAGCTGTGAGCTGCTTCACTCTGCGCTGAGGC

CTGTCCCTGGCCAGGGCCTGAGTCTCAGCA

-continued

```
TCTCCGACTCCTCCATCCGGGTCCAGGGCAGGTGGAAGGTGCGCAAGTCATTCTTCA

AACTACAGGGCTCCTTTGATGTCAGTGTCAAGGGCATCAGCATTTCGGTCAACCTCC

TGTTGGGCAGCGAGTCCTCCGGGAGGCCCACAGTTACTGCCTCCAGCTGCAGCAGTG

ACATCGCTGACGTGGAGGTGGACATGTCGGGAGACTTGGGGTGGCTGTTGAACCTCT

TCCACAACCAGATTGAGTCCAAGTTCCAGAAAGTACTGGAGAGCAGGATTTGCGAA

ATGATCCAGAAATCGGTGTCCTCCGATCTACAGCCTTATCTCCAAACTCTGCCAGTT

ACAACAGAGATTGACAGTTTCGCCGACATTGATTATAGCTTAGTGGAAGCCCCTCGG

GCAACAGCCCAGATGCTGGAGGTGATGTTTAAGGGTGAAATCTTTCATCGTAACCAC

CGTTCTCCAGTTACCCTCCTTGCTGCAGTCATGAGCCTTCCTGAGGAACACAACAAA

ATGGTCTACTTTGCCATCTCGGATTATGTCTTCAACACGGCCAGCCTGGTTTATCATG

AGGAAGGATATCTGAACTTCTCCATCACAGATGACATGATACCGCCTGACTCTAATA

TCCGACTGACCACCAAGTCCTTCCGACCCTTCGTCCCACGGTTAGCCAGGCTCTACC

CCAACATGAACCTGGAACTCCAGGGATCAGTGCCCTCTGCTCCGCTCCTGAACTTCA

GCCCTGGGAATCTGTCTGTGGACCCCTATATGGAGATAGATGCCTTTGTGCTCCTGC

CCAGCTCCAGCAAGGAGCCTGTCTTCCGGCTCAGTGTGGCCA

CTAATGTGTCCGCCACCTTGACCTTCAATACCAGCAAGATCACTGGGTTCCTGAAGC

CAGGAAAGGTAAAAGTGGAACTGAAAGAATCCAAAGTTGGACTATTCAATGCAGAG

CTGTTGGAAGCGCTCCTCAACTATTACATCCTTAACACCCTCTACCCCAAGTTCAAT

GATAAGTTGGCCGAAGGCTTCCCCCTTCCTCTGCTGAAGCGTGTTCAGCTCTACGAC

CTTGGGCTGCAGATCCATAAGGACTTCCTGTTCTTGGGTGCCAATGTCCAATACATG

AGAGTTTGA
```

Human MEK1 CDS (SEQ ID NO: 16)
```
ATGCCCAAGAAGAAGCCGACGCCCATCCAGCTGAACCCGGCCCCCGACGGCTCTGC

AGTTAACGGGACCAGCTCTGCGGAGACCAACTTGGAGGCCTTGCAGAAGAAGCTGG

AGGAGCTAGAGCTTGATGAGCAGCAGCGAAAGCGCCTTGAGGCCTTTCTTACCCAG

AAGCAGAAGGTGGGAGAACTGAAGGATGACGACTTTGAGAAGATCAGTGAGCTGG

GGGCTGGCAATGGCGGTGTGGTGTTCAAGGTCTCCCACAAGCCTTCTGGCCTGGTCA

TGGCCAGAAAGCTAATTCATCTGGAGATCAAACCCGCAATCCGGAACCAGATCATA

AGGGAGCTGCAGGTTCTGCATGAGTGCAACTCTCCGTACATCGTGGGCTTCTATGGT

GCGTTCTACAGCGATGGCGAGATCAGTATCTGCATGGAGCACATGGATGGAGGTTCT

CTGGATCAAGTCCTGAAGAAAGCTGGAAGAATTCCTGAACAAATTTTAGGAAAAGT

TAGCATTGCTGTAATAAAAGGCCTGACATATCTGAGGGAGAAGCACAAGATCATGC

ACAGAGATGTCAAGCCCTCCAACATCCTAGTCAACTCCCGTGGGGAGATCAAGCTCT

GTGACTTTGGGGTCAGCGGGCAGCTCATCGACTCCATGGCCAACTCCTTCGTGGGC

ACAAGGTCCTACATGTCGCCAGAAAGACTCCAGGGGACTCATTACTCTGTGCAGTCA

GACATCTGGAGCATGGGACTGTCTCTGGTAGAGATGGCGGTTGGGAGGTATCCCATC

CCTCCTCCAGATGCCAAGGAGCTGGAGCTGATGTTTGGGTGCCAGGTGGAAGGAGA

TGCGGCTGAGACCCCACCCAGGCCAAGGACCCCCGGGAGGCCCCTTAGCTCATACG

GAATGGACAGCCGACCTCCCATGGCAATTTTTGAGTTGTTGGATTACATAGTCAACG

AGCCTCCTCCAAAACTGCCCAGTGGAGTGTTCAGTCTGGAATTTCAAGATTTTGTGA

ATAAATGCTTAATAAAAAACCCCGCAGAGAGAGCAGATTTGAAGCAACTCATGGTT
```

```
CATGCTTTTATCAAGAGATCTGATGCTGAGGAAGTGGATTTTGCAGGTTGGCTCTGC

TCCACCATCGGCCTTAACCAGCCCAGCACACCAACCCATGCTGCTGGCGTCTAA
```

Human MEK2 CDS (SEQ ID NO: 17)

```
ATGCTGGCCCGGAGGAAGCCGGTGCTGCCGGCGCTCACCATCAACCCTACCATCGC

CGAGGGCCCATCCCCTACCAGCGAGGGCGCCTCCGAGGCAAACCTGGTGGACCTGC

AGAAGAAGCTGGAGGAGCTGGAACTTGACGAGCAGCAGAAGAAGCGGCTGGAAGC

CTTTCTCACCCAGAAAGCCAAGGTCGGCGAACTCAAAGACGATGACTTCGAAAGGA

TCTCAGAGCTGGGCGCGGGCAACGGCGGGGTGGTCACCAAAGTCCAGCACAGACCC

TCGGGCCTCATCATGGCCAGGAAGCTGATCCACCTTGAGATCAAGCCGGCCATCCG

GAACCAGATCATCCGCGAGCTGCAGGTCCTGCACGAATGCAACTCGCCGTACATCG

TGGGCTTCTACGGGGCCTTCTACAGTGACGGGGAGATCAGCATTTGCATGGAACACA

TGGACGGCGGCTCCCTGGACCAGGTGCTGAAAGAGGCCAAGAGGATTCCCGAGGAG

ATCCTGGGGAAAGTCAGCATCGCGGTTCTCCGGGGCTTGGCGTACCTCCGAGAGAA

GCACCAGATCATGCACCGAGATGTGAAGCCCTCCAACATCCTCGTGAACTCTAGAG

GGGAGATCAAGCTGTGTGACTTCGGGGTGAGCGGCCAGCTCATCGACTCCATGGCC

AACTCCTTCGTGGGCACGCGCTCCTACATGGCTCCGGAGCGGTTGCAGGGCACA

CATTACTCGGTGCAGTCGGACATCTGGAGCATGGGCCTGTCCCTGGTGGAGCTGGCC

GTCGGAAGGTACCCCATCCCCCCGCCCGACGCCAAAGAGCTGGAGGCCATCTTTGG

CCGGCCCGTGGTCGACGGGGAAGAAGGAGAGCCTCACAGCATCTCGCCTCGGCCGA

GGCCCCCCGGGCGCCCCGTCAGCGGTCACGGGATGGATAGCCGGCCTGCCATGGCC

ATCTTTGAACTCCTGGACTATATTGTGAACGAGCCACCTCCTAAGCTGCCCAACGGT

GTGTTCACCCCCGACTTCCAGGAGTTTGTCAATAAATGCCTCATCAAGAACCCAGCG

GAGCGGGCGGACCTGAAGATGCTCACAAACCACACCTTCATCAAGCGGTCCGAGGT

GGAAGAAGTGGATTTTGCCGGCTGGTTGTGTAAAACCCTGCGGCTGAACCAGCCCG

GCACACCCACGCGCACCGCCGTGTGA
```

Human MEK3 CDS (SEQ ID NO: 18)

```
ATGTCCAAGCCACCCGCACCCAACCCCACACCCCCCGGAACCTGGACTCCCGGAC

CTTCATCACCATTGGAGACAGAAACTTTGAGGTGGAGGCTGATGACTTGGTGACCAT

CTCAGAACTGGGCCGTGGAGCCTATGGGGTGGTAGAGAAGGTGCGGCACGCCCAGA

GCGGCACCATCATGGCCGTGAAGCGGATCCGGGCCACCGTGAACTCACAGGAGCAG

AAGCGGCTGCTCATGGACCTGGACATCAACATGCGCACGGTCGACTGTTTCTACACT

GTCACCTTCTACGGGGCACTATTCAGAGAGGGAGACGTGTGGATCTGCATGGAGCTC

ATGGACACATCCTTGGACAAGTTCTACCGGAAGGTGCTGGATAAAAACATGACAAT

TCCAGAGGACATCCTTGGGGAGATTGCTGTGTCTATCGTGCGGGCCCTGGAGCATCT

GCACAGCAAGCTGTCGGTGATCCACAGAGATGTGAAGCCCTCCAATGTCCTTATCAA

CAAGGAGGGCCATGTGAAGATGTGTGACTTTGGCATCAGTGGCTACTTGGTGGACTC

TGTGGCCAAGACGATGGATGCCGGCTGCAAGCCCTACATGGCCCCTGAGAGGATCA

ACCCAGAGCTGAACCAGAAGGGCTACAATGTCAAGTCCGACGTCTGGAGCCTGGGC

ATCACCATGATTGAGATGGCCATCCTGCGCTTCCCTTACGAGTCCTGGGGGACCCCG

TTCCAGCAGCTGAAGCAGGTGGTGGAGGAGCCGTCCCCCCAGCTCCCAGCCGACCG
```

-continued

```
TTTCTCCCCCGAGTTTGTGGACTTCACTGCTCAGTGCCTGAGGAAGAACCCCGCAGA

GCGTATGAGCTACCTGGAGCTGATGGAGCACCCCTTCTTCACCTTGCACAAAACCAA

GAAGACGGACATTGCTGCCTTCGTGAAGGAGATCCTGGGAGAAGACTCATAG
```

Human MEK6 CDS  
(SEQ ID NO: 19)
```
ATGTCTCAGTCGAAAGGCAAGAAGCGAAACCCTGGCCTTAAAATTCCAAAGAAGC

ATTTGAACAACCTCAGACCAGTTCCACACCACCTCGAGATTTAGACTCCAAGGCTTG

CATTTCTATTGGAAATCAGAACTTTGAGGTGAAGGCAGATGACCTGGAGCCTATAAT

GGAACTGGGACGAGGTGCGTACGGGGTGGTGGAGAAGATGCGGCACGTGCCCAGC

GGGCAGATCATGGCAGTGAAGCGGATCCGAGCCACAGTAAATAGCCAGGAACAGA

AACGGCTACTGATGGATTTGGATATTTCCATGAGGACGGTGGACTGTCCATTCACTG

TCACCTTTTATGGCGCACTGTTTCGGGAGGGTGATGTGTGGATCTGCATGGAGCTCA

TGGATACATCACTAGATAAATTCTACAAACAAGTTATTGATAAAGGCCAGACAATTC

CAGAGGACATCTTAGGGAAAATAGCAGTTTCTATTGTAAAAGCATTAGAACATTTAC

ATAGTAAGCTGTCTGTCATTCACAGAGACGTCAAGCCTTCTAATGTACTCATCAATG

CTCTCGGTCAAGTGAAGATGTGCGATTTTGGAATCAGTGGCTACTTGGTGGACTCTG

TTGCTAAAACAATTGATGCAGGTTGCAAACCATACATGGCCCCTGAAAGAATAAAC

CCAGAGCTCAACCAGAAGGGATACAGTGTGAAGTCTGACATTTGGAGTCTGGGCAT

CACGATGATTGAGTTGGCCATCCTTCGATTTCCCTATGATTCATGGGGAACTCCATTT

CAGCAGCTCAAACAGGTGGTAGAGGAGCCATCGCCACAACTCCCAGCAGACAAGTT

CTCTGCAGAGTTTGTTGACTTTACCTCACAGTGCTTAAAGAAGAATTCCAAAGAACG

GCCTACATACCCAGAGCTAATGCAACATCCATTTTTCACCCTACATGAATCCAAAGG

AACAGATGTGGCATCTTTTGTAAAACTGATTCTTGGAGACTAA
```

Human MEKK1 CDS  
(SEQ ID NO: 20)
```
ATGGCGGCGGCGGCGGGGAATCGCGCCTCGTCGTCGGGATTCCCGGGCGCCAGGGC

TACGAGCCCTGAGGCAGGCGGCGGCGGAGGAGCCCTCAAGGCGAGCAGCGCGCCC

GCGGCTGCCGCGGGACTGCTGCGGGAGGCGGGCAGCGGGGGCCGCGAGCGGGCGG

ACTGGCGGCGGCGGCAGCTGCGCAAAGTGCGGAGTGTGGAGCTGGACCAGCTGCCT

GAGCAGCCGCTCTTCCTTGCCGCCTCACCGCCGGCCTCCTCGACTTCCCCGTCGCCG

GAGCCCGCGGACGCAGCGGGGAGTGGGACCGGCTTCCAGCCTGTGGCGGTGCCGCC

GCCCCACGGAGCCGCGAGCCGCGGCGGCGCCCACCTTACCGAGTCGGTGGCGGCGC

CGGACAGCGGCGCCTCGAGTCCCGCAGCGGCCGAGCCCGGGGAGAAGCGGGCGCC

CGCCGCCGAGCCGTCTCCTGCAGCGGCCCCCGCCGGTCGTGAGATGGAGAATAAAG

AAACTCTCAAAGGGTTGCACAAGATGGATGATCGTCCAGAGGAACGAATGATCAGG

GAGAAACTGAAGGCAACCTGTATGCCAGCCTGGAAGCACGAATGGTTGGAAAGGAG

AAATAGGCGAGGGCCTGTGGTGGTAAAACCAATCCCAGTTAAAGGAGATGGATCTG

AAATGAATCACTTAGCAGCTGAGTCTCCAGGAGAGGTCCAGGCAAGTGCGGCTTCA

CCAGCTTCCAAAGGCCGACGCAGTCCTTCTCCTGGCAACTCCCCATCAGGTCGCACA

GTGAAATCAGAATCTCCAGGAGTAAGGAGAAAAAGAGTTTCCCCAGTGCCTTTTCA

GAGTGGCAGAATCACACCACCCCGAAGAGCCCCTTCACCAGATGGCTTCTCACCAT

ATAGCCCTGAGGAAACAAACCGCCGTGTTAACAAAGTGATGCGGGCCAGACTGTAC

TTACTGCAGCAGATAGGGCCTAACTCTTTCCTGATTGGAGGAGACAGCCCAGACAAT
```

-continued

```
AAATACCGGGTGTTTATTGGGCCTCAGAACTGCAGCTGTGCACGTGGAACATTCTGT

ATTCATCTGCTATTTGTGATGCTCCGGGTGTTTCAACTAGAACCTTCAGACCCAATGT

TATGGAGAAAAACTTTAAAGAATTTTGAGGTTGAGAGTTTGTTCCAGAAATATCACA

GTAGGCGTAGCTCAAGGATCAAAGCTCCATCTCGTAACACCATCCAGAAGTTTGTTT

CACGCATGTCAAATTCTCATACATTGTCATCATCTAGTACTTCTACGTCTAGTTCAGA

AAACAGCATAAAGGATGAAGAGGAACAGATGTGTCCTATTTGCTTGTTGGGCATGC

TTGATGAAGAAAGTCTTACAGTGTGTGAAGACGGCTGCAGGAACAAGCTGCACCAC

CACTGCATGTCAATTTGGGCAGAAGAGTGTAGAAGAAATAGAGAACCTTTAATATG

TCCCCTTTGTAGATCTAAGTGGAGATCTCATGATTTCTACAGCCACGAGTTGTCAAG

TCCTGTGGATTCCCCTTCTTCCCTCAGAGCTGCACAGCAGCAAACCGTACAGCAGCA

GCCTTTGGCTGGATCACGAAGGAATCAAGAGAGCAATTTTAACCTTACTCATTATGG

AACTCAGCAAATCCCTCCTGCTTACAAAGATTTAGCTGAGCCATGGATTCAGGTGTT

TGGAATGGAACTCGTTGGCTGCTTATTTTCTAGAAACTGGAATGTGAGAGAGATGGC

CCTCAGGCGTCTTTCCCATGATGTCAGTGGGCCCTGCTGTTGGCAAATGGGGAGAG

CACTGGAAATTCTGGGGGCAGCAGTGGAAGCAGCCCGAGTGGGGAGCCACCAGTG

GGTCTTCCCAGACCAGTATCTCAGGAGATGTGGTGGAGGCATGCTGCAGCGTTCTGT

CAATGGTCTGTGCTGACCCTGTCTACAAAGTGTACGTTGCTGCTTTAAAAACATTGA

GAGCCATGCTGGTATATACTCCTTGCCACAGTTTAGCGGAAAGAATCAAACTTCAGA

GACTTCTCCAGCCAGTTGTAGACACCATCCTAGTCAAATGTGCAGATGCCAATAGCC

GCACAAGTCAGCTGTCCATATCAACACTGTTGGAACTGTGCAAAGGCCAAGCAGGA

GAGTTGGCAGTTGGCAGAGAAATACTAAAAGCTGGATCCATTGGTATTGGTGGTGTT

GATTATGTCTTAAATTGTATTCTTGGAAACCAAACTGAATCAAACAATTGGCAAGAA

CTTCTTGGCCGCCTTTGTCTTATAGATAGACTGTTGTTGGAATTTCCTGCTGAATTTT

ATCCTCATATTGTCAGTACTGATGTTTCACAAGCTGAGCCTGTTGAAATCAGGTATA

AGAAGCTGCTGTCCCTCTTAACCTTTGCTTTGCAGTCCATTGATAATTCCCACTCAAT

GGTTGGCAAACTTTCCAGAAGGATCTACTTGAGTTCTGCAAGAATGGTTACTACAGT

ACCCCATGTGTTTTCAAAACTGTTAGAAATGCTGAGTGTTTCCAGTTCCACTCACTTC

ACCAGGATGCGTCGCCGTTTGATGGCTATTGCAGATGAGGTGGAAATTGCCGAAGC

CATCCAGTTGGGCGTAGAAGACACTTTGGATGGTCAACAGGACAGCTTCTTGCAGGC

ATCTGTTCCCAACAACTATCTGGAAACCACAGAGAACAGTTCCCCTGAGTGCACAGT

CCATTTAGAGAAAACTGGAAAAGGATTATGTGCTACAAAATTGAGTGCCAGTTCAG

AGGACATTTCTGAGAGACTGGCCAGCATTTCAGTAGGACCTTCTAGTTCAACAACAA

CAACAACAACAACAGAGCAACCAAAGCCAATGGTTCAAACAAAAGGCAGACC

CCACAGTCAGTGTTTGAACTCCTCTCCTTTATCTCATCATTCCCAATTAATGTTTCCA

GCCTTGTCAACCCCTTCTTCTTCTACCCCATCTGTACCAGCTGGCACTGCAACAGATG

TCTCTAAGCATAGACTTCAGGGATTCATTCCCTGCAGAATACCTTCTGCATCTCCTCA

AACACAGCGCAAGTTTTCTCTACAATTCCACAGAAACTGTCCTGAAAACAAAGACTC

AGATAAACTTTCCCCAGTCTTTACTCAGTCAAGACCCTTGCCCTCCAGTAACATACA

CAGGCCAAAGCCATCTAGACCTACCCCAGGTAATACAAGTAAACAGGGAGATCCCT

CAAAAAATAGCATGACACTTGATCTGAACAGTAGTTCCAAATGTGATGACAGCTTTG
```

```
-continued
GCTGTAGCAGCAATAGTAGTAATGCTGTTATACCCAGTGACGAGACAGTGTTCACCC

CAGTAGAGGAGAAATGCAGATTAGATGTCAATACAGAGCTCAACTCCAGTATTGAG

GACCTTCTTGAAGCATCTATGCCTTCAAGTGATACAACAGTAACTTTTAAGTCAGAA

GTTGCTGTCCTGTCTCCTGAAAAGGCTGAAAATGATGATACCTACAAAGATGATGTG

AATCATAATCAAAAGTGCAAAGAGAAGATGGAAGCTGAAGAAGAAGAAGCTTTAG

CAATTGCCATGGCAATGTCAGCGTCTCAGGATGCCCTCCCCATAGTTCCTCAGCTGC

AGGTTGAAAATGGAGAAGATATCATCATTATTCAACAGGATACACCAGAGACTCTA

CCAGGACATACCAAAGCAAAACAACCGTATAGAGAAGACACTGAATGGCTGAAAG

GTCAACAGATAGGCCTTGGAGCATTTTCTTCTTGTTATCAGGCTCAAGATGTGGGAA

CTGGAACTTTAATGGCTGTTAAACAGGTGACTTATGTCAGAAACACATCTTCTGAGC

AAGAAGAAGTAGTAGAAGCACTAAGAGAAGAGATAAGAATGATGAGCCATCTGAA

TCATCCAAACATCATTAGGATGTTGGGAGCCACGTGTGAGAAGAGCAATTACAATCT

CTTCATTGAATGGATGGCAGGGGGATCGGTGGCTCATTTGCTGAGTAAATATGGAGC

CTTCAAAGAATCAGTAGTTATTAACTACACTGAACAGTTACTCCGTGGCCTTTCGTA

TCTCCATGAAAACCAAATCATTCACAGAGATGTCAAAGGTGCCAATTTGCTAATTGA

CAGCACTGGTCAGAGACTAAGAATTGCAGATTTTGGAGCTGCAGCCAGGTTGGCAT

CAAAAGGAACTGGTGCAGGAGAGTTTCAGGGACAATTACTGGGGACAATTGCATTT

ATGGCACCTGAGGTACTAAGAGGTCAACAGTATGGAAGGAGCTGTGATGTATGGAG

TGTTGGCTGTGCTATTATAGAAATGGCTTGTGCAAAACCACCATGGAATGCAGAAAA

ACACTCCAATCATCTTGCTTTGATATTTAAGATTGCTAGTGCAACTACTGCTCCATCG

ATCCCTTCACATTTGTCTCCTGGTTTACGAGATGTGGCTCTTCGTTGTTTAGAACTTC

AACCTCAGGACAGACCTCCATCAAGAGAGCTACTGAAGCATCCAGTCTTTCGTACTA

CATGGTAG

Human MEKK 3 CDS
                                                      (SEQ ID NO: 21)
ATGGACGAACAGGAGGCATTGAACTCAATCATGAACGATCTGGTGGCCCTCCAGAT

GAACCGACGTCACCGGATGCCTGGATATGAGACCATGAAGAACAAAGACACAGGTC

ACTCAAATAGGCAGAAAAAAACACAACAGCAGCAGCTCAGCCCTTCTGAACAGCCCC

ACAGTAACAACAAGCTCATGTGCAGGGGCCAGTGAGAAAAAGAAATTTTTGAGTGA

CGTCAGAATCAAGTTCGAGCACAACGGGGAGAGGCGAATTATAGCGTTCAGCCGGC

CTGTGAAATATGAAGATGTGGAGCACAAGGTGACAACAGTATTTGGACAACCTCTT

GATCTACATTACATGAACAATGAGCTCTCCATCCTGCTGAAAAACCAAGATGATCTT

GATAAAGCAATTGACATTTTAGATAGAAGCTCAAGCATGAAAAGCCTTAGGATATT

GCTGTTGTCCCAGGACAGAAACCATAACAGTTCCTCTCCCCACTCTGGGGTGTCCAG

ACAGGTGCGGATCAAGGCTTCCCAGTCCGCAGGGGATATAAATACTATCTACCAGC

CCCCGAGCCCAGAAGCAGGCACCTCTCTGTCAGCTCCCAGAACCCTGGCCGAAGC

TCACCTCCCCCTGGCTATGTTCCTGAGCGGCAGCAGCACATTGCCCGGCAGGGGTCC

TACACCAGCATCAACAGTGAGGGGGAGTTCATCCCAGAGACCAGCGAGCAGTGCAT

GCTGGATCCCCTGAGCAGTGCAGAAAATTCCTTGTCTGGAAGCTGCCAATCCTTGGA

CAGGTCAGCAGACAGCCCATCCTTCCGGAAATCACGAATGTCCCGTGCCCAGAGCTT

CCCTGACAACAGACAGGAATACTCAGATCGGGAAACTCAGCTTTATGACAAAGGGG

TCAAAGGTGGAACCTACCCCCGGCGCTACCACGTGTCTGTGCACCACAAGGACTAC
```

-continued

AGTGATGGCAGAAGAACATTTCCCCGAATACGGCGTCATCAAGGCAACTTGTTCACC

CTGGTGCCCTCCAGCCGCTCCCTGAGCACAAATGGCGAGAACATGGGTCTGGCTGTG

CAATACCTGGACCCCGTGGGCGCCTGCGGAGTGCGGACAGCGAGAATGCCCTCTC

TGTGCAGGAGAGGAATGTGCCAACCAAGTCTCCCAGTGCCCCCATCAACTGGCGCC

GGGGAAAGCTCCTGGGCCAGGGTGCCTTCGGCAGGGTCTATTTGTGCTATGACGTGG

ACACGGGACGTGAACTTGCTTCCAAGCAGGTCCAATTTGATCCAGACAGTCCTGAGA

CAAGCAAGGAGGTGAGTGCTCTGGAGTGCGAGATCCAGTTGCTAAAGAACTTGCAG

CATGAGCGCATCGTGCAGTACTATGGCTGTCTGCGGGACCGCGCTGAGAAGACCCT

GACCATCTTCATGGAGTACATGCCAGGGGGCTCGGTGAAAGACCAGTTGAAGGCTT

ACGGTGCTCTGACAGAGAGCGTGACCCGAAAGTACACGCGGCAGATCCTGGAGGGC

ATGTCCTACCTGCACAGCAACATGATTGTTCACCGGGACATTAAGGGAGCCAACATC

CTCCGAGACTCTGCTGGGAATGTAAAGCTGGGGGACTTTGGGGCCAGCAAACGCCT

GCAGACGATCTGTATGTCGGGGACGGGCATGCGCTCCGTCACTGGCACACCCTACTG

GATGAGCCCTGAGGTGATCAGCGGCGAGGGCTATGGAAGGAAAGCAGACGTGTGG

AGCCTGGGCTGCACTGTGGTGGAGATGCTGACAGAGAAACCACCGTGGGCAGAGTA

TGAAGCTATGGCCGCCATCTTCAAGATTGCCACCCAGCCCACCAATCCTCAGCTGCC

CTCCCACATCTCTGAACATGGCCGGGACTTCCTGAGGCGCATTTTTGTGGAGGCTCG

CCAGAGACCTTCAGCTGAGGAGCTGCTCA

CACACCACTTTGCACAGCTCATGTACTGA

Human MEKK4 CDS (SEQ ID NO: 22)

ATGAGAGAAGCCGCTGCCGCGCTGGTCCCTCCTCCCGCCTTTGCCGTCACGCCTGCC

GCCGCCATGGAGGAGCCGCCGCCACCGCCGCCGCCACCACCGCCACCGGAACC

CGAGACCGAGTCAGAACCCGAGTGCTGCTTGGCGGCGAGGCAAGAGGGCACATTGG

GAGATTCAGCTTGCAAGAGTCCTGAATCTGATCTAGAAGACTTCTCCGATGAAACAA

ATACAGAGAATCTTTATGGTACCTCTCCCCCCAGCACACCTCGACAGATGAAACGCA

TGTCAACCAAACATCAGAGGAATAATGTGGGGAGGCCAGCCAGTCGGTCTAATTTG

AAAGAAAAAATGAATGCACCAAATCAGCCTCCACATAAAGACACTGGAAAAACAGT

GGAGAATGTGGAAGAATACAGCTATAAGCAGGAGAAAAAGATCCGAGCAGCTCTTA

GAACAACAGAGCGTGATCATAAAAAAAATGTACAGTGCTCATTCATGTTAGACTCA

GTGGGTGGATCTTTGCCAAAAAAATCAATTCCAGATGTGGATCTCAATAAGCCTTAC

CTCAGCCTTGGCTGTAGCAATGCTAAGCTTCCAGTATCTGTGCCCATGCCTATAGCC

AGACCTGCACGCCAGACTTCTAGGACTGACTGTCCAGCAGATCGTTTAAAGTTTTTT

GAAACTTTACGACTTTTGCTAAAGCTTACCTCAGTCTCAAAGAAAAAAGACAGGGA

GCAAAGAGGACAAGAAAATACGTCTGGTTTCTGGCTTAACCGATCTAACGAACTGA

TCTGGTTAGAGCTACAAGCCTGGCATGCAGGACGGACAATTAACGACCAGGACTTC

TTTTTATATACAGCCCGTCAAGCCATCCCAGATATTATTAATGAAATCCTTACTTTCA

AAGTCGACTATGGGAGCTTCGCCTTTGTTAGAGATAGAGCTGGTTTTAATGGTACTT

CAGTAGAAGGGCAGTGCAAAGCCACTCCTGGAACAAAGATTGTAGGTTACTCAACA

CATCATGAGCATCTCCAACGCCAGAGGGTCTCATTTGAGCAGGTAAAACGGATAAT

GGAGCTGCTAGAGTACATAGAAGCACTTTATCCATCATTGCAGGCTCTTCAGAAGGA

-continued

```
CTATGAAAAATATGCTGCAAAAGACTTCCAGGACAGGGTGCAGGCACTCTGTTTGTG

GTTAAACATCACAAAAGACTTAAATCAGAAATTAAGGATTATGGGCACTGTTTTGGG

CATCAAGAATTTATCAGACATTGGCTGGCCAGTGTTTGAAATCCCTTCCCCTCGACC

ATCCAAAGGTAATGAGCCGGAGTATGAGGGTGATGACACAGAAGGAGAATTAAAG

GAGTTGGAAAGTAGTACGGATGAGAGTGAAGAAGAACAAATCTCTGATCCTAGGGT

ACCGGAAATCAGACAGCCCATAGATAACAGCTTCGACATCCAGTCGCGGGACTGCA

TATCCAAGAAGCTTGAGAGGCTCGAATCTGAGGATGATTCTCTTGGCTGGGGAGCAC

CAGACTGGAGCACAGAAGCAGGCTTTAGTAGACATTGTCTGACTTCTATTTATAGAC

CATTTGTAGACAAAGCACTGAAGCAGATGGGGTTAAGAAAGTTAATTTTAAGACTTC

ACAAGCTAATGGATGGTTCCTTGCAAAGGGCACGTATAGCATTGGTAAAGAACGAT

CGTCCAGTGGAGTTTTCTGAATTTCCAGATCCCATGTGGGGTTCAGATTATGTGCAG

TTGTCAAGGACACCACCTTCATCTGAGGAGAAATGCAGTGCTGTGTCGTGGGAGGA

GCTGAAGGCCATGGATTTACCTTCATTCGAACCTGCCTTCCTAGTTCTCTGCCGAGTC

CTTCTGAATGTCATACATGAGTGTCTGAAGTTAAGATTGGAGCAGAGACCTGCTGGA

GAACCATCTCTCTTGAGTATTAAGCAGCTGGTGAGAGAGTGTAAGGAGGTCCTGAA

GGGCGG

CCTGCTGATGAAGCAGTACTACCAGTTCATGCTGCAGGAGGTTCTGGAGGACTTGGA

GAAGCCCGACTGCAACATTGACGCTTTTGAAGAGGATCTACATAAAATGCTTATGGT

GTATTTTGATTACATGAGAAGCTGGATCCAAATGCTACAGCAATTACCTCAAGCATC

GCATAGTTTAAAAAATCTGTTAGAAGAAGAATGGAATTTCACCAAAGAAATAACTC

ATTACATACGGGGAGGAGAAGCACAGGCCGGGAAGCTTTTCTGTGACATTGCAGGA

ATGCTGCTGAAATCTACAGGAAGTTTTTTAGAATTTGGCTTACAGGAGAGCTGTGCT

GAATTTTGGACTAGTGCGGATGACAGCAGTGCTTCCGACGAAATCAGGAGGTCTGTT

ATAGAGATCAGTCGAGCCCTGAAGGAGCTCTTCCATGAAGCCAGAGAAAGGGCTTC

CAAAGCACTTGGATTTGCTAAAATGTTGAGAAAGGACCTGGAAATAGCAGCAGAAT

TCAGGCTTTCAGCCCCAGTTAGAGACCTCCTGGATGTTCTGAAATCAAAACAGTATG

TCAAGGTGCAAATTCCTGGGTTAGAAAACTTGCAAATGTTTGTTCCAGACACTCTTG

CTGAGGAGAAGAGTATTATTTTGCAGTTACTCAATGCAGCTGCAGGAAAGGACTGTT

CAAAAGATTCAGATGACGTACTCATCGATGCCTATCTGCTTCTGACCAAGCACGGTG

ATCGAGCCCGTGATTCAGAGGACAGCTGGGCACCTGGGAGGCACAGCCTGTCAAA

GTCGTGCCTCAGGTGGAGACTGTTGACACCCTGAGAAGCATGCAGGTGGATAATCTT

TTACTAGTTGTCATGCAGTCTGCGCATCTCACAATTCAGAGAAAAGCTTTCCAGCAG

TCCATTGAGGGACTTATGACTCTGTGCCAGGAGCAGACATCCAGTCAGCCGGTCATC

GCCAAAGCTTTGCAGCAGCTGAAGAATGATGCATTGGAGCTATGCAACAGGATAAG

CAATGCCATTGACCGCGTGGACCACATGTTCACATCAGAATTTGATGCTGAGGTTGA

TGAATCTGAATCTGTCACCTTGCAACAGTACTACCGAGAAGCAATGATTCAGGGGTA

CAATTTTGGATTTGAGTATCATAAAGAAGTTGTTCGTTTGATGTCTGGGGAGTTTAG

ACAGAAGAT

AGGAGACAAATATATAAGCTTTGCCCGGAAGTGGATGAATTATGTCCTGACTAAAT

GTGAGAGTGGTAGAGGTACAAGACCCAGGTGGGCGACTCAAGGATTTGATTTTCTA

CAAGCAATTGAACCTGCCTTTATTTCAGCTTTACCAGAAGATGACTTCTTGAGTTTAC
```

-continued

AAGCCTTGATGAATGAATGCATTGGCCATGTCATAGGAAAACCACACAGTCCTGTTA

CAGGTTTGTACCTTGCCATTCATCGGAACAGCCCCCGTCCTATGAAGGTACCTCGAT

GCCATAGTGACCCTCCTAACCCACACCTCATTATCCCCACTCCAGAGGGATTCAGCA

CTCGGAGCATGCCTTCCGACGCGCGGAGCCATGGCAGCCCTGCTGCTGCTGCTGCTG

CTGCTGCTGCTGTTGCTGCCAGTCGGCCCAGCCCCTCTGGTGGTGACTCTGTGCT

GCCCAAATCCATCAGCAGTGCCCATGATACCAGGGGTTCCAGCGTTCCTGAAAATG

ATCGATTGGCTTCCATAGCTGCTGAATTGCAGTTTAGGTCCCTGAGTCGTCACTCAA

GCCCCACGGAGGAGCGAGATGAACCAGCATATCCAAGAGGAGATTCAAGTGGGTCC

ACAAGAAGAAGTTGGGAACTTCGGACACTAATCAGCCAGAGTAAAGATACTGCTTC

TAAACTAGGACCCATAGAAGCTATCCAGAAGTCAGTCCGATTGTTTGAAGAAAGA

GGTACCGAGAAATGAGGAGAAAGAATATCATTGGTCAAGTTTGTGATACGCCTAAG

TCCTATGATAATGTTATGCACGTTGGCTTGAGGAAGGTGACCTTCAAATGGCAAAGA

GGAAACAAAATTGGAGAAGGCCAGTATGGGAAGGTGTACACCTGCATCAGCGTCGA

CACCGGGGAGCTGATGGCCATGAAAGAGATTCGATTTCAACCTAATGACCATAAGA

CTATCAAGGAAACTGCAGACGAATTGAAAATATTCGAAGGCATCAAACACCCCAAT

CTGGTTCGGTATTTTGGTGTGGAGCTCCATAGAGAAGAAATGTACATCTTCATGGAG

TACTGCGATGAGGGGACTTTAGAAGAGGTGTCAAGGCTGGGACTTCAGGAACATGT

GATTAGGCTGTATTCAAAGCAGATCACCATTGCGATCAACGTCCTCCATGAGCATGG

CATAGTCCACCGTGACATTAAAGGTGCCAATATCTTCCTTACCTCATCTGGATTAATC

AAACTGGGAGATTTTGGATGTTCAGTAAAGCTCAAAAACAATGCCCAGACCATGCC

TGGTGAAGTGAACAGCACCCTGGGGACAGCAGCATACATGGCACCTGAAGTCATCA

CTCGTGCCAAAGGAGAGGGCCATGGGCGTGCGGCCGACATCTGGAGTCTGGGGTGT

GTTGTCATAGAGATGGTGACTGGCAAGAGGCCTTGGCATGAGTATGAGCACAACTTT

CAAATTATGTATAAAGTGGGGATGGGACATAAGCCACCAATCCCTGAAAGATTAAG

CCCTGAAGGAAAGGACTTCCTTTCTCACTGCCTTGAGAGTGACCCAAAGATGAGATG

GACCGCCAGCCAGCTCCTCGACCATTCGTTTGTCAA

GGTTTGCACAGATGAAGAATG

Human MEKK 6 CDS (SEQ ID NO: 23)
ATGGCGGGGCCGTGTCCCCGGTCCGGGGCGGAGCGCGCCGGCAGCTGCTGGCAGGA

CCCGCTGGCCGTGGCGCTGAGCCGGGGCCGGCAGCTCGCGGCGCCCCCGGGCCGGG

GCTGCGCGCGGAGCCGGCCGCTCAGCGTGGTCTACGTGCTGACCCGGGAGCCGCAG

CCCGGGCTCGAGCCTCGGGAGGGAACCGAGGCGGAGCCGCTGCCCCTGCGCTGCCT

GCGCGAGGCTTGCGCGCAGGTCCCCCGGCCGCGGCCGCCCCCGCAGCTGCGCAGCC

TGCCCTTCGGGACGCTGGAGCTAGGCGACACCGCGGCTCTGGATGCCTTCTACAACG

CGGATGTGGTGGTGCTGGAGGTGAGCAGCTCGCTGGTACAGCCCTCCCTGTTCTACC

ACCTTGGTGTGCGTGAGAGCTTCAGCATGACCAACAATGTGCTCCTCTGCTCCCAGG

CCGACCTCCCTGACCTGCAGGCCCTGCGGAGGATGTTTTCCAGAAGAACTCGGATT

GCGTTGGCAGCTACACACTGATCCCCTATGTGGTGACGGCCACTGGTCGGGTGCTGT

GTGGTGATGCAGGCCTTCTGCGGGGCCTGGCTGATGGGCTGGTACAGGCTGGAGTG

GGGACCGAGGCCCTGCTCACTCCCCTGGTGGGCCGGCTTGCCCGCCTGCTGGAGGCC

-continued

```
ACACCCACAGACTCTTGTGGCTATTTCCGGGAGACCATTCGGCGGGACATCCGGCAG

GCGCGGGAGCGGTTCAGTGGGCCACAGCTGCGGCAGGAGCTGGCTC

GCCTGCAGCGGAGACTGGACAGCGTGGAGCTGCTGAGCCCCGACATCATCATGAAC

TTGCTGCTCTCCTACCGCGATGTGCAGGACTACTCGGCCATCATTGAGCTGGTGGAG

ACGCTGCAGGCCTTGCCCACCTGTGATGTGGCCGAGCAGCATAATGTCTGCTTCCAC

TACACTTTTGCCCTCAACCGGAGGAACAGGCCTGGGGACCGGGCGAAGGCCCTGTC

TGTGCTGCTGCCGCTGGTACAGCTTGAGGGCTCTGTGGCGCCCGATCTGTACTGCAT

GTGTGGCCGTATCTACAAGGACATGTTCTTCAGCTCGGGTTTCCAGGATGCTGGGCA

CCGGGAGCAGGCCTATCACTGGTATCGCAAGGCTTTTGACGTAGAGCCCAGCCTTCA

CTCAGGCATCAATGCAGCTGTGCTCCTCATTGCTGCCGGGCAGCACTTTGAGGATTC

CAAAGAGCTCCGGCTAATAGGCATGAAGCTGGGCTGCCTGCTGGCCCGCAAAGGCT

GCGTGGAGAAGATGCAGTATTACTGGGATGTGGGTTTCTACCTGGGAGCCCAGATCC

TCGCCAATGACCCCACCCAGGTGGTGCTGGCTGCAGAGCAGCTGTATAAGCTCAAT

GCCCCCATATGGTACCTGGTGTCCGTGATGGAGACCTTCCTGCTCTACCAGCACTTC

AGGCCCACGCCAGAGCCCCCTGGAGGGCCACCACGCCGTGCCCACTTCTGGCTCCA

CTTCTTGCTACAGTCCTGCCAACCATTCAAGACAGCCTGTGCCCAGGGCGACCAGTG

CTTGGTGCTGGTCCTGGAGATGAACAAGGTGCTGCTGCCTGCAAAGCTCGAGGTTCG

GGGTACTGACCCAGTAAGCACAGTGACCCTGAGCCTGCTGGAGCCTGAGACCCAGG

ACATTCCCTCCAGCTGGACCTTCCCAGTCGCCTCCATATGCGGAGTCAGCGCCTCAA

AGCGCGACGAGCGCTGCTGCTTCCTCTATGCACTCCCCCCGGCTCAGGACGTCCAGC

TGTGCTTCCCCAGCGTAGGGCACTGCCAGTGGTTCTGCGGCCTGATCCAGGCCTGGG

TGACGAACCCGGATTCCACGGCGCCCGCGGAGGAGGCGGAGGGCGCGGGGGAGAT

GTTGGAGTTTGATTATGA

GTACACGGAGACGGGCGAGCGGCTGGTGCTGGGCAAGGGCACGTATGGGGTGGTGT

ACGCGGGCCGCGATCGCCACACGAGGGTGCGCATCGCCATCAAGGAGATCCCGGAG

CGGGACAGCAGGTTCTCTCAGCCCCTGCATGAAGAGATCGCTCTTCACAGACGCCTG

CGCCACAAGAACATAGTGCGCTATCTGGGCTCAGCTAGCCAGGGCGGCTACCTTAA

GATCTTCATGGAGGAAGTGCCTGGAGGCAGCCTGTCCTCCTTGCTGCGGTCGGTGTG

GGGACCCCTGAAGGACAACGAGAGCACCATCAGTTTCTACACCCGCCAGATCCTGC

AGGGACTTGGCTACTTGCACGACAACCACATCGTGCACAGGGACATAAAAGGGGAC

AATGTGCTGATCAACACCTTCAGTGGGCTGCTCAAGATTTCTGACTTCGGCACCTCC

AAGCGGCTGGCAGGCATCACACCTTGCACTGAGACCTTCACAGGAACTCTGCAGTA

TATGGCCCCAGAAATCATTGACCAGGGCCCACGCGGGTATGGGAAAGCAGCTGACA

TCTGGTCACTGGGCTGCACTGTCATTGAGATGGCCACAGGTCGCCCCCCCTTCCACG

AGCTCGGGAGCCCACAGGCTGCCATGTTTCAGGTGGGTATGTACAAGGTCCATCCGC

CAATGCCCAGCTCTCTGTCGGCCGAGGCCCAAGCCTTTCTCCTCCGAACTTTTGAGC

CAGACCCCCGCCTCCGAGCCAGCGCCCAGACACTGCTGGGGACCCCTTCCTGCAG

CCTGGGAAAAGGAGCCGCAGCCCCAGCTCCCACGACATGCTCCACGGCCCTCAGA

TGCCCCTTCTGCCAGTCCCACTCCTTCAGCCAACTCAACCACCCAGTCTCAGACATTC

CCGTGCCCTCAGGCACCCTCTCAGCACCCACCCAGCCCCCGAAGCGCTGCCTCAGT

TATGGGGGCACCAGCCAGCTCCGGGTGCCCGAGGAGCCTGCGGCCGAGGAGCCTGC
```

-continued

```
GTCTCCGGAGGAGAGTTCGGGGCTGAGCCTGCTGCACCAGGAGAGCAAGCGTCGGG

CCATGCTGGCCGCAGTATTGGAGCAGGAGCTGCCAGCGCTGGCGGAGAATCTGCAC

CAGGAGCAGAAGCAAGAGCAGGGGCCCGTCTGGGCAGAAACCATGTGGAAGAGC

TGCTGCGCTGCCTCGGGCACACATCCACACTCCCAACCGCCGGCAGCTCGCCCAGG

AGCTGCGGGCGCTGCAAGGACGGCTGAGGGCCCAGGGCCTTGGGCCTGCGCTTCTG

CACAGACCGCTGTTTGCCTTCCCGGATGCGGTGAAGCAGATCCTCCGCAAGCGCCAG

ATCCGTCCACACTGGATGTTCGTTCTGGACTCACTGCTCAGCCGTGCTGTGCGGGCA

GCCCTGGGTGTGCTAGGACCGGAGGTGGAGAAGGAGGCGGTCTCACCGAGGTCAGA

GGAGCTGAGTAATGAAGGGGACTCCCAGCAGAGCCCAGGCCAGCAGAGCCCGCTTC

CGGTGGAGCCCGAGCAGGGCCCCGCTCCTCTGATGGTGCAGCTGAGCCTCTTGAGG

GCAGAGACTGATCGGCTGCGCGAAATCCTGG

CGGGGAAGGAACGGGAGTACCAGGCCCTGGTGCAGCGGGCTCTACAGCGGCTGAAT

GAGGAAGCCCGGACCTATGTCCTGGCCCCAGAGCCTCCAACTGCTCTTTCAACGGAC

CAGGGCCTGGTGCAGTGGCTACAGGAACTGAATGTGGATTCAGGCACCATCCAAAT

GCTGTTGAACCATAGCTTCACCCTCCACACTCTGCTCACCTATGCCACTCGAGATGA

CCTCATCTACACCCGCATCAGGGGAGGGATGGTATGCCGCATCTGGAGGGCCATCTT

GGCACAGCGAGCAGGATCCACACCAGTCACCTCTGGACCCTGA
```

Human MEKK7 CDS
(SEQ ID NO: 24)

```
ATGTCTACAGCCTCTGCCGCCTCCTCCTCCTCCTCGTCTTCGGCCGGTGAGATGATCG

AAGCCCCTTCCCAGGTCCTCAACTTTGAAGAGATCGACTACAAGGAGATCGAGGTG

GAAGAGGTTGTTGGAAGAGGAGCCTTTGGAGTTGTTTGCAAAGCTAAGTGGAGAGC

AAAAGATGTTGCTATTAAACAAATAGAAAGTGAATCTGAGAGGAAAGCGTTTATTG

TAGAGCTTCGGCAGTTATCCCGTGTGAACCATCCTA

ATATTGTAAAGCTTTATGGAGCCTGCTTGAATCCAGTGTGTCTTGTGATGGAATATG

CTGAAGGGGGCTCTTTATATAATGTGCTGCATGGTGCTGAACCATTGCCATATTATA

CTGCTGCCCACGCAATGAGTTGGTGTTTACAGTGTTCCCAAGGAGTGGCTTATCTTC

ACAGCATGCAACCCAAAGCGCTAATTCACAGGGACCTGAAACCACCAAACTTACTG

CTGGTTGCAGGGGGACAGTTCTAAAAATTTGTGATTTTGGTACAGCCTGTGACATT

CAGACACACATGACCAATAACAAGGGGAGTGCTGCTTGGATGGCACCTGAAGTTTT

TGAAGGTAGTAATTACAGTGAAAAATGTGACGTCTTCAGCTGGGGTATTATTCTTTG

GGAAGTGATAACGCGTCGGAAAC

CCTTTGATGAGATTGGTGGCCCAGCTTTCCGAATCATGTGGGCTGTTCATAATGGTA

CTCGACCACCACTGATAAAAAATTTACCTAAGCCCATTGAGAGCCTGATGACTCGTT

GTTGGTCTAAAGATCCTTCCCAGCGCCCTTCAATGGAGGAAATTGTGAAAATAATGA

CTCACTTGATGCGGTACTTTCCAGGAGCAGATGAGCCATTACAGTATCCTTGTCAGT

ATTCAGATGAAGGACAGAGCAACTCTGCCACCAGTACAGGCTCATTCATGGACATT

GCTTCTACAAATACGAGTAACAAAAGTGACACTAATATGGAGCAAGTTCCTGCCAC

AAATGATACTATTAAGCGCTTAGAATCAAAATTGTTGAAAAATCAGGCAAAGCAAC

AGAGTGAATCTGGACGTTTAAGCTTGGGAGCCTCCCGTGGGAGCAGTGTGGAGAGC

TTGCCCCCAACCTCTGAGGGCAAGAGGATGAGTGCTGACATGTCTGAAATAGAAGC
```

-continued

```
TAGGATCGCCGCAACCACAGGCAACGGACAGCCAAGACGTAGATCCATCCAAGACT

TGACTGTAACTGGAACAGAACCTGGTCAGGTGAGCAGTAGGTCATCCAGTCCCAGT

GTCAGAATGATTACTACCTCAGGACCAACCTCAGAAAAGCCAACTCGAAGTCATCC

ATGGACCCTGATGATTCCACAGATACCAATGGATCAGATAACTCCATCCCAATGGC

TTATCTTACACTGGATCACCAACTACAGCCTCTAGCACCGTGCCCAAACTCCAAAGA

ATCTATGGCAGTGTTTGAACAGCATTGTAAAATGGCACAAGAATATATGAAAGTTCA

AACAGAAATTGCATTGTTATTACAGAGAAAGCAAGAACTAGTTGCAGAACTGGACC

AGGATGAAAAGGACCAGCAAAATACATCTCGCCTGGTACAGGAACATAAAAAGCTT

TTAGATGAAAACAAAAGCCTTTCTACTTACTACCAGCAATGCAAAAAACAACTAGA

GGTCATCAGAAGTCAGCAGCAGAAACGACAAGGCACTTCATGA
```

Human MK2 CDS (SEQ ID NO: 25)
```
ATGCTGTCCAACTCCCAGGGCCAGAGCCCGCCGGTGCCGTTCCCCGCCCCGGCCCCG

CCGCCGCAGCCCCCCACCCCTGCCCTGCCGCACCCCCCGGCGCAGCCGCCGCCGCCG

CCCCCGCAGCAGTTCCCGCAGTTCCACGTCAAGTCCGGCCTGCAGATCAAGAAGAA

CGCCATCATCGATGACTACAAGGTCACCAGCCAGGTCCTGGGGCTGGGCATCAACG

GCAAAGTTTTGCAGATCTTCAACAAGAGGACCCAGGAGAAATTCGCCCTCAAAATG

CTTCAGGACTGCCCCAAGGCCCGCAGGGAGGTGGAGCTGCACTGGCGGGCCTCCCA

GTGCCCGCACATCGTACGGATCGTGGATGTGTACGAGAATCTGTACGCAGGGAGGA

AGTGCCTGCTGATTGTCATGGAATGTTTGGACGGTGGAGAACTCTTTAGCCGAATCC

AGGATCGAGGAGACCAGGCATTCACAGAAAGAGAAGCATCCGAAATCATGAAGAG

CATCGGTGAGGCCATCCAGTATCTGCATTCAATCAACATTGCCCATCGGATGTCAA

GCCTGAGAATCTCTTATACACCTCCAAAAGGCCCAACGCCATCCTGAAACTCACTGA

CTTTGGCTTTGCCAAGGAAACCACCAGCCACAACTCTTTGACCACTCCTTGTTATAC

ACCGTACTATGTGGCTCCAGAAGTGCTGGGTCCAGAGAAGTATGACAAGTCCTGTG

ACATGTGGTCCCTGGGTGTCATCATGTACATCCTGCTGTGTGGGTATCCCCCCTTCTA

CTCCAACCACGGCCTTGCCATCTCTCCGGGCATGAAGACTCGCATCCGAATGGGCCA

GTATGAATTTCCCAACCCAGAATGGTCAGAAGTATCAGAGGAAGTGAAGATGCTCA

TTCGGAATCTGCTGAAAACAGAGCCCACCCAGAGAATGACCATCACCGAGTTTATG

AACCACCCTTGGATCATGCAATCAACAAAGGTCCCTCAAACCCCACTGCACACCAG

CCGGGTCCTGAAGGAGGACAAGGAGCGGTGGGAGGATGTCAAGGGGTGTCTTCATG

ACAAGAACAGCGACCAGGCCACTTGGCTGACCAGGTTGTGA
```

Human MyD88 CDS (SEQ ID NO: 26)
```
ATGCGACCCGACCGCGCTGAGGCTCCAGGACCGCCCGCCATGGCTGCAGGAGGTCC

CGGCGCGGGGTCTGCGGCCCCGGTCTCCTCCACATCCTCCCTTCCCCTGGCTGCTCTC

AACATGCGAGTGCGGCGCCGCCTGTCTCTGTTCTTGAACGTGCGGACACAGGTGGCG

GCCGACTGGACCGCGCTGGCGGAGGAGATGGACTTTGAGTACTTGGAGATCCGGCA

ACTGGAGACACAAGCGGACCCCACTGGCAGGCTGCTGGACGCCTGGCAGGGACGCC

CTGGCGCCTCTGTAGGCCGACTGCTCGAGCTGCTTACCAAGCTGGGCCGCGACGACG

TGCTGCTGGAGCTGGGACCCAGCATTGAGGAGGATTGCCAAAAGTATATCTTGAAG

CAGCAGCAGGAGGAGGCTGAGAAGCCTTTACAGGTGGCCGCTGTAGACAGCAGTGT

CCCACGGACAGCAGAGCTGGCGGGCATCACCACACTTGATGACCCCCTGGGGCATA
```

-continued

TGCCTGAGCGTTTCGATGCCTTCATCTGCTATTGCCCCAGCGACATCCAGTTTGTGCA

GGAGATGATCCGGCAACTGGAACAGACAAACTATCGACTGAAGTTGTGTGTGTCTG

ACCGCGATGTCCTGCCTGGCACCTGTGTCTGGTCTATTGCTAGTGAGCTCATCGAAA

AGAGGTTGGCTAGAAGGCCACGGGTGGGTGCCGCCGGATGGTGGTGGTTGTCTCT

GATGATTACCTGCAGAGCAAGGAATGTGACTTCCAGACCAAATTTGCACTCAGCCTC

TCTCCAGGTGCCCATCAGAAGCGACTGATCCCCATCAAGTACAAGGCAATGAAGAA

AGAGTTCCCCAGCATCCTGAGGTTCATCACTGTCTGCGACTACACCAACCCCTGCAC

CAAATCTTGGTTCTGGACTCGCCTTGCCAAGGCCTTGTCCCTGCCCTGA

Human NF-κB CDS (SEQ ID NO: 27)

ATGGCAGAAGATGATCCATATTTGGGAAGGCCTGAACAAATGTTTCATTTGGATCCT

TCTTTGACTCATACAATATTTAATCCAGAAGTATTTCAACCACAGATGGCACTGCCA

ACAGATGGCCCATACCTTCAAATATTAGAGCAACCTAAACAGAGAGGATTTCGTTTC

CGTTATGTATGTGAAGGCCCATCCCATGGTGGACTACCTGGTGCCTCTAGTGAAAAG

AACAAGAAGTCTTACCCTCAGGTCAAAATCTGCAACTATGTGGGACCAGCAAAGGT

TATTGTTCAGTTGGTCACAAATGGAAAAAATATCCACCTGCATGCCCACAGCCTGGT

GGGAAAACACTGTGAGGATGGGATCTGCACTGTAACTGCTGGACCCAAGGACATGG

TGGTCGGCTTCGCAAACCTGGGTATACTTCATGTGACAAAGAAAAAGTATTTGAAA

CACTGGAAGCACGAATGACAGAGGCGTGTATAAGGGCTATAATCCTGGACTCTTG

GTGCACCCTGACCTTGCCTATTTGCAAGCAGAAGGTGGAGGGGACCGGCAGCTGGG

AGATCGGGAAAAGAGCTAATCCGCCAAGCAGCTCTGCAGCAGACCAAGGAGATG

GACCTCAGCGTGGTGCGGCTCATGTTTACAGCTTTTCTTCCGGATAGCACTGGCAGC

TTCACAAGGCGCCTGGAACCCGTGGTATCAGACGCCATCTATGACAGTAAAGCCCC

CAATGCATCCAACTTGAAAATTGTAAGAATGGACAGGACAGCTGGATGTGTGACTG

GAGGGGAGGAAATTTATCTTCTTTGTGACAAAGTTCAGAAAGATGACATCCAGATTC

GATTTTATGAAGAGGAAGAAATGGTGGAGTCTGGGAAGGATTTGGAGATTTTTCC

CCCACAGATGTTCATAGACAATTTGCCATTGTCTTCAAAACTCCAAAGTATAAAGAT

ATTAATATTACAAAACCAGCCTCTGTGTTTGTCCAGCTTCGGAGGAAATCTGACTTG

GAAACTAGTGAACCAAAACCTTTCCTCTACTATCCTGAAATCAAAGATAAAGAAGA

AGTGCAGAGGAAACGTCAGAAGCTCATGCCCAATTTTTCGGATAGTTTCGGCGGTGG

TAGTGGTGCTGGAGCTGGAGGCGGAGGCATGTTTGGTAGTGGCGGTGGAGGAGGGG

GCACTGGAAGTACAGGTCCAGGGTATAGCTTCCCACACTATGGATTTCCTACTTATG

GTGGGATTACTTTCCATCCTGGAACTACTAAATCTAATGCTGGGATGAAGCATGGAA

CCATGGACACTGAATCTAAAAAGGACCCTGAAGGTTGTGACAAAAGTGATGACAAA

AACACTGTAAACCTCTTTGGGAAAGTTATTGAAACCACAGAGCAAGATCAGGAGCC

CAGCGAGGCCACCGTTGGGAATGGTGAGGTCACTCTAACGTATGCAACAGGAACAA

AAGAAGAGAGTGCTGGAGTTCAGGATAACCTCTTTCTAGAGAAGGCTATGCAGCTT

GCAAAGAGGCATGCCAATGCCCTTTTCGACTACGCGGTGACAGGAGACGTGAAGAT

GCTGCTGGCCGTCCAGCGCCATCTCACTGCTGTGCAGGATGAGAATGGGGACAGTGT

CTTACACTTAGCAATCATCCACCTTCATTCTCAACTTGTGAGGGATCTACTAGAAGTC

ACATCTGGTTTGATTTCTGATGACATTATCAACATGAGAAATGATCTGTACCAGACG

-continued

```
CCCTTGCACTTGGCAGTGATCACTAAGCAGGAAGATGTGGTGGAGGATTTGCTGAG
GGCTGGGGCCGACCTGAGCCTTCTGGACCGCTTGGGTAACTCTGTTTTGCACCTAGC
TGCCAAAGAAGGACATGATAAAGTTCTCAGTATCTTACTCAAGCACAAAAAGGCAG
CACTACTTCTTGACCACCCCAACGGGGACGGTCTGAATGCCATTCATCTAGCCATGA
TGAGCAATAGCCTGCCATGTTTGCTGCTGCTGGTGGCCGCTGGGGCTGACGTCAATG
CTCAGGAGCAGAAGTCCGGGCGCACAGCACTGCACCTGGCTGTGGAGCACGACAAC
ATCTCATTGGCAGGCTGCCTGCTCCTGGAGGGTGATGCCCATGTGGACAGTACTACC
TACGATGGAACCACACCCCTGCATATAGCAGCTGGGAGAGGGTCCACCAGGCTGGC
AGCTCTTCTCAAAGCAGCAGGAGCAGATCCCCTGGTGGAGAACTTTGAGCCTCTCTA
TGACCTGGATGACTCTTGGGAAAATGCAGGAGAGGATGAAGGAGTTGTGCCTGGAA
CCACGCCTCTAGATATGGCCACCAGCTGGCAGGTATTTGACATATTAAATGGGAAAC
CATATGAGCCAGAGTTTACATCTGATGATTTACTAGCACAAGGAGACATGAAACAG
CTGGCTGAAGATGTGAAGCTGCAGCTGTATAAGTTACTAGAAATTCCTGATCCAGAC
AAAAACTGGGCTACTCTGGCGCAGAAATTAGGTCTGGGGATACTTAATAATGCCTTC
CGGCTGAGTCCTGCTCCTTCCAAAACACTTATGGACAACTATGAGGTCTCTGGGGGT
ACAGTCAGAGAGCTGGTGGAGGCCCTGAGACAAATGGGCTACACCGAAGCAATTGA
AGTGATCCAGGCAGCCTCCAGCCCAGTGAAGACCACCTCTCAGGCCCACTCGCTGCC
TCTCTCGCCTGCCTCCACAAGGCAGCAAATAGACGAGCTCCGAGACAGTGACAGTG
TCTGCGACAGCGGCGTGGAGACATCCTTCCGCAAACTCAGCTTTACCGAGTCTCTGA
CCAGTGGTGCCTCACTGCTAACTCTCAACAAAATGCCCCATGATTATGGGCAGGAAG
GACCTCTAGAAGGCAAAATTTAG
```

Human NIK CDS (SEQ ID NO: 28)
```
ATGGCAGTGATGGAAATGGCCTGCCCAGGTGCCCCTGGCTCAGCAGTGGGGCAGCA
GAAGGAACTCCCCAAAGCCAAGGAGAAGACGCCGCCACTGGGGAAGAAACAGAGC
TCCGTCTACAAGCTTGAGGCCGTGGAGAAGAGCCCTGTGTTCTGCGGAAAGTGGGA
GATCCTGAATGACGTGATTACCAAGGGCACAGCCAAGGAAGGCTCCGAGGCAGGGC
CAGCTGCCATCTCTATCATCGCCCAGGCTGAGTGTGAGAATAGCCAAGAGTTCAGCC
CCACCTTTTCAGAACGCATTTTCATCGCTGGGTCCAAACAGTACAGCCAGTCCGAGA
GTCTTGATCAGATCCCCAACAATGTGGCCCATGCTACAGAGGGCAAAATGGCCCGT
GTGTGTTGGAAGGGAAAGCGTCGCAGCAAAGCCCGGAAGAAACGGAAGAAGAAGA
GCTCAAAGTCCCTGGCTCATGCAGGAGTGGCCTTGGCCAAACCCCTCCCCAGGACCC
CTGAGCAGGAGAGCTGCACCATCCCAGTGCAGGAGGATGAGTCTCCACTCGGCGCC
CCATATGTTAGAAACACCCCGCAGTTCACCAAGCCTCTGAAGGAACCAGGCCTTGG
GCAACTCTGTTTTAAGCAGCTTGGCGAGGGCCTACGGCCGGCTCTGCCTCGATCAGA
ACTCCACAAACTGATCAGCCCCTTGCAATGTCTGAACCACGTGTGGAAACTGCACCA
CCCCCAGGACGGAGGCCCCCTGCCCCTGCCCACGCACCCCTTCCCCTATAGCAGACT
GCCTCATCCCTTCCCATTCCACCCTCTCCAGCCCTGGAAACCTCACCCTCTGGAGTCC
TTCCTGGGCAAACTGGCCTGTGTAGACAGCCAGAAACCCTTGCCTGACCCACACCTG
AGCAAACTGGCCTGTGTAGACAGTCCAAAGCCCCTGCCTGGCCCACACCTGGAGCC
CAGCTGCCTGTCTCGTGGTGCCCATGAGAAGTTTTCTGTGGAGGAATACCTAGTGCA
TGCTCTGCAAGGCAGCGTGAGCTCAGGCCAGGCCCACAGCCTGACCAGCCTGGCCA
```

-continued

```
AGACCTGGGCAGCAAGGGGCTCCAGATCCCGGGAGCCCAGCCCCAAAACTGAGGAC
AACGAGGGTGTCCTGCTCACTGAGAAACTCAAGCCAGTGGATTATGAGTACCGAGA
AGAAGTCCACTGGGCCACGCACCAGCTCCGCCTGGGCAGAGGCTCCTTCGGAGAGG
TGCACAGGATGGAGGACAAGCAGACTGGCTTCCAGTGCGCTGTCAAAAAGGTGCGG
CTGGAAGTATTTCGGGCAGAGGAGCTGATGGCATGTGCAGGATTGACCTCACCCAG
AATTGTCCCTTTGTATGGAGCTGTGAGAGAAGGGCCTTGGGTCAACATCTTCATGGA
GCTGCTGGAAGGTGGCTCCCTGGGCCAGCTGGTCAAGGAGCAGGGCTGTCTCCCAG
AGGACCGGGCCCTGTACTACCTGGGCCAGGCCCTGGAGGGTCTG
GAATACCTCCACTCACGAAGGATTCTGCATGGGGACGTCAAAGCTGACAACGTGCT
CCTGTCCAGCGATGGGAGCCACGCAGCCCTCTGTGACTTTGGCCATGCTGTGTGTCT
TCAACCTGATGGCCTGGGAAAGTCCTTGCTCACAGGGGACTACATCCCTGGCACAG
AGACCCACATGGCTCCGGAGGTGGTGCTGGGCAGGAGCTGCGACGCCAAGGTGGAT
GTCTGGAGCAGCTGCTGTATGATGCTGCACATGCTCAACGGCTGCCACCCCTGGACT
CAGTTCTTCCGAGGGCCGCTCTGCCTCAAGATTGCCAGCGAGCCTCCGCCTGTGAGG
GAGATCCCACCCTCCTGCGCCCCTCTCACAGCCCAGGCCATCCAAGAGGGGCTGAG
GAAAGAGCCCATCCACCGCGTGTCTGCAGCGGAGCTGGGAGGGAAGGTGAACCGG
GCACTACAGCAAGTGGGAGGTCTGAAGAGCCCTTGGAGGGGAGAATATAAAGAACC
AAGACATCCACCGCCAAATCAAGCCAATTACCACCAGACCCTCCATGCCCAGCCGA
GAGAGCTTTCGCCAAGGGCCCCAGGGCCCCGGCCAGCTGAGGAGACAACAGGCAG
AGCCCCTAAGCTCCAGCCTCCTCTCCCACCAGAGCCCCCAGAGCCAAACAAGTCTCC
TCCCTTGACTTTGAGCAAGGAGGAGTCTGGGATGTGGGAACCCTTACCTCTGTCCTC
CCTGGAGCCAGCCCCTGCCAGAAACCCCAGCTCACCAGAGCGGAAAGCAACCGTCC
CGGAGCAGGAACTGCAGCAGCTGGAAATAGAATTATTCCTCAACAGCCTGTCCCAG
CCATTTTCTCTGGAGGAGCAGGAGCAAATTCTCTCGTGCCTCAGCATCGACAGCCTC
TCCCTGTCGGATGACAGTGAGAAGAACCCATCAAAGGCCTCTCAAAGCTCGCGGGA
CACCCTGAGCTCAGGCGTACACTCCTGGAGCAGCCAGGCCGAGGCTCGAAGCTCCA
GCTGGAACATGGTGCTGGCCCGGGGGCGGCCCACCGACACCCCAAGCTATTTCAAT
GGTGTGAAAGTCCAAATACAGTCTCTTAATGGTGAACACCTGCACATCCGGGAGTTC
CACCGGGTCAAAGTGGGAGACATCGCCACTGGCATCAGCAGCCAGATCCCAGCTGC
AGCCTTCAGCTTGGTCACCAAAGACGGGCAGCCTGTTCGCTACGACATGGAGGTGC
CAGACTCGGGCATCGACCTGCAGTGCACACTGGCCCCTGATGGCAGCTTCGCCTGGA
GCTGGAGGGTCAAGCATGGCCAGCTGGAGAACAGGCCCTAA
Human p38 CDS
                                         (SEQ ID NO: 29)
ATGTCTCAGGAGAGGCCCACGTTCTACCGGCAGGAGCTGAACAAGACAATCTGGGA
GGTGCCCGAGCGTTACCAGAACCTGTCTCCAGTGGGCTCTGGCGCCTATGGCTCTGT
GTGTGCTGCTTTTGACACAAAAACGGGGTTACGTGTGGCAGTGAAGAAGCTCTCCAG
ACCATTTCAGTCCATCATTCATGCGAAAAGAACCTACAGAGAACTGCGGTTACTTAA
ACATATGAAACATGAAAATGTGATTGGTCTGTTGGACGTTTTTACACCTGCAAGGTC
TCTGGAGGAATTCAATGATGTGTATCTGGTGACCCATCTCATGGGGGCAGATCTGAA
CAACATTGTGAAATGTCAGAAGCTTACAGATGACCATGTTCAGTTCCTTATCTACCA
```

-continued

```
AATTCTCCGAGGTCTAAAGTATATACATTCAGCTGACATAATTCACAGGGACCTAAA

ACCTAGTAATCTAGCTGTGAATGAAGACTGTGAGCTGAAGATTCTGGATTTTGGACT

GGCTCGGCACACAGATGATGAAATGACAGGCTACGTGGCCACTAGGTGGTACAGGG

CTCCTGAGATCATGCTGAACTGGATGCATTACAACCAGACAGTTGATATTTGGTCAG

TGGGATGCATAATGGCCGAGCTGTTGACTGGAAGAACATTGTTTCCTGGTACAGACC

ATATTAACCAGCTTCAGCAGATTATGCGTCTGACAGGAACACCCCCCGCTTATCTCA

TTAACAGGATGCCAAGCCATGAGGCAAGAAACTATATTCAGTCTTTGACTCAGATGC

CGAAGATGAACTTTGCGAATGTATTTATTGGTGCCAATCCCCTGGCTGTCGACTTGC

TGGAGAAGATGCTTGTATTGGACTCAGATAAGAGAATTACAGCGGCCCAAGCCCTT

GCACATGCCTACTTTGCTCAGTACCACGATCCTGATGATGAACCAGTGGCCGATCCT

TATGATCAGTCCTTTGAAAGCAGGGACCTCCTTATAGATGAGTGGAAAAGCCTGACC

TATGATGAAGTCATCAGCTTTGTGCCACCACCCCTTGACCAAGAAGAGATGGAGTCC

TGA
```

Human PKR CDS (SEQ ID NO: 30)

```
ATGGCTGGTGATCTTTCAGCAGGTTTCTTCATGGAGGAACTTAATACATACCG

TCAGAAGCAGGGAGTAGTACTTAAATATCAAGAACTGCCTAATTCAGGACCTCCAC

ATGATAGGAGGTTTACATTTCAAGTTATAATAGATGGAAGAGAATTTCCAGAAGGT

GAAGGTAGATCAAAGAAGGAAGCAAAAAATGCCGCAGCCAAATTAGCTGTTGAGAT

ACTTAATAAGGAAAAGAAGGCAGTTAGTCCTTTATTATTGACAACAACGAATTCTTC

AGAAGGATTATCCATGGGGAATTACATAGGCCTTATCAATAGAATTGCCCAGAAGA

AAAGACTAACTGTAAATTATGAACAGTGTGCATCGGGGGTGCATGGGCCAGAAGGA

TTTCATTATAAATGCAAATGGGACAGAAAGAATATAGTATTGGTACAGGTTCTACT

AAACAGGAAGCAAAACAATTGGCCGCTAAACTTGCATATCTTCAGATATTATCAGA

AGAAACCTCAGTGAAATCTGACTACCTGTCCTCTGGTTCTTTTGCTACTACGTGTGAG

TCCCAAAGCAACTCTTTAGTGACCAGCACACTCGCTTCTGAATCATCATCTGAAGGT

GACTTCTCAGCAGATACATCAGAGATAAATTCTAACAGTGACAGTTTAAACAGTTCT

TCGTTGCTTATGAATGGTCTCAGAAATAATCAAAGGAAGGCAAAAAGATCTTTGGC

ACCCAGATTTGACCTTCCTGACATGAAAGAAACAAAGTATACTGTGGACAAGAGGT

TTGGCATGGATTTTAAAGAAATAGAATTAATTGGCTCAGGTGGATTTGGCCAAGTTT

TCAAAGCAAAACACAGAATTGACGGAAAGACTTACGTTATTAAACGTGTTAAATAT

AATAACGAGAAGGCGGAGCGTGAAGTAAAAGCATTGGCAAAACTTGATCATGTAAA

TATTGTTCACTACAATGGCTGTTGGGATGGATTTGATTATGATCCTGAGACCAGTGA

TGATTCTCTTGAGAGCAGTGATTATGATCCTGAGAACAGCAAAAATAGTTCAAGGTC

AAAGACTAAGTGCCTTTTCATCCAAATGGAATTCTGTGATAAAGGGACCTTGGAACA

ATGGATTGAAAAAGAAGAGGCGAGAAACTAGACAAAGTTTTGGCTTTGGAACTCT

TTGAACAAATAACAAAAGGGGTGGATTATATACATTCAAAAAAATTAATTCATAGA

GATCTTAAGCCAAGTAATATATTCTTAGTAGATACAAAACAAGTAAAGATTGGAGA

CTTTGGACTTGTAACATCTCTGAAAAATGATGGAAAGCGAACAAGGAGTAAGGGAA

CTTTGCGATACATGAGCCCAGAACAGATTTCTTCGCAAGACTATGGAAAGGAAGTG

GACCTCTACGCTTTGGGGCTAATTCTTGCTGAACTTCTTCATGTATGTGACACTGCTT

TTGAAACATCAAAGTTTTTCACAGACCTACGGGATGGCATCATCTCAGATATATTTG
```

-continued

ATAAAAAAGAAAAAACTCTTCTACAGAAATTACTCTCAAAGAAACCTGAGGATCGA

CCTAACACATCTGAAATACTAAGGACCTTGACTGTGTGGAAGAAAAGCCCAGAGAA

AAATGAACGACACACATGTTAG

Human Rac CDS (SEQ ID NO: 31)

ATGAGCGACGTGGCTATTGTGAAGGAGGGTTGGCTGCACAAACGAGGGGAGTACAT

CAAGACCTGGCGGCCACGCTACTTCCTCCTCAAGAATGATGGCACCTTCATTGGCTA

CAAGGAGCGGCCGCAGGATGTGGACCAACGTGAGGCTCCCCTCAACAACTTCTCTG

TGGCGCAGTGCCAGCTGATGAAGACGGAGCGGCCCCGGCCCAACACCTTCATCATC

CGCTGCCTGCAGTGGACCACTGTCATCGAACGCACCTTCCATGTGGAGACTCCTGAG

GAGCGGGAGGAGTGGACAACCGCCATCCAGACTGTGGCTGACGGCCTCAAGAAGCA

GGAGGAGGAGGAGATGGACTTCCGGTCGGGCTCACCCAGTGACAACTCAGGGGCTG

AAGAGATGGAGGTGTCCCTGGCCAAGCCCAAGCACCGCGTGACCATGAACGAGTTT

GAGTACCTGAAGCTGCTGGGCAAGGGCACTTTCGGCAAGGTGATCCTGGTGAAGGA

GAAGGCCACAGGCCGCTACTACGCCATGAAGATCCTCAAGAAGGAAGTCATCGTGG

CCAAGGACGAGGTGGCCCACACACTCACCGAGAACCGCGTCCTGCAGAACTCCAGG

CACCCCTTCCTCACAGCCCTGAAGTACTCTTTCCAGACCCACGACCGCCTCTGCTTTG

TCATGGAGTACGCCAACGGGGGCGAGCTGTTCTTCCACCTGTCCCGGGAGCGTGTGT

TCTCCGAGGACCGGGCCCGCTTCTATGGCGCTGAGATTGTGTCAGCCCTGGACTACC

TGCACTCGGAGAAGAACGTGGTGTACCGGGACCTCAAGCTGGAGAACCTCATGCTG

GACAAGGACGGGCACATTAAGATCACAGACTTCGGGCTGTGCAAGGAGGGGATCAA

GGACGGTGCCACCATGAAGACCTTTTGCGGCACACCTGAGTACCTGGCCCCCGAGG

TGCTGGAGGACAATGACTACGGCCGTGCAGTGGACTGGTGGGGGCTGGGCGTGGTC

ATGTACGAGATGATGTGCGGTCGCCTGCCCTTCTACAACCAGGACCATGAGAAGCTT

TTTGAGCTCATCCTCATGGAGGAGATCCGCTTCCCGCGCACGCTTGGTCCCGAGGCC

AAGTCCTTGCTTTCAGGG

CTGCTCAAGAAGGACCCCAAGCAGAGGCTTGGCGGGGGCTCCGAGGACGCCAAGG

AGATCATGCAGCATCGCTTCTTTGCCGGTATCGTGTGGCAGCACGTGTACGAGAAGA

AGCTCAGCCCACCCTTCAAGCCCCAGGTCACGTCGGAGACTGACACCAGGTATTTTG

ATGAGGAGTTCACGGCCCAGATGATCACCATCACACCACCTGACCAAGATGACAGC

ATGGAGTGTGTGGACAGCGAGCGCAGGCCCCACTTCCCCCAGTTCTCCTACTCGGCC

AGCGGCACGGCCTGA

Human Raf CDS (SEQ ID NO: 32)

ATGGCTAGCAAACGAAAATCTACAACTCCATGCATGGTTCGGACATCACAAGTAGT

AGAACAAGATGTGCCCGAGGAAGTAGACAGGGCCAAAGAGAAAGGAATCGGCACA

CCACAGCCTGACGTGGCCAAGGACAGTTGGGCAGCAGAACTTGAAAACTCTTCCAA

AGAAAACGAAGTGATAGAGGTGAAATCTATGGGGAAAGCCAGTCCAAAAAACTC

CAAGGTGGTTATGAGTGCAAATACTGCCCCTACTCCACGCAAAACCTGAACGAGTTC

ACGGAGCATGTCGACATGCAGCATCCCAACGTGATTCTCAACCCCCTCTACGTGTGT

GCAGAATGTAACTTCACAACCAAAAAGTACGACTCCCTATCCGACCACAACTCCAA

GTTCCATCCCGGGGAGGCCAACTTCAAGCTGAAGTTAATTAAACGCAATAATCAAA

-continued

```
CTGTCTTGGAACAGTCCATCGAAACCACCAACCATGTCGTGTCCATCACCACCAGTG
GCCCTGGAACTGGTGACAGTGATTCTGGGATCTCGGTGAGTAAAACCCCCATCATGA
AGCCTGGAAAACCAAAAGCGGATGCCAAGAAGGTGCCCAAGAAGCCCGAGGAGAT
CACCCCCGAGAACCACGTGGAAGGGACCGCCCGCCTGGTGACAGACACAGCTGAGA
TCCTCTCGAGACTCGGCGGGGTGGAGCTCCTCCAAGACACATTAGGACACGTCATGC
CTTCTGTACAGCTGCCACCAAATATCAACCTTGTGCCCAAGGTCCCTGTCCCACTAA
ATACTACCAAATACAACTCTGCCCTGGATACAAATGCCACGATGATCAACTCTTTCA
ACAAGTTTCCTTACCCGACCCAGGCTGAGTTGTCCTGGCTGACAGCTGCCTCCAAAC
ACCCAGAGGAGCACATCAGAATCTGGTTTGCCACCCAGCGCTTAAAGCATGGCATC
AGCTGGTCCCCAGAAGAGGTGGAGGAGGCCCGGAAGAAGATGTTCAACGGCACCAT
CCAGTCAGTACCCCCGACCATCACTGTGCTGCCCGCCCAGTTGGCCCCCACAAAGGT
GACGCAGCCCATCCTCCAGACGGCTCTACCGTGCCAGATCCTCGGCCAGACTAGCCT
GGTGCTGACTCAGGTGACCAGCGGGTCAACAACCGTCTCTTGCTCCCCCATCACACT
TGCCGTGGCAGGAGTCACCAACCATGGCCAGAAGAGACCCTTGGTGACTCCCCAAG
CTGCCCCCGAACCCAAGCGTCCACACATCGCTCAGGTGCCAGAGCCCCCACCCAAG
GTGGCCAACCCCCCGCTCACACCAGCCAGTGACCGCAAGAAGACAAAGGAGCAGAT
AGCACATCTCAAGGCCAGCTTTCTCCAGAGCCAGTTCCCTGACGATGCCGAGGTTTA
CCGGCTCATCGAGGTGACTGGCCTTGCCAGGAGCGAGATCAAGAAGTGGTTCAGTG
ACCACCGATATCGGTGTCAAAGGGGCATCGTCCACATCACCAGCGAATCCCTTGCCA
AAGACCAGTTGGCCATCGCGGCCTCCCGACACGGTCGCACGTATCATGCGTACCCA
GACTTTGCCCCCCAGAAGTTCAAAGAGAAAACACAGGGTCAGGTTAAAATCTTGGA
AGACAGCTTTTTGAAAAGTTCTTTTCCTACCCAAGCAGAACTGGATCGGCTAAGGGT
GGGAGACCAAGCTGAGCAGGAGAGAGATCGACTCCTGGTTCTCGGAGAGGCGGAAGC
TTCGAGACAGCATGGAACAAGCTGTCTTGGATTCCATGGGGTCTGGCAAAAAAGGC
CAAGATGTGGGAGCCCCCAATGGTGCTCTGTCTCGACTCGACCAGCTCTCCGGTGCC
CAGTTAACAAGTTCTCTGCCCAGCCCTTCGCCAGCAATTGCAAAAAGTCAAGAACA
GGTTCATCTCCTGAGGAGCACGTTTGCAAGAACCCAGTGGCCTACTCCCAGGAGTA
CGACCAGTTAGCGGCCAAGACTGGCCTGGTCCGAACTGAGATTGTGCGTTGGTTCAA
GGAGAACAGATGCTTGCTGAAAACGGGAACCGTGAAGTGGATGGAGCAGTACCAGC
ACCAGCCCATGGCAGATGATCACGGCTACGATGCCGTAGCAAGGAAAGCAACAAAA
CCCATGGCCGAGAGCCCAAAGAACGGGGGTGATGTGGTTCCACAATATTACAAGGA
CCCCAAAAAGCTCTGCGAAGAGGACTTGGAGAAGTTGGTGACCAGGGTAAAAGTAG
GCAGCGAGCCAGCAAAAGACTGTTTGCCAGCAAAGCCCTCAGAGGCCACCTCAGAC
CGGTCAGAGGGCAGCAGCCGGGACGGCCAGGGTAGCGACGAGAACGAGGAGTCGA
GCGTTGTGGATTACGTGGAGGTGACGGTCGGGGAGGAGGATGCGATCTCAGATAGA
TCAGATAGCTGGAGTCAGGCTGCGGCAGAAGGTGTGTCGGAACTGGCTGAATCAGA
CTCCGACTGCGTCCCTGCAGAGGCTGGCCAGGCCTAG
```

Human K-Ras CDS (SEQ ID NO: 33)
```
ATGACTGAATATAAACTTGTGGTAGTTGGAGCTGGTGGCGTAGGCAAGAGTGCCTTG
ACGATACAGCTAATTCAGAATCATTTTGTGGACGAATATGATCCAACAATAGAGGAT
TCCTACAGGAAGCAAGTAGTAATTGATGGAGAAACCTGTCTCTTGGATATTCTCGAC
```

-continued

ACAGCAGGTCAAGAGGAGTACAGTGCAATGAGGGACCAGTACATGAGGACTGGGG

AGGGCTTTCTTTGTGTATTTGCCATAAATAATACTAAATCATTTGAAGATATTCACCA

TTATAGAGAACAAATTAAAAGAGTTAAGGACTCTGAAGATGTACCTATGGTCCTAGT

AGGAAATAAATGTGATTTGCCTTCTAGAACAGTAGACACAAAACAGGCTCAGGACT

TAGCAAGAAGTTATGGAATTCCTTTTATTGAAACATCAGCAAAGACAAGACAGGGT

GTTGATGATGCCTTCTATACATTAGTTCGAGAAATTCGAAAACATAAAGAAAAGATG

AGCAAAGATGGTAAAAAGAAGAAAAAGAAGTCAAAGACAAAGTGTGTAATTATGT

AA

Human N-Ras CDS (SEQ ID NO: 34)

ATGACTGAGTACAAACTGGTGGTGGTTGGAGCAGGTGGTGTTGGGAAAAGCGCACT

GACAATCCAGCTAATCCAGAACCACTTTGTAGATGAATATGATCCCACCATAGAGG

ATTCTTACAGAAAACAAGTGGTTATAGATGGTGAAACCTGTTTGTTGGACATACTGG

ATACAGCTGGACAAGAAGAGTACAGTGCCATGAGAGACCAATACATGAGGACAGG

CGAAGGCTTCCTCTGTGTATTTGCCATCAATAATAGCAAGTCATTTGCGGATATTAA

CCTCTACAGGGAGCAGATTAAGCGAGTAAAAGACTCGGATGATGTACCTATGGTGC

TAGTGGGAAACAAGTGTGATTTGCCAACAAGGACAGTTGATACAAAACAAGCCCAC

GAACTGGCCAAGAGTTACGGGATTCCATTCATTGAAACCTCAGCCAAGACCAGACA

GGGTGTTGAAGATGCTTTTTACACACTGGTAAGAGAAATACGCCAGTACCGAATGA

AAAAACTCAACAGCAGTGATGATGGGACTCAGGGTTGTATGGGATTGCCATGTGTG

GTGATGTAA

Human RIP CDS (SEQ ID NO: 35)

ATGCAACCAGACATGTCCTTGAATGTCATTAAGATGAAATCCAGTGACTTCCTGGAG

AGTGCAGAACTGGACAGCGGAGGCTTTGGGAAGGTGTCTCTGTGTTTCCACAGAAC

CCAGGGACTCATGATCATGAAAACAGTGTACAAGGGGCCCAACTGCATTGAGCACA

ACGAGGCCCTCTTGGAGGAGGCGAAGATGATGAACAGACTGAGACACAGCCGGGTG

GTGAAGCTCCTGGGCGTCATCATAGAGGAAGGGAAGTACTCCCTGGTGATGGAGTA

CATGGAGAAGGGCAACCTGATGCACGTGCTGAAAGCCGAGATGAGTACTCCGCTTT

CTGTAAAAGGAAGGATAATTTTGGAAATCATTGAAGGAATGTGCTACTTACATGGA

AAAGGCGTGATACACAAGGACCTGAAGCCTGAAAATATCCTTGTTGATAATGACTTC

CACATTAAGATCGCAGACCTCGGCCTTGCCTCCTTTAAGATGTGGAGCAAACTGAAT

AATGAAGAGCACAATGAGCTGAGGGAAGTGGACGGCACCGCTAAGAAGAATGGCG

GCACCCTCTACTACATGGCGCCCGAGCACCTGAATGACGTCAACGCAAAGCCCACA

GAGAAGTCGGATGTGTACAGCTTTGCTGTAGTACTCTGGGCGATATTTGCAAATAAG

GAGCCATATGAAAATGCTATCTGTGAGCAGCAGTTGATAATGTGCATAAAATCTGG

GAACAGGCCAGATGTGGATGACATCACTGAGTACTGCCCAAGAGAAATTATCAGTC

TCATGAAGCTCTGCTGGGAAGCGAATCCGGAAGCTCGGCCGACATTTCCTGGCATTG

AAGAAAAATTTAGGCCTTTTTATTTAAGTCAATTAGAAGAAAGTGTAGAAGAGGAC

GTGAAGAGTTTAAAGAAAGAGTATTCAAACGAAATGCAGTTGTGAAGAGAATGCA

GTCTCTTCAACTTGATTGTGTGGCAGTACCTTCAAGCCGGTCAAATTCAGCCACAGA

ACAGCCTGGTTCACTGCACAGTTCCCAGGGACTTGGGATGGGTCCTGTGGAGGAGTC

-continued
```
CTGGTTTGCTCCTTCCCTGGAGCACCCACAAGAAGAGAATGAGCCCAGCCTGCAGA

GTAAACTCCAAGACGAAGCCAACTACCATCTTTATGGCAGCCGCATGGACAGGCAG

ACGAAACAGCAGCCCAGACAGAATGTGGCTTACAACAGAGAGGAGGAAAGGAGAC

GCAGGGTCTCCCATGACCCTTTTGCACAGCAAAGACCTTACGAGAATTTTCAGAATA

CAGAGGGAAAAGGCACTGCTTATTCCAGTGCAGCCAGTCATGGTAATGCAGTGCAC

CAGCCCTCAGGGCTCACCAGCCAACCTCAAGTACTGTATCAGAACAATGGATTATAT

AGCTCACATGGCTTTGGAACAAGACCACTGGATCCAGGAACAGCAGGTCCCAGAGT

TTGGTACAGGCCAATTCCAAGTCATATGCCTAGTCTGCATAATATCCCAGTGCCTGA

GACCAACTATCTAGGAAATACACCCACCATGCCATTCAGCTCCTTGCCACCAACAGA

TGAATCTATAAAATATACCATATACAATAGTACTGGCATTCAGATTGGAGCCTACAA

TTATATGGAGATTGGTGGGACGAGTTCATCACTACTAGACAGCACAAATACGAACTT

CAAAGAAGAGCCAGCTGCTAAGTACCAAGCTATCTTTGATAATACCACTAGTCTGAC

GGATAAACACCTGGACCCAATCAGGGAAAATCTGGGAAAGCACTGGAAAAACTGTG

CCCGTAAACTGGGCTTCACACAGTCTCAGATTGATGAAATTGACCATGACTATGAGC

GAGATGGACTGAAAGAAAAGGTTTACCAGATGCTCCAAAAGTGGGTGATGAGGGAA

GGCATAAAGGGAGCCACGGTGGGGAAGCTGGCCCAGGCGCTCCACCAGTGTTCCAG

GATCGACCTTCTGAGCAGCTTGATTTACGTCAGCCAGAACTAA
```

Human TRAF6 CDS (SEQ ID NO: 36)
```
ATGAGTCTGCTAAACTGTGAAAACAGCTGTGGATCCAGCCAGTCTGAAAGTGACTG

CTGTGTGGCCATGGCCAGCTCCTGTAGCGCTGTAACAAAAGATGATAGTGTGGGTGG

AACTGCCAGCACGGGGAACCTCTCCAGCTCATTTATGGAGGAGATCCAGGGATATG

ATGTAGAGTTTGACCCACCCCTGGAAAGCAAGTATGAATGCCCCATCTGCTTGATGG

CATTACGAGAAGCAGTGCAAACGCCATGCGGCCATAGGTTCTGCAAAGCCTGCATC

ATAAAATCAATAAGGGATGCAGGTCACAAATGTCCAGTTGACAATGAAATACTGCT

GGAAAATCAACTATTTCCAGACAATTTTGCAAAACGTGAGATTCTTTCTCTGATGGT

GAAATGTCCAAATGAAGGTTGTTTGCACAAGATGGAACTGAGACATCTTGAGGATC

ATCAAGCACATTGTGAGTTTGCTCTTATGGATTGTCCCAATGCCAGCGTCCCTTCCA

AAAATTCCATATTAATATTCACATTCTGAAGGATTGTCCAAGGAGACAGGTTTCTTG

TGACAACTGTGCTGCATCAATGGCATTTGAAGATAAAGAGATCCATGACCAGAACT

GTCCTTTGGCAAATGTCATCTGTGAATACTGCAATACTATACTCATCAGAGAACAGA

TGCCTAATCATTATGATCTAGACTGCCCTACAGCCCCAATTCCATGCACATTCAGTA

CTTTTGGTTGCCATGAAAAGATGCAGAGGAATCACTTGGCACGCCACCTACAAGAG

AACACCCAGTCACACATGAGAATGTTGGCCCAGGCTGTTCATAGTTTGAGCGTTATA

CCCGACTCTGGGTATATCTCAGAGGTCCGGAATTTCCAGGAAACTATTCACCAGTTA

GAGGGTCGCCTTGTAAGACAAGACCATCAAATCCGGGAGCTGACTGCTAAAATGGA

AACTCAGAGTATGTATGTAAGTGAGCTCAAACGAACCATTCGAACCCTTGAGGACA

AAGTTGCTGAAATCGAAGCACAGCAGTGCAATGGAATTTATATTTGGAAGATTGGC

AACTTTGGAATGCATTTGAAATGTCAAGAAGAGGAGAAACCTGTTGTGATTCATAGC

CCTGGATTCTACACTGGCAAACCCGGGTACAAACTGTGCATGCGCTTGCACCTTCAG

TTACCGACTGCTCAGCGCTGTGCAAACTATATATCCCTTTTTGTCCACACAATGCAA

GGAGAATATGACAGCCACCTCCCTTGGCCCTTCCAGGGTACAATACGCCTTACAATT
```

-continued

CTTGATCAGTCTGAAGCACCTGTAAGGCAAAACCACGAAGAGATAATGGATGCCAA

ACCAGAGCTGCTTGCTTTCCAGCGACCCACAATCCCACGGAACCCAAAAGGTTTTGG

CTATGTAACTTTTATGCATCTGGAAGCCCTAAGACAAAGAACTTTCATTAAGGATGA

CACATTATTAGTGCGCTGTGAGGTCTCCACCCGCTTTGACATGGGTAGCCTTCGGAG

GGAGGGTTTTCAGCCACGAAGTACTGATGCAGGGGTATAG

Human TTP CDS (SEQ ID NO: 37)

ATGGCCAACCGTTACACCATGGATCTGACTGCCATCTACGAGAGCCTCCTGTCGCTG

AGCCCTGACGTGCCCGTGCCATCCGACCATGGAGGGACTGAGTCCAGCCCAGGCTG

GGGCTCCTCGGGACCCTGGAGCCTGAGCCCCTCCGACTCCAGCCCGTCTGGGGTCAC

CTCCCGCCTGCCTGGCCGCTCCACCAGCCTAGTGGAGGGCCGCAGCTGTGGCTGGGT

GCCCCCACCCCCTGGCTTCGCACCGCTGGCTCCCCGCCTGGGCCCTGAGCTGTCACC

CTCACCCACTTCGCCCACTGCAACCTCCACCACCCCCTCGCGCTACAAGACTGAGCT

ATGTCGGACCTTCTCAGAGAGTGGGCGCTGCCGCTACGGGCCAAGTGCCAGTTTGC

CCATGGCCTGGGCGAGCTGCGCCAGGCCAATCGCCACCCCAAATACAAGACGGAAC

TCTGTCACAAGTTCTACCTCCAGGGCCGCTGCCCCTACGGCTCTCGCTGCCACTTCAT

CCACAACCCTAGCGAAGACCTGGCGGCCCCGGGCCACCCTCCTGTGCTTCGCCAGA

GCATCAGCTTCTCCGGCCTGCCCTCTGGCCGCCGGACCTCACCACCACCACCAGGCC

TGGCCGGCCCTTCCCTGTCCTCCAGCTCCTTCTCGCCCTCCAGCTCCCCACCACCACC

TGGGGACCTTCCACTGTCACCCTCTGCCTTCTCTGCTGCCCCTGGCACCCCCCTGGCT

CGAAGAGACCCCACCCCAGTCTGTTGCCCCTCCTGCCGAAGGGCCACTCCTATCAGC

GTCTGGGGGCCCTTGGGTGGCCTGGTTCGGACCCCCTCTGTACAGTCCCTGGGATCC

GACCCTGATGAATATGCCAGCAGCGGCAGCAGCCTGGGGGGCTCTGACTCTCCCGT

CTTCGAGGCGGGAGTTTTTGCACCACCCCAGCCCGTGGCAGCCCCCCGGCGACTCCC

CATCTTCAATCGCATCTCTGTTTCTGAGTGA

An antisense nucleic acid molecule can be complementary to all or part of a non-coding region of the coding strand of a nucleotide sequence encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP-MEKK1 protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense nucleic acids to target a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein described herein. Antisense nucleic acids targeting a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTPMEKK1protein can be designed using the software available at the Integrated DNA Technologies website.

An antisense nucleic acid can be, for example, about 5, 10, 15, 18, 20, 22, 24, 25, 26, 28, 30, 32, 35, 36, 38, 40, 42, 44, 45, 46, 48, or 50 nucleotides or more in length. An antisense oligonucleotide can be constructed using enzymatic ligation reactions and chemical synthesis using procedures known in the art. For example, an antisense nucleic acid can be chemically synthesized using variously modified nucleotides or naturally occurring nucleotides designed to increase the physical stability of the duplex formed between the antisense and sense nucleic acids, e.g., phosphorothioate derivatives and acridine substituted nucleotides or to increase the biological stability of the molecules.

Examples of modified nucleotides which can be used to generate an antisense nucleic acid include 1-methylguanine, 1-methylinosine, 2,2-dimethylguanine, 2-methyladenine, 2-methylguanine, 3-methylcytosine, 2-methylthio-N6-isopentenyladenine, uracil-5-oxyacetic acid (v), wybutoxosine, pseudouracil, queosine, 2-thiocytosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein can be prepared in vitro and administered to a subject, e.g., a human subject. Alternatively, they can be generated in situ such that they hybridize with or bind to cellular mRNA and/or genomic DNA encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. The antisense nucleic acid molecules can be delivered to a mammalian cell using a vector (e.g., an adenovirus vector, a lentivirus, or a retrovirus).

An antisense nucleic acid can be an α-anomeric nucleic acid molecule. An α-anomeric nucleic acid molecule forms specific double-stranded hybrids with complementary RNA in which, contrary to the usual, p-units, the strands run parallel to each other (Gaultier et al., *Nucleic Acids Res.* 15:6625-6641, 1987). The antisense nucleic acid can also comprise a chimeric RNA-DNA analog (Inoue et al., *FEBS Lett.* 215:327-330, 1987) or a 2'-O-methylribonucleotide (Inoue et al., *Nucleic Acids Res.* 15:6131-6148, 1987).

Another example of an inhibitory nucleic acid is a ribozyme that has specificity for a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA, e.g., specificity for any one of SEQ ID NOs: 1-37). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature* 334:585-591, 1988)) can be used to catalytically cleave mRNA transcripts to thereby inhibit translation of the protein encoded by the mRNA. An AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be used to select a catalytic RNA having a specific ribonuclease activity from a pool of RNA molecules. See, e.g., Bartel et al., *Science* 261:1411-1418, 1993.

Alternatively, a ribozyme having specificity for an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be designed based upon the nucleotide sequence of any of the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA sequences disclosed herein. For example, a derivative of a Tetrahymena L-19 IVS RNA can be constructed in which the nucleotide sequence of the active site is complementary to the nucleotide sequence to be cleaved in an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (see, e.g., U.S. Pat. Nos. 4,987,071 and 5,116,742).

An inhibitory nucleic acid can also be a nucleic acid molecule that forms triple helical structures. For example, expression of an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide can be inhibited by targeting nucleotide sequences complementary to the regulatory region of the gene encoding the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Maher, *Bioassays* 14(12):807-15, 1992; Helene, *Anticancer Drug Des.* 6(6):569-84, 1991; and Helene, *Ann. N.Y. Acad. Sci.* 660:27-36, 1992.

In various embodiments, inhibitory nucleic acids can be modified at the sugar moiety, the base moiety, or phosphate backbone to improve, e.g., the solubility, stability, or hybridization, of the molecule. For example, the deoxyribose phosphate backbone of the nucleic acids can be modified to generate peptide nucleic acids (see, e.g., Hyrup et al., *Bloorganic Medicinal Chem.* 4(1):5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to RNA and DNA under conditions of low ionic strength. PNA oligomers can be synthesized using standard solid phase peptide synthesis protocols (see, e.g., Perry-O'Keefe et al., *Proc. Natl. Acad. Sci. U.S.A.* 93:14670-675, 1996). PNAs can be used as antisense or antigene agents for sequence-specific modulation of gene expression by, e.g., inducing transcription or translation arrest or inhibiting replication.

Small Molecules

In some embodiments, the anti-TNFα agent is a small molecule. In some embodiments, the small molecule is a tumor necrosis factor-converting enzyme (TACE) inhibitor (e.g., Moss et al., *Nature Clinical Practice Rheumatology* 4: 300-309, 2008). In some embodiments, the anti-TNFα agent is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the TACE inhibitor is TMI-005 and BMS-561392. Additional examples of small molecule inhibitors are described in, e.g., He et al., *Science* 310(5750):1022-1025, 2005.

In some examples, the anti-TNFα agent is a small molecule that inhibits the activity of one of AP-1, ASK1, IKK, JNK, MAPK, MEKK 1/4, MEKK4/7, MEKK 3/6, NIK, TRADD, RIP, NF-κB, and TRADD in a cell (e.g., in a cell obtained from a subject, a mammalian cell).

In some examples, the anti-TNFα agent is a small molecule that inhibits the activity of one of CD14, MyD88 (see, e.g., Olson et al., *Scientific Reports* 5:14246, 2015), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, R05126766 (CH5126766), PLX7904, and MLN2480).

In some examples, the anti-TNFα agent TNFα inhibitor is a small molecule that inhibits the activity of one of MK2 (PF 3644022 and PHA 767491), JNK (e.g., AEG 3482, BI 78D3, CEP 1347, c-JUN peptide, IQ 1S, JIP-1 (153-163), SP600125, SU 3327, and TCS JNK6o), c-jun (e.g., AEG 3482, BI 78D3, CEP 1347, c-JUN peptide, IQ 1S, JIP-1 (153-163), SP600125, SU 3327, and TCS JNK6o), MEK3/6 (e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), MEK1/2 (e.g., Facciorusso et al., *Expert Review Gastroentrol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, IRAK (Chaudhary et al., *J. Med. Chem.* 58(1):96-110, 2015), LBP (see, e.g., U.S. Pat. No. 5,705,398), and TRAF6 (e.g., 3-[(2,5-Dimethylphenyl) amino]-1-phenyl-2-propen-1-one).

In some embodiments of any of the methods described herein, the inhibitory nucleic acid can be about 10 nucleotides to about 50 nucleotides (e.g., about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 28 nucleotides, about 10 nucleotides to about 26 nucleotides, about 10 nucleotides to about 25 nucleotides, about 10 nucleotides to about 24 nucleotides, about 10 nucleotides to about 22 nucleotides, about 10 nucleotides to about 20 nucleotides, about 10 nucleotides to about 18 nucleotides, about 10 nucleotides to about 16 nucleotides, about 10 nucleotides to about 14 nucleotides, about 10 nucleotides to about 12 nucleotides, about 12 nucleotides to about 50 nucleotides, about 12 nucleotides to about 45 nucleotides, about 12 nucleotides to about 40 nucleotides, about 12 nucleotides to about 35 nucleotides, about 12 nucleotides to about 30 nucleotides, about 12 nucleotides to about 28 nucleotides, about 12 nucleotides to about 26 nucleotides, about 12 nucleotides to about 25 nucleotides, about 12 nucleotides to about 24 nucleotides, about 12 nucleotides to about 22 nucleotides, about 12 nucleotides to about 20 nucleotides, about 12 nucleotides to about 18 nucleotides, about 12 nucleotides to about 16 nucleotides, about 12 nucleotides to about 14 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 28 nucleotides, about 15 nucleotides to about 26 nucleotides, about 15 nucleotides to about 25 nucleotides, about 15 nucleotides to about 24 nucleotides, about 15 nucleotides to about 22 nucleotides, about 15 nucleotides to about 20 nucleotides, about 15 nucleotides to about 18 nucleotides, about 15 nucleotides to about 16 nucleotides, about 16 nucleotides to about 50 nucleotides, about 16 nucleotides to about 45 nucleotides, about 16 nucleotides to about 40 nucleotides, about 16 nucleotides to about 35 nucleotides, about 16 nucleotides to about 30 nucleotides, about 16 nucleotides to about 28 nucleotides, about 16 nucleotides to about 26 nucleotides, about 16 nucleotides to about 25 nucleotides, about 16 nucleotides to about 24 nucleotides, about 16 nucleotides to about 22 nucleotides, about 16 nucleotides to about 20 nucleotides, about 16 nucleotides to about 18 nucleotides, about 18 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 28 nucleotides, about 20 nucleotides to about 26 nucleotides, about 20 nucleotides to about 25 nucleotides, about 20 nucleotides to about 24 nucleotides, about 20 nucleotides to about 22 nucleotides, about 24 nucleotides to about 50 nucleotides, about 24 nucleotides to about 45 nucleotides, about 24 nucleotides to about 40 nucleotides, about 24 nucleotides to about 35 nucleotides, about 24 nucleotides to about 30 nucleotides, about 24 nucleotides to about 28 nucleotides, about 24 nucleotides to about 26 nucleotides, about 24 nucleotides to about 25 nucleotides, about 26 nucleotides to about 50 nucleotides, about 26 nucleotides to about 45 nucleotides, about 26 nucleotides to about 40 nucleotides, about 26 nucleotides to about 35 nucleotides, about 26 nucleotides to about 30 nucleotides, about 26 nucleotides to about 28 nucleotides, about 28 nucleotides to about 50 nucleotides, about 28 nucleotides to about 45 nucleotides, about 28 nucleotides to about 40 nucleotides, about 28 nucleotides to about 35 nucleotides, about 28 nucleotides to about 30 nucleotides, about 30 nucleotides to about 50 nucleotides, about 30 nucleotides to about 45 nucleotides, about 30 nucleotides to about 40 nucleotides, about 30 nucleotides to about 38 nucleotides, about 30 nucleotides to about 36 nucleotides, about 30 nucleotides to about 34 nucleotides, about 30 nucleotides to about 32 nucleotides, about 32 nucleotides to about 50 nucleotides, about 32 nucleotides to about 45 nucleotides, about 32 nucleotides to about 40 nucleotides, about 32 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, about 42 nucleotides to about 50 nucleotides, about 42 nucleotides to about 45 nucleotides, or about 45 nucleotides to about 50 nucleotides) in length. One skilled in the art will appreciate that inhibitory nucleic acids may comprises at least one modified nucleic acid at either the 5' or 3' end of DNA or RNA.

In some embodiments, the inhibitory nucleic acid can be formulated in a liposome, a micelle (e.g., a mixed micelle), a nanoemulsion, or a microemulsion, a solid nanoparticle, or a nanoparticle (e.g., a nanoparticle including one or more synthetic polymers). Additional exemplary structural features of inhibitory nucleic acids and formulations of inhibitory nucleic acids are described in US 2016/0090598.

In some embodiments, the inhibitory nucleic acid (e.g., any of the inhibitory nucleic acid described herein) can include a sterile saline solution (e.g., phosphate-buffered saline (PBS)). In some embodiments, the inhibitory nucleic acid (e.g., any of the inhibitory nucleic acid described herein) can include a tissue-specific delivery molecule (e.g., a tissue-specific antibody).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

PREPARATIVE EXAMPLES

The following abbreviations have the indicated meanings:
ACN=acetonitrile
BTC=trichloromethyl chloroformate
DCM=dichloromethane
DEA=diethylamine
DMF=N,N-dimethylformamide
DMSO=dimethyl sulfoxide
EtOH=ethanol
Hex=hexane
HPLC=high performance liquid chromatography
LC-MS=liquid chromatography-mass spectrometry
Me=methyl
MeOH=methanol
NBS=N-brornosuccinimide
NCS=N-chlorosuccinimide
NMR=nuclear magnetic resonance
Pd(dppf)Cl$_2$ dichloro[1,1'-bis(diphenylphosphino)ferrocene]palladium
Ph=phenyl
PPh$_3$Cl$_2$=dichlorotriphenylphosphorane
Py=pyridine
RT=room temperature
TBAF=tetrabutylammonium fluoride
TBS=tert-butyldinethylsilyl
TBSCl=tert-butyldimethylsilyl chloride
TEA=triethylamine
TFA=trifluoroacetic acid
THF=tetrahydrofuran
TLC=thin layer chromatography
UV=ultraviolet General The progress of reactions was often monitored by TLC or LC-MS. The identity of the products was often confirmed by LC-MS. The LC-MS was recorded using one of the following methods.

Method A: Shim-pack XR-ODS, C18, 3×50 mm, 2.5 um column, 1.0 uL injection, 1.5 mL/min flow rate, 90-900 amu scan range, 190-400 nm IV range, 5-100% (1.1 min), 100% (0.6 min) gradient with ACN (0.05% TFA) and water (0.05% TFA), 2 minute total run time.

Method B: Kinetex EVO, C18, 3×50 mm, 2.2 um column, 1.0 uL injection, 1.5 mL/min flow rate. 90-900 amu scan range, 190-400 nm UV range, 10-95% (1.1 min), 95% (0.6 min) gradient with ACN and water (0.5% NH$_4$HCO$_3$), 2 minute total run time.

Method C: Shim-pack XR-ODS, C18, 3×50 mm, 2.5 um column, 1.0 uL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D: Kinetex EVO, C18, 3×50 mm, 2.2 um column, 1.0 uL injection, 1.5 mi/min flow rate, 90-900 amu scan range, 190-400 nm JV range, 10-95% (2.1 min), 95% (0.6 min) gradient with ACN and water (0.5% NH$_4$HCO$_3$), 3 minute total run time.

The final targets were purified by Prep-HPLC. The Prep-HPLC was carried out using the following method.

Method E: Prep-HPLC: Column, XBridge Shield RP18 OBD (19×250 mm, 10 um); mobile phase, Water (10 mmol/L NH$_4$HCO$_3$) and ACN, UV detection 254/210 nm.

The final targets were purified by Prep-HPLC. The Prep-HPLC was carried out using the following method.

Method F: Prep-HPLC: Higgins Analytical Proto 200, C18 Column, 250×20 mm, 10 um; mobile phase, Water (0.1% TFA) and ACN (0.1% TFA), UV detection 254/210 nm.

NMR was recorded on BRUKER NMR 300.03 MHz, DUL-C-H, ULTRASHIELD™300,
AVANCE II 300 B-ACS™120 or BRUKER NMR 400.13 MHz, BBFO,
ULTRASHIELD™400, AVANCE III 400, B-ACS™120.
NMR was recorded on 250 MHz, BRUKER AC 250 NMR Racemic compounds of this invention can be resolved to give individual enantiomers using a variety of known methods. For example, chiral stationary phases can used and the elution conditions can include normal phase or super-critical fluid with or without acidic or basic additives. Enantiomerically pure acids or bases can be used to form diatereomeric salts with the racemic compounds whereby pure enantiomers can be obtained by fractional crystallization. The racemates can also be derivatized with enantiomerically pure auxiliary reagents to form diastereomeric mixtures that can be separated. The auxiliary is then removed to give pure enantiomers.

The compounds herein may be prepared, for example, using the synthetic route as shown in Scheme 1.

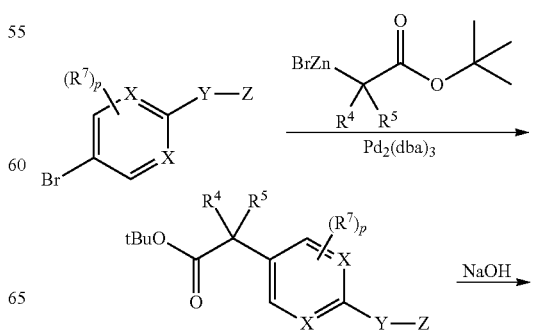

Scheme 1

-continued
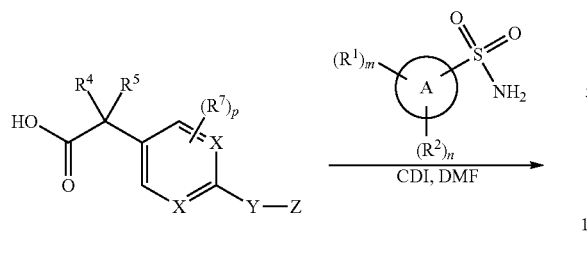
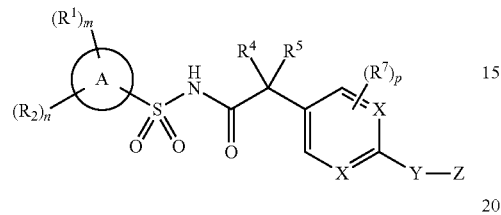
Scheme of final targets: Schemes A-E illustrate several conditions used for coupling of acid 1 and sulfonamide 2 to afford acyl sulfonamide 3.
Scheme A
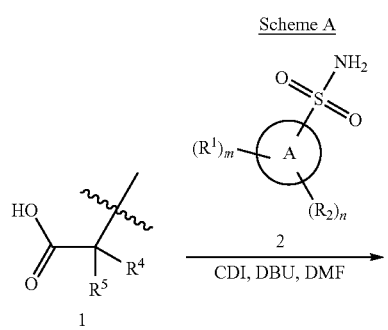
Scheme B
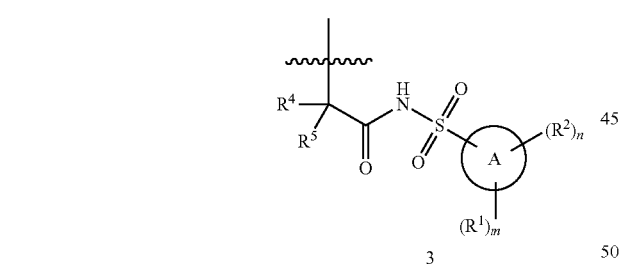
-continued
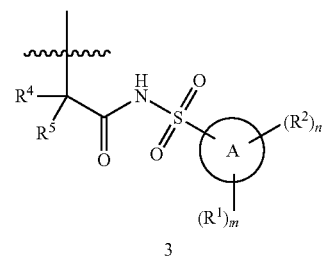
Scheme C:
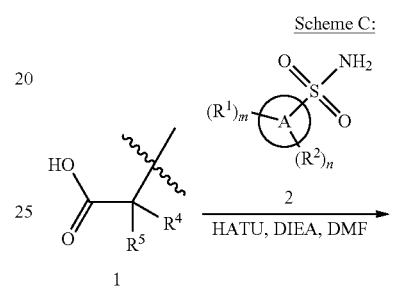
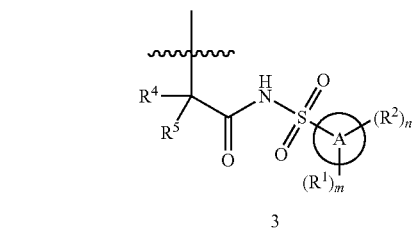
Scheme D
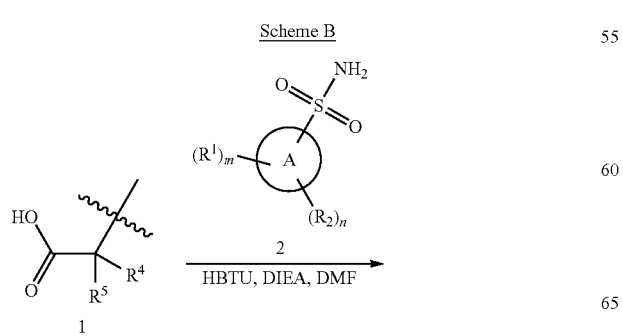

Scheme E

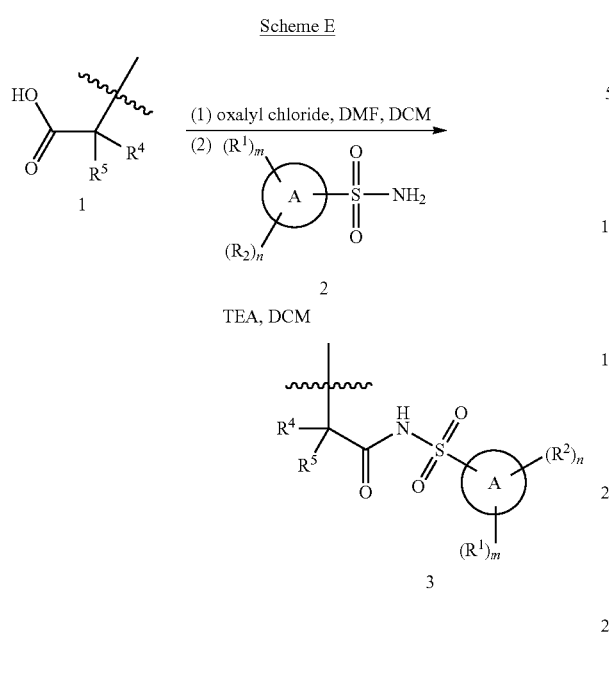

Scheme E1

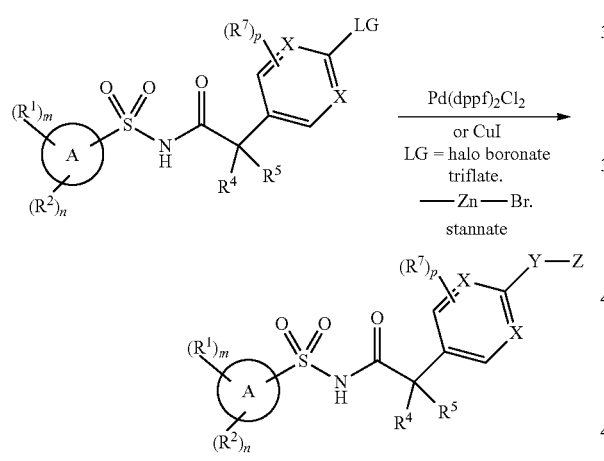

Scheme of Sulfonamides Intermediates:

Schemes F-Z illustrate the preparation of sulfonamide intermediates. It is understood that the numbering used in the schemes below refers only to the intermediates and that the intermediates are distinct from compounds of formula A, I, and/or II. that may have the same numerical designation. Thus, by way of example, intermediate number "116" in Scheme AB below is distinct from compound 116 disclosed herein.

Scheme F

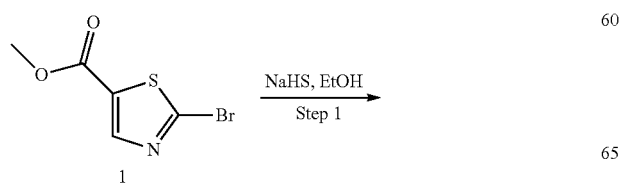

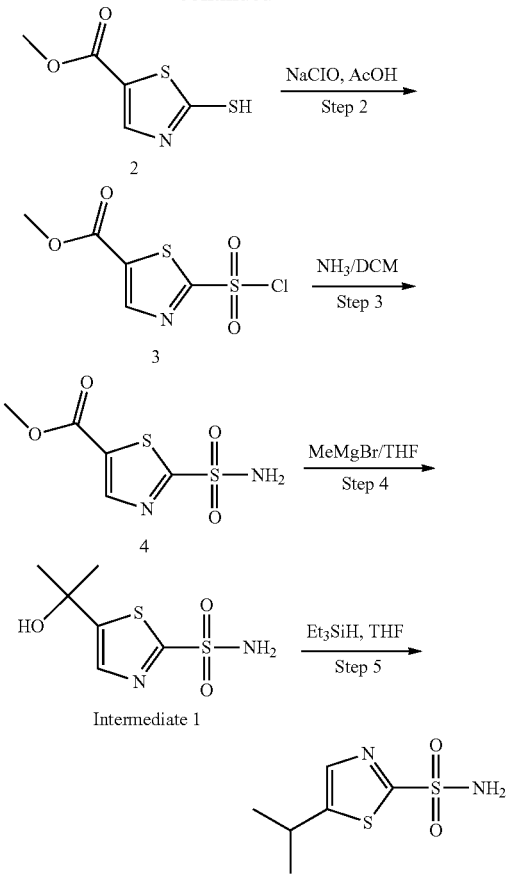

Intermediate 1

5-(2-Hydroxypropan-2-yl)thiazole-2-sulfonamide

Step 1: Methyl 2-mercaptothiazole-5-carboxylate

Into a 250-mL round-bottom flask, was placed methyl 2-bromothiazole-5-carboxylate (10 g, 45 mmol), EtOH (100 mL), and sodium hydrogensulfide (5 g, 89 mmol). The resulting solution was stirred for 2 h at 80° C. and then was cooled to 0° C. with a water/ice bath. The pH value of the solution was adjusted to 3 with hydrogen chloride (1 N). The solids were collected by filtration. This resulted in 6 g (76%) of the title compound as a light yellow solid. MS-ESI: 176.0 (M+1).

Step 2: Methyl 2-(chlorosulfonyl)thiazole-5-carboxylate

Into a 250-mL round-bottom flask, was placed methyl 2-mercaptothiazole-5-carboxylate (6 g, 34 mmol), and acetic acid (60 mL). This was followed by the addition of sodium hypochlorite (60 mL, 8%-10% wt) in portions at 0° C. The resulting solution was stirred for 1 h at RT and then was diluted with 100 mL of water. The solution was extracted with 3×50 mL of DCM and the organic layers combined and dried over anhydrous Na₂SO₄, then concentrated under vacuum. This resulted in 5 g (crude, 60%) of the title compound as yellow oil. The crude product was used in the next step.

Step 3: Methyl 2-sulfamoylthiazole-5-carboxylate

Into a 250-mL round-bottom flask, was placed methyl 2-(chlorosulfonyl)thiazole-5-carboxylate (5 g, 21 mmol), and DCM (50 mL). This was followed by the addition of a saturated solution of ammonia in DCM (10 mL) in portions at RT. The resulting solution was stirred for 2 h at RT and then was concentrated under vacuum. The residue was applied onto a silica gel column and eluted with ethyl acetate/petroleum ether (1:5 to 1:3). This resulted in 3 g (65%) of the title compound as a white solid. MS-ESI: 223.0 (M+1).

Step 4: 5-(2-Hydroxypropan-2-yl)thiazole-2-sulfonamide

Into a 250-mL round-bottom flask purged with and maintained under nitrogen, was placed a solution of methyl 2-sulfamoylthiazole-5-carboxylate (3 g, 13.5 mmol) in THF (25 mL). This was followed by the addition of MeMgBr/THF (3 M, 18 mL) dropwise with stirring at 0° C. The resulting solution was stirred for 14 h at RT and then was quenched by the addition of 20 mL of NH₄Cl (sat.). The resulting solution was extracted with 3×30 mL of DCM and the organic layers combined and dried over anhydrous Na₂SO₄, then concentrated under vacuum. The residue was applied onto a silica gel column and eluted with ethyl acetate/petroleum ether (1:5 to 1:3). This resulted in 2.3 g (78%) of the title compound as a white solid. MS-ESI: 223.0 (M+1), 221.0 (M−1).

Intermediate 2

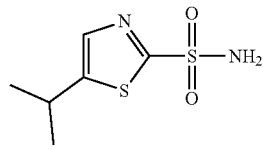

5-Isopropylthiazole-2-sulfonamide

Step 5: 5-Isopropylthiazole-2-sulfonamide

Into a 40-mL sealed tube, was placed 5-(2-hydroxypropan-2-yl)thiazole-2-sulfonamide (500 mg, 2.25 mmol) in TFA (5 mL), and Et₃SiH (5 mL). The resulting solution was stirred for 4 h at 70° C. and then was concentrated under vacuum. The residue was applied onto a silica gel column and eluted with ethyl acetate/petroleum ether (1:4 to 1:2). This resulted in 380 mg (82%) of the title compound as a yellow solid. MS-ESI: 205.0 (M−1).

Scheme G

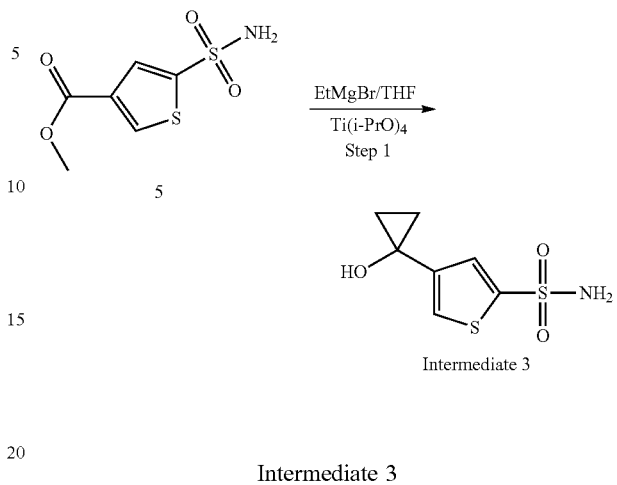

Intermediate 3

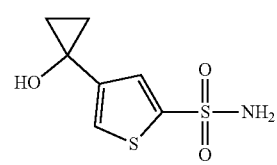 [SMILES: NS(=O)(=O)c1cc(C2(O)CC2)cs1]

4-(1-Hydroxycyclopropyl)thiophene-2-sulfonamide

Step 1: 4-(1-Hydroxycyclopropyl)thiophene-2-sulfonamide

Into a 500-mL 3-necked round-bottom flask purged with and maintained under nitrogen, was placed methyl 5-sulfamoylthiophene-3-carboxylate (5.525 g, 24.97 mmol), THF (80 mL), Ti(i-PrO)₄ (1.5 mL). This was followed by the addition of EtMgBr/THF (3 M, 21 mL) dropwise with stirring at 0° C. The resulting solution was stirred for 2 h at RT and then was quenched by the addition of 30 mL of NH₄Cl (sat.). The resulting solution was extracted with 3×40 mL of ethyl acetate and the organic layers combined and concentrated under vacuum. The residue was applied onto a silica gel column and eluted with ethyl acetate/petroleum ether (1:3 to 1:1). This resulted in 662 mg (12%) of the title compound as a light yellow solid. MS-ESI: 218.0 (M−1).

Scheme H

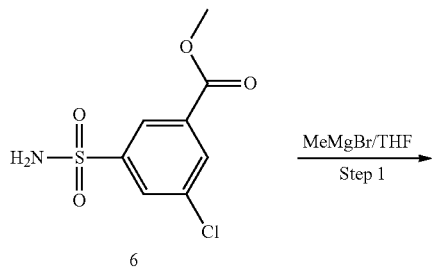

-continued

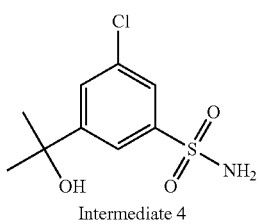

Intermediate 4

Intermediate 4

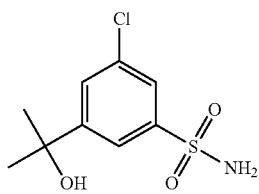

3-Chloro-5-(2-hydroxypropan-2-yl)benzenesulfonamide

Step 1: 3-Chloro-5-(2-hydroxypropan-2-yl)benzenesulfonamide

Into a 100-mL 3-necked round-bottom flask purged with and maintained under nitrogen, was placed a solution of methyl 3-chloro-5-sulfamoylbenzoate (579 mg, 2.32 mmol) in THF (30 mL). This was followed by the addition of MeMgBr/THF (3 M, 3.5 mL) dropwise with stirring at 0° C. The resulting solution was stirred for 12 h at RT and then was quenched by the addition of 20 mL of NH$_4$Cl (sat.). The solution was extracted with 3×20 mL of ethyl acetate and the organic layers combined and concentrated under vacuum. The residue was applied onto a silica gel column and eluted with ethyl acetate/petroleum ether (1:3 to 1:1). This resulted in 415 mg (72%) of the title compound as a light yellow solid. MS-ESI: 248.0, 250.0 (M−1).

Scheme I

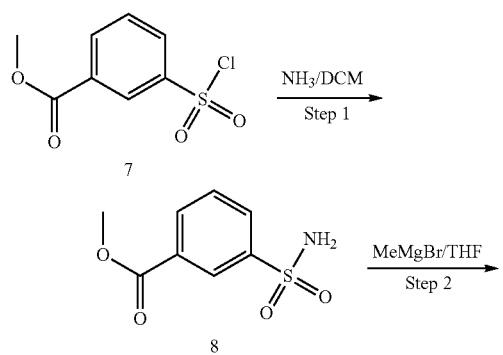

-continued

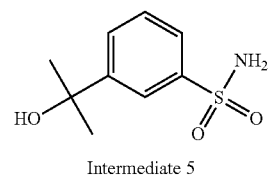

Intermediate 5

Intermediate 5

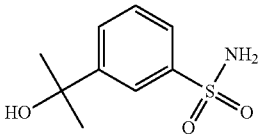

3-(2-Hydroxypropan-2-yl)benzenesulfonamide

Step 1: Methyl 3-sulfamoylbenzoate

Into a 100-mL round-bottom flask, was placed a solution of methyl 3-(chlorosulfonyl)benzoate (2 g, 8.5 mmol) in DCM (35 mL). To the above was added a saturated solution of ammonia in DCM (15 mL). The resulting solution was stirred for 2 h at RT and then was concentrated under vacuum. The residue was applied onto a silica gel column and eluted with ethyl acetate/petroleum ether (1:3 to 1:1). This resulted in 1.753 g (93%) of the title compound as a white solid. MS-ESI: 214.0 (M−1).

Step 2: 3-(2-Hydroxypropan-2-yl)benzenesulfonamide

Into a 250-mL 3-necked round-bottom flask purged with and maintained under nitrogen, was placed a solution of methyl 3-sulfamoylbenzoate (1.753 g, 8.14 mmol) in THF (70 mL). This was followed by the addition of MeMgBr/THF (3 M, 12.2 mL) dropwise with stirring at 0° C. The resulting solution was stirred for 12 h at RT and then was quenched by the addition of 30 mL of NH$_4$Cl (sat.). The resulting solution was extracted with 5×30 mL of ethyl acetate and the organic layers combined and concentrated under vacuum. The residue was applied onto a silica gel column and eluted with ethyl acetate/petroleum ether (1:3 to 1:1). This resulted in 1.642 g (94%) of the title compound as a white solid. MS-ESI: 214.0 (M−1).

TABLE 2

The Intermediates in the following Table were prepared using the similar procedure for converting compound 7 to compound 8 shown in Scheme 1.

| Intermediate # | Structure | IUPAC Name | Mass Spec [M + H]+ |
|---|---|---|---|
| Intermediate 6 | 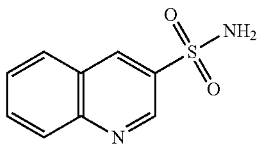 [SMILES: NS(=O)(=O)c1cnc2ccccc2c1] | quinoline-3-sulfonamide | 209.0 (M + 1) |
| Intermediate 7 | 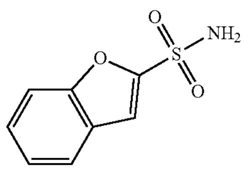 [SMILES: NS(=O)(=O)c1cc2ccccc2o1] | benzofuran-2-sulfonamide | 196.0 (M − 1) |

Intermediate 8

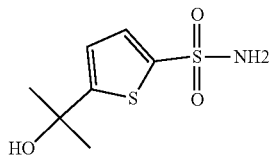

5-(2-Hydroxypropan-2-yl)thiophene-2-sulfonamide

Intermediate 8 was prepared using the similar procedures for converting compound 7 to Intermediate 5 shown in Scheme I. MS-ESI: 220.0 (M−1).

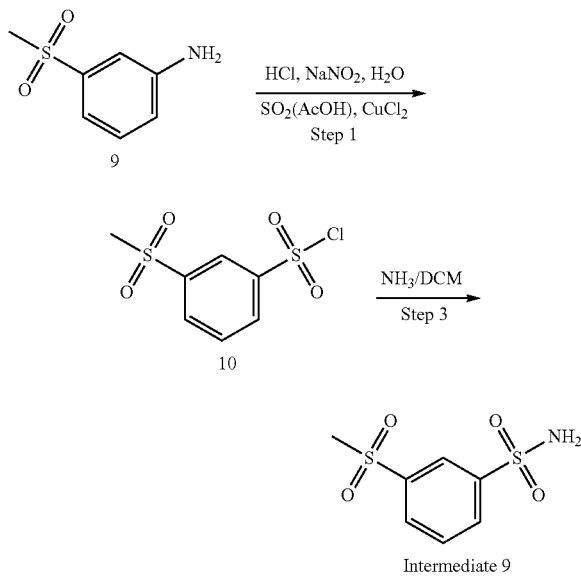

Scheme J

Intermediate 9

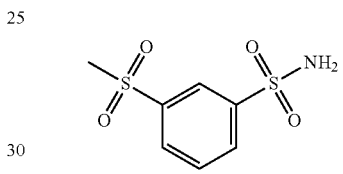

3-(Methylsulfonyl)benzenesulfonamide

Step 1: 3-(Methylsulfonyl)benzene-1-sulfonyl chloride

Into a 100-mL round-bottom flask, was placed a solution of 3-(methylsulfonyl)benzenamine (200 mg, 1.17 mmol) in HCl (6 M, 5 mL). This was followed by the addition of a solution of NaNO$_2$ (97 mg, 1.41 mmol) in water (0.5 mL) dropwise with stirring at 0° C. The resulting solution was stirred for 20 min at 0° C. The above mixture was added to a saturated solution of SO$_2$ in AcOH (5 mL) dropwise with stirring at 0° C. Then to the above was added CuCl$_2$ (157 mg, 1.17 mmol). The resulting solution was stirred for 1 h at RT and then was quenched by the addition of 10 mL of water. The resulting solution was extracted with 3×10 mL of DCM and the organic layers combined and dried over anhydrous Na$_2$SO$_4$, then concentrated under vacuum. This resulted in 250 mg (84%) of the title compound as a light yellow solid. The crude product was used in the next step.

Step 2: 3-(Methylsulfonyl)benzenesulfonamide

Into a 50-mL round-bottom flask, was placed 3-(methylsulfonyl)benzene-1-sulfonyl chloride (250 mg, 0.98 mmol) and DCM (3 mL). To the above was added a saturated solution of ammonia in DCM (5 mL). The resulting solution was stirred for 1 h at RT and then was diluted with 5 mL of water. The resulting solution was extracted with 3×10 mL of ethyl acetate; and the organic layers combined and dried over anhydrous Na$_2$SO$_4$, then concentrated under vacuum. This resulted in 220 mg (crude, 95%) of the title compound as a white solid. MS-ESI: 234.0 (M−1).

TABLE 3

The Intermediates in the following Table were prepared using the similar procedures for converting compound 9 to Intermediate 9 shown in Scheme J.

| Intermediate # | Structure | IUPAC Name | Mass Spec [M − H]⁻ |
|---|---|---|---|
| Intermediate 10 | 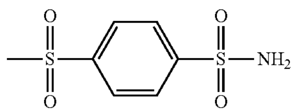 | (methylsulfonyl)benzenesulfonamide | 234.0 |
| Intermediate 11 | 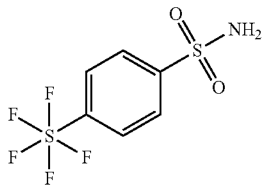 [SMILES: NS(=O)(=O)c1ccc(S(F)(F)(F)(F)F)cc1] | 4-pentafluorobenzenesulfonamide | 282.0 |
| Intermediate 12 | 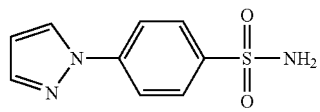 [SMILES: NS(=O)(=O)c1ccc(-n2cccn2)cc1] | 4-(1H-pyrazol-1-yl)benzenesulfonamide | 222.0 |

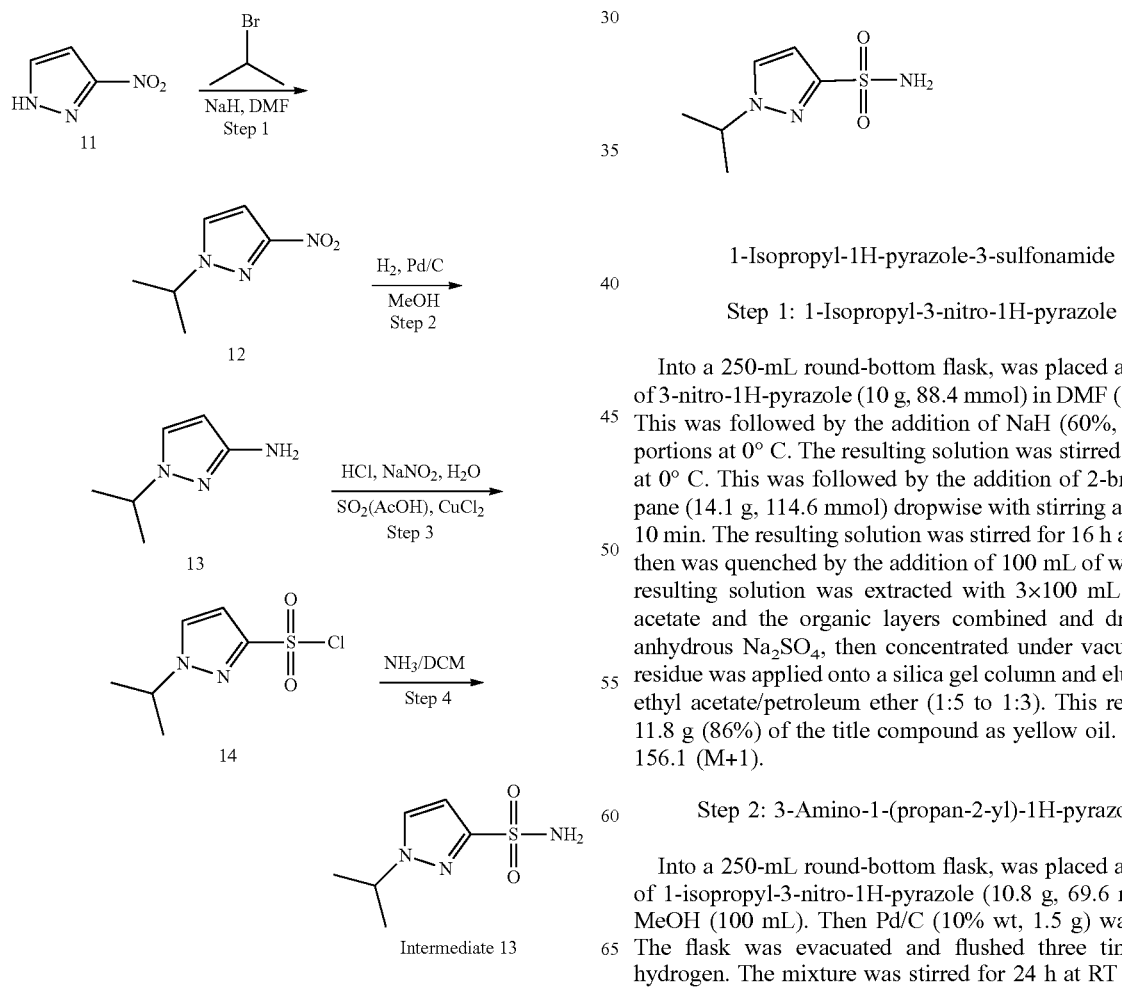

Intermediate 13

1-Isopropyl-1H-pyrazole-3-sulfonamide

Step 1: 1-Isopropyl-3-nitro-1H-pyrazole

Into a 250-mL round-bottom flask, was placed a solution of 3-nitro-1H-pyrazole (10 g, 88.4 mmol) in DMF (100 mL). This was followed by the addition of NaH (60%, 3.9 g) in portions at 0° C. The resulting solution was stirred for 0.5 h at 0° C. This was followed by the addition of 2-bromopropane (14.1 g, 114.6 mmol) dropwise with stirring at 0° C. in 10 min. The resulting solution was stirred for 16 h at RT and then was quenched by the addition of 100 mL of water. The resulting solution was extracted with 3×100 mL of ethyl acetate and the organic layers combined and dried over anhydrous Na$_2$SO$_4$, then concentrated under vacuum. The residue was applied onto a silica gel column and eluted with ethyl acetate/petroleum ether (1:5 to 1:3). This resulted in 11.8 g (86%) of the title compound as yellow oil. MS-ESI: 156.1 (M+1).

Step 2: 3-Amino-1-(propan-2-yl)-1H-pyrazole

Into a 250-mL round-bottom flask, was placed a solution of 1-isopropyl-3-nitro-1H-pyrazole (10.8 g, 69.6 mmol) in MeOH (100 mL). Then Pd/C (10% wt, 1.5 g) was added. The flask was evacuated and flushed three times with hydrogen. The mixture was stirred for 24 h at RT under an atmosphere of hydrogen. The solids were filtered out. The resulting mixture was concentrated under vacuum. This resulted in 7.27 g (83%) of the title compound as yellow oil. MS-ESI: 126.1 (M+1).

Steps 3-4 used similar procedures for converting compound 9 to Intermediate 9 shown in Scheme J to afford Intermediate 13. MS-ESI: 188.0 (M−1).

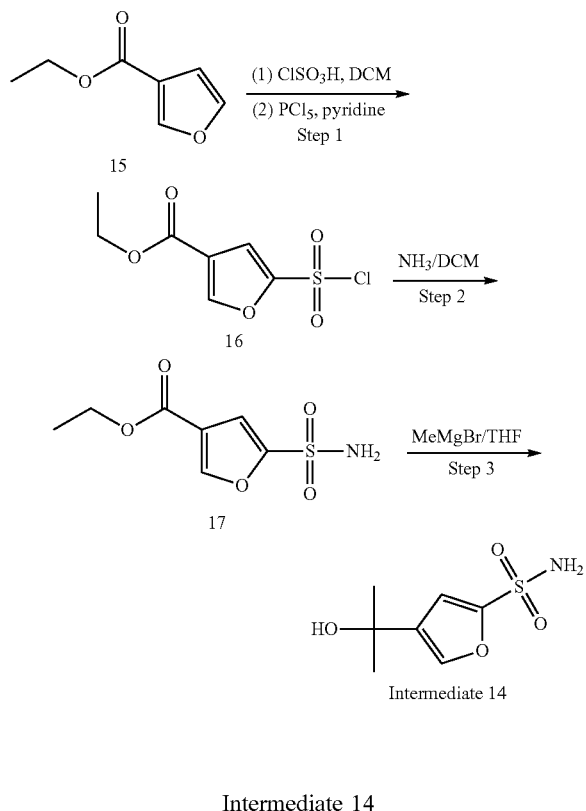

Intermediate 14

4-(2-Hydroxypropan-2-yl)furan-2-sulfonamide

Step 1: Ethyl 5-(chlorosulfonyl)furan-3-carboxylate

Into a 500-mL 3-necked round-bottom flask, was placed ethyl furan-3-carboxylate (7 g, 50 mmol), DCM (200 mL). This was followed by the addition of chlorosulfonic acid (5.8 g, 49.8 mmol) dropwise with stirring at −10° C. Then the reaction was stirred for 48 h at RT and the system was cooled to −10° C. Then to the above was added pyridine (3.96 g, 50.1 mmol), phosphorus pentachloride (11.46 g, 55.0 mmol). The resulting solution was stirred for 12 h at RT and then was quenched by the addition of 200 mL of water. The resulting solution was extracted with 3×200 mL of DCM and the organic layers combined and dried over anhydrous $Na_2SO_4$, then concentrated under vacuum. This resulted in 7.13 g (60%) of the title compound as light brown oil. The crude product was used in the next step.

Step 2: Ethyl 5-sulfamoylfuran-3-carboxylate

Into a 250-mL round-bottom flask, was placed a solution of ethyl 5-(chlorosulfonyl)furan-3-carboxylate (6.111 g, 25.61 mmol) in DCM (60 mL). To the above was added a saturated solution of ammonia in DCM (40 mL). The resulting solution was stirred for 3 h at RT and then was concentrated under vacuum. The residue was applied onto a silica gel column and eluted with ethyl acetate/petroleum ether (1:4 to 1:2). This resulted in 3.698 g (66%) of the title compound as a light yellow solid. MS-ESI: 218.0 (M−1).

Step 3: 4-(2-Hydroxypropan-2-yl)furan-2-sulfonamide

Into a 250-mL 3-necked round-bottom flask purged with and maintained under nitrogen, was placed a solution of ethyl 5-sulfamoylfuran-3-carboxylate (3.698 g, 16.87 mmol) in THF (100 mL). This was followed by the addition of MeMgBr/THF (3 M, 25 mL) dropwise with stirring at −10° C. The resulting solution was stirred for 10 h at RT and then was quenched by the addition of 50 mL of $NH_4Cl$ (sat.). The resulting solution was extracted with 3×50 mL of ethyl acetate and the organic layers combined and dried over anhydrous $Na_2SO_4$, then concentrated under vacuum. The residue was applied onto a silica gel column and eluted with ethyl acetate/petroleum ether (1:3 to 1:1). This resulted in 2.6 g (75%) of the title compound as a light yellow solid. MS-ESI: 204.0 (M−1).

TABLE 4

The Intermediates in the following Table were prepared using the similar procedures for converting compound 15 to Intermediate 14 shown in Scheme L.

| Intermediate # | Structure | IUPAC Name | Mass Sec [M − H]⁻ |
| --- | --- | --- | --- |
| Intermediate 15 | 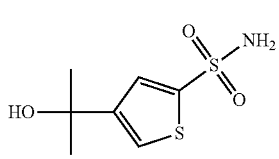 | 4-(2-hydroxypropan-2-yl) thiophene-2-sulfonamide | 220.0 |

TABLE 4-continued

The Intermediates in the following Table were prepared using the similar procedures for converting compound 15 to Intermediate 14 shown in Scheme L.

| Intermediate # | Structure | IUPAC Name | Mass Sec [M − H]⁻ |
|---|---|---|---|
| Intermediate 16 | 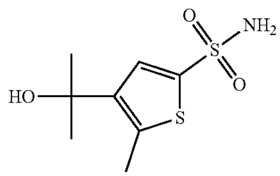 | 4-(2-hydroxypropan-2-yl)-5-methylthiophene-2-sulfonamide | 234.0 |
| Intermediate 17 | 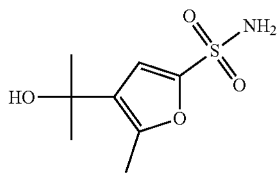 | 4-(2-hydroxypropan-2-yl)-5-methylfuran-2-sulfonamide | 218.1 |
| Intermediate 18 | 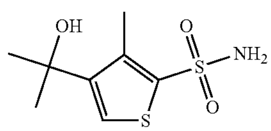 | 4-(2-hydroxypropan-2-yl)-3-methylthiophene-2-sulfonamide | 234.1 |

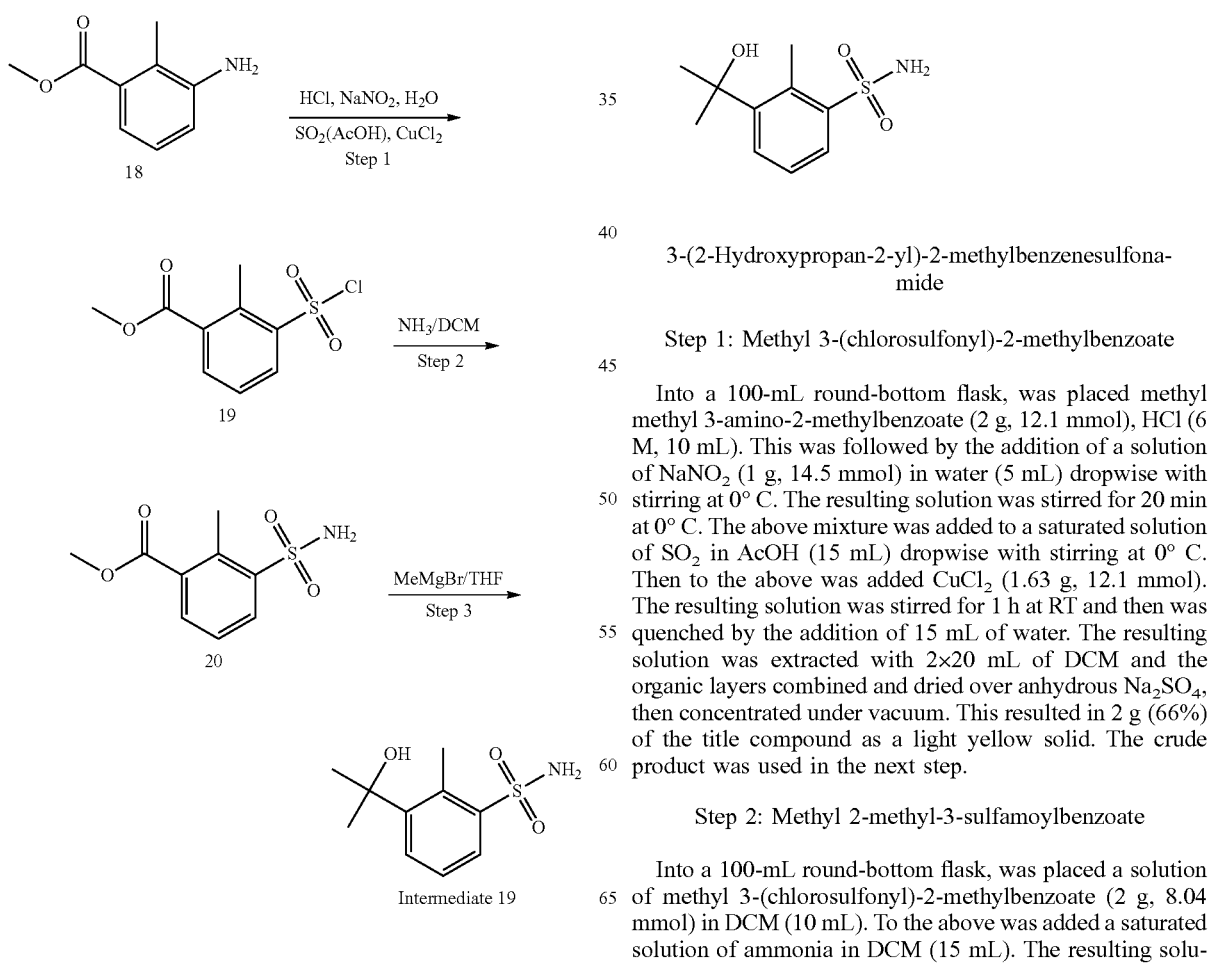

Intermediate 19

3-(2-Hydroxypropan-2-yl)-2-methylbenzenesulfonamide

Step 1: Methyl 3-(chlorosulfonyl)-2-methylbenzoate

Into a 100-mL round-bottom flask, was placed methyl methyl 3-amino-2-methylbenzoate (2 g, 12.1 mmol), HCl (6 M, 10 mL). This was followed by the addition of a solution of NaNO₂ (1 g, 14.5 mmol) in water (5 mL) dropwise with stirring at 0° C. The resulting solution was stirred for 20 min at 0° C. The above mixture was added to a saturated solution of SO₂ in AcOH (15 mL) dropwise with stirring at 0° C. Then to the above was added CuCl₂ (1.63 g, 12.1 mmol). The resulting solution was stirred for 1 h at RT and then was quenched by the addition of 15 mL of water. The resulting solution was extracted with 2×20 mL of DCM and the organic layers combined and dried over anhydrous Na₂SO₄, then concentrated under vacuum. This resulted in 2 g (66%) of the title compound as a light yellow solid. The crude product was used in the next step.

Step 2: Methyl 2-methyl-3-sulfamoylbenzoate

Into a 100-mL round-bottom flask, was placed a solution of methyl 3-(chlorosulfonyl)-2-methylbenzoate (2 g, 8.04 mmol) in DCM (10 mL). To the above was added a saturated solution of ammonia in DCM (15 mL). The resulting solution was stirred for 1 h at RT and then was concentrated under vacuum. The residue was applied onto a silica gel column and eluted with ethyl acetate/petroleum ether (1:3 to 1:1). This resulted in 1.2 g (65%) of the title compound as a white solid. MS-ESI: 228.0 (M−1).

Step 3: 3-(2-Hydroxypropan-2-yl)-2-methylbenzenesulfonamide

Into a 100-mL 3-necked round-bottom flask purged with and maintained under nitrogen, was placed a solution of methyl 2-methyl-3-sulfamoylbenzoate (1.2 g, 5.23 mmol) in THF (20 mL). This was followed by the addition MeMgBr/THF (3 M, 8.7 mL) dropwise with stirring at 0° C. The resulting solution was stirred for 12 h at RT. The reaction was then quenched by the addition of 15 mL of NH$_4$Cl (sat.). The resulting solution was extracted with 3×20 mL of ethyl acetate and the organic layers combined and dried over anhydrous Na$_2$SO$_4$, then concentrated under vacuum. This resulted in 1.1 g (crude, 92%) of the title compound as an off-white solid. MS-ESI: 228.1 (M−1).

TABLE 5

The Intermediates in the following Table were prepared using the similar procedures for converting compound 18 to Intermediate 19 shown in Scheme M.

| Intermediate # | Structure | IUPAC Name | Mass Spec [M − H]⁻ |
|---|---|---|---|
| Intermediate 20 | 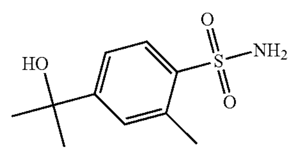 | 4-(2-hydroxypropan-2-yl)-2-methylbenzenesulfonamide | 228.1 |
| Intermediate 21 | 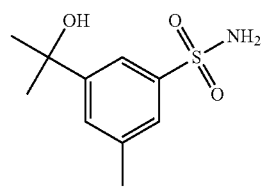 | 3-(2-hydroxypropan-2-yl)-5-methylbenzenesulfonamide | 228.1 |
| Intermediate 22 | 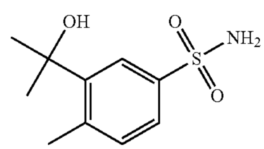 | 3-(2-hydroxypropan-2-yl)-4-methylbenzenesulfonamide | 228.1 |
| Intermediate 23 | 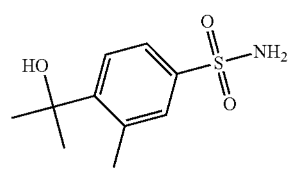 | 4-(2-hydroxypropan-2-yl)-3-methylbenzenesulfonamide | 228.1 |
| Intermediate 24 | 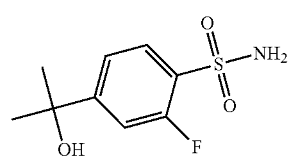 | 2-fluoro-4-(2-hydroxypropan-2-yl)benzenesulfonamide | 232.1 |
| Intermediate 25 | 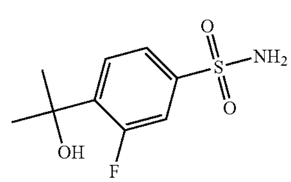 | 3-fluoro-4-(2-hydroxypropan-2-yl)benzenesulfonamide | 232.1 |

TABLE 5-continued

The Intermediates in the following Table were prepared using the similar procedures for converting compound 18 to Intermediate 19 shown in Scheme M.

| Intermediate # | Structure | IUPAC Name | Mass Spec [M − H]⁻ |
|---|---|---|---|
| Intermediate 26 | 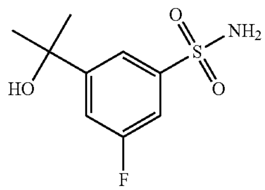 | 3-fluoro-5-(2-hydroxypropan-2-yl)benzenesulfonamide | 232.1 |
| Intermediate 27 | 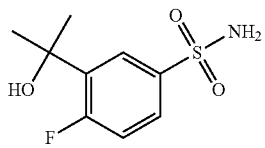 | 4-fluoro-3-(2-hydroxypropan-2-yl)benzenesulfonamide | 232.1 |
| Intermediate 28 | 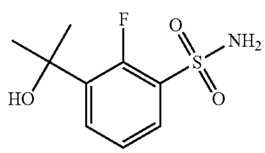 | 2-fluoro-3-(2-hydroxypropan-2-yl)benzenesulfonamide | 232.1 |
| Intermediate 29 | 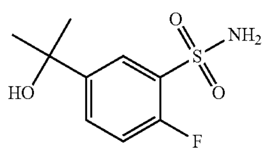 | 2-fluoro-5-(2-hydroxypropan-2-yl)benzenesulfonamide | 232.1 |
| Intermediate 30 | 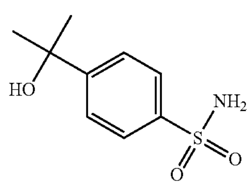 | 4-(2-hydroxypropan-2-yl)benzenesulfonamide | 214.1 |
| Intermediate 31 | 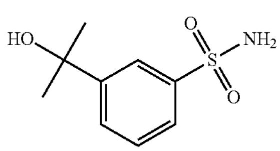 | 3-(2-hydroxypropan-2-yl)benzenesulfonamide | 214.1 |
| Intermediate 32 | 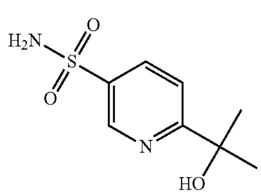 | 6-(2-hydroxypropan-2-yl)pyridine-3-sulfonamide | 217.1 (M + 1) |
| Intermediate 33 | 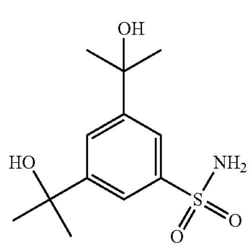 [SMILES: CC(C)(O)c1cc(C(C)(C)O)cc(S(N)(=O)=O)c1] | 3,5-bis(2-hydroxypropan-2-yl)benzenesulfonamide | 272.1 |

Scheme N

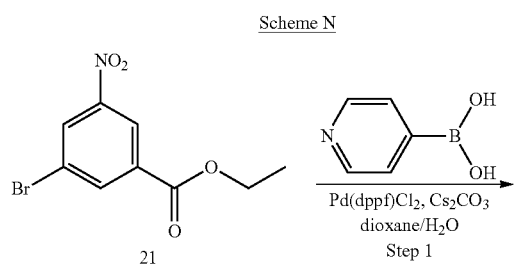

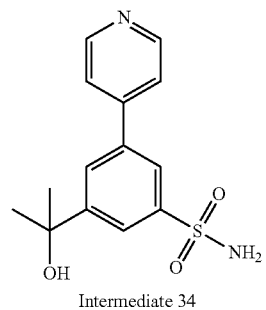 [SMILES: CC(C)(O)c1cc(-c2ccncc2)cc(S(N)(=O)=O)c1]

Intermediate 34

3-(2-Hydroxypropan-2-yl)-5-(pyridin-4-yl)benzenesulfonamide

Step 1: Ethyl 3-nitro-5-(pyridin-4-yl)benzoate

Into a 500-mL round-bottom flask purged with and maintained under nitrogen, was placed ethyl 3-bromo-5-nitrobenzoate (5.5 g, 20.1 mmol), dioxane (250 mL), water (50 mL), (pyridin-4-yl)boronic acid (3.0 g, 24.4 mmol), $Cs_2CO_3$ (12.7 g, 38.98 mmol), and $Pd(dppf)Cl_2$ (600 mg, 0.82 mmol). The resulting solution was stirred for 12 h at 90° C. and then was concentrated under vacuum. The residue was applied onto a silica gel column and eluted with ethyl acetate/petroleum ether (1:1 to 3:1). This resulted in 4.2 g (77%) of the title compound as a white solid. MS-ESI: 273.1 (M+1).

Step 2: Ethyl 3-amino-5-(pyridin-4-yl)benzoate

Into a 250-mL round-bottom flask, was placed ethyl 3-nitro-5-(pyridin-4-yl)benzoate (4.2 g, 15.4 mmol), MeOH (150 mL). Then Pd/C (10% wt, 500 mg) was added. The flask was evacuated and flushed three times with hydrogen. The resulting solution was stirred for 2 days at RT under an atmosphere of hydrogen. The solids were filtered out. The resulting solution was concentrated under vacuum. This resulted in 3.7 g (99%) of the title compound as a white solid. MS-ESI: 243.1 (M+1).

Steps 3-5 used similar procedures for converting compound 18 to Intermediate 19 shown in Scheme M to afford Intermediate 34. MS-ESI: 293.1 (M+1), 291.1 (M−1).

Intermediate 35

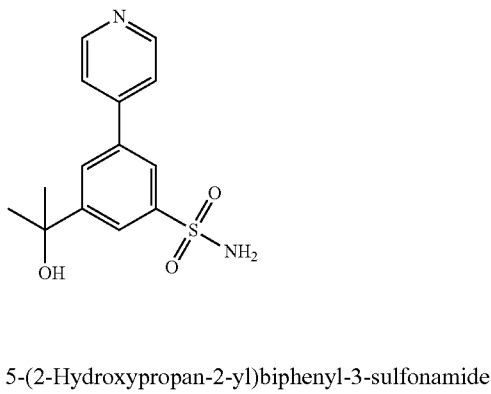

5-(2-Hydroxypropan-2-yl)biphenyl-3-sulfonamide

Intermediate 35 was prepared using the similar procedures for converting compound 21 to Intermediate 34 shown in Scheme N. MS-ESI: 290.1 (M−1).

Scheme O

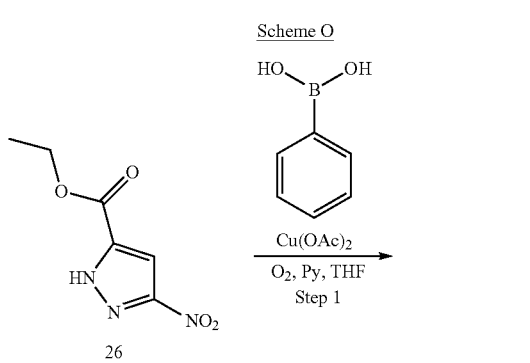

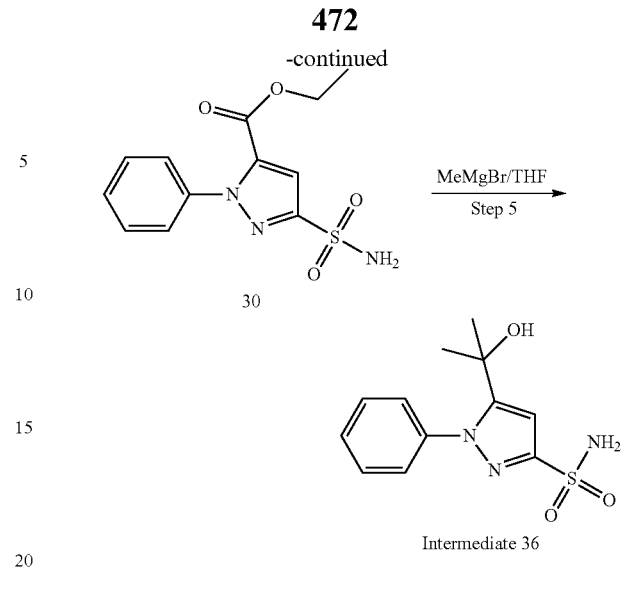

Intermediate 36

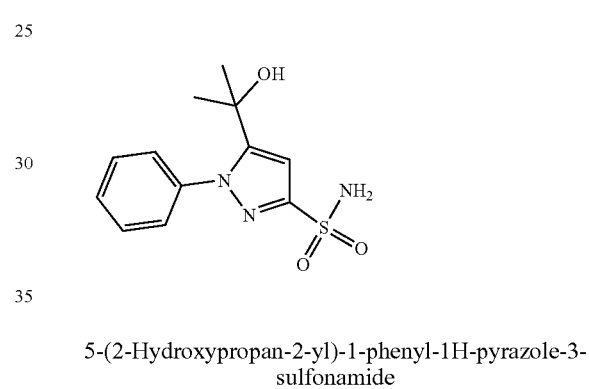

5-(2-Hydroxypropan-2-yl)-1-phenyl-1H-pyrazole-3-sulfonamide

Step 1: Ethyl 3-nitro-1-phenyl-1H-pyrazole-5-carboxylate

Into a 500-mL round-bottom flask, was placed ethyl 3-nitro-1H-pyrazole-5-carboxylate (5 g, 27.0 mmol), THF (150 mL), phenylboronic acid (6.59 g, 54.1 mmol), Cu(OAc)$_2$ (7.36 g, 40.5 mmol), and pyridine (8.54 g, 108 mmol). The resulting solution was stirred for 14 h at 55° C. and then was concentrated under vacuum. The residue was applied onto a silica gel column and eluted with ethyl acetate/petroleum ether (1:7 to 1:4). This resulted in 2 g (28%) of the title compound as an off-white solid. MS-ESI: 262.1 (M+1).

Step 2: Ethyl 3-amino-1-phenyl-1H-pyrazole-5-carboxylate

Into a 100-mL round-bottom flask, was placed ethyl 3-nitro-1-phenyl-1H-pyrazole-5-carboxylate (2 g, 7.66 mmol), EtOH (50 mL). Then Pd/C (10% wt, 200 mg) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:3 to 1:1). This resulted in 1 g (56%) of the title compound as a light yellow solid. MS-ESI: 232.1 (M+1).

Steps 3-5 used similar procedures for converting compound 18 to Intermediate 19 shown in Scheme M to afford Intermediate 36. MS-ESI: 280.1 (M−1).

Scheme P

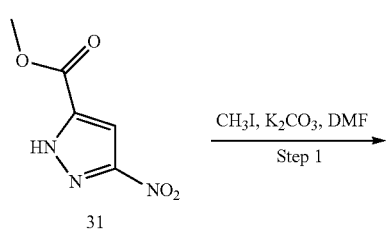
31

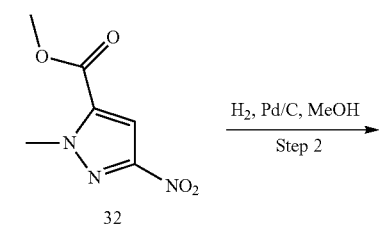
32

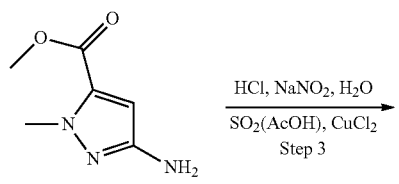
33

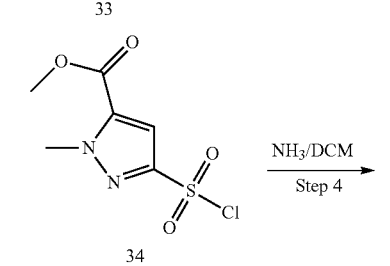
34

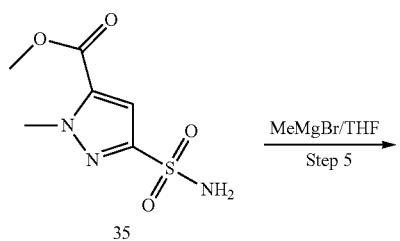
35

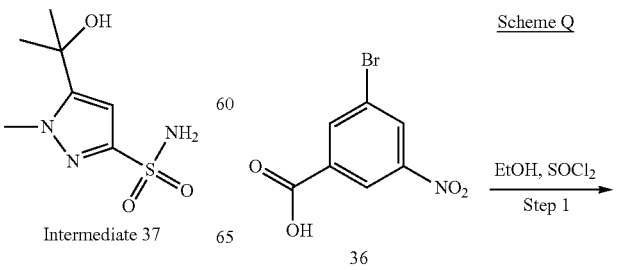
Intermediate 37

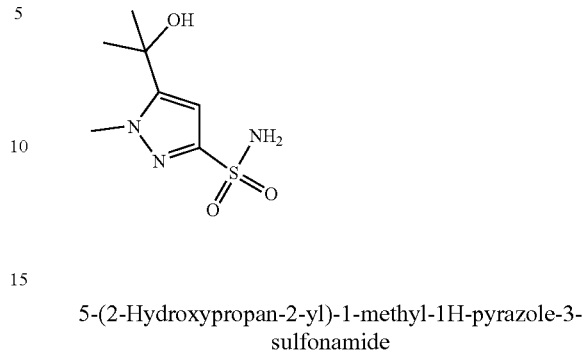

5-(2-Hydroxypropan-2-yl)-1-methyl-1H-pyrazole-3-sulfonamide

Step 1: Methyl 1-methyl-3-nitro-1H-pyrazole-5-carboxylate

Into a 250-mL round-bottom flask purged with and maintained under nitrogen, was placed methyl 3-nitro-1H-pyrazole-5-carboxylate (15 g, 87.7 mmol), DMF (50 mL), potassium carbonate (22.4 g, 162 mmol), and CH$_3$I (18.5 g, 130 mmol). The resulting solution was stirred for 15 h at RT and then was quenched by the addition of 50 mL of water. The resulting solution was extracted with 3×40 mL of ethyl acetate and the organic layers combined and dried over anhydrous Na$_2$SO$_4$, then concentrated under vacuum. This resulted in 17 g (crude) of the title compound as a yellow solid. MS-ESI: 186.0 (M+1).

Step 2: Methyl 3-amino-1-methyl-1H-pyrazole-5-carboxylate

Into a 500-mL round-bottom flask, was placed methyl 1-methyl-3-nitro-1H-pyrazole-5-carboxylate (17 g, 91.8 mmol), and MeOH (100 mL). Then Pd/C (10% wt, 2 g) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:4 to 2:3). This resulted in 11.6 g (81%) of the title compound as a yellow solid. MS-ESI: 156.1 (M+1).

Steps 3-5 used similar procedures for converting compound 18 to Intermediate 19 shown in Scheme M to afford Intermediate 37. MS-ESI: 218.0 (M−1).

Scheme Q

475
-continued

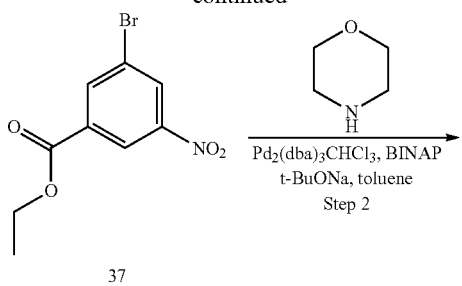

37

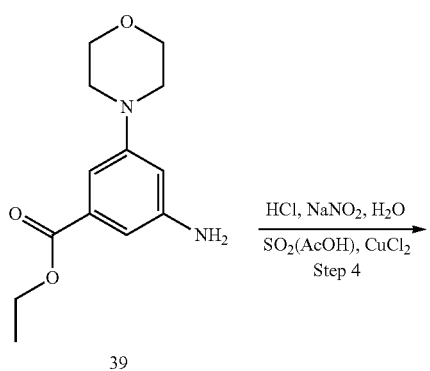

38

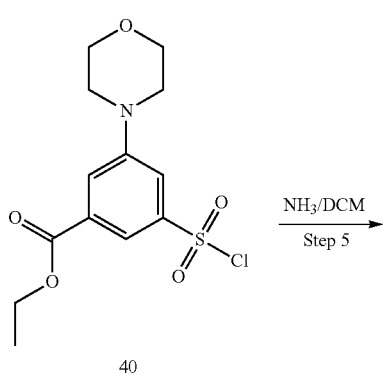

39

40

476
-continued

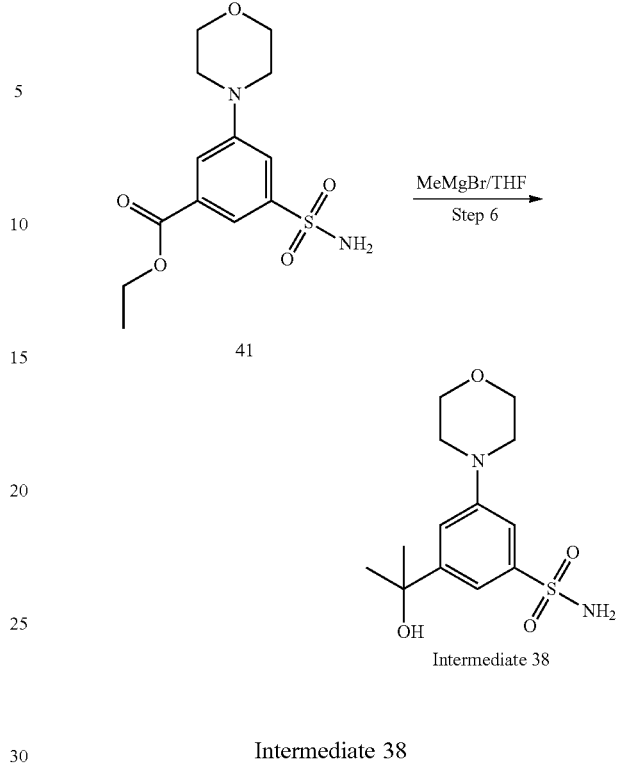

3-(2-Hydroxypropan-2-yl)-5-morpholinobenzene-sulfonamide

Step 1: Ethyl 3-bromo-5-nitrobenzoate

Into a 500-mL round-bottom flask, was placed 3-bromo-5-nitrobenzoic acid (25 g, 101.6 mmol), EtOH (200 mL). This was followed by the addition of thionyl chloride (15 mL) dropwise with stirring at 0° C. The resulting solution was stirred for 4 h at 80° C. and then was quenched by the addition of 50 mL water. The resulting solution was extracted with 3×50 mL of DCM and the organic layers combined and concentrated under vacuum. The residue was applied onto a silica gel column and eluted with ethyl acetate/petroleum ether (1:20 to 1:10). This resulted in 27.5 g (99%) of the title compound as a white solid.

Step 2: Ethyl 3-(morpholin-4-yl)-5-nitrobenzoate

Into a 500-mL round-bottom flask purged with and maintained under nitrogen, was placed ethyl 3-bromo-5-nitrobenzoate (10 g, 36.5 mmol), toluene (250 mL), morpholine (4.6 g, 52.8 mmol), t-BuONa (5 g, 52.0 mmol), Pd₂(dba)₃CHCl₃ (1.9 g, 1.93 mmol), BINAP (1.2 g, 1.93 mmol). The resulting solution was stirred for 18 h at 60° C. and then was concentrated under vacuum. The residue was applied onto a silica gel column and eluted with ethyl acetate/petroleum ether (1:30 to 1:10). This resulted in 2.8 g (27%) of the title compound as a yellow solid. MS-ESI: 281.1 (M+1).

Step 3: Ethyl 3-amino-5-(morpholin-4-yl benzoate

Into a 250-mL round-bottom flask, was placed ethyl 3-(morpholin-4-yl)-5-nitrobenzoate (3.0 g, 10.7 mmol), MeOH (100 mL). Then Pd/C (10% wt, 300 mg) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether (1:5 to 1:3). This resulted in 2.6 g (97%) of the title compound as a yellow solid. MS-ESI: 251.1 (M+1).

Steps 4-6 used similar procedures for converting compound 18 to Intermediate 19 shown in Scheme M to afford Intermediate 38. MS-ESI: 299.1 (M−1).

Scheme R

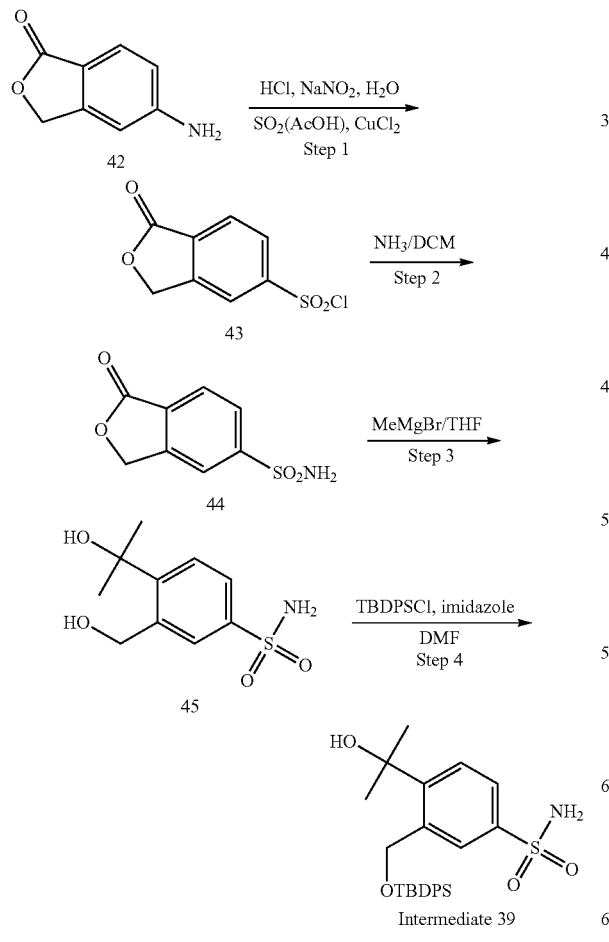

Intermediate 39

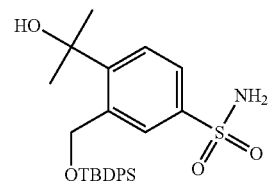

3-((Tert-butyldiphenylsilyloxy)methyl)-4-(2-hydroxypropan-2-yl)benzenesulfonamide Steps 1-3 used similar procedures for converting compound 18 to Intermediate 19 shown in Scheme M to afford compound 45. MS-ESI: 212.1 (M−1).

Step 4: 3-((Tert-butyldiphenylsilyloxy)methyl)-4-(2-hydroxypropan-2-yl)benzenesulfonamide Into a 100-mL round-bottom flask, was placed 3-(hydroxymethyl)-4-(2-hydroxypropan-2-yl)benzenesulfonamide (1.9 g, 7.75 mmol), DMF (20 mL), imidazole (1.06 g, 15.57 mmol), and TBDPSCl (3.2 g, 11.64 mmol). The resulting solution was stirred overnight at RT and then was diluted with 20 mL of water. The resulting solution was extracted with 2×20 mL of DCM and the organic layers combined and dried over anhydrous Na₂SO₄, then concentrated under vacuum. The crude product was purified by Flash-Prep-HPLC with the following conditions (IntelFlash-1): Column, C18 silica gel; mobile phase, ACN/H₂O (10 mmol/NH₄HCO₃)=1:4 increasing to ACN/H₂O (10 mmol/NH₄HCO₃)=4:1 within 30 min; Detector, UV 210 nm. This resulted in 1.4 g (37%) of the title compound as an off-white solid. MS-ESI: 482.2 (M−1).

Scheme S

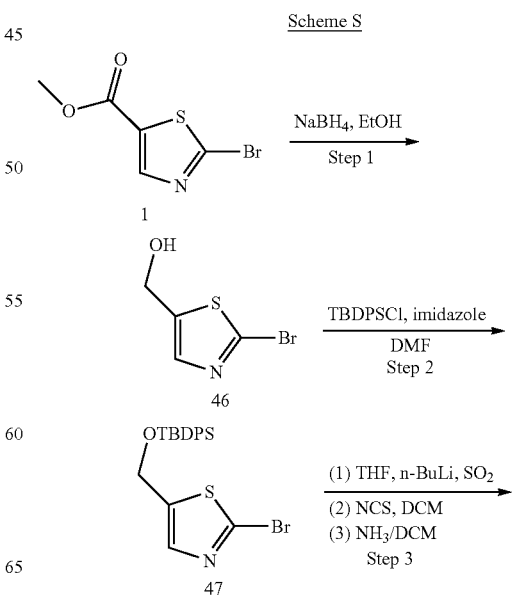

-continued

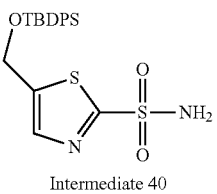

Intermediate 40

Intermediate 40

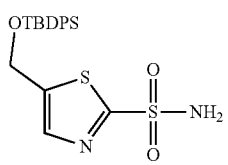

5-((Tert-butyldiphenylsilyloxy)methyl)thiazole-2-sulfonamide

Step 1: (2-Bromothiazol-5-yl)methanol

Into a 250-mL round-bottom flask, was placed a solution of methyl 2-bromothiazole-5-carboxylate (15 g, 67.55 mmol) in EtOH (100 mL). This was followed by the addition of sodium borohydride (5.13 g, 139.3 mmol) in portions at 0° C. The resulting solution was stirred for 12 h at RT and then was quenched by the addition of 100 mL of water. The resulting solution was extracted with 3×50 mL of DCM and the organic layers combined and dried over anhydrous $Na_2SO_4$, then concentrated under vacuum. This resulted in 10 g (crude, 76%) of the title compound as a light yellow oil. MS-ESI: 195.9, 193.9 (M+1).

Step 2: 2-Bromo-5-((tert-butyldiphenylsilyloxy)methyl)thiazole

Into a 250-mL round-bottom flask, was placed (2-bromothiazol-5-yl)methanol (8 g, 41.2 mmol), DMF (50 mL), TBDPSCl (12.5 g, 45.5 mmol), and imidazole (5.6 g, 82.4 mmol). The resulting solution was stirred for 2 h at RT and then was concentrated under vacuum. The residue was applied onto a silica gel column and eluted with ethyl acetate/petroleum ether (1:100 to 1:80). This resulted in 15 g (84%) of the title compound as a light yellow solid. MS-ESI: 434.0, 432.0 (M+1).

Step 3: 5-((Tert-butyldiphenylsilyloxy)methyl)thiazole-2-sulfonamide

Into a 500-mL 3-necked round-bottom flask purged with and maintained under nitrogen, was placed a solution of 2-bromo-5-((tert-butyldiphenylsilyloxy)methyl)thiazole (15 g, 34.7 mmol) in THF (200 mL). This was followed by the addition of n-BuLi (2.5 M, 16.7 mL) dropwise with stirring at −78° C. The resulting solution was stirred for 30 min at −78° C. To the above $SO_2$ was introduced. The reaction was warmed to RT and stirred for 30 min and then was concentrated under vacuum. The residue diluted in DCM (150 mL) and then NCS (5.7 g, 42.69 mmol) was added. The resulting solution was stirred for 30 min at RT. To the above was added a saturated solution of ammonia in DCM (100 mL). The resulting solution was stirred for 2 h at RT and then was concentrated under vacuum. The residue was applied onto a silica gel column and eluted with ethyl acetate/petroleum ether (1:20 to 1:10). This resulted in 7.5 g (50%) of the title compound as a light yellow solid. MS-ESI: 431.1 (M−1).

Scheme T

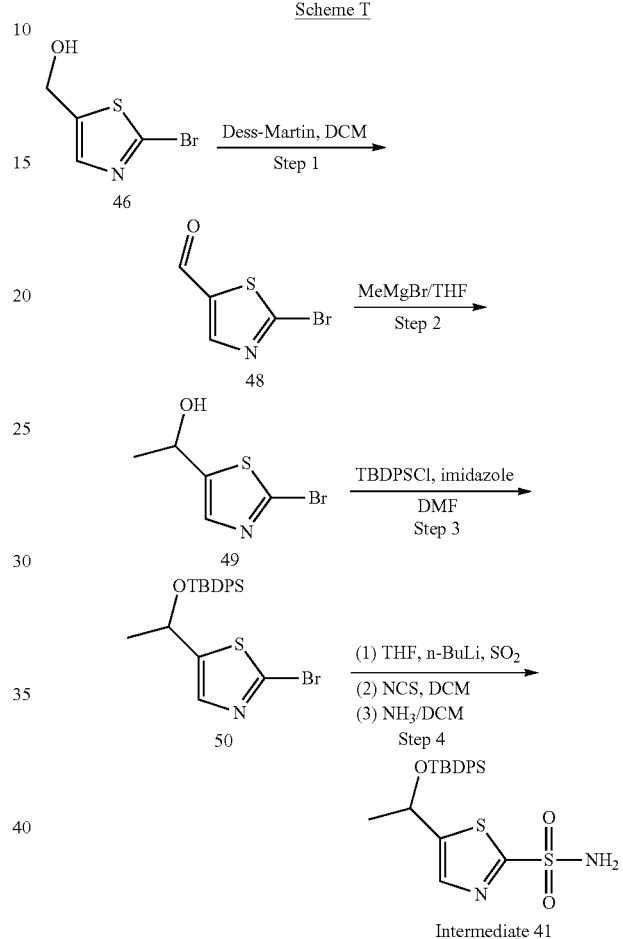

Intermediate 41

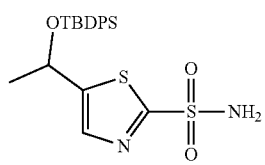

5-(1-(Tert-butyldiphenylsilyloxy)ethyl)thiazole-2-sulfonamide

Step 1: 2-Bromothiazole-5-carbaldehyde

Into a 500-mL round-bottom flask, was placed (2-bromothiazol-5-yl)methanol (20 g, 103 mmol), DCM (200 mL). This was followed by the addition of Dess-Martin reagent (46 g, 103 mmol) in portions at 0° C. The resulting solution was stirred for 2 h at RT and then was concentrated under vacuum. The residue was applied onto a silica gel column and eluted with ethyl acetate/petroleum ether (1:20 to 1:10). This resulted in 18 g (91%) of the title compound as a white solid. MS-ESI: 193.9, 191.9 (M+1).

Step 2: 1-(2-Bromothiazol-5-yl)ethanol

Into a 500-mL 3-necked round-bottom flask purged with and maintained under nitrogen, was placed a solution of 2-bromothiazole-5-carbaldehyde (18 g, 93.7 mmol) in THF (200 mL). This was followed by the addition of MeMgBr/THF (3 M, 33 mL) dropwise with stirring at 0° C. The resulting solution was stirred for 0.5 h at 0° C. The reaction was then quenched by the addition of 200 mL of NH$_4$Cl (sat.). The resulting solution was extracted with 2×200 mL of DCM and the organic layers combined and concentrated under vacuum. The residue was applied onto a silica gel column and eluted with ethyl acetate/petroleum ether (1:20 to 1:15). This resulted in 15 g (77%) of the title compound as colorless oil. MS-ESI: 209.9, 207.9 (M+1).

Steps 3-4 used similar procedures for converting compound 46 to Intermediate 40 shown in Scheme S to afford Intermediate 41. MS-ESI: 445.1 (M−1).

Scheme U

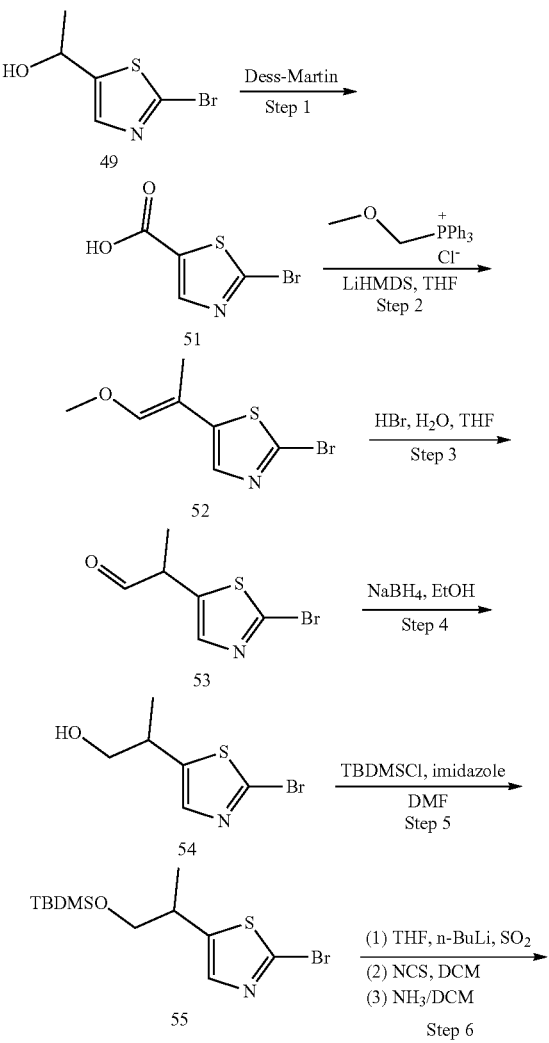

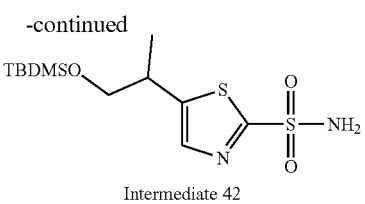

Intermediate 42

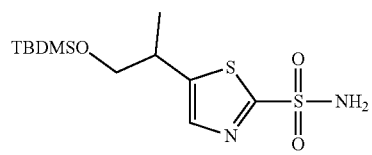 [SMILES: CC(CO[Si](C)(C)C(C)(C)C)c1cnc(S(N)(=O)=O)s1]

5-(1-(Tert-butyldimethylsilyloxy)propan-2-yl)thiazole-2-sulfonamide

Step 1: 1-(2-Bromothiazol-5-yl)ethanone

Into a 250-mL round-bottom flask, was placed 1-(2-bromothiazol-5-yl)ethanol (5.792 g, 27.84 mmol), DCM (150 mL), and Dess-Martin reagent (17.72 g, 41.78 mmol). The resulting solution was stirred for 2 h at RT and then was concentrated under vacuum. The residue was applied onto a silica gel column and eluted with ethyl acetate/petroleum ether (1:10 to 1:5). This resulted in 5.29 g (92%) of the title compound as an off-white solid. MS-ESI: 207.9, 205.9 (M+1).

Step 2: 2-Bromo-5-(1-methoxyprop-1-en-2-yl)thiazole

Into a 250-mL 3-necked round-bottom flask purged with and maintained under nitrogen, was placed (methoxymethyl)triphenylphosphanium chloride (13.16 g, 38.39 mmol) and THF (100 mL). This was followed by the addition of LiHMDS (1 M, 38.52 mL) dropwise with stirring at 0° C. The resulting solution was stirred for 0.5 h at 0° C. To this was added a solution of 1-(2-bromothiazol-5-yl)ethanone (5.29 g, 25.67 mmol) in THF (30 mL) dropwise with stirring at 0° C. The resulting solution was stirred for 1 h at RT and then was quenched by the addition of 100 mL of NH$_4$Cl (sat.). The resulting solution was extracted with 3×80 mL of DCM and the organic layers combined and dried over anhydrous Na$_2$SO$_4$, then concentrated under vacuum. The residue was applied onto a silica gel column and eluted with ethyl acetate/petroleum ether (1:5 to 1:3). This resulted in 4.38 g (73%) of the title compound as light yellow oil. MS-ESI: 235.9, 234.0 (M+1).

Step 3: 2-(2-Bromothiazol-5-yl)propanal

Into a 250-mL round-bottom flask, was placed 2-bromo-5-(1-methoxyprop-1-en-2-yl)thiazole (4.38 g, 18.7 mmol), THF (30 mL), water (50 mL), and HBr (47% wt, 50 mL). The resulting solution was stirred for 4 h at 70° C. and then was diluted with 30 mL of water. The resulting solution was extracted with 3×50 mL of DCM and the organic layers combined and dried over anhydrous Na$_2$SO$_4$, then concentrated under vacuum. This resulted in 3.79 g (crude, 92%) of the title compound as light yellow oil. MS-ESI: 221.9, 219.9 (M+1).

Step 4: 2-(2-Bromothiazol-5-yl)propan-1-ol

Into a 250-mL round-bottom flask, was placed 2-(2-bromothiazol-5-yl)propanal (4 g, 18.2 mmol) and EtOH (60 mL). This was followed by the addition of $NaBH_4$ (1.38 g, 36.5 mmol) in portions at 0° C. The resulting solution was stirred overnight at RT and then was quenched by the addition of 50 mL of water. The resulting solution was extracted with 3×50 mL of DCM and the organic layers combined and dried over anhydrous $Na_2SO_4$, then concentrated under vacuum. This resulted in 3.79 g (94%) of the title compound as light yellow oil. MS-ESI: 223.9, 222.0 (M+1).

Step 5: 2-Bromo-5-(1-(tert-butyldimethylsilyloxy)propan-2-yl)thiazole

Into a 100-mL round-bottom flask, was placed 2-(2-bromothiazol-5-yl)propan-1-ol (3.79 g, 17.1 mmol), DMF (25 mL), imidazole (2.33 g, 34.2 mmol), TBDMSCl (3.87 g, 25.7 mmol). The resulting solution was stirred overnight at RT and then was diluted with 30 mL of water. The resulting solution was extracted with 3×30 mL of DCM and the organic layers combined and dried over anhydrous $Na_2SO_4$, then concentrated under vacuum. The residue was applied onto a silica gel column and eluted with ethyl acetate/petroleum ether (1:15 to 1:10). This resulted in 3.12 g (54%) of the title compound as a white solid. MS-ESI: 338.0, 336.0 (M+1).

Step 6 used similar procedure for converting compound 47 to Intermediate 40 shown in Scheme S to afford Intermediate 42. MS-ESI: 335.1 (M−1).

Scheme V

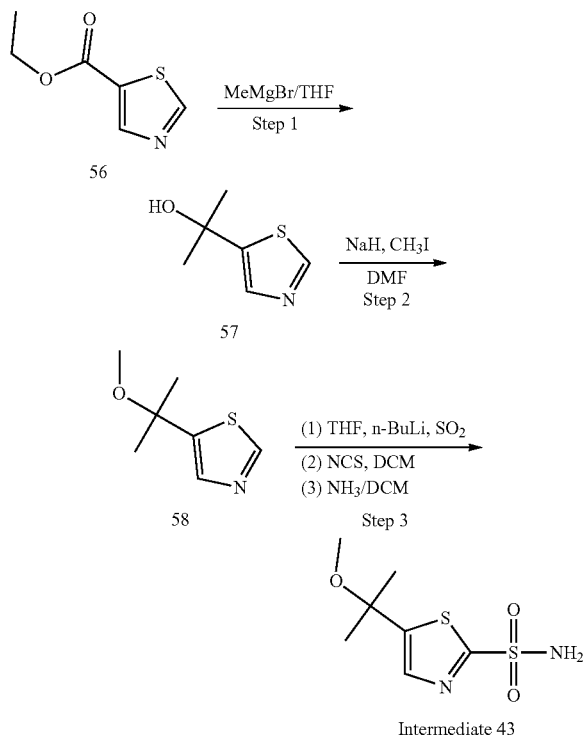

Intermediate 43

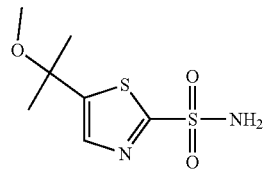

5-(2-Methoxypropan-2-yl)thiazole-2-sulfonamide

Step 1: 2-(Thiazol-5-yl)propan-2-ol

Into a 250-mL 3-necked round-bottom flask purged with and maintained under nitrogen, was placed a solution of ethyl ethyl thiazole-5-carboxylate (3.75 g, 23.9 mmol) in THF (50 mL). This was followed by the addition of MeMgBr/THF (3 M, 40 mL) dropwise with stirring at 0° C. The resulting solution was stirred for 2 h at RT and then was quenched by the addition of 50 mL of $NH_4Cl$ (sat.). The resulting solution was extracted with 3×80 mL of DCM and the organic layers combined and dried over anhydrous $Na_2SO_4$, then concentrated under vacuum. The residue was applied onto a silica gel column and eluted with ethyl acetate/petroleum ether (1:3 to 1:1). This resulted in 2.1 g (61%) of the title compound as yellow oil. MS-ESI: 144.0 (M+1).

Step 2: 5-(2-Methoxypropan-2-yl)thiazole

Into a 100-mL round-bottom flask, was placed a solution of 2-(thiazol-5-yl)propan-2-ol (2.06 g, 14.4 mmol) in DMF (20 mL). This was followed by the addition of NaH (60%, 1.15 g, 28.8 mmol) in portions at 0° C. To this was added $CH_3I$ (3.07 g, 21.6 mmol) dropwise with stirring at 0° C. The resulting solution was stirred for 1 h at RT and then was quenched by the addition of 20 mL of water. The resulting solution was extracted with 3×30 mL of ethyl acetate and the organic layers combined and dried over anhydrous $Na_2SO_4$, then concentrated under vacuum. The residue was applied onto a silica gel column and eluted with ethyl acetate/petroleum ether (1:5 to 1:3). This resulted in 1.42 g (63%) of the title compound as yellow oil. MS-ESI: 158.1 (M+1).

Step 3 used similar procedure for converting compound 47 to Intermediate 40 shown in Scheme S to afford Intermediate 43. MS-ESI: 235.0 (M−1).

Scheme W

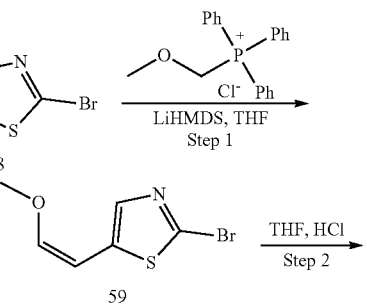

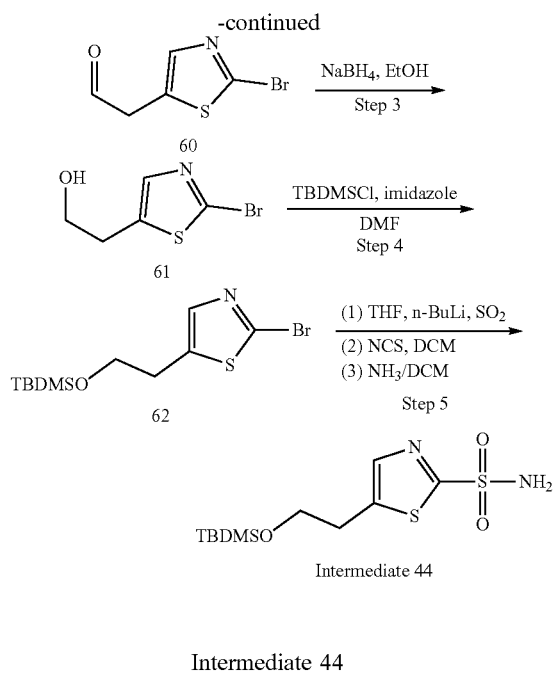

Intermediate 44

5-(2-(Tert-butyldimethylsilyloxy)ethyl)thiazole-2-sulfonamide

Step 1: 2-Bromo-5-(2-methoxyvinyl)thiazole

Into a 100-mL 3-necked round-bottom flask purged with and maintained under nitrogen, was placed (methoxymethyl)triphenylphosphanium chloride (3.2 g, 9.33 mmol), THF (15 mL). This was followed by the addition of LiHMDS (1 M, 9.4 mL) dropwise with stirring at 0° C. To this was added a solution of 2-bromo-1,3-thiazole-5-carbaldehyde (1.5 g, 7.81 mmol) in THF (10 mL) dropwise with stirring at 0° C. The resulting solution was stirred for 0.5 h at 0° C. and then was quenched by the addition of 50 mL of NH$_4$Cl (sat.). The resulting solution was extracted with 3×50 mL of DCM and the organic layers combined and concentrated under vacuum. The residue was applied onto a silica gel column and eluted with ethyl acetate/petroleum ether (1:100 to 1:80). This resulted in 1.3 g (76%) of the title compound as brown oil. The crude product was used in the next step.

Step 2: 2-(2-Bromo-1,3-thiazol-5-yl)acetaldehyde

Into a 50-mL round-bottom flask purged with and maintained under nitrogen, was placed 2-bromo-5-(2-methoxyvinyl)thiazole (1.3 g, 5.91 mmol), THF (10 mL). This was followed by the addition of aqueous hydrogen chloride (4 M, 5 mL) dropwise with stirring at 0° C. The resulting solution was stirred for 4 h at 60° C. The resulting solution was extracted with 3×30 mL of DCM and the organic layers combined and dried over anhydrous Na$_2$SO$_4$, then concentrated under vacuum. This resulted in 1.1 g (90%) of the title compound as light yellow oil. MS-ESI: 205.9, 207.9 (M+1).

Step 3: 2-(2-Bromo-1,3-thiazol-5-yl)ethan-1-ol

Into a 50-mL round-bottom flask, was placed 2-(2-bromo-1,3-thiazol-5-yl)acetaldehyde (1.1 g, 5.34 mmol), EtOH (10 mL), and sodium borohydride (200 mg, 5.43 mmol). The resulting solution was stirred for 2 h at RT and then was quenched by the addition of 20 mL of water. The resulting solution was extracted with 3×30 mL of DCM and the organic layers combined and dried over anhydrous Na$_2$SO$_4$, then concentrated under vacuum. This resulted in 1.0 g (90%) of the title compound as light yellow oil. MS-ESI: 207.9, 209.9 (M+1).

Step 4: 2-Bromo-5-(2-(tert-butyldimethylsilyloxy)ethyl thiazole

Into a 50-mL round-bottom flask, was placed 2-(2-bromo-1,3-thiazol-5-yl)ethan-1-ol (1.0 g, 4.81 mmol), DMF (10 mL), imidazole (650 mg, 9.56 mmol), and TBDMSCl (1.1 g, 7.30 mmol). The resulting solution was stirred for 2 h at RT and then was diluted with 20 mL of water. The resulting solution was extracted with 2×20 mL of DCM and the organic layers combined and concentrated under vacuum. This resulted in 1.2 g (77%) of the title compound as light yellow oil. MS-ESI: 324.0, 322.0 (M+1).

Step 5 used similar procedure for converting compound 47 to Intermediate 40 shown in Scheme S to afford Intermediate 44. MS-ESI: 321.1 (M−1).

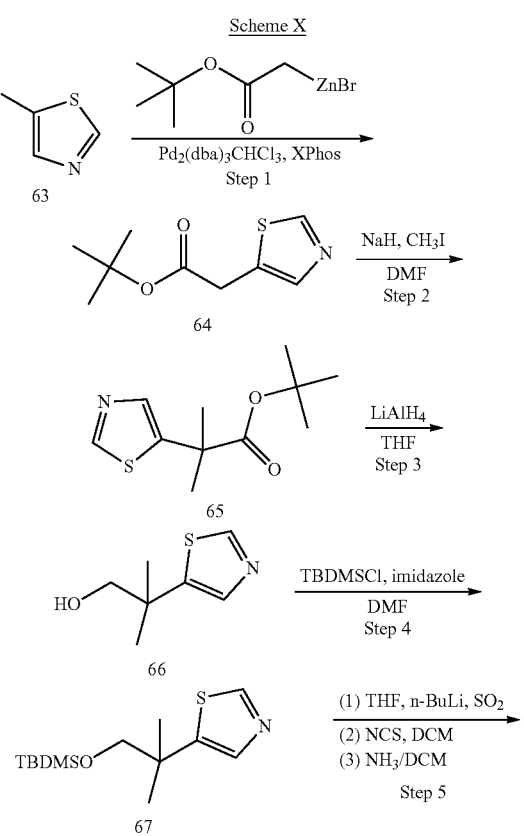

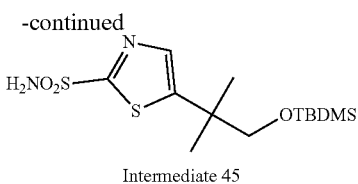

Intermediate 45

Intermediate 45

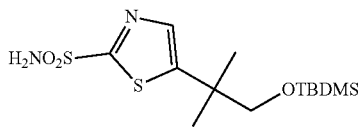 [SMILES: CC(C)(CO[Si](C)(C)C(C)(C)C)c1cnc(S(N)(=O)=O)s1]

5-(1-(Tert-butyldimethylsilyloxy)-2-methylpropan-2-yl)thiazole-2-sulfonamide

Step 1: Tert-butyl 2-(thiazol-5-yl)acetate

Into a 100-mL 3-necked round-bottom flask purged with and maintained under nitrogen, was placed 5-bromothiazole (3 g, 18.29 mmol), THF (30 mL), X-phos (1.74 g, 3.66 mmol), and Pd$_2$(dba)$_3$CHCl$_3$ (950 mg, 0.91 mmol). The resulting solution was stirred for 0.5 h at RT. To the above was added tert-butyl 2-(bromozincio)acetate (7.13 g, 27.37 mmol). The resulting solution was stirred for 4 h at 70° C. and then was concentrated under vacuum. The residue was applied onto a silica gel column and eluted with ethyl acetate/petroleum ether (1:10 to 1:3). This resulted in 2.4 g (66%) of the title compound as brown oil. MS-ESI: 200.1 (M+1).

Step 2: Tert-butyl 2-methyl-2-(thiazol-5-yl)propanoate

Into a 100-mL round-bottom flask purged with and maintained under nitrogen, was placed tert-butyl 2-(thiazol-5-yl)acetate (1 g, 5.02 mmol), DMF (20 mL). This was followed by the addition of NaH (60%, 600 mg, 25.00 mmol) in portions at 0° C. The solution was stirred for 0.5 h at 0° C. This was followed by the addition of CH$_3$I (2.13 g, 15.06 mmol) dropwise with stirring at 0° C. The resulting solution was stirred for 2 h at RT and then was quenched by the addition of 40 mL of NH$_4$Cl (sat.). The resulting solution was extracted with 3×50 mL of DCM and the organic layers combined and concentrated under vacuum. The residue was applied onto a silica gel column and eluted with ethyl acetate/petroleum ether (1:10 to 1:3). This resulted in 0.7 g (61%) of the title compound as light yellow oil. MS-ESI: 228.1 (M+1).

Step 3: 2-Methyl-2-(thiazol-5-yl)propan-1-ol

Into a 100-mL round-bottom flask, was placed tert-butyl 2-methyl-2-(thiazol-5-yl)propanoate (700 mg, 3.08 mmol), THF (20 mL). This was followed by the addition of LiAlH$_4$ (200 mg, 5.27 mmol) in portions at 0° C. and was stirred for 2 h at 0° C. and then was quenched by the addition of 1 mL of water. The solids were filtered out. The resulting mixture was concentrated under vacuum. This resulted in 400 mg (83%) of the title compound as brown oil. MS-ESI: 158.1 (M+1).

Steps 4-5 used similar procedures for converting compound 54 to Intermediate 42 shown in in Scheme U to afford Intermediate 45. MS-ESI: 349.1 (M−1).

Scheme Y

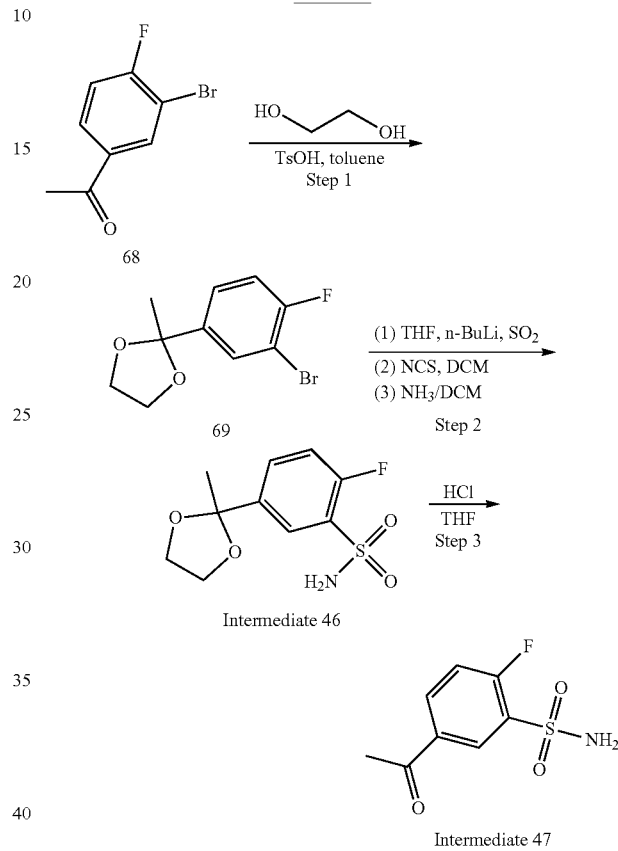

Intermediate 46

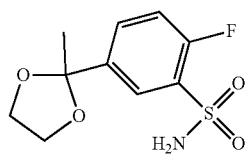 [SMILES: CC1(c2ccc(F)c(S(N)(=O)=O)c2)OCCO1]

2-Fluoro-5-(2-methyl-1,3-dioxolan-2-yl)benzenesulfonamide

Step 1: 2-(3-Bromo-4-fluorophenyl)-2-methyl-1,3-dioxolane

Into a 250-mL round-bottom flask, was placed a solution of 1-(3-bromo-4-fluorophenyl)ethan-1-one (5 g, 23.0 mmol) in toluene (50 mL), ethane-1,2-diol (4 mL), and TsOH (200 mg, 1.16 mmol). The resulting solution was stirred for 6 h at 120° C. The reaction was then quenched by the addition of 100 mL of water. The resulting solution was extracted with 3×100 mL of ethyl acetate and the organic layers combined and dried over anhydrous Na$_2$SO$_4$, then concentrated under vacuum. The residue was applied onto a silica gel column and eluted with ethyl acetate/petroleum ether (1:5 to 1:4). This resulted in 5.5 g (91%) of the title compound as yellow oil.

Step 2 used similar procedure for converting compound 47 to Intermediate 40 shown in Scheme S to afford Intermediate 46. MS-ESI: 260.0 (M−1).

Intermediate 47

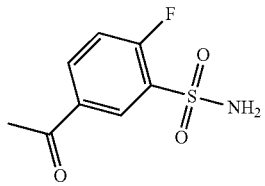

5-Acetyl-2-fluorobenzenesulfonamide

Step 3: 5-Acetyl-2-fluorobenzenesulfonamide

Into a 50-mL round-bottom flask, was placed 2-fluoro-5-(2-methyl-1,3-dioxolan-2-yl)benzene-1-sulfonamide (300 mg, 1.15 mmol), THF (5 mL), and hydrogen chloride (1 N, 5 mL). The resulting solution was stirred for 12 h at RT. The pH value of the solution was adjusted to 7~8 with NaOH (2 N). The resulting solution was extracted with 3×30 mL of ethyl acetate and the organic layers combined and concentrated under vacuum. This resulted in 240 mg (crude, 96%) of the title compound as a light yellow solid. MS-ESI: 216.0 (M−1).

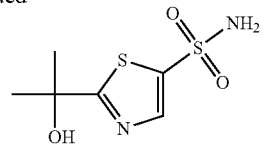

Intermediate 48

Intermediate 48

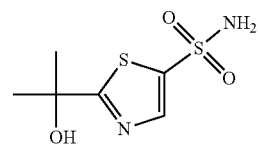

2-(2-Hydroxypropan-2-yl)thiazole-5-sulfonamide

Compound 73 was prepared using similar procedures for converting compound 68 to Intermediate 47 shown in Scheme Y.

Step 4: 2-(2-Hydroxypropan-2-yl)thiazole-5-sulfonamide

Into a 100-mL 3-necked round-bottom flask purged with and maintained under nitrogen, was placed 2-acetylthiazole-5-sulfonamide (1 g, 4.85 mmol), and THF (20 mL). This was followed by the addition of MeMgBr (3 M, 7 mL) dropwise with stirring at 0° C. The resulting solution was stirred for 14 h at RT and then was quenched by the addition of 20 mL of NH$_4$Cl (sat.). The resulting solution was extracted with 2×30 mL of DCM and the organic layers combined and concentrated under vacuum. The residue was applied onto a silica gel column and eluted with ethyl acetate/petroleum ether (1:5 to 1:3). This resulted in 580 mg (54%) of the title compound as a light yellow solid. MS-ESI: 221.0 (M−1).

Scheme Z

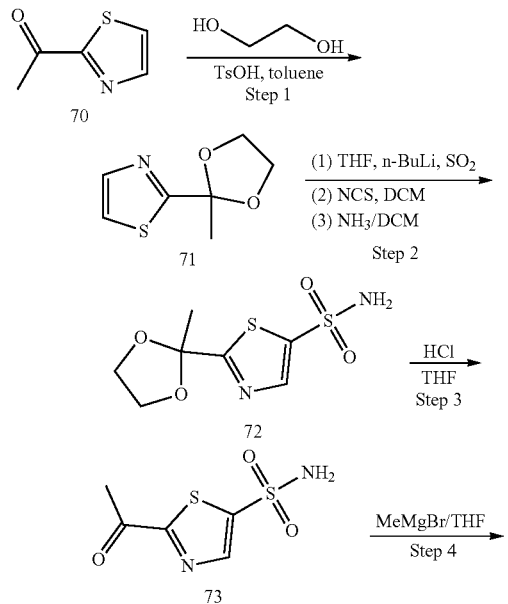

Scheme MM

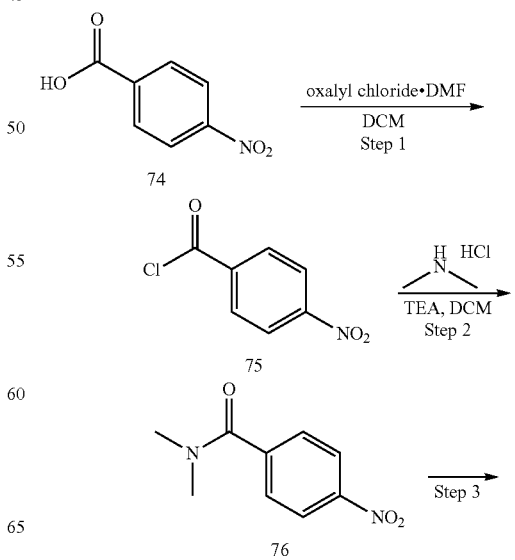

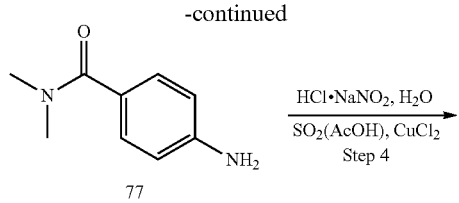

77

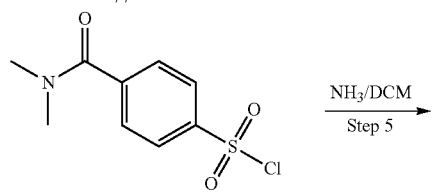

78

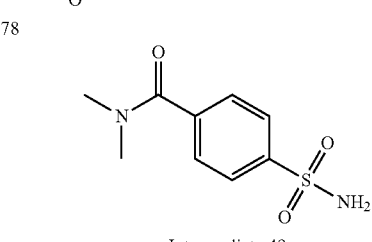

Intermediate 49

Intermediate 49

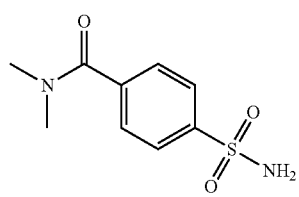

Step 1: 4-Nitrobenzoyl Chloride

Into a 500-mL round-bottom flask was placed 4-nitrobenzoic acid (20 g, 120 mmol), DCM (200 mL), and DMF (0.2 mL). This was followed by the addition of oxalyl chloride (15 mL) dropwise with stirring at 0° C. The resulting solution was stirred for 4 h at RT and then was concentrated under vacuum. This resulted in 22 g (crude) of the title compound as yellow oil. The crude product was used in the next step.

Step 2: N,N-dimethyl-4-nitrobenzamide

Into a 500-mL round-bottom flask was placed dimethylamine hydrochloride (6.5 g, 79.7 mmol), DCM (200 mL), and TEA (50 mL). This was followed by the addition of 4-nitrobenzoyl chloride (22 g, 119 mmol) dropwise with stirring at 0° C. The resulting solution was stirred for 6 h at RT and then was concentrated under vacuum. The resulting mixture was washed with 2×50 mL of water. The solids were collected by filtration. This resulted in 16 g (69% over two steps) of the title compound as a white solid. MS-ESI: 195.1 (M+1).

Step 3: 4-Amino-N,N-dimethylbenzamide

Into a 250-mL round-bottom flask was placed N,N-dimethyl-4-nitrobenzamide (16 g, 82.4 mmol), MeOH (100 mL). Then Pd/C (10% wt., 1 g) was added. The flask was evacuated and flushed three times with hydrogen. The resulting solution was stirred for 12 h at RT under an atmosphere of hydrogen. The solids were filtered out. The resulting filtrate was concentrated under vacuum. This resulted in 13 g (96%) of the title compound as a white solid. MS-ESI: 165.1 (M+1).

Steps 4-5 used similar steps as described for intermediate 38 shown in Scheme Q to afford compound 41. MS-ESI: 229.1 (M+1).

Scheme NN

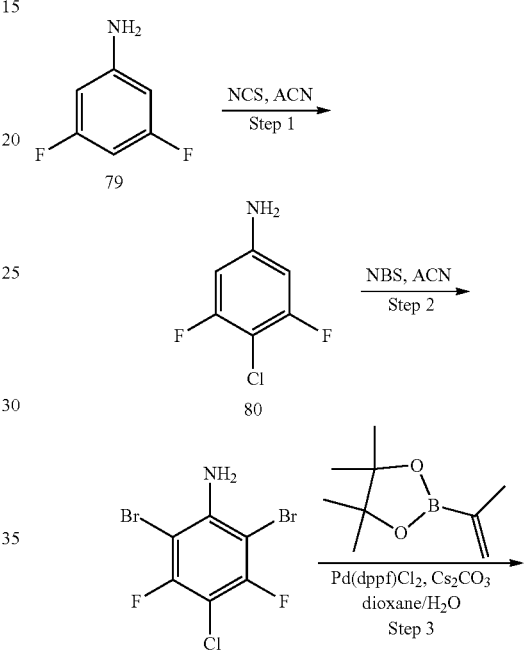

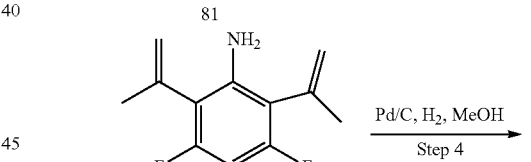

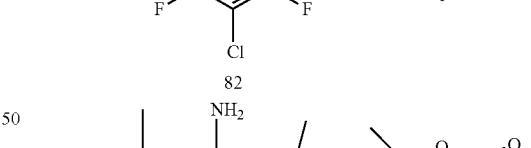

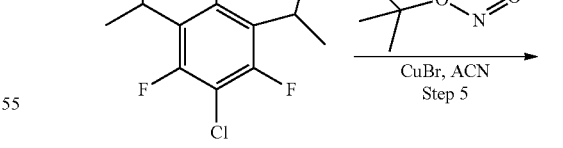

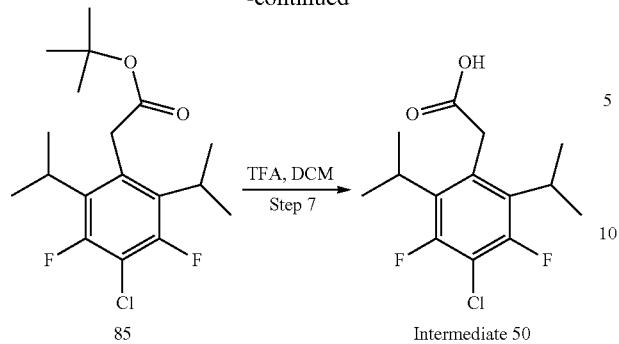

Scheme OO

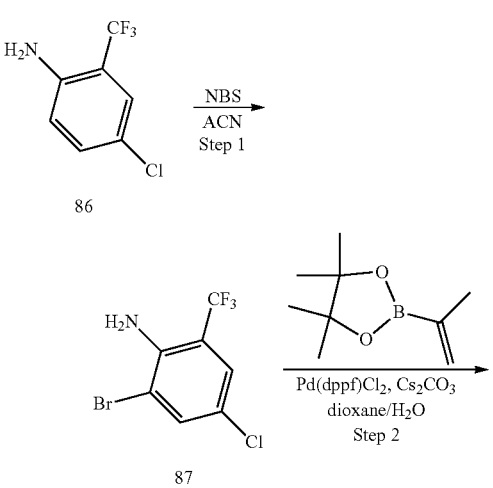

Intermediate 50

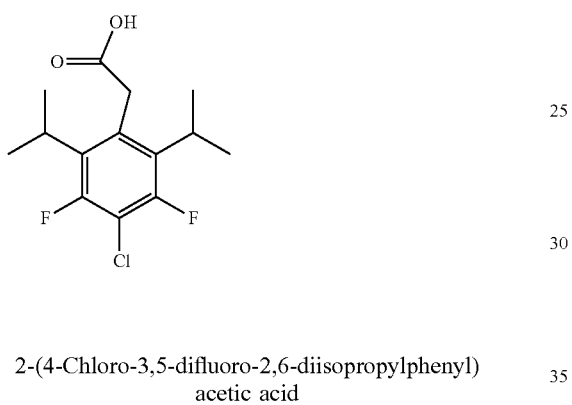

2-(4-Chloro-3,5-difluoro-2,6-diisopropylphenyl) acetic acid

Step 1: 4-Chloro-3,5-difluorobenzenamine

Into a 500-mL round-bottom flask, was placed 3,5-difluorobenzenamine (10.3 g, 79.8 mmol), ACN (100 mL), NCS (10.8 g, 80.9 mmol). The resulting solution was stirred for 5 h at 80° C. and then was concentrated under vacuum. The residue was applied onto a silica gel column and eluted with ethyl acetate/petroleum ether (1:3 to 1:1). This resulted in 7.1 g (54%) of the title compound as a gray solid. 164.0, 166.0 (M+1).

Step 2: 2,6-Dibromo-4-chloro-3,5-difluorobenzenamine

Into a 250-mL round-bottom flask, was placed 4-chloro-3,5-difluorobenzenamine (4.0 g, 24.5 mmol), ACN (100 mL), NBS (13.0 g, 73.0 mmol). The resulting solution was stirred for 1 h at RT and then was concentrated under vacuum. The residue was applied onto a silica gel column and eluted with ethyl acetate/petroleum ether (1:6 to 1:4). This resulted in 7.4 g (94%) of the title compound as a yellow solid. MS-ESI: 319.8, 321.8, 323.8 (M+1).

Steps 3-7 used similar procedures for converting compound 87 to Intermediate 51 shown in Scheme OO (below) to afford Intermediate 50. MS-ESI: 289.1, 291.1 (M−1).

Compound 84: $^1$H NMR (400 MHz, CDCl$_3$-d) δ 3.67 (hept, J=7.2 Hz, 2H), 1.33 (d, J=7.2 Hz, 12H).

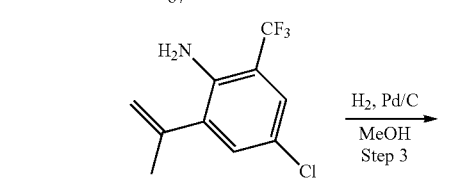

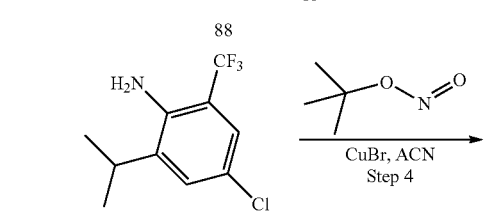

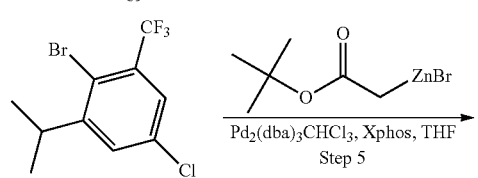

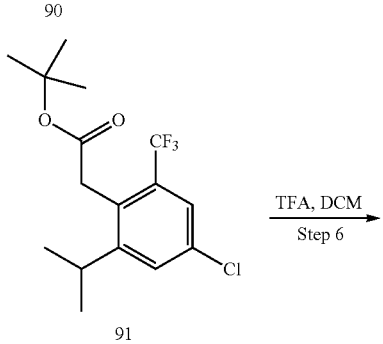

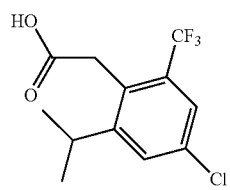

Intermediate 51

Intermediate 51

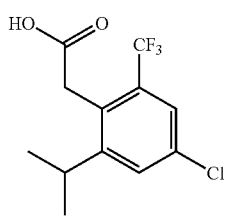 [SMILES: CC(C)c1cc(Cl)cc(C(F)(F)F)c1CC(=O)O]

2-(4-Chloro-2-isopropyl-6-(trifluoromethyl)phenyl)
acetic acid

Step 1: 2-Bromo-4-chloro-6-(trifluoromethyl)aniline

Into a 250-mL round-bottom flask, was placed 4-chloro-2-(trifluoromethyl)aniline (5 g, 25.6 mmol), ACN (150 mL), NBS (9.2 g, 51.7 mmol). The resulting solution was stirred overnight at RT and then was concentrated under vacuum. The residue was applied onto a silica gel column and eluted with ethyl acetate/petroleum ether (1:15 to 1:10). This resulted in 6 g (86%) of the title compound as a white solid. MS-ESI: 275.9, 273.9 (M+1).

Step 2: 4-chloro-2-(prop-1-en-2-yl)-6-(trifluoromethyl)aniline

Into a 500-mL round-bottom flask purged with and maintained under nitrogen, was placed 2-bromo-4-chloro-6-(trifluoromethyl)aniline (1 equiv.), dioxane (0.372 M in limiting reagent), water (14.9 equiv.), $Cs_2CO_3$ (3.0 equiv.), 4,4,5,5-tetramethyl-2-(prop-1-en-2-yl)-1,3,2-dioxaborolane (2.67 equiv.), and $Pd(dppf)Cl_2$ (9.8 mol %). The resulting solution was stirred for 15 h at 100° C. and then was concentrated under vacuum. The residue was applied onto a silica gel column and eluted with ethyl acetate/petroleum ether. This resulted in the title compound.

Step 3: 4-chloro-2-isopropyl-6-(trifluoromethyl)aniline

Into a 500-mL round-bottom flask, was placed 4-chloro-2-(prop-1-en-2-yl)-6-(trifluoromethyl)aniline (1 equiv.) and MeOH (0.24 M in limiting reagent). Then Pd/C (10% wt, ca. 1.76 mol % Pd) was added. The flask was evacuated and flushed three times with hydrogen. The resulting solution was stirred for 12 h at RT under an atmosphere of hydrogen. The solids were filtered out. The resulting mixture was concentrated under vacuum. The residue was applied onto a silica gel column and eluted with ethyl acetate/petroleum ether. This resulted in the title compound.

Step 4: 2-bromo-5-chloro-1-isopropyl-3-(trifluoromethyl)benzene

Into a 500-mL round-bottom flask purged with and maintained under nitrogen, was placed 4-chloro-2-isopropyl-6-(trifluoromethyl)aniline (1.0 equiv.), ACN (0.12 M in limiting reagent), and CuBr (1.50 equiv.). This was followed by the addition of tert-butyl nitrite (1.50 equiv.) dropwise with stirring at 0° C. The resulting solution was stirred for 3 h at 60° C. and then was concentrated under vacuum. The residue was applied onto a silica gel column with petroleum ether. This resulted in the title compound.

Step 5: tert-butyl 2-(4-chloro-2-isopropyl-6-(trifluoromethyl)phenyl)acetate Into a 250-mL 3-necked round-bottom flask purged with and maintained under nitrogen, was placed 2-bromo-5-chloro-1-isopropyl-3-(trifluoromethyl)benzene (1.0 equiv.), THF (0.077 M in limiting reagent), X-phos (10 mol %), and $Pd_2(dba)_3CHCl_3$ (5 mol %). The resulting solution was stirred for 0.5 h at RT. Then to the above tert-butyl 2-(bromozincio)acetate (1.9 equiv.) was added. The resulting solution was stirred for 5 h at 70° C. and then was quenched by the addition of $NH_4Cl$ (sat.). The resulting solution was extracted with ethyl acetate and the organic layers combined and concentrated under vacuum. The residue was applied onto a silica gel column and eluted with ethyl acetate/petroleum ether (1:100 to 3:97). This resulted in the title compound.

Step 6: 2-(4-chloro-2-isopropyl-6-(trifluoromethyl)phenyl)acetic acid

Into a 50-mL round-bottom flask, was placed tert-butyl 2-(4-chloro-2-isopropyl-6-(trifluoromethyl)phenyl)acetate (1.0 equiv.), DCM (0.53 M in limiting reagent), TFA (0.53 M in limiting reagent). The resulting solution was stirred for 3 h at RT and then was concentrated under vacuum. This resulted in the title compound as a light yellow solid. MS-ESI: 279.0 (M−1).

Compound 91: $^1$H NMR (300 MHz, DMSO-$d_6$) δ 7.70 (s, 1H), 7.58 (s, 1H), 3.77 (s, 2H), 3.11-2.97 (m, 1H), 1.35 (s, 9H), 1.17 (d, J=6.8 Hz, 6H).

Scheme PP

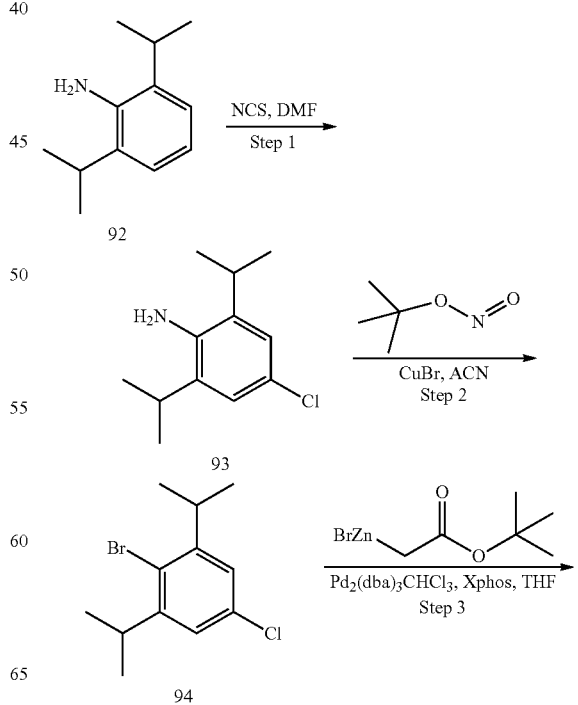

497

-continued

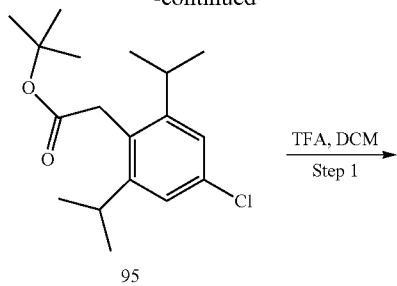
95

TFA, DCM
Step 1

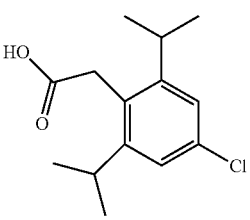
Intermediate 52

Intermediate 52

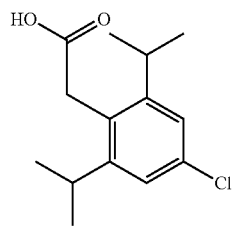 [SMILES: CC(C)c1cc(Cl)cc(C(C)C)c1CC(=O)O]

2-(4-Chloro-2,6-diisopropylphenyl)acetic acid

Step 1: 4-Chloro-2,6-bis(propan-2-yl)aniline

Into a 100-mL round-bottom flask, was placed 2,6-bis(propan-2-yl)aniline (5 g, 28.2 mmol), DMF (20 mL), NCS (4.9 g, 36.7 mmol). The resulting solution was stirred for 15 h at RT and then was diluted with 20 mL of water. The resulting solution was extracted with 3×20 mL of DCM and the organic layers combined and concentrated under vacuum. The residue was applied onto a silica gel column and eluted with ethyl acetate/petroleum ether (1:10 to 1:5). This resulted in 3.7 g (62%) of the title compound as brown oil. MS-ESI: 212.1, 214.1 (M+1).

Steps 2-4 used similar procedures for converting compound 89 to Intermediate 51 shown in Scheme OO to afford Intermediate 58. MS-ESI: 253.1, 255.1 (M−1).

Scheme QQ

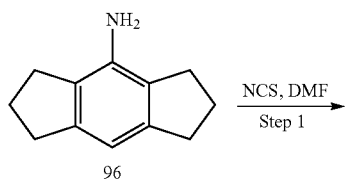
96

NCS, DMF
Step 1

498

-continued

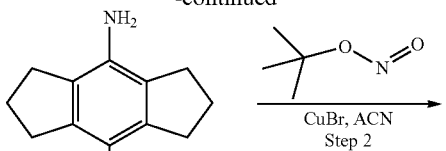
97 tBuO-N=O
CuBr, ACN
Step 2

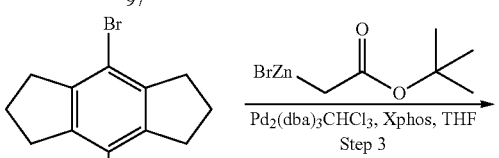
98

BrZn-CH2-C(O)-OtBu
Pd2(dba)3CHCl3, Xphos, THF
Step 3

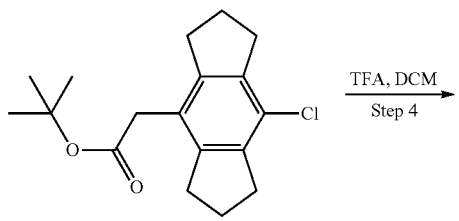
99

TFA, DCM
Step 4

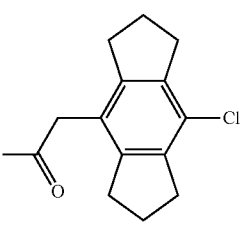

Intermediate 53

Intermediate 53

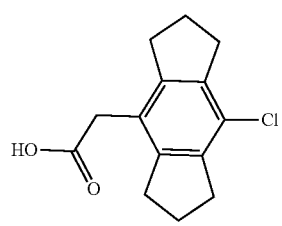 [SMILES: O=C(O)Cc1c2c(c(Cl)c3c1CCC3)CCC2]

2-(8-Chloro-1,2,3,5,6,7-hexahydros-indacen-4-yl)acetic acid

Step 1:
8-Chloro-1,2,3,5,6,7-hexahydros-indacen-4-amine

Into a 100-mL round-bottom flask, was placed 1,2,3,5,6,7-hexahydros-indacen-4-amine (1.73 g, 9.99 mmol), DMF (10 mL), NCS (1.47 g, 11.0 mmol). The resulting solution was stirred for 12 h at RT and then was diluted with 50 mL of DCM. The resulting mixture was washed with 3×10 mL of water. The resulting mixture was concentrated under vacuum. The residue was applied onto a silica gel column and eluted with ethyl acetate/petroleum ether (1:5 to 1:10). This resulted in 1.88 g (91%) of the title compound as a yellow solid. MS-ESI: 208.1, 210.1 (M+1).

Steps 2-4 used similar procedures for converting compound 89 to Intermediate 51 shown in Scheme OO to afford Intermediate 60. MS-ESI: 249.1, 251.1 (M−1).

Intermediate 54

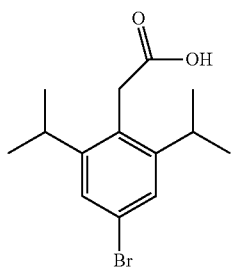 [SMILES: CC(C)c1cc(Br)cc(C(C)C)c1CC(=O)O]

Scheme RR: Preparation of 2-(4-bromo-2,6-diisopropylphenyl)acetic acid

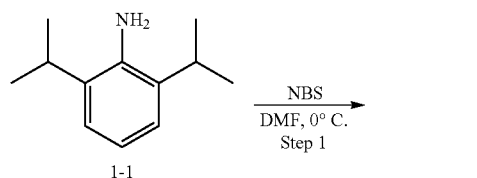

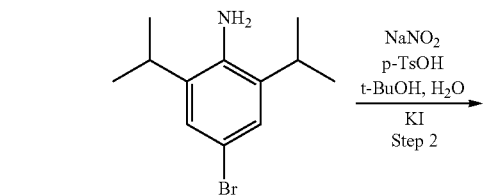

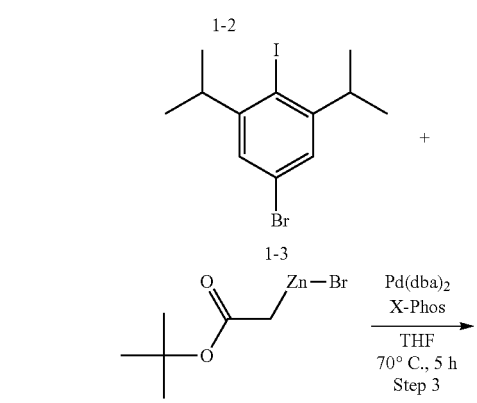

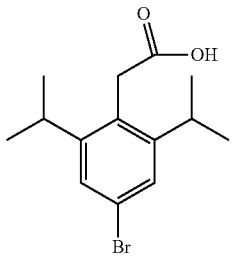

Intermediate 54

Step 1: Preparation of 4-bromo-2,6-diisopropylaniline

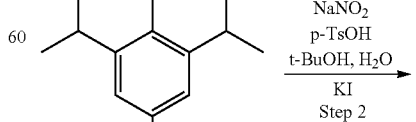

To a stirred solution of 2,6-diisopropylaniline (5.05 g, 28.4 mmol, 1.00 equiv) in N,N-dimethylformamide (70 mL) at 0° C. was added a solution of NBS (5.05 g, 28.4 mmol, 1.00 equiv) in N,N-dimethylformamide (30 mL) dropwise over 60 min. The reaction was stirred for another hour at 0° C., at which time water (300 mL) was added. The resulting mixture was extracted with ethyl acetate (2×300 mL), and the combined organic layers were washed with saturated NH$_4$Cl solution (3×100 mL) followed by water (100 mL) and dried over anhydrous sodium sulfate. Concentration of the solution under vacuum afforded 4-bromo-2,6-diisopropylaniline (6.5 g, 88% yield). LCMS (Method A): 256.1 [M+H]$^+$, retention time 2.97 min.

Step 2: Preparation of 5-bromo-2-iodo-1,3-diisopropylbenzene

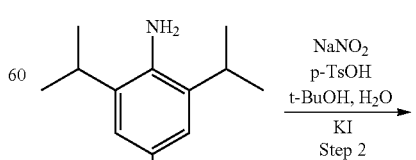

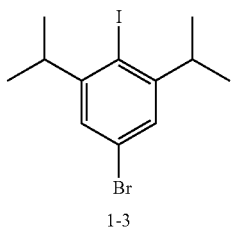

4-Bromo-2,6-diisopropylaniline (35.6 g, 138.96 mmol) was added to a suspension of p-TsOH monohydrate (118.95 g, 625.34 mmol) in a mixture of t-BuOH (500 mL) and water (30 mL). The mixture was cooled to 0° C. in an ice bath and a solution of sodium nitrite (28.76 g, 416.89 mmol) and potassium iodide (86.51 g, 521.11 mmol) in water (70 mL) was then added dropwise over 2.5 h, keeping the temperature of the mixture at 10-15° C. Following the addition, the temperature was then allowed to rise to 25° C., and the mixture was stirred for an additional 1.5 h. The reaction mixture was poured into water and extracted with $Et_2O$. The ether layer was then washed with 10% sodium bisulfite solution to remove iodine related by-products. The organic layer was dried over $MgSO_4$ and concentrated under reduced pressure. The residue was flushed through the silica gel plug eluting with hexane/EtOAc (100/0 to 90/10). Fractions containing the desired product were combined and concentrated under reduced pressure to afford pure 5-bromo-2-iodo-1,3-diisopropylbenzene (34.5 g, 67% yield). LCMS (Method A): 366.0 [M*], retention time 4.31 min.

Step 3: Preparation of tert-butyl 2-(4-bromo-2,6-diisopropylphenyl)acetate

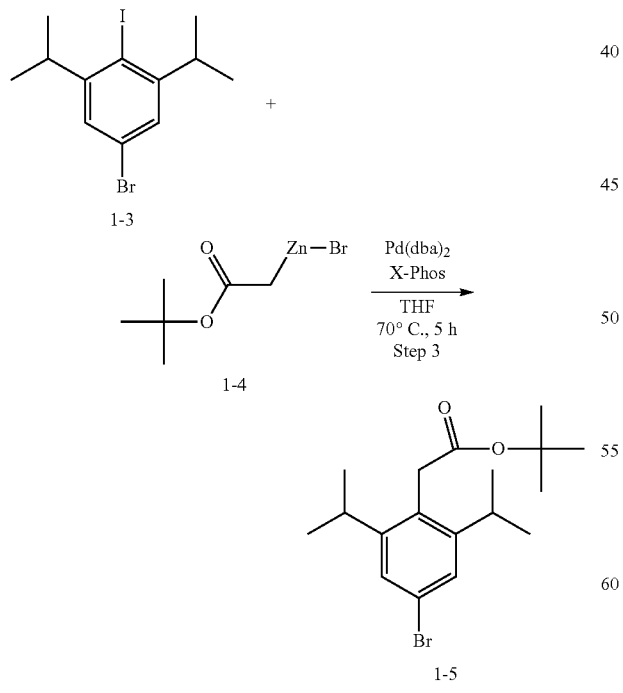

(2-(tert-butoxy)-2-oxoethyl)zinc(II) bromide solution: Under a $N_2$ atmosphere, to a 500 mL round-bottom flask were added zinc powder (32.19 g, 492.17 mmol), dry THF (200 mL), and TMSCl (2.08 mL, 16.41 mmol). The suspension was warmed to 56° C. and stirred at this temperature for 30 min. A solution of t-butyl bromoacetate (32 g, 164.06 mmol) in THF (50 mL) was added dropwise to the suspension. After insoluble matter precipitated, the light yellow supernatant solution was decanted and used for subsequent experiment as is. tert-Butyl 2-(4-bromo-2,6-diisopropylphenyl)acetate: Into a 5 L 3-necked round-bottom flask purged with and maintained under nitrogen, was placed 5-bromo-2-iodo-1,3-diisopropylbenzene (34.5 g, 93.99 mmol), THF (150 mL), X-phos (4.48 g, 9.4 mmol), $Pd_2(dba)_3CHCl_3$ (3.2 g, 4.7 mmol). The resulting solution was stirred for 0.5 h at room temperature, at which time the previously prepared solution of 2-(tert-butoxy)-2-oxoethyl)zinc(II) bromide was added. The resulting solution was stirred for 3 h at 76° C. and then quenched by the addition of 200 mL of $NH_4Cl$ (saturated). The organic layer was separated and the aqueous layer was back extracted with EtOAc (200 mL). The combined organic layers were washed with brine, dried over anhydrous sodium sulfate, filtered and concentrated. The crude product was purified by percolation through silica gel, eluting with mixtures of hexane and EtOAc. The product was analyzed on HPLC and had a retention time of 4.11 min using method A. Fractions containing pure product were concentrated and used in the next step without further purification.

Step 4: Preparation of 2-(4-bromo-2,6-diisopropylphenyl) acetic acid

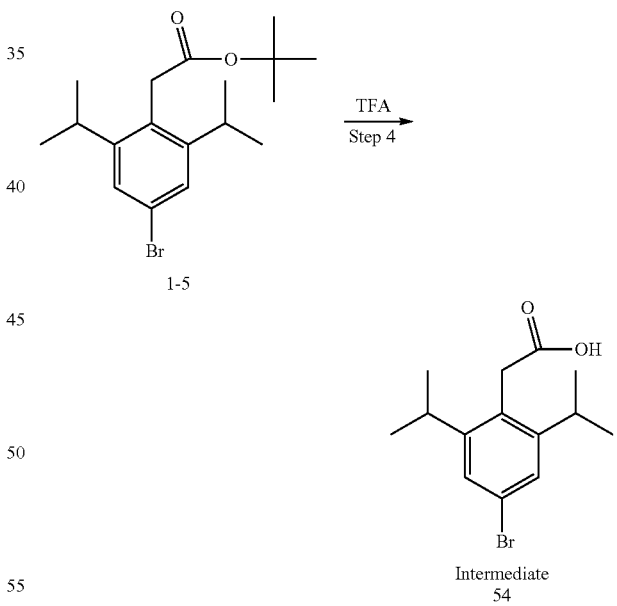

tert-Butyl 2-(4-bromo-2,6-diisopropylphenyl)acetate from the previous step was dissolved in dichloromethane (60 mL) and treated with TFA (35 mL). The reaction mixture was stirred overnight at room temperature and then concentrated and partially purified by silica gel flash chromatography. The majority of the desired product eluted with 100% hexanes, but further fractions collected from 1-20% EtOAc/hexanes also contained product. Those fractions which contained product were combined, concentrated in vacuo, and then partitioned between hexane and aqueous 10% $Na_2CO_3$.

The product-containing aqueous layer was washed once with hexanes and then acidified to pH-1 using 2N HCl. The product was extracted into EtOAc (150 mL×3). The combined organic layers were washed with brine, dried over anhydrous sodium sulfate, filtered and concentrated to give desired product 2-(4-bromo-2,6-diisopropylphenyl)acetic acid as white solid (7 g, 25% yield over two steps).

The product does not have discernible [M+H]$^+$ but does have a UV and ELSD signal. The retention time was 3.2 min on an LCMS run using method A. $^1$H NMR (250 MHz, DMSO-d$_6$): 7.26 (s, 2H), 3.68 (s, 2H), 3.08 (m, 2H), 1.13 (d, J=7.5 Hz, 12H).

Intermediates 55 and its Use in the Preparation of a Compound of Formula AA

Scheme SS: Preparation of 2-(4-bromo-2,6-diisopropylphenyl)-N-((4-((dimethylamino)methyl)phenyl)sulfonyl)acetamide)

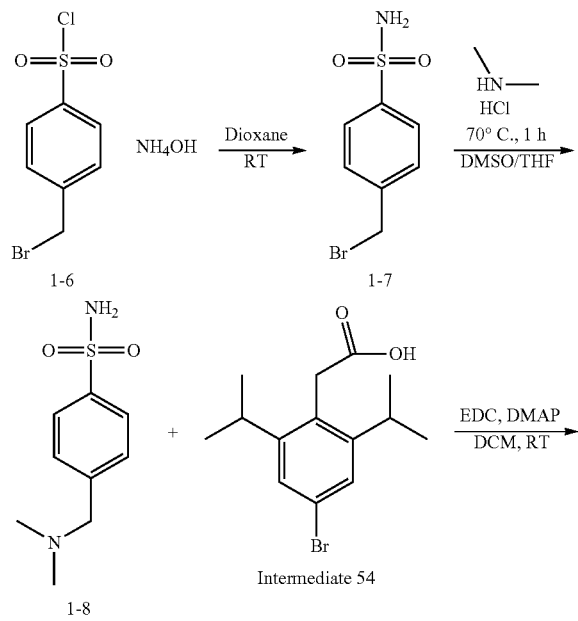

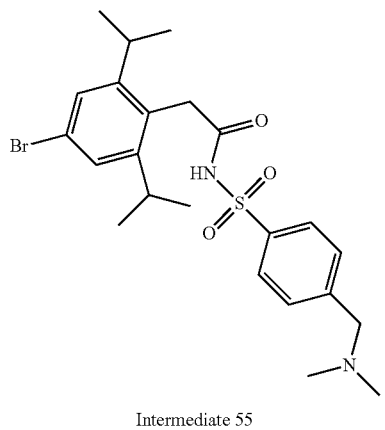

Intermediate 55

Step 1: Preparation of 4-(bromomethyl)benzenesulfonamide

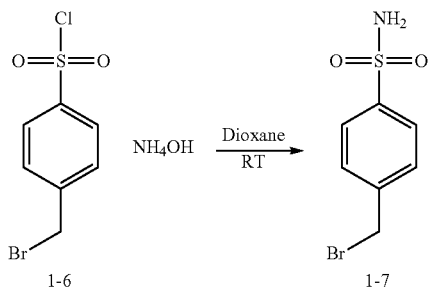

4-(bromomethyl)benzenesulfonyl chloride (2.5 g, 9.3 mmol) was dissolved in dioxane (20 mL). To this solution was added concentrated NH$_4$OH (5 mL). The solution was stirred at room temperature for 5 min. After the initial exotherm, the solution was poured into the water and extracted with EtOAc several times. The combined organic extracts were dried over MgSO$_4$, filtered and concentrated under reduced pressure. The resulting sulfonamide was used without further purification. Product does not ionize on LCMS but has a UV (254 nm) signal at 2.0 min (Method A).

Step 2: Preparation of 4-((dimethylamino)methyl)benzenesulfonamide

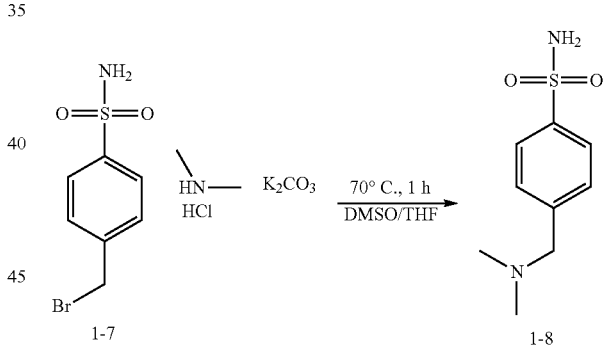

To a solution of 4-(bromomethyl)benzenesulfonamide (2.5 g, 10 mmol) in DMSO (10 mL) was added dimethylamine hydrochloride followed by K$_2$CO$_3$. The reaction mixture was heated at 70° C. for 1 h. LCMS showed complete conversion of the starting material and the mixture was poured into the water and extracted with EtOAc several times. The the product in the combined organic layers was extracted with 1M HCL. The aqueous phase was washed with EtOAc and dichloromethane to remove impurities and the aqueous layer was basified with 2M NaOH and extracted with EtOAc. The solution was dried over MgSO$_4$, filtered and concentrated under reduced pressure to afford pure 4-((dimethylamino)methyl) benzenesulfonamide as white crystals (0.800 g, 37% yield over two steps). LCMS (Method A): 215.1 [M+H]$^+$, retention time 0.86 min. H NMR (250 MHz, DMSO-d$_6$): 7.77 (d, J=7.5 Hz, 2H), 7.46 (d, J=7.5 Hz, 2H), 3.45 (s, 2H), 2.15 (s, 6H).

Step 3: Preparation of 2-(4-bromo-2,6-diisopropylphenyl)-N-((4-((dimethylamino)methyl)phenyl)-sulfonyl)acetamide

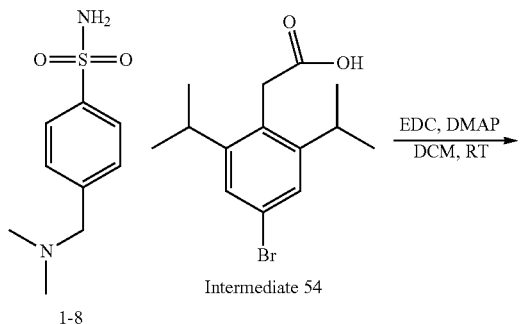

A solution of 2-(4-bromo-2,6-diisopropylphenyl)acetic acid (0.598 g, 2 mmol), 4-((dimethylamino)-methyl) benzene sulfonamide (0.643 g, 3 mmol, 1.5 eq.), 4-dimethyaminopyridine (DMAP, 0.489 g, 4 mmol, 2 equiv), and 1-[3-(dimethyamino)-propyl]-3-ethylcarbodiimide hydrochloride (EDCI, 0.767 g, 4 mmol, 2 eq.) in CH$_2$Cl$_2$ (15 mL) was stirred at room temperature for 1 h. After LCMS showed complete conversion of the acid, the reaction was quenched by the addition of water, and aqueous phase was extracted with DCM (3×50 mL). The combined organic layers were washed with brine and dried over MgSO$_4$, and evaporated in vacuo to afford 2-(4-bromo-2,6-diisopropylphenyl)-N-((4-((dimethylamino)methyl)phenyl)-sulfonyl)acetamide (0.891 g, 90% yield) of sufficient purity to be used as a scaffold for the cross coupling reactions without further purification. An analytically pure sample was obtained when the product was purified on HPLC with TFA buffer. LCMS (Method A): 497.3, 495.3 [M+H]$^+$, retention time 2.63 min. $^1$H NMR (250 MHz, DMSO-d$_6$): 7.79 (d, J=7.5 Hz, 2H), 7.46 (d, J=7.5 Hz, 2H), 7.14 (s, 2H), 3.86 (s, 2H), 3.58 (s, 2H), 2.97 (m, 2H), 2.41 (s, 6H), 0.97 (d, J=7.5 Hz, 12H).

General Protocol 1: General Procedure for Suzuki Coupling of 2-(4-bromo-2,6-diisopropylphenyl)-N-((4-((dimethylamino)methyl)phenyl)sulfonyl)acetamide with Boronic Acids/Esters

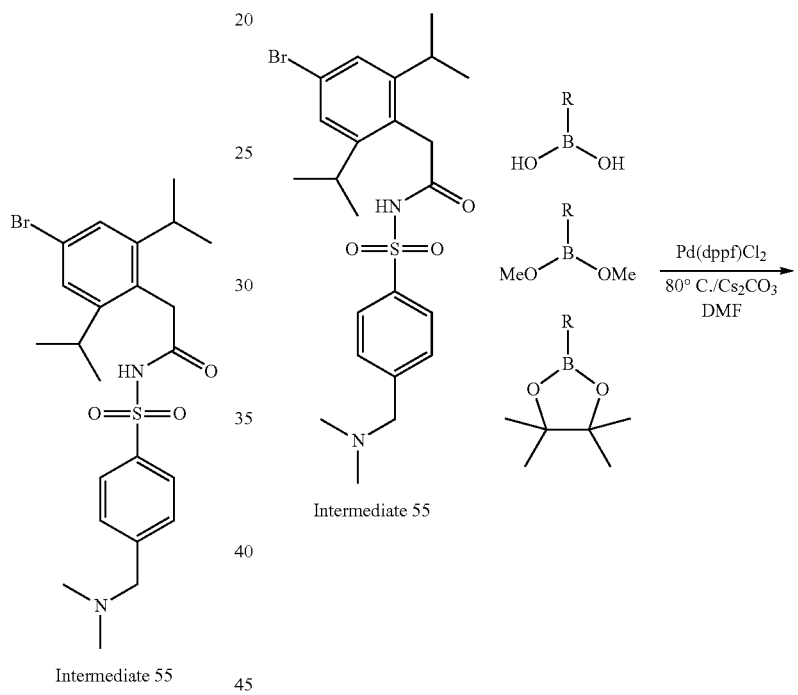

Scheme TT

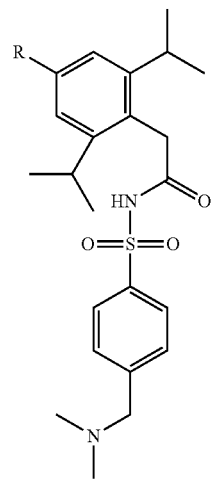

2-(4-bromo-2,6-diisopropylphenyl)-N-((4-((dimethyl-amino)methyl)phenyl)sulfonyl)acetamide (30.0 mg, 0.06 mmol, 1 equiv), a boronic acid or ester (0.18 mmol, 3 equiv), [1,1'-Bis(diphenylphosphino)ferrocene]dichloropalladium (II) (Pd(dppf)Cl₂, 22.15 mg, 0.5 equiv) and cesium carbonate (59.18 mg, 0.16 mmol, 3 equiv, 1M aqueous, 181.6 μL) were mixed with DMF (1 mL) and heated overnight at 80° C. The cooled mixture was filtered and the filtrate was purified by preparative HPLC method F. R in Scheme TT is as defined for Y—Z in Formula AA.

General Protocol 2: For Stille Coupling of 2-(4-bromo-2,6-diisopropylphenyl)-N-((4-((dimethyl-amino)methyl)phenyl)sulfonyl)acetamide with Aryl (Heteroaryl) Tributylstannanes Scheme UU

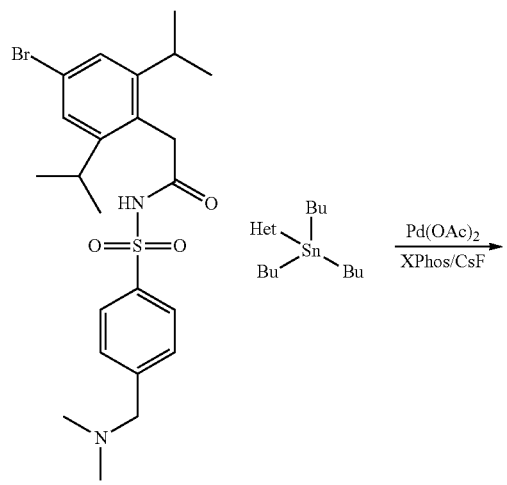

Intermediate 55

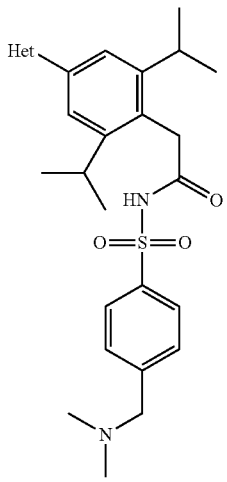

An intimate mixture of palladium acetate (11 mg, 0.05 mmol) and XPhos (53 mg, 0.11 mmol) was prepared in a 4 mL vial. Cesium fluoride was added (34 mg, 0.22 mmol) and the vial was purged with dry nitrogen. The heteroaryl tributylstannane (0.406 mmol) was added followed by 2-(4-bromo-2,6-diisopropylphenyl)-N-((4-((dimethylamino)methyl)phenyl)sulfonyl)acetamide (50 mg, 0.10 mmol) suspended/dissolved in anhydrous dimethoxyethane (1.5 mL). The reaction mixture was stirred vigorously at 80° C. for 2-4 h or until LCMS analysis indicated complete reaction. The cooled reaction mixture was filtered through a pad of Celite to remove solids and the Celite was washed with methanol and the combined organic solvents were evaporated to dryness. Purification was carried out by preparative HPLC method E. Het in Scheme UU is as defined for Y—Z in Formula AA.

Examples of compounds that may be prepared in a manner analogous to Schemes UU and TT are as follows:

| Structure | Example # Method | Compound Number | LCMS: [M + H]⁺ | Retention time (min) Method B | IUPAC NAME | ¹H NMR Tabulation |
|---|---|---|---|---|---|---|
| 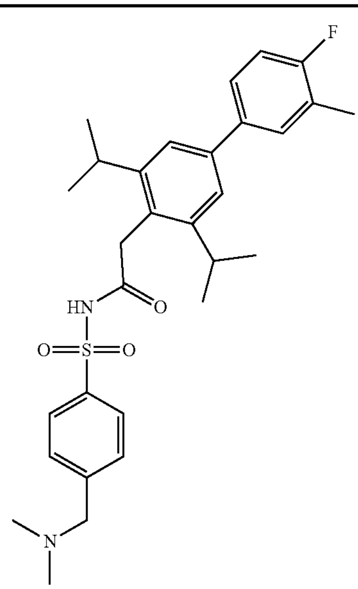 | 14 Suzuki | 101 | 525.4 | 2.37 | N-[4-[(dimethylamino)methyl]phenyl]sulfonyl-2-[4-(4-fluoro-3-methylphenyl)-2,6-di(propan-2-yl-phenyl]acetamide | |

-continued

| Structure | Example # Method | Compound Number | LCMS: [M + H]+ | Retention time (min) Method B | IUPAC NAME | ¹H NMR Tabulation |
|---|---|---|---|---|---|---|
| 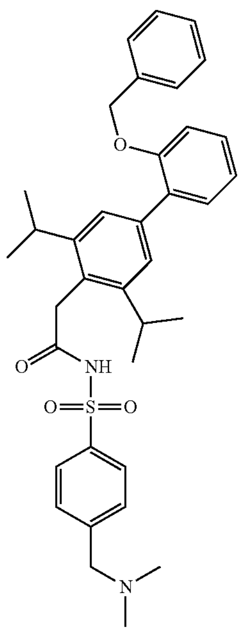 [SMILES: CC(C)c1cc(-c2ccccc2OCc2ccccc2)cc(C(C)C)c1CC(=O)NS(=O)(=O)c1ccc(CN(C)C)cc1] | 15 Suzuki | 102 | 599.6 | 2.49 | N-[4-[(dimethylamino)methyl]phenyl]sulfonyl-2-[4-(2-phenylmethoxyphenyl)-2,6-di(propan-2-yl)phenyl]acetamide | |
| 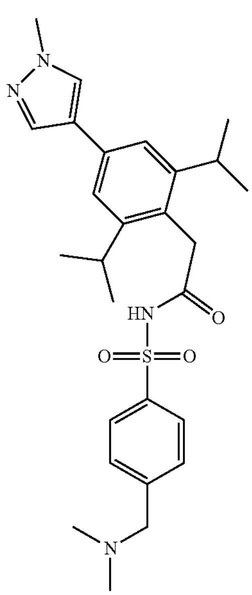 [SMILES: CC(C)c1cc(-c2cnn(C)c2)cc(C(C)C)c1CC(=O)NS(=O)(=O)c1ccc(CN(C)C)cc1] | 19 Suzuki | 106 | 497.5 | 1.77 | N-[4-[(dimethylamino)methyl]phenyl]sulfonyl-2-[4-(1-methylpyrazol-4-yl)-2,6-di(propan-2-yl)phenyl]acetamide | |

-continued

| Structure | Example # Method | Compound Number | LCMS: [M + H]+ | Retention time (min) Method B | IUPAC NAME | ¹H NMR Tabulation |
|---|---|---|---|---|---|---|
| 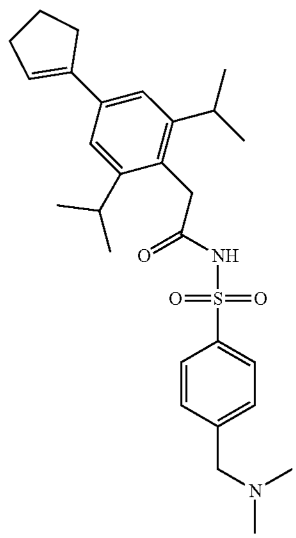 [SMILES: CC(C)c1cc(C2=CCCC2)cc(C(C)C)c1CC(=O)NS(=O)(=O)c1ccc(CN(C)C)cc1] | 20 Suzuki | 107 | 483.4 | 2.37 | 2-[4-(cyclopenten-1-yl)-2,6-di(propan-2-yl)phenyl]-N-[4-[(dimethylamino)methyl]phenyl]sulfonylacetamide | |
| 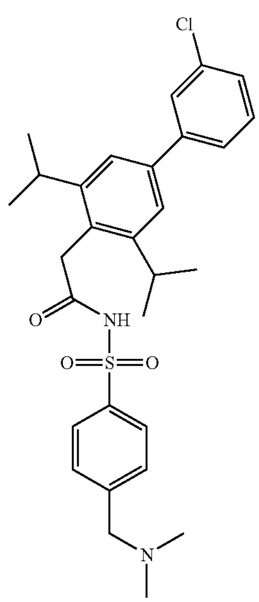 [SMILES: CC(C)c1cc(-c2cccc(Cl)c2)cc(C(C)C)c1CC(=O)NS(=O)(=O)c1ccc(CN(C)C)cc1] | 21 Suzuki | 108 | 527.2 | 2.37 | 2-[4-(3-chlorophenyl)-2,6-di(propan-2-yl)phenyl]-N-[4-[(dimethylamino)methyl]phenyl]sulfonylacetamide | |

-continued

| Structure | Example # Method | Compound Number | LCMS: [M + H]+ | Retention time (min) Method B | IUPAC NAME | ¹H NMR Tabulation |
|---|---|---|---|---|---|---|
| 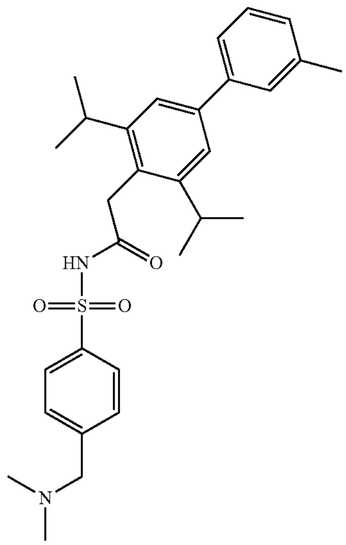 | 22 Suzuki | 109 | 507.4 | 2.36 | N-[4-[(dimethylamino)methyl]phenyl]sulfonyl-2-[4-(3-methylphenyl)-2,6-di(propan-2-yl)phenyl]acetamide | |
| 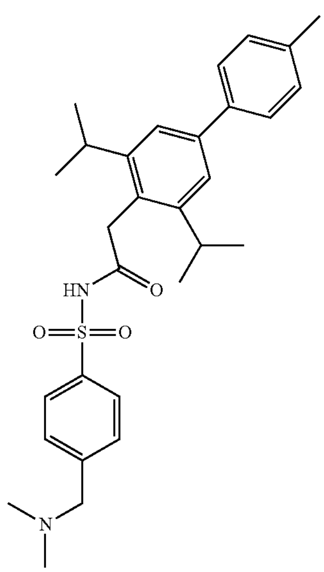 | 23 Suzuki | 110 | 507.4 | 2.33 | N-[4-[(dimethylamino)methyl]phenyl]sulfonyl-2-[4-(4-methylphenyl)-2,6-di(propan-2-yl)phenyl]acetamide | |

-continued

| Structure | Example # Method | Compound Number | LCMS: [M + H]+ | Retention time (min) Method B | IUPAC NAME | 1H NMR Tabulation |
|---|---|---|---|---|---|---|
| 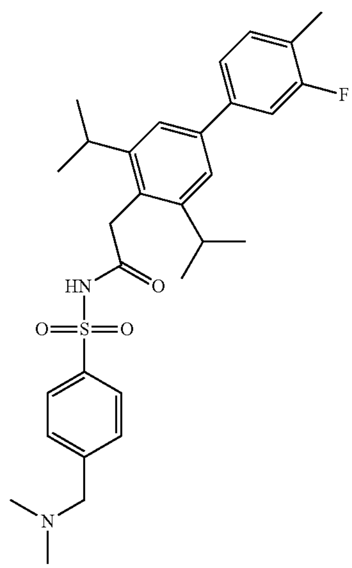 [SMILES: Cc1ccc(-c2cc(C(C)C)c(CC(=O)NS(=O)(=O)c3ccc(CN(C)C)cc3)c(C(C)C)c2)cc1F] | 24 Suzuki | 111 | 525.4 | 2.38 | N-[4-[(dimethylamino)methyl]phenyl]sulfonyl-2-[4-(3-fluoro-4-methylphenyl)-2,6-di(propan-2-yl)phenyl]acetamide | |
| 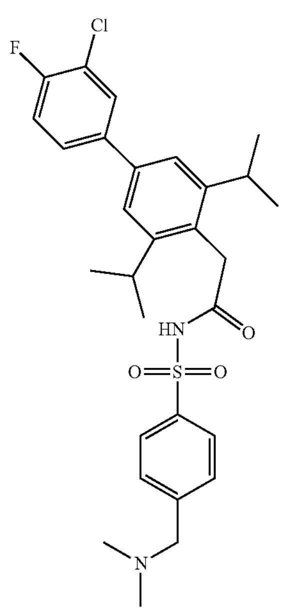 [SMILES: CC(C)c1cc(-c2ccc(F)c(Cl)c2)cc(C(C)C)c1CC(=O)NS(=O)(=O)c1ccc(CN(C)C)cc1] | 25 Suzuki | 112 | 545.2 | 2.38 | 2-[4-(3-chloro-4-fluorophenyl)-2,6-di(propan-2-yl)phenyl]-N-[4-[(dimethylamino)methyl]phenyl]sulfonylacetamide | |

-continued

| Structure | Example # Method | Compound Number | LCMS: [M + H]+ | Retention time (min) Method B | IUPAC NAME | ¹H NMR Tabulation |
|---|---|---|---|---|---|---|
| 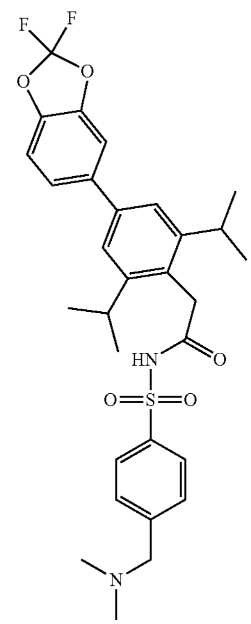 [SMILES: CC(C)c1cc(-c2ccc3c(c2)OC(F)(F)O3)cc(C(C)C)c1CC(=O)NS(=O)(=O)c1ccc(CN(C)C)cc1] | 26 Suzuki | 113 | 573.4 | 2.46 | 2-[4-(2,2-difluoro-1,3-benzodioxol-5-yl)-2,6-di(propan-2-yl)phenyl]-N-[4-[(dimethylamino)methyl]phenyl]sulfonylacetamide | |
| 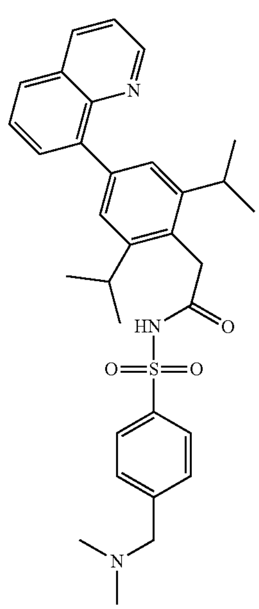 [SMILES: CC(C)c1cc(-c2cccc3cccnc23)cc(C(C)C)c1CC(=O)NS(=O)(=O)c1ccc(CN(C)C)cc1] | 27 Suzuki | 114 | 544.3 | 1.69 | N-[4-[(dimethylamino)methyl]phenyl]sulfonyl-2-[2,6-di(propan-2-yl)-4-quinolin-8-yl)phenyl]acetamide | |

-continued

| Structure | Example # Method | Compound Number | LCMS: [M + H]+ | Retention time (min) Method B | IUPAC NAME | ¹H NMR Tabulation |
|---|---|---|---|---|---|---|
| 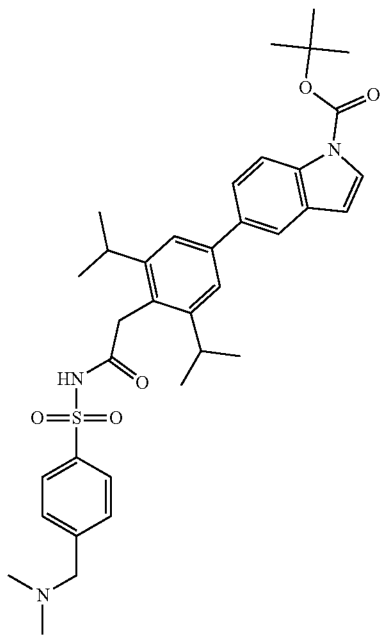 [SMILES: CC(C)c1cc(-c2ccc3c(ccn3C(=O)OC(C)(C)C)c2)cc(C(C)C)c1CC(=O)NS(=O)(=O)c1ccc(CN(C)C)cc1] | 28 Suzuki | 115 | 632.6 | 2.69 | tert-butyl 5-[4-[2-[[4-[(dimethylamino)methyl]phenyl]sulfonylamino]-2-oxoethyl]-3,5-di(propan-2-yl)phenyl]indole-1-carboxylate | 8.07 (d, J = 7.5 Hz, 1H), 8.0 (d, J = 7.5 Hz, 2H), 7.84 (s, 1H), 7.69 (m, 3H), 7.56 (d, J = 7.5 Hz, 1H), 7.33 (s, 2H), 6.76 (d, J = 2.5 Hz, 1H), 4.36 (s, 2H), 3.83 (s, 2H), 2.91 (m, 2H), 2.71 (s, 6H), 1.64 (s, 9H), 1.05 (d, J = 5 Hz, 12H). |
| 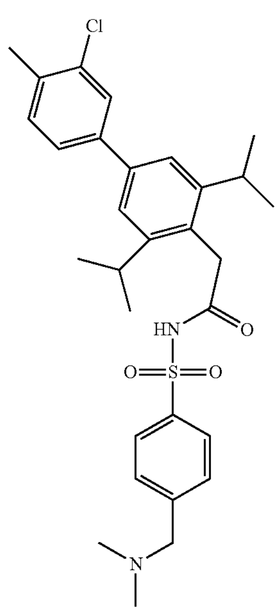 [SMILES: Cc1ccc(-c2cc(C(C)C)c(CC(=O)NS(=O)(=O)c3ccc(CN(C)C)cc3)c(C(C)C)c2)cc1Cl] | 29 Suzuki | 117 | 541.3 | 2.51 | 2-[4-(3-chloro-4-methylphenyl)-2,6-di(propan-2-yl)phenyl]-N-[4-[(dimethylamino)methyl]phenyl]sulfonylacetamide | |

-continued

| Structure | Example # Method | Compound Number | LCMS: [M + H]+ | Retention time (min) Method B | IUPAC NAME | ¹H NMR Tabulation |
|---|---|---|---|---|---|---|
| 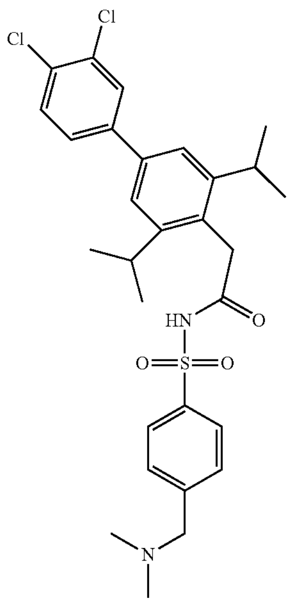 [SMILES: CC(C)c1cc(-c2ccc(Cl)c(Cl)c2)cc(C(C)C)c1CC(=O)NS(=O)(=O)c1ccc(CN(C)C)cc1] | 30 Suzuki | 119 | 561.1 | 2.54 | 2-[4-(3,4-dichlorophenyl)-2,6-di(propan-2-yl)phenyl]-N-[4-[(dimethylamino)methyl]phenyl]sulfonylacetamide | 7.98 (d, J = 7.5 Hz, 2H), 7.88 (d, J = 2.5 Hz, 1H), 7.59-7.72 (m, 4H), 7.31 (s, 2H), 4.35 (s, 2H), 3.82 (s, 2H), 2.91 (m, 2H), 2.70 (s, 6H), 1.03 (d, J = 5 Hz, 12H). |
| 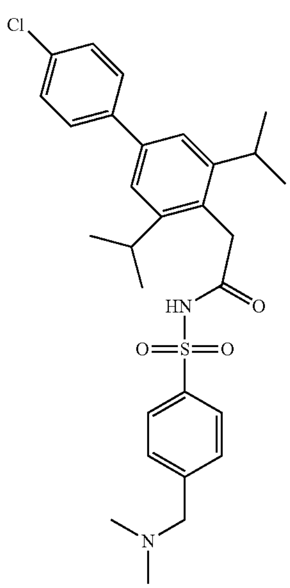 [SMILES: CC(C)c1cc(-c2ccc(Cl)cc2)cc(C(C)C)c1CC(=O)NS(=O)(=O)c1ccc(CN(C)C)cc1] | 31 Suzuki | 116 | 527.2 | 2.41 | 2-[4-(4-chlorophenyl)-2,6-di(propan-2-yl)phenyl]-N-[4-[(dimethylamino)methyl]phenyl]sulfonylacetamide | |

-continued
| Structure | Example # Method | Compound Number | LCMS: [M + H]+ | Retention time (min) Method B | IUPAC NAME | 1H NMR Tabulation |
|---|---|---|---|---|---|---|
| 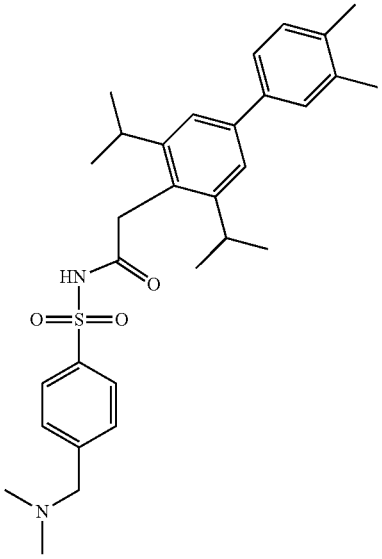 | 32 Suzuki | 118 | 521.5 | 2.46 | N-[4-[(dimethylamino)methyl]phenyl]sulfonyl-2-[4-(3,4-dimethylphenyl)-2,6-di(propan-2-yl)phenyl]acetamide | |
| 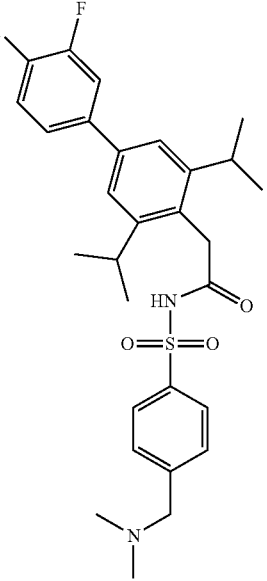 | 33 Suzuki | 120 | 545.2 | 2.43 | 2-[4-(4-chloro-3-fluorophenyl)-2,6-di(propan-2-yl)phenyl]-N-[4-[(dimethylamino)methyl]phenyl]sulfonylacetamide | |

| Structure | Example # Method | Compound Number | LCMS: [M + H]+ | Retention time (min) Method B | IUPAC NAME | 1H NMR Tabulation |
|---|---|---|---|---|---|---|
| 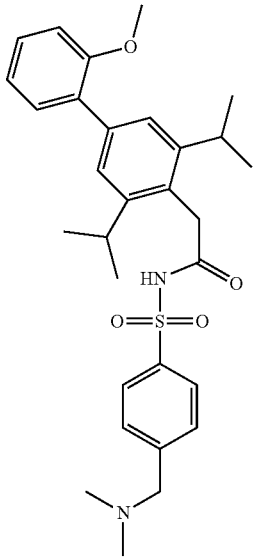 [SMILES: COc1ccccc1-c1cc(C(C)C)c(CC(=O)NS(=O)(=O)c2ccc(CN(C)C)cc2)c(C(C)C)c1] | 34 Suzuki | 121 | 523.3 | 2.23 | N-[4-[(dimethylamino)methyl]phenyl]sulfonyl-2-[4-(2-methoxyphenyl)-2,6-di(propan-2-yl)phenyl]acetamide | |
| 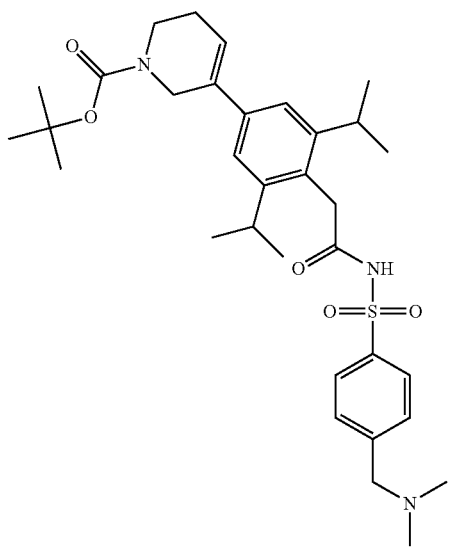 [SMILES: CC(C)c1cc(C2=CCCN(C(=O)OC(C)(C)C)C2)cc(C(C)C)c1CC(=O)NS(=O)(=O)c1ccc(CN(C)C)cc1] | 35 Suzuki | 122 | 598.4 | 2.37 | tert-butyl 5-[4-[2-[[4-[(dimethylamino)methyl]phenyl]sulfonylamino]-2-oxoethyl]-3,5-di(propan-2-yl)phenyl]-3,6-dihydro-2H-pyridine-1-carboxylate | |

-continued

| Structure | Example # Method | Compound Number | LCMS: [M + H]+ | Retention time (min) Method B | IUPAC NAME | ¹H NMR Tabulation |
|---|---|---|---|---|---|---|
| 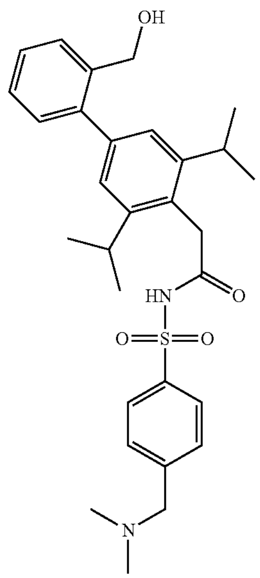 [SMILES: CC(C)c1cc(-c2ccccc2CO)cc(C(C)C)c1CC(=O)NS(=O)(=O)c1ccc(CN(C)C)cc1] | 37 Suzuki | 124 | 523.6 | 1.92 | N-[4-[(dimethylamino)methyl]phenyl]sulfonyl-2-[4-[2-(hydroxymethyl)phenyl]-2,6-di(propan-2-yl)phenyl]acetamide | |
| 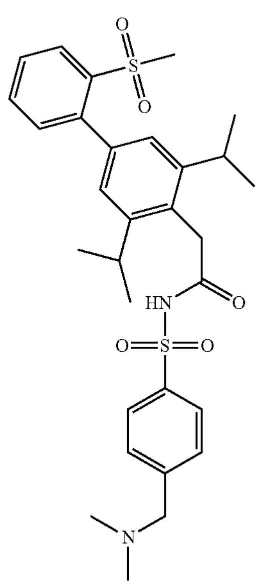 [SMILES: CC(C)c1cc(-c2ccccc2S(C)(=O)=O)cc(C(C)C)c1CC(=O)NS(=O)(=O)c1ccc(CN(C)C)cc1] | 38 Suzuki | 125 | 571.3 | 1.93 | N-[4-[(dimethylamino)methyl]phenyl]sulfonyl-2-[4-(2-methylsulfonylphenyl)-2,6-di(propan-2-yl)phenyl]acetamide | |

| Structure | Example # Method | Compound Number | LCMS: [M + H]+ | Retention time (min) Method B | IUPAC NAME | 1H NMR Tabulation |
|---|---|---|---|---|---|---|
| 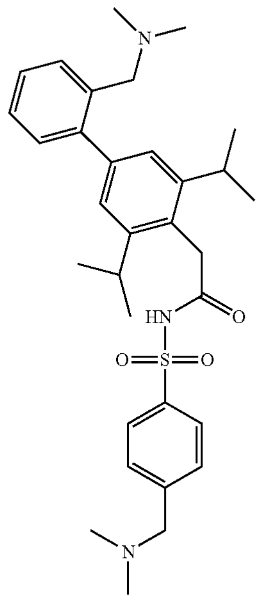 [SMILES: CC(C)c1cc(-c2ccccc2CN(C)C)cc(C(C)C)c1CC(=O)NS(=O)(=O)c1ccc(CN(C)C)cc1] | 41 Suzuki | 128 | 550.6 | 1.58 | 2-[4-[2-[(dimethylamino)methyl]phenyl]-2,6-di(propan-2-yl)phenyl]-N-[4-[(dimethylamino)methyl]phenyl]sulfonyl-acetamide | |
| 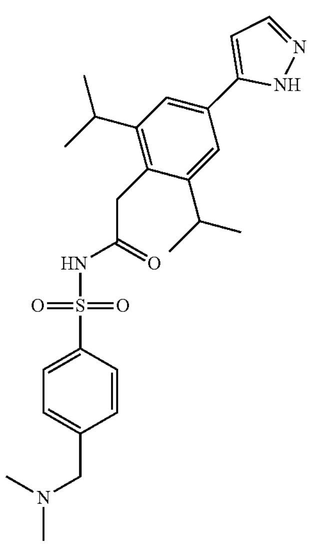 [SMILES: CC(C)c1cc(-c2ccn[nH]2)cc(C(C)C)c1CC(=O)NS(=O)(=O)c1ccc(CN(C)C)cc1] | 45 Suzuki | 134 | 483.39 | 1.66 | N-[4-[(dimethylamino)methyl]phenyl]sulfonyl-2-[2,6-di(propan-2-yl)-4-(1H-pyrazol-5-yl)phenyl]acetamide | |

| Structure | Example # Method | Compound Number | LCMS: [M + H]+ | Retention time (min) Method B | IUPAC NAME | ¹H NMR Tabulation |
|---|---|---|---|---|---|---|
| 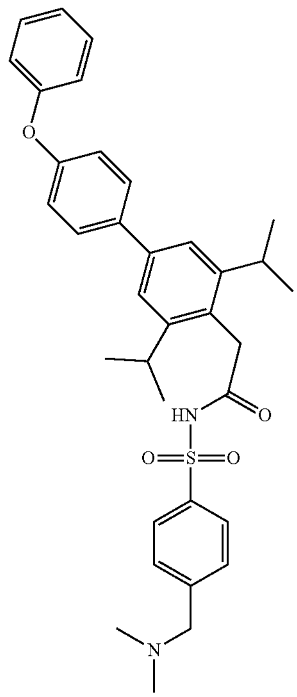 [SMILES: CC(C)c1cc(-c2ccc(Oc3ccccc3)cc2)cc(C(C)C)c1CC(=O)NS(=O)(=O)c1ccc(CN(C)C)cc1] | 46 Suzuki | 131 | 585.45 | 2.60 | N-[4-[(dimethylamino)methyl]phenyl]sulfonyl-2-[4-(4-phenoxyphenyl)-2,6-di(propan-2-yl)phenyl]acetamide | |
| 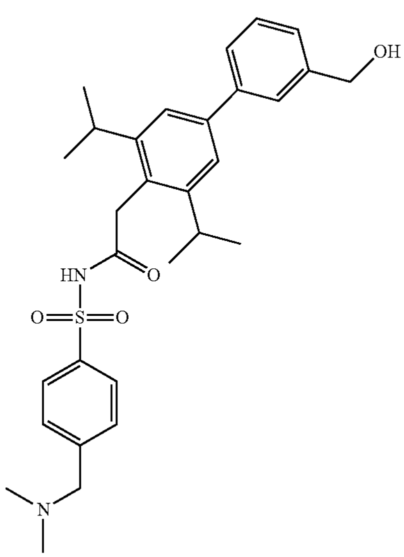 [SMILES: CC(C)c1cc(-c2cccc(CO)c2)cc(C(C)C)c1CC(=O)NS(=O)(=O)c1ccc(CN(C)C)cc1] | 47 Suzuki | 132 | 523.61 | 1.87 | N-[4-[(dimethylamino)methyl]phenyl]sulfonyl-2-[4-[3-(hydroxymethyl)phenyl]-2,6-di(propan-2-yl)phenyl]acetamide | |

-continued
| Structure | Example # Method | Compound Number | LCMS: [M + H]+ | Retention time (min) Method B | IUPAC NAME | 1H NMR Tabulation |
|---|---|---|---|---|---|---|
| 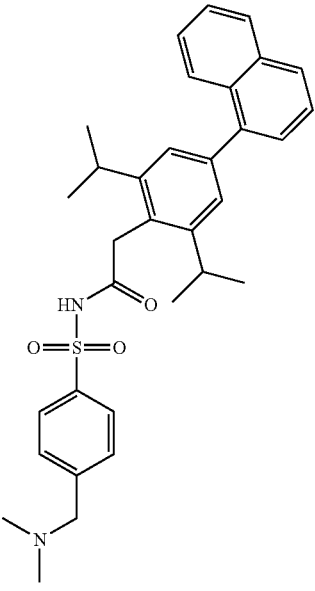 [SMILES: CC(C)c1cc(-c2cccc3ccccc23)cc(C(C)C)c1CC(=O)NS(=O)(=O)c1ccc(CN(C)C)cc1] | 50 Suzuki | 137 | 543.42 | 2.53 | N-[4-[(dimethylamino)methyl]phenyl]sulfonyl-2-[4-naphthalen-1-yl-2,6-di(propan-2-yl)phenyl]acetamide | |
| 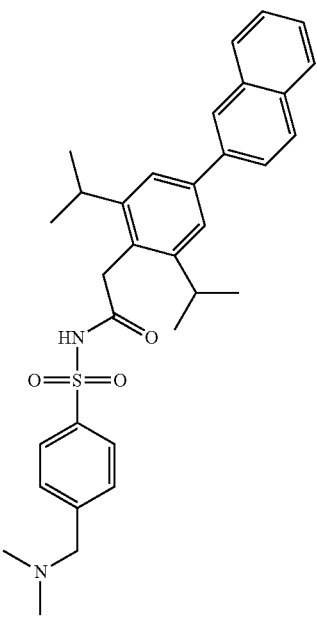 [SMILES: CC(C)c1cc(-c2ccc3ccccc3c2)cc(C(C)C)c1CC(=O)NS(=O)(=O)c1ccc(CN(C)C)cc1] | 51 Suzuki | 139 | 543.42 | 2.46 | N-[4-[(dimethylamino)methyl]phenyl]sulfonyl-2-[4-naphthalen-2-yl-2,6-di(propan-2-yl)phenyl]acetamide | |

-continued

| Structure | Example # Method | Compound Number | LCMS: [M + H]+ | Retention time (min) Method B | IUPAC NAME | 1H NMR Tabulation |
|---|---|---|---|---|---|---|
| 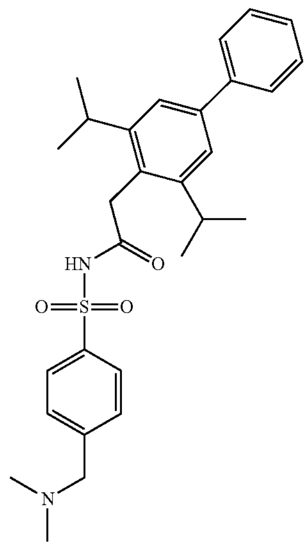 [SMILES: CC(C)c1cc(-c2ccccc2)cc(C(C)C)c1CC(=O)NS(=O)(=O)c1ccc(CN(C)C)cc1] | 52 Suzuki | 140 | 493.3 | 2.24 | N-[4-[(dimethylamino)methyl]phenyl]sulfonyl-2-[4-phenyl-2,6-di(propan-2-yl)phenyl]acetamide | |
| 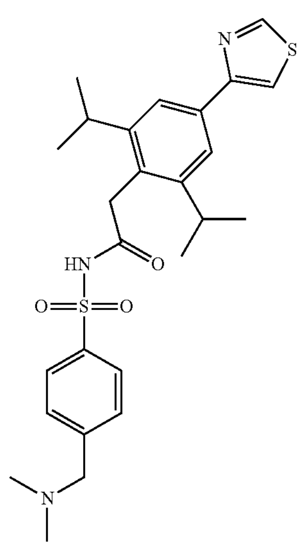 [SMILES: CC(C)c1cc(-c2cscn2)cc(C(C)C)c1CC(=O)NS(=O)(=O)c1ccc(CN(C)C)cc1] | 53 Stille | 143 | 500.2 | 1.85 | N-[4-[(dimethylamino)methyl]phenyl]sulfonyl-2-[2,6-di(propan-2-yl)-4-(1,3-thiazol-4-yl)phenyl]acetamide | |

-continued

| Structure | Example # Method | Compound Number | LCMS: [M + H]+ | Retention time (min) Method B | IUPAC NAME | ¹H NMR Tabulation |
|---|---|---|---|---|---|---|
| 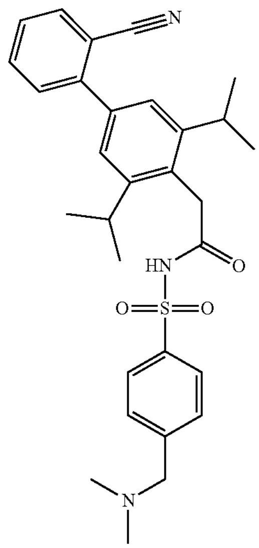 [SMILES: CC(C)c1cc(-c2ccccc2C#N)cc(C(C)C)c1CC(=O)NS(=O)(=O)c1ccc(CN(C)C)cc1] | 56 Suzuki | 138 | 518.21 | 2.08 | 2-[4-(2-cyanophenyl)-2,6-di(propan-2-yl)phenyl]-N-[4-[(dimethylamino)methyl]phenyl]sulfonylacetamide | |
| 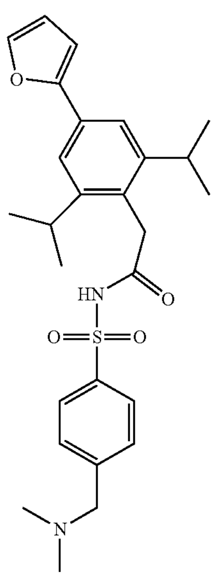 [SMILES: CC(C)c1cc(-c2ccco2)cc(C(C)C)c1CC(=O)NS(=O)(=O)c1ccc(CN(C)C)cc1] | 57 Suzuki | 144 | 483.39 | 2.13 | N-[4-[(dimethylamino)methyl]phenyl]sulfonyl-2-[4-(furan-2-yl)-2,6-di(propan-2-yl)phenyl]acetamide | |

| Structure | Example # Method | Compound Number | LCMS: [M + H]+ | Retention time (min) Method B | IUPAC NAME | 1H NMR Tabulation |
|---|---|---|---|---|---|---|
| 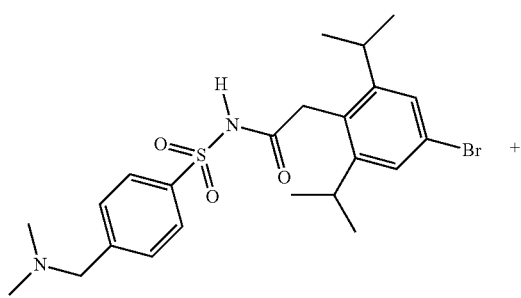 | 59 Suzuki | 161 | 541.3 | 2.63 | 2-[4-(4-chloro-3-methylphenyl)-2,6-bis(propan-2-yl)phenyl]-N-{4-[(dimethylamino)methyl]benzenesulfonyl}acetamide | |

Preparation of 2-[2,6-bis(propan-2-yl)-4-(tetramethyl-1,3,2-dioxaborolan-2-yl)phenyl]-N-{4-[(dimethylamino)methyl]benzenesulfonyl}acetamide Scheme VV

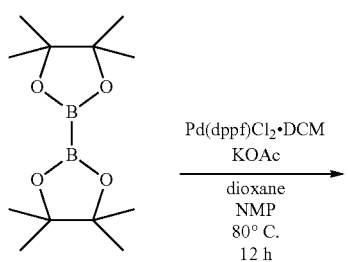

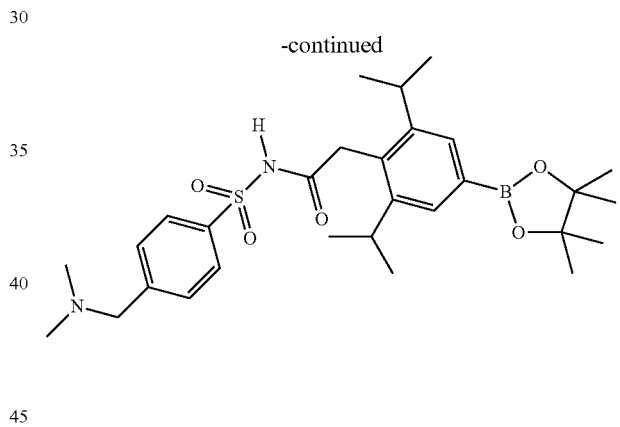

To a solution of 2-(4-bromo-2,6-diisopropylphenyl)-N-((4-((dimethylamino)methyl)phenyl)-sulfonyl)acetamide (530 mg, 1.06 mmol) in dioxane (20 mL) and NMP (2 mL) was added 4,4,5,5-tetramethyl-2-(4,4,5,5-tetramethyl-1,3,2-dioxaborolan-2-yl)-1,3,2-dioxaborolane (410 mg, 1.61 mmol), Pd(dppf)Cl$_2$·DCM (86 mg, 0.106 mmol) and potassium acetate (312 mg, 3.18 mmol). The resulting mixture was stirred at 80° C. for 12 h. Reaction mixture was brought to room temperature, filtered through a pad of celite, diluted with water (50 mL) and extracted with EtOAc (3×30 mL). The combined organic layer was washed water and brine, dried over anhydrous sodium sulfate, filtered and concentrated in vacuo to provide titled compound (437 mg, 75%) as light buff color solid.

541

General Procedure for Reverse Suzuki Coupling of 2-[2,6-bis(propan-2-yl)-4-(tetramethyl-1,3,2-dioxaborolan-2-yl)phenyl]-N-{4-[(dimethylamino)methyl]benzenesulfonyl}acetamide with Aryl Bromides and Heteroaryl Chlorides/Bromides

542

General Procedure for Sonogashira Coupling of 2-(4-bromo-2,6-diisopropylphenyl)-N-((4-((dimethylamino)methyl)phenyl)sulfonyl)acetamide with Alkynes

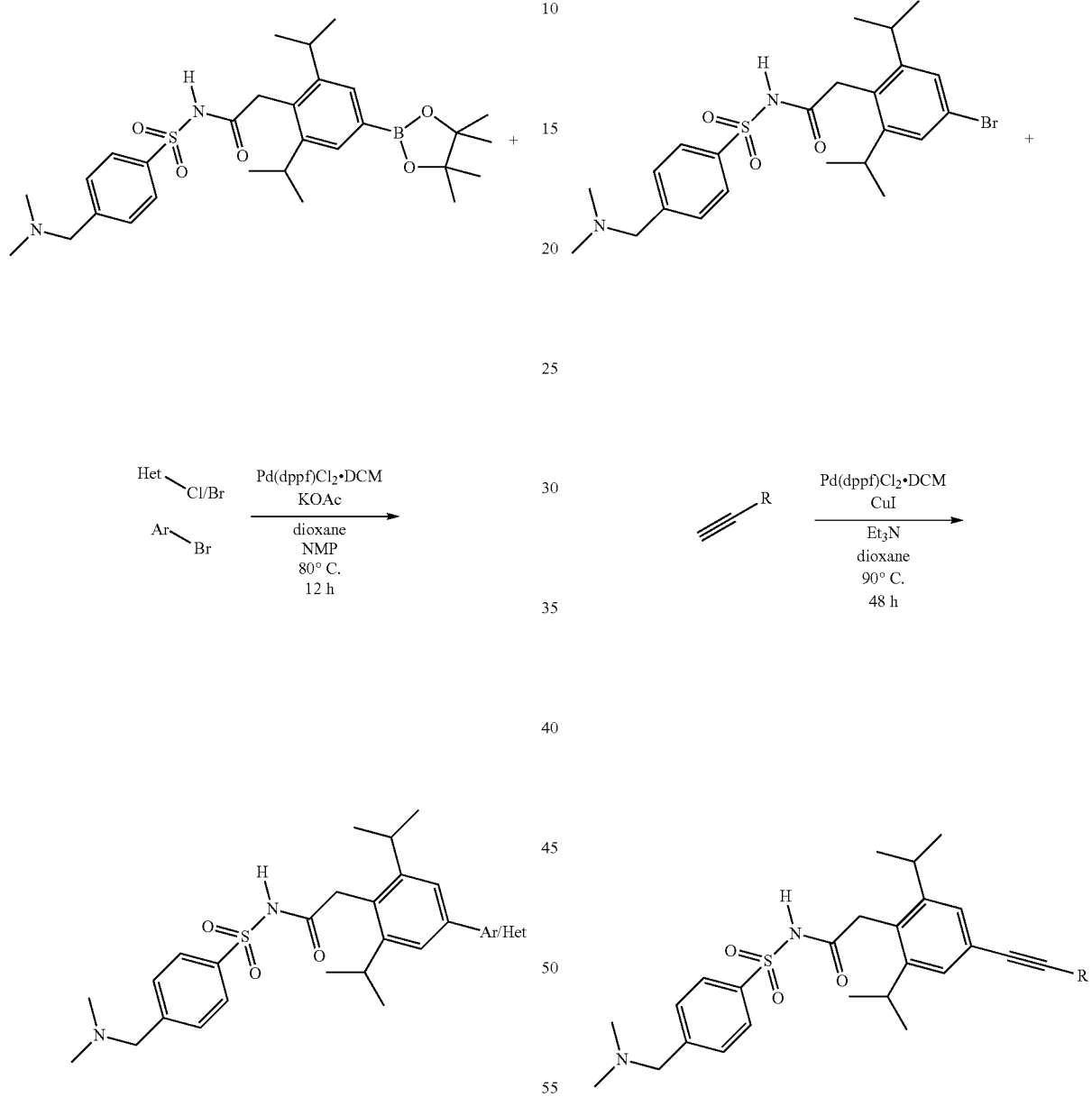

To a solution of 2-[2,6-bis(propan-2-yl)-4-(tetramethyl-1,3,2-dioxaborolan-2-yl)phenyl]-N-{4-[(dimethylamino)methyl]benzenesulfonyl}acetamide (0.1 mmol) in dioxane (1.5 mL) was added arylbromide or heteroaryl chloride or bromide (0.2 mmol), Pd(dppf)Cl$_2$·DCM (0.01 mmol) and 1M aqueous cesium carbonate solution (0.3 mL). The resulting mixture was stirred at 80° C. for 12 h. Reaction mixture was brought to room temperature, filtered through a pad of celite and rinsed with EtOAc (5 mL). Filtrates were concentrated in vacuo and purified by prep-HPLC to obtain desired product.

To a solution of 2-(4-bromo-2,6-diisopropylphenyl)-N-((4-((dimethylamino)methyl)phenyl)-sulfonyl)acetamide (0.2 mmol) in dioxane (0.8 mL) was added alkyne (0.4 mol), Pd(dppf)Cl$_2$·DCM (0.02 mmol), CuI (0.02 mmol) and triethylamine (0.6 mmol) at room temperature. The resulting mixture was then stirred at 90° C. for 48 h. Reaction mixture was brought to room temperature, filtered through a pad of celite and rinsed with EtOAc (5 mL). Filtrates were concentrated in vacuo and purified by prep-HPLC to obtain desired product.

General Procedure for the Hydrogenation of Unsaturated Compounds

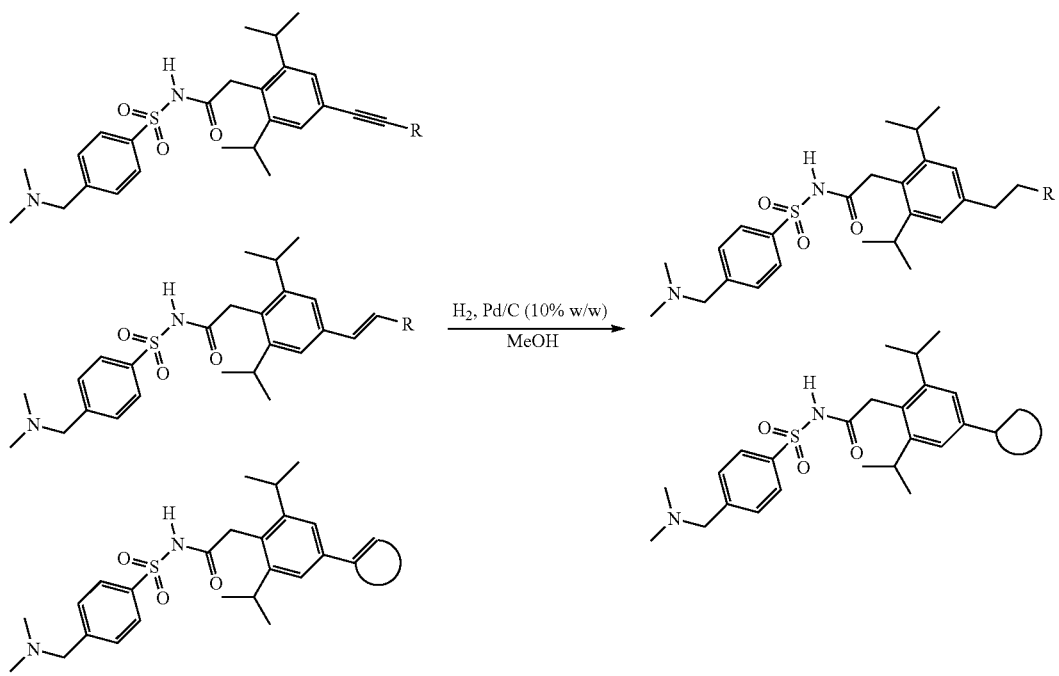

Scheme YY

Hydrogenation Method A

To a solution of unsaturated starting material (0.1 mmol) in MeOH (15 mL) was added 10 weight % Pd/C (10% w/w), trifluoroacetic acid (0.5 mL) and the resulting mixture was hydrogenated at 45 psi for 12 h. Reaction mixture was filtered through a pad of celite, filtrates were concentrated and purified by prep-HPLC.

Hydrogenation Method B

To a solution of unsaturated starting material (crude obtained either from Suzuki or Sonogashira coupling at 0.1 mmol scale) in ethyl acetate (15 mL) was added Pd(OH)$_2$ (22 mg) and trifluoroacetic acid (0.2 mL) and the resulting mixture was hydrogenated at 45 psi for 12 h. Reaction mixture was filtered through a pad of celite, filtrates were concentrated and purified by prep-HPLC.

General Procedure for the De-protection of tert-Butyloxycarbonyl (Boc) Group 25% TFA/DCM solution (1.3 mL) was added to Boc-protected amine (0.065 mmol) at 0° C. The resulting solution was then warmed up to room temperature and stirred until the completion of reaction. Reaction mixture was concentrated in vacuo and purified by prep-HPLC.

Examples of compounds that may be prepared in a manner analogous to Schemes VV, WW, XX and/or YY are as follows:

| Structure | Example # Method | Compound # | LCMS: [M + H]+ | Retention time (min) Method B | IUPAC NAME |
|---|---|---|---|---|---|
| 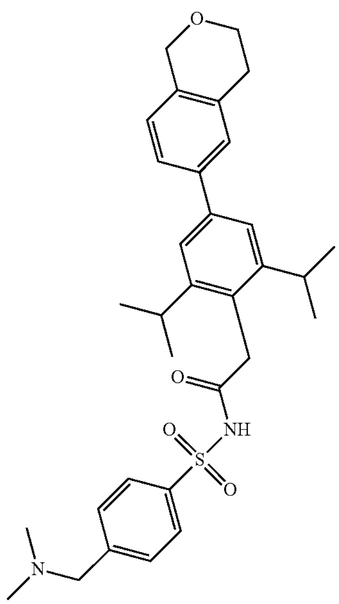 [SMILES: CC(C)c1cc(-c2ccc3c(c2)CCOC3)cc(C(C)C)c1CC(=O)NS(=O)(=O)c1ccc(CN(C)C)cc1] | 62 Suzuki | 301 | 549.43 | 2.17 | 2-[4-(3,4-dihydro-1H-2-benzopyran-6-yl)-2,6-bis(propan-2-yl)phenyl]-N-{4-[(dimethylamino)methyl]benzene-sulfonyl}-acetamide |
| 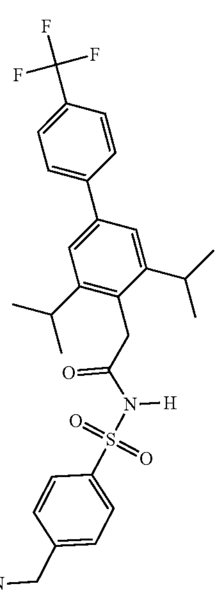 | 63 Suzuki | 302 | 561.44 | 2.50 | 2-[2,6-bis(propan-2-yl)-4-[4-(trifluoromethyl)phenyl]phenyl]-N-{4-[(dimethylamino)methyl]benzene-sulfonyl}acetamide |

| Structure | Example # Method | Compound # | LCMS: [M + H]+ | Retention time (min) Method B | IUPAC NAME |
|---|---|---|---|---|---|
| 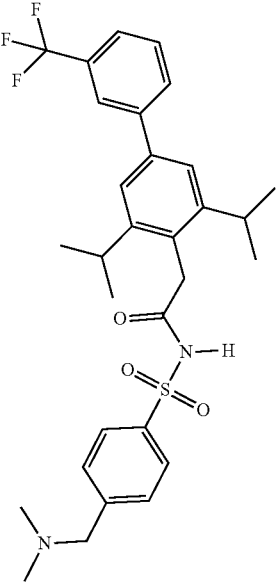 [SMILES: CC(C)c1cc(-c2cccc(C(F)(F)F)c2)cc(C(C)C)c1CC(=O)NS(=O)(=O)c1ccc(CN(C)C)cc1] | 64 Suzuki | 303 | 561.44 | 2.47 | 2-[2,6-bis(propan-2-yl)-4-[3-(trifluoromethyl)phenyl]phenyl]-N-{4-[(dimethylamino)methyl]benzene-sulfonyl}acetamide |
| 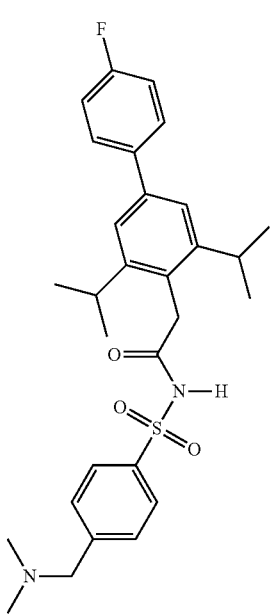 [SMILES: CC(C)c1cc(-c2ccc(F)cc2)cc(C(C)C)c1CC(=O)NS(=O)(=O)c1ccc(CN(C)C)cc1] | 65 Suzuki | 304 | 511.61 | 2.31 | N-{4-[(dimethylamino)methyl]benzene-sulfonyl}-2-[4-(4-fluorophenyl)-2,6-bis(propan-2-yl)phenyl]acetamide |

-continued

| Structure | Example # Method | Compound # | LCMS: [M + H]+ | Retention time (min) Method B | IUPAC NAME |
|---|---|---|---|---|---|
| 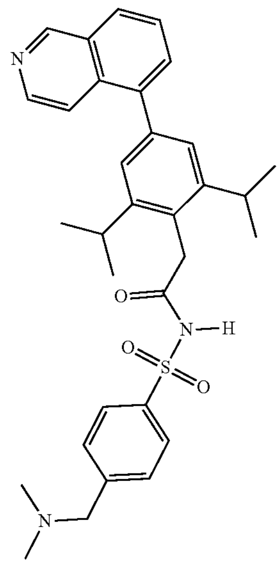 [SMILES: CC(C)c1cc(-c2cccc3cnccc23)cc(C(C)C)c1CC(=O)NS(=O)(=O)c1ccc(CN(C)C)cc1] | 66 Suzuki | 305 | 544.33 | 1.55 | N-{4-[(dimethylamino)methyl]benzene-sulfonyl}-2-[4-(isoquinolin-5-yl)-2,6-bis(propan-2-yl)phenyl]acetamide |
| 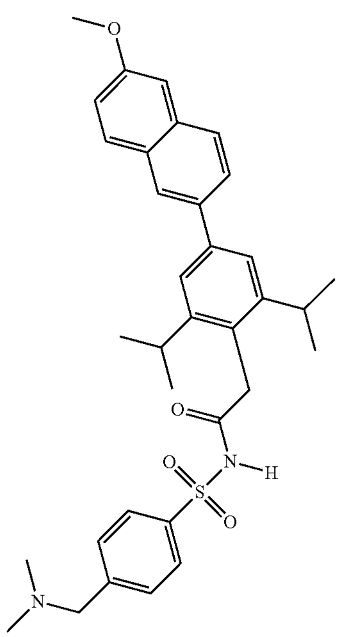 [SMILES: COc1ccc2cc(-c3cc(C(C)C)c(CC(=O)NS(=O)(=O)c4ccc(CN(C)C)cc4)c(C(C)C)c3)ccc2c1] | 67 Suzuki | 306 | 573.44 | 2.46 | N-{4-[(dimethylamino)methyl]benzene-sulfonyl}-2-[4-(6-methoxynaphthalen-2-yl)-2,6-bis(propan-2-yl)phenyl]acetamide |

-continued

| Structure | Example # Method | Compound # | LCMS: [M + H]⁺ | Retention time (min) Method B | IUPAC NAME |
|---|---|---|---|---|---|
| 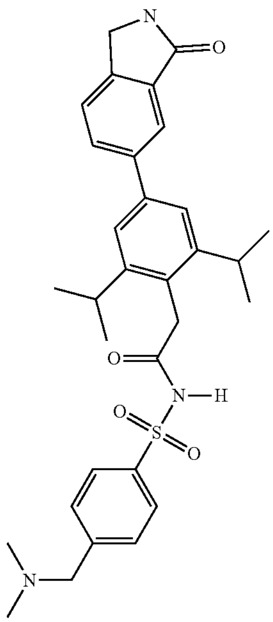 [SMILES: CC(C)c1cc(-c2ccc3c(c2)C(=O)NC3)cc(C(C)C)c1CC(=O)NS(=O)(=O)c1ccc(CN(C)C)cc1] | 68 Suzuki | 307 | 548.23 | 1.75 | N-{4-[(dimethylamino)methyl]benzene-sulfonyl}-2-[4-(3-oxo-2,3-dihydro-1H-isoindol-5-yl)-2,6-bis(propan-2-yl)phenyl]acetamide |
| 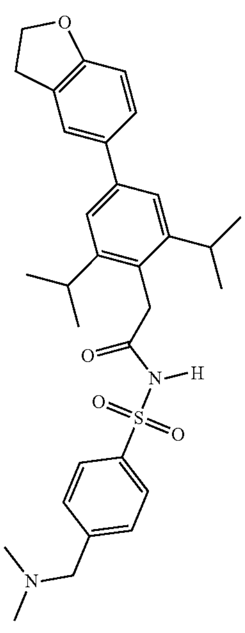 [SMILES: CC(C)c1cc(-c2ccc3c(c2)CCO3)cc(C(C)C)c1CC(=O)NS(=O)(=O)c1ccc(CN(C)C)cc1] | 69 Suzuki | 308 | 535.32 | 2.22 | 2-[4-(2,3-dihydro-1-benzofuran-5-yl)-2,6-bis(propan-2-yl)phenyl]-N-{4-[(dimethylamino)methyl]benzene-sulfonyl}acetamide |

-continued
| Structure | Example # Method | Compound # | LCMS: [M + H]+ | Retention time (min) Method B | IUPAC NAME |
|---|---|---|---|---|---|
| 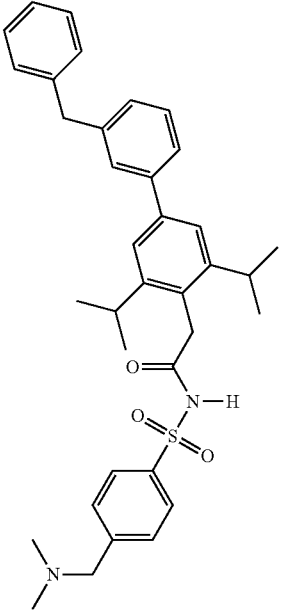 [SMILES: CC(C)c1cc(-c2cccc(Cc3ccccc3)c2)cc(C(C)C)c1CC(=O)NS(=O)(=O)c1ccc(CN(C)C)cc1] | 70 Suzuki | 309 | 583.35 | 2.67 | 2-[4-(3-benzylphenyl)-2,6-bis(propan-2-yl)phenyl]-N-{4-[(dimethylamino)methyl]benzene-sulfonyl}acetamide |
| 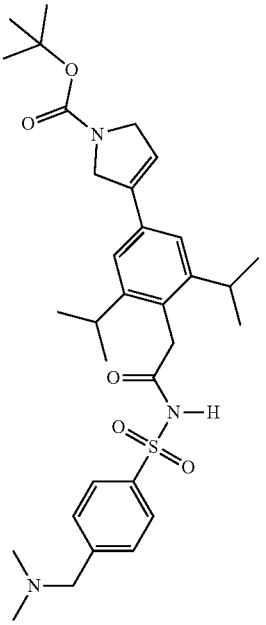 [SMILES: CC(C)c1cc(C2=CCN(C(=O)OC(C)(C)C)C2)cc(C(C)C)c1CC(=O)NS(=O)(=O)c1ccc(CN(C)C)cc1] | 71 Suzuki | 310 | 584.55 | 2.32 | tert-butyl 3-{4-[({4-[(dimethylamino)methyl]benzene-sulfonyl}carbamoyl)methyl]-3,5-bis(propan-2-yl)phenyl}-2,5-dihydro-1H-pyrrole-1-carboxylate |

-continued

| Structure | Example # Method | Compound # | LCMS: [M + H]+ | Retention time (min) Method B | IUPAC NAME |
|---|---|---|---|---|---|
| 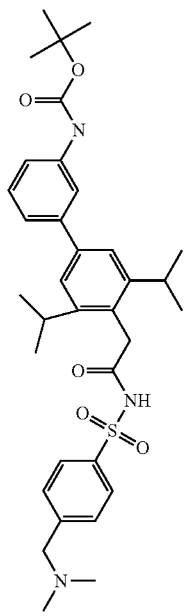 [SMILES: CC(C)c1cc(-c2cccc(NC(=O)OC(C)(C)C)c2)cc(C(C)C)c1CC(=O)NS(=O)(=O)c1ccc(CN(C)C)cc1] | 72 Suzuki | 311 | 608.56 | 2.41 | tert-butyl N-(3-{4-[({4-[(dimethylamino)methyl]benzenesulfonyl}carbamoyl)methyl]-3,5-bis(propan-2-yl)phenyl}phenyl)carbamate |
| 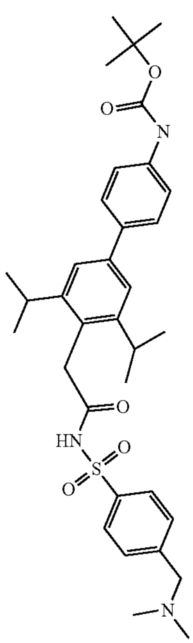 [SMILES: CC(C)c1cc(-c2ccc(NC(=O)OC(C)(C)C)cc2)cc(C(C)C)c1CC(=O)NS(=O)(=O)c1ccc(CN(C)C)cc1] | 73 Suzuki | 312 | 608.56 | 2.40 | tert-butyl N-(4-{4-[({4-[(dimethylamino)methyl]benzenesulfonyl}carbamoyl)methyl]-3,5-bis(propan-2-yl)phenyl}phenyl)carbamate |

-continued

| Structure | Example # Method | Compound # | LCMS: [M + H]⁺ | Retention time (min) Method B | IUPAC NAME |
|---|---|---|---|---|---|
| 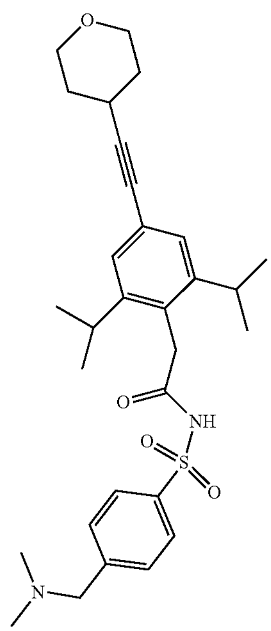 [SMILES: CC(C)c1cc(C#CC2CCOCC2)cc(C(C)C)c1CC(=O)NS(=O)(=O)c1ccc(CN(C)C)cc1] | 74 Sonogashira | 313 | 525.42 | 2.07 | N-{4-[(dimethylamino)methyl]benzenesulfonyl}-2-{4-[2-(oxan-4-yl)ethynyl]-2,6-bis(propan-2-yl)phenyl}acetamide |
| 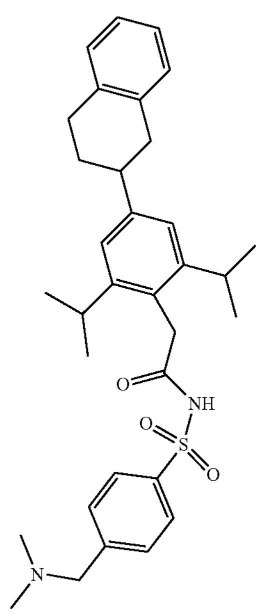 [SMILES: CC(C)c1cc(C2CCc3ccccc3C2)cc(C(C)C)c1CC(=O)NS(=O)(=O)c1ccc(CN(C)C)cc1] | 75 Suzuki Hydrogenation Method (A) | 314 | 547.33 | 2.51 | 2-[2,6-bis(propan-2-yl)-4-(1,2,3,4-tetrahydronaphthalen-2-yl)phenyl]-N-{4-[(dimethylamino)methyl]benzenesulfonyl}acetamide |

-continued

| Structure | Example # Method | Compound # | LCMS: [M + H]⁺ | Retention time (min) Method B | IUPAC NAME |
|---|---|---|---|---|---|
| | 76 Suzuki Hydrogenation Method (A) | 315 | 487.29 | 1.81 | N-{4-[(dimethylamino)methyl]benzenesulfonyl}-2-[4-(oxolan-3-yl)-2,6-bis(propan-2-yl)phenyl]acetamide |
| | 77 Suzuki Hydronation Method (A) | 316 | 527.20 | 2.67 | N-{4-[(dimethylamino)methyl]benzenesulfonyl}-2-[4-(4,4-dimethylcyclohexyl)-2,6-bis(propan-2-yl)phenyl]acetamide |

-continued

| Structure | Example # Method | Compound # | LCMS: [M + H]+ | Retention time (min) Method B | IUPAC NAME |
|---|---|---|---|---|---|
| 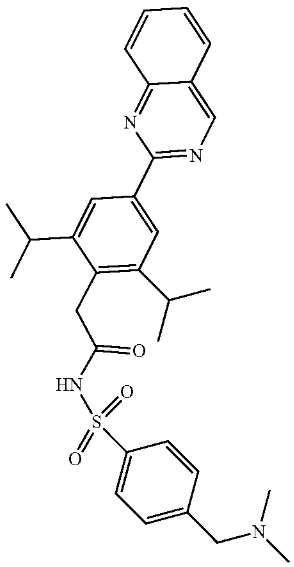 [SMILES: CC(C)c1cc(-c2ncc3ccccc3n2)cc(C(C)C)c1CC(=O)NS(=O)(=O)c1ccc(CN(C)C)cc1] | 78 Reverse Suzuki | 317 | 545.20 | 2.04 | 2-[2,6-bis(propan-2-yl)-4-(quinazolin-2-yl)phenyl]-N-{4-[(dimethylamino)methyl]benzenesulfonyl}acetamide |
| 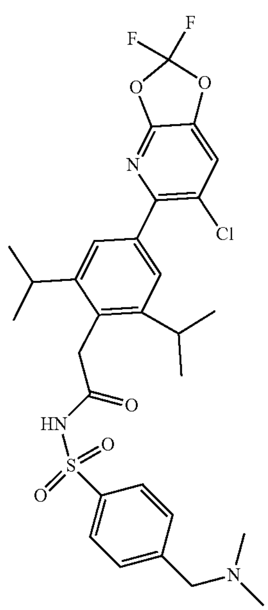 [SMILES: CC(C)c1cc(-c2nc3c(cc2Cl)OC(F)(F)O3)cc(C(C)C)c1CC(=O)NS(=O)(=O)c1ccc(CN(C)C)cc1] | 79 Reverse Suzuki | 318 | 607.10 | 2.62 | 2-[4-(6-chloro-2,2-difluoro-2H-1,3-benzodioxol-5-yl)-2,6-bis(propan-2-yl)phenyl]-N-{4-[(dimethylamino)methyl]benzenesulfonyl}acetamide |

-continued

| Structure | Example # Method | Compound # | LCMS: [M + H]+ | Retention time (min) Method B | IUPAC NAME |
|---|---|---|---|---|---|
| 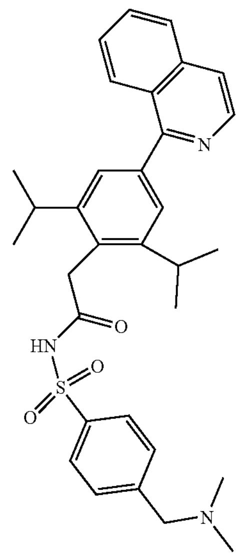 [SMILES: CC(C)c1cc(-c2nccc3ccccc23)cc(C(C)C)c1CC(=O)NS(=O)(=O)c1ccc(CN(C)C)cc1] | 80 Reverse Suzuki | 319 | 544.30 | 1.58 | N-{4-[(dimethylamino)methyl]benzene-sulfonyl}-2-[4-(isoquinolin-1-yl)-2,6-bis(propan-2-yl)phenyl]acetamide |
| 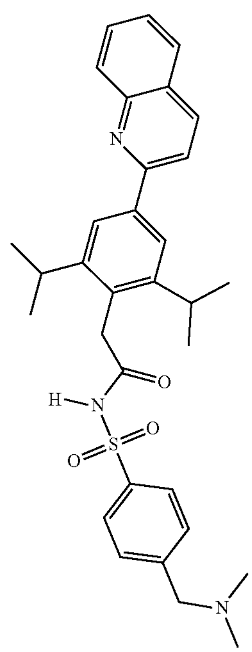 [SMILES: CC(C)c1cc(-c2ccc3ccccc3n2)cc(C(C)C)c1CC(=O)NS(=O)(=O)c1ccc(CN(C)C)cc1] | 81 Reverse Suzuki | 320 | 544.30 | 1.67 | 2-[2,6-bis(propan-2-yl)-4-(quinolin-2-yl)phenyl]-N-{4-[(dimethylamino)methyl]benzene-sulfonyl}acetamide |

-continued

| Structure | Example # Method | Compound # | LCMS: [M + H]+ | Retention time (min) Method B | IUPAC NAME |
|---|---|---|---|---|---|
| 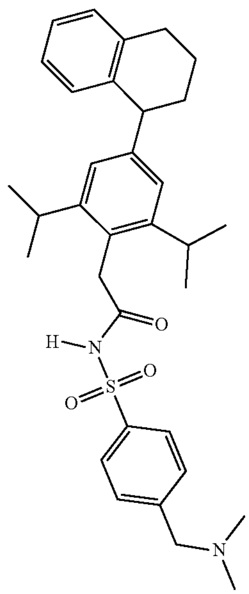 [SMILES: CC(C)c1cc(C2CCCc3ccccc32)cc(C(C)C)c1CC(=O)NS(=O)(=O)c1ccc(CN(C)C)cc1] | 82 Suzuki Hydrogenation Method (B) | 321 | 547.33 | 2.55 | 2-[2,6-bis(propan-2-yl)-4-(1,2,3,4-tetrahydronaphthalen-1-yl)phenyl]-N-{4-[(dimethylamino)methyl]benzenesulfonyl}acetamide |
| 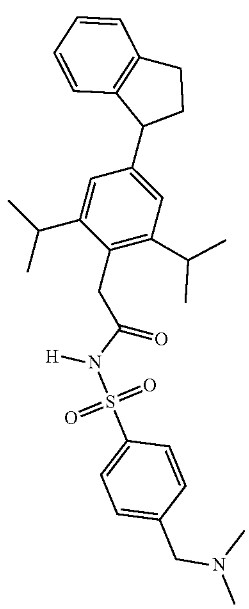 [SMILES: CC(C)c1cc(C2CCc3ccccc32)cc(C(C)C)c1CC(=O)NS(=O)(=O)c1ccc(CN(C)C)cc1] | 83 Suzuki Hydrogenation Method (A) | 322 | 533.22 | 2.48 | 2-[4-(2,3-dihydro-1H-inden-1-yl)-2,6-bis(propan-2-yl)phenyl]-N-{4-[(dimethylamino)methyl]benzenesulfonyl}acetamide |

| Structure | Example # Method | Compound # | LCMS: [M + H]+ | Retention time (min) Method B | IUPAC NAME |
|---|---|---|---|---|---|
| 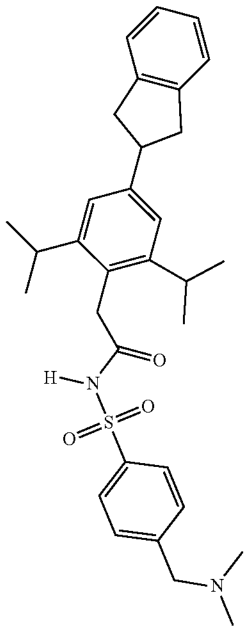 [SMILES: CC(C)c1cc(C2Cc3ccccc3C2)cc(C(C)C)c1CC(=O)NS(=O)(=O)c1ccc(CN(C)C)cc1] | 84 Suzuki Hydrogenation Method (B) | 323 | 533.22 | 2.48 | 2-[4-(2,3-dihydro-1H-inden-2-yl)-2,6-bis(propan-2-yl)phenyl]-N-{4-[(dimethylamino)methyl]benzenesulfonyl}acetamide |
| 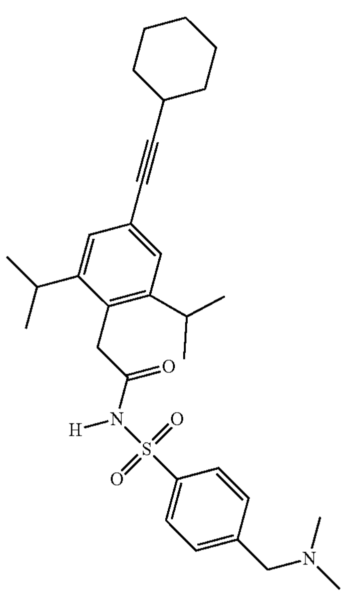 [SMILES: CC(C)c1cc(C#CC2CCCCC2)cc(C(C)C)c1CC(=O)NS(=O)(=O)c1ccc(CN(C)C)cc1] | 85 Sonogashira | 324 | 523.62 | 2.66 | 2-[4-(2-cyclohexylethynyl)-2,6-bis(propan-2-yl)phenyl]-N-{4-[(dimethylamino)methyl]benzenesulfonyl}acetamide |

-continued

| Structure | Example # Method | Compound # | LCMS: [M + H]+ | Retention time (min) Method B | IUPAC NAME |
|---|---|---|---|---|---|
| 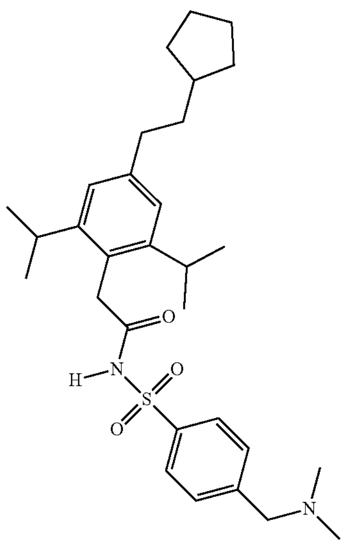 [SMILES: CC(C)c1cc(CCC2CCCC2)cc(C(C)C)c1CC(=O)NS(=O)(=O)c1ccc(CN(C)C)cc1] | 86 Sonogashira Hydrogenation (Method A) | 325 | 513.41 | 2.72 | 2-[4-(2-cyclopentylethyl)-2,6-bis(propan-2-yl)phenyl]-N-{4-[(dimethylamino)methyl]benzene-sulfonyl}acetamide |
| 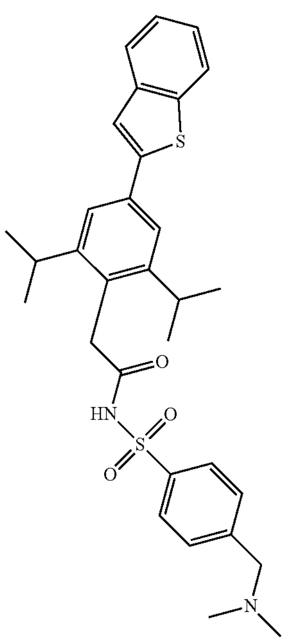 [SMILES: CC(C)c1cc(-c2cc3ccccc3s2)cc(C(C)C)c1CC(=O)NS(=O)(=O)c1ccc(CN(C)C)cc1] | 87 Suzuki | 326 | 549.43 | 2.49 | 2-[4-(1-benzothiophen-2-yl)-2,6-bis(propan-2-yl)phenyl]-N-{4-[(dimethylamino)methyl]benzene-sulfonyl}acetamide |

-continued
| Structure | Example # Method | Compound # | LCMS: [M + H]+ | Retention time (min) Method B | IUPAC NAME |
|---|---|---|---|---|---|
| 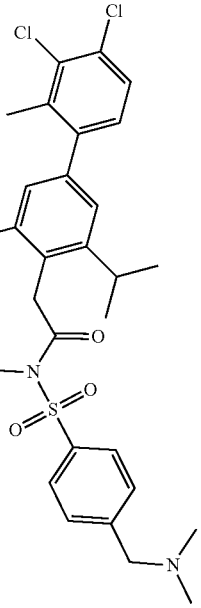 | 88 Suzuki | 327 | 575.24 | 2.70 | 2-[4-(3,4-dichloro-2-methylphenyl)-2,6-bis(propan-2-yl)phenyl]-N-{4-[(dimethylamino)methyl]benzenesulfonyl}acetamide |
| 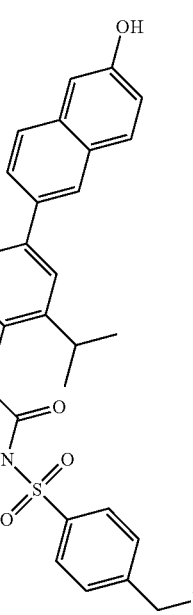 | 89 Suzuki | 328 | 559.34 | 2.04 | N-{4-[(dimethylamino)methyl]benzenesulfonyl}-2-[4-(6-hydroxynaphthalen-2-yl)-2,6-bis(propan-2-yl)phenyl]acetamide |

-continued

| Structure | Example # Method | Compound # | LCMS: [M + H]+ | Retention time (min) Method B | IUPAC NAME |
|---|---|---|---|---|---|
| 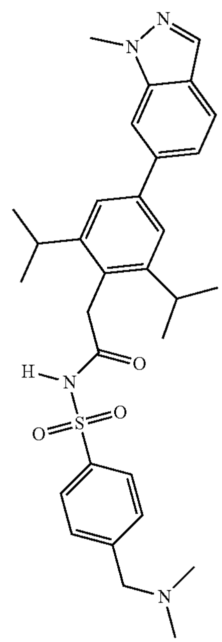 [SMILES: CC(C)c1cc(-c2ccc3cnn(C)c3c2)cc(C(C)C)c1CC(=O)NS(=O)(=O)c1ccc(CN(C)C)cc1] | 90 Suzuki | 329 | 547.33 | 2.04 | N-{4-[(dimethylamino)methyl]benzene-sulfonyl}-2-[4-(1-methyl-1H-indazol-6-yl)-2,6-bis(propan-2-yl)phenyl]acetamide |
| 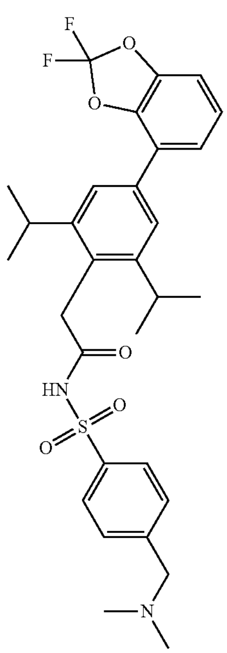 [SMILES: CC(C)c1cc(-c2cccc3c2OC(F)(F)O3)cc(C(C)C)c1CC(=O)NS(=O)(=O)c1ccc(CN(C)C)cc1] | 91 Suzuki | 330 | 573.44 | 2.46 | 2-[4-(2,2-difluoro-2H-1,3-benzodioxol-4-yl)-2,6-bis(propan-2-yl)phenyl]-N-{4-[(dimethylamino)methyl]benzene-sulfonyl}acetamide |

| Structure | Example # Method | Compound # | LCMS: [M + H]+ | Retention time (min) Method B | IUPAC NAME |
|---|---|---|---|---|---|
| 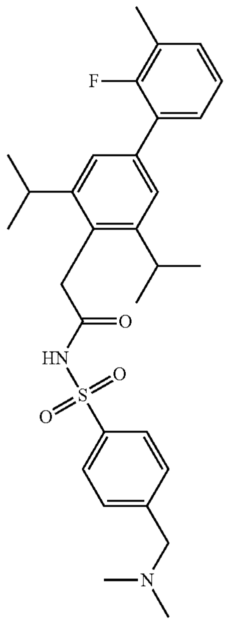 [SMILES: Cc1cccc(-c2cc(C(C)C)c(CC(=O)NS(=O)(=O)c3ccc(CN(C)C)cc3)c(C(C)C)c2)c1F] | 92 Suzuki | 331 | 525.42 | 2.41 | N-{4-[(dimethylamino)methyl]benzene-sulfonyl}-2-[4-(2-fluoro-3-methylphenyl)-2,6-bis(propan-2-yl)phenyl]acetamide |
| 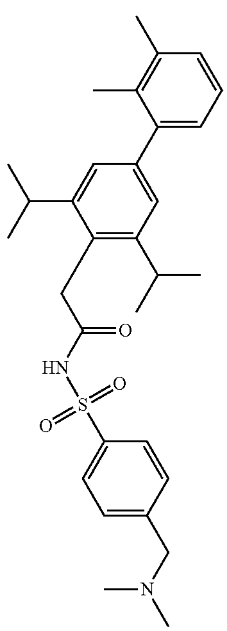 [SMILES: Cc1cccc(-c2cc(C(C)C)c(CC(=O)NS(=O)(=O)c3ccc(CN(C)C)cc3)c(C(C)C)c2)c1C] | 93 Suzuki | 332 | 521.52 | 2.51 | N-{4-[(dimethylamino)methyl]benzene-sulfonyl}-2-[4-(2,3-dimethylphenyl)-2,6-bis(propan-2-yl)phenyl]acetamide |

-continued

| Structure | Example # Method | Compound # | LCMS: [M + H]+ | Retention time (min) Method B | IUPAC NAME |
|---|---|---|---|---|---|
| 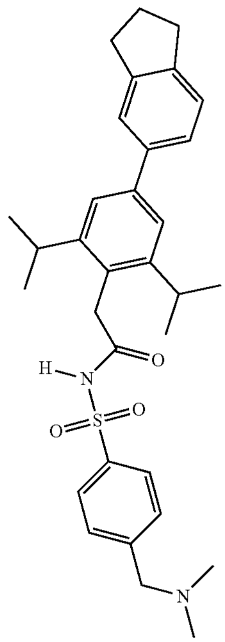 [SMILES: CC(C)c1cc(-c2ccc3c(c2)CCC3)cc(C(C)C)c1CC(=O)NS(=O)(=O)c1ccc(CN(C)C)cc1] | 94 Suzuki | 333 | 533.22 | 2.58 | 2-[4-(2,3-dihydro-1H-inden-5-yl)-2,6-bis(propan-2-yl)phenyl]-N-{4-[(dimethylamino)methyl]benzenesulfonyl}acetamide |
| 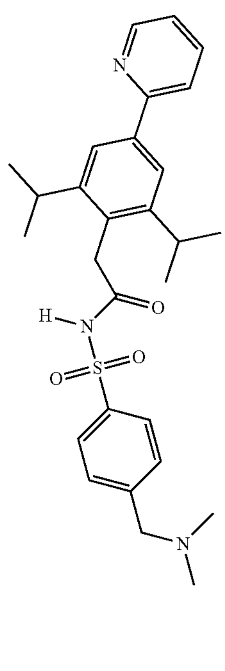 [SMILES: CC(C)c1cc(-c2ccccn2)cc(C(C)C)c1CC(=O)NS(=O)(=O)c1ccc(CN(C)C)cc1] | 95 Stille | 334 | 494.50 | 1.38 | 2-[2,6-bis(propan-2-yl)-4-(pyridin-2-yl)phenyl]-N-{4-[(dimethylamino)methyl]benzenesulfonyl}acetamide |

-continued

| Structure | Example # Method | Compound # | LCMS: [M + H]⁺ | Retention time (min) Method B | IUPAC NAME |
|---|---|---|---|---|---|
| 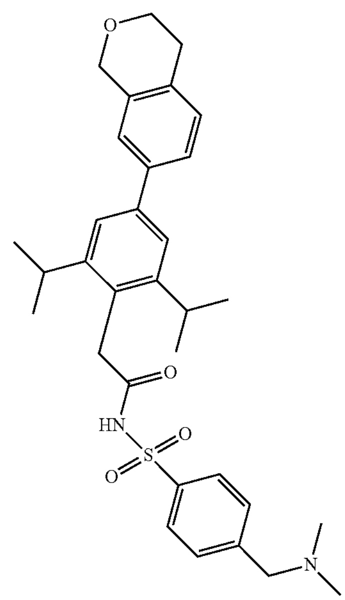 [SMILES: CC(C)c1cc(-c2ccc3c(c2)COCC3)cc(C(C)C)c1CC(=O)NS(=O)(=O)c1ccc(CN(C)C)cc1] | 96 Suzuki | 335 | 549.43 | 2.18 | 2-[4-(3,4-dihydro-1H-2-benzopyran-7-yl)-2,6-bis(propan-2-yl)phenyl]-N-{4-[(dimethylamino)methyl]benzenesulfonyl}acetamide |
| 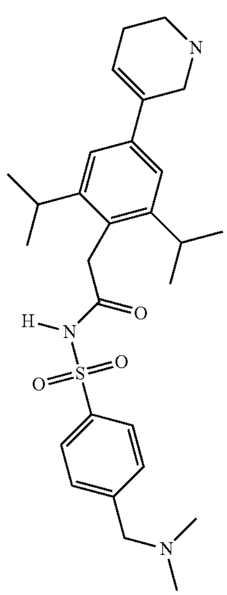 [SMILES: CC(C)c1cc(C2=CCCNC2)cc(C(C)C)c1CC(=O)NS(=O)(=O)c1ccc(CN(C)C)cc1] | 97 Suzuki Boc de-protection | 336 | 498.41 | 1.44 | 2-[2,6-bis(propan-2-yl)-4-(1,2,5,6-tetrahydropyridin-3-yl)phenyl]-N-{4-[(dimethylamino)methyl]benzenesulfonyl}acetamide |

| Structure | Example # Method | Compound # | LCMS: [M + H]+ | Retention time (min) Method B | IUPAC NAME |
|---|---|---|---|---|---|
| 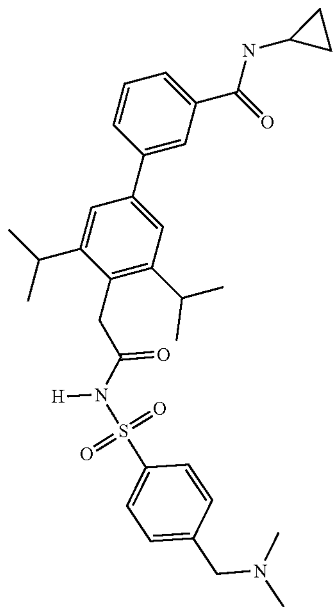 [SMILES: CC(C)c1cc(-c2cccc(C(=O)NC3CC3)c2)cc(C(C)C)c1CC(=O)NS(=O)(=O)c1ccc(CN(C)C)cc1] | 98 Suzuki | 337 | 576.45 | 1.93 | N-cyclopropyl-3-{4-[({4-[(dimethylamino)methyl]benzene-sulfonyl}carbamoyl)methyl]-3,5-bis(propan-2-yl)phenyl}benzamide |
| 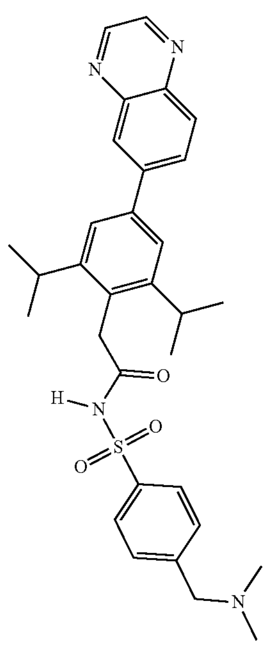 [SMILES: CC(C)c1cc(-c2ccc3nccnc3c2)cc(C(C)C)c1CC(=O)NS(=O)(=O)c1ccc(CN(C)C)cc1] | 99 Suzuki | 338 | 545.23 | 1.95 | 2-[2,6-bis(propan-2-yl)-4-(quinoxalin-6-yl)phenyl]-N-{4-[(dimethylamino)methyl]benzene-sulfonyl}acetamide |

| Structure | Example # Method | Compound # | LCMS: [M + H]+ | Retention time (min) Method B | IUPAC NAME |
|---|---|---|---|---|---|
| 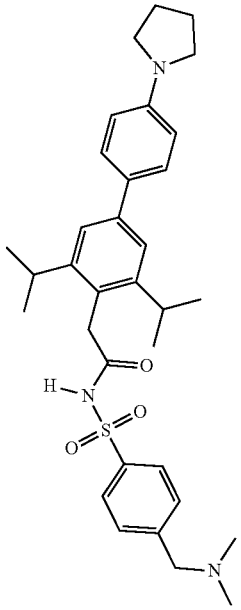 [SMILES: CC(C)c1cc(-c2ccc(N3CCCC3)cc2)cc(C(C)C)c1CC(=O)NS(=O)(=O)c1ccc(CN(C)C)cc1] | 100 Suzuki | 339 | 562.34 | 2.14 | 2-[2,6-bis(propan-2-yl)-4-[4-(pyrrolidin-1-yl)phenyl]phenyl]-N-{4-[(dimethylamino)methyl]benzene-sulfonyl}acetamide |
| 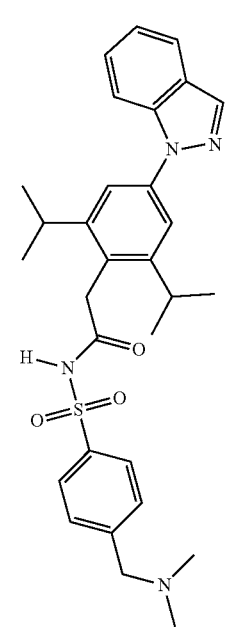 [SMILES: CC(C)c1cc(-n2ncc3ccccc32)cc(C(C)C)c1CC(=O)NS(=O)(=O)c1ccc(CN(C)C)cc1] | 102 Ullmann | 340 | 533.22 | 2.10 | N-{4-[(dimethylamino)methyl]benzene-sulfonyl}-2-[4-(1H-indazol-1-yl)-2,6-bis(propan-2-yl)phenyl]acetamide |

-continued

| Structure | Example # Method | Compound # | LCMS: [M + H]+ | Retention time (min) Method B | IUPAC NAME |
|---|---|---|---|---|---|
| 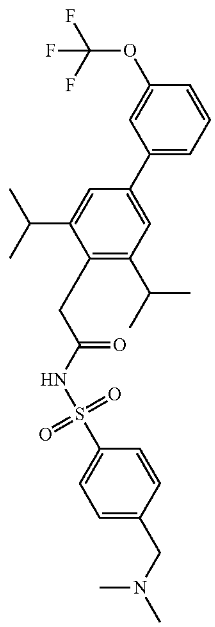 [SMILES: CC(C)c1cc(-c2cccc(OC(F)(F)F)c2)cc(C(C)C)c1CC(=O)NS(=O)(=O)c1ccc(CN(C)C)cc1] | 103 Suzuki | 341 | 577.65 | 2.51 | 2-[2,6-bis(propan-2-yl)-4-[3-(trifluoromethoxy)phenyl]phenyl]-N-{4-[(dimethylamino)methyl]benzenesulfonyl}acetamide |
| 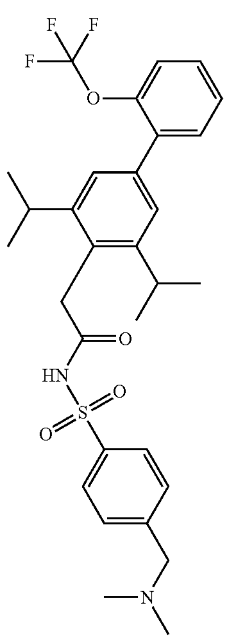 [SMILES: CC(C)c1cc(-c2ccccc2OC(F)(F)F)cc(C(C)C)c1CC(=O)NS(=O)(=O)c1ccc(CN(C)C)cc1] | 104 Suzuki | 342 | 577.65 | 2.44 | 2-[2,6-bis(propan-2-yl)-4-[2-(trifluoromethoxy)phenyl]phenyl]-N-{4-[(dimethylamino)methyl]benzenesulfonyl}acetamide |

-continued

| Structure | Example # Method | Compound # | LCMS: [M + H]+ | Retention time (min) Method B | IUPAC NAME |
|---|---|---|---|---|---|
| 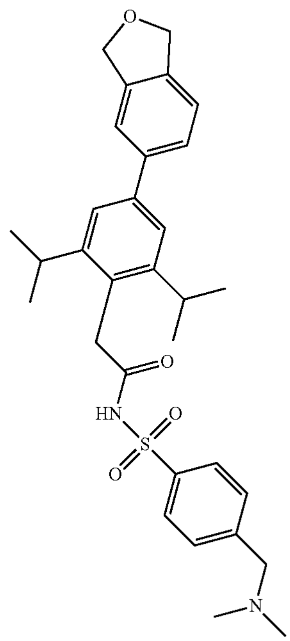 [SMILES: CC(C)c1cc(-c2ccc3c(c2)COC3)cc(C(C)C)c1CC(=O)NS(=O)(=O)c1ccc(CN(C)C)cc1] | 105 Suzuki | 343 | 535.32 | 2.10 | 2-[4-(1,3-dihydro-2-benzofuran-5-yl)-2,6-bis(propan-2-yl)phenyl]-N-{4-[(dimethylamino)methyl]benzene-sulfonyl}acetamide |
| 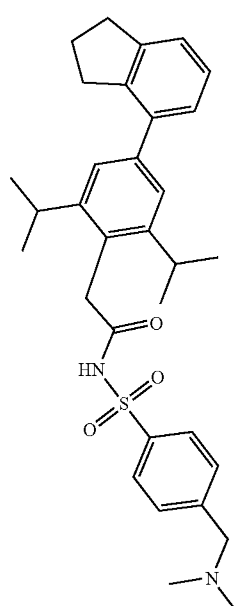 | 106 Suzuki | 344 | 533.22 | 2.52 | 2-[4-(2,3-dihydro-1H-inden-4-yl)-2,6-bis(propan-2-yl)phenyl]-N-{4-[(dimethylamino)methyl]benzene-sulfonyl}acetamide |

-continued

| Structure | Example # Method | Compound # | LCMS: [M + H]+ | Retention time (min) Method B | IUPAC NAME |
|---|---|---|---|---|---|
| 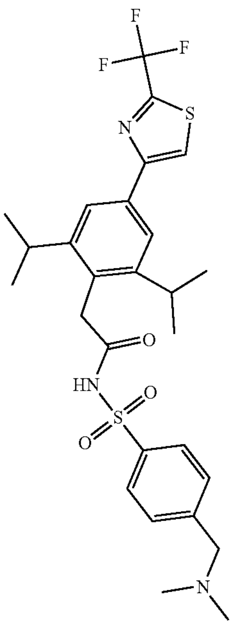 [SMILES: CC(C)c1cc(-c2csc(C(F)(F)F)n2)cc(C(C)C)c1CC(=O)NS(=O)(=O)c1ccc(CN(C)C)cc1] | 107 Suzuki | 345 | 568.34 | 2.33 | 2-[2,6-bis(propan-2-yl)-4-[2-(trifluoromethyl)-1,3-thiazol-4-yl]phenyl]-N-{4-[(dimethylamino)methyl]benzene-sulfonyl}acetamide |
| 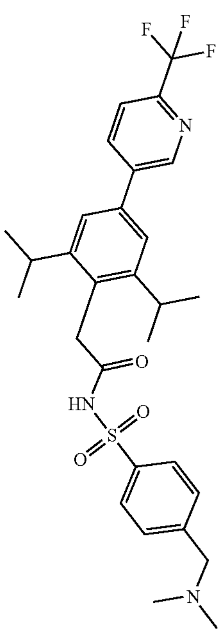 [SMILES: CC(C)c1cc(-c2ccc(C(F)(F)F)nc2)cc(C(C)C)c1CC(=O)NS(=O)(=O)c1ccc(CN(C)C)cc1] | 110 Suzuki | 346 | 562.34 | 2.17 | 2-[2,6-bis(propan-2-yl)-4-[6-(trifluoromethyl)pyridin-3-yl]phenyl]-N-{4-[(dimethylamino)methyl]benzene-sulfonyl}acetamide |

-continued

| Structure | Example # Method | Compound # | LCMS: [M + H]+ | Retention time (min) Method B | IUPAC NAME |
|---|---|---|---|---|---|
| 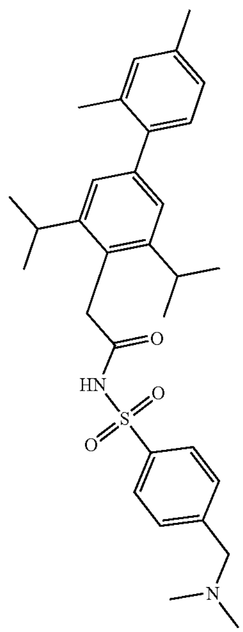 [SMILES: Cc1ccc(-c2cc(C(C)C)c(CC(=O)NS(=O)(=O)c3ccc(CN(C)C)cc3)c(C(C)C)c2)c(C)c1] | 111 Suzuki | 347 | 521.52 | 2.49 | N-{4-[(dimethylamino)methyl]benzenesulfonyl}-2-[4-(2,4-dimethylphenyl)-2,6-bis(propan-2-yl)phenyl]acetamide |
| | 112 Suzuki Hydrogenation Method (A) | 348 | 586.35 | 2.29 | tert-butyl 3-{4-[({4-[(dimethylamino)methyl]benzenesulfonyl}carbamoyl)methyl]-3,5-bis(propan-2-yl)phenyl}pyrrolidine-1-carboxylate |

-continued

| Structure | Example # Method | Compound # | LCMS: [M + H]+ | Retention time (min) Method B | IUPAC NAME |
|---|---|---|---|---|---|
| 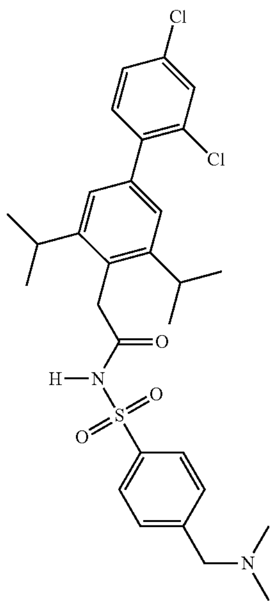 [SMILES: CC(C)c1cc(-c2ccc(Cl)cc2Cl)cc(C(C)C)c1CC(=O)NS(=O)(=O)c1ccc(CN(C)C)cc1] | 113 Suzuki | 349 | 561.14 | 2.61 | 2-[4-(2,4-dichlorophenyl)-2,6-bis(propan-2-yl)phenyl]-N-{4-[(dimethylamino)methyl]benzenesulfonyl}acetamide |
| 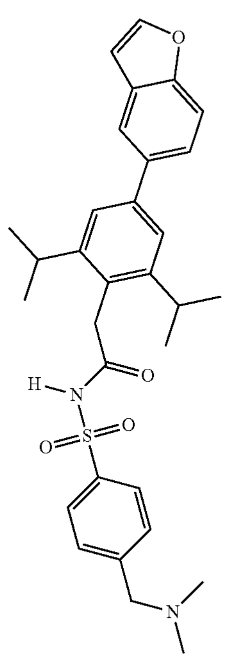 [SMILES: CC(C)c1cc(-c2ccc3occc3c2)cc(C(C)C)c1CC(=O)NS(=O)(=O)c1ccc(CN(C)C)cc1] | 114 Suzuki | 350 | 533.22 | 2.32 | 2-[4-(1-benzofuran-5-yl)-2,6-bis(propan-2-yl)phenyl]-N-{4-[(dimethylamino)methyl]benzenesulfonyl}acetamide |

-continued

| Structure | Example # Method | Compound # | LCMS: [M + H]+ | Retention time (min) Method B | IUPAC NAME |
|---|---|---|---|---|---|
| 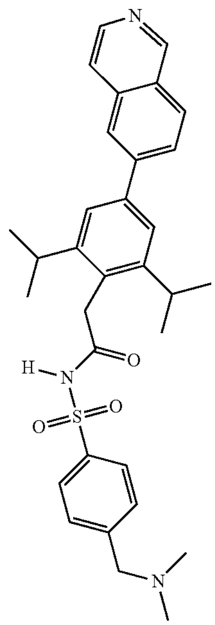 [SMILES: CC(C)c1cc(-c2ccc3cnccc3c2)cc(C(C)C)c1CC(=O)NS(=O)(=O)c1ccc(CN(C)C)cc1] | 115 Suzuki | 351 | 544.33 | 1.52 | N-{4-[(dimethylamino)methyl]benzene-sulfonyl}-2-[4-(isoquinolin-6-yl)-2,6-bis(propan-2-yl)phenyl]acetamide |
| 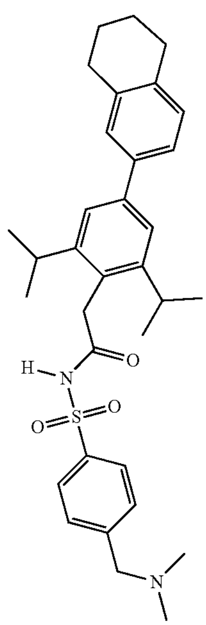 [SMILES: CC(C)c1cc(-c2ccc3c(c2)CCCC3)cc(C(C)C)c1CC(=O)NS(=O)(=O)c1ccc(CN(C)C)cc1] | 116 Suzuki | 352 | 547.33 | 2.69 | 2-[2,6-bis(propan-2-yl)-4-(5,6,7,8-tetrahydronaphthalen-1-yl)phenyl]-N-{4-[(dimethylamino)methyl]benzene-sulfonyl}acetamide |

-continued
| Structure | Example # Method | Compound # | LCMS: [M + H]+ | Retention time (min) Method B | IUPAC NAME |
|---|---|---|---|---|---|
| 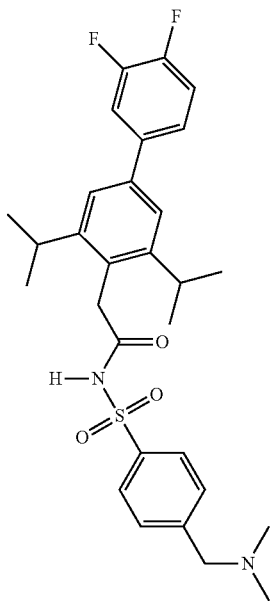 [SMILES: CC(C)c1cc(-c2ccc(F)c(F)c2)cc(C(C)C)c1CC(=O)NS(=O)(=O)c1ccc(CN(C)C)cc1] | 117 Suzuki | 353 | 529.32 | 2.32 | 2-[4-(3,4-difluorophenyl)-2,6-bis(propan-2-yl)phenyl]-N-{4-[(dimethylamino)methyl]benzenesulfonyl}acetamide |
| 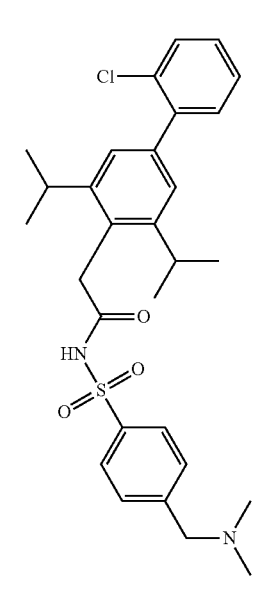 [SMILES: CC(C)c1cc(-c2ccccc2Cl)cc(C(C)C)c1CC(=O)NS(=O)(=O)c1ccc(CN(C)C)cc1] | 118 Suzuki | 354 | 527.22 | 2.35 | 2-[4-(2-chlorophenyl)-2,6-bis(propan-2-yl)phenyl]-N-{4-[(dimethylamino)methyl]benzenesulfonyl}acetamide |

| Structure | Example # Method | Compound # | LCMS: [M + H]+ | Retention time (min) Method B | IUPAC NAME |
|---|---|---|---|---|---|
| 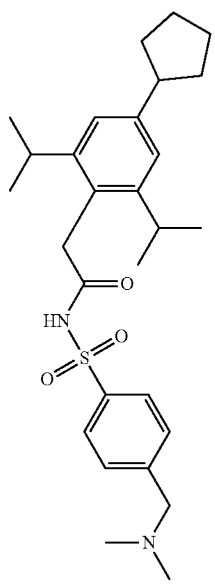 [SMILES: CC(C)c1cc(C2CCCC2)cc(C(C)C)c1CC(=O)NS(=O)(=O)c1ccc(CN(C)C)cc1] | 119 Suzuki Hydrogenation Method (A) | 355 | 485.49 | 2.44 | 2-[4-cyclopentyl-2,6-bis(propan-2-yl)phenyl]-N-{4-[(dimethylamino)methyl]benzenesulfonyl}acetamide |
| 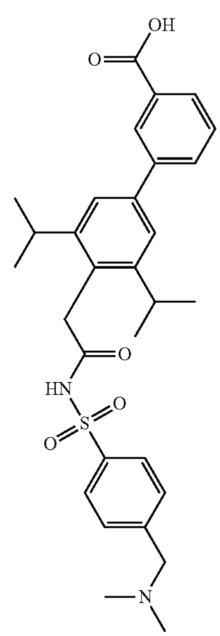 [SMILES: CC(C)c1cc(-c2cccc(C(=O)O)c2)cc(C(C)C)c1CC(=O)NS(=O)(=O)c1ccc(CN(C)C)cc1] | 120 Suzuki | 356 | 537.43 | 1.85 | 3-{4-[({4-[(dimethylamino)methyl]benzenesulfonyl}carbamoyl)methyl]-3,5-bis(propan-2-yl)phenyl}benzoic acid |

-continued

| Structure | Example # Method | Compound # | LCMS: [M + H]+ | Retention time (min) Method B | IUPAC NAME |
|---|---|---|---|---|---|
| 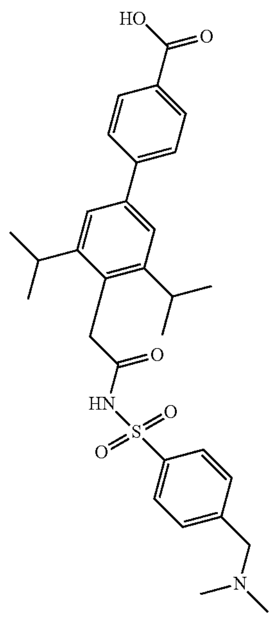 [SMILES: CC(C)c1cc(-c2ccc(C(=O)O)cc2)cc(C(C)C)c1CC(=O)NS(=O)(=O)c1ccc(CN(C)C)cc1] | 121 Suzuki | 357 | 537.43 | 1.91 | 4-{4-[({4-[(dimethylamino)methyl]benzene-sulfonyl}carbamoyl)methyl]-3,5-bis(propan-2-yl)phenyl}benzoic acid |
| 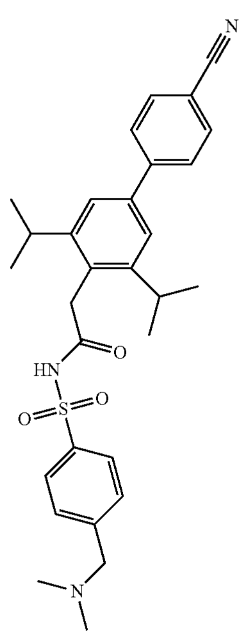 [SMILES: CC(C)c1cc(-c2ccc(C#N)cc2)cc(C(C)C)c1CC(=O)NS(=O)(=O)c1ccc(CN(C)C)cc1] | 122 Suzuki | 358 | 518.22 | 2.14 | 2-{4-(4-cyanophenyl)-2,6-bis(propan-2-yl)phenyl]-N-{4-[(dimethylamino)methyl]benzene-sulfonyl}acetamide |

-continued

| Structure | Example # Method | Compound # | LCMS: [M + H]+ | Retention time (min) Method B | IUPAC NAME |
|---|---|---|---|---|---|
| 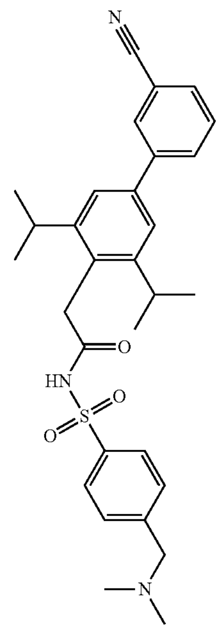 [SMILES: CC(C)c1cc(-c2cccc(C#N)c2)cc(C(C)C)c1CC(=O)NS(=O)(=O)c1ccc(CN(C)C)cc1] | 123 Suzuki | 359 | 518.22 | 2.13 | 2-[4-(3-cyanophenyl)-2,6-bis(propan-2-yl)phenyl]-N-{4-[(dimethylamino)methyl]benzenesulfonyl}acetamide |
| 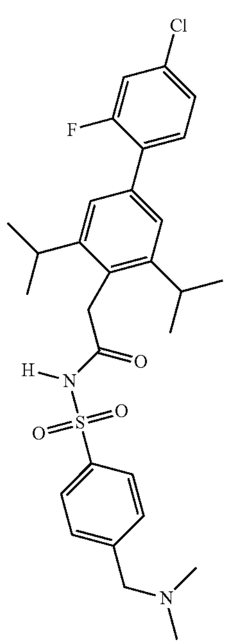 [SMILES: CC(C)c1cc(-c2ccc(Cl)cc2F)cc(C(C)C)c1CC(=O)NS(=O)(=O)c1ccc(CN(C)C)cc1] | 124 Suzuki | 360 | 545.23 | 2.49 | 2-[4-(4-chloro-2-fluorophenyl)-2,6-bis(propan-2-yl)phenyl]-N-{4-[(dimethylamino)methyl]benzenesulfonyl}acetamide |

-continued

| Structure | Example # Method | Compound # | LCMS: [M + H]+ | Retention time (min) Method B | IUPAC NAME |
|---|---|---|---|---|---|
| 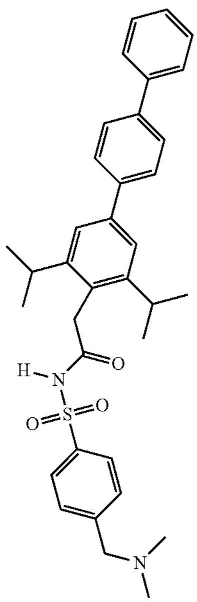 [SMILES: CC(C)c1cc(-c2ccc(-c3ccccc3)cc2)cc(C(C)C)c1CC(=O)NS(=O)(=O)c1ccc(CN(C)C)cc1] | 125 Suzuki | 361 | 569.54 | 2.64 | N-{4-[(dimethylamino)methyl]benzenesulfonyl}-2-[4-(4-phenylphenyl)-2,6-bis(propan-2-yl)phenyl]acetamide |
| 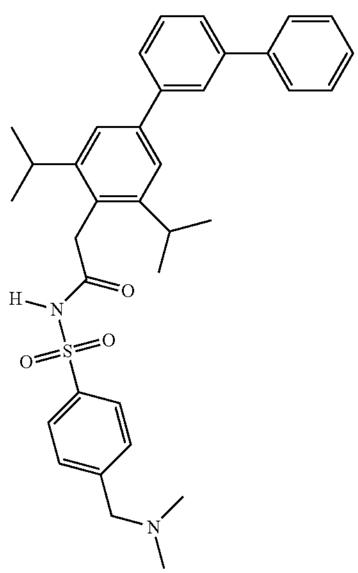 [SMILES: CC(C)c1cc(-c2cccc(-c3ccccc3)c2)cc(C(C)C)c1CC(=O)NS(=O)(=O)c1ccc(CN(C)C)cc1] | 126 Suzuki | 362 | 569.54 | 2.62 | N-{4-[(dimethylamino)methyl]benzenesulfonyl}-2-[4-(3-phenylphenyl)-2,6-bis(propan-2-yl)phenyl]acetamide |

| Structure | Example # Method | Compound # | LCMS: [M + H]+ | Retention time (min) Method B | IUPAC NAME |
|---|---|---|---|---|---|
| 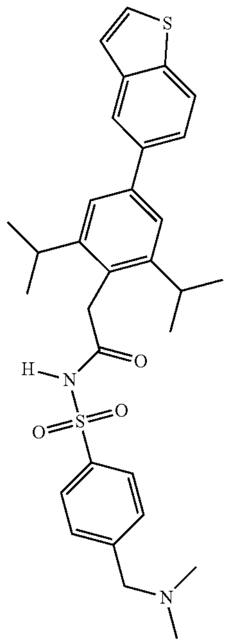 [SMILES: CC(C)c1cc(-c2ccc3sccc3c2)cc(C(C)C)c1CC(=O)NS(=O)(=O)c1ccc(CN(C)C)cc1] | 127 Suzuki | 363 | 549.43 | 2.43 | 2-[4-(1-benzothiophen-5-yl)-2,6-bis(propan-2-yl)phenyl]-N-{4-[(dimethylamino)methyl]benzenesulfonyl}acetamide |
| 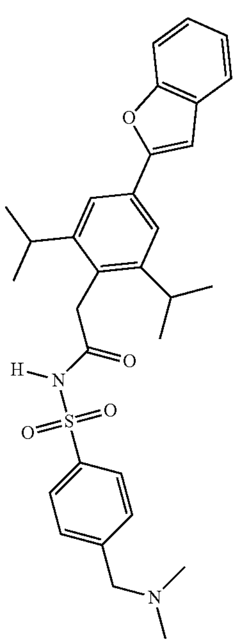 [SMILES: CC(C)c1cc(-c2cc3ccccc3o2)cc(C(C)C)c1CC(=O)NS(=O)(=O)c1ccc(CN(C)C)cc1] | 128 Suzuki | 364 | 533.22 | 2.42 | 2-[4-(1-benzofuran-2-yl)-2,6-bis(propan-2-yl)phenyl]-N-{4-[(dimethylamino)methyl]benzenesulfonyl}acetamide |

-continued

| Structure | Example # Method | Compound # | LCMS: [M + H]+ | Retention time (min) Method B | IUPAC NAME |
|---|---|---|---|---|---|
| 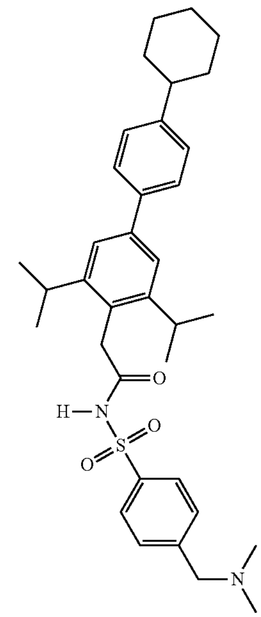 [SMILES: CC(C)c1cc(-c2ccc(C3CCCCC3)cc2)cc(C(C)C)c1CC(=O)NS(=O)(=O)c1ccc(CN(C)C)cc1] | 129 Suzuki | 365 | 575.55 | 2.99 | 2-[4-(4-cyclohexylphenyl)-2,6-bis(propan-2-yl)phenyl]-N-{4-[(dimethylamino)methyl]benzenesulfonyl}acetamide |
| 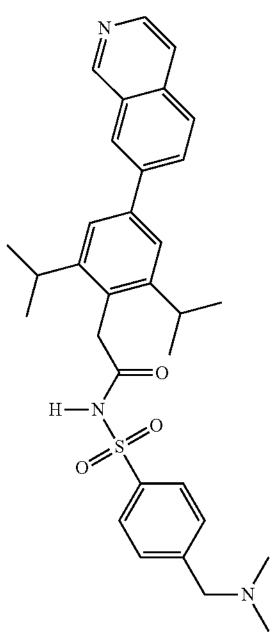 [SMILES: CC(C)c1cc(-c2ccc3ccncc3c2)cc(C(C)C)c1CC(=O)NS(=O)(=O)c1ccc(CN(C)C)cc1] | 130 Suzuki | 366 | 544.33 | 1.55 | N-{4-[(dimethylamino)methyl]benzenesulfonyl}-2-[4-(isoquinolin-7-yl)-2,6-bis(propan-2-yl)phenyl]acetamide |

-continued

| Structure | Example # Method | Compound # | LCMS: [M + H]+ | Retention time (min) Method B | IUPAC NAME |
| --- | --- | --- | --- | --- | --- |
| 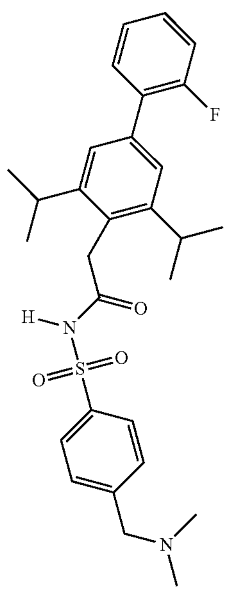 [SMILES: CC(C)c1cc(-c2ccccc2F)cc(C(C)C)c1CC(=O)NS(=O)(=O)c1ccc(CN(C)C)cc1] | 131 Suzuki | 367 | 511.61 | 2.28 | N-{4-[(dimethylamino)methyl]benzene-sulfonyl}-2-[4-(2-fluorophenyl)-2,6-bis(propan-2-yl)phenyl]acetamide |
| 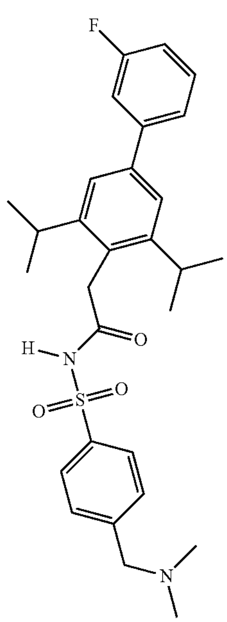 [SMILES: CC(C)c1cc(-c2cccc(F)c2)cc(C(C)C)c1CC(=O)NS(=O)(=O)c1ccc(CN(C)C)cc1] | 132 Suzuki | 368 | 511.61 | 2.31 | N-{4-[(dimethylamino)methyl]benzene-sulfonyl}-2-[4-(3-fluorophenyl)-2,6-bis(propan-2-yl)phenyl]acetamide |

-continued

| Structure | Example # Method | Compound # | LCMS: [M + H]+ | Retention time (min) Method B | IUPAC NAME |
|---|---|---|---|---|---|
| 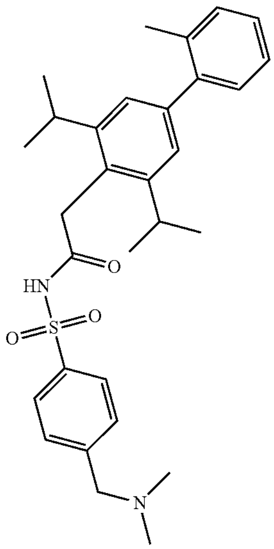 [SMILES: Cc1ccccc1-c1cc(C(C)C)c(CC(=O)NS(=O)(=O)c2ccc(CN(C)C)cc2)c(C(C)C)c1] | 133 Suzuki | 369 | 507.41 | 2.38 | N-{4-[(dimethylamino)methyl]benzenesulfonyl}-2-[4-(2-methylphenyl)-2,6-bis(propan-2-yl)phenyl]acetamide |
| | 134 Sonogashira | 370 | 509.51 | 2.55 | 2-[4-(2-cyclopentylethynyl)-2,6-bis(propan-2-yl)phenyl]-N-{4-[(dimethylamino)methyl]benzenesulfonyl}acetamide |

-continued

| Structure | Example # Method | Compound # | LCMS: [M + H]+ | Retention time (min) Method B | IUPAC NAME |
|---|---|---|---|---|---|
| 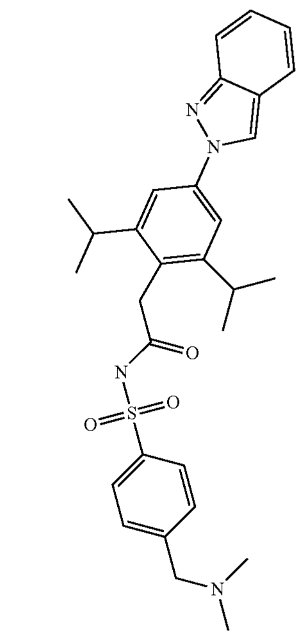 [SMILES: CC(C)c1cc(-n2cc3ccccc3n2)cc(C(C)C)c1CC(=O)NS(=O)(=O)c1ccc(CN(C)C)cc1] | 135 Ullmann | 371 | 533.22 | 2.16 | N-{4-[(dimethylamino)methyl]benzenesulfonyl}-2-[4-(2H-indazol-2-yl)-2,6-bis(propan-2-yl)phenyl]acetamide |

Example #137: Preparation of N-{4-[(dimethylamino)methyl]benzenesulfonyl}-2-(4-[hydroxy(phenyl)methyl]-2,6-bis(propan-2-yl)phenyl)acetamide (Compound 372)

Scheme AAA

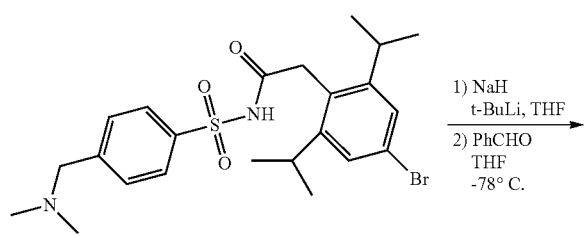

To a solution of 2-(4-bromo-2,6-diisopropylphenyl)-N-((4-((dimethylamino)methyl)phenyl)-sulfonyl)acetamide (83 mg, 0.167 mmol) (83 mg, 0.167 mmol) in anhydrous THF (3.8 mL) was added NaH (6.7 mg, 0.167 mmol, 60% dispersed in oil) under nitrogen at −78° C. t-BuLi (0.107 mL, 0.182 mmol, 1.7M in pentane) was added slowly and after 3 min benzaldehyde (0.12 mL) was added quickly. Reaction mixture was further stirred at −78° C. for 5 min before quenching with water. Reaction mixture froze. Dry ice/acetone cooling bath was removed. The reaction mixture was gradually warmed up to room temperature and extracted with EtOAc (3×5 mL). Combined organic layer was concentrated in vacuo to obtain crude material which was purified by prep-HPLC to obtain titled compound (10 mg, 11%). LCMS (Method A): 523.32 [M+H]+, retention time 2.19 min.

Example #138: Preparation of 2-[4-benzoyl-2,6-bis(propan-2-yl)phenyl]-N-{4-[(dimethylamino)methyl]benzenesulfonyl}acetamide (Compound 373)

Scheme BBB

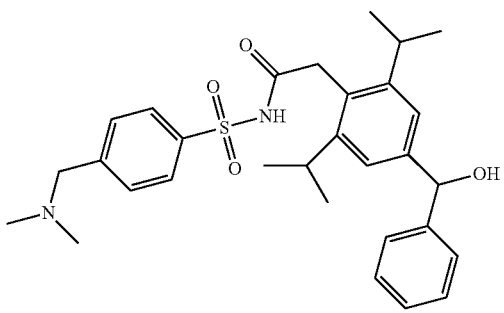

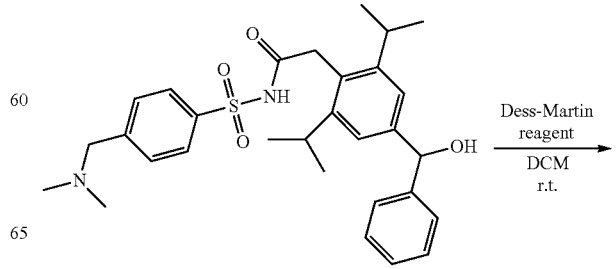

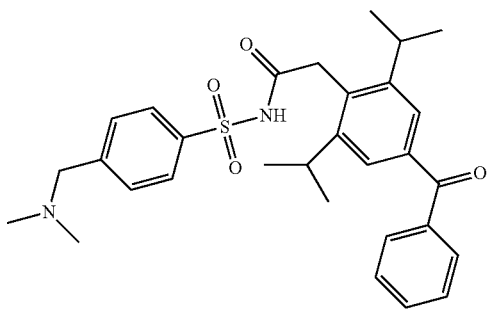

To the crude material of N-{4-[(dimethylamino)methyl]benzenesulfonyl}-2-{4-[hydroxy(phenyl)methyl]-2,6-bis(propan-2-yl)phenyl}acetamide obtained from 2-(4-bromo-2,6-diisopropylphenyl)-N-((4-((dimethylamino)methyl)phenyl)-sulfonyl)acetamide (83 mg, 0.167 mmol) as described in example 137, in DCM (4 mL) was added Dess-Martin reagent (140 mg, 0.33 mmol) portion wise over 1.5 h at room temperature. 10% aqueous Na$_2$S$_2$O$_3$ solution (1 mL), water (3 mL) and EtOAc (4 mL) was added. A sticky solid appeared which was collected and purified by prep-HPLC to give titled compound (9 mg, 10%). LCMS (Method A): 521.22 [M+H]$^+$, retention time 2.37 min.

Example #139: Preparation of N-cyclohexyl-4-[({4-[(dimethylamino)methyl]benzene-sulfonyl}carbamoyl)methyl]-3,5-bis(propan-2-yl)benzamide (Compound 374)

Scheme CCC

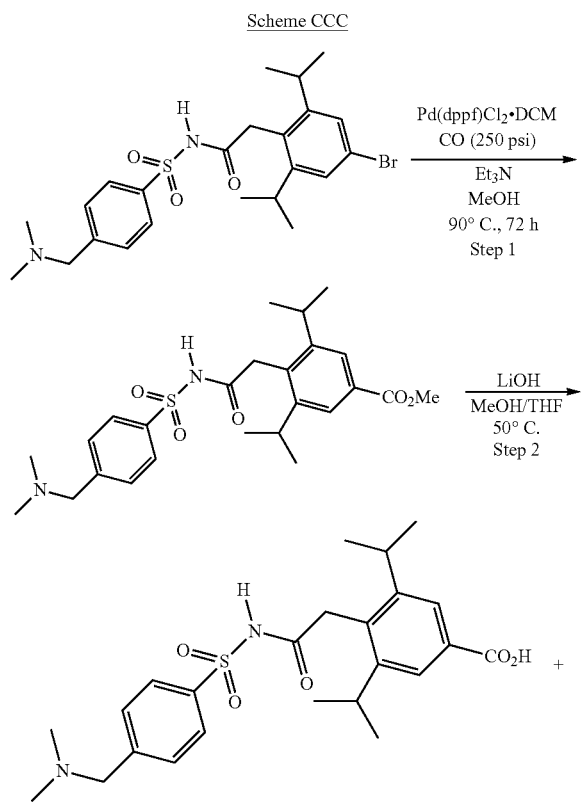

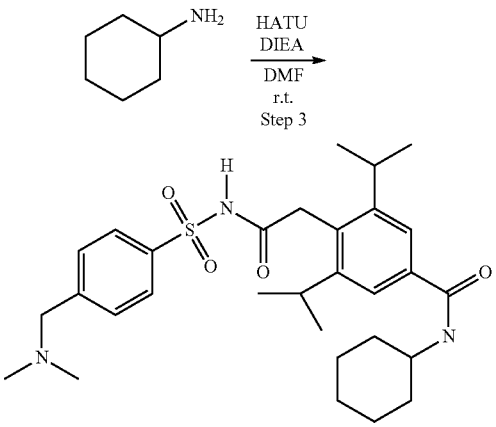

Step 1: Preparation of methyl 4-[({4-[(dimethylamino)methyl]benzenesulfonyl}-carbamoyl)methyl]-3,5-bis(propan-2-yl)benzoate To a solution of 2-(4-bromo-2,6-diisopropylphenyl)-N-((4-((dimethylamino)methyl)phenyl)-sulfonyl)acetamide (200 mg, 0.404 mmol) in MeOH (35 mL) was added Pd(dppf)Cl$_2$·DCM (29 mg, 0.035 mmol) and triethylamine (0.169 mL, 1.21 mmol). The resulting mixture was autoclaved under CO (250 psi) at 90° C. for 72 h. Reaction mixture was filtered through a pad of celite, rinsed with MeOH and concentrated to give titled compound (158 mg, 83%) which was used in the next step without any further purification.

Step 2: Preparation of 4-[({4-[(dimethylamino)methyl]benzenesulfonyl}carbamoyl)methyl]-3,5-bis(propan-2-yl)benzoic acid To a solution of methyl 4-[({4-[(dimethylamino)methyl]benzenesulfonyl}carbamoyl)methyl]-3,5-bis(propan-2-yl)benzoate (158 mg, 0.332 mmol) in a 1:1 mixture of THF and MeOH (3 mL) was added LiOH (10 mg, 0.39 mmol) and the resulting mixture was heated at 50° C. for 2 h. Reaction mixture was brought to room temperature and basified with aqueous 1 N NaOH solution. The resulting precipitates were filtered and dried under high vacuum to give titled compound (113 mg, 74%).

Step 3: Preparation of N-cyclohexyl-4-[({4-[(dimethylamino)methyl]benzene-sulfonyl}-carbamoyl)methyl]-3,5-bis(propan-2-yl)benzamide (Compound 374)

A solution of 4-[({4-[(dimethylamino)methyl]benzenesulfonyl}carbamoyl)methyl]-3,5-bis(propan-2-yl)benzoic acid (46 mg, 0.1 mmol), cyclohexylamine (0.034 mL, 0.3 mmol), DIEA (0.068 mL, 0.4 mmol) and HATU (45 mg, 0.12 mmol) in DMF (0.5 mL) was stirred at room temperature for 1 h. Subsequently the reaction mixture was directly purified using prep-HPLC to obtain titled compound (19 mg, 35%). LCMS (Method A): 542.53 [M+H]$^+$, retention time 1.96 min.

Example #140: Preparation of N-{4-[(dimethyl-amino)methyl]benzenesulfonyl}-2-[4-(piperidine-1-carbonyl)-2,6-bis(propan-2-yl)phenyl]acetamide (Compound 375)

Scheme DDD

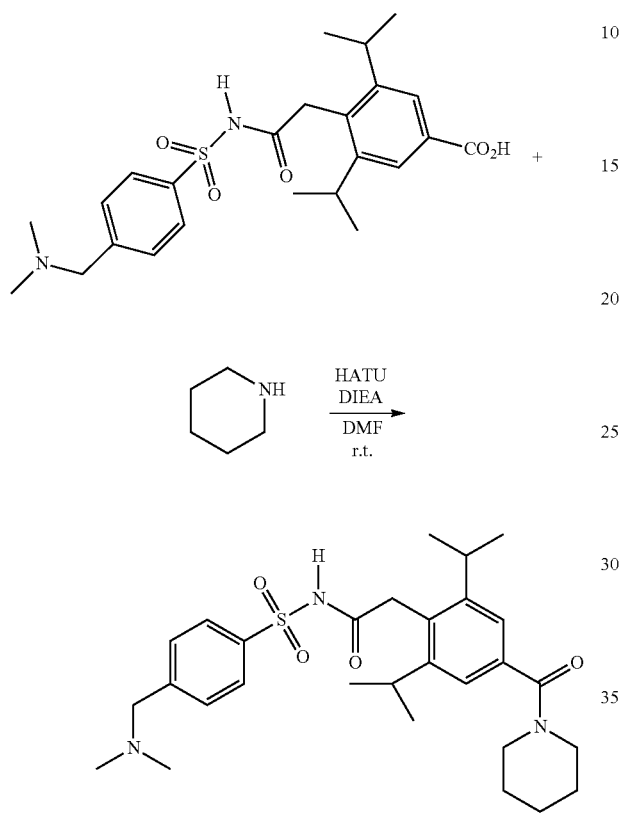

Using the same method as described above in Step 3 of example 139, by replacing cyclohexylamine with piperidine (0.029 mL, 0.3 mmol), the titled compound was obtained (19 mg, 37%). LCMS (Method A): 528.42 [M+H]$^+$, retention time 1.83 min.

Example #141: Preparation of 2-[4-cyclopropyl-2,6-bis(propan-2-yl)phenyl]-N-{4-[(dimethylamino)methyl]benzenesulfonyl}acetamide (Compound 376)

Scheme EEE

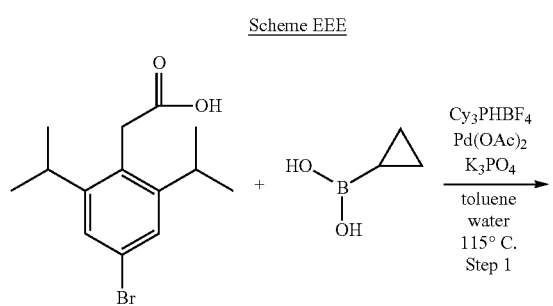

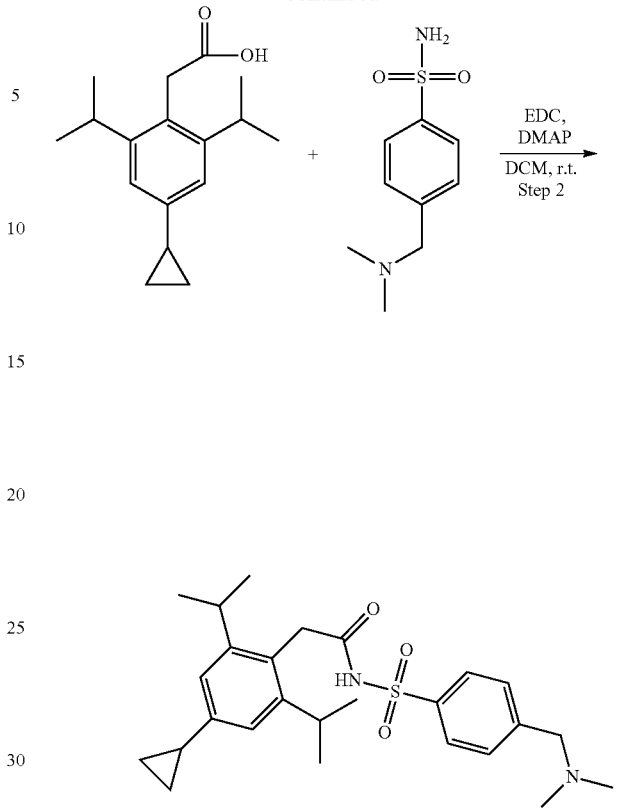

Step 1: Preparation of 2-(4-cyclopropyl-2,6-diisopropylphenyl)acetic acid

In the 20 mL vial were placed 2-(4-bromo-2,6-diisopropylphenyl) acetic acid (20 mg, 0.067 mmol), tricyclohexylphosphine tetrafluoroborate (25 mg, 0.067 mmol), Pd(OAc)$_2$ (7.5 mg, 0.033 mmol) K$_3$PO$_4$, (42 mg, 0.20 mmol) and cyclopropylboronic acid (17.2 mg, 0.020 mmol). A solution of toluene (3 mL) and water (0.3 mL) was added and the resulting mixture was stirred at 115° C. for 2 h. Reaction mixture was brought to room temperature and filtered through a pad of celite. Filtrate was concentrated in vacuo to afford crude titled compound which was directly used in the next without any purification.

Step 2: Preparation of 2-[4-cyclopropyl-2,6-bis(propan-2-yl)phenyl]-N-{4-[(dimethylamino)-methyl]benzenesulfonyl}acetamide A solution of 2-(4-cyclopropyl-2,6-diisopropylphenyl) acetic acid (crude from step 1), 4-((dimethylamino)methyl) benzene sulfonamide (120 mg, 0.56 mmol), 4-dimethyaminopyridine (DMAP, 137 mg, 1.12 mmol), and 1-[3-(dimethyamino)-propyl]-3-ethylcarbodiimide hydrochloride (EDCI, 214.7 mg, 1.12 mmol) in CH$_2$Cl$_2$ (10 mL) was stirred at room temperature for 1 h. Reaction mixture was then concentrated under reduced pressure and purified by prep-HPLC to obtain titled compound (4.7 mg, 16% over two steps). LCMS (Method A): 457.58 [M+H]$^+$, retention time 2.13 min.

Example #142 and 143: Preparation of 2-[4-(cyclohex-1-en-1-ylmethyl)-2,6-bis(propan-2-yl)phenyl]-N-{4-[(dimethylamino)methyl]benzenesulfonyl}acetamide (Compound 377) and 2-[4-(cyclohexylmethyl)-2,6-bis(propan-2-yl)phenyl]-N-{4-[(dimethylamino)methyl]benzenesulfonyl}acetamide (Example 378)

Scheme FFF

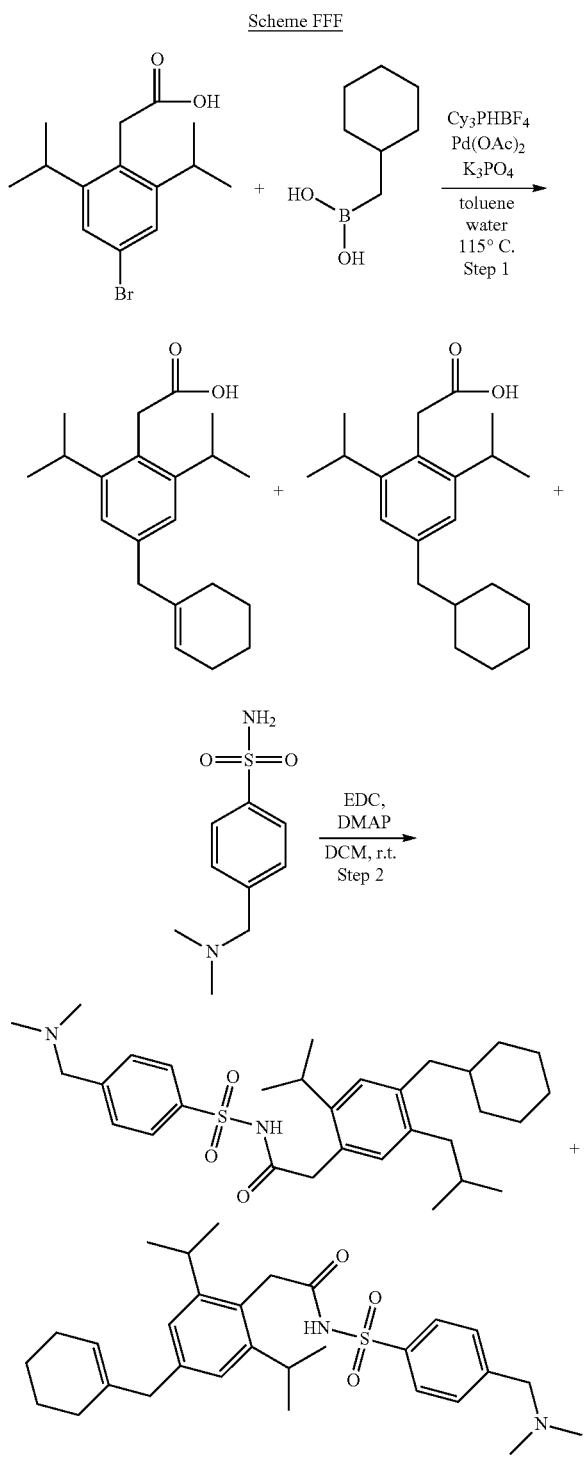

Step 1: Preparation of a mixture of 2-(4-(cyclohexenylmethyl)-2,6-diisopropylphenyl)acetic acid and 2-(4-(cyclohexylmethyl)-2,6-diisopropylphenyl) acetic acid In the 20 mL vial were placed 2-(4-bromo-2,6-diisopropylphenyl) acetic acid (20 mg, 0.067 mmol), tricyclohexylphosphine tetrafluoroborate (25 mg, 0.067 mmol), $Pd(OAc)_2$ (7.5 mg, 0.033 mmol) $K_3PO_4$, (42 mg, 0.20 mmol) and cyclohexylmethylboronic acid (28.5 mg, 0.20 mmol). A solution of toluene (3 mL) and water (0.3 mL) was added and the resulting mixture was stirred at 115° C. for 2 h. Reaction mixture was brought to room temperature and filtered through a pad of celite. Filtrate was concentrated in vacuo to afford crude titled compounds which were directly used in the next without any purification.

Step 2: Preparation of 2-[4-(cyclohex-1-en-1-ylmethyl)-2,6-bis(propan-2-yl)phenyl]-N-{4-[(dimethylamino)methyl]benzenesulfonyl}acetamide and 2-[4-(cyclohexylmethyl)-2,6-bis(propan-2-yl)phenyl]-N-{4-[(dimethylamino)methyl]benzenesulfonyl}acetamide A solution of 2-(4-(cyclohexenylmethyl)-2,6-diisopropylphenyl)acetic acid and 2-(4-(cyclohexylmethyl)-2,6-diisopropylphenyl)acetic acid (crude from step 1), 4-((dimethylamino)methyl) benzene sulfonamide (200 mg, 0.93 mmol), 4-dimethyaminopyridine (DMAP, 228 mg, 1.86 mmol), and 1-[3-(dimethyamino)-propyl]-3-ethylcarbodiimide hydrochloride (EDCI, 358 mg, 1.86 mmol) in $CH_2Cl_2$ (10 mL) was stirred at room temperature for 1 h. Reaction mixture was then concentrated under reduced pressure and purified by prep-HPLC to obtain titled compound 2-[4-(cyclohex-1-en-1-ylmethyl)-2,6-bis(propan-2-yl)phenyl]-N-{4-[(dimethylamino)methyl]benzenesulfonyl}acetamide (6.1 mg, 18% over two steps), LCMS (Method A): 511.61 $[M+H]^+$, retention time 2.57 min and 2-[4-(cyclohexylmethyl)-2,6-bis(propan-2-yl)phenyl]-N-{4-[(dimethylamino)methyl]benzenesulfonyl}-acetamide (3.4 mg, 10% over two steps), LCMS (Method A): 513.41 $[M+H]^+$, retention time 2.69 min.

PROPHETIC EXAMPLES

The following schemes depict synthetic sequences that can be used to prepare a variety of sulfonamide intermediates. The sulfonamide intermediates may be coupled, according to any one of schemes A-E above, to carboxylic acids (such as the carboxylic acids prepared according to schemes MM-RR or schemes EEE-FFF) to form a variety of N-acyl sulfonamides which can, optionally, be functionalized using conditions described in Schemes TT-YY and AAA-DDD.

Intermediate 56

Scheme GGG

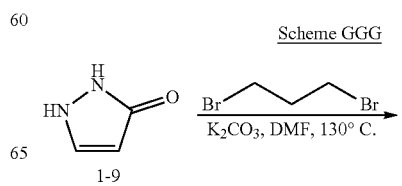

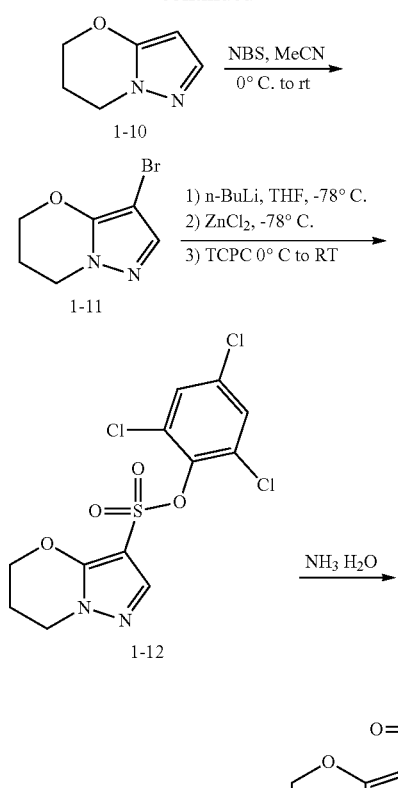

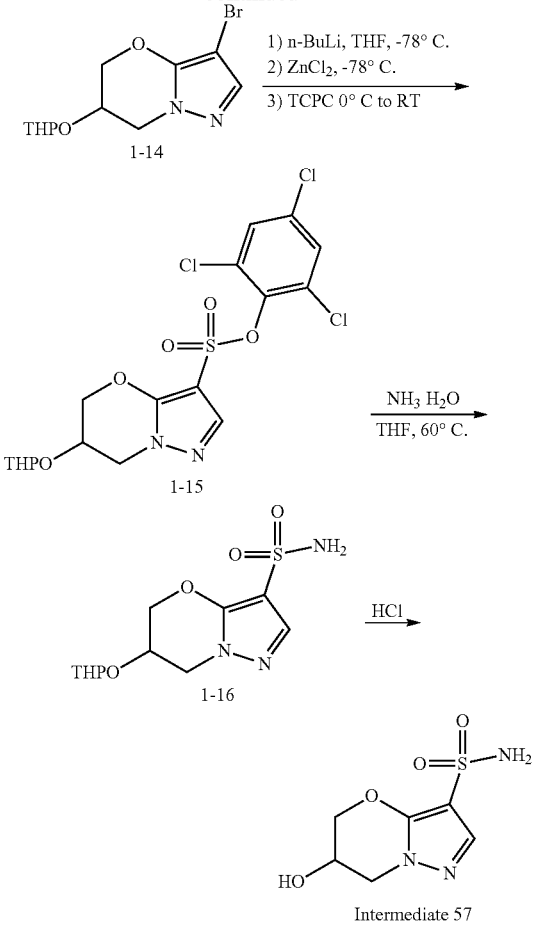

Referring to Scheme GGG, Intermediate 56 is prepared from compound 1-9. Pyrazolone 1-9 is reacted with 1,3-dibromopropane (e.g., using potassium carbonate as a base at elevated temperatures (e.g., 130° C.)) to provide compound 1-10. Bromination of 1-10 (e.g., using NBS) allows the formation of compound 1-11. Treatment of 1-11 with n-BuLi leads to lithium-halogen exchange. The resulting organolithium species is contacted with ZnCl$_2$, whereupon treatment of the intermediate with TCPC leads to compound 1-12. Intermediate 56 is obtained by reacting 1-12 with aqueous ammonia.

Referring to Scheme HHH, pyrazolone 1-9 is reacted with 2-((1,3-dibromopropan-2-yl)oxy)tetrahydro-2H-pyran to produce compound 1-13 which is brominated (e.g., with NBS) to provide compound 1-14. Sequential treatment of compound 1-14 with n-butyl lithium, zinc chloride, and TCPC affords compound 1-15. The reaction between 1-15 and aqueous ammonia then provides 1-16. The THP protecting group in 1-16 is removed with HCl, affording Intermediate 57.

Intermediate 58

Intermediate 57

Scheme HHH

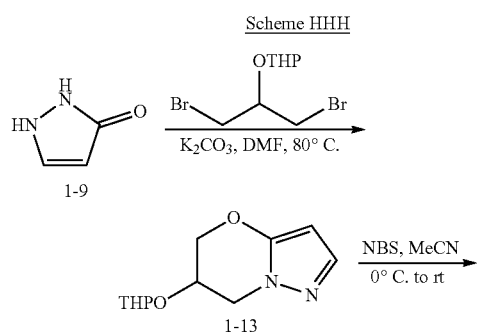

Scheme III

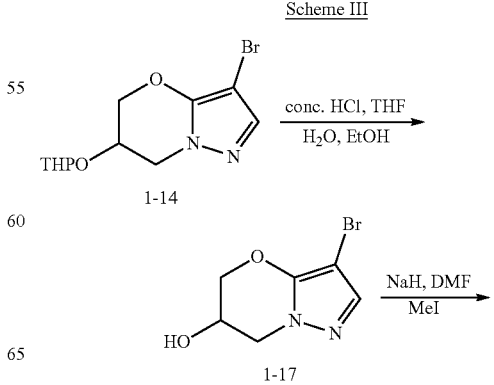

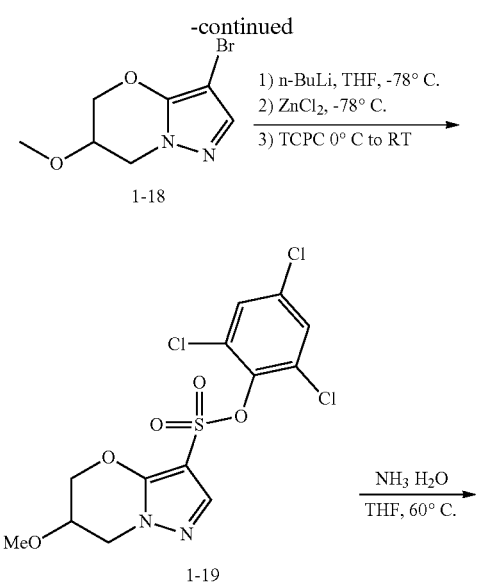

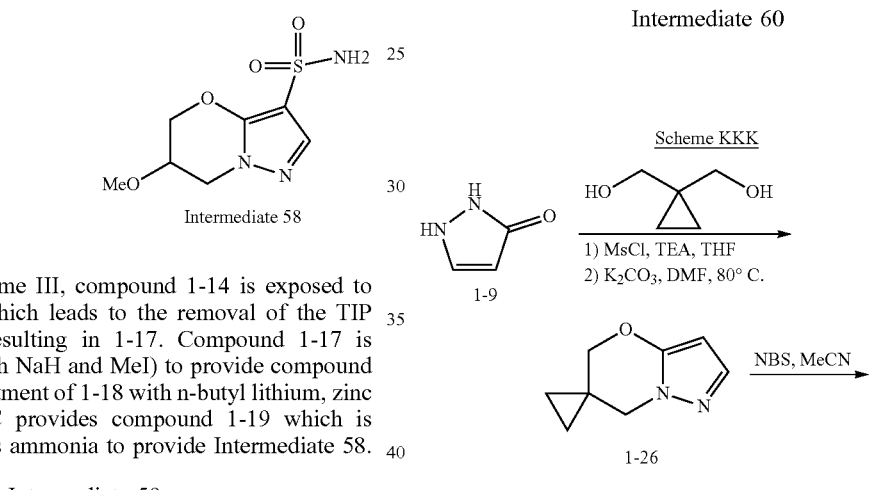

Referring to Scheme JJJ, pyrazolone 1-9 is acetylated (e.g., with acetic anhydride and pyridine at elevated temperatures) to provide compound 1-20. The non-acylated nitrogen of 1-20 can engage (R)-oxiran-2-ylmethanol in a Mitsunobu reaction (e.g., with DEAD, PPh₃) to afford compound 1-21. The epoxide moiety in 1-21 is opened with a chloride nucleophile (e.g., LiCl), leading to the formation of 1-22. Removal of the acetyl protecting group (e.g, with aqueous potassium carbonate) allows the formation of 1-23, which is brominated (e.g., with NBS) to provide compound 1-24. Compound 1-24 is methylated (e.g., with MeI and NaH) to provide compound 1-25. Sequential treatment of 1-25 with n-butyl lithium, zinc chloride, TCPC, and ammonium hydroxide provides Intermediate 59. The (S)-enantiomer of Intermediate 59 can be prepared in an analogous fashion using (S)-oxiran-2-ylmethanol in the reaction with 1-20.

Referring to Scheme III, compound 1-14 is exposed to concentrated HCl which leads to the removal of the TIP protecting group, resulting in 1-17. Compound 1-17 is methylated (e.g., with NaH and MeI) to provide compound 1-18. Sequential treatment of 1-18 with n-butyl lithium, zinc chloride, and TCPC provides compound 1-19 which is reacted with aqueous ammonia to provide Intermediate 58.

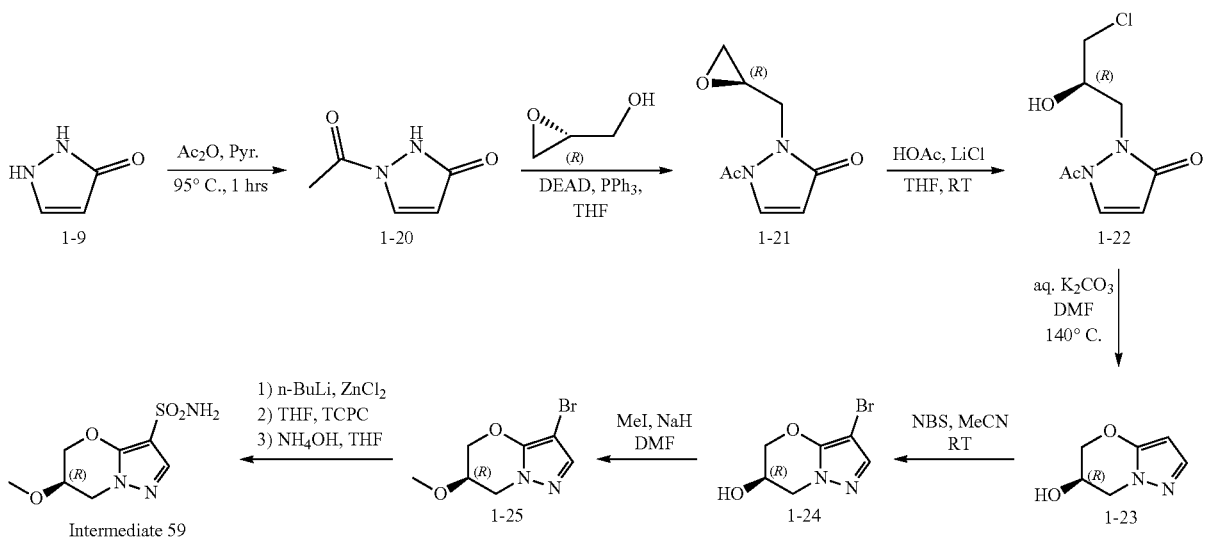

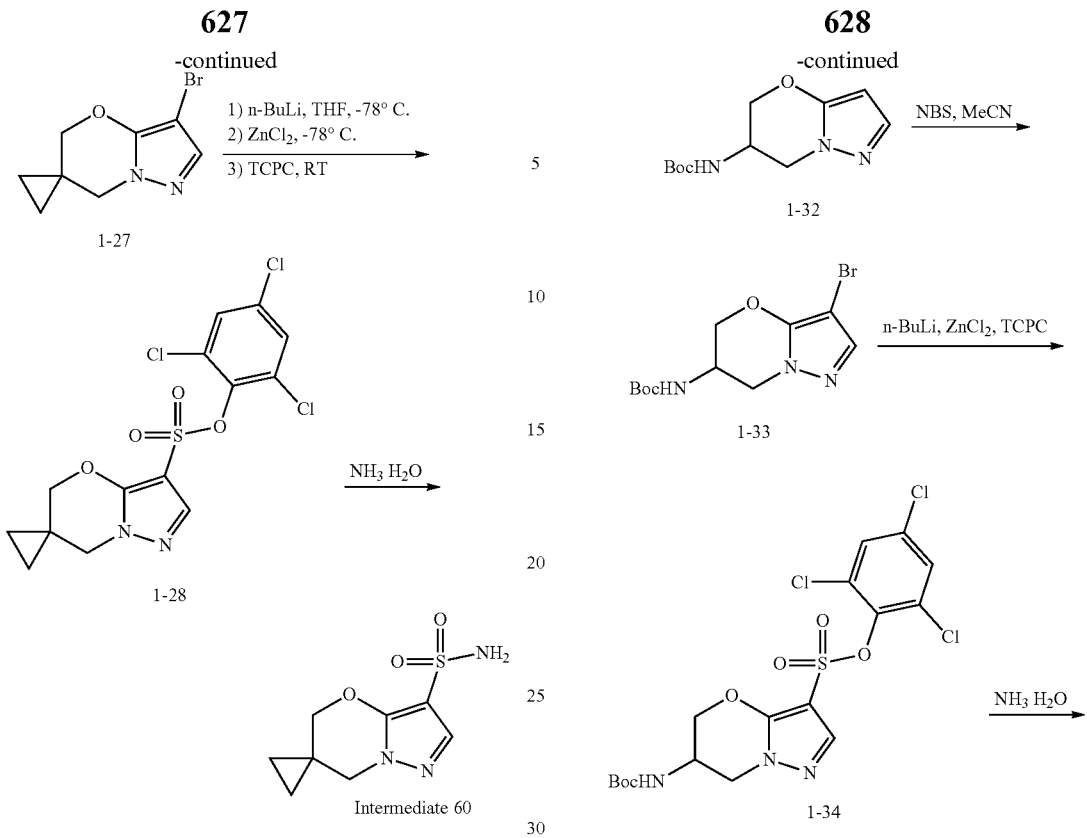

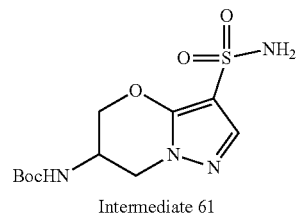

Referring to Scheme KKK, cyclopropane-1,1-diyldimethanol is mesylated (e.g., with MsCl and TEA). Treatment of the ensuing mesylate with pyrazolone 1-9 affords compound 1-26 (e.g., using potassium carbonate as the base and DMF as the solvent). Compound 1-26 is brominated (e.g., with NBS) to afford 1-27 which is reacted sequentially with n-butyl lithium, zinc chloride, and TCPC to furnish compound 1-28. Intermediate 60 is obtained by reacting compound 1-28 with aqueous ammonia.

Intermediate 61

Scheme LLL

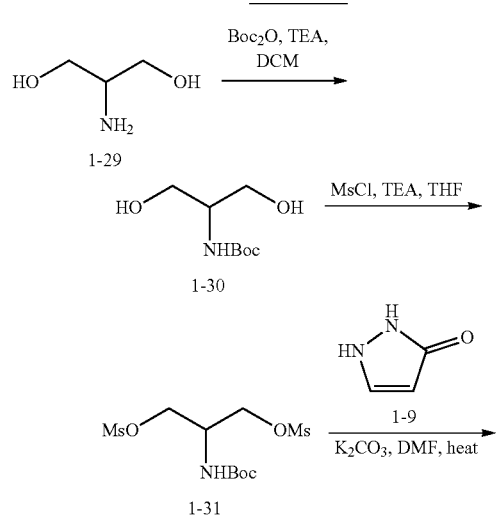

Referring to Scheme LLL, the amino group in diol 1-29 is protected with Boc₂O to provide compound 1-30 which is mesylated (e.g., with MsCl and TEA) to afford compound 1-31. Compound 1-31 is subjected to a double nucleophilic substitution with pyrazolone 1-9, providing 1-32, which is brominated (e.g., with NBS) to afford compound 1-33. Sequential treatment of 1-33 with n-butyl lithium, zinc chloride, and TCPC provides compound 1-34. Intermediate 61 is obtained when 1-34 is reacted with aqueous ammonia.

Intermediate 62

Scheme MMM

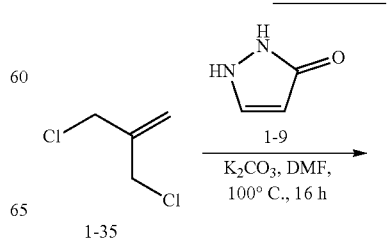

629

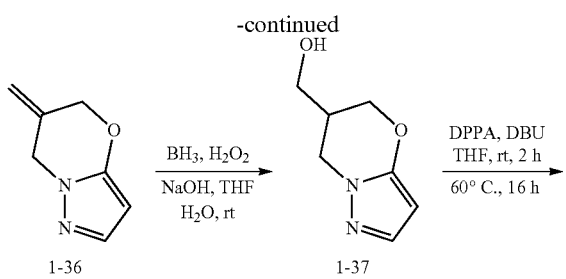

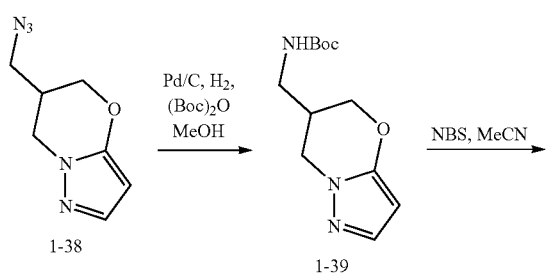

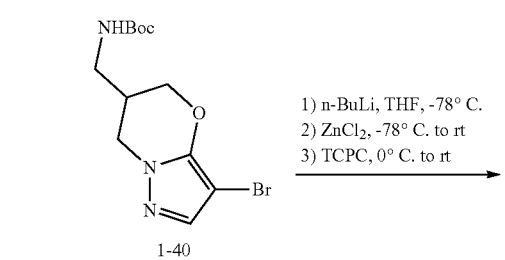

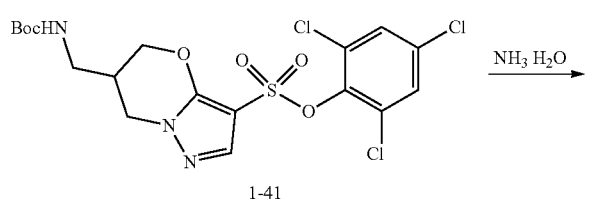

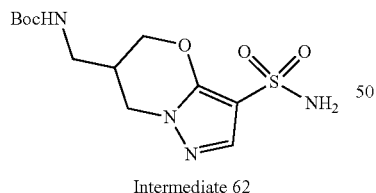

Intermediate 62

Referring to Scheme MMM, bis-chloride 1-35 is reacted with pyrazolone 1-9 to yield compound 1-36. Hydroboration-oxidation of 1-36 provides compound 1-37, whereupon the primary alcohol is converted into an azido group (e.g., with DPPA and DBU). The azide moiety in the resulting 1-38 is then reduced (e.g., with Pd/C, H₂); and the ensuing amino group is protected with Boc₂O to afford 1-39. Compound 1-39 is brominated to provide 1-40. Sequential treatment of 1-40 with n-butyl lithium, zinc chloride, and TCPC affords compound 1-41. Intermediate 62 is obtained by treating 1-41 with aqueous ammonia.

630

Intermediate 63, 63a and 63b

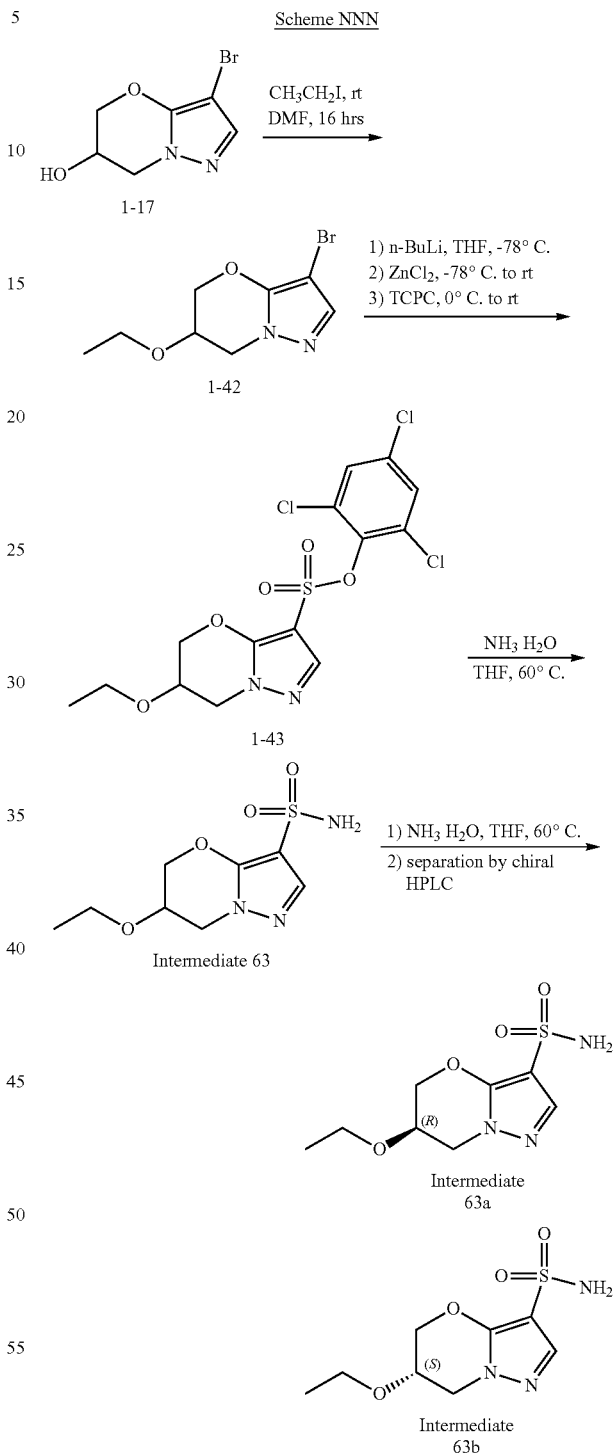

Referring to Scheme NNN, compound 1-17 is ethylated (e.g., with ethyl iodide) to provide 1-42. Sequential treatment of 1-42 with n-butyl lithium, zinc chloride, and TCPC affords 1-43 which is reacted with aqueous ammonia to provide Intermediate 63. Chiral resolution of Intermediate 63 affords Intermediate 63a and 63b.

Intermediate 64

Scheme OOO

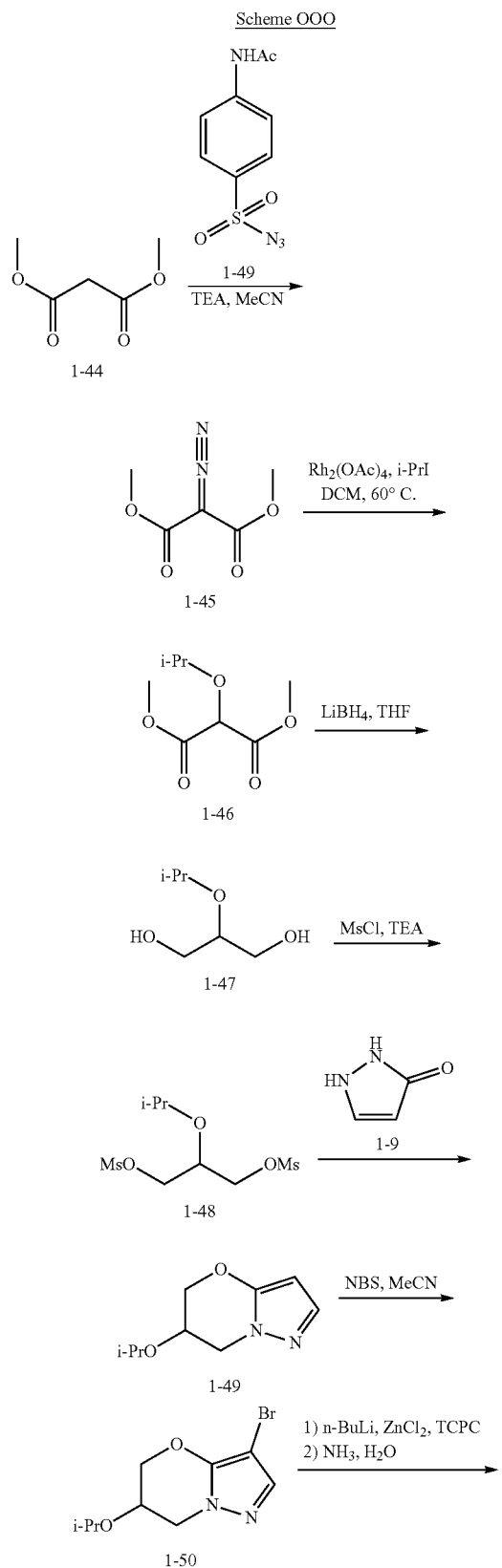

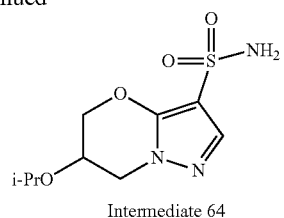

Intermediate 64

Referring to Scheme OOO, compound 1-44 is reacted with sulfonyl azide 1-49 (in a Regitz-type diazo transfer) to provide compound 1-45. Compound 1-45 is subjected to Rh$_2$(OAc)$_4$ and i-PrI to afford compound 1-46. The ester groups in 1-46 is reduced (e.g., with lithium borohydride) to afford diol compound 1-47 which is mesylated (e.g., with MsCl) to provide compound 48. Compound 48 is reacted with pyrazolone 1-9 to furnish 1-49, whereupon bromination of the pyrazole ring affords 1-50. Sequential treatment of 1-50 with n-butyl lithium, zinc chloride, TCPC, and aqueous ammonia provide Intermediate 64.

Intermediate 65

Scheme PPP

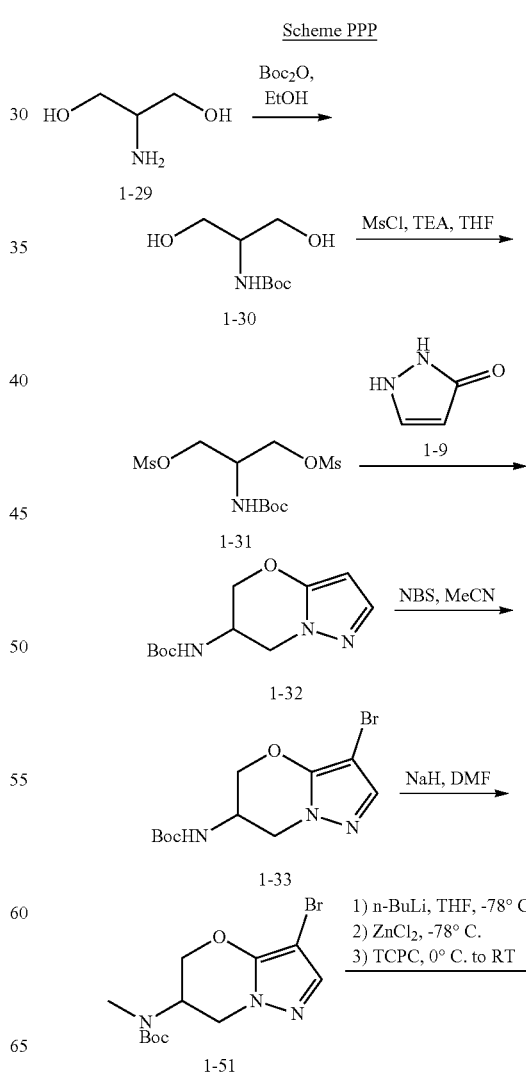

633

-continued

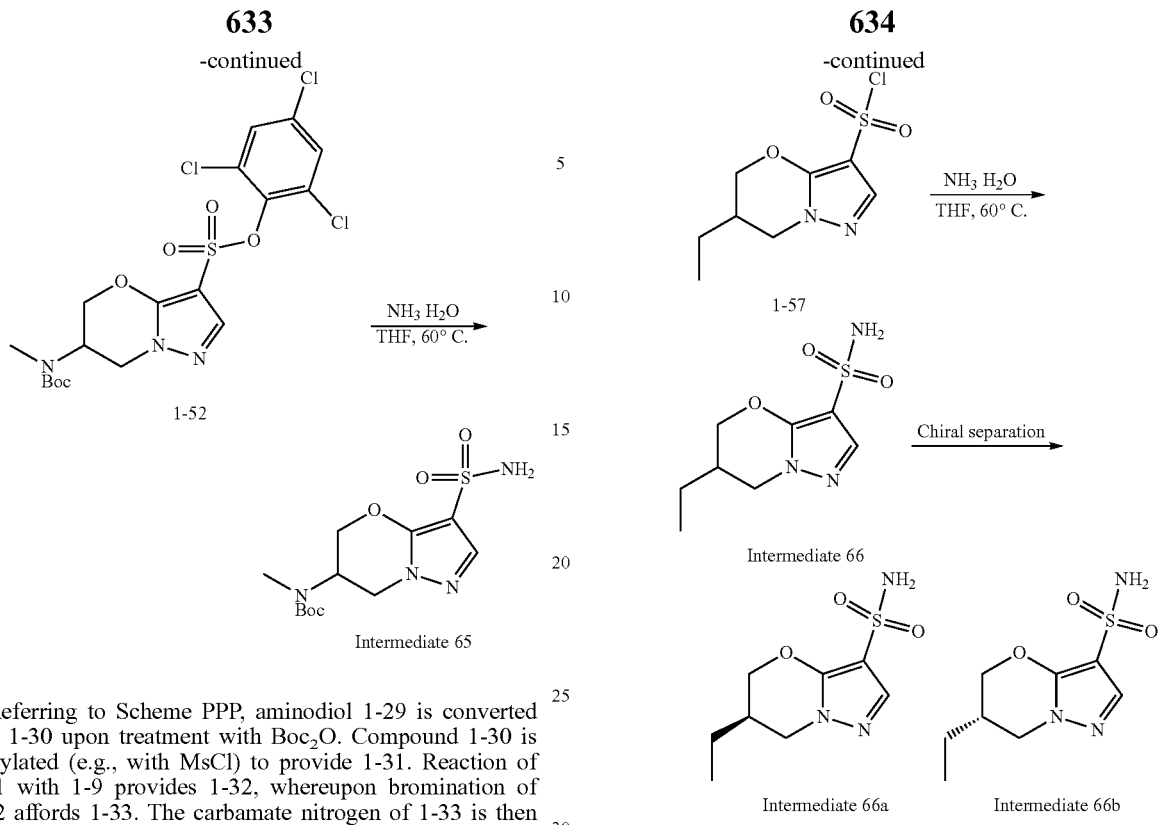

Intermediate 65

Referring to Scheme PPP, aminodiol 1-29 is converted into 1-30 upon treatment with Boc₂O. Compound 1-30 is mesylated (e.g., with MsCl) to provide 1-31. Reaction of 1-31 with 1-9 provides 1-32, whereupon bromination of 1-32 affords 1-33. The carbamate nitrogen of 1-33 is then methylated (e.g., with MeI and NaH) to provide 1-51. Sequential treatment of 1-51 with n-butyl lithium, zinc chloride, and TCPC provides 1-52, whereupon treatment with aqueous ammonia provide Intermediate 65.

Intermediate 66, 66a and 66b

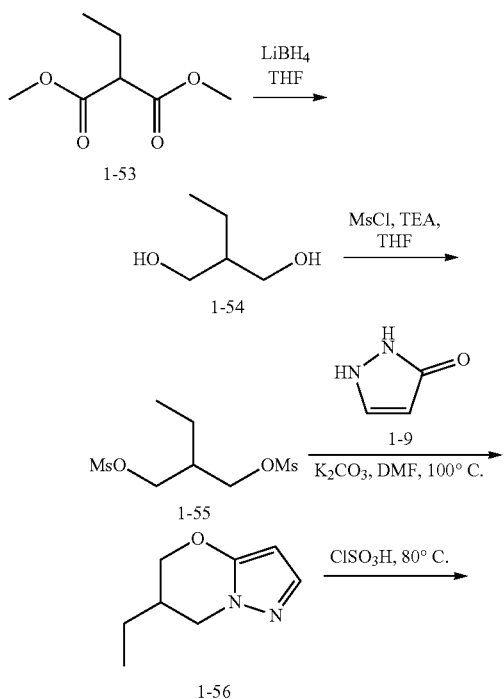

634

-continued

Intermediate 66

Referring to Scheme QQQ, diester compound 1-53 is reduced to give rise to diol 1-54 which is mesylated (e.g., with MsCl) to provide 1-55. Treatment of 1-55 with pyrazolone 1-9 affords bicyclic compound 1-56. Exposure of 1-56 to ClSO₃H (e.g., at elevated temperatures) provides 1-57, whereupon treatment with aqueous ammonia affords Intermediate 66. Chiral separation of Intermediate 66 affords Intermediate 66a and 66b.

Intermediate 67

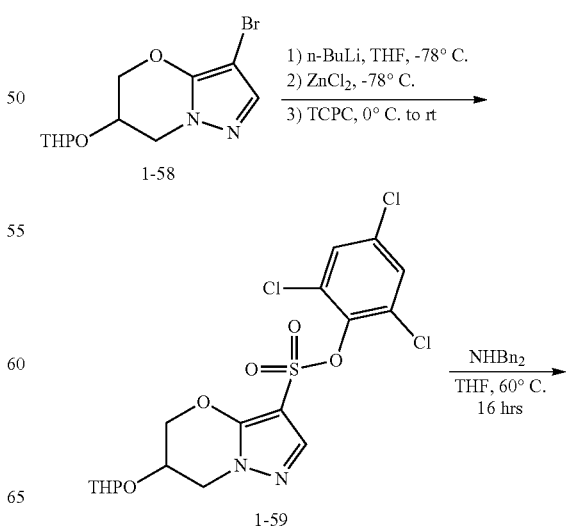

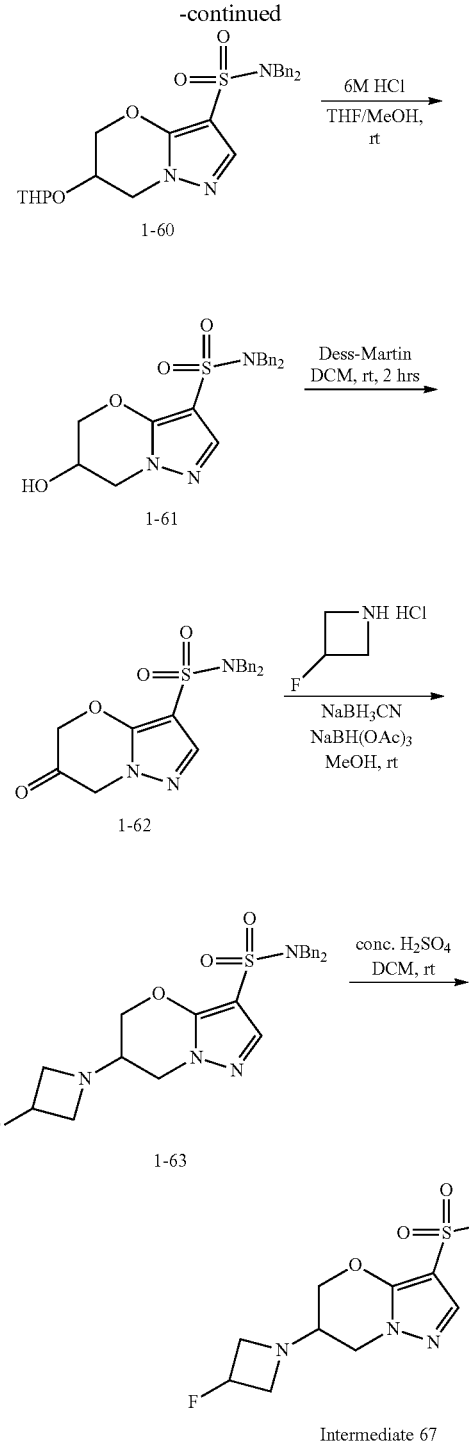

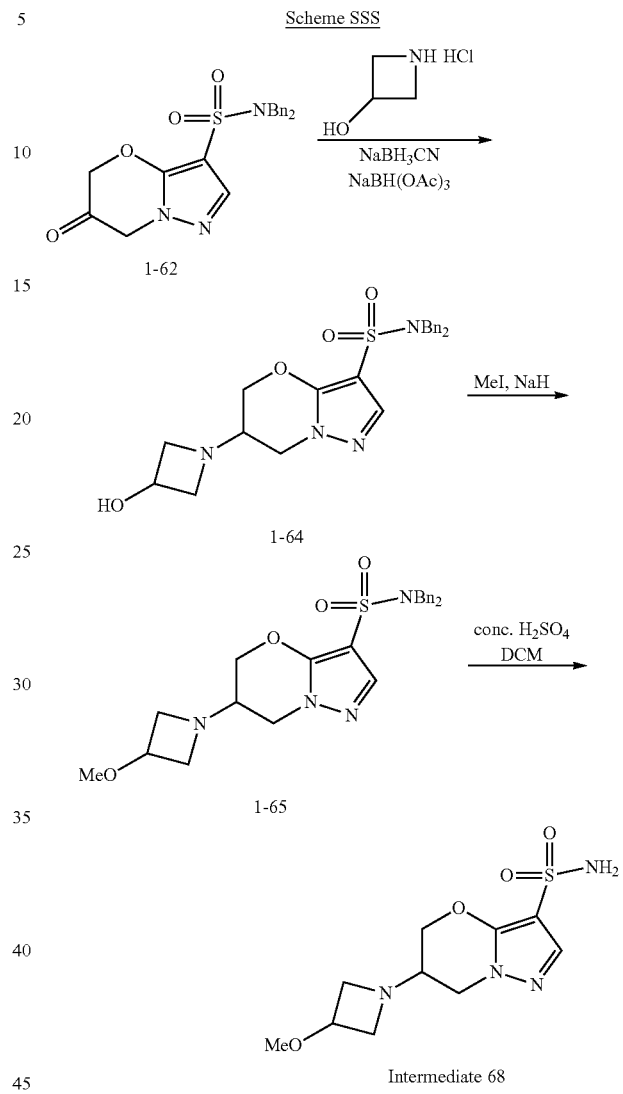

Referring to Scheme RRR, compound 1-58 is treated sequentially with n-butyl lithium, zinc chloride, and TCPC to provide compound 1-59. Reaction of 1-59 with dibenzylamine provides 1-60. The THP group in 1-60 is removed (e.g., with concentrated HCl) to afford compound 1-61. The secondary alcohol in 1-61 is oxidized to a ketone (e.g., with Dess-Martin's reagent). The resulting 1-62 is subjected to a reductive amination with 3-fluoroazetidine to provide 1-63, whereupon removal of the benzyl protecting groups affords Intermediate 67.

Referring to Scheme SSS, compound 1-62 is subjected to a reductive amination with 3-hydroxyazetidine to provide compound 1-64 which is then methylated (e.g., with MeI) to afford 1-65. Removal of the benzyl protecting groups on 1-65 affords Intermediate 68.

The Following Protocols are Suitable for Testing the Activity of the Compounds Disclosed Herein.

IL-1β Production in PMA-Differentiated THP-1 Cells Stimulated with Gramicidin.

THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 μg/ml)), and maintained in log phase prior to experimental setup. Prior to the experiment THP-1 were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 μg/ml). The cells were plated in a 384-well plate at a density of 50,000 cells/well (final assay volume 50 μl). Compounds were dissolved in dimethyl sulfoxide (DMSO) and added to the culture medium to achieve desired concentration (e.g. 100, 33, 11, 3.7, 1.2, 0.41, 0.14, 0.046, 0.015, 0.0051, 0.0017 μM). Cells were incubated with compounds for 1 hour and then stimulated with gramicidin (5 μM) (Enzo) for 2 hours. Cell free supernatant was collected and the production of IL-1β was evaluated by HTRF (cisbio). A vehicle only control was run concurrently with each experiment. Final DMSO concentration was 0.38%. Compounds exhibited a concentration-dependent inhibition of IL-1p production in PMA-differentiated THP-1 cells.

IL-1β Production in PMA-Differentiated THP-1 Cells Stimulated with Gramicidin.

THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 μg/ml)), and maintained in log phase prior to experimental setup. Prior to the experiment THP-1 were treated with PMA (Phorbol 12-myristate 13-acetate) (20 ng/ml) for 16-18 hours. Compounds were dissolved in dimethyl sulfoxide (DMSO) to generate a 30 mM stock. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 μg/ml). The cells were plated in a 384-well plate at a density of 50,000 cells/well (final assay volume 50 μl). Compounds were first dissolved in assay medium to obtain a 5× top concentration of 500 μM. 10 step dilutions (1:3) were then undertaken in assay medium containing 1.67% DMSO. 5× compound solutions were added to the culture medium to achieve desired final concentration (e.g. 100, 33, 11, 3.7, 1.2, 0.41, 0.14, 0.046, 0.015, 0.0051, 0.0017 μM). Final DMSO concentration was at 0.37%. Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1p was evaluated by HTRF (cisbio). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1p production in PMA-differentiated THP-1 cells.

IL-1p Production in PMA-Differentiated THP-1 Cells Stimulated with Gramicidin.

THP-1 cells were purchased from the American Type Culture Collection and sub-cultured according to instructions from the supplier. Cells were cultured in complete RPMI 1640 (containing 10% heat inactivated FBS, penicillin (100 units/ml) and streptomycin (100 μg/ml)), and maintained in log phase prior to experimental setup. Prior to the experiment, compounds were dissolved in dimethyl sulfoxide (DMSO) to generate a 30 mM stock. The compound stock was first pre-diluted in DMSO to 3, 0.34, 0.042 and 0.0083 mM intermediate concentrations and subsequently spotted using Echo550 liquid handler into an empty 384-well assay plate to achieve desired final concentration (e.g. 100, 33, 11, 3.7, 1.2, 0.41, 0.14, 0.046, 0.015, 0.0051, 0.0017 μM). DMSO was backfilled in the plate to achieve a final DMSO assay concentration of 0.37%. The plate was then sealed and stored at room temperature until required.

THP-1 cells were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, and resuspended in RPMI 1640 (containing 2% heat inactivated FBS, penicillin (100 units/ml) and streptomycin (100 μg/ml). The cells were plated in the 384-well assay plate containing the spotted compounds at a density of 50,000 cells/well (final assay volume 50 μl). Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1β was evaluated by HTRF (cisbio). The plates were incubated for 18 h at 4° C. and read using the preset HTRF program (donor emission at 620 nm, acceptor emission at 668 nm) of the SpectraMax i3x spectrophotometer (Molecular Devices, software SoftMax 6). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1p production in PMA-differentiated THP-1 cells.

TABLE 6

Average IC$_{50}$ of compounds in hTHP-1 assay

| Compound Number | NLRP3 Antagonist, human THP1 NLRP3, IL-1b, Normalized: GeoMean IC50 (uM) |
| --- | --- |
| 101 | +++ |
| 102 | + |
| 106 | >30.0000 |
| 107 | ++ |
| 107 | ++ |
| 108 | +++ |
| 109 | ++ |
| 110 | ++ |
| 111 | ++ |
| 112 | +++ |
| 113 | +++ |
| 114 | ++ |
| 115 | + |
| 116 | ++ |
| 117 | +++ |
| 118 | +++ |
| 119 | +++ |
| 120 | ++ |
| 121 | ++ |
| 122 | >30.0000 |
| 124 | + |
| 125 | + |
| 137 | ++++ |
| 139 | ++++ |
| 145 | ++ |
| 146 | +++ |
| 147 | ++ |
| 147 | ++ |
| 148 | ++ |
| 149 | ++ |
| 313 | ++ |
| 314 | ++ |
| 315 | >30.0000 |
| 316 | ++ |

TABLE 6-continued

Average IC$_{50}$ of compounds in hTHP-1 assay

| Compound Number | NLRP3 Antagonist, human THP1 NLRP3, IL-1b, Normalized: GeoMean IC50 (uM) |
|---|---|
| 321 | ++ |
| 322 | +++ |
| 323 | ++ |
| 324 | ++++ |
| 325 | ++ |
| 355 | + |
| 370 | ++++ |
| 372 | >30.0000 |
| 373 | >30.0000 |
| 377 | ++ |
| 378 | + |
| 379 | ++ |

Table 6 shows the biological activity of compounds in hTHP-1 assay containing 2% fetal bovine serum: <0.008 μM = "+++++"; ≥0.008 and <0.04 μM = "++++"; ≥0.04 and <0.2 μM = "+++"; ≥0.2 and <1 μM = "+++"; ≥1 and <5 μM = "++"; ≥5 and <30 μM = "+".

A number of embodiments of the invention have been described. Nevertheless, it will be understood that various modifications may be made without departing from the spirit and scope of the invention. Accordingly, other embodiments are within the scope of the following claims.

What is claimed is:
1. A compound, selected from the group consisting of the compounds below:
| Compound | Structure |
|---|---|
| 101 | 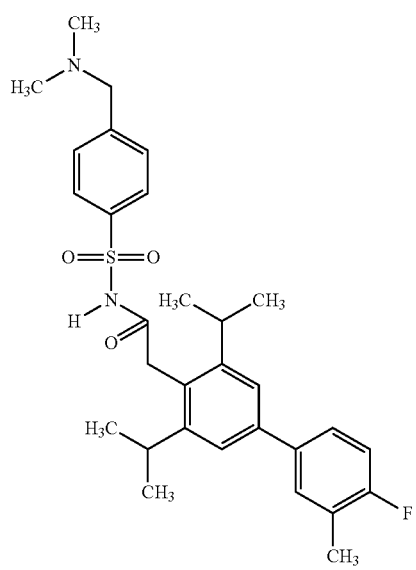 [SMILES: Cc1cc(-c2cc(C(C)C)c(CC(=O)NS(=O)(=O)c3ccc(CN(C)C)cc3)c(C(C)C)c2)ccc1F] |
| 102 | 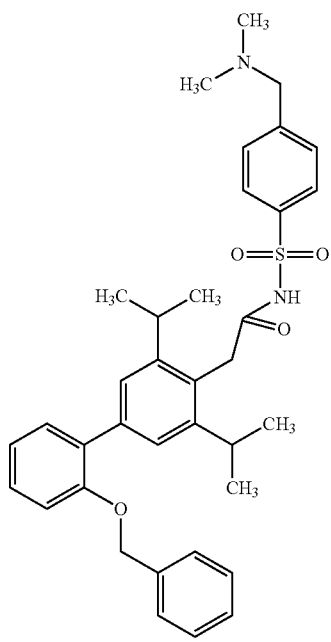 [SMILES: CC(C)c1cc(-c2ccccc2OCc2ccccc2)cc(C(C)C)c1CC(=O)NS(=O)(=O)c1ccc(CN(C)C)cc1] |

| Compound | Structure |
|---|---|
| 106 | 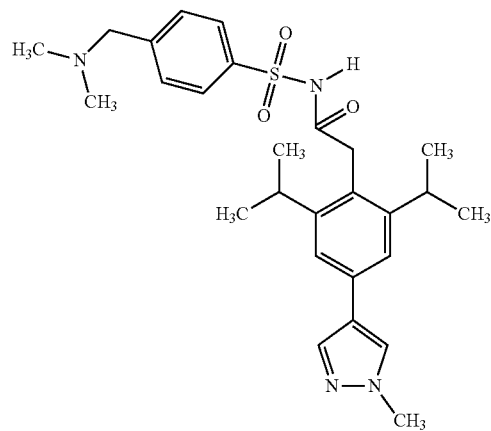 [SMILES: CC(C)c1cc(-c2cnn(C)c2)cc(C(C)C)c1CC(=O)NS(=O)(=O)c1ccc(CN(C)C)cc1] |
| 107 | 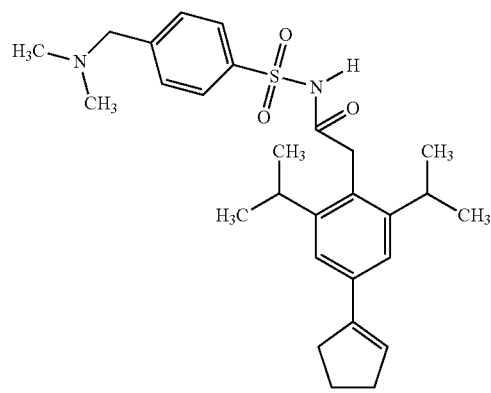 [SMILES: CC(C)c1cc(C2=CCCC2)cc(C(C)C)c1CC(=O)NS(=O)(=O)c1ccc(CN(C)C)cc1] |
| 108 | 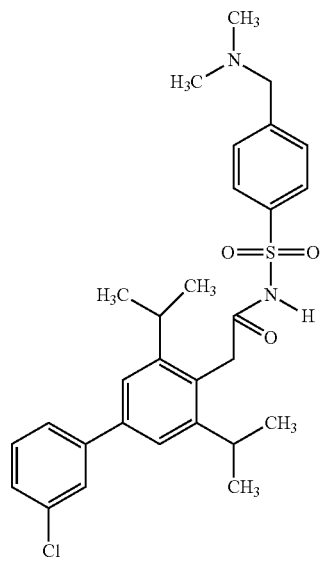 [SMILES: CC(C)c1cc(-c2cccc(Cl)c2)cc(C(C)C)c1CC(=O)NS(=O)(=O)c1ccc(CN(C)C)cc1] |

-continued
| Compound | Structure |
|---|---|
| 109 | 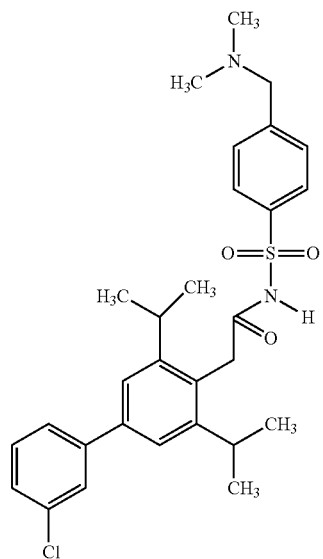 [SMILES: CC(C)c1cc(-c2cccc(Cl)c2)cc(C(C)C)c1CC(=O)NS(=O)(=O)c1ccc(CN(C)C)cc1] |
| 110 | 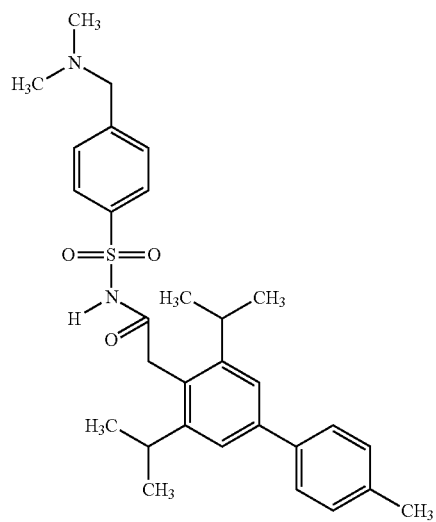 |

| Compound | Structure |
|---|---|
| 111 | 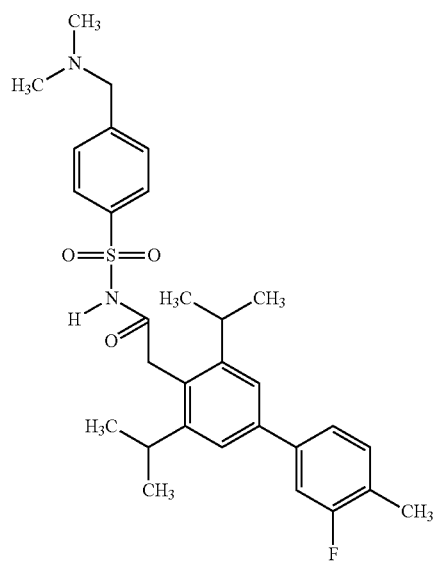 |
| 112 | 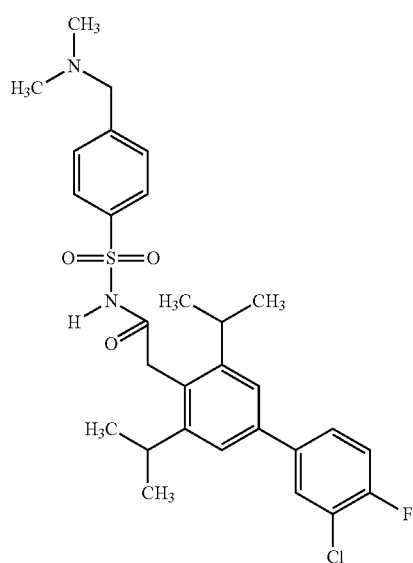 [SMILES: CC(C)c1cc(-c2ccc(F)c(Cl)c2)cc(C(C)C)c1CC(=O)NS(=O)(=O)c1ccc(CN(C)C)cc1] |
| 113 | 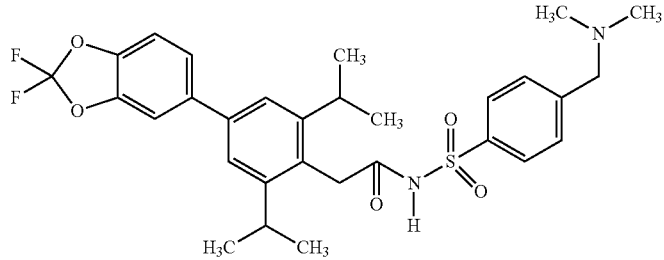 [SMILES: CC(C)c1cc(-c2ccc3c(c2)OC(F)(F)O3)cc(C(C)C)c1CC(=O)NS(=O)(=O)c1ccc(CN(C)C)cc1] |

| Compound | Structure |
|---|---|
| 114 | 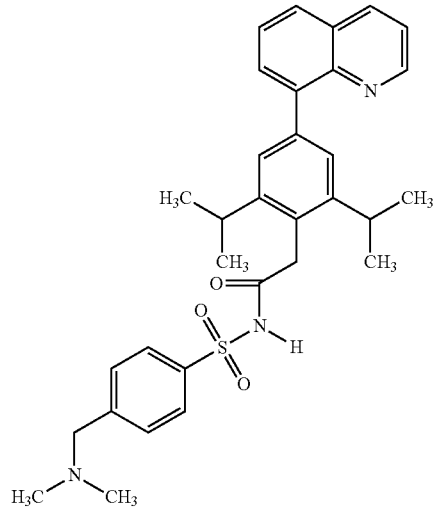 |
| 115 | 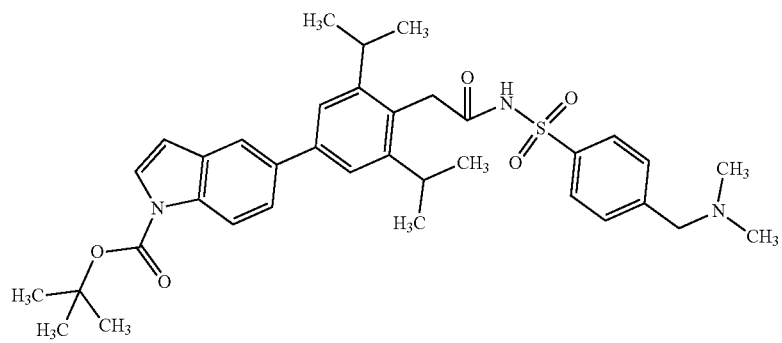 [SMILES: CC(C)c1cc(-c2ccc3c(ccn3C(=O)OC(C)(C)C)c2)cc(C(C)C)c1CC(=O)NS(=O)(=O)c1ccc(CN(C)C)cc1] |
| 116 | 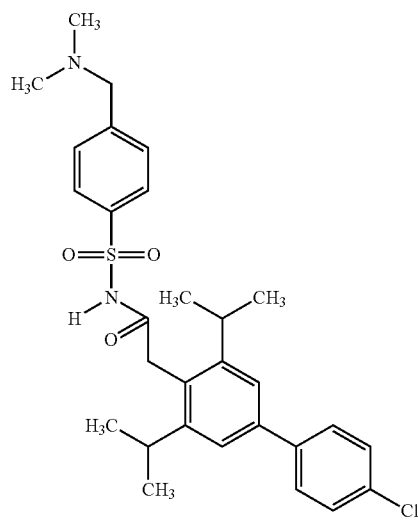 [SMILES: CC(C)c1cc(-c2ccc(Cl)cc2)cc(C(C)C)c1CC(=O)NS(=O)(=O)c1ccc(CN(C)C)cc1] |

-continued
| Compound | Structure |
|---|---|
| 117 | 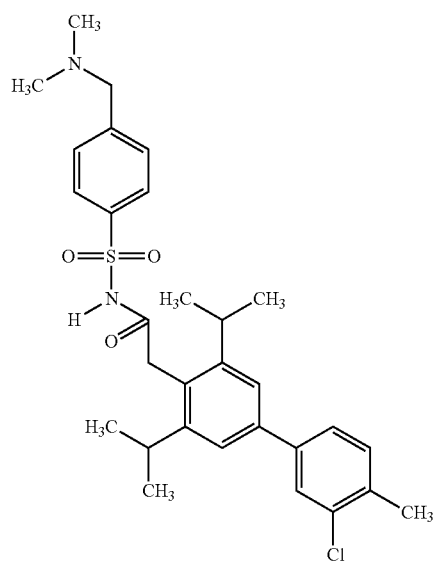 |
| 118 | 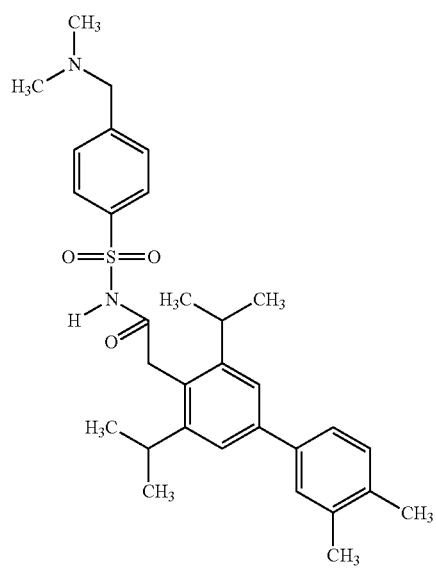 |

-continued
| Compound | Structure |
|---|---|
| 119 | 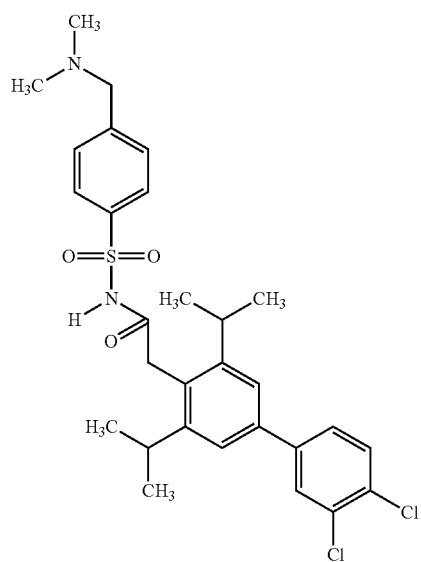 [SMILES: CC(C)c1cc(-c2ccc(Cl)c(Cl)c2)cc(C(C)C)c1CC(=O)NS(=O)(=O)c1ccc(CN(C)C)cc1] |
| 120 | 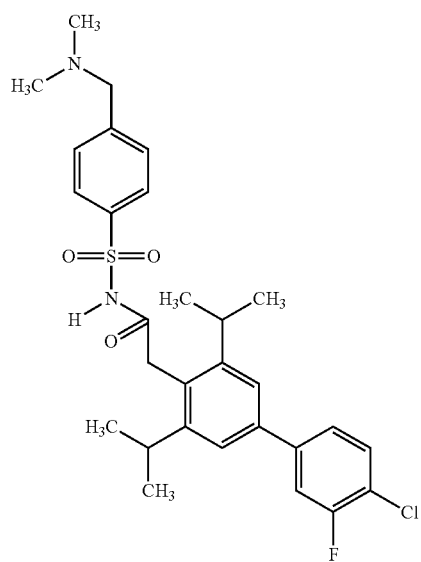 [SMILES: CC(C)c1cc(-c2ccc(Cl)c(F)c2)cc(C(C)C)c1CC(=O)NS(=O)(=O)c1ccc(CN(C)C)cc1] |

-continued
| Compound | Structure |
|---|---|
| 121 | 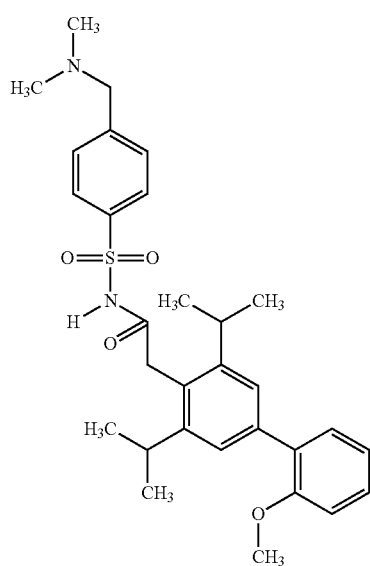 [SMILES: COc1ccccc1-c1cc(C(C)C)c(CC(=O)NS(=O)(=O)c2ccc(CN(C)C)cc2)c(C(C)C)c1] |
| 122 | 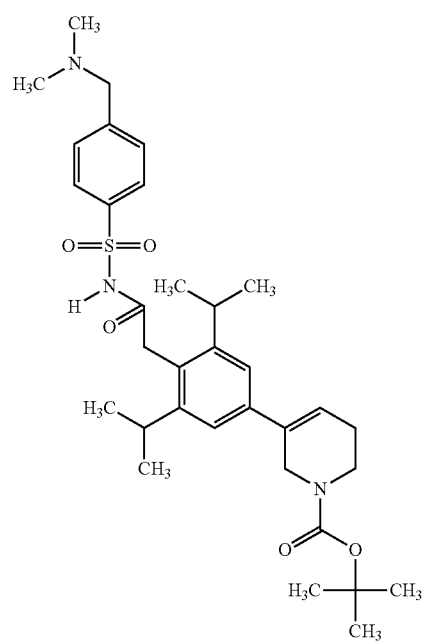 [SMILES: CC(C)c1cc(C2=CCCN(C(=O)OC(C)(C)C)C2)cc(C(C)C)c1CC(=O)NS(=O)(=O)c1ccc(CN(C)C)cc1] |

| Compound | Structure |
|---|---|
| 124 | 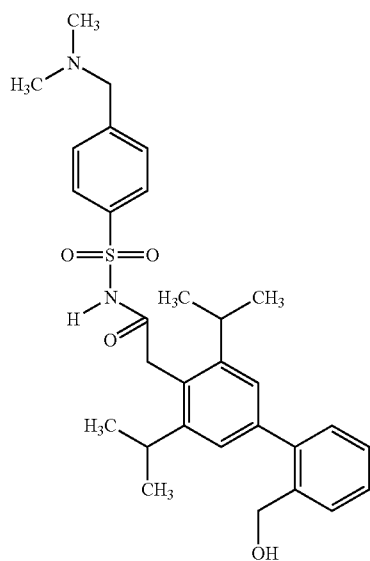 [SMILES: CC(C)c1cc(-c2ccccc2CO)cc(C(C)C)c1CC(=O)NS(=O)(=O)c1ccc(CN(C)C)cc1] |
| 125 | 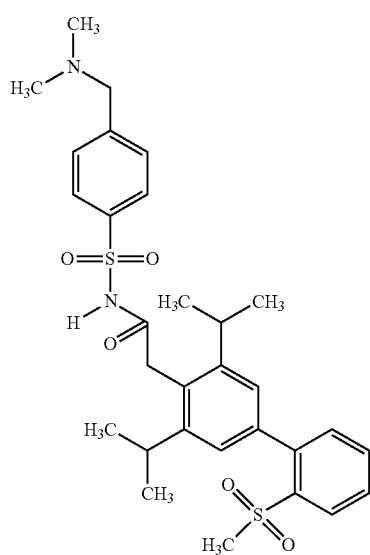 [SMILES: CC(C)c1cc(-c2ccccc2S(C)(=O)=O)cc(C(C)C)c1CC(=O)NS(=O)(=O)c1ccc(CN(C)C)cc1] |

-continued
| Compound | Structure |
|---|---|
| 131 | 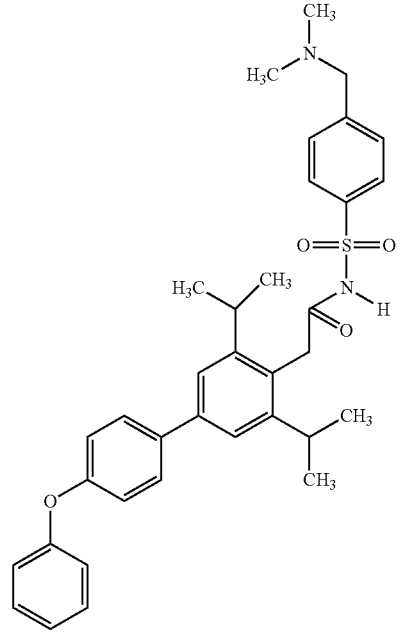 [SMILES: CC(C)c1cc(-c2ccc(Oc3ccccc3)cc2)cc(C(C)C)c1CC(=O)NS(=O)(=O)c1ccc(CN(C)C)cc1] |
| 134 | 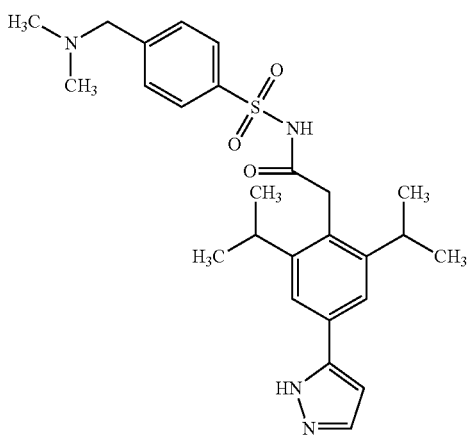 [SMILES: CC(C)c1cc(-c2ccn[nH]2)cc(C(C)C)c1CC(=O)NS(=O)(=O)c1ccc(CN(C)C)cc1] |
| 137 | 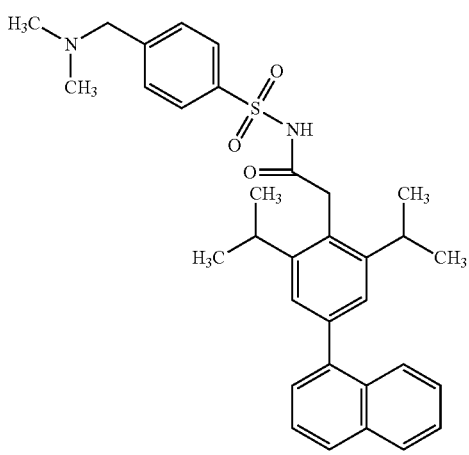 [SMILES: CC(C)c1cc(-c2cccc3ccccc23)cc(C(C)C)c1CC(=O)NS(=O)(=O)c1ccc(CN(C)C)cc1] |

-continued
| Compound | Structure |
|---|---|
| 138 | 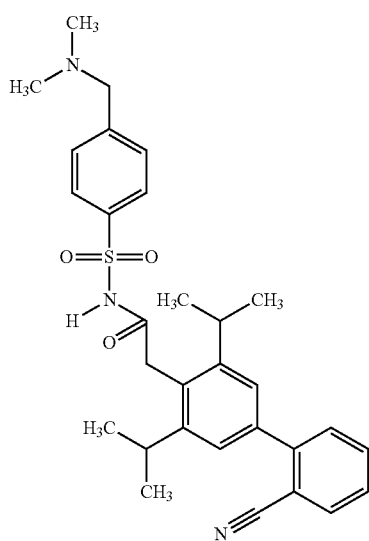 [SMILES: CC(C)c1cc(-c2ccccc2C#N)cc(C(C)C)c1CC(=O)NS(=O)(=O)c1ccc(CN(C)C)cc1] |
| 139 | 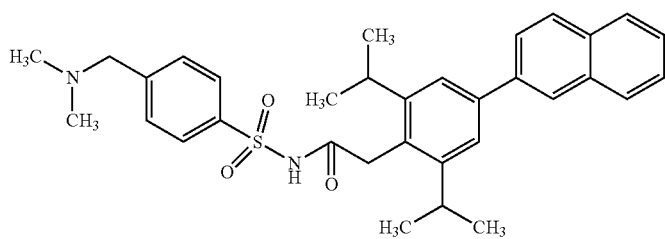 [SMILES: CC(C)c1cc(-c2ccc3ccccc3c2)cc(C(C)C)c1CC(=O)NS(=O)(=O)c1ccc(CN(C)C)cc1] |
| 140 | 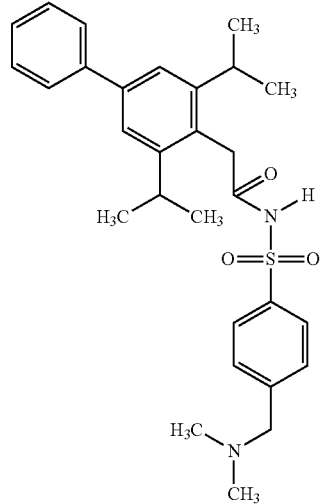 [SMILES: CC(C)c1cc(-c2ccccc2)cc(C(C)C)c1CC(=O)NS(=O)(=O)c1ccc(CN(C)C)cc1] |

| Compound | Structure |
|---|---|
| 143 | 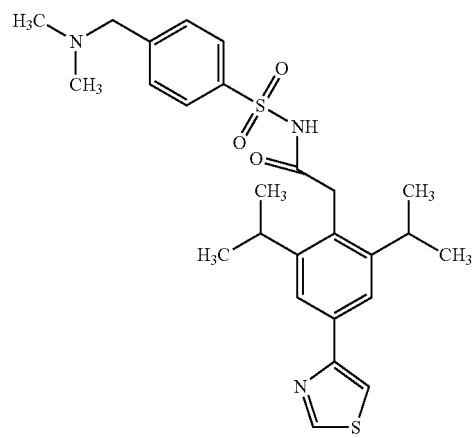 [SMILES: CC(C)c1cc(-c2cscn2)cc(C(C)C)c1CC(=O)NS(=O)(=O)c1ccc(CN(C)C)cc1] |
| 144 | 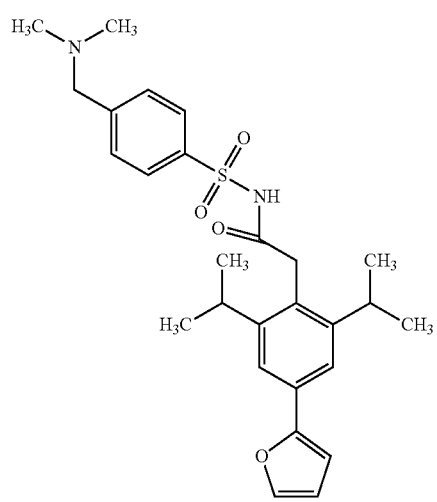 [SMILES: CC(C)c1cc(-c2ccco2)cc(C(C)C)c1CC(=O)NS(=O)(=O)c1ccc(CN(C)C)cc1] |
| 145 | 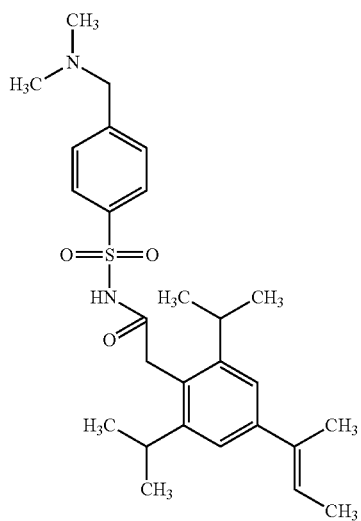 [SMILES: C/C=C(\C)c1cc(C(C)C)c(CC(=O)NS(=O)(=O)c2ccc(CN(C)C)cc2)c(C(C)C)c1] |

| Compound | Structure |
|---|---|
| 146 | 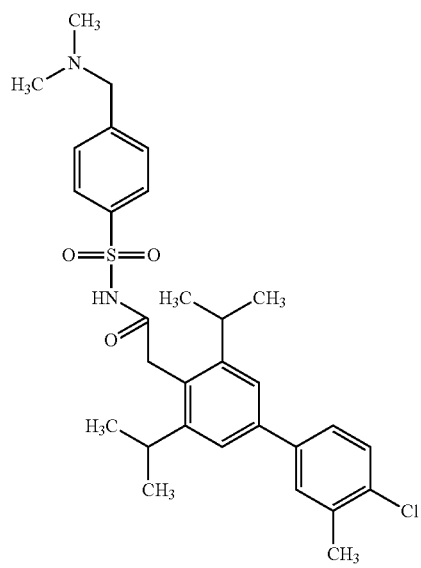 [SMILES: Cc1cc(-c2cc(C(C)C)c(CC(=O)NS(=O)(=O)c3ccc(CN(C)C)cc3)c(C(C)C)c2)ccc1Cl] |
| 147 | 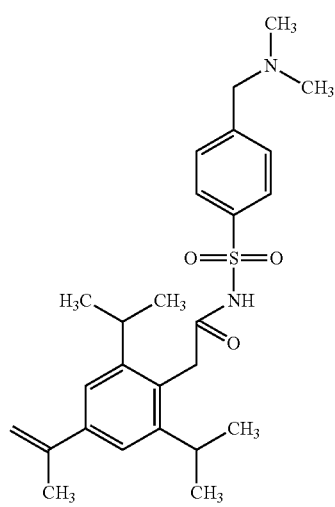 [SMILES: C=C(C)c1cc(C(C)C)c(CC(=O)NS(=O)(=O)c2ccc(CN(C)C)cc2)c(C(C)C)c1] |
| 201 | 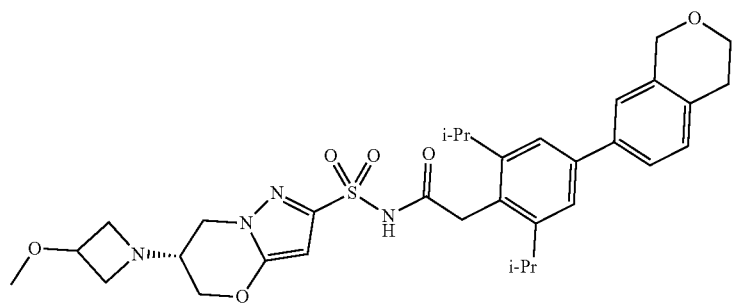 [SMILES: COC1CN([C@H]2COc3cc(S(=O)(=O)NC(=O)Cc4c(C(C)C)cc(-c5ccc6c(c5)COCC6)cc4C(C)C)nn3C2)C1] |

-continued

| Compound | Structure |
|---|---|
| 202 | 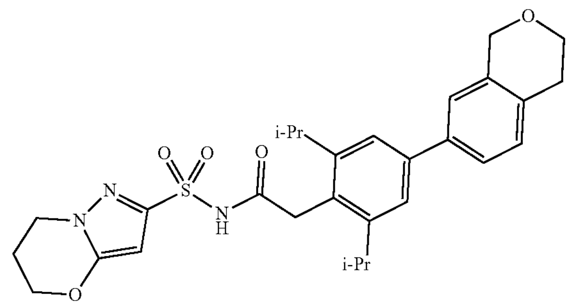 [SMILES: CC(C)c1cc(-c2ccc3c(c2)COCC3)cc(C(C)C)c1CC(=O)NS(=O)(=O)c1cc2n(n1)CCCO2] |
| 203 | 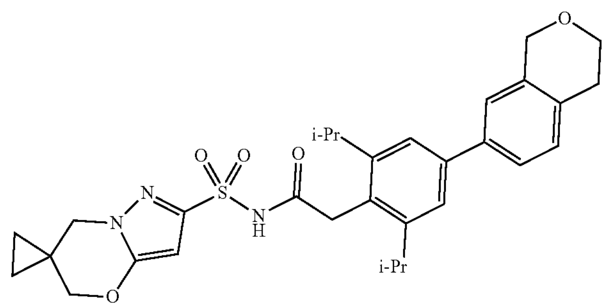 [SMILES: CC(C)c1cc(-c2ccc3c(c2)COCC3)cc(C(C)C)c1CC(=O)NS(=O)(=O)c1cc2n(n1)CC1(CC1)CO2] |
| 204 | 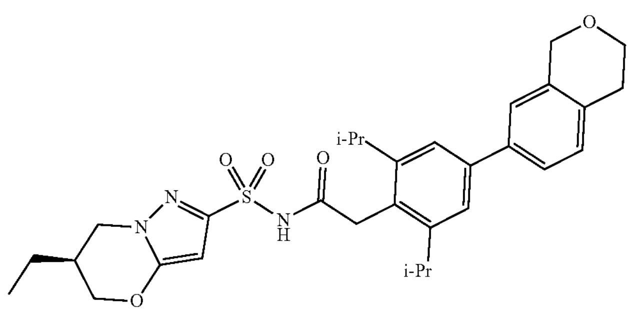 [SMILES: CC[C@@H]1COc2cc(S(=O)(=O)NC(=O)Cc3c(C(C)C)cc(-c4ccc5c(c4)COCC5)cc3C(C)C)nn2C1] |
| 205 | 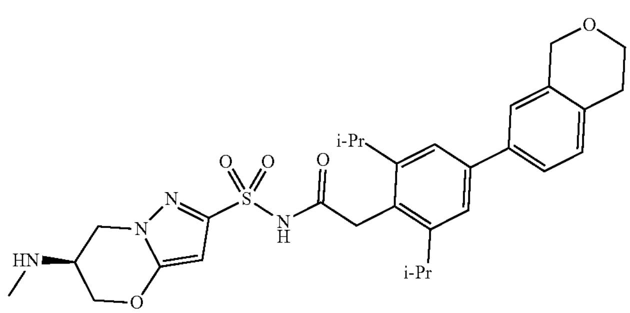 |
| 206 | 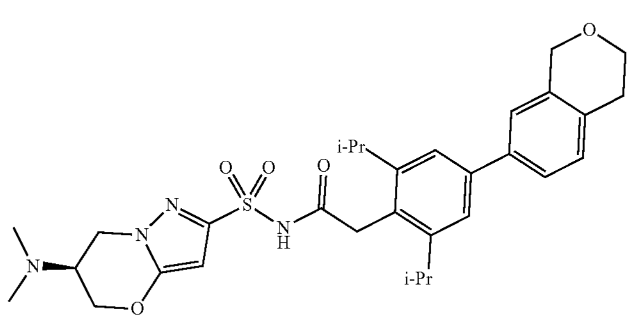 [SMILES: CC(C)c1cc(-c2ccc3c(c2)COCC3)cc(C(C)C)c1CC(=O)NS(=O)(=O)c1cc2n(n1)C[C@H](N(C)C)CO2] |

-continued
| Compound | Structure |
|---|---|
| 207 | 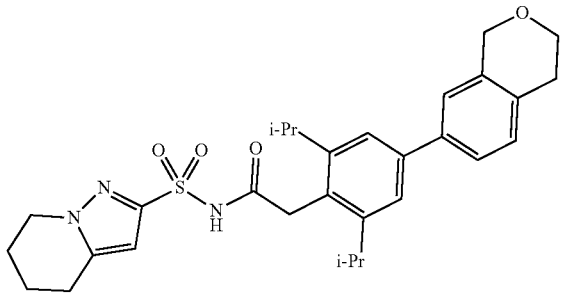 [SMILES: CC(C)c1cc(-c2ccc3c(c2)COCC3)cc(C(C)C)c1CC(=O)NS(=O)(=O)c1cc2n(n1)CCCC2] |
| 208 | 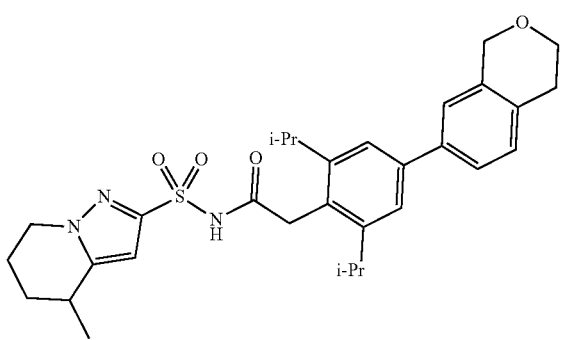 [SMILES: CC(C)c1cc(-c2ccc3c(c2)COCC3)cc(C(C)C)c1CC(=O)NS(=O)(=O)c1cc2n(n1)CCCC2C] |
| 209 | 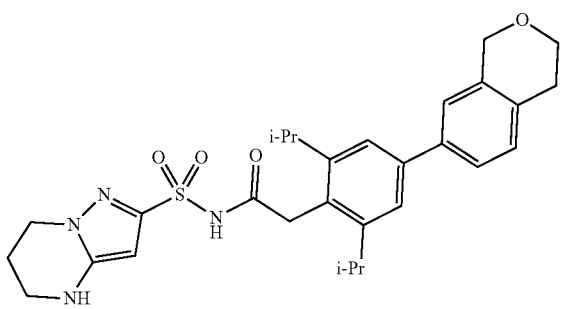 [SMILES: CC(C)c1cc(-c2ccc3c(c2)COCC3)cc(C(C)C)c1CC(=O)NS(=O)(=O)c1cc2n(n1)CCCN2] |
| 210 | 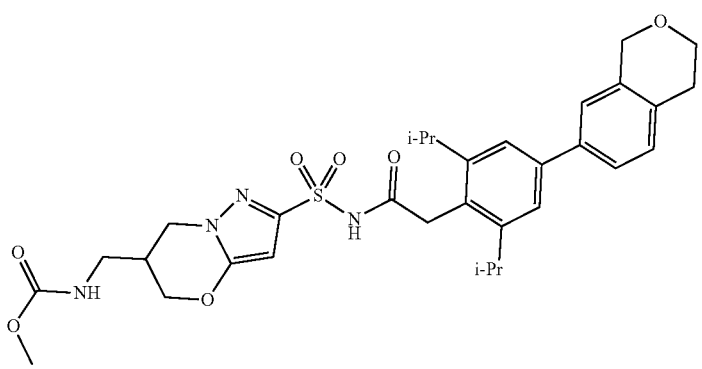 [SMILES: COC(=O)NCC1COc2cc(S(=O)(=O)NC(=O)Cc3c(C(C)C)cc(-c4ccc5c(c4)COCC5)cc3C(C)C)nn2C1] |

-continued
| Compound | Structure |
|---|---|
| 211 | 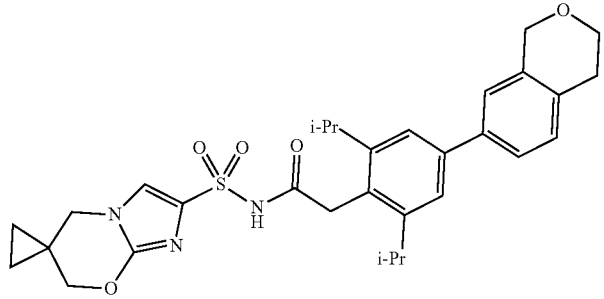 [SMILES: CC(C)c1cc(-c2ccc3c(c2)COCC3)cc(C(C)C)c1CC(=O)NS(=O)(=O)c1cn2c(n1)OCC1(CC1)C2] |
| 212 | 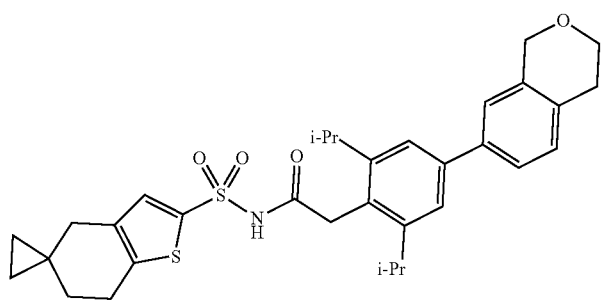 [SMILES: CC(C)c1cc(-c2ccc3c(c2)COCC3)cc(C(C)C)c1CC(=O)NS(=O)(=O)c1cc2c(s1)CCC1(CC1)C2] |
| 213 | 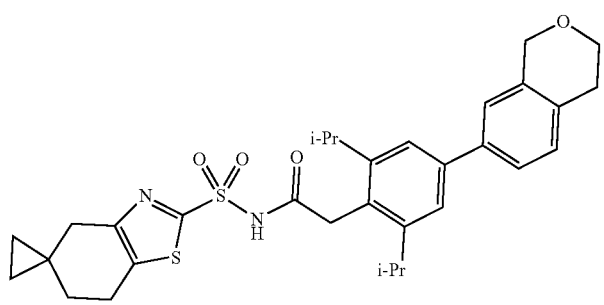 [SMILES: CC(C)c1cc(-c2ccc3c(c2)COCC3)cc(C(C)C)c1CC(=O)NS(=O)(=O)c1nc2c(s1)CCC1(CC1)C2] |
| 214 | 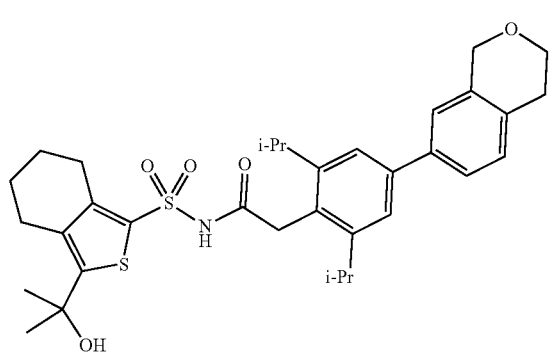 [SMILES: CC(C)c1cc(-c2ccc3c(c2)COCC3)cc(C(C)C)c1CC(=O)NS(=O)(=O)c1sc(C(C)(C)O)c2c1CCCC2] |
| 215 | 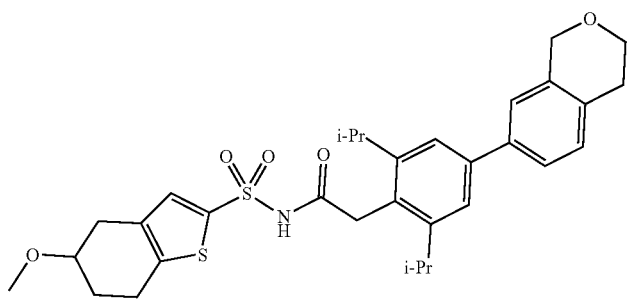 [SMILES: COC1CCc2sc(S(=O)(=O)NC(=O)Cc3c(C(C)C)cc(-c4ccc5c(c4)COCC5)cc3C(C)C)cc2C1] |

-continued

| Compound | Structure |
|---|---|
| 216 | 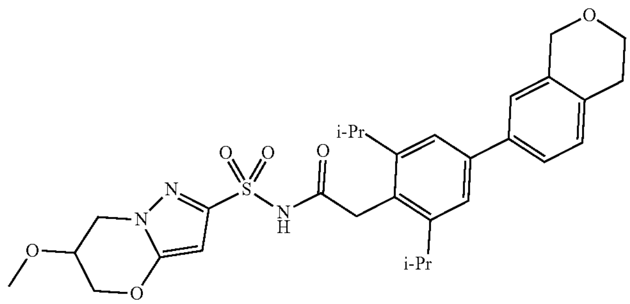 [SMILES: COC1COc2cc(S(=O)(=O)NC(=O)Cc3c(C(C)C)cc(-c4ccc5c(c4)COCC5)cc3C(C)C)nn2C1] |
| 217 | 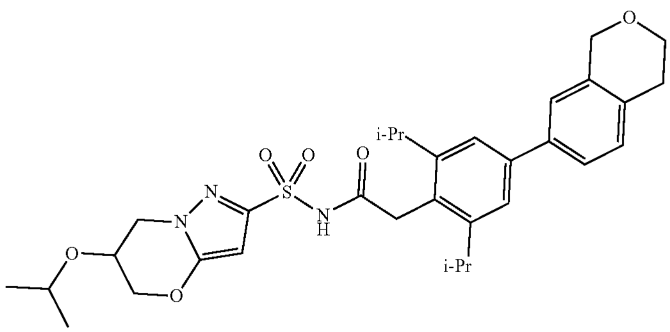 [SMILES: CC(C)OC1COc2cc(S(=O)(=O)NC(=O)Cc3c(C(C)C)cc(-c4ccc5c(c4)COCC5)cc3C(C)C)nn2C1] |
| 218 | 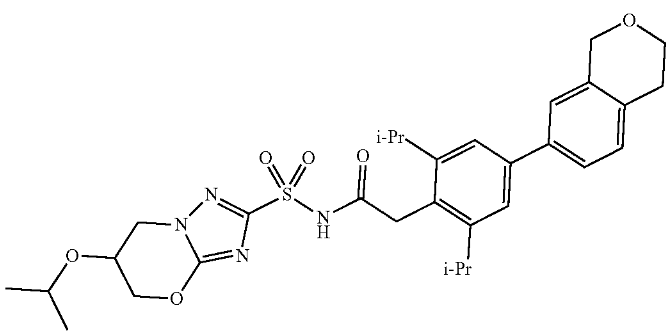 [SMILES: CC(C)OC1COc2nc(S(=O)(=O)NC(=O)Cc3c(C(C)C)cc(-c4ccc5c(c4)COCC5)cc3C(C)C)nn2C1] |
| 219 | 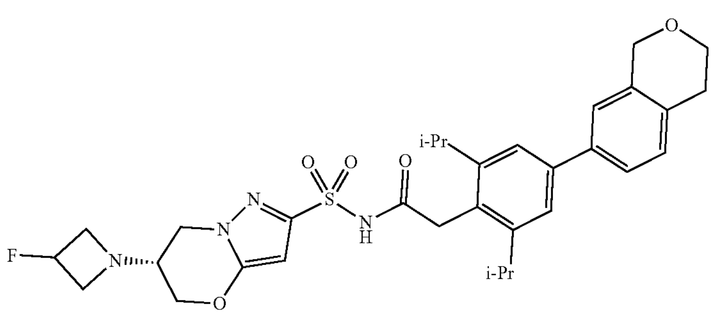 [SMILES: CC(C)c1cc(-c2ccc3c(c2)COCC3)cc(C(C)C)c1CC(=O)NS(=O)(=O)c1cc2n(n1)C[C@@H](N1CC(F)C1)CO2] |
| 220 | 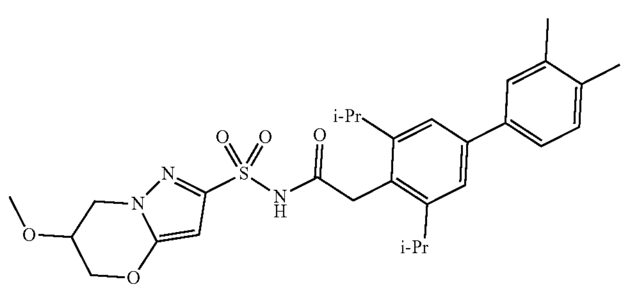 |

-continued

| Compound | Structure |
|---|---|
| 221 | 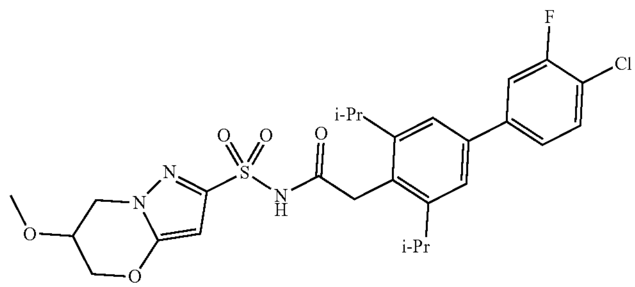 [SMILES: COC1COc2cc(S(=O)(=O)NC(=O)Cc3c(C(C)C)cc(-c4ccc(Cl)c(F)c4)cc3C(C)C)nn2C1] |
| 222 | 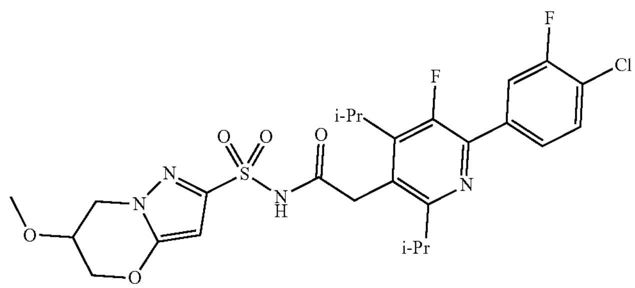 [SMILES: COC1COc2cc(S(=O)(=O)NC(=O)Cc3c(C(C)C)nc(-c4ccc(Cl)c(F)c4)c(F)c3C(C)C)nn2C1] |
| 223 | 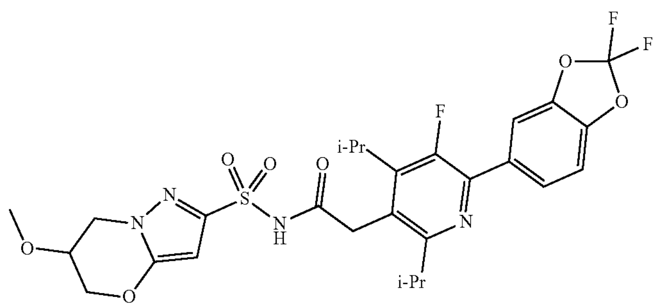 [SMILES: COC1COc2cc(S(=O)(=O)NC(=O)Cc3c(C(C)C)nc(-c4ccc5c(c4)OC(F)(F)O5)c(F)c3C(C)C)nn2C1] |
| 224 | 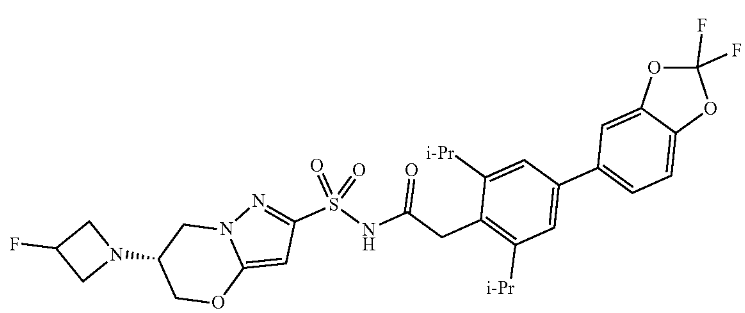 [SMILES: CC(C)c1cc(-c2ccc3c(c2)OC(F)(F)O3)cc(C(C)C)c1CC(=O)NS(=O)(=O)c1cc2n(n1)C[C@@H](N1CC(F)C1)CO2] |
| 225 | 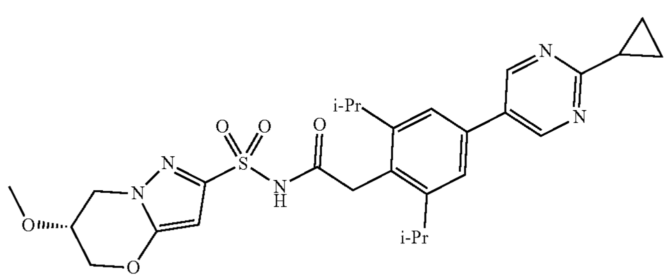 [SMILES: CO[C@H]1COc2cc(S(=O)(=O)NC(=O)Cc3c(C(C)C)cc(-c4cnc(C5CC5)nc4)cc3C(C)C)nn2C1] |

-continued

| Compound | Structure |
|---|---|
| 226 | 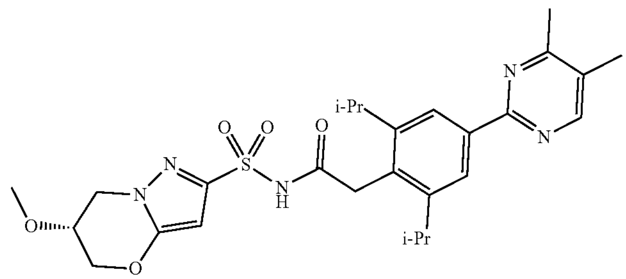 |
| 227 | 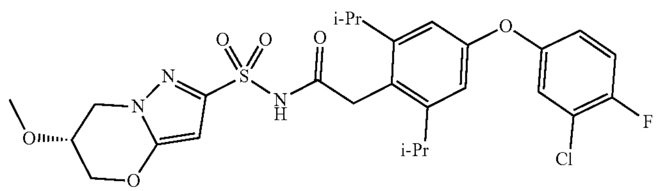 [SMILES: CO[C@H]1COc2cc(S(=O)(=O)NC(=O)Cc3c(C(C)C)cc(Oc4ccc(F)c(Cl)c4)cc3C(C)C)nn2C1] |
| 228 | 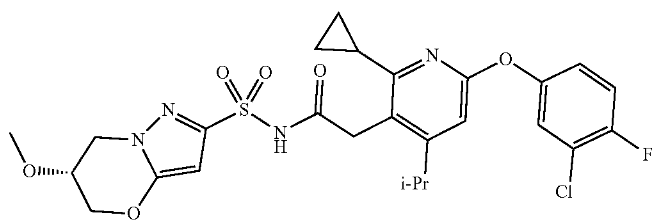 [SMILES: CO[C@H]1COc2cc(S(=O)(=O)NC(=O)Cc3c(C(C)C)cc(Oc4ccc(F)c(Cl)c4)nc3C3CC3)nn2C1] |
| 229 | 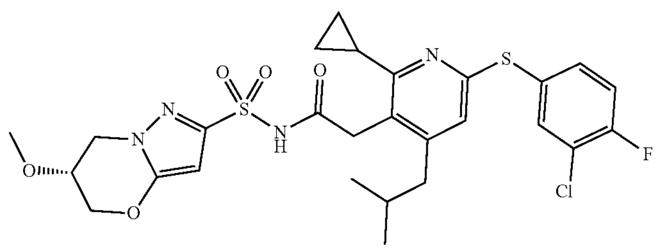 [SMILES: CO[C@H]1COc2cc(S(=O)(=O)NC(=O)Cc3c(CC(C)C)cc(Sc4ccc(F)c(Cl)c4)nc3C3CC3)nn2C1] |
| 230 | 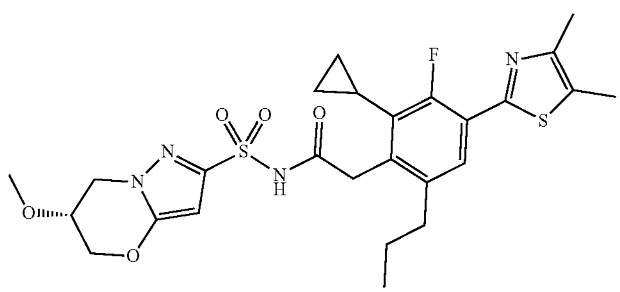 |
| 231 | 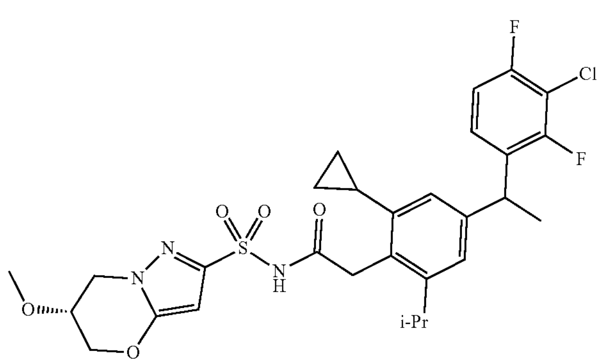 [SMILES: CO[C@H]1COc2cc(S(=O)(=O)NC(=O)Cc3c(C(C)C)cc(C(C)c4ccc(F)c(Cl)c4F)cc3C3CC3)nn2C1] |

| Compound | Structure |
|---|---|
| 232 | 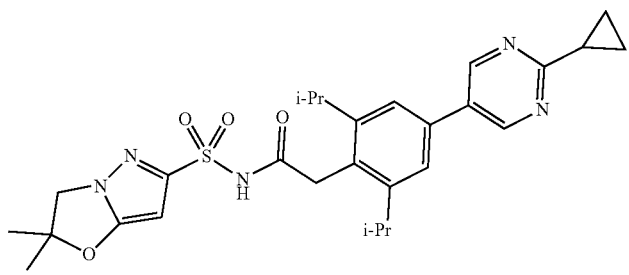 [SMILES: CC(C)c1cc(-c2cnc(C3CC3)nc2)cc(C(C)C)c1CC(=O)NS(=O)(=O)c1cc2n(n1)CC(C)(C)O2] |
| 233 | 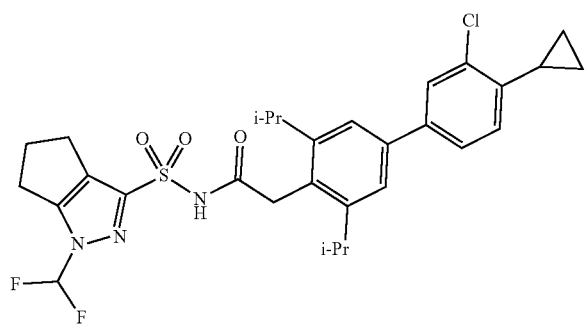 [SMILES: CC(C)c1cc(-c2ccc(C3CC3)c(Cl)c2)cc(C(C)C)c1CC(=O)NS(=O)(=O)c1nn(C(F)F)c2c1CCC2] |
| 234 | 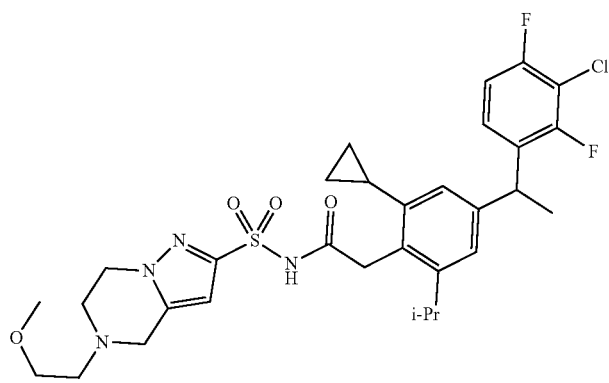 [SMILES: COCCN1CCn2nc(S(=O)(=O)NC(=O)Cc3c(C(C)C)cc(C(C)c4ccc(F)c(Cl)c4F)cc3C3CC3)cc2C1] |

| Compound | Structure |
|---|---|
| 235 | 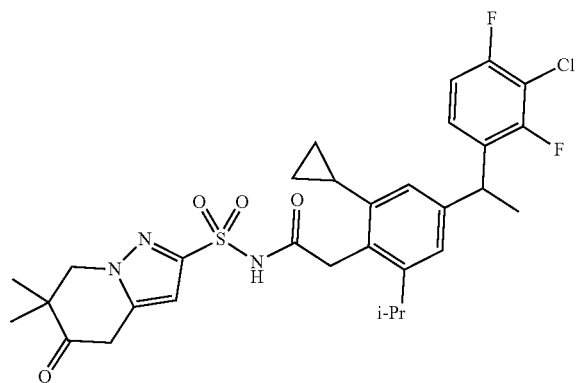 [SMILES: CC(C)c1cc(C(C)c2ccc(F)c(Cl)c2F)cc(C2CC2)c1CC(=O)NS(=O)(=O)c1cc2n(n1)CC(C)(C)C(=O)C2] |
| 236 | 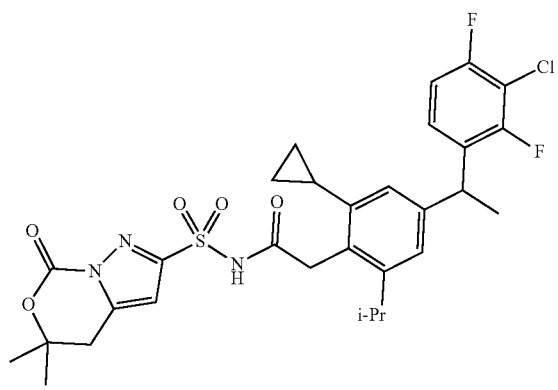 [SMILES: CC(C)c1cc(C(C)c2ccc(F)c(Cl)c2F)cc(C2CC2)c1CC(=O)NS(=O)(=O)c1cc2n(n1)C(=O)OC(C)(C)C2] |
| 301 | 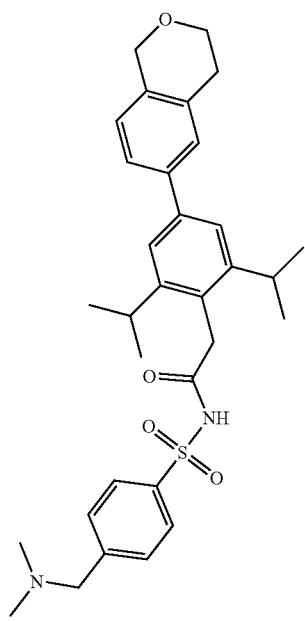 [SMILES: CC(C)c1cc(-c2ccc3c(c2)CCOC3)cc(C(C)C)c1CC(=O)NS(=O)(=O)c1ccc(CN(C)C)cc1] |

| Compound | Structure |
|---|---|
| 302 | 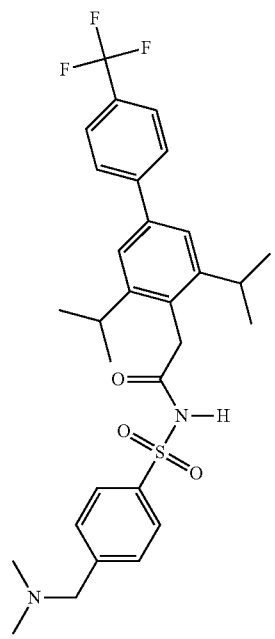 [SMILES: CC(C)c1cc(-c2ccc(C(F)(F)F)cc2)cc(C(C)C)c1CC(=O)NS(=O)(=O)c1ccc(CN(C)C)cc1] |
| 303 | 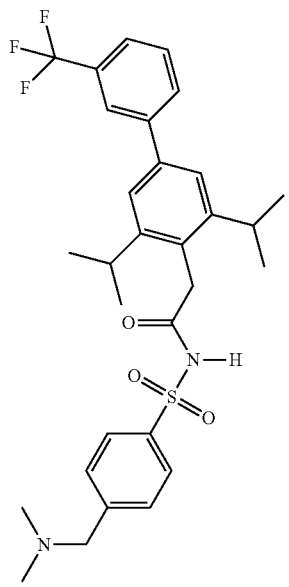 [SMILES: CC(C)c1cc(-c2cccc(C(F)(F)F)c2)cc(C(C)C)c1CC(=O)NS(=O)(=O)c1ccc(CN(C)C)cc1] |

-continued
| Compound | Structure |
|---|---|
| 304 | 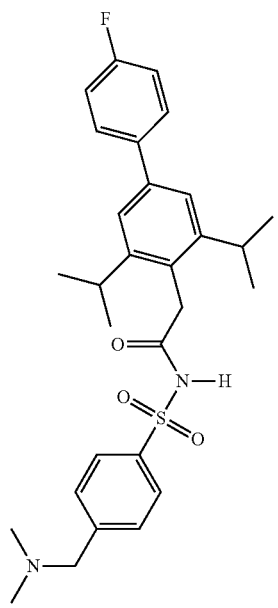 [SMILES: CC(C)c1cc(-c2ccc(F)cc2)cc(C(C)C)c1CC(=O)NS(=O)(=O)c1ccc(CN(C)C)cc1] |
| 305 | 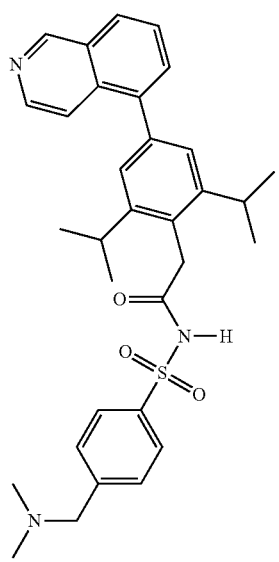 [SMILES: CC(C)c1cc(-c2cccc3cnccc23)cc(C(C)C)c1CC(=O)NS(=O)(=O)c1ccc(CN(C)C)cc1] |

-continued
| Compound | Structure |
|---|---|
| 306 | 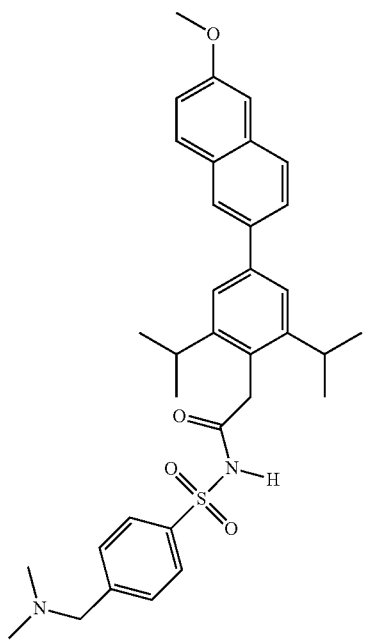 [SMILES: COc1ccc2cc(-c3cc(C(C)C)c(CC(=O)NS(=O)(=O)c4ccc(CN(C)C)cc4)c(C(C)C)c3)ccc2c1] |
| 307 | 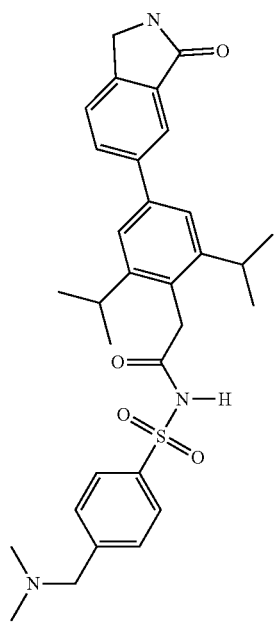 [SMILES: CC(C)c1cc(-c2ccc3c(c2)C(=O)NC3)cc(C(C)C)c1CC(=O)NS(=O)(=O)c1ccc(CN(C)C)cc1] |

| Compound | Structure |
|---|---|
| 308 | 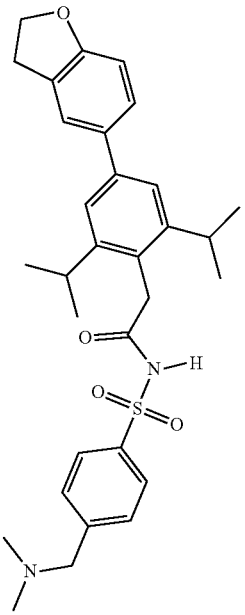 [SMILES: CC(C)c1cc(-c2ccc3c(c2)CCO3)cc(C(C)C)c1CC(=O)NS(=O)(=O)c1ccc(CN(C)C)cc1] |
| 309 | 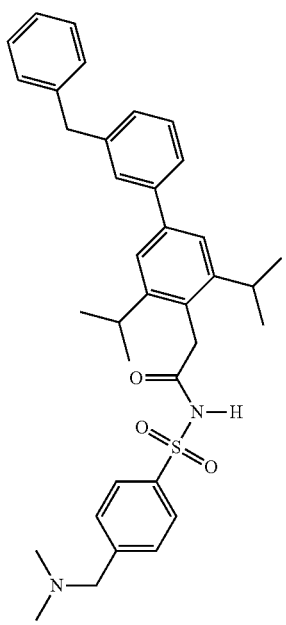 [SMILES: CC(C)c1cc(-c2cccc(Cc3ccccc3)c2)cc(C(C)C)c1CC(=O)NS(=O)(=O)c1ccc(CN(C)C)cc1] |

| Compound | Structure |
|---|---|
| 310 | 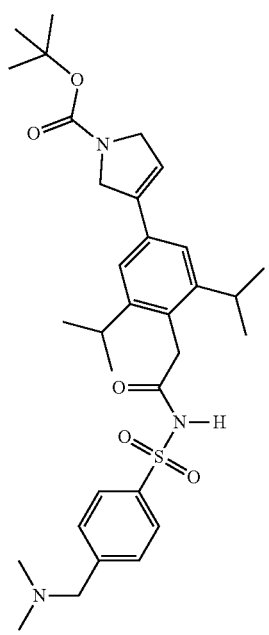 [SMILES: CC(C)c1cc(C2=CCN(C(=O)OC(C)(C)C)C2)cc(C(C)C)c1CC(=O)NS(=O)(=O)c1ccc(CN(C)C)cc1] |
| 311 | 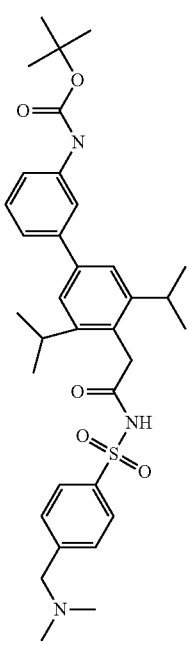 [SMILES: CC(C)c1cc(-c2cccc(NC(=O)OC(C)(C)C)c2)cc(C(C)C)c1CC(=O)NS(=O)(=O)c1ccc(CN(C)C)cc1] |

-continued
| Compound | Structure |
|---|---|
| 312 | 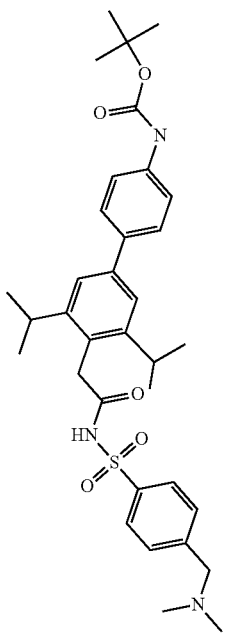 [SMILES: CC(C)c1cc(-c2ccc(NC(=O)OC(C)(C)C)cc2)cc(C(C)C)c1CC(=O)NS(=O)(=O)c1ccc(CN(C)C)cc1] |
| 313 | 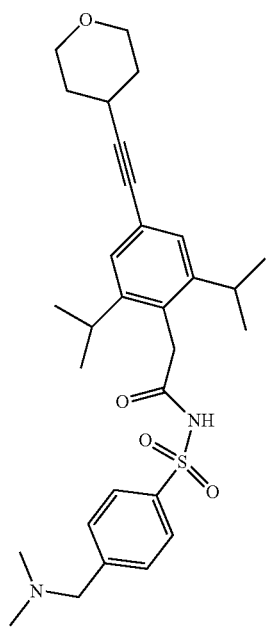 [SMILES: CC(C)c1cc(C#CC2CCOCC2)cc(C(C)C)c1CC(=O)NS(=O)(=O)c1ccc(CN(C)C)cc1] |

| Compound | Structure |
|---|---|
| 314 | 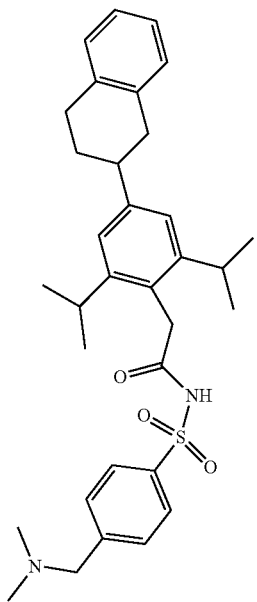 [SMILES: CC(C)c1cc(C2CCc3ccccc3C2)cc(C(C)C)c1CC(=O)NS(=O)(=O)c1ccc(CN(C)C)cc1] |
| 315 | 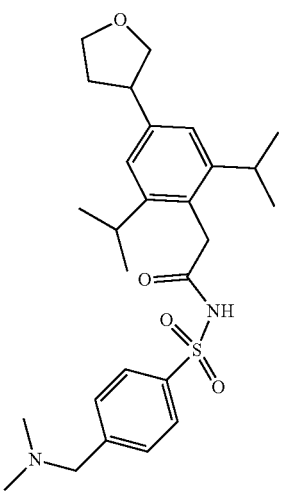 [SMILES: CC(C)c1cc(C2CCOC2)cc(C(C)C)c1CC(=O)NS(=O)(=O)c1ccc(CN(C)C)cc1] |

| Compound | Structure |
|---|---|
| 316 | 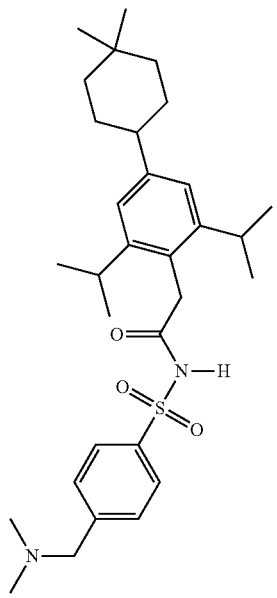 [SMILES: CC(C)c1cc(C2CCC(C)(C)CC2)cc(C(C)C)c1CC(=O)NS(=O)(=O)c1ccc(CN(C)C)cc1] |
| 317 | 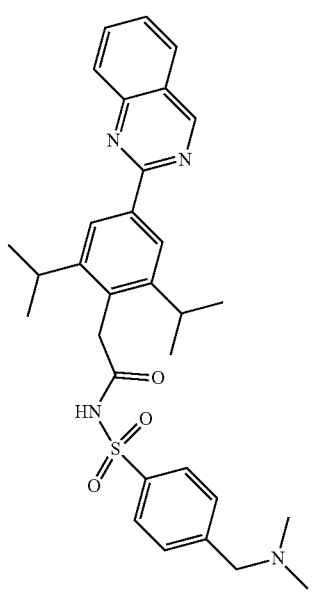 [SMILES: CC(C)c1cc(-c2ncc3ccccc3n2)cc(C(C)C)c1CC(=O)NS(=O)(=O)c1ccc(CN(C)C)cc1] |

| Compound | Structure |
|---|---|
| 318 | 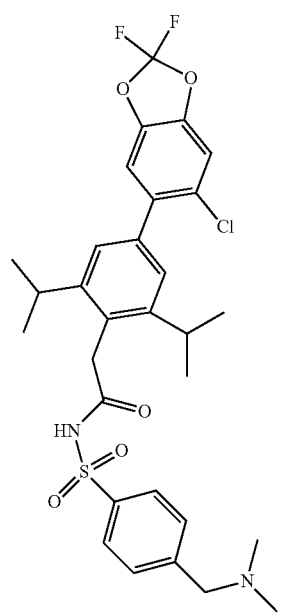 [SMILES: CC(C)c1cc(-c2cc3c(cc2Cl)OC(F)(F)O3)cc(C(C)C)c1CC(=O)NS(=O)(=O)c1ccc(CN(C)C)cc1] |
| 319 | 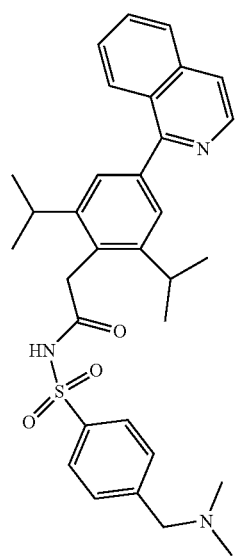 [SMILES: CC(C)c1cc(-c2nccc3ccccc23)cc(C(C)C)c1CC(=O)NS(=O)(=O)c1ccc(CN(C)C)cc1] |

| Compound | Structure |
|---|---|
| 320 | 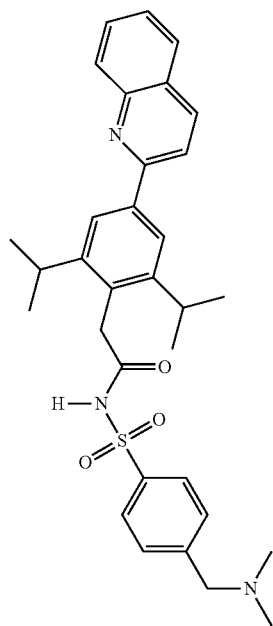 [SMILES: CC(C)c1cc(-c2ccc3ccccc3n2)cc(C(C)C)c1CC(=O)NS(=O)(=O)c1ccc(CN(C)C)cc1] |
| 321 | 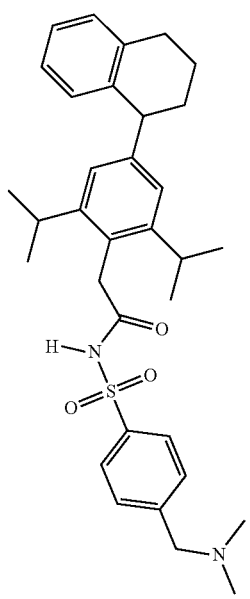 [SMILES: CC(C)c1cc(C2CCCc3ccccc32)cc(C(C)C)c1CC(=O)NS(=O)(=O)c1ccc(CN(C)C)cc1] |

-continued
| Compound | Structure |
|---|---|
| 322 | 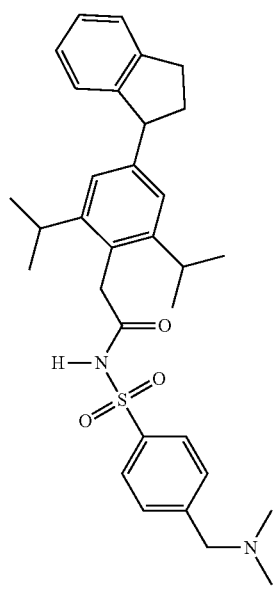 [SMILES: CC(C)c1cc(C2CCc3ccccc32)cc(C(C)C)c1CC(=O)NS(=O)(=O)c1ccc(CN(C)C)cc1] |
| 323 | 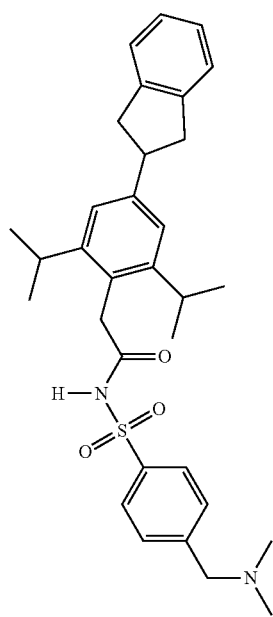 [SMILES: CC(C)c1cc(C2Cc3ccccc3C2)cc(C(C)C)c1CC(=O)NS(=O)(=O)c1ccc(CN(C)C)cc1] |

| Compound | Structure |
|---|---|
| 324 | 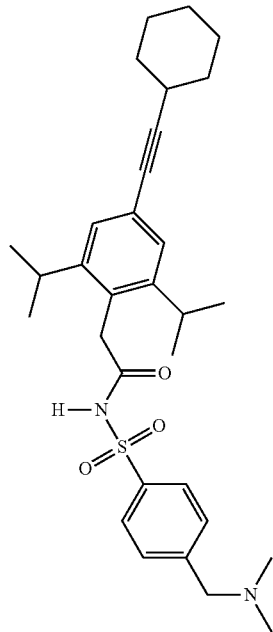 [SMILES: CC(C)c1cc(C#CC2CCCCC2)cc(C(C)C)c1CC(=O)NS(=O)(=O)c1ccc(CN(C)C)cc1] |
| 325 | 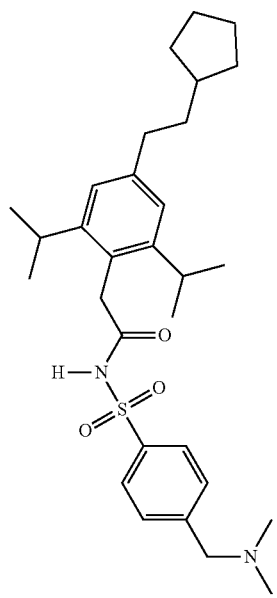 [SMILES: CC(C)c1cc(CCC2CCCC2)cc(C(C)C)c1CC(=O)NS(=O)(=O)c1ccc(CN(C)C)cc1] |

| Compound | Structure |
|---|---|
| 326 | 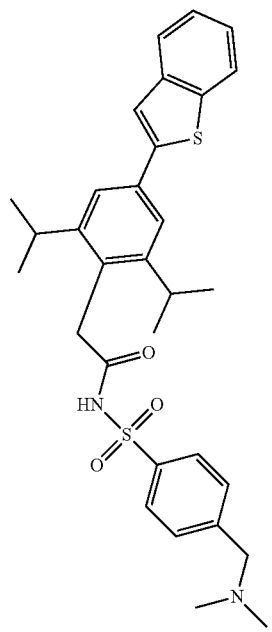 [SMILES: CC(C)c1cc(-c2cc3ccccc3s2)cc(C(C)C)c1CC(=O)NS(=O)(=O)c1ccc(CN(C)C)cc1] |
| 327 | 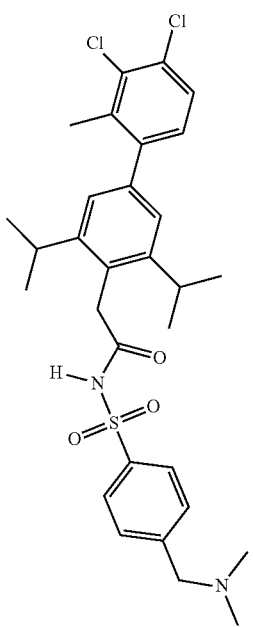 [SMILES: Cc1c(-c2cc(C(C)C)c(CC(=O)NS(=O)(=O)c3ccc(CN(C)C)cc3)c(C(C)C)c2)ccc(Cl)c1Cl] |

| Compound | Structure |
|---|---|
| 328 | 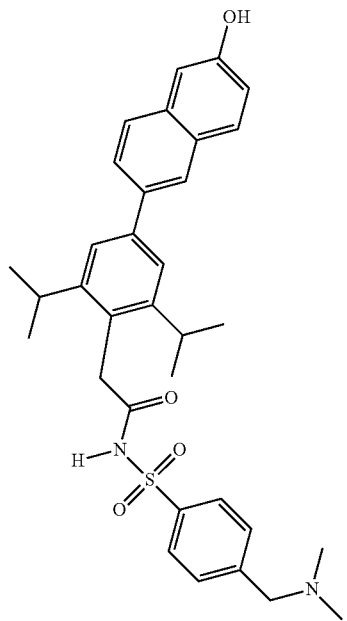 [SMILES: CC(C)c1cc(-c2ccc3cc(O)ccc3c2)cc(C(C)C)c1CC(=O)NS(=O)(=O)c1ccc(CN(C)C)cc1] |
| 329 | 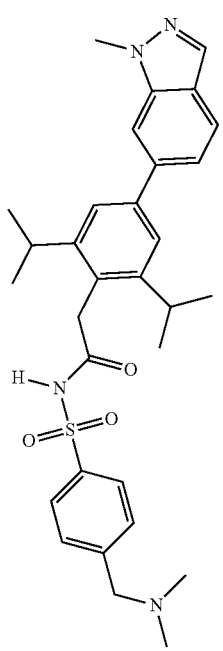 [SMILES: CC(C)c1cc(-c2ccc3cnn(C)c3c2)cc(C(C)C)c1CC(=O)NS(=O)(=O)c1ccc(CN(C)C)cc1] |

| Compound | Structure |
|---|---|
| 330 | 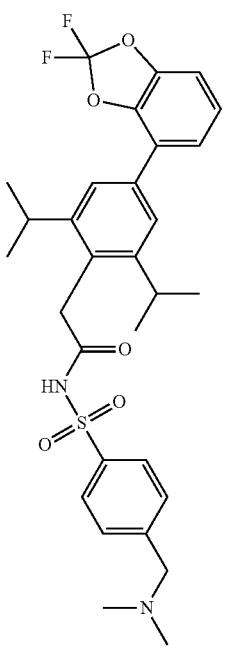 [SMILES: CC(C)c1cc(-c2cccc3c2OC(F)(F)O3)cc(C(C)C)c1CC(=O)NS(=O)(=O)c1ccc(CN(C)C)cc1] |
| 331 | 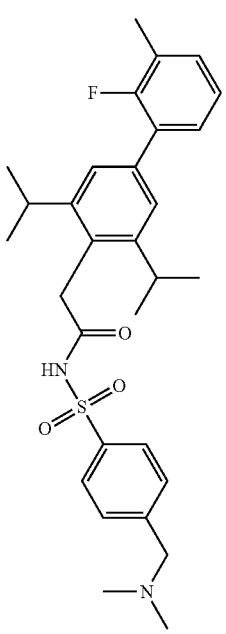 [SMILES: Cc1cccc(-c2cc(C(C)C)c(CC(=O)NS(=O)(=O)c3ccc(CN(C)C)cc3)c(C(C)C)c2)c1F] |

-continued
| Compound | Structure |
|---|---|
| 332 | 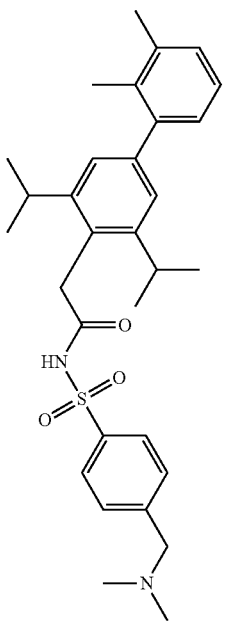 [SMILES: Cc1cccc(-c2cc(C(C)C)c(CC(=O)NS(=O)(=O)c3ccc(CN(C)C)cc3)c(C(C)C)c2)c1C] |
| 333 | 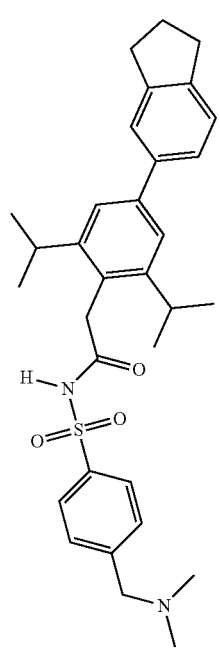 [SMILES: CC(C)c1cc(-c2ccc3c(c2)CCC3)cc(C(C)C)c1CC(=O)NS(=O)(=O)c1ccc(CN(C)C)cc1] |

-continued
| Compound | Structure |
|---|---|
| 334 | 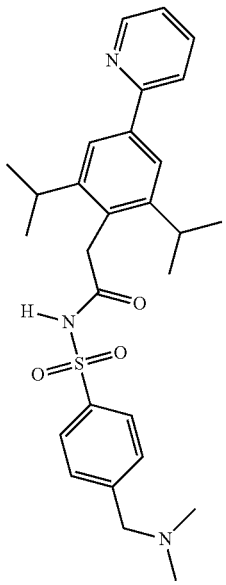 [SMILES: CC(C)c1cc(-c2ccccn2)cc(C(C)C)c1CC(=O)NS(=O)(=O)c1ccc(CN(C)C)cc1] |
| 335 | 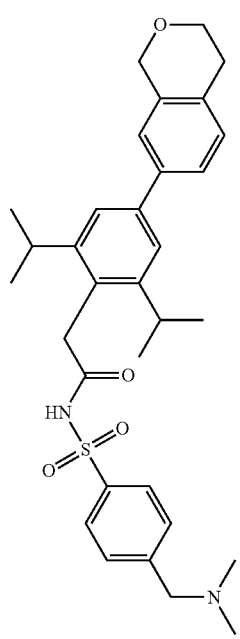 [SMILES: CC(C)c1cc(-c2ccc3c(c2)COCC3)cc(C(C)C)c1CC(=O)NS(=O)(=O)c1ccc(CN(C)C)cc1] |

| Compound | Structure |
|---|---|
| 336 | 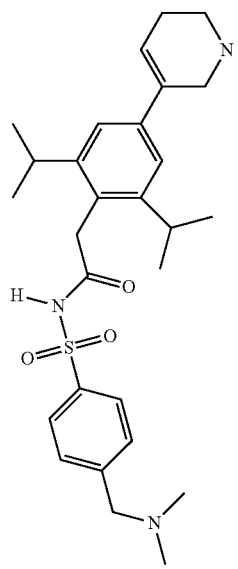 [SMILES: CC(C)c1cc(C2=CCCNC2)cc(C(C)C)c1CC(=O)NS(=O)(=O)c1ccc(CN(C)C)cc1] |
| 337 | 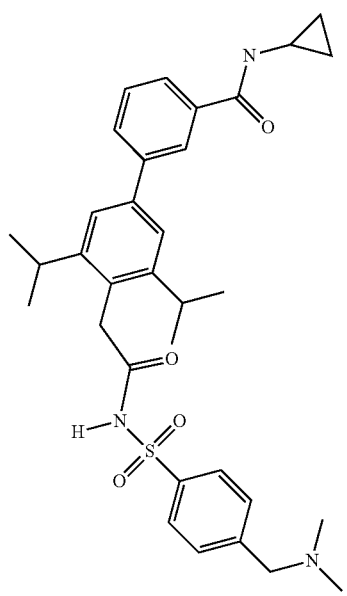 [SMILES: CC(C)c1cc(-c2cccc(C(=O)NC3CC3)c2)cc(C(C)C)c1CC(=O)NS(=O)(=O)c1ccc(CN(C)C)cc1] |

| Compound | Structure |
|---|---|
| 338 | 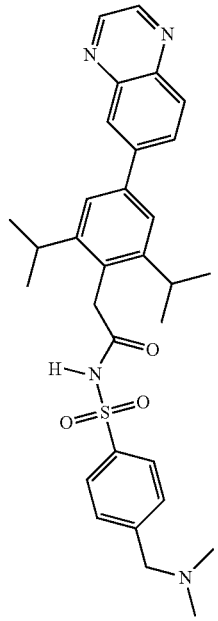 [SMILES: CC(C)c1cc(-c2ccc3nccnc3c2)cc(C(C)C)c1CC(=O)NS(=O)(=O)c1ccc(CN(C)C)cc1] |
| 339 | 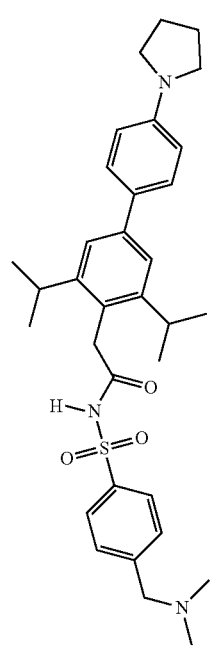 [SMILES: CC(C)c1cc(-c2ccc(N3CCCC3)cc2)cc(C(C)C)c1CC(=O)NS(=O)(=O)c1ccc(CN(C)C)cc1] |

-continued
| Compound | Structure |
|---|---|
| 340 | 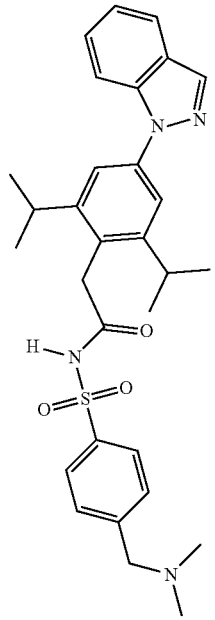 [SMILES: CC(C)c1cc(-n2ncc3ccccc32)cc(C(C)C)c1CC(=O)NS(=O)(=O)c1ccc(CN(C)C)cc1] |
| 341 | 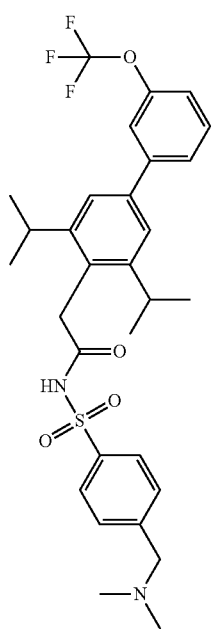 [SMILES: CC(C)c1cc(-c2cccc(OC(F)(F)F)c2)cc(C(C)C)c1CC(=O)NS(=O)(=O)c1ccc(CN(C)C)cc1] |

| Compound | Structure |
|---|---|
| 342 | 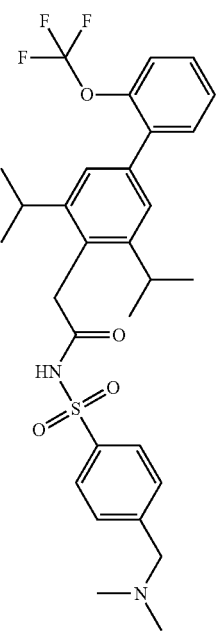 [SMILES: CC(C)c1cc(-c2ccccc2OC(F)(F)F)cc(C(C)C)c1CC(=O)NS(=O)(=O)c1ccc(CN(C)C)cc1] |
| 343 | 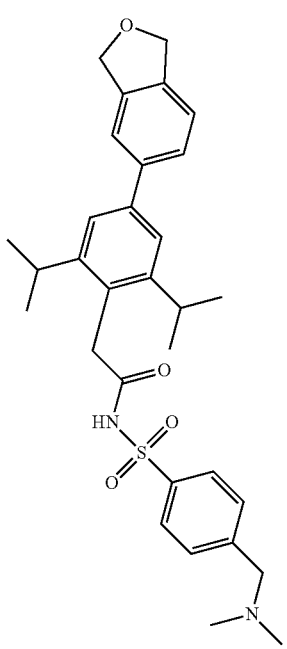 [SMILES: CC(C)c1cc(-c2ccc3c(c2)COC3)cc(C(C)C)c1CC(=O)NS(=O)(=O)c1ccc(CN(C)C)cc1] |

| Compound | Structure |
|---|---|
| 344 | 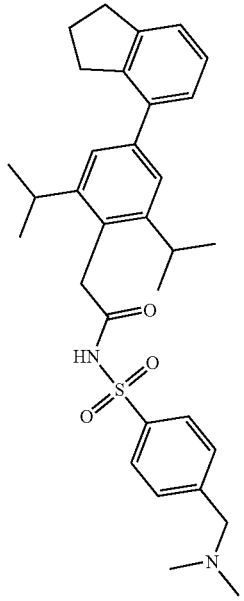 [SMILES: CC(C)c1cc(-c2cccc3c2CCC3)cc(C(C)C)c1CC(=O)NS(=O)(=O)c1ccc(CN(C)C)cc1] |
| 345 | 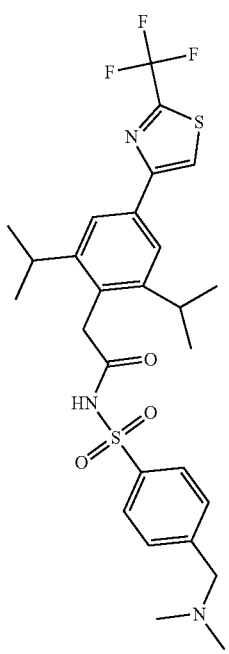 [SMILES: CC(C)c1cc(-c2csc(C(F)(F)F)n2)cc(C(C)C)c1CC(=O)NS(=O)(=O)c1ccc(CN(C)C)cc1] |

-continued
| Compound | Structure |
|---|---|
| 346 | 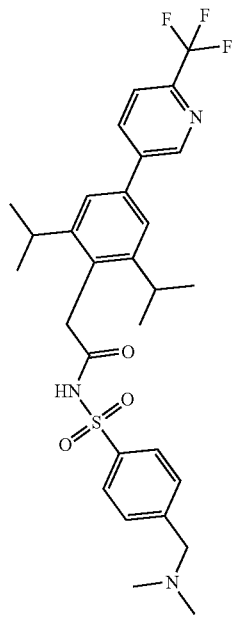 [SMILES: CC(C)c1cc(-c2ccc(C(F)(F)F)nc2)cc(C(C)C)c1CC(=O)NS(=O)(=O)c1ccc(CN(C)C)cc1] |
| 347 | 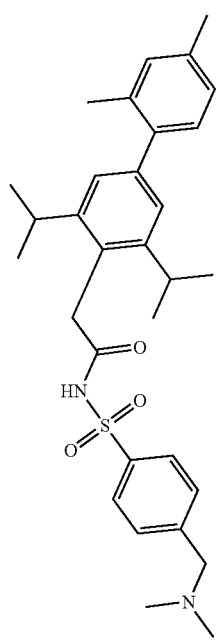 [SMILES: Cc1ccc(-c2cc(C(C)C)c(CC(=O)NS(=O)(=O)c3ccc(CN(C)C)cc3)c(C(C)C)c2)c(C)c1] |

| Compound | Structure |
|---|---|
| 348 | 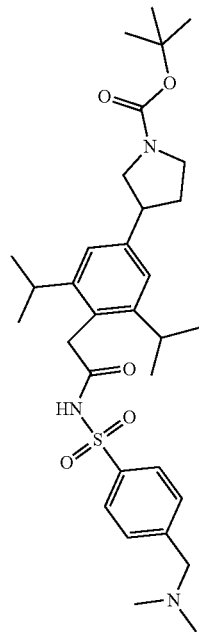 [SMILES: CC(C)c1cc(C2CCN(C(=O)OC(C)(C)C)C2)cc(C(C)C)c1CC(=O)NS(=O)(=O)c1ccc(CN(C)C)cc1] |
| 349 | 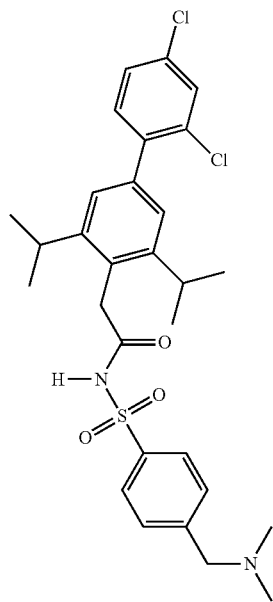 [SMILES: CC(C)c1cc(-c2ccc(Cl)cc2Cl)cc(C(C)C)c1CC(=O)NS(=O)(=O)c1ccc(CN(C)C)cc1] |

| Compound | Structure |
|---|---|
| 350 | 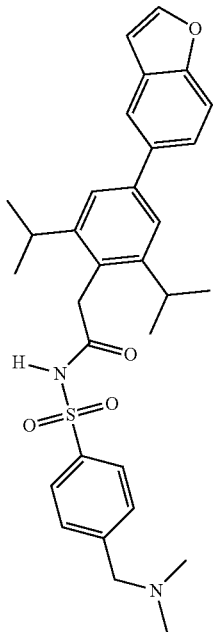 [SMILES: CC(C)c1cc(-c2ccc3occc3c2)cc(C(C)C)c1CC(=O)NS(=O)(=O)c1ccc(CN(C)C)cc1] |
| 351 | 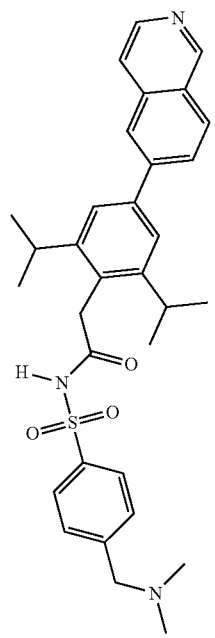 [SMILES: CC(C)c1cc(-c2ccc3cnccc3c2)cc(C(C)C)c1CC(=O)NS(=O)(=O)c1ccc(CN(C)C)cc1] |

| Compound | Structure |
|---|---|
| 352 | 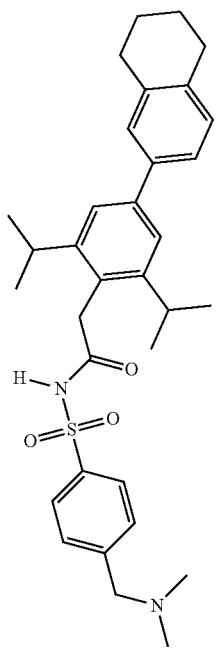 [SMILES: CC(C)c1cc(-c2ccc3c(c2)CCCC3)cc(C(C)C)c1CC(=O)NS(=O)(=O)c1ccc(CN(C)C)cc1] |
| 353 | 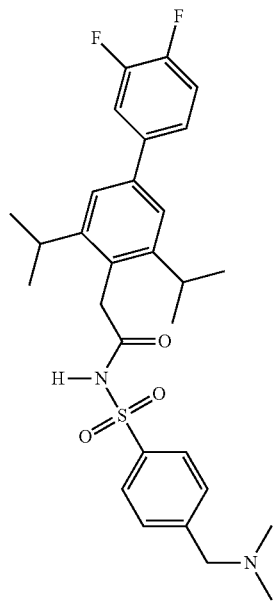 [SMILES: CC(C)c1cc(-c2ccc(F)c(F)c2)cc(C(C)C)c1CC(=O)NS(=O)(=O)c1ccc(CN(C)C)cc1] |

| Compound | Structure |
|---|---|
| 354 | 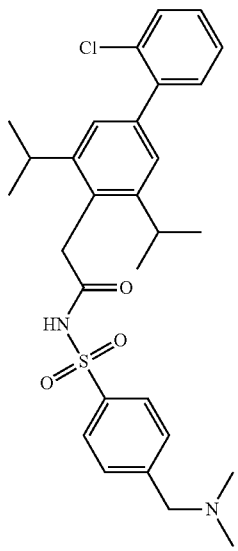 [SMILES: CC(C)c1cc(-c2ccccc2Cl)cc(C(C)C)c1CC(=O)NS(=O)(=O)c1ccc(CN(C)C)cc1] |
| 355 | 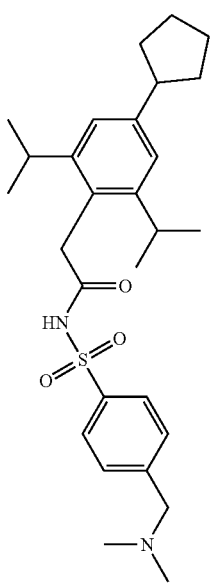 [SMILES: CC(C)c1cc(C2CCCC2)cc(C(C)C)c1CC(=O)NS(=O)(=O)c1ccc(CN(C)C)cc1] |

-continued
| Compound | Structure |
|---|---|
| 356 | 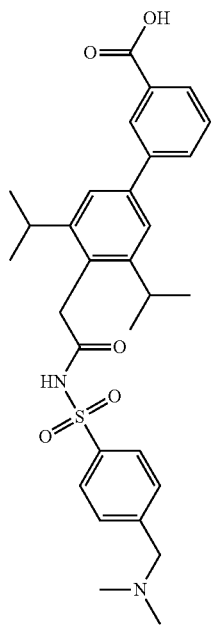 [SMILES: CC(C)c1cc(-c2cccc(C(=O)O)c2)cc(C(C)C)c1CC(=O)NS(=O)(=O)c1ccc(CN(C)C)cc1] |
| 357 | 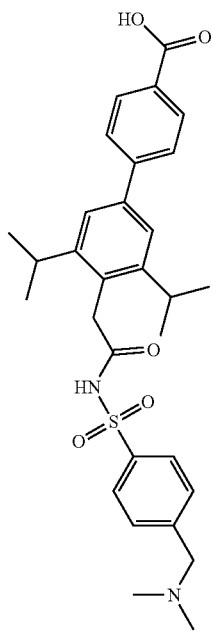 [SMILES: CC(C)c1cc(-c2ccc(C(=O)O)cc2)cc(C(C)C)c1CC(=O)NS(=O)(=O)c1ccc(CN(C)C)cc1] |

| Compound | Structure |
|---|---|
| 358 | 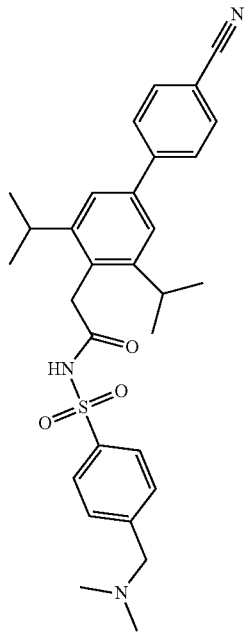 [SMILES: CC(C)c1cc(-c2ccc(C#N)cc2)cc(C(C)C)c1CC(=O)NS(=O)(=O)c1ccc(CN(C)C)cc1] |
| 359 | 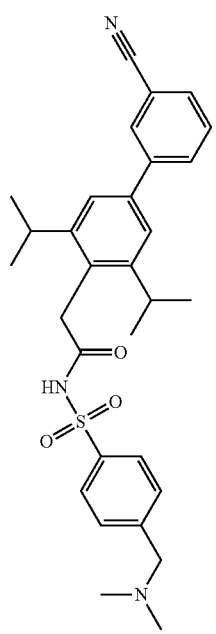 [SMILES: CC(C)c1cc(-c2cccc(C#N)c2)cc(C(C)C)c1CC(=O)NS(=O)(=O)c1ccc(CN(C)C)cc1] |

| Compound | Structure |
|---|---|
| 360 | 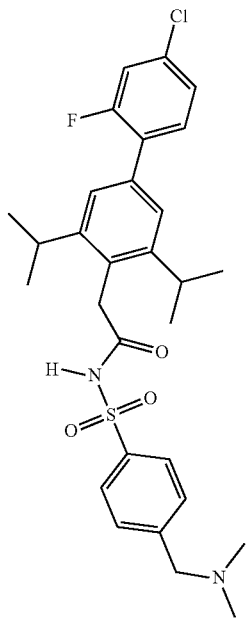 [SMILES: CC(C)c1cc(-c2ccc(Cl)cc2F)cc(C(C)C)c1CC(=O)NS(=O)(=O)c1ccc(CN(C)C)cc1] |
| 361 | 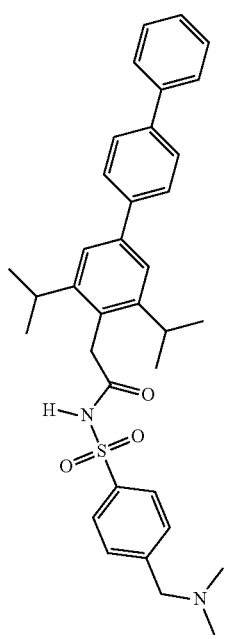 [SMILES: CC(C)c1cc(-c2ccc(-c3ccccc3)cc2)cc(C(C)C)c1CC(=O)NS(=O)(=O)c1ccc(CN(C)C)cc1] |

| Compound | Structure |
|---|---|
| 362 | 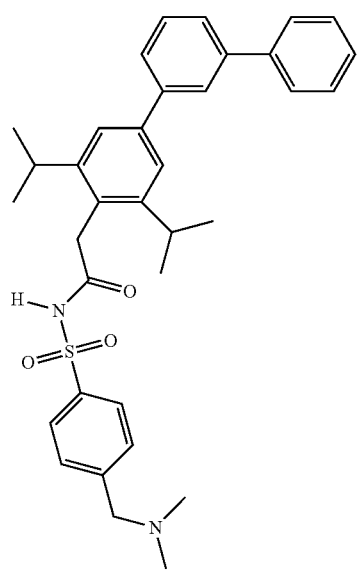 |
| 363 | 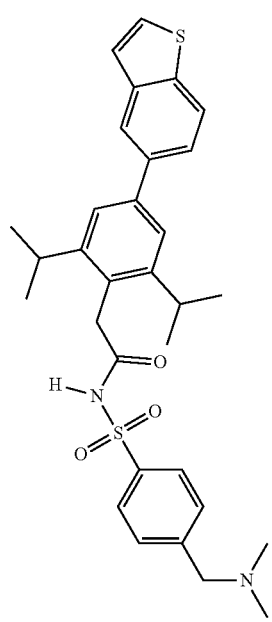 [SMILES: CC(C)c1cc(-c2ccc3sccc3c2)cc(C(C)C)c1CC(=O)NS(=O)(=O)c1ccc(CN(C)C)cc1] |

| Compound | Structure |
|---|---|
| 364 | 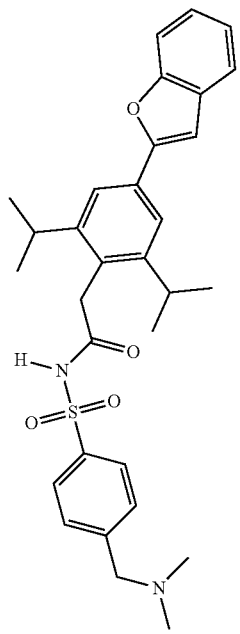 [SMILES: CC(C)c1cc(-c2cc3ccccc3o2)cc(C(C)C)c1CC(=O)NS(=O)(=O)c1ccc(CN(C)C)cc1] |
| 365 | 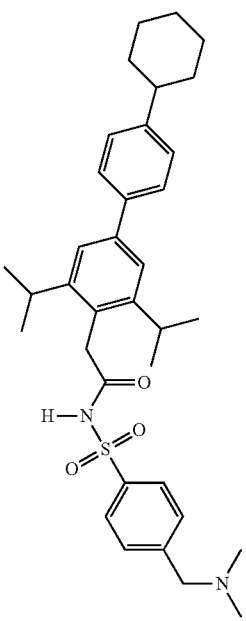 [SMILES: CC(C)c1cc(-c2ccc(C3CCCCC3)cc2)cc(C(C)C)c1CC(=O)NS(=O)(=O)c1ccc(CN(C)C)cc1] |

| Compound | Structure |
|---|---|
| 366 | 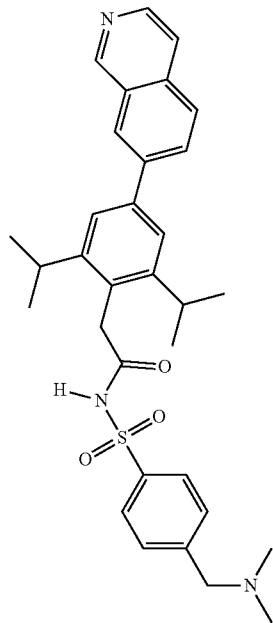 [SMILES: CC(C)c1cc(-c2ccc3ccncc3c2)cc(C(C)C)c1CC(=O)NS(=O)(=O)c1ccc(CN(C)C)cc1] |
| 367 | 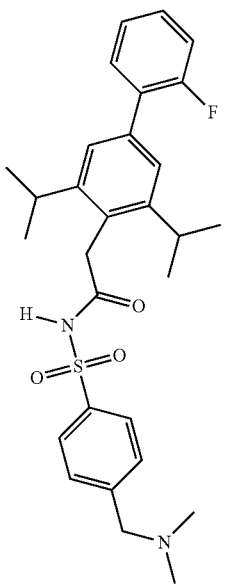 [SMILES: CC(C)c1cc(-c2ccccc2F)cc(C(C)C)c1CC(=O)NS(=O)(=O)c1ccc(CN(C)C)cc1] |

| Compound | Structure |
|---|---|
| 368 | 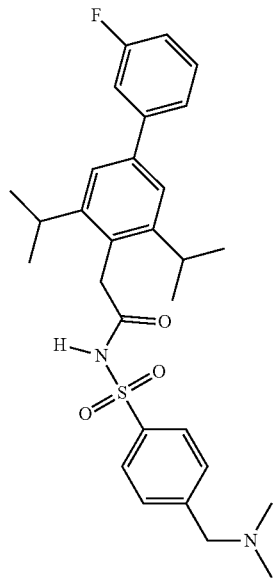 [SMILES: CC(C)c1cc(-c2cccc(F)c2)cc(C(C)C)c1CC(=O)NS(=O)(=O)c1ccc(CN(C)C)cc1] |
| 369 | 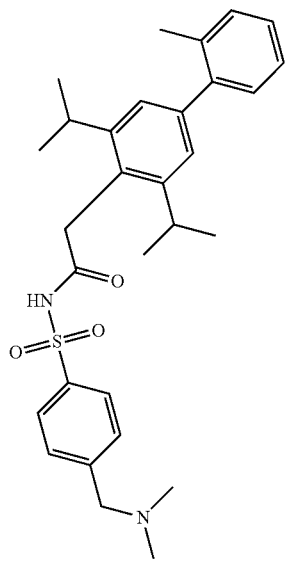 [SMILES: Cc1ccccc1-c1cc(C(C)C)c(CC(=O)NS(=O)(=O)c2ccc(CN(C)C)cc2)c(C(C)C)c1] |

| Compound | Structure |
|---|---|
| 370 | 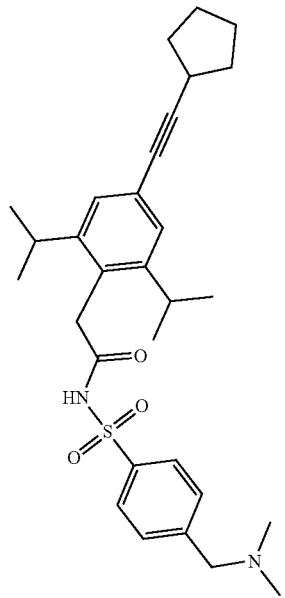 [SMILES: CC(C)c1cc(C#CC2CCCC2)cc(C(C)C)c1CC(=O)NS(=O)(=O)c1ccc(CN(C)C)cc1] |
| 371 | 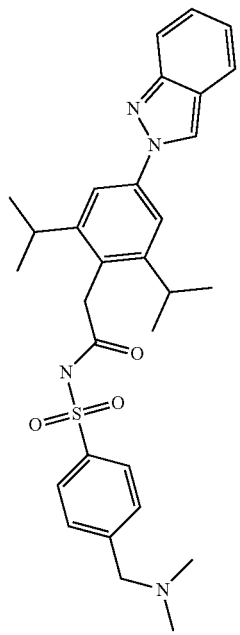 [SMILES: CC(C)c1cc(-n2cc3ccccc3n2)cc(C(C)C)c1CC(=O)NS(=O)(=O)c1ccc(CN(C)C)cc1] |
| 372 | 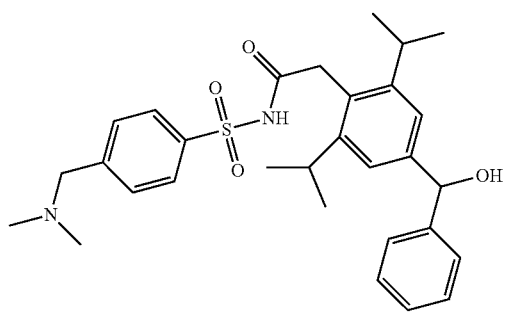 [SMILES: CC(C)c1cc(C(O)c2ccccc2)cc(C(C)C)c1CC(=O)NS(=O)(=O)c1ccc(CN(C)C)cc1] |

| Compound | Structure |
|---|---|
| 373 | 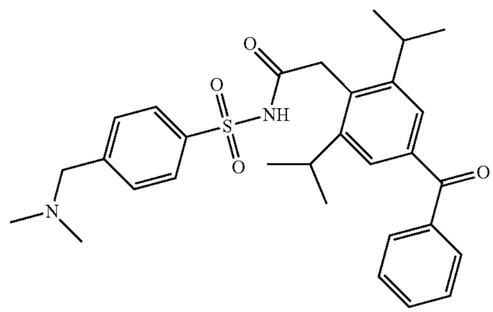 [SMILES: CC(C)c1cc(C(=O)c2ccccc2)cc(C(C)C)c1CC(=O)NS(=O)(=O)c1ccc(CN(C)C)cc1] |
| 374 | 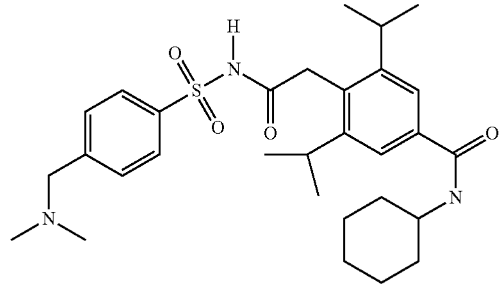 [SMILES: CC(C)c1cc(C(=O)NC2CCCCC2)cc(C(C)C)c1CC(=O)NS(=O)(=O)c1ccc(CN(C)C)cc1] |
| 375 | 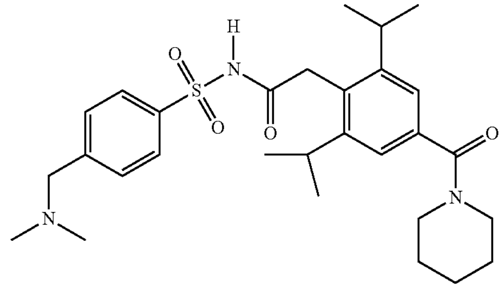 [SMILES: CC(C)c1cc(C(=O)N2CCCCC2)cc(C(C)C)c1CC(=O)NS(=O)(=O)c1ccc(CN(C)C)cc1] |
| 376 | 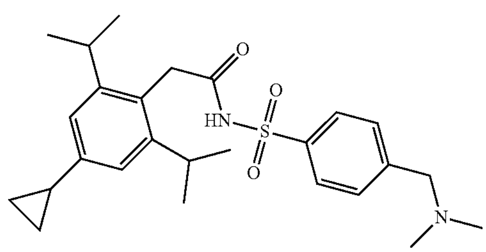 [SMILES: CC(C)c1cc(C2CC2)cc(C(C)C)c1CC(=O)NS(=O)(=O)c1ccc(CN(C)C)cc1] |
| 377 | 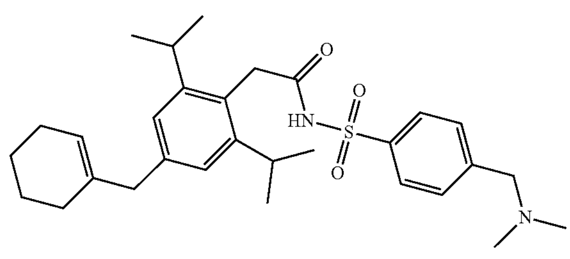 [SMILES: CC(C)c1cc(CC2=CCCCC2)cc(C(C)C)c1CC(=O)NS(=O)(=O)c1ccc(CN(C)C)cc1] |

| Compound | Structure |
| --- | --- |
| 378 | *(structure)* |
| 379 | *(structure)* | and pharmaceutically acceptable salts thereof.

2. A pharmaceutical composition comprising a compound or salt as claimed in claim 1 and one or more pharmaceutically acceptable excipients.

* * * * *

SEQUENCE LISTING

<160> NUMBER OF SEQ ID NOS: 37

<210> SEQ ID NO 1
<211> LENGTH: 702
<212> TYPE: DNA
<213> ORGANISM: Homo sapiens

<400> SEQUENCE: 1

```
atgagcactg aaagcatgat ccgggacgtg gagctggccg aggaggcgct ccccaagaag    60
acaggggggc cccagggctc caggcggtgc ttgttcctca gcctcttctc cttcctgatc   120
gtggcaggcg ccaccacgct cttctgcctg ctgcactttg gagtgatcgg cccccagagg   180
gaagagttcc cagggacct ctctctaatc agccctctgg cccaggcagt cagatcatct   240
tctcgaaccc cgagtgacaa gcctgtagcc catgttgtag caaaccctca agctgagggg   300
cagctccagt ggctgaaccg ccgggccaat gccctcctgg ccaatggcgt ggagctgaga   360
gataaccagc tggtggtgcc atcagagggc ctgtacctca tctactccca ggtcctcttc   420
aagggccaag gctgcccctc cacccatgtg ctcctcaccc acaccatcag ccgcatcgcc   480
gtctcctacc agaccaaggt caacctcctc tctgccatca gagccctg ccagaggag    540
accccagagg gggctgaggc caagccctgg tatgagccca tctatctggg aggggtcttc   600
cagctggaga agggtgaccg actcagcgct gagatcaatc ggcccgacta tctcgacttt   660
gccgagtctg ggcaggtcta ctttgggatc attgccctgt ga                      702
```

<210> SEQ ID NO 2
<211> LENGTH: 1368
<212> TYPE: DNA
<213> ORGANISM: Homo sapiens

<400> SEQUENCE: 2

```
atgggcctct ccaccgtgcc tgacctgctg ctgccactgg tgctcctgga gctgttggtg    60
ggaatatacc cctcaggggt tattggactg gtccctcacc taggggacag ggagaagaga   120
gatagtgtgt gtcccaagg aaaatatatc caccctcaaa ataattcgat ttgctgtacc   180
aagtgccaca aaggaaccta cttgtacaat gactgtccag gccgggggca ggatacggac   240
tgcagggagt gtgagagcgg ctccttcacc gcttcagaaa accacctcag acactgcctc   300
agctgctcca atgccgaaa ggaaatgggt caggtggaga tctcttcttg cacagtggac   360
cgggacaccg tgtgtggctg caggaagaac cagtaccggc attattggag tgaaaacctt   420
```

```
ttccagtgct tcaattgcag cctctgcctc aatgggaccg tgcacctctc ctgccaggag    480
aaacagaaca ccgtgtgcac ctgccatgca ggtttctttc taagagaaaa cgagtgtgtc    540
tcctgtagta actgtaagaa aagcctggag tgcacgaagt tgtgcctacc ccagattgag    600
aatgttaagg gcactgagga ctcaggcacc acagtgctgt tgcccctggt cattttcttt    660
ggtctttgcc ttttatccct cctcttcatt ggtttaatgt atcgctacca acggtggaag    720
tccaagctct actccattgt ttgtgggaaa tcgacacctg aaaaagaggg ggagcttgaa    780
ggaactacta ctaagcccct ggccccaaac ccaagcttca gtcccactcc aggcttcacc    840
cccaccctgg gcttcagtcc cgtgcccagt tccaccttca cctccagctc cacctatacc    900
cccggtgact gtcccaactt tgcggctccc cgcagagagg tggcaccacc ctatcagggg    960
gctgacccca tccttgcgac agccctcgcc tccgacccca tccccaaccc ccttcagaag   1020
tgggaggaca gcgcccacaa gccacagagc ctagacactg atgacccccgc gacgctgtac   1080 gccgtggtgg agaacgtgcc cccgttgcgc tggaaggaat tcgtgcggcg cctagggctg   1140
agcgaccacg agatcgatcg gctggagctg cagaacgggc gctgcctgcg cgaggcgcaa   1200
tacagcatgc tggcgacctg gaggcggcgc acgccgcggc gcgaggccac gctggagctg   1260
ctgggacgcg tgctccgcga catggacctg ctgggctgcc tggaggacat cgaggaggcg   1320
ctttgcggcc ccgccgccct cccgcccgcg cccagtcttc tcagatga                1368

<210> SEQ ID NO 3
<211> LENGTH: 281
<212> TYPE: DNA
<213> ORGANISM: Homo sapiens

<400> SEQUENCE: 3
attcttcccc tggtggccat gggacccagg tcaatgtcac ctgcatcgtg aacgtctgta     60
gcagctctga ccacagctca cagtgctcct cccaagccag ctccacaatg ggagacacag    120
attccagccc ctcggagtcc ccgaaggacg agcaggtccc cttctccaag gaggaatgtg    180
cctttcggtc acagctggag acgccagaga ccctgctggg gagcaccgaa gagaagcccc    240
tgccccttgg agtgcctgat gctgggatga agcccagtta a                        281

<210> SEQ ID NO 4
<211> LENGTH: 939
<212> TYPE: DNA
<213> ORGANISM: Homo sapiens

<400> SEQUENCE: 4
atggcagctg ggcaaaatgg gcacgaagag tgggtgggca gcgcatacct gtttgtggag     60
tcctcgctgg acaaggtggt cctgtcggat gcctacgcgc accccagca gaaggtggca    120 gtgtacaggg ctctgcaggc tgccttggca gagagcggcg ggagcccgga cgtgctgcag    180
atgctgaaga tccaccgcag cgacccgcag ctgatcgtgc agctgcgatt ctgcgggcgg    240
cagccctgtg gccgcttcct ccgcgcctac cgcgaggggc gctgcgcgc cgcgctgcag    300 aggagcctgg cggccgcgct cgcccagcac tcggtgccgc tgcaactgga gctgcgcgcc    360
ggcgccgagc ggctggacgc tttgctggcg gacgaggagc gctgtttgag ttgcatccta    420
gcccagcagc ccgaccggct ccgggatgaa gaactggctg agctggagga tgcgctgcga    480
aatctgaagt gcggctcggg ggccggggt ggcgacgggg aggtcgcttc ggccccttg     540 cagccccgg tgcctctcct gtcggaggtg aagccgccgc cgccgccgcc acctgcccag    600
acttttctgt tccagggtca gcctgtagtg aatcggccgc tgagcctgaa ggaccaacag    660
```

```
acgttcgcgc gctctgtggg tctcaaatgg cgcaaggtgg ggcgctcact gcagcgaggc    720
tgccgggcgc tgcgggaccc ggcgctggac tcgctggcct acgagtacga gcgcgaggga    780
ctgtacgagc aggccttcca gctgctgcgg cgcttcgtgc aggccgaggg ccgccgcgcc    840
acgctgcagc gcctggtgga ggcactcgag gagaacgagc tcaccagcct ggcagaggac    900
ttgctgggcc tgaccgatcc caatggcggc ctggcctag                           939
```

<210> SEQ ID NO 5
<211> LENGTH: 1506
<212> TYPE: DNA
<213> ORGANISM: Homo sapiens

<400> SEQUENCE: 5

```
atggctgcag ctagcgtgac ccccctggc tccctggagt tgctacagcc cggcttctcc      60
aagaccctcc tggggaccaa gctggaagcc aagtacctgt gctccgcctg cagaaacgtc    120
ctccgcaggc ccttccaggc gcagtgtggc accggtact gctccttctg cctggccagc    180
atcctcagct ctgggcctca gaactgtgct gcctgtgttc acgagggcat atatgaagaa    240
ggcatttcta ttttagaaag cagttcggcc ttcccagata tgctgcccg caggggaggtg    300
gagagcctgc cggccgtctg tcccagtgat ggatgcacct ggaaggggac cctgaaagaa    360
tacgagagct gccacgaagg ccgctgcccg ctcatgctga ccgaatgtcc cgcgtgcaaa    420
ggcctggtcc gccttggtga aaaggagcgc cacctggagc acgagtgccc ggagagaagc    480
ctgagctgcc ggcattgccg ggcaccctgc tgcggagcag acgtgaaggc gcaccacgag    540
gtctgcccca gttccccctt aacttgtgac ggctgcggca agaagaagat ccccgggag     600
aagtttcagg accacgtcaa gacttgtggc aagtgtcgag tcccttgcag attccacgcc    660
atcggctgcc tcgagacggt agagggtgag aaacagcagg agcacgaggt gcagtggctg    720
cgggagcacc tggccatgct actgagctcg gtgctggagg caaagcccct cttgggagac    780
cagagccacg cggggtcaga gctcctgcag aggtgcgaga gctggagaa gaagacggcc     840
acttttgaga acattgtctg cgtcctgaac cgggaggtgg agagggtggc catgactgcc    900
gaggcctgca gccggcagca ccggctggac caagacaaga ttgaagccct gagtagcaag    960
gtgcagcagc tggagaggag cattggcctc aaggacctgg cgatggctga cttggagcag   1020
aaggtcttgg agatggaggc atccacctac gatgggtctc tcatctggaa gatctcagac   1080
ttcgccagga agcgccagga agctgtggct ggccgcatac ccgccatctt ctccccagcc   1140
ttctacacca gcaggtacgg ctacaagatg tgtctgcgta tctacctgaa cggcgacggc   1200
accgggcgag gaacacacct gtccctcttc tttgtggtga tgaagggccc gaatgacgcc   1260
ctgctgcggt ggcccttcaa ccagaaggtg accttaatgc tgctcgacca gaataaccgg   1320
gagcacgtga ttgacgcctt caggcccgac gtgacttcat cctctttca gaggccagtc    1380
aacgacatga acatcgcaag cggctgcccc ctcttctgcc ccgtctccaa gatgaaggca    1440
aagaattcct acgtgcggga cgatgccatc ttcatcaagg ccattgtgga cctgacaggg   1500
ctctaa                                                              1506
```

<210> SEQ ID NO 6
<211> LENGTH: 1044
<212> TYPE: DNA
<213> ORGANISM: Homo sapiens

<400> SEQUENCE: 6

| | |
|---|---|
| atggaaacac ccttctacgg cgatgaggcg ctgagcggcc tgggcggcgg cgccagtggc | 60 |
| agcggcggca gcttcgcgtc cccgggccgc ttgttccccg gggcgccccc gacggccgcg | 120 |
| gccggcagca tgatgaagaa ggacgcgctg acgctgagcc tgagtgagca ggtggcggca | 180 |
| gcgctcaagc ctgcggccgc gccgcctcct accccctgc gcgccgacgg cgcccccagc | 240 |
| gcggcacccc ccgacggcct gctcgcctct cccgacctgg ggctgctgaa gctggcctcc | 300 |
| cccgagctcg agcgcctcat catccagtcc aacgggctgg tcaccaccac gccgacgagc | 360 |
| tcacagttcc tctaccccaa ggtggcggcc agcgaggagc aggagttcgc cgagggcttc | 420 |
| gtcaaggccc tggaggattt acacaagcag aaccagctcg gcgcgggcgc ggccgctgcc | 480 |
| gccgccgccg ccgccgccgg ggggccctcg ggcacggcca cgggctccgc gccccccggc | 540 |
| gagctggccc cggcggcggc cgcgcccgaa gcgcctgtct acgcgaacct gagcagctac | 600 |
| gcgggcggcg ccggggggcgc gggggcgcc gcgacggtcg ccttcgctgc cgaacctgtg | 660 |
| cccttcccgc cgccgccacc cccaggcgcg ttggggccgc cgcgcctggc tgcgctcaag | 720 |
| gacgagccac agacggtgcc cgacgtgccg agcttcggcg agagcccgcc gttgtcgccc | 780 |
| atcgacatgg acacgcagga gcgcatcaag gcggagcgca gcggctgcg caaccgcatc | 840 |
| gccgcctcca agtgccgcaa gcgcaagctg gagcgcatct cgcgcctgga agagaaagtg | 900 |
| aagaccctca gagtcagaa cacggagctg cgtccacgg cgagcctgct gcgcgagcag | 960 |
| gtggcgcagc tcaagcagaa agtcctcagc cacgtcaaca gcggctgcca gctgctgccc | 1020 |
| cagcaccagg tgcccgcgta ctga | 1044 |

<210> SEQ ID NO 7
<211> LENGTH: 4124
<212> TYPE: DNA
<213> ORGANISM: Homo sapiens

<400> SEQUENCE: 7

| | |
|---|---|
| atgagcacgg aggcggacga gggcatcact ttctctgtgc cacccttcgc ccctcgggc | 60 |
| ttctgcacca tccccgaggg cggcatctgc aggaggggag gagcggcggc ggtgggcgag | 120 |
| ggcgaggagc accagctgcc accgccgccg ccgggcagtt tctggaacgt ggagagcgcc | 180 |
| gctgccctg gcatcggttg tccggcggcc acctcctcga gcagtgccac ccgaggccgg | 240 |
| ggcagctctt ttggcggggg cagccgacgg accacggtgg catatgtgat caacgaagcg | 300 |
| agccaagggc aactggtggt ggccgagagc gaggccctgc agagcttgcg ggaggcgtgc | 360 |
| gagacagtgg gcgccaccct ggaacccctgc atttgggaa actcgacttt ggagaaacca | 420 |
| ccgtgctgga ccgcttttac aatgcagata ttgcggtggt ggagatgagc gatgccttcc | 480 |
| ggcagccgtc cttgttttac caccttgggg tgagagaaag tttcagcatg gccaacaaca | 540 |
| tcatcctcta ctgcgatact aactcggact ctctgcagtc actgaaggaa atcatttgcc | 600 |
| agaagaatac tatgtgcact gggaactaca cctttgttcc ttacatgata actccacata | 660 |
| acaaagtcta ctgctgtgac agcagcttca tgaaggggtt gacagagctc atgcaaccga | 720 |
| acttcgagct gcttcttgga cccatctgct tacctcttgt ggatcgtttt attcaacttt | 780 |
| tgaaggtggc acaagcaagt tctagccagt acttccggga atctatactc aatgacatca | 840 |
| ggaaagctcg taatttatac actggtaaag aattggcagc tgagttggca agaattcggc | 900 |
| agcgagtaga taatatcgaa gtcttgacag cagatattgt cataaatctg ttacttccct | 960 |
| acagagatat ccaggactat gattctattg tgaagctgg agagacttta gaaaactgc | 1020 |
| caacctttga tttggcctcc catcaccatg tgaagtttca ttatgcattt gcactgaata | 1080 |

```
ggagaaatct ccctggtgac agagcaaaag ctcttgatat tatgattccc atggtgcaaa    1140
gcgaaggaca agttgcttca gatatgtatt gcctagttgg tcgaatctac aaagatatgt    1200 tttggactc taatttcacg gacactgaaa gcagagacca tggagcttct tggttcaaaa    1260
aggcatttga atctgagcca acactacagt caggaattaa ttatgcggtc ctcctcctgg    1320
cagctggaca ccagtttgaa tcttcctttg agctccggaa agttggggtg aagctaagta    1380
gtcttcttgg taaaaaggga aacttggaaa actccagag ctactgggaa gttggatttt     1440
ttctgggggc cagcgtccta gccaatgacc acatgagagt cattcaagca tctgaaaagc    1500
tttttaaact gaagacacca gcatggtacc tcaagtctat tgtagagaca attttgatat    1560
ataagcattt tgtgaaactg accacagaac agcctgtggc caagcaagaa cttgtggact    1620
tttggatgga tttcctggtc gaggccacaa agacagatgt tactgtggtt aggtttccag    1680
tattaatatt agaaccaacc aaaatctatc aaccttctta tttgtctatc aacaatgaag    1740
ttgaggaaaa gacaatctct atttggcacg tgcttcctga tgacaagaaa ggtatacatg    1800
agtggaattt tagtgcctct tctgtcaggg gagtgagtat ttctaaattt gaagaaagat    1860
gctgctttct ttatgtgctt cacaattctg atgatttcca atctatttc tgtacagaac     1920 ttcattgtaa aaagtttttt gagatggtga acaccattac cgaagagaag gggagaagca    1980
cagaggaagg agactgtgaa agtgacttgc tggagtatga ctatgaatat gatgaaaatg    2040
gtgacagagt cgttttagga aaaggcactt atgggatagt ctacgcaggt cgggacttga    2100
gcaaccaagt cagaattgct attaaggaaa tcccagagag agacagcaga tactctcagc    2160
ccctgcatga agaaatagca ttgcataaac acctgaagca caaaatatt gtccagtatc     2220 tgggctcttt cagtgagaat ggtttcatta aaatcttcat ggagcaggtc cctggaggaa    2280
gtctttctgc tctccttcgt tccaaatggg gtccattaaa agacaatgag caaacaattg    2340
gcttttatac aaagcaaata ctggaaggat taaaatatct ccatgacaat cagatagttc    2400
accgggacat aaagggtgac aatgtgttga ttaataccta cagtggtgtt ctcaagatct    2460
ctgacttcgg aacatcaaag aggcttgctg catcaaaccc ctgtactgaa acttttactg    2520
gtaccctcca gtatatggca ccagaaataa tagataaagg accaagaggc tacggaaaag    2580
cagcagacat ctggtctctg ggctgtacaa tcattgaaat ggccacagga aaaccccat     2640 tttatgaact gggagaacca caagcagcta tgttcaaggt gggaatgttt aaagtccacc    2700
ctgagatccc agagtccatg tctgcagagg ccaaggcatt catactgaaa tgttttgaac    2760
cagatcctga caagagagcc tgtgctaacg acttgcttgt tgatgagttt ttaaaagttt    2820
caagcaaaaa gaaaagaca caacctaagc tttcagctct ttcagctgga tcaaatgaat     2880
atctcaggag tatatccttg ccggtacctg tgctggtgga ggacaccagc agcagcagtg    2940
agtacggctc agtttcaccc gacacggagt tgaaagtgga ccccttctct ttcaaaacaa    3000
gagccaagtc ctgcgagaa agagatgtca agggaattcg acactctttt tgggcattc      3060 cagatgagaa ttttgaagat cacagtgctc ctccttcccc tgaagaaaaa gattctggat    3120
tcttcatgct gaggaaggac agtgagaggc gagctaccct tcacaggatc ctgacggaag    3180
accaagacaa aattgtgaga aacctaatgg aatctttagc tcaggggggct gaagaaccga    3240 aactaaaatg ggaacacatc acaaccctca ttgcaagcct cagagaattt gtgagatcca    3300
ctgaccgaaa aatcatagcc accacactgt caaagctgaa actggagctg gacttcgaca    3360
gccatggcat tagccaagtc caggtggtac tctttggttt tcaagatgct gtcaataaag    3420
```

| | |
|---|---|
| ttcttcggaa tcataacatc aagccgcact ggatgtttgc cttagacagt atcattcgga | 3480 |
| aggcggtaca gacagccatt accatcctgg ttccagaact aaggccacat ttcagccttg | 3540 |
| catctgagag tgatactgct gatcaagaag acttggatgt agaagatgac catgaggaac | 3600 |
| agccttcaaa tcaaactgtc cgaagacctc aggctgtcat tgaagatgct gtggctacct | 3660 |
| caggcgtgag cacgctcagt tctactgtgt ctcatgattc ccagagtgct caccggtcac | 3720 |
| tgaatgtaca gcttggaagg atgaaaatag aaaccaatag attactggaa gaattggttc | 3780 |
| ggaaagagaa agaattacaa gcactccttc atcgagctat tgaagaaaaa gaccaagaaa | 3840 |
| ttaaacacct gaagcttaag tcccaaccca tagaaattcc tgaattgcct gtatttcatc | 3900 |
| taaattcttc tggcacaaat actgaagatt ctgaacttac cgactggctg agagtgaatg | 3960 |
| gagctgatga agacactata agccggtttt tggctgaaga ttatacacta ttggatgttc | 4020 |
| tctactatgt tacacgtgat gacttaaaat gcttgagact aaggggaggg atgctgtgca | 4080 |
| cactgtggaa ggctatcatt gactttcgaa acaaacagac ttga | 4124 |

<210> SEQ ID NO 8
<211> LENGTH: 1128
<212> TYPE: DNA
<213> ORGANISM: Homo sapiens

<400> SEQUENCE: 8

| | |
|---|---|
| atggagcgcg cgtcctgctt gttgctgctg ctgctgccgc tggtgcacgt ctctgcgacc | 60 |
| acgccagaac cttgtgagct ggacgatgaa gatttccgct gcgtctgcaa cttctccgaa | 120 |
| cctcagcccg actggtccga agccttccag tgtgtgtctg cagtagaggt ggagatccat | 180 |
| gccggcggtc tcaacctaga gccgtttcta aagcgcgtcg atgcggacgc cgacccgcgg | 240 |
| cagtatgctg acacggtcaa ggctctccgc gtgcggcggc tcacagtggg agccgcacag | 300 |
| gttcctgctc agctactggt aggcgccctg cgtgtgctag cgtactcccg cctcaaggaa | 360 |
| ctgacgctcg aggacctaaa gataaccggc accatgcctc cgctgcctct ggaagccaca | 420 |
| ggacttgcac tttccagctt gcgcctacgc aacgtgtcgt gggcgacagg gcgttcttgg | 480 |
| ctcgccgagc tgcagcagtg gctcaagcca ggcctcaagg tactgagcat tgcccaagca | 540 |
| cactcgcctg ccttttcctg cgaacaggtt cgcgccttcc cggcccttac cagcctagac | 600 |
| ctgtctgaca tcctggact gggcgaacgc ggactgatgg cggctctctg tccccacaag | 660 |
| ttccccggcc atccagaatct agcgctgcgc aacacaggaa tggagacgcc cacaggcgtg | 720 |
| tgcgccgcac tggcggcggc aggtgtgcag ccccacagcc tagacctcag ccacaactcg | 780 |
| ctgcgcgcca ccgtaaaccc tagcgctccg agatgcatgt ggtccagcgc cctgaactcc | 840 |
| ctcaatctgt cgttcgctgg gctggaacag gtgcctaaag gactgccagc caagctcaga | 900 |
| gtgctcgatc tcagctgcaa cagactgaac agggcgccgc agcctgacga gctgcccgag | 960 |
| gtggataacc tgacactgga cgggaatccc ttcctggtcc ctggaactgc cctcccccac | 1020 |
| gagggctcaa tgaactccgg cgtggtccca gcctgtgcac gttcgaccct gtcggtgggg | 1080 |
| gtgtcgggaa ccctggtgct gctccaaggg gcccggggct tgcctaa | 1128 |

<210> SEQ ID NO 9
<211> LENGTH: 1140
<212> TYPE: DNA
<213> ORGANISM: Homo sapiens

<400> SEQUENCE: 9

| | |
|---|---|
| atggcggcgg cggcggctca ggggggcggg ggcggggagc cccgtagaac cgaggggtc | 60 |

```
ggcccggggg tcccggggga ggtggagatg gtgaagggc agccgttcga cgtgggcccg    120
cgctacacgc agttgcagta catcggcgag ggcgcgtacg gcatggtcag ctcggcctat    180
gaccacgtgc gcaagactcg cgtggccatc aagaagatca gccccttcga acatcagacc    240
tactgccagc gcacgctccg ggagatccag atcctgctgc gcttccgcca tgagaatgtc    300
atcggcatcc gagacattct gcgggcgtcc accctggaag ccatgagaga tgtctacatt    360
gtgcaggacc tgatggagac tgacctgtac aagttgctga aaagccagca gctgagcaat    420
gaccatatct gctacttcct ctaccagatc ctgcggggcc tcaagtacat ccactccgcc    480
aacgtgctcc accgagatct aaagccctcc aacctgctca tcaacaccac ctgcgacctt    540
aagatttgtg atttcggcct ggccggatt gccgatcctg agcatgacca caccggcttc    600
ctgacggagt atgtggctac gcgctggtac cgggccccag agatcatgct gaactccaag    660
ggctatacca agtccatcga catctggtct gtgggctgca ttctggctga gatgctctct    720
aaccggccca tcttccctgg caagcactac ctggatcagc tcaaccacat tctgggcatc    780
ctgggctccc catcccagga ggacctgaat tgtatcatca acatgaaggc ccgaaactac    840
ctacagtctc tgccctccaa gaccaaggtg gcttgggcca gcttttccc caagtcagac    900 tccaaagccc ttgacctgct ggaccggatg ttaacctta accccaataa acggatcaca    960
gtggaggaag cgctggctca cccctacctg gagcagtact atgacccgac ggatgagcca   1020
gtggccgagg agcccttcac cttcgccatg gagctggatg acctacctaa ggagcggctg   1080
aaggagctca tcttccagga gacagcacgc ttccagcccg gagtgctgga ggccccctag   1140
```

<210> SEQ ID NO 10
<211> LENGTH: 1083
<212> TYPE: DNA
<213> ORGANISM: Homo sapiens

<400> SEQUENCE: 10

```
atggcggcgg cggcggcggc gggcgcgggc ccggagatgg tccgcgggca ggtgttcgac     60
gtggggccgc gctacaccaa cctctcgtac atcggcgagg gcgcctacgg catggtgtgc    120
tctgcttatg ataatgtcaa caaagttcga gtagctatca agaaaatcag cccctttgag    180
caccagacct actgccagag aaccctgagg gagataaaaa tcttactgcg cttcagacat    240
gagaacatca ttggaatcaa tgacattatt cgagcaccaa ccatcgagca atgaaagat    300 gtatatatag tacaggacct catggaaaca gatctttaca gctcttgaa gacacaacac    360 ctcagcaatg accatatctg ctattttctc taccagatcc tcagagggtt aaaatatatc    420
cattcagcta acgttctgca ccgtgacctc aagccttcca acctgctgct caacaccacc    480
tgtgatctca agatctgtga ctttggcctg gcccgtgttg cagatccaga ccatgatcac    540
acagggttcc tgacagaata tgtggccaca cgttggtaca gggctccaga aattatgttg    600
aattccaagg gctacaccaa gtccattgat atttggtctg taggctgcat tctggcagaa    660
atgctttcta acaggcccat ctttccaggg aagcattatc ttgaccagct gaaccacatt    720
ttgggtattc ttggatcccc atcacaagaa gacctgaatt gtataataaa tttaaaagct    780
aggaactatt tgctttctct tccacacaaa ataaggtgc catggaacag gctgttccca    840
aatgctgact ccaaagctct ggacttattg gacaaaatgt tgacattcaa cccacacaag    900
aggattgaag tagaacaggc tctggcccac ccatatctgg agcagtatta cgacccgagt    960
gacgagccca tcgccgaagc accattcaag ttcgacatgg aattggatga cttgcctaag   1020
```

| | |
|---|---|
| gaaaagctca aagaactaat ttttgaagag actgctagat tccagccagg atacagatct | 1080 |
| taa | 1083 |

<210> SEQ ID NO 11
<211> LENGTH: 2265
<212> TYPE: DNA
<213> ORGANISM: Homo sapiens

<400> SEQUENCE: 11

| | |
|---|---|
| atgttttcag gggggtgtca tagccccggg tttggccgcc ccagccccgc cttcccgcc | 60 |
| ccggggagcc cgcccctgc cccgcgtccc tgccgacagg aaacaggtga gcagattgcc | 120 |
| atcaagcagt gccggcagga gctcagcccc cggaaccgag agcggtggtg cctggagatc | 180 |
| cagatcatga aaggctgac ccaccccaat gtggtggctg cccgagatgt ccctgagggg | 240 |
| atgcagaact tggcgcccaa tgacctgccc ctgctggcca tggagtactg ccaaggagga | 300 |
| gatctccgga gtacctgaa ccagtttgag aactgctgtg gtctgcggga aggtgccatc | 360 |
| ctcaccttgc tgagtgacat tgcctctgcg cttagatacc ttcatgaaaa cagaatcatc | 420 |
| catcgggatc taaagccaga aaacatcgtc ctgcagcaag agaacagag gttaatacac | 480 |
| aaaattattg acctaggata tgccaaggag ctggatcagg cagtctttg cacatcattc | 540 |
| gtggggaccc tgcagtacct ggccccagag ctactggagc agcagaagta cacagtgacc | 600 |
| gtcgactact ggagcttcgg caccctggcc tttgagtgca tcacgggctt ccggcccttc | 660 |
| ctccccaact ggcagcccgt gcagtggcat tcaaaagtgc ggcagaagag tgaggtggac | 720 |
| attgttgtta gcgaagactt gaatggaacg gtgaagtttt caagctcttt accctacccc | 780 |
| aataatctta cagtgtcct ggctgagcga ctggagaagt ggctgcaact gatgctgatg | 840 |
| tggcacccccc gacagagggg cacgatccc acgtatgggc caatggctg cttcaaggcc | 900 |
| ctggatgaca tcttaaactt aaagctggtt catatcttga acatggtcac gggcaccatc | 960 |
| cacacctacc ctgtgacaga ggatgagagt ctgcagagct tgaaggccag aatccaacag | 1020 |
| gacacgggca tcccagagga ggaccaggag ctgctgcagg aagcgggcct ggcgttgatc | 1080 |
| cccgataagc ctgccactca gtgtatttca gacggcaagt taaatgaggg ccacacattg | 1140 |
| gacatggatc ttgttttct cttttgacaac agtaaaatca cctatgagac tcagatctcc | 1200 |
| ccacggcccc aacctgaaag tgtcagctgt atccttcaag agcccaagag gaatctcgcc | 1260 |
| ttcttccagc tgaggaaggt gtggggccag gtctggcaca gcatccagac cctgaaggaa | 1320 |
| gattgcaacc ggctgcagca gggacagcga gccgccatga tgaatctcct ccgaaacaac | 1380 |
| agctgcctct ccaaaatgaa gaattccatg gcttccatgt ctcagcagct caaggccaag | 1440 |
| ttggatttct tcaaaccag catccagatt gacctggaga agtacagcga gcaaaccgag | 1500 |
| tttgggatca catcagataa actgctgctg gcctggaggg aaatggagca ggctgtggag | 1560 |
| ctctgtgggc gggagaacga agtgaaactc ctggtagaac ggatgatggc tctgcagacc | 1620 |
| gacattgtgg acttacagag gagccccatg ggccggaagc agggggggaac gctggacgac | 1680 |
| ctagaggagc aagcaaggga gctgtacagg agactaaggg aaaaacctcg agaccagcga | 1740 |
| actgagggtg acagtcagga aatggtacgc tgctgcttc aggcaattca gagcttcgag | 1800 |
| aagaaagtgc gagtgatcta tacgcagctc agtaaaactg tggtttgcaa gcagaaggcg | 1860 |
| ctggaactgt tgcccaaggt ggaagaggtg gtgagcttaa tgaatgagga tgagaagact | 1920 |
| gttgtccggc tgcaggagaa gcggcagaag gagctctgga tctcctgaa gattgcttgt | 1980 |
| agcaaggtcc gtggtcctgt cagtggaagc ccggatagca tgaatgcctc tcgacttagc | 2040 |

| | |
|---|---|
| cagcctgggc agctgatgtc tcagccctcc acggcctcca acagcttacc tgagccagcc | 2100 |
| aagaagagtg aagaactggt ggctgaagca cataacctct gcaccctgct agaaaatgcc | 2160 |
| atacaggaca ctgtgaggga acaagaccag agtttcacgg ccctagactg gagctggtta | 2220 |
| cagacggaaa aagaagagca cagctgcctg gagcaggcct catga | 2265 |

<210> SEQ ID NO 12
<211> LENGTH: 954
<212> TYPE: DNA
<213> ORGANISM: Homo sapiens

<400> SEQUENCE: 12

| | |
|---|---|
| atgttccagg cggccgagcg cccccaggag tgggccatgg agggccccg cgacgggctg | 60 |
| aagaaggagc ggctactgga cgaccgccac gacagcggcc tggactccat gaaagacgag | 120 |
| gagtacgagc agatggtcaa ggagctgcag gagatccgcc tcgagccgca ggaggtgccg | 180 |
| cgcggctcgg agccctggaa gcagcagctc accgaggacg ggactcgtt cctgcacttg | 240 |
| gccatcatcc atgaagaaaa ggcactgacc atggaagtga tccgccaggt gaagggagac | 300 |
| ctggccttcc tcaacttcca gaacaacctg cagcagactc cactccactt ggctgtgatc | 360 |
| accaaccagc cagaaattgc tgaggcactt ctgggagctg gctgtgatcc tgagctccga | 420 |
| gactttcgag gaaataccc cctacacctt gcctgtgagc agggctgcct ggccagcgtg | 480 |
| ggagtcctga ctcagtcctg caccaccccg cacctccact ccatcctgaa ggctaccaac | 540 |
| tacaatggcc acacgtgtct acacttagcc tctatccatg ctacctggg catcgtggag | 600 |
| cttttggtgt ccttgggtgc tgatgtcaat gctcaggagc cctgtaatgg ccggactgcc | 660 |
| cttcacctcg cagtggacct gcaaaatcct gacctggtgt cactcctgtt gaagtgtggg | 720 |
| gctgatgtca acagagttac ctaccagggc tattctccct accagctcac ctggggccgc | 780 |
| ccaagcaccc ggatacagca gcagctgggc cagctgacac tagaaaacct tcagatgctg | 840 |
| ccagagagtg aggatgagga gagctatgac acagagtcag agttcacgga gttcacagag | 900 |
| gacgagctgc cctatgatga ctgtgtgttt ggaggccagc gtctgacgtt atga | 954 |

<210> SEQ ID NO 13
<211> LENGTH: 2139
<212> TYPE: DNA
<213> ORGANISM: Homo sapiens

<400> SEQUENCE: 13

| | |
|---|---|
| atggccgggg ggccgggccc gggggagccc gcagccccg gcgcccagca cttcttgtac | 60 |
| gaggtgccgc cctgggtcat gtgccgcttc tacaaagtga tggacgccct ggagcccgcc | 120 |
| gactggtgcc agttcgccgc cctgatcgtg cgcgaccaga ccgagctgcg gctgtgcgag | 180 |
| cgctccgggc agcgcacggc cagcgtcctg tggccctgga tcaaccgcaa cgcccgtgtg | 240 |
| gccgacctcg tgcacatcct cacgcacctg cagctgctcc gtgcgcggga catcatcaca | 300 |
| gcctggcacc ctcccgcccc gcttccgtcc ccaggcacca ctgccccgag gcccagcagc | 360 |
| atccctgcac ccgccgaggc cgaggcctgg agccccgga agttgccatc ctcagcctcc | 420 |
| accttcctct cccagctttt ccaggcctcc agacccatt cagggcctga gctcggcctg | 480 |
| gtcccaagcc ctgcttccct gtggcctcca ccgccatctc cagcccttc ttctaccaag | 540 |
| ccaggcccag agagctcagt gtccctcctg caggagccc gccctttcc gttttgctgg | 600 |
| cccctctgtg agatttcccg gggcacccac aacttctcgg aggagctcaa gatcggggag | 660 |

```
ggtggctttg ggtgcgtgta ccgggcggtg atgaggaaca cggtgtatgc tgtgaagagg      720
ctgaaggaga acgctgacct ggagtggact gcagtgaagc agagcttcct gaccgaggtg      780
gagcagctgt ccaggtttcg tcacccaaac attgtggact ttgctggcta ctgtgctcag      840
aacggcttct actgcctggt gtacggcttc ctgcccaacg ctccctgga ggaccgtctc       900 cactgccaga cccaggcctg cccacctctc tcctggcctc agcgactgga catccttctg      960
ggtacagccc gggcaattca gtttctacat caggacagcc ccagcctcat ccatggagac     1020
atcaagagtt ccaacgtcct tctggatgag aggctgacac ccaagctggg gactttggc     1080 ctggcccggt tcagccgctt tgccgggtcc agccccagcc agagcagcat ggtgccccgg     1140
acacagacag tgcggggcac cctggcctac ctgcccgagg agtacatcaa gacgggaagg    1200
ctggctgtgg acacggacac cttcagcttt ggggtggtag tgctagagac cttggctggt     1260
cagagggctg tgaagacgca cggtgccagg accaagtatc tgaaagacct ggtggaagag    1320
gaggctgagg aggctggagt ggctttgaga agcacccaga gcacactgca agcaggtctg    1380
gctgcagatg cctgggctgc tcccatcgcc atgcagatct acaagaagca cctggacccc    1440
aggcccgggc cctgcccacc tgagctgggc ctgggcctgg ccagctggc ctgctgctgc      1500 ctgcaccgcc gggccaaaag gaggcctcct atgacccagg tgtacgagag ctagagaag     1560 ctgcaggcag tggtgcgggg ggtgcccggg cattcggagg ccgccagctg catcccccct     1620
tccccgcagg agaactccta cgtgtccagc actggcagag cccacagtgg ggctgctcca    1680
tggcagcccc tggcagcgcc atcaggagcc agtgcccagg cagcagagca gctgcagaga    1740
ggccccaacc agcccgtgga gagtgacgag agcctaggcg gcctctctgc tgccctgcgc    1800
tcctggcact tgactccaag ctgccctctg acccagcac ccctcaggga ggccggctgt     1860
cctcaggggg acacggcagg agaatcgagc tgggggagtg gcccaggatc ccggcccaca    1920
gccgtggaag gactggccct tggcagctct gcatcatcgt cgtcagagcc accgcagatt    1980
atcatcaacc ctgcccgaca gaagatggtc cagaagctgg ccctgtacga ggatggggcc    2040
ctggacagcc tgcagctgct gtcgtccagc tccctcccag gcttgggcct ggaacaggac    2100
aggcaggggc ccgaagaaag tgatgaattt cagagctga                          2139
```

<210> SEQ ID NO 14
<211> LENGTH: 1284
<212> TYPE: DNA
<213> ORGANISM: Homo sapiens

<400> SEQUENCE: 14

```
atgagcagaa gcaagcgtga caacaatttt tatagtgtag agattggaga ttctacattc       60
acagtcctga aacgatatca gaatttaaaa cctataggct caggagctca aggaatagta      120
tgcgcagctt atgatgccat tcttgaaaga aatgttgcaa tcaagaagct aagccgacca     180
tttcagaatc agactcatgc caagcgggcc tacagagagc tagttcttat gaaatgtgtt      240
aatcacaaaa atataattgg cctttttgaat gttttcacac cacagaaatc cctagaagaa      300
tttcaagatg tttacatagt catggagctc atggatgcaa atctttgcca agtgattcag      360
atggagctag atcatgaaag aatgtcctac cttctctatc agatgctgtg tggaatcaag    420
caccttcatt ctgctggaat tattcatcgg gacttaaagc ccagtaatat agtagtaaaa       480
tctgattgca ctttgaagat tcttgactt ggtctggcca ggactgcagg aacgagtttt       540
atgatgacgc cttatgtagt gactcgctac tacagagcac ccgaggtcat ccttggcatg     600
ggctacaagg aaaacgttga catttggtca gttgggtgca tcatgggaga aatgatcaaa     660
```

```
ggtggtgttt tgttcccagg tacagatcat attgatcagt ggaataaagt tattgaacag      720
cttggaacac catgtcctga attcatgaag aaactgcaac caacagtaag gacttacgtt      780 gaaacagac ctaaatatgc tggatatagc tttgagaaac tcttccctga tgtcctttc       840 ccagctgact cagaacacaa caaacttaaa gccagtcagg caagggattt gttatccaaa      900
atgctggtaa tagatgcatc taaaaggatc tctgtagatg aagctctcca cacccgtac       960 atcaatgtct ggtatgatcc ttctgaagca gaagctccac caccaaagat ccctgacaag     1020
cagttagatg aaagggaaca cacaatagaa gagtggaaag aattgatata aaggaagtt     1080 atggacttgg aggagagaac caagaatgga gttatacggg gcagccctc tcctttaggt      1140 gcagcagtga tcaatggctc tcagcatcca tcatcatcgt cgtctgtcaa tgatgtgtct     1200
tcaatgtcaa cagatccgac tttggcctct gatacagaca gcagtctaga agcagcagct     1260
gggcctctgg gctgctgtag atga                                             1284

<210> SEQ ID NO 15
<211> LENGTH: 1446
<212> TYPE: DNA
<213> ORGANISM: Homo sapiens

<400> SEQUENCE: 15 atggggcct tggccagagc cctgccgtcc atactgctgg cattgctgct tacgtccacc        60
ccagaggctc tgggtgccaa ccccggcttg gtcgccagga tcaccgacaa gggactgcag      120
tatgcggccc aggaggggct attagctctg cagagtgagc tgctcaggat cacgctgcct      180
gacttcaccg gggacttgag gatccccac gtcggccgtg ggcgctatga gttccacagc       240
ctgaacatcc acagctgtga gctgcttcac tctgcgctga ggcctgtccc tggccagggc     300
ctgagtctca gcatctccga ctcctccatc cgggtccagg gcaggtggaa ggtgcgcaag     360
tcattcttca aactacaggg ctccttggat gtcagtgtca agggcatcag catttcggtc      420
aacctcctgt tgggcagcga gtcctccggg aggcccacag ttactgcctc cagctgcagc     480
agtgacatcg ctgacgtgga ggtggacatg tcgggagact ggggtggct gttgaacctc      540 ttccacaacc agattgagtc caagttccag aaagtactgg agagcaggat ttgcgaaatg      600
atccagaaat cggtgtcctc cgatctacag ccttatctcc aaactctgcc agttacaaca      660
gagattgaca gtttcgccga cattgattat agcttagtgg aagccctcg ggcaacagcc      720 cagatgctgg aggtgatgtt taagggtgaa atctttcatc gtaaccaccg ttctccagtt      780 acctccttg ctgcagtcat gagccttcct gaggaacaca caaaatggt ctactttgcc       840 atctcggatt atgtcttcaa cacggccagc ctggtttatc atgaggaagg atatctgaac      900
ttctccatca cagatgacat gatccgcct gactctaata tccgactgac caccaagtcc      960
ttccgaccct tcgtcccacg gttagccagg ctctaccca acatgaacct ggaactccag     1020
ggatcagtgc cctctgctcc gctcctgaac ttcagccctg gaatctgtc tgtgaccccc    1080 tatatggaga tagatgcctt tgtgctcctg cccagctcca gcaaggagcc tgtcttccgg     1140
ctcagtgtgg ccactaatgt gtccgccacc ttgaccttca ataccagcaa gatcactggg     1200
ttcctgaagc aggaaaggt aaagtggaa ctgaaagaat ccaagttgg actattcaat     1260 gcagagctgt tggaagcgct cctcaactat acatccttta caccctcta ccccaagttc     1320 aatgataagt tggccgaagg cttccccctt cctctgctga gcgtgttcca gctctacgac     1380
cttgggctgc agatccataa ggacttcctg ttcttgggtg ccaatgtcca atacatgaga     1440
```

| | |
|---|---|
| gtttga | 1446 |

<210> SEQ ID NO 16
<211> LENGTH: 1182
<212> TYPE: DNA
<213> ORGANISM: Homo sapiens

<400> SEQUENCE: 16

| | |
|---|---|
| atgcccaaga agaagccgac gcccatccag ctgaacccgg cccccgacgg ctctgcagtt | 60 |
| aacgggacca gctctgcgga gaccaacttg gaggccttgc agaagaagct ggaggagcta | 120 |
| gagcttgatg agcagcagcg aaagcgcctt gaggcctttc ttacccagaa gcagaaggtg | 180 |
| ggagaactga aggatgacga cttgagaag atcagtgagc tggggctgg caatggcggt | 240 |
| gtggtgttca aggtctccca caagccttct ggcctggtca tggccagaaa gctaattcat | 300 |
| ctggagatca aacccgcaat ccggaaccag atcataaggg agctgcaggt tctgcatgag | 360 |
| tgcaactctc cgtacatcgt gggcttctat ggtgcgttct acagcgatgg cgagatcagt | 420 |
| atctgcatgg agcacatgga tggaggttct ctggatcaag tcctgaagaa gctggaaga | 480 |
| attcctgaac aaattttagg aaaagttagc attgctgtaa taaaaggcct gacatatctg | 540 |
| agggagaagc acaagatcat gcacagagat gtcaagccct ccaacatcct agtcaactcc | 600 |
| cgtgggga tcaagctctg tgactttggg gtcagcgggc agctcatcga ctccatggcc | 660 |
| aactccttcg tgggcacaag gtcctacatg tcgccagaaa gactccaggg gactcattac | 720 |
| tctgtgcagt cagacatctg gagcatggga ctgtctctgg tagagatggc ggttgggagg | 780 |
| tatcccatcc ctcctccaga tgccaaggag ctggagctga tgtttgggtg ccaggtggaa | 840 |
| ggagatgcgg ctgagacccc acccaggcca aggaccccg ggaggcccct tagctcatac | 900 |
| ggaatggaca gccgacctcc catggcaatt tttgagttgt tggattacat agtcaacgag | 960 |
| cctcctccaa aactgcccag tggagtgttc agtctggaat tcaagattt tgtgaataaa | 1020 |
| tgcttaataa aaaaccccgc agagagagca gatttgaagc aactcatggt tcatgctttt | 1080 |
| atcaagagat ctgatgctga ggaagtggat tttgcaggtt ggctctgctc caccatcggc | 1140 |
| cttaaccagc ccagcacacc aacccatgct gctggcgtct aa | 1182 |

<210> SEQ ID NO 17
<211> LENGTH: 1203
<212> TYPE: DNA
<213> ORGANISM: Homo sapiens

<400> SEQUENCE: 17

| | |
|---|---|
| atgctggccc ggaggaagcc ggtgctgccg gcgctcacca tcaaccctac catcgccgag | 60 |
| ggcccatccc ctaccagcga gggcgcctcc gaggcaaacc tggtggacct gcagaagaag | 120 |
| ctggaggagc tggaacttga cgagcagcag aagaagcggc tggaagcctt tctcacccag | 180 |
| aaagccaagg tcggcgaact caaagacgat gacttcgaaa ggatctcaga gctgggcgcg | 240 |
| ggcaacggcg gggtggtcac caaagtccag cacagaccct cgggcctcat catggccagg | 300 |
| aagctgatcc accttgagat caagccggcc atccggaacc agatcatccg cgagctgcag | 360 |
| gtcctgcacg aatgcaactc gccgtacatc gtgggcttct acggggcctt ctacagtgac | 420 |
| ggggagatca gcatttgcat ggaacacatg gacgcggct ccctggacca ggtgctgaaa | 480 |
| gaggccaaga ggattcccga ggagatcctg ggaaagtca gcatcgcggt tctccggggc | 540 |
| ttggcgtacc tccgagagaa gcaccagatc atgcaccgag atgtgaagcc ctccaacatc | 600 |
| ctcgtgaact ctagagggga gatcaagctg tgtgacttcg gggtgagcgg ccagctcatc | 660 |

```
gactccatgg ccaactcctt cgtgggcacg cgctcctaca tggctccgga gcggttgcag      720
ggcacacatt actcggtgca gtcggacatc tggagcatgg gcctgtccct ggtggagctg      780
gccgtcggaa ggtaccccat cccccgccc gacgccaaag agctggaggc catctttggc      840
cggcccgtgg tcgacgggga agaaggagag cctcacagca tctcgcctcg ccgaggccc      900 cccgggcgcc ccgtcagcgg tcacgggatg gatagccggc ctgccatggc catctttgaa      960
ctcctggact atattgtgaa cgagccacct cctaagctgc ccaacggtgt gttcaccccc     1020
gacttccagg agtttgtcaa taaatgcctc atcaagaacc cagcggagcg ggcggacctg     1080
aagatgctca caaaccacac cttcatcaag cggtccgagg tggaagaagt ggattttgcc     1140
ggctggttgt gtaaaaccct gcggctgaac cagcccggca cccacgcg caccgccgtg     1200 tga                                                                  1203

<210> SEQ ID NO 18
<211> LENGTH: 957
<212> TYPE: DNA
<213> ORGANISM: Homo sapiens

<400> SEQUENCE: 18
atgtccaagc caccgcacc caaccccaca ccccccgga acctggactc ccggaccttc        60
atcaccattg gagacagaaa ctttgaggtg gaggctgatg acttggtgac catctcagaa      120
ctgggccgtg gagcctatgg ggtggtagag aaggtgcggc acgcccagag cggcaccatc      180
atggccgtga agcggatccg ggccaccgtg aactcacagg agcagaagcg gctgctcatg      240
gacctggaca tcaacatgcg cacggtcgac tgtttctaca ctgtcacctt ctacggggca      300
ctattcagag agggagacgt gtggatctgc atggagctca tggacacatc cttggacaag      360
ttctaccgga aggtgctgga taaaaacatg acaattccag aggacatcct tggggagatt      420
gctgtgtcta tcgtgcgggc cctggagcat ctgcacagca gctgtcggt gatccacaga      480 gatgtgaagc cctccaatgt ccttatcaac aaggagggcc atgtgaagat gtgtgacttt      540
ggcatcagtg gctacttggt ggactctgtg ccaagacga tggatgccgg ctgcaagccc      600
tacatggccc ctgagaggat caacccagag ctgaaccaga agggctacaa tgtcaagtcc      660
gacgtctgga gcctgggcat caccatgatt gagatggcca tcctgcggtt cccttacgag      720 tcctgggga ccccgttcca gcagctgaag caggtggtgg aggagccgtc cccccagctc      780
ccagccgacc gtttctcccc cgagtttgtg gacttcactg ctcagtgcct gaggaagaac      840
cccgcagagc gtatgagcta cctggagctg atggagcacc ccttcttcac cttgcacaaa      900
accaagaaga cggacattgc tgccttcgtg aaggagatcc tgggagaaga ctcatag       957

<210> SEQ ID NO 19
<211> LENGTH: 1005
<212> TYPE: DNA
<213> ORGANISM: Homo sapiens

<400> SEQUENCE: 19
atgtctcagt cgaaaggcaa gaagcgaaac cctggcctta aaattccaaa agaagcattt       60
gaacaacctc agaccagttc cacaccacct cgagatttag actccaaggc ttgcatttct      120
attggaaatc agaactttga ggtgaaggca gatgacctgg agcctataat ggaactggga      180
cgaggtgcgt acgggtggt ggagaagatg cggcacgtgc ccagcgggca gatcatggca      240
gtgaagcgga tccgagccac agtaaatagc caggaacaga aacggctact gatggatttg      300
```

-continued

| | |
|---|---|
| gatatttcca tgaggacggt ggactgtcca ttcactgtca ccttttatgg cgcactgttt | 360 |
| cgggagggtg atgtgtggat ctgcatggag ctcatggata tcatcactag ataaattctac | 420 |
| aaacaagtta ttgataaagg ccagacaatt ccagaggaca tcttagggaa aatagcagtt | 480 |
| tctattgtaa aagcattaga acatttacat agtaagctgt ctgtcattca cagagacgtc | 540 |
| aagccttcta atgtactcat caatgctctc ggtcaagtga agatgtgcga ttttggaatc | 600 |
| agtggctact tggtggactc tgttgctaaa acaattgatg caggttgcaa accatacatg | 660 |
| gccccctgaaa gaataaaccc agagctcaac agaagggat acagtgtgaa gtctgacatt | 720 |
| tggagtctgg gcatcacgat gattgagttg gccatccttc gatttcccta tgattcatgg | 780 |
| ggaactccat ttcagcagct caaacaggtg gtagaggagc catcgccaca actcccagca | 840 |
| gacaagttct ctgcagagtt tgttgacttt acctcacagt gcttaaagaa gaattccaaa | 900 |
| gaacggccta catacccaga gctaatgcaa catccatttt tcaccctaca tgaatccaaa | 960 |
| ggaacagatg tggcatcttt tgtaaaactg attcttggag actaa | 1005 |

<210> SEQ ID NO 20
<211> LENGTH: 4539
<212> TYPE: DNA
<213> ORGANISM: Homo sapiens

<400> SEQUENCE: 20

| | |
|---|---|
| atggcggcgg cggcggggaa tcgcgcctcg tcgtcgggat cccgggcgc cagggctacg | 60 |
| agccctgagg caggcggcgg cggaggagcc ctcaaggcga gcagcgcgcc cgcggctgcc | 120 |
| gcgggactgc tgcgggaggc gggcagcggg ggccgcgagc gggcggactg gcggcggcgg | 180 |
| cagctgcgca aagtgcggag tgtggagctg gaccagctgc ctgagcagcc gctcttcctt | 240 |
| gccgcctcac cgccggcctc ctcgacttcc ccgtcgccgg agcccgcgga cgcagcgggg | 300 |
| agtgggaccg gcttccagcc tgtggcggtg ccgccgcccc acggagccgc gagccgcggc | 360 |
| ggcgcccacc ttaccgagtc ggtggcggcg ccggacagcg cgcctcgag tcccgcagcg | 420 |
| gccgagcccg ggagaagcg ggcgcccgcc gccgagccgt ctcctgcagc ggccccccgcc | 480 |
| ggtcgtgaga tggagaataa agaaactctc aaagggttgc acaagatgga tgatcgtcca | 540 |
| gaggaacgaa tgatcaggga gaaactgaag gcaacctgta tgccagcctg gaagcacgaa | 600 |
| tggttggaaa ggagaaatag gcgagggcct gtggtggtaa aaccaatccc agttaaagga | 660 |
| gatggatctg aaatgaatca cttagcagct gagtctccag agaggtcca ggcaagtgcg | 720 |
| gcttcaccag cttccaaagg ccgacgcagt ccttctcctg caactcccc atcaggtcgc | 780 |
| acagtgaaat cagaatctcc aggagtaagg agaaaaagag tttccccagt gccttttcag | 840 |
| agtggcagaa tcacaccacc ccgaagagcc ccttcaccag atggcttctc accatatagc | 900 |
| cctgaggaaa caaaccgccg tgttaacaaa gtgatgcggg ccagactgta cttactgcag | 960 |
| cagatagggc ctaactcttt cctgattgga ggagacagcc cagacaataa ataccgggtg | 1020 |
| tttattgggc ctcagaactg cagctgtgca cgtggaacat tctgtattca tctgctattt | 1080 |
| gtgatgctcc gggtgtttca actagaacct tcagacccaa tgttatggag aaaaactta | 1140 |
| aagaattttg aggttgagag tttgttccag aaatatcaca gtaggcgtag ctcaaggatc | 1200 |
| aaagctccat ctcgtaacac catccagaag tttgtttcac gcatgtcaaa ttctcataca | 1260 |
| ttgtcatcat ctagtacttc tacgtctagt tcagaaaaca gcataaagga tgaagaggaa | 1320 |
| cagatgtgtc ctatttgctt gttgggcatg cttgatgaag aaagtcttac agtgtgtgaa | 1380 |
| gacggctgca ggaacaagct gcaccaccac tgcatgtcaa tttgggcaga agagtgtaga | 1440 |

```
agaaatagag aacctttaat atgtcccctt tgtagatcta agtggagatc tcatgatttc    1500
tacagccacg agttgtcaag tcctgtggat tccccttctt ccctcagagc tgcacagcag    1560
caaaccgtac agcagcagcc tttggctgga tcacgaagga atcaagagag caattttaac    1620
cttactcatt atggaactca gcaaatccct cctgcttaca aagatttagc tgagccatgg    1680
attcaggtgt ttggaatgga actcgttggc tgcttatttt ctagaaactg aatgtgaga    1740 gagatggccc tcaggcgtct ttcccatgat gtcagtgggg ccctgctgtt ggcaaatggg    1800
gagagcactg gaaattctgg gggcagcagt ggaagcagcc cgagtggggg agccaccagt    1860
gggtcttccc agaccagtat ctcaggagat gtggtggagg catgctgcag cgttctgtca    1920
atggtctgtg ctgaccctgt ctacaaagtg tacgttgctg cttaaaaac attgagagcc      1980 atgctggtat atactccttg ccacagttta gcggaaagaa tcaaacttca gagacttctc    2040
cagccagttg tagacaccat cctagtcaaa tgtgcagatg ccaatagccg cacaagtcag    2100
ctgtccatat caacactgtt ggaactgtgc aaaggccaag caggagagtt ggcagttggc    2160
agagaaatac taaaagctgg atccattggt attggtggtg ttgattatgt cttaaattgt    2220
attcttggaa accaaactga atcaaacaat tggcaagaac ttcttggccg cctttgtctt    2280
atagatagac tgttgttgga atttcctgct gaattttatc ctcatattgt cagtactgat    2340
gtttcacaag ctgagcctgt tgaaatcagg tataagaagc tgctgtccct cttaaccttt    2400
gctttgcagt ccattgataa ttcccactca atggttggca aactttccag aaggatctac    2460
ttgagttctg caagaatggt tactacagta ccccatgtgt tttcaaaact gttagaaatg    2520
ctgagtgttt ccagttccac tcacttcacc aggatgcgtc gccgtttgat ggctattgca    2580
gatgaggtgg aaattgccga agccatccag ttgggcgtag aagacacttt ggatggtcaa    2640
caggacagct tcttgcaggc atctgttccc aacaactatc tggaaccac agagaacagt      2700 tcccctgagt gcacagtcca tttagagaaa actggaaaag gattatgtgc tacaaaattg    2760
agtgccagtt cagaggacat ttctgagaga ctggccagca tttcagtagg accttctagt    2820
tcaacaacaa caacaacaac aacaacagag caaccaaagc caatggttca aacaaaggc      2880 agaccccaca gtcagtgttt gaactcctct cctttatctc atcattccca attaatgttt    2940
ccagccttgt caaccccttc ttcttctacc ccatctgtac cagctggcac tgcaacagat    3000
gtctctaagc atagacttca gggattcatt ccctgcagaa taccttctgc atctcctcaa    3060
acacagcgca agttttctct acaattccac agaaactgtc ctgaaaacaa agactcagat    3120
aaactttccc cagtctttac tcagtcaaga cccttgccct ccagtaacat acacaggcca    3180
aagccatcta gacctacccc aggtaataca agtaaacagg gagatccctc aaaaaatagc    3240
atgacacttg atctgaacag tagttccaaa tgtgatgaca gctttggctg tagcagcaat    3300
agtagtaatg ctgttatacc cagtgacgag acagtgttca ccccagtaga ggagaaatgc    3360
agattagatg tcaatacaga gctcaactcc agtattgagg accttcttga agcatctatg    3420
ccttcaagtg atacaacagt aactttttaag tcagaagttg ctgtcctgtc tcctgaaaag    3480
gctgaaaatg atgataccta caaagatgat gtgaatcata atcaaaagtg caaagagaag    3540
atggaagctg aagaagaaga agctttagca attgccatgg caatgtcagc gtctcaggat    3600
gccctcccca tagttcctca gctgcaggtt gaaaatggag aagatatcat cattattcaa    3660
caggatacac cagagactct accaggacat accaaagcaa acaaccgta tagaagagac      3720 actgaatggc tgaaaggtca acagataggc cttggagcat tttcttcttg ttatcaggct    3780
```

-continued

| | |
|---|---|
| caagatgtgg gaactggaac tttaatggct gttaaacagg tgacttatgt cagaaacaca | 3840 |
| tcttctgagc aagaagaagt agtagaagca ctaagagaag agataagaat gatgagccat | 3900 |
| ctgaatcatc caaacatcat taggatgttg ggagccacgt gtgagaagag caattacaat | 3960 |
| ctcttcattg aatggatggc aggggatcg gtggctcatt tgctgagtaa atatggagcc | 4020 |
| ttcaaagaat cagtagttat taactacact gaacagttac tccgtggcct ttcgtatctc | 4080 |
| catgaaaacc aaatcattca cagagatgtc aaggtgcca atttgctaat tgacagcact | 4140 |
| ggtcagagac taagaattgc agattttgga gctgcagcca ggttggcatc aaaaggaact | 4200 |
| ggtgcaggag agtttcaggg acaattactg gggacaattg catttatggc acctgaggta | 4260 |
| ctaagaggtc aacagtatgg aaggagctgt gatgtatgga gtgttggctg tgctattata | 4320 |
| gaaatggctt gtgcaaaacc accatggaat gcagaaaaac actccaatca tcttgctttg | 4380 |
| atatttaaga ttgctagtgc aactactgct ccatcgatcc cttcacattt gtctcctggt | 4440 |
| ttacgagatg tggctcttcg ttgtttagaa cttcaacctc aggacagacc tccatcaaga | 4500 |
| gagctactga agcatccagt ctttcgtact acatggtag | 4539 |

<210> SEQ ID NO 21
<211> LENGTH: 1974
<212> TYPE: DNA
<213> ORGANISM: Homo sapiens

<400> SEQUENCE: 21

| | |
|---|---|
| atggacgaac aggaggcatt gaactcaatc atgaacgatc tggtggccct ccagatgaac | 60 |
| cgacgtcacc ggatgcctgg atatgagacc atgaagaaca aagacacagg tcactcaaat | 120 |
| aggcagaaaa aacacaacag cagcagctca gcccttctga acagccccac agtaacaaca | 180 |
| agctcatgtg caggggccag tgagaaaaag aaattttga gtgacgtcag aatcaagttc | 240 |
| gagcacaacg gggagaggcg aattatagcg ttcagccggc ctgtgaaata tgaagatgtg | 300 |
| gagcacaagg tgacaacagt atttggacaa cctcttgatc tacattacat gaacaatgag | 360 |
| ctctccatcc tgctgaaaaa ccaagatgat cttgataaag caattgacat tttagataga | 420 |
| agctcaagca tgaaaagcct taggatattg ctgttgtccc aggacagaaa ccataacagt | 480 |
| tcctctcccc actctggggt gtccagacag gtgcggatca aggcttccca gtccgcaggg | 540 |
| gatataaata ctatctacca gccccccgag cccagaagca ggcacctctc tgtcagctcc | 600 |
| cagaaccctg gccgaagctc acctcccccct ggctatgttc ctgagcggca gcagcacatt | 660 |
| gcccggcagg ggtcctacac cagcatcaac agtgaggggg agttcatccc agagaccagc | 720 |
| gagcagtgca tgctggatcc cctgagcagt gcagaaaatt ccttgtctgg aagctgccaa | 780 |
| tccttggaca ggtcagcaga cagcccatcc ttccggaaat cacgaatgtc ccgtgcccag | 840 |
| agcttccctg acaacagaca ggaatactca gatcgggaaa ctcagcttta tgacaaaggg | 900 |
| gtcaaaggtg gaacctaccc ccggcgctac cacgtgtctg tgcaccacaa ggactacagt | 960 |
| gatggcagaa gaacatttcc ccgaatacgg cgtcatcaag caacttgtt cacctgggtg | 1020 |
| ccctccagcc gctccctgag cacaaatggc gagaacatgg tctggctgt gcaatacctg | 1080 |
| gaccccgtg gcgcctgcg gagtgcggac agcgagaatg ccctctctgt gcaggagagg | 1140 |
| aatgtgccaa ccaagtctcc cagtgccccc atcaactggc gccggggaaa gctcctgggc | 1200 |
| cagggtgcct cggcagggt ctatttgtgc tatgacgtgg acacgggacg tgaacttgct | 1260 |
| tccaagcagg tccaatttga tccagacagt cctgagacaa gcaaggaggt gagtgctctg | 1320 |
| gagtgcgaga tccagttgct aaagaacttg cagcatgagc gcatcgtgca gtactatgc | 1380 |

| | |
|---|---|
| tgtctgcggg accgcgctga gaagaccctg accatcttca tggagtacat gccaggggc | 1440 |
| tcggtgaaag accagttgaa ggcttacggt gctctgacag agagcgtgac ccgaaagtac | 1500 |
| acgcggcaga tcctggaggg catgtcctac ctgcacagca acatgattgt tcaccgggac | 1560 |
| attaagggag ccaacatcct ccgagactct gctgggaatg taaagctggg ggactttggg | 1620 |
| gccagcaaac gcctgcagac gatctgtatg tcggggacgg gcatgcgctc cgtcactggc | 1680 |
| acaccctact ggatgagccc tgaggtgatc agcggcgagg gctatggaag gaaagcagac | 1740 |
| gtgtggagcc tgggctgcac tgtggtggag atgctgacag agaaaccacc gtgggcagag | 1800 |
| tatgaagcta tggccgccat cttcaagatt gccaccagc ccaccaatcc tcagctgccc | 1860 |
| tcccacatct ctgaacatgg ccgggacttc ctgaggcgca ttttgtgga ggctcgccag | 1920 |
| agaccttcag ctgaggagct gctcacacac cactttgcac agctcatgta ctga | 1974 |

<210> SEQ ID NO 22
<211> LENGTH: 4826
<212> TYPE: DNA
<213> ORGANISM: Homo sapiens

<400> SEQUENCE: 22

| | |
|---|---|
| atgagagaag ccgctgccgc gctggtccct cctcccgcct ttgccgtcac gcctgccgcc | 60 |
| gccatggagg agccgccgcc accgccgccg ccgccaccac cgccaccgga acccgagacc | 120 |
| gagtcagaac ccgagtgctg cttggcggcg aggcaagagg gcacattggg agattcagct | 180 |
| tgcaagagtc ctgaatctga tctagaagac ttctccgatg aaacaaatac agagaatctt | 240 |
| tatggtacct ctcccccag cacacctcga cagatgaaac gcatgtcaac caaacatcag | 300 |
| aggaataatg tggggaggcc agccagtcgg tctaatttga agaaaaaat gaatgcacca | 360 |
| aatcagcctc cacataaaga cactggaaaa acagtggaga atgtggaaga atacagctat | 420 |
| aagcaggaga aaaagatccg agcagctctt gaacaacag agcgtgatca taaaaaaat | 480 |
| gtacagtgct cattcatgtt agactcagtg ggtggatctt tgccaaaaaa atcaattcca | 540 |
| gatgtggatc tcaataagcc ttacctcagc cttggctgta gcaatgctaa gcttccagta | 600 |
| tctgtgccca tgcctatagc cagacctgca cgccagactt ctaggactga ctgtccagca | 660 |
| gatcgtttaa agttttttga aactttacga cttttgctaa agcttacctc agtctcaaag | 720 |
| aaaaaagaca gggagcaaag aggacaagaa aatacgtctg gtttctggct taaccgatct | 780 |
| aacgaactga tctggttaga gctacaagcc tggcatgcag acggacaat taacgaccag | 840 |
| gacttcttt tatatacagc ccgtcaagcc atcccagata ttattaatga aatccttact | 900 |
| ttcaaagtcg actatgggag cttcgccttt gttagagata gagctggttt taatggtact | 960 |
| tcagtagaag ggcagtgcaa agccactcct ggaacaaaga ttgtaggtta ctcaacacat | 1020 |
| catgagcatc tccaacgcca gagggtctca tttgagcagg taaaacggat aatggagctg | 1080 |
| ctagagtaca tagaagcact ttatccatca ttgcaggctc ttcagaagga ctatgaaaaa | 1140 |
| tatgctgcaa aagacttcca ggacagggtg caggcactct gtttgtggtt aaacatcaca | 1200 |
| aaagacttaa atcagaaatt aaggattatg ggcactgttt tggcatcaa gaatttatca | 1260 |
| gacattggct ggccagtgtt tgaaatccct tcccctcgac catccaaagg taatgagccg | 1320 |
| gagtatgagg gtgatgacac agaaggagaa ttaaaggagt tggaaagtag tacggatgag | 1380 |
| agtgaagaag aacaaatctc tgatcctagg gtaccgaaaa tcagacagcc catagataac | 1440 |
| agcttcgaca tccagtcgcg ggactgcata tccaagaagc ttgagaggct cgaatctgag | 1500 |

```
gatgattctc ttggctgggg agcaccagac tggagcacag aagcaggctt tagtagacat    1560
tgtctgactt ctatttatag accatttgta gacaaagcac tgaagcagat ggggttaaga    1620
aagttaattt taagacttca caagctaatg gatggttcct tgcaaagggc acgtatagca    1680
ttggtaaaga acgatcgtcc agtggagttt tctgaatttc cagatcccat gtggggttca    1740
gattatgtgc agttgtcaag gacaccacct tcatctgagg agaaatgcag tgctgtgtcg    1800
tgggaggagc tgaaggccat ggatttacct tcattcgaac ctgccttcct agttctctgc    1860
cgagtccttc tgaatgtcat acatgagtgt ctgaagttaa gattggagca gagacctgct    1920
ggagaaccat ctctcttgag tattaagcag ctggtgagag agtgtaagga ggtcctgaag    1980
ggcggcctgc tgatgaagca gtactaccag ttcatgctgc aggaggttct ggaggacttg    2040
gagaagcccg actgcaacat tgacgctttt gaagaggatc tacataaaat gcttatggtg    2100
tattttgatt acatgagaag ctggatccaa atgctacagc aattacctca agcatcgcat    2160
agtttaaaaa atctgttaga agaagaatgg aatttcacca agaaataac tcattacata     2220 cggggaggag aagcacaggc cgggaagctt ttctgtgaca ttgcaggaat gctgctgaaa    2280
tctacaggaa gttttttaga atttggctta caggagagct gtgctgaatt ttggactagt    2340
gcggatgaca gcagtgcttc cgacgaaatc aggaggtctg ttatagagat cagtcgagcc    2400
ctgaaggagc tcttccatga agccagagaa agggcttcca aagcacttgg atttgctaaa    2460
atgttgaaga aggacctgga aatagcagca gaattcaggc tttcagcccc agttagagac    2520
ctcctggatg ttctgaaatc aaaacagtat gtcaaggtgc aaattcctgg gttagaaaac    2580
ttgcaaatgt ttgttccaga cactcttgct gaggagaaga gtattatttt gcagttactc    2640
aatgcagctg caggaaagga ctgttcaaaa gattcagatg acgtactcat cgatgcctat    2700
ctgcttctga ccaagcacgg tgatcgagcc cgtgattcag aggacagctg ggcacctgg    2760 gaggcacagc ctgtcaaagt cgtgcctcag gtggagactg ttgacaccct gagaagcatg    2820
caggtggata atcttttact agttgtcatg cagtctgcgc atctcacaat tcagagaaaa    2880
gctttccagc agtccattga gggacttatg actctgtgcc aggagcagac atccagtcag    2940
ccggtcatcg ccaaagcttt gcagcagctg aagaatgatg cattggagct atgcaacagg    3000
ataagcaatg ccattgaccg cgtggaccac atgttcacat cagaatttga tgctgaggtt    3060
gatgaatctg aatctgtcac cttgcaacag tactaccgag aagcaatgat tcaggggtac    3120
aattttggat ttgagtatca taaagaagtt gttcgtttga tgtctgggga gtttagacag    3180
aagataggag acaaatatat aagctttgcc cggaagtgga tgaattatgt cctgactaaa    3240
tgtgagagtg gtagaggtac aagacccagg tgggcgactc aaggatttga ttttctacaa    3300
gcaattgaac ctgcctttat ttcagcttta ccagaagatg acttcttgag tttacaagcc    3360
ttgatgaatg aatgcattgg ccatgtcata ggaaaaccac acagtcctgt tacaggtttg    3420
taccttgcca ttcatcggaa cagccccgt cctatgaagg tacctcgatg ccatagtgac     3480
cctcctaacc cacacctcat tatccccact ccagagggat tcagcactcg gagcatgcct    3540
tccgacgcgc ggagccatgg cagccctgct gctgctgctg ctgctgctgc tgctgctgtt    3600
gctgccagtc ggcccagccc ctctggtggt gactctgtgc tgcccaaatc catcagcagt    3660
gcccatgata ccaggggttc cagcgttcct gaaaatgatc gattggcttc catagctgct    3720
gaattgcagt ttaggtccct gagtcgtcac tcaagcccca cggaggagcg agatgaacca    3780
gcatatccaa gaggagattc aagtgggtcc acaagaagaa gttgggaact tcggacacta    3840
atcagccaga gtaaagatac tgcttctaaa ctaggaccca tagaagctat ccagaagtca    3900
```

-continued

```
gtccgattgt tgaagaaaa gaggtaccga gaaatgagga gaaagaatat cattggtcaa    3960
gtttgtgata cgcctaagtc ctatgataat gttatgcacg ttggcttgag gaaggtgacc    4020
ttcaaatggc aaagaggaaa caaaattgga gaaggccagt atgggaaggt gtacacctgc    4080
atcagcgtcg acaccgggga gctgatggcc atgaaagaga ttcgatttca acctaatgac    4140
cataagacta tcaaggaaac tgcagacgaa ttgaaaatat tcgaaggcat caaacacccc    4200
aatctggttc ggtattttgg tgtggagctc catagaaag aaatgtacat cttcatggag    4260
tactgcgatg aggggacttt agaagaggtg tcaaggctgg gacttcagga acatgtgatt    4320
aggctgtatt caaagcagat caccattgcg atcaacgtcc tccatgagca tggcatagtc    4380
caccgtgaca ttaaaggtgc caatatcttc cttacctcat ctggattaat caaactggga    4440
gattttggat gttcagtaaa gctcaaaaac aatgcccaga ccatgcctgg tgaagtgaac    4500
agcaccctgg ggacagcagc atacatggca cctgaagtca tcactcgtgc caaggagag    4560 ggccatgggc gtgcggccga catctggagt ctggggtgtg ttgtcataga gatggtgact    4620
ggcaagaggc cttggcatga gtatgagcac aactttcaaa ttatgtataa agtggggatg    4680
ggacataagc caccaatccc tgaaagatta agccctgaag gaaaggactt cctttctcac    4740
tgccttgaga gtgacccaaa gatgagatgg accgccagcc agctcctcga ccattcgttt    4800
gtcaaggttt gcacagatga agaatg                                         4826
```

<210> SEQ ID NO 23
<211> LENGTH: 3867
<212> TYPE: DNA
<213> ORGANISM: Homo sapiens

<400> SEQUENCE: 23

```
atggcggggc cgtgtccccg gtccggggcg gagcgcgccg gcagctgctg gcaggacccg     60
ctggccgtgg cgctgagccg gggcggcag ctcgcggcgc cccgggccg gggctgcgcg    120 cggagccggc cgctcagcgt ggtctacgtg ctgacccggg agccgcagcc cgggctcgag    180 cctcggagg gaaccgaggc ggagccgctg cccctgcgct gcctgcgcga ggcttgcgcg    240
caggtccccc ggccgcggcc gccccgcag ctgcgcagcc tgcccttcgg gacgctggag    300
ctaggcgaca ccgcggctct ggatgccttc tacaacgcgg atgtggtggt gctggaggtg    360
agcagctcgc tggtacagcc ctccctgttc taccaccttg gtgtgcgtga gagcttcagc    420
atgaccaaca atgtgctcct ctgctcccag gccgacctcc ctgacctgca ggccctgcgg    480
gaggatgttt tccagaagaa ctcggattgc gttggcagct acacactgat ccctatgtg    540 gtgacggcca ctggtcgggt gctgtgtggt gatgcaggcc ttctgcgggg cctggctgat    600
gggctggtac aggctggagt ggggaccgag gccctgctca ctccctggt gggccggctt    660 gcccgcctgc tggaggccac acccacagac tcttgtggct atttccggga gaccattcgg    720
cgggacatcc ggcaggcgcg ggagcggttc agtgggccac agctgcggca ggagctggct    780
cgcctgcagc ggagactgga cagcgtggag ctgctgagcc ccgacatcat catgaacttg    840
ctgctctcct accgcgatgt gcaggactac tcggccatca ttgagctggt ggagacgctg    900
caggccttgc ccacctgtga tgtggccgag cagcataatg tctgcttcca ctacactttt    960
gccctcaacc ggaggaacag gcctggggac cgggcgaagg ccctgtctgt gctgctgccg    1020
ctggtacagc ttgagggctc tgtggcgccc gatctgtact gcatgtgtgg ccgtatctac    1080
aaggacatgt tcttcagctc gggtttccag gatgctgggc accggagca ggcctatcac    1140
```

```
tggtatcgca aggcttttga cgtagagccc agccttcact caggcatcaa tgcagctgtg   1200
ctcctcattg ctgccgggca gcactttgag gattccaaag agctccggct aataggcatg   1260
aagctgggct gcctgctggc ccgcaaaggc tgcgtggaga agatgcagta ttactgggat   1320
gtgggtttct acctgggagc ccagatcctc gccaatgacc ccacccaggt ggtgctggct   1380
gcagagcagc tgtataagct caatgccccc atatggtacc tggtgtccgt gatggagacc   1440
ttcctgctct accagcactt caggcccacg ccagagcccc tggagggcc accacgccgt   1500 gcccacttct ggctccactt cttgctacag tcctgccaac cattcaagac agcctgtgcc   1560
cagggcgacc agtgcttggt gctggtcctg gagatgaaca aggtgctgct gcctgcaaag   1620
ctcgaggttc ggggtactga cccagtaagc acagtgaccc tgagcctgct ggagcctgag   1680
acccaggaca ttccctccag ctggaccttc ccagtcgcct ccatatgcgg agtcagcgcc   1740
tcaaagcgcg acgagcgctg ctgcttcctc tatgcactcc ccccggctca ggacgtccag   1800
ctgtgcttcc ccagcgtagg gcactgccag tggttctgcg gcctgatcca ggcctgggtg   1860
acgaacccgg attccacggc gcccgcggag gaggcggagg gcgcggggga gatgttggag   1920
tttgattatg agtacacgga gacgggcgag cggctggtgc tgggcaaggg cacgtatggg   1980
gtggtgtacg cgggccgcga tcgccacacg agggtgcgca tcgccatcaa ggagatcccg   2040
gagcgggaca gcaggttctc tcagcccctg catgaagaga tcgctcttca cagacgcctg   2100
cgccacaaga acatagtgcg ctatctgggc tcagctagcc agggcggcta ccttaagatc   2160
ttcatggagg aagtgcctgg aggcagcctg tcctccttgc tgcggtcggt gtggggaccc   2220
ctgaaggaca acgagagcac catcagtttc tacacccgcc agatcctgca gggacttggc   2280
tacttgcacg acaaccacat cgtgcacagg gacataaaag gggacaatgt gctgatcaac   2340
accttcagtg ggctgctcaa gatttctgac ttcggcacct ccaagcggct ggcaggcatc   2400
acaccttgca ctgagacctt cacaggaact ctgcagtata tggccccaga aatcattgac   2460
cagggcccac gcgggtatgg gaaagcagct gacatctggt cactgggctg cactgtcatt   2520
gagatggcca caggtcgccc ccccttccac gagctcggga gcccacaggc tgccatgttt   2580
caggtgggta tgtacaaggt ccatccgcca atgcccagct ctctgtcggc cgaggcccaa   2640
gcctttctcc tccgaacttt tgagccagac ccccgcctcc gagccagcgc cagacactg   2700 ctggggacc ccttcctgca gcctgggaaa aggagccgca gccccagctc cccacgacat   2760
gctccacggc cctcagatgc ccttctgcc agtcccactc cttcagccaa ctcaaccacc   2820
cagtctcaga cattcccgtg ccctcaggca ccctctcagc acccaccag ccccccgaag   2880 cgctgcctca gttatggggg caccagccag ctccgggtgc ccgaggagcc tgcggccgag   2940
gagcctgcgt ctccggagga gagttcgggg ctgagcctgc tgcaccagga gagcaagcgt   3000
cgggccatgc tggccgcagt attggagcag gagctgccag cgctggcgga gaatctgcac   3060
caggagcaga agcaagagca gggggcccgt ctgggcagaa accatgtgga agagctgctg   3120
cgctgcctcg gggcacacat ccacactccc aaccgccggc agctcgccca ggagctgcgg   3180
gcgctgcaag acggctgag ggccagggc cttgggcctg cgcttctgca cagaccgctg   3240
tttgccttcc cggatgcggt gaagcagatc ctccgcaagc gccagatccg tccacactgg   3300
atgttcgttc tggactcact gctcagccgt gctgtgcggg cagccctggg tgtgctagga   3360
ccggaggtgg agaaggaggc ggtctccacc g aggtcagagg agctgagtaa tgaaggggac   3420
tcccagcaga gcccaggcca gcagagcccg cttccggtgg agcccgagca gggccccgct   3480
cctctgatgg tgcagctgag cctcttgagg gcagagactg atcggctgcg cgaaatcctg   3540
```

```
gcggggaagg aacgggagta ccaggccctg gtgcagcggg ctctacacgg gctgaatgag    3600
gaagcccgga cctatgtcct ggccccagag cctccaactg ctctttcaac ggaccagggc    3660
ctggtgcagt ggctacagga actgaatgtg gattcaggca ccatccaaat gctgttgaac    3720
catagcttca ccctccacac tctgctcacc tatgccactc gagatgacct catctacacc    3780
cgcatcaggg gagggatggt atgccgcatc tggagggcca tcttggcaca gcgagcagga    3840
tccacaccag tcacctctgg accctga                                        3867

<210> SEQ ID NO 24
<211> LENGTH: 1740
<212> TYPE: DNA
<213> ORGANISM: Homo sapiens

<400> SEQUENCE: 24
atgtctacag cctctgccgc ctcctcctcc tcctcgtctt cggccggtga gatgatcgaa      60
gccccttccc aggtcctcaa ctttgaagag atcgactaca aggagatcga ggtggaagag     120
gttgttggaa gaggagcctt tggagttgtt tgcaaagcta agtggagagc aaaagatgtt     180
gctattaaac aaatagaaag tgaatctgag aggaaagcgt ttattgtaga gcttcggcag     240
ttatcccgtg tgaaccatcc taatattgta aagctttatg gagcctgctt gaatccagtg     300
tgtcttgtga tggaatatgc tgaaggggggc tctttatata atgtgctgca tggtgctgaa     360
ccattgccat attatactgc tgcccacgca atgagttggt gtttacagtg ttcccaagga     420
gtggcttatc ttcacagcat gcaacccaaa gcgctaattc acagggacct gaaaccacca     480
aacttactgc tggttgcagg ggggacagtt ctaaaaattt gtgattttgg tacagcctgt     540
gacattcaga cacacatgac caataacaag gggagtgctg cttggatggc acctgaagtt     600
tttgaaggta gtaattacag tgaaaaatgt gacgtcttca gctggggtat tattctttgg     660
gaagtgataa cgcgtcggaa acccttttgat gagattggtg gcccagcttt ccgaatcatg     720
tgggctgttc ataatggtac tcgaccacca ctgataaaaa atttacctaa gcccattgag     780
agcctgatga ctcgttgttg gtctaaagat ccttcccagc gccctcaat ggaggaaatt     840 gtgaaaataa tgactcactt gatgcggtac tttccaggag cagatgagcc attacagtat     900
ccttgtcagt attcagatga aggacagagc aactctgcca ccagtacagg ctcattcatg     960
gacattgctt ctcaaaatac gagtaacaaa agtgacacta tatgagca agttcctgcc    1020 acaaatgata ctattaagcg cttagaatca aaattgttga aaaatcaggc aaagcaacag    1080
agtgaatctg gacgtttaag cttgggagcc tcccgtggga gcagtgtgga gagcttgccc    1140
ccaacctctg agggcaagag gatgagtgct gacatgtctg aaatagaagc taggatcgcc    1200
gcaaccacag caacggaca gccaagacgt agatccatcc aagacttgac tgtaactgga    1260
acagaacctg gtcaggtgag cagtaggtca tccagtccca gtgtcagaat gattactacc    1320
tcaggaccaa cctcagaaaa gccaactcga agtcatccat ggaccctga tgattccaca    1380 gataccaatg gatcagataa ctccatccca atggcttatc ttacactgga tcaccaacta    1440
cagcctctag caccgtgccc aaactccaaa gaatctatgg cagtgtttga acagcattgt    1500
aaaatggcac aagaatatat gaaagttcaa acagaaattg cattgttatt acagagaaag    1560
caagaactag ttgcagaact ggaccaggat gaaaaggacc agcaaaatac atctcgcctg    1620
gtacaggaac ataaaagct tttagatgaa acaaaagcc tttctactta ctaccagcaa    1680
tgcaaaaaac aactagaggt catcagaagt cagcagcaga aacgacaagg cacttcatga    1740
```

<210> SEQ ID NO 25
<211> LENGTH: 1113
<212> TYPE: DNA
<213> ORGANISM: Homo sapiens

<400> SEQUENCE: 25

| | | | | | |
|---|---|---|---|---|---|
| atgctgtcca | actcccaggg | ccagagcccg | ccggtgccgt | tccccgcccc | ggccccgccg | 60 |
| ccgcagcccc | ccacccctgc | cctgccgcac | ccccggcgc | agccgccgcc | gccgcccccg | 120 |
| cagcagttcc | cgcagttcca | cgtcaagtcc | ggcctgcaga | tcaagaagaa | cgccatcatc | 180 |
| gatgactaca | aggtcaccag | ccaggtcctg | gggctgggca | tcaacggcaa | agttttgcag | 240 |
| atcttcaaca | gaggaccca | ggagaaattc | gccctcaaaa | tgcttcagga | ctgccccaag | 300 |
| gcccgcaggg | aggtggagct | gcactggcgg | gcctcccagt | gcccgcacat | cgtacggatc | 360 |
| gtggatgtgt | acgagaatct | gtacgcaggg | aggaagtgcc | tgctgattgt | catggaatgt | 420 |
| ttggacggtg | agaactctt | tagccgaatc | caggatcgag | agaccaggc | attcacagaa | 480 |
| agagaagcat | ccgaaatcat | gaagagcatc | ggtgaggcca | tccagtatct | gcattcaatc | 540 |
| aacattgccc | atcgggatgt | caagcctgag | aatctcttat | acacctccaa | aaggcccaac | 600 |
| gccatcctga | aactcactga | ctttggcttt | gccaaggaaa | ccaccagcca | caactctttg | 660 |
| accactcctt | gttatacacc | gtactatgtg | gctccagaag | tgctgggtcc | agagaagtat | 720 |
| gacaagtcct | gtgacatgtg | gtccctgggt | gtcatcatgt | acatcctgct | gtgtgggtat | 780 |
| ccccccttct | actccaacca | cggccttgcc | atctctccgg | gcatgaagac | tcgcatccga | 840 |
| atgggccagt | atgaatttcc | caacccagaa | tggtcagaag | tatcagagga | agtgaagatg | 900 |
| ctcattcgga | atctgctgaa | acagagccc | accagagaa | tgaccatcac | cgagtttatg | 960 |
| aaccacccctt | ggatcatgca | atcaacaaag | gtccctcaaa | ccccactgca | caccagccgg | 1020 |
| gtcctgaagg | aggacaagga | gcggtgggag | gatgtcaagg | ggtgtcttca | tgacaagaac | 1080 |
| agcgaccagg | ccacttggct | gaccaggttg | tga | | | 1113 |

<210> SEQ ID NO 26
<211> LENGTH: 954
<212> TYPE: DNA
<213> ORGANISM: Homo sapiens

<400> SEQUENCE: 26

| | | | | | |
|---|---|---|---|---|---|
| atgcgacccg | accgcgctga | ggctccagga | ccgcccgcca | tggctgcagg | aggtcccggc | 60 |
| gcggggtctg | cggccccggt | ctcctccaca | tcctcccttc | ccctggctgc | tctcaacatg | 120 |
| cgagtgcggc | gccgcctgtc | tctgttcttg | aacgtgcgga | cacaggtggc | ggccgactgg | 180 |
| accgcgctgg | cggaggagat | ggactttgag | tacttggaga | tccggcaact | ggagacacaa | 240 |
| gcggacccca | ctggcaggct | gctggacgcc | tggcagggac | gccctggcgc | tctctgtaggc | 300 |
| cgactgctcg | agctgcttac | caagctgggc | cgcgacgacg | tgctgctgga | gctgggaccc | 360 |
| agcattgagg | aggattgcca | aaagtatatc | ttgaagcagc | agcaggagga | ggctgagaag | 420 |
| cctttacagg | tggccgctgt | agacagcagt | gtcccacgga | cagcagagct | ggcgggcatc | 480 |
| accacacttg | atgaccccct | ggggcatatg | cctgagcgtt | tcgatgcctt | catctgctat | 540 |
| tgccccagcg | acatccagtt | tgtgcaggag | atgatccggc | aactggaaca | gacaaactat | 600 |
| cgactgaagt | tgtgtgtgtc | tgaccgcgat | gtcctgcctg | gcacctgtgt | ctggtctatt | 660 |
| gctagtgagc | tcatcgaaaa | gaggttggct | agaaggccac | ggggtgggtg | ccgccggatg | 720 |
| gtggtggttg | tctctgatga | ttacctgcag | agcaaggaat | gtgacttcca | gaccaaattt | 780 |

-continued

| | |
|---|---|
| gcactcagcc tctctccagg tgcccatcag aagcgactga tccccatcaa gtacaaggca | 840 |
| atgaagaaag agttccccag catcctgagg ttcatcactg tctgcgacta caccaacccc | 900 |
| tgcaccaaat cttggttctg gactcgcctt gccaaggcct tgtccctgcc ctga | 954 |

<210> SEQ ID NO 27
<211> LENGTH: 2907
<212> TYPE: DNA
<213> ORGANISM: Homo sapiens

<400> SEQUENCE: 27

| | |
|---|---|
| atggcagaag atgatccata tttgggaagg cctgaacaaa tgtttcattt ggatccttct | 60 |
| ttgactcata caatatttaa tccagaagta tttcaaccac agatggcact gccaacagat | 120 |
| ggcccatacc ttcaaatatt agagcaacct aaacagagag gatttcgttt ccgttatgta | 180 |
| tgtgaaggcc catcccatgg tggactacct ggtgcctcta gtgaaaagaa caagaagtct | 240 |
| taccctcagg tcaaaatctg caactatgtg ggaccagcaa aggttattgt tcagttggtc | 300 |
| acaaatggaa aaaatatcca cctgcatgcc cacagcctgg tgggaaaaca ctgtgaggat | 360 |
| gggatctgca ctgtaactgc tggacccaag gacatggtgg tcggcttcgc aaacctgggt | 420 |
| atacttcatg tgacaaagaa aaagtatttt gaaacactgg aagcacgaat gacagaggcg | 480 |
| tgtataaggg gctataatcc tggactcttg gtgcaccctg accttgccta tttgcaagca | 540 |
| gaaggtggag gggaccggca gctgggagat cgggaaaaag agctaatccg ccaagcagct | 600 |
| ctgcagcaga ccaaggagat ggacctcagc gtggtgcggc tcatgtttac agcttttctt | 660 |
| ccggatagca ctggcagctt cacaaggcgc ctggaacccg tggtatcaga cgccatctat | 720 |
| gacagtaaag cccccaatgc atccaacttg aaaattgtaa gaatggacag acagctgga | 780 |
| tgtgtgactg gaggggagga aatttatctt ctttgtgaca agttcagaa agatgacatc | 840 |
| cagattcgat tttatgaaga ggaagaaaat ggtggagtct gggaaggatt ggagattttt | 900 |
| tcccccacag atgttcatag acaatttgcc attgtcttca aaactccaaa gtataaagat | 960 |
| attaatatta caaaaccagc ctctgtgttt gtccagcttc ggaggaaatc tgacttggaa | 1020 |
| actagtgaac caaaaccttt cctctactat cctgaaatca agataaaga agaagtgcag | 1080 |
| aggaaacgtc agaagctcat gcccaatttt tcggatagtt tcggcggtgg tagtggtgct | 1140 |
| ggagctggag gcggaggcat gtttggtagt ggcggtggag gaggggcac tggaagtaca | 1200 |
| ggtccagggt atagcttccc acactatgga tttcctactt atggtgggat tactttccat | 1260 |
| cctggaacta ctaaatctaa tgctgggatg aagcatgaa ccatgacac tgaatctaaa | 1320 |
| aaggaccctg aaggttgtga caaaagtgat gacaaaaaca ctgtaaacct ctttgggaaa | 1380 |
| gttattgaaa ccacagagca agatcaggag cccagcgagg ccaccgttgg aatggtgag | 1440 |
| gtcactctaa cgtatgcaac aggaacaaaa aagagagtg ctggagttca ggataacctc | 1500 |
| tttctagaga aggctatgca gcttgcaaag aggcatgcca atgccctttt cgactacgcg | 1560 |
| gtgacaggag acgtgaagat gctgctggcc gtccagcgcc atctcactgc tgtgcaggat | 1620 |
| gagaatgggg acagtgtctt acacttagca atcatccacc ttcattctca acttgtgagg | 1680 |
| gatctactag aagtcacatc tggtttgatt tctgatgaca ttatcaacat gagaaatgat | 1740 |
| ctgtaccaga cgcccttgca cttggcagtg atcactaagc aggaagatgt ggtggaggat | 1800 |
| ttgctgaggg ctggggccga cctgagcctt ctggaccgct gggtaactc tgttttgcac | 1860 |
| ctagctgcca agaaggaca tgataaagtt ctcagtatct tactcaagca caaaaggca | 1920 |

```
gcactacttc ttgaccaccc caacggggac ggtctgaatg ccattcatct agccatgatg    1980
agcaatagcc tgccatgttt gctgctgctg gtggccgctg gggctgacgt caatgctcag    2040
gagcagaagt ccgggcgcac agcactgcac ctggctgtgg agcacgacaa catctcattg    2100
gcaggctgcc tgctcctgga gggtgatgcc catgtggaca gtactaccta cgatggaacc    2160
acacccctgc atatagcagc tgggagaggg tccaccaggc tggcagctct tctcaaagca    2220
gcaggagcag atcccctggt ggagaacttt gagcctctct atgacctgga tgactcttgg    2280
gaaaatgcag gagaggatga aggagttgtg cctggaacca cgcctctaga tatggccacc    2340
agctggcagg tatttgacat attaaatggg aaaccatatg agccagagtt tacatctgat    2400
gatttactag cacaaggaga catgaaacag ctggctgaag atgtgaagct gcagctgtat    2460
aagttactag aaattcctga tccagacaaa actgggcta ctctggcgca gaaattaggt    2520
ctggggatac ttaataatgc cttccggctg agtcctgctc cttccaaaac acttatggac    2580
aactatgagg tctctggggg tacagtcaga gagctggtgg aggccctgag acaaatgggc    2640
tacaccgaag caattgaagt gatccaggca gcctccagcc cagtgaagac cacctctcag    2700
gcccactcgc tgcctctctc gcctgcctcc acaaggcagc aaatagacga gctccgagac    2760
agtgacagtg tctgcgacag cggcgtggag acatccttcc gcaaactcag ctttaccgag    2820
tctctgacca gtggtgcctc actgctaact ctcaacaaaa tgccccatga ttatgggcag    2880
gaaggacctc tagaaggcaa aatttag                                         2907

<210> SEQ ID NO 28
<211> LENGTH: 2844
<212> TYPE: DNA
<213> ORGANISM: Homo sapiens

<400> SEQUENCE: 28
atggcagtga tggaaatggc ctgcccaggt gcccctggct cagcagtggg gcagcagaag      60
gaactcccca agccaaggaa gaagacgccg ccactgggga gaaacagag ctccgtctac      120 aagcttgagg ccgtggagaa gagccctgtg ttctgcggaa agtgggagat cctgaatgac     180
gtgattacca agggcacagc caaggaaggc tccgaggcag ggccagctgc catctctatc     240
atcgcccagg ctgagtgtga aatagccaa gagttcagcc ccaccttttc agaacgcatt      300
ttcatcgctg gtccaaaaca gtacagccag tccgagagtc ttgatcagat ccccaacaat     360
gtggcccatg ctacagaggg caaaatggcc cgtgtgtgtt ggaagggaaa gcgtcgcagc     420
aaagcccgga gaaacggaa gaagaagagc tcaaagtccc tggctcatgc aggagtggcc     480
ttggccaaac ccctccccag gacccctgag caggagagct gcaccatccc agtgcaggag     540
gatgagtctc cactcggcgc ccatatgtt agaaacaccc cgcagttcac caagcctctg     600
aaggaaccag gccttgggca actctgtttt aagcagcttg gcgagggcct acggccggct     660
ctgcctcgat cagaactcca caaactgatc agccccttgc aatgtctgaa ccacgtgtgg     720
aaactgcacc accccagga cggaggcccc ctgcccctgc ccacgcaccc cttcccctat     780
agcagactgc ctcatccctt cccattccac cctctccagc cctggaaacc tcaccctctg     840
gagtccttcc tgggcaaact ggctgtgta gacagccaga aacccttgcc tgacccacac     900
ctgagcaaac tggcctgtgt agacagtcca aagcccctgc ctgcccaca cctggagccc     960 agctgcctgt ctcgtggtgc ccatgagaag ttttctgtgg aggaatacct agtgcatgct    1020
ctgcaaggca gcgtgagctc aggccaggcc cacagcctga ccagcctggc caagacctgg    1080
gcagcaaggg gctccagatc ccgggagccc agccccaaaa ctgaggacaa cgagggtgtc    1140
```

```
ctgctcactg agaaactcaa gccagtggat tatgagtacc gagaagaagt ccactgggcc      1200
acgcaccagc tccgcctggg cagaggctcc ttcggagagg tgcacaggat ggaggacaag      1260
cagactggct tccagtgcgc tgtcaaaaag gtgcggctgg aagtatttcg ggcagaggag      1320
ctgatggcat gtgcaggatt gacctcaccc agaattgtcc ctttgtatgg agctgtgaga      1380
gaagggcctt gggtcaacat cttcatggag ctgctggaag gtggctccct gggccagctg      1440
gtcaaggagc agggctgtct cccagaggac cgggccctgt actacctggg ccaggccctg      1500
gagggtctgg aatacctcca ctcacgaagg attctgcatg gggacgtcaa agctgacaac      1560
gtgctcctgt ccagcgatgg gagccacgca gccctctgtg actttggcca tgctgtgtgt      1620
cttcaacctg atggcctggg aaagtccttg ctcacagggg actacatccc tggcacagag      1680
acccacatgg ctccggaggt ggtgctgggc aggagctgcg acgccaaggt ggatgtctgg      1740
agcagctgct gtatgatgct gcacatgctc aacggctgcc accctggac tcagttcttc       1800 cgagggccgc tctgcctcaa gattgccagc gagcctccgc ctgtgaggga gatcccaccc      1860
tcctgcgccc ctctcacagc ccaggccatc aagagggggc tgaggaaaga gcccatccac      1920
cgcgtgtctg cagcggagct gggagggaag gtgaaccggg cactacagca agtgggaggt      1980
ctgaagagcc cttggagggg agaatataaa gaaccaagac atccaccgcc aaatcaagcc      2040
aattaccacc agaccctcca tgcccagccg agagagcttt cgccaagggc cccagggccc      2100
cggccagctg aggagacaac aggcagagcc cctaagctcc agcctcctct cccaccagag      2160
cccccagagc caaacaagtc tcctcccttg actttgagca aggaggagtc tgggatgtgg      2220
gaacccttac ctctgtcctc cctggagcca gcccctgcca gaaacccag ctcaccagag       2280 cggaaagcaa ccgtcccgga gcaggaactg cagcagctgg aaatagaatt attcctcaac      2340
agcctgtccc agccatttc tctggaggag caggagcaaa ttctctcgtg cctcagcatc       2400
gacagcctct ccctgtcgga tgacagtgag aagaacccat caaaggcctc tcaaagctcg      2460
cgggacaccc tgagctcagg cgtacactcc tggagcagca aggccgaggc tcgaagctcc      2520
agctggaaca tggtgctggc ccgggggcgc cccaccgaca cccccaagcta tttcaatggt      2580 gtgaaagtcc aaatacagtc tcttaatggt gaacacctgc acatccggga gttccaccgg      2640
gtcaaagtgg gagacatcgc cactggcatc agcagccaga tcccagctgc agccttcagc      2700
ttggtcacca agacgggca gcctgttcgc tacgacatga ggtgccagat tcgggcatc       2760 gacctgcagt gcacactggc ccctgatggc agcttcgcct ggagctggag ggtcaagcat      2820
ggccagctgg agaacaggcc ctaa                                             2844
```

<210> SEQ ID NO 29
<211> LENGTH: 1083
<212> TYPE: DNA
<213> ORGANISM: Homo sapiens

<400> SEQUENCE: 29

```
atgtctcagg agaggcccac gttctaccgg caggagctga acaagacaat ctgggaggtg       60
cccgagcgtt accagaacct gtctccagtg ggctctggcg cctatggctc tgtgtgtgct      120
gcttttgaca caaaaacggg gttacgtgtg gcagtgaaga agctctccag accatttcag      180
tccatcattc atgcgaaaag aacctacaga gaactgcggt tacttaaaca tatgaaacat      240
gaaaatgtga ttggtctgtt ggacgttttt acacctgcaa ggtctctgga ggaattcaat      300
gatgtgtatc tggtgaccca tctcatgggg gcagatctga caacattgt gaaatgtcag      360
```

```
aagcttacag atgaccatgt tcagttcctt atctaccaaa ttctccgagg tctaaagtat    420
atacattcag ctgacataat tcacagggac ctaaaaccta gtaatctagc tgtgaatgaa    480
gactgtgagc tgaagattct ggattttgga ctggctcggc acacagatga tgaaatgaca    540
ggctacgtgg ccactaggtg gtacagggct cctgagatca tgctgaactg gatgcattac    600
aaccagacag ttgatatttg gtcagtggga tgcataatgg ccgagctgtt gactggaaga    660
acattgtttc ctggtacaga ccatattaac cagcttcagc agattatgcg tctgacagga    720
acaccccccg cttatctcat taacaggatg ccaagccatg aggcaagaaa ctatattcag    780
tctttgactc agatgccgaa gatgaacttt gcgaatgtat ttattggtgc caatcccctg    840
gctgtcgact tgctggagaa gatgcttgta ttggactcag ataagagaat tacagcggcc    900
caagcccttg cacatgccta ctttgctcag taccacgatc ctgatgatga accagtggcc    960
gatccttatg atcagtcctt tgaaagcagg gacctcctta tagatgagtg gaaaagcctg   1020
acctatgatg aagtcatcag ctttgtgcca ccacccttg accaagaaga gatggagtcc    1080
tga                                                                 1083

<210> SEQ ID NO 30
<211> LENGTH: 1656
<212> TYPE: DNA
<213> ORGANISM: Homo sapiens

<400> SEQUENCE: 30
atggctggtg atctttcagc aggtttcttc atggaggaac ttaatacata ccgtcagaag     60
cagggagtag tacttaaata tcaagaactg cctaattcag acctccaca tgataggagg    120
tttacatttc aagttataat agatggaaga gaatttccag aaggtgaagg tagatcaaag    180
aaggaagcaa aaatgccgc agccaaatta gctgttgaga tacttaataa ggaaaagaag    240
gcagttagtc ctttattatt gacaacaacg aattcttcag aaggattatc catggggaat    300
tacataggcc ttatcaatag aattgcccag aagaaaagac taactgtaaa ttatgaacag    360
tgtgcatcgg gggtgcatgg ccagaagga tttcattata aatgcaaaat gggacagaaa    420
gaatatagta ttggtacagg ttctactaaa caggaagcaa acaattggc cgctaaactt    480
gcatatcttc agatattatc agaagaaacc tcagtgaaat ctgactacct gtcctctggt    540
tcttttgcta ctacgtgtga gtcccaaagc aactctttag tgaccagcac actcgcttct    600
gaatcatcat ctgaaggtga cttctcagca gatacatcag agataaattc taacagtgac    660
agtttaaaca gttcttcgtt gcttatgaat ggtctcagaa ataatcaaag gaaggcaaaa    720
agatctttgg cacccagatt tgaccttcct gacatgaaag aaacaaagta tactgtggac    780
aagaggtttg gcatggattt taagaaaata gaattaattg gctcaggtgg atttggccaa    840
gttttcaaag caaaacacag aattgacgga aagacttacg ttattaaacg tgttaaatat    900
aataacgaga aggcggagcg tgaagtaaaa gcattggcaa acttgatca tgtaaatatt    960
gttcactaca tggctgttg ggatggattt gattatgatc ctgagaccag tgatgattct   1020
cttgagagca gtgattatga tcctgagaac agcaaaaata gttcaaggtc aaagactaag   1080
tgccttttca tccaaatgga attctgtgat aaagggacct ggaacaatg gattgaaaaa   1140
agaagaggcg agaaactaga caaagttttg ctttggaac tctttgaaca aataacaaaa   1200
ggggtggatt atacattc aaaaaaatta attcatagag atcttaagcc aagtaatata    1260
ttcttagtag atacaaaaca gtaaagatt ggagactttg gacttgtaac atctctgaaa   1320
aatgatggaa agcgaacaag gagtaaggga actttgcgat acatgagccc agaacagatt   1380
```

| | |
|---|---|
| tcttcgcaag actatggaaa ggaagtggac ctctacgctt tggggctaat tcttgctgaa | 1440 |
| cttcttcatg tatgtgacac tgcttttgaa acatcaaagt ttttcacaga cctacgggat | 1500 |
| ggcatcatct cagatatatt tgataaaaaa gaaaaaactc ttctacagaa attactctca | 1560 |
| aagaaacctg aggatcgacc taacacatct gaaatactaa ggaccttgac tgtgtggaag | 1620 |
| aaaagcccag agaaaaatga acgacacaca tgttag | 1656 |

<210> SEQ ID NO 31
<211> LENGTH: 1443
<212> TYPE: DNA
<213> ORGANISM: Homo sapiens

<400> SEQUENCE: 31

| | |
|---|---|
| atgagcgacg tggctattgt gaaggagggt tggctgcaca aacgagggga gtacatcaag | 60 |
| acctggcggc cacgctactt cctcctcaag aatgatggca ccttcattgg ctacaaggag | 120 |
| cggccgcagg atgtgaccca acgtgaggct cccctcaaca acttctctgt ggcgcagtgc | 180 |
| cagctgatga agacggagcg gccccggccc aacaccttca tcatccgctg cctgcagtgg | 240 |
| accactgtca tcgaacgcac cttccatgtg gagactcctg aggagcggga ggagtggaca | 300 |
| accgccatcc agactgtggc tgacggcctc aagaagcagg aggaggagga gatggacttc | 360 |
| cggtcgggct cacccagtga caactcaggg gctgaagaga tggaggtgtc cctggccaag | 420 |
| cccaagcacc gcgtgaccat gaacgagttt gagtacctga gctgctggg caagggcact | 480 |
| ttcggcaagg tgatcctggt gaaggagaag gccacaggcc gctactacgc catgaagatc | 540 |
| ctcaagaagg aagtcatcgt ggccaaggac gaggtggccc acacactcac cgagaaccgc | 600 |
| gtcctgcaga actccaggca cccccttcctc acagccctga gtactctttt ccagacccac | 660 |
| gaccgcctct gctttgtcat ggagtacgcc aacggggcg agctgttctt ccacctgtcc | 720 |
| cgggagcgtg tgttctccga ggaccgggcc cgcttctatg cgctgagat tgtgtcagcc | 780 |
| ctggactacc tgcactcgga agaaacgtg gtgtaccggg acctcaagct ggagaacctc | 840 |
| atgctggaca aggacgggca cattaagatc acagacttcg ggctgtgcaa ggagggatc | 900 |
| aaggacggtg ccaccatgaa gacctttgc ggcacacctg agtacctggc ccccgaggtg | 960 |
| ctggaggaca tgactacgg ccgtgcagtg gactggtggg gctgggcgt ggtcatgtac | 1020 |
| gagatgatgt gcggtcgcct gccccttctac aaccaggacc atgagaagct tttttgagctc | 1080 |
| atcctcatgg aggagatccg cttccgcgc acgcttggtc ccgaggccaa gtccttgctt | 1140 |
| tcagggctgc tcaagaagga ccccaagcag aggcttggcg ggggctccga ggacgccaag | 1200 |
| gagatcatgc agcatcgctt ctttgccggt atcgtgtggc agcacgtgta cgagaagaag | 1260 |
| ctcagcccac ccttcaagcc ccaggtcacg tcggagactg acaccaggta ttttgatgag | 1320 |
| gagttcacgg cccagatgat caccatcaca ccacctgacc aagatgacag catggagtgt | 1380 |
| gtggacagcg agcgcaggcc ccacttcccc cagttctcct actcggccag cggcacggcc | 1440 |
| tga | 1443 |

<210> SEQ ID NO 32
<211> LENGTH: 2514
<212> TYPE: DNA
<213> ORGANISM: Homo sapiens

<400> SEQUENCE: 32

| | |
|---|---|
| atggctagca acgaaaaatc tacaactcca tgcatggttc ggacatcaca agtagtagaa | 60 |

```
caagatgtgc ccgaggaagt agacagggcc aaagagaaag gaatcggcac accacagcct    120
gacgtggcca aggacagttg ggcagcagaa cttgaaaact cttccaaaga aaacgaagtg    180
atagaggtga atctatggg ggaaagccag tccaaaaaac tccaaggtgg ttatgagtgc     240
aaatactgcc cctactccac gcaaaacctg aacgagttca cggagcatgt cgacatgcag    300
catcccaacg tgattctcaa ccccctctac gtgtgtgcag aatgtaactt cacaaccaaa    360
aagtacgact ccctatccga ccacaactcc aagttccatc ccggggaggc caacttcaag    420
ctgaagttaa ttaaacgcaa taatcaaact gtcttggaac agtccatcga aaccaccaac    480
catgtcgtgt ccatcaccac cagtggccct ggaactggtg acagtgattc tgggatctcg    540
gtgagtaaaa cccccatcat gaagcctgga aaaccaaaag cggatgccaa gaaggtgccc    600
aagaagcccg aggagatcac ccccgagaac cacgtggaag ggaccgcccg cctggtgaca    660
gacacagctg agatcctctc gagactcggc ggggtggagc tcctccaaga cacattagga    720
cacgtcatgc cttctgtaca gctgccacca aatatcaacc ttgtgcccaa ggtccctgtc    780
ccactaaata ctaccaaata caactctgcc ctggatacaa atgccacgat gatcaactct    840
ttcaacaagt tccttaccc gacccaggct gagttgtcct ggctgacagc tgcctccaaa    900
cacccagagg agcacatcag aatctggttt gccaccagc gcttaaagca tggcatcagc    960
tggtccccag aagaggtgga ggaggcccgg aagaagatgt tcaacggcac catccagtca   1020 gtaccccga ccatcactgt gctgcccgcc cagttggccc ccacaaaggt gacgcagccc   1080
atcctccaga cggctctacc gtgccagatc ctcggccaga ctagcctggt gctgactcag   1140
gtgaccagcg ggtcaacaac cgtctcttgc tccccccatca cacttgccgt ggcaggagtc   1200
accaaccatg gccagaagag acccttggtg actccccaag ctgccccccga acccaagcgt   1260 ccacacatcg ctcaggtgcc agagcccca cccaaggtgg ccaaccccc gctcacacca   1320 gccagtgacc gcaagaagac aaaggagcag atagcacatc tcaaggccag ctttctccag   1380
agccagttcc ctgacgatgc cgaggtttac cggctcatcg aggtgactgg ccttgccagg   1440
agcgagatca agaagtggtt cagtgaccac cgatatcggt gtcaaagggg catcgtccac   1500
atcaccagcg aatcccttgc caaagaccag ttggccatcg cggcctcccg acacggtcgc   1560
acgtatcatg cgtacccaga cttttgcccc cagaagttca agagaaaac acagggtcag   1620 gttaaaatct tggaagacag cttttttgaaa agttcttttc ctacccaagc agaactggat   1680
cggctaaggg tggagaccaa gctgagcagg agagagatcg actcctggtt ctcggagagg   1740
cggaagcttc gagacagcat ggaacaagct gtcttggatt ccatgggtc tggcaaaaaa   1800 ggccaagatg tgggagcccc caatggtgct ctgtctcgac tcgaccagct ctccggtgcc   1860
cagttaacaa gttctctgcc cagcccttcg ccagcaattg caaaaagtca gaacaggtt   1920 catctcctga ggagcacgtt tgcaagaacc cagtggccta ctccccagga gtacgaccag   1980
ttagcggcca agactggcct ggtccgaact gagattgtgc gttggttcaa ggagaacaga   2040
tgcttgctga aaacgggaac cgtgaagtgg atggagcagt accagcacca gcccatggca   2100
gatgatcacg gctacgatgc cgtagcaagg aaagcaacaa acccatggc cgagagccca   2160 aagaacgggg gtgatgtggt tccacaatat tacaaggacc ccaaaaagct ctgcgaagag   2220
gacttggaga agttggtgac cagggtaaaa gtaggcagcg agccagcaaa agactgtttg   2280
ccagcaaagc cctcagaggc cacctcagac cggtcagagg gcagcagccg ggacggccag   2340
ggtagcgacg agaacgagga gtcgagcgtt gtggattacg tggaggtgac ggtcggggag   2400
gaggatgcga tctcagatag atcagatagc tggagtcagg ctgcggcaga aggtgtgtcg   2460
```

```
gaactggctg aatcagactc cgactgcgtc cctgcagagg ctggccaggc ctag        2514
```

<210> SEQ ID NO 33
<211> LENGTH: 567
<212> TYPE: DNA
<213> ORGANISM: Homo sapiens

<400> SEQUENCE: 33

```
atgactgaat ataaacttgt ggtagttgga gctggtggcg taggcaagag tgccttgacg    60
atacagctaa ttcagaatca ttttgtggac gaatatgatc caacaataga ggattcctac   120
aggaagcaag tagtaattga tggagaaacc tgtctcttgg atattctcga cacagcaggt   180
caagaggagt acagtgcaat gagggaccag tacatgagga ctggggaggg ctttctttgt   240
gtatttgcca taataatac taaatcattt gaagatattc accattatag agaacaaatt    300
aaaagagtta aggactctga agatgtacct atggtcctag taggaaataa atgtgatttg   360
ccttctagaa cagtagacac aaaacaggct caggacttag caagaagtta tggaattcct   420
tttattgaaa catcagcaaa gacaagacag ggtgttgatg atgccttcta tacattagtt   480
cgagaaattc gaaaacataa agaaaagatg agcaaagatg gtaaaaagaa gaaaaagaag   540
tcaaagacaa agtgtgtaat tatgtaa                                       567
```

<210> SEQ ID NO 34
<211> LENGTH: 570
<212> TYPE: DNA
<213> ORGANISM: Homo sapiens

<400> SEQUENCE: 34

```
atgactgagt acaaactggt ggtggttgga gcaggtggtg ttgggaaaag cgcactgaca    60
atccagctaa tccagaacca cttttgtagat gaatatgatc ccaccataga ggattcttac   120
agaaaacaag tggttataga tggtgaaacc tgtttgttgg atatactgga tacagctgga   180
caagaagagt acagtgccat gagagaccaa tacatgagga caggcgaagg cttcctctgt   240
gtatttgcca tcaataatag caagtcattt gcggatatta acctctacag ggagcagatt   300
aagcgagtaa aagactcgga tgatgtacct atggtgctag tgggaaacaa gtgtgatttg   360
ccaacaagga cagttgatac aaaacaagcc cacgaactgg ccaagagtta cgggattcca   420
ttcattgaaa cctcagccaa gaccagacag ggtgttgaag atgctttta cacactggta   480
agagaaatac gccagtaccg aatgaaaaaa ctcaacagca gtgatgatgg gactcagggt   540
tgtatgggat tgccatgtgt ggtgatgtaa                                    570
```

<210> SEQ ID NO 35
<211> LENGTH: 2016
<212> TYPE: DNA
<213> ORGANISM: Homo sapiens

<400> SEQUENCE: 35

```
atgcaaccag acatgtcctt gaatgtcatt aagatgaaat ccagtgactt cctggagagt    60
gcagaactgg acagcggagg ctttgggaag gtgtctctgt gtttccacag aacccaggga   120
ctcatgatca tgaaaacagt gtacaagggg cccaactgca ttgagcacaa cgaggccctc   180
ttggaggagg cgaagatgat gaacagactg agacacagcc gggtggtgaa gctcctgggc   240
gtcatcatag aggaagggaa gtactcccctg gtgatggagt acatggagaa gggcaacctg   300
atgcacgtgc tgaaagccga gatgagtact ccgcttttctg taaaaggaag gataatttg   360
```

```
gaaatcattg aaggaatgtg ctacttacat ggaaaaggcg tgatacacaa ggacctgaag        420
cctgaaaata tccttgttga taatgacttc cacattaaga tcgcagacct cggccttgcc        480
tcctttaaga tgtggagcaa actgaataat gaagagcaca atgagctgag ggaagtggac        540
ggcaccgcta agaagaatgg cggcaccctc tactacatgg cgcccgagca cctgaatgac        600
gtcaacgcaa agcccacaga gaagtcggat gtgtacagct ttgctgtagt actctgggcg        660
atatttgcaa ataaggagcc atatgaaaat gctatctgtg agcagcagtt gataatgtgc        720
ataaaatctg ggaacaggcc agatgtggat gacatcactg agtactgccc aagagaaatt        780
atcagtctca tgaagctctg ctgggaagcg aatccggaag ctcggccgac atttcctggc        840
attgaagaaa aatttaggcc ttttttattta agtcaattag aagaaagtgt agaagaggac       900
gtgaagagtt taagaaaga gtattcaaac gaaaatgcag ttgtgaagag aatgcagtct         960
cttcaacttg attgtgtggc agtaccttca agccggtcaa attcagccac agaacagcct       1020
ggttcactgc acagttccca gggacttggg atgggtcctg tggaggagtc ctggtttgct       1080
ccttccctgg agcacccaca agaagagaat gagcccagcc tgcagagtaa actccaagac       1140
gaagccaact accatcttta tggcagccgc atggacaggc agacgaaaca gcagcccaga       1200
cagaatgtgg cttacaacag agaggaggaa aggagacgaa gggtctccca tgaccctttt       1260
gcacagcaaa gaccttacga gaattttcag aatacagagg gaaaaggcac tgcttattcc       1320
agtgcagcca gtcatggtaa tgcagtgcac cagccctcag ggctcaccag ccaacctcaa       1380
gtactgtatc agaacaatgg attatatagc tcacatggct ttggaacaag accactggat       1440
ccaggaacag caggtcccag agtttggtac aggccaattc caagtcatat gcctagtctg       1500
cataatatcc cagtgcctga gaccaactat ctaggaaata cacccaccat gccattcagc       1560
tccttgccac caacagatga atctataaaa tataccatat acaatagtac tggcattcag       1620
attggagcct acaattatat ggagattggt gggacgagtt catcactact agacagcaca       1680
aatacgaact tcaaagaaga gccagctgct aagtaccaag ctatctttga taataccact       1740
agtctgacgg ataaacacct ggacccaatc agggaaaatc tgggaaagca ctggaaaaac       1800
tgtgcccgta aactgggctt cacacagtct cagattgatg aaattgacca tgactatgag       1860
cgagatggac tgaaagaaaa ggtttaccag atgctccaaa agtgggtgat gagggaaggc       1920
ataaagggag ccacggtggg gaagctggcc caggcgctcc accagtgttc caggatcgac       1980
cttctgagca gcttgattta cgtcagccag aactaa                                 2016

<210> SEQ ID NO 36
<211> LENGTH: 1569
<212> TYPE: DNA
<213> ORGANISM: Homo sapiens

<400> SEQUENCE: 36
atgagtctgc taaactgtga aaacagctgt ggatccagcc agtctgaaag tgactgctgt         60
gtggccatgg ccagctcctg tagcgctgta acaaaagatg atagtgtggg tggaactgcc        120
agcacgggga acctctccag ctcatttatg gaggagatcc agggatatga tgtagagttt        180
gacccacccc tggaaagcaa gtatgaatgc cccatctgct tgatggcatt acgagaagca        240
gtgcaaacgc catgcggcca taggttctgc aaagcctgca tcataaaatc aataagggat        300
gcaggtcaca atgtccagt tgacaatgaa atactgctgg aaaatcaact atttccagac        360
aattttgcaa aacgtgagat tctttctctg atggtgaaat gtccaaatga aggttgtttg        420
cacaagatgg aactgagaca tcttgaggat catcaagcac attgtgagtt tgctcttatg        480
```

```
gattgtcccc aatgccagcg tcccttccaa aaattccata ttaatattca cattctgaag      540
gattgtccaa ggagacaggt ttcttgtgac aactgtgctg catcaatggc atttgaagat      600
aaagagatcc atgaccagaa ctgtcctttg gcaaatgtca tctgtgaata ctgcaatact      660
atactcatca gagaacagat gcctaatcat tatgatctag actgccctac agccccaatt      720
ccatgcacat tcagtacttt tggttgccat gaaaagatgc agaggaatca cttggcacgc      780
cacctacaag agaacaccca gtcacacatg agaatgttgg cccaggctgt tcatagtttg      840
agcgttatac ccgactctgg gtatatctca gaggtccgga atttccagga aactattcac      900
cagttagagg gtcgccttgt aagacaagac catcaaatcc gggagctgac tgctaaaatg      960
gaaactcaga gtatgtatgt aagtgagctc aaacgaacca ttcgaaccct tgaggacaaa     1020
gttgctgaaa tcgaagcaca gcagtgcaat ggaatttata tttggaagat tggcaacttt     1080
ggaatgcatt tgaaatgtca agaagaggag aaacctgttg tgattcatag ccctggattc     1140
tacactggca aacccgggta caaactgtgc atgcgcttgc accttcagtt accgactgct     1200
cagcgctgtg caaactatat atccctttttt gtccacacaa tgcaaggaga atatgacagc     1260
cacctccctt ggcccttcca gggtacaata cgccttacaa ttcttgatca gtctgaagca     1320
cctgtaaggc aaaaccacga agagataatg gatgccaaac cagagctgct tgctttccag     1380
cgacccacaa tcccacggaa cccaaaaggt tttggctatg taacttttat gcatctggaa     1440
gccctaagac aaagaacttt cattaaggat gacacattat tagtgcgctg tgaggtctcc     1500
acccgctttg acatgggtag ccttcggagg gagggttttc agccacgaag tactgatgca     1560
ggggtatag                                                              1569

<210> SEQ ID NO 37
<211> LENGTH: 999
<212> TYPE: DNA
<213> ORGANISM: Homo sapiens

<400> SEQUENCE: 37
atggccaacc gttacaccat ggatctgact gccatctacg agagcctcct gtcgctgagc       60
cctgacgtgc ccgtgccatc cgaccatgga gggactgagt ccagcccagg ctggggctcc      120
tcgggaccct ggagcctgag cccctccgac tccagcccgt ctggggtcac ctcccgcctg      180
cctggccgct ccaccagcct agtggagggc cgcagctgtg gctgggtgcc cccaccccct      240
ggcttcgcac cgctggctcc ccgcctgggc cctgagctgt caccctcacc cacttcgccc      300
actgcaacct ccaccacccc ctcgcgctac aagactgagc tatgtcggac cttctcagag      360
agtgggcgct gccgctacgg ggccaagtgc cagtttgccc atggcctggg cgagctgcgc      420
caggccaatc gccacccccaa atacaagacg gaactctgtc acaagttcta cctccagggc      480
cgctgcccct acgctctccg ctgccacttc atccacaacc tagcgaaga cctggcggcc      540 ccgggccacc ctcctgtgct cgccagagc atcagcttct ccggcctgcc ctctggccgc      600
cggacctcac caccaccacc aggcctggcc ggcccttccc tgtcctccag ctccttctcg      660
ccctccagct cccaccacc acctggggac cttccactgt cacctctgc cttctctgct      720 gcccctggca ccccctggc tcgaagagac cccaccccag tctgttgccc ctcctgccga      780
agggccactc ctatcagcgt ctgggggccc ttgggtggcc tggttcggac cccctctgta      840
```

```
cagtccctgg gatccgaccc tgatgaatat gccagcagcg gcagcagcct gggggctct    900
gactctcccg tcttcgaggc gggagttttt gcaccacccc agcccgtggc agcccccgg    960
cgactcccca tcttcaatcg catctctgtt tctgagtga                          999
```